US010539566B2

(12) United States Patent
Narain et al.

(10) Patent No.: US 10,539,566 B2
(45) Date of Patent: Jan. 21, 2020

(54) USE OF MARKERS INCLUDING FILAMIN A IN THE DIAGNOSIS AND TREATMENT OF PROSTATE CANCER

(71) Applicant: Berg LLC, Framingham, MA (US)

(72) Inventors: Niven Rajin Narain, Cambridge, MA (US); Vivek K. Vishnudas, Bedford, MA (US); Rangaprasad Sarangarajan, Boylston, MA (US); Viatcheslav R. Akmaev, Sudbury, MA (US)

(73) Assignee: Berg LLC, Framingham, MA (US)

( * ) Notice: Subject to any disclaimer, the term of this patent is extended or adjusted under 35 U.S.C. 154(b) by 21 days.

(21) Appl. No.: 14/962,966

(22) Filed: Dec. 8, 2015

(65) Prior Publication Data

US 2016/0258958 A1 Sep. 8, 2016

Related U.S. Application Data

(60) Provisional application No. 62/148,294, filed on Apr. 16, 2015, provisional application No. 62/134,956, filed on Mar. 18, 2015, provisional application No. 62/088,931, filed on Dec. 8, 2014.

(51) Int. Cl.
*G01N 33/574* (2006.01)
*C12Q 1/6886* (2018.01)

(52) U.S. Cl.
CPC ..... *G01N 33/57434* (2013.01); *C12Q 1/6886* (2013.01); *C12Q 2600/106* (2013.01); *C12Q 2600/158* (2013.01); *G01N 2333/47* (2013.01); *G01N 2333/4742* (2013.01)

(58) Field of Classification Search
CPC ................................................ G01N 33/57434
See application file for complete search history.

(56) References Cited

U.S. PATENT DOCUMENTS

| | | | |
|---|---|---|---|
| 5,288,614 | A | 2/1994 | Bodenmuller et al. |
| 5,399,482 | A | 3/1995 | Bodenmueller et al. |
| 6,207,380 | B1 | 3/2001 | Billing-Medel et al. |
| 6,329,179 | B1 | 12/2001 | Kopreski |
| 7,901,902 | B2 | 3/2011 | Bae et al. |
| 8,008,032 | B2 | 8/2011 | Forsyth et al. |
| 8,030,031 | B2 | 10/2011 | Kopreski |
| 8,076,080 | B2 | 12/2011 | Tada et al. |
| 8,293,485 | B2 | 10/2012 | Krizman et al. |
| 8,383,357 | B2 | 2/2013 | Haley et al. |
| 8,492,328 | B2 | 7/2013 | Huang et al. |
| 8,524,493 | B2 | 9/2013 | Panabieres et al. |
| 8,557,777 | B2 | 10/2013 | Perambakam et al. |
| 8,609,345 | B2 | 12/2013 | Krisman et al. |
| 8,642,349 | B1 | 2/2014 | Yeatman et al. |
| 8,669,058 | B2 | 3/2014 | Liew |
| 8,741,587 | B2 | 6/2014 | Roessler et al. |
| 8,748,108 | B2 | 6/2014 | McKeegan et al. |
| 8,889,361 | B2 | 11/2014 | Chen |
| 8,980,573 | B2 | 3/2015 | Rollinger et al. |
| 2002/0012931 | A1 | 1/2002 | Waldman et al. |
| 2002/0137086 | A1 | 9/2002 | Olek et al. |
| 2003/0073144 | A1 | 4/2003 | Benson et al. |
| 2003/0225528 | A1 | 12/2003 | Baker et al. |
| 2004/0029151 | A1 | 2/2004 | Mahadevappa et al. |
| 2004/0109863 | A1 | 6/2004 | Emtage |
| 2005/0064455 | A1 | 3/2005 | Baker et al. |
| 2005/0259483 | A1 | 11/2005 | Nakamura et al. |
| 2006/0019256 | A1 | 1/2006 | Clarke et al. |
| 2006/0057127 | A1 | 3/2006 | Liu et al. |
| 2006/0134663 | A1 | 6/2006 | Harkin et al. |
| 2006/0172303 | A1 | 8/2006 | Lehnert |
| 2006/0234259 | A1 | 10/2006 | Rubin et al. |
| 2007/0042945 | A1 | 2/2007 | Bodary et al. |
| 2007/0048297 | A1 | 3/2007 | Rosen et al. |

(Continued)

FOREIGN PATENT DOCUMENTS

| | | | |
|---|---|---|---|
| EP | 1124572 | A2 | 8/2001 |
| EP | 1678503 | A2 | 7/2006 |

(Continued)

OTHER PUBLICATIONS

Flam et al, J Urol, 172:108-111, 2004.*
Alaiya et al., Proteomics-based signature for human benign prostate hyperplasia and prostate adenocarcinoma. Int J Oncol. Apr. 2011;38(4):1047-57.
Baldassarre et al., Filamins Regulate Cell Spreading and Initiation of Cell Migration. PLoS One. Nov. 2009;4(11):e7830. 16 pages.
Bedolla et al., Nuclear vs. Cytoplasmic Localization of Filamin A in Prostate Cancer: Immunohistochemical Correlation with Metastases. Clin Cancer Res. 2009;15(3):788-796.
Ernst et al., Decrease and gain of gene expression are equally discriminatory markers for prostate carcinoma: a gene expression analysis on total and microdissected prostate tissue. Am J Pathol. Jun. 2002;160(6):2169-80.
Filella et al., Measurement of Complexed PSA in the Differential Diagnosis Between Prostate Cancer and Benign Prostate Hyperplasia. The Prostate. 2000;42(3):181-185.

(Continued)

*Primary Examiner* — Mark Halvorson
(74) *Attorney, Agent, or Firm* — McCarter & English, LLP; Jill Mello

(57) ABSTRACT

Methods for diagnosing the presence of prostate cancer in a subject are provided, such methods including the detection of levels of variety of biomarkers diagnostic of prostate cancer, including filamin A alone, or in combination with one or more additional biomarkers of prostate cancer, including, PSA, keratin 4, keratin 7, keratin 8, keratin 15, keratin 18, keratin 19, tubulin-beta 3, filamin B, and LY9. Additionally, age can be used as a predictor variable. The invention also provides methods of treating prostate cancer which rely on diagnostic information obtained based on the detection of biomarkers of prostate cancer, including filamin A alone, or in combination with one or more additional biomarkers of prostate cancer, including, PSA, keratin 4, keratin 7, keratin 8, keratin 15, keratin 18, keratin 19, tubulin-beta 3, filamin B, LY9, and/or age. Compositions in the form of kits and panels of reagents for detecting the biomarkers of the invention are also provided.

23 Claims, 54 Drawing Sheets

Specification includes a Sequence Listing.

(56) References Cited

U.S. PATENT DOCUMENTS

| | | | |
|---|---|---|---|
| 2007/0048738 | A1 | 3/2007 | Donkena et al. |
| 2007/0054271 | A1 | 3/2007 | Polyak et al. |
| 2007/0099209 | A1 | 5/2007 | Clarke et al. |
| 2007/0099251 | A1 | 5/2007 | Zhang et al. |
| 2007/0105114 | A1 | 5/2007 | Li et al. |
| 2007/0122856 | A1 | 5/2007 | Georges et al. |
| 2007/0141587 | A1 | 6/2007 | Baker et al. |
| 2007/0207508 | A1 | 9/2007 | Yao et al. |
| 2007/0218496 | A1 | 9/2007 | Kitagawa et al. |
| 2007/0220621 | A1 | 9/2007 | Clarke et al. |
| 2007/0231822 | A1 | 10/2007 | Mitas |
| 2008/0003624 | A1 | 1/2008 | Takata et al. |
| 2008/0305558 | A1 | 12/2008 | Loveday et al. |
| 2009/0081659 | A1 | 3/2009 | Hornbeck et al. |
| 2009/0098533 | A1 | 4/2009 | Munnes et al. |
| 2009/0176235 | A1 | 7/2009 | Cargill et al. |
| 2009/0186024 | A1 | 7/2009 | Nevins et al. |
| 2009/0186815 | A1 | 7/2009 | Boutros et al. |
| 2009/0215636 | A1 | 8/2009 | Krizman et al. |
| 2009/0221004 | A1 | 9/2009 | Hong |
| 2009/0232773 | A1 | 9/2009 | Kato et al. |
| 2010/0093556 | A1 | 4/2010 | Clarke et al. |
| 2010/0137164 | A1 | 6/2010 | Rubin et al. |
| 2010/0184125 | A1 | 7/2010 | Huang et al. |
| 2010/0216660 | A1 | 8/2010 | Nikolsky et al. |
| 2010/0272640 | A1 | 10/2010 | Alper |
| 2010/0279957 | A1 | 11/2010 | Potti et al. |
| 2010/0330593 | A1 | 12/2010 | Alper |
| 2011/0171124 | A1 | 7/2011 | Bugaj et al. |
| 2011/0177525 | A1 | 7/2011 | Shuber et al. |
| 2011/0177967 | A1 | 7/2011 | Carstens et al. |
| 2011/0212464 | A1 | 9/2011 | Hagmann et al. |
| 2011/0212465 | A1 | 9/2011 | Roessler et al. |
| 2011/0236903 | A1 | 9/2011 | McClelland et al. |
| 2011/0265197 | A1 | 10/2011 | Depinho et al. |
| 2011/0271357 | A1 | 11/2011 | Kim et al. |
| 2011/0271359 | A1 | 11/2011 | Langham |
| 2011/0311443 | A1 | 12/2011 | Schubert |
| 2012/0021929 | A1 | 1/2012 | Swiatek-de Lange et al. |
| 2012/0071335 | A1 | 3/2012 | Manaresi et al. |
| 2012/0087862 | A1 | 4/2012 | Hood et al. |
| 2012/0101084 | A1 | 4/2012 | Haley et al. |
| 2012/0183552 | A1 | 7/2012 | Joseloff et al. |
| 2012/0244531 | A1 | 9/2012 | Lee et al. |
| 2012/0264154 | A1* | 10/2012 | Mann ................ G01N 33/5091 435/23 |
| 2013/0022974 | A1 | 1/2013 | Chinnaiyan et al. |
| 2013/0029868 | A1 | 1/2013 | Orfao de Matos Correia E Vale |
| 2013/0095503 | A1 | 4/2013 | Lu |
| 2013/0131194 | A1 | 5/2013 | Skog et al. |
| 2013/0203164 | A1 | 8/2013 | Rosen et al. |
| 2013/0244256 | A1 | 9/2013 | Clarke et al. |
| 2013/0260388 | A1 | 10/2013 | Shen et al. |
| 2013/0288233 | A1 | 10/2013 | Murray |
| 2013/0316361 | A1 | 11/2013 | Bastia et al. |
| 2013/0317083 | A1 | 11/2013 | Rigoutsos |
| 2014/0011861 | A1 | 1/2014 | McClelland et al. |
| 2014/0038838 | A1 | 2/2014 | Narain et al. |
| 2014/0045915 | A1 | 2/2014 | Skog et al. |
| 2014/0065612 | A1 | 3/2014 | Tsai et al. |
| 2014/0066319 | A1 | 3/2014 | Gertler et al. |
| 2014/0106981 | A1 | 4/2014 | Hood et al. |
| 2014/0162888 | A1 | 6/2014 | Kuslich et al. |
| 2014/0235479 | A1 | 8/2014 | Depinho et al. |
| 2014/0242069 | A1 | 8/2014 | Shin et al. |
| 2014/0271672 | A1 | 9/2014 | Iakoubova et al. |
| 2014/0286961 | A1 | 9/2014 | Bergstein |
| 2014/0296096 | A1* | 10/2014 | Llorente .......... G01N 33/57434 506/9 |
| 2014/0343451 | A1 | 11/2014 | Pannell et al. |
| 2014/0364326 | A1 | 12/2014 | Guergova-Kuras et al. |
| 2015/0051104 | A1 | 2/2015 | Schubert |
| 2015/0055614 | A1 | 2/2015 | Mazzarese et al. |
| 2015/0079590 | A1 | 3/2015 | Pandolfi et al. |
| 2015/0086570 | A1 | 3/2015 | Violette et al. |
| 2015/0125456 | A1 | 5/2015 | Kim et al. |
| 2015/0152474 | A1 | 6/2015 | Pawlowski et al. |
| 2015/0153363 | A1 | 6/2015 | Jarvi et al. |
| 2016/0178632 | A1 | 6/2016 | Narain et al. |

FOREIGN PATENT DOCUMENTS

| | | | |
|---|---|---|---|
| EP | 1845167 | A1 | 10/2007 |
| EP | 1364069 | B1 | 4/2009 |
| EP | 2057465 | A2 | 5/2009 |
| EP | 2177615 | A1 | 4/2010 |
| EP | 1861715 | B1 | 8/2010 |
| EP | 2270226 | A2 | 1/2011 |
| EP | 2403877 | A1 | 1/2012 |
| EP | 2520935 | A2 | 11/2012 |
| WO | WO-2000/23100 | A2 | 4/2000 |
| WO | WO-2001/053837 | A1 | 7/2001 |
| WO | WO-2002/014500 | A2 | 2/2002 |
| WO | WO-2004/076614 | A2 | 9/2004 |
| WO | WO-2005/043165 | A2 | 5/2005 |
| WO | WO-2006/048291 | A2 | 5/2006 |
| WO | WO-2007/071947 | A1 | 6/2007 |
| WO | WO-2008/079269 | A2 | 7/2008 |
| WO | WO-2008/121307 | A2 | 10/2008 |
| WO | WO-2010/100899 | A1 | 9/2010 |
| WO | WO-2011/040532 | A1 | 4/2011 |
| WO | WO-2011/053837 | A1 | 5/2011 |
| WO | WO-2011/073131 | A1 | 6/2011 |
| WO | WO-2011/149402 | A2 | 12/2011 |
| WO | WO-2012/006634 | A2 | 1/2012 |
| WO | WO-2012/021969 | A1 | 2/2012 |
| WO | WO-2012/024543 | A1 | 2/2012 |
| WO | WO-2012/031008 | A2 | 3/2012 |
| WO | WO-2012/077139 | A1 | 6/2012 |
| WO | WO-2012/083338 | A1 | 6/2012 |
| WO | WO-2012/101283 | A1 | 8/2012 |
| WO | WO-2012/116248 | A1 | 8/2012 |
| WO | WO-2012/135397 | A2 | 10/2012 |
| WO | 2012/149522 | A1 | 11/2012 |
| WO | WO-2013/022995 | A2 | 2/2013 |
| WO | 2013/173476 | A1 | 11/2013 |
| WO | 2014/004931 | A1 | 1/2014 |
| WO | WO-2014/041185 | A2 | 3/2014 |
| WO | WO-2014/160499 | A2 | 10/2014 |
| WO | WO-2014/163557 | A1 | 10/2014 |
| WO | WO-2015/042465 | A1 | 3/2015 |

OTHER PUBLICATIONS

Glen et al., Eight-plex iTRAQ analysis of variant metastatic human prostate cancer cells identifies candidate biomarkers of progression: An exploratory study. Prostate. Sep. 1, 2010;70(12):1313-32.

Higano et al., Phase 1/2 dose-escalation study of a GM-CSF-secreting, allogeneic, cellular immunotherapy for metastatic hormone-refractory prostate cancer. Cancer. Sep 1, 2008;113(5):975-84.

Hudson et al., Epithelial cell differentiation pathways in the human prostate: identification of intermediate phenotypes by keratin expression. J Histochem Cytochem. Feb. 2001;49(2):271-8.

Loy et al., Filamin-A Fragment Localizes to the Nucleaus to Regulate Androgen Receptor and Coactivator Functions. International Journal of Oncology. 2003;44(2):467-472.

Narain et al., Identification and validation of novel prostate cancer biomarkers using the Berg interrogative Biology™ platform. Cancer Res. Aug. 2014;75. Abstract No. 538. 1 page.

Panteleakou et al., Detection of Circulating Tumor Cells in Prostate Cancer Patients: Methodological Pitfalls and Clinical Relevance. Molecular Medicine. 2009;15(3-4):101-114.

Ploussard et al., Class III beta-tubulin expression predicts prostate tumor aggressiveness and patient response to docetaxel-based chemotherapy. Cancer Res. Nov. 15, 2010;70(22):9253-64.

Sakamoto et al., Down-regulation of keratin 4 and keratin 13 expression in oral squamous cell carcinoma and epithelial dysplasia: a clue for histopathogenesis. Histopathology. Mar. 2011;58(4):531-42.

Tobias-Machado et al., Cytokeratin 19 expression by reverse transcriptase-polymerase chain reaction in the peripheral blood of prostate cancer patients. Tumori. May-Jun. 2005;91(3):248-52.

(56) References Cited

OTHER PUBLICATIONS

Tockman et al., Considerations in bringing a cancer biomarker to clinical application. Cancer Res. May 1, 1992;52(9 Suppl):2711s-2718s.
Van den Eertwegh et al., Combined immunotherapy with granulocyte-macrophage colony-stimulating factor-transduced allogeneic prostate cancer cells and ipilimumab in patients with metastatic castration-resistant prostate cancer: a phase 1 dose-escalation trial. Lancet Oncol. May 2012;13(5):509-17.
International Search Report for Application No. PCT/US2015/064530, dated Apr. 1, 2016. 5 pages.
International Preliminary Report on Patentability for Application No. PCT/US2015/064530, dated Jun. 22, 2017. 11 pages.
Fredolini et al., Investigation of the ovarian and prostate cancer peptidome for candidate early detection markers using a novel nanoparticle biomarker capture technology. AAPS J. Dec. 2010;12(4):504-18.
Sarangarajan et al., Berg Interrogative Biology™ platform unravels novel biomarkers FLNB and LY9 in combination with PSA enhances specificity in serum of patients with prostate cancer. Proceedings: AACR 104th Annual Meeting. Cancer Research. Apr. 15, 2013;73, Abstract 7.

* cited by examiner

Bars represent median with interquartile range

| Marker | AUC |
| --- | --- |
| PSA | 0.87 |
| FLNB | 0.78 |
| PSA + FLNB | 0.975 |

Linear scoring function

ROC curves for PSA, FLNB, LY9 and combinations

Non-Linear scoring function

ROC curves for PSA, FLNB, LY9 and combinations:
Non-linear model:

FIG. 11

| Human Serum (Prostate Cancer) | | | | | | | |
|---|---|---|---|---|---|---|---|
| **Label** | **Lot Number** | **UID** | **Gender** | **Medications** | **Race** | **Diagnosis** | **Age** |
| **1** | BRH590798 | 71152 | Male | Vitamin D, Citracal | Hispanic | Prostate cancer | 59 |
| **2** | BRH590799 | 70021 | Male | Multivitamins | African American | Prostate Cancer | 50 |
| **3** | BRH590800 | 7074 | Male | Multivitamin; Aspirin; Paxil; Albuterol;Levitra | Caucasian | Prostate Cancer | 63 |
| **4** | BRH590801 | 72295 | Male | Aredia,Trelstar | Caucasian | Prostate cancer | 76 |
| **5** | BRH590802 | 72297 | Male | Casodex, Metoprolol, Clonidine, Amlodipine, Zometa, Lupron | African American | Prostate cancer | 59 |
| **6** | BRH590803 | 23738 | Male | Lexapro; Pravastatn | Caucasian | Prostate Cancer | 49 |
| **7** | BRH590804 | 23796 | Male | Keppra; Aspirin; Calcium; Prilosec;Taxotere | Caucasian | Prostate Cancer | 62 |
| **8** | BRH590805 | 71712 | Male | Aredia, Lupron, Casodex, Restoril, Hydroxycodone | Caucasian | Prostate cancer, 5'11 bone LN,Hypoproliferative anemia | 75 |
| **9** | BRH590806 | 71119 | Male | Lipitor | Caucasian | Prostate cancer, Acid reflux, High Cholesterol | 47 |
| **10** | BRH590807 | 25716 | Male | Prilosec; Lipitor | Caucasian | Prostate Cancer; High Cholesterol | 54 |

FIG. 11 (cont.)

| | | | Normal Serum | | | | |
|---|---|---|---|---|---|---|---|
| **Stage** | **Surgery** | **Other Comments** | **Label** | **Lot Number** | **Gender** | **Race** | **Age** |
| TNM, T1C | Radiation for prostate cancer | Date of diagnosis 4/29/11, Stage of prostate cancer TNM, T1C | **21** | BRH590923 | Male | Caucasian | 57 |
| Pre-Treatment, 1C | Hernia | PSA Level: 4, grade = 3 | **22** | BRH590924 | Male | Caucasian | 48 |
| Stage T1C; PSA Level:6; Gleason Score:7 | Double Hernia | | **23** | BRH590925 | Male | Caucasian | 59 |
| Stable disease state; 4 | | Patient undergoing chemotherapy | **24** | BRH590926 | Male | Caucasian | 72 |
| Stable disease state; 4 | | | **25** | BRH590927 | Male | African American | 57 |
| Stage T1C | | | **26** | BRH590928 | Male | Caucasian | 48 |
| Stage 4; Flare-Up | | | **27** | BRH590929 | Male | Caucasian | 59 |
| Stable disease state; 4 | | | **28** | BRH590930 | Male | Caucasian | 68 |
| T1C | Arthroscopic Knee Tonsillectomy, Appendectomy, Fissurectomy | Prostate cancer stage T1C, Date of diagnosis 7/11, PSA level 2.6, Gleason score 6 | **29** | BRH590931 | Male | Caucasian | 45 |
| Stable; Stage T1C | | | **30** | BRH590932 | Male | Caucasian | 50 |

FIG. 11 (cont.)

| | | | | | | | |
|---|---|---|---|---|---|---|---|
| **11** | BRH590808 | 30186 | Male | Vytorin; Atenolol; Altace; Aspirin | Hispanic | Prostate Cancer; High Cholesterol | 62 |
| **12** | BRH590809 | 72135 | Male | ASA; MVI; Vantin; Septra | African American | Prostate cancer | 48 |
| **13** | BRH590810 | 100989 | Male | Casodex, Lupron | Caucasian | Prostate cancer | 80 |
| **14** | BRH590811 | 49545 | Male | Tri-Cor; Prilosec; Klor-Con; Edecrin; Simvastatin; Vitamin D | Caucasian | Prostate Cancer; High Cholesterol | 69 |
| **15** | BRH590812 | 49568 | Male | Lupron; Depot; synthroid | Caucasian | Prostate Cancer; High Cholesterol; HTN; Thyroid | 54 |
| **16** | BRH590813 | 49564 | Male | Benicar; Atenolol; Neurotin; Plavix; Prednisone; Cymbalta; Zometa | Caucasian | Prostate Cancer | 75 |
| **17** | BRH590814 | 103500 | Male | Prochlorperazine, maleate, Prednisone,Resveratrol, Synthroid, Lisinopril, Lasix | Caucasian | Prostate Cancer | 86 |
| **18** | BRH590815 | 45168 | Male | None | Caucasian | Prostate Cancer | 58 |
| **19** | BRH590816 | 61323 | Male | Aspirin; Benicar; Amlodipine; Triamterene; Multaq | Caucasian | Prostate Cancer; Atrial Fibrillation; High Cholesterol | 60 |
| **20** | BRH590817 | 61324 | Male | Allopurinol; Aspirin; Vitamins | Caucasian | Prostate Cancer; Atrial Fibrillation | 68 |

FIG. 11 (cont.)

| | | | | | | | |
|---|---|---|---|---|---|---|---|
| Stage T1C | Robotic Prostatectomy (8/16/10) ; Heart Stents x4 | | **31** | BRH590933 | | Hispanic | 58 |
| T1C | Back surgery | Prostate cancer stage TIC; Date of diagnosis 9/16/11; PSA value 4.23; Gleason score 7 | **32** | BRH590934 | Male | African American | 46 |
| Stable Disease State | Ulcers, Hernia | Date of diagnosis 4/17/01, Grade T1C, Gleason score 7; PSA=12.33 | **33** | BRH590935 | Male | Caucasian | 71 |
| Stage 4; Stable | Appendectomy; Craniotomy; Thoracoscopy | | **34** | BRH590936 | Male | Caucasian | 66 |
| Stage 4; Stable | | | **35** | BRH590937 | Male | Caucasian | 52 |
| Stage 4; Stable | Bariatric Surgery; Prostate Seed Implants | | **36** | BRH590938 | Male | Caucasian | 70 |
| 4 | Partial Thyroidectomy 1958 | Date of diagnosis 4/17/01, Grade T1C, Gleason score 7 | **37** | BRH590939 | Male | Caucasian | 71 |
| PreTreatment | | PSA= 4.4, Grade 7, Stage 3b | **38** | BRH590940 | Male | Caucasian | 56 |
| Stage T1C; PreTreatment | Cardiac Ablation | PSA Level= 2.6; Gleason Score=6 | **39** | BRH590941 | Male | Caucasian | 58 |
| Stage T2b; PreTreatment | Valve Replacement Repair | PSA Level=9.3; Gleason Score=7, grade = 4 | **40** | BRH590942 | Male | Caucasian | 63 |

FIG. 12

| Label | Vendor | Prostate Cancer Stage | Case ID / Lot | Specimen ID | Age | Sex | Ethnicity | Clinical Test Results |
|---|---|---|---|---|---|---|---|---|
| 111 | Bioreclamation | | BRH621393 | | 67 | Male | Hispanic | |
| 112 | Bioreclamation | | BRH621389 | | 49 | Male | African American | |
| 113 | Bioreclamation | | BRH621390 | | 63 | Male | African American | |
| 114 | Bioreclamation | | BRH621391 | | 54 | Male | Hispanic | |
| 115 | Bioreclamation | | BRH621392 | | 66 | Male | African American | |

FIG. 12 (cont.)

| Clinical Diagnosis (specimen) | Clinical Diagnoses (patient) | Medications |
|---|---|---|
| Normal control donor | Normal control donor (Status: Ongoing) | |
| Normal control donor | Normal control donor (Status: Ongoing) | |
| Normal control donor | Normal control donor (Status: Ongoing) | |
| Normal control donor | Normal control donor (Status: Ongoing) | |
| Normal control donor | Normal control donor (Status: Ongoing) | |

FIG. 12 (cont.)

| | | | | | | | | |
|---|---|---|---|---|---|---|---|---|
| **116** | Asterand | | 69871 | 248975A8 | 65 | Male | Caucasian | |
| **117** | Asterand | | 66017 | 220676A8 | 56 | Male | Caucasian | |
| **118** | Asterand | | 66010 | 220673A8 | 56 | Male | Caucasian | |
| **119** | Asterand | | 65953 | 220643A8 | 59 | Male | Caucasian | |
| **120** | Asterand | | 69874 | 248976A8 | 66 | Male | Caucasian | |
| **121** | Asterand | | 67494 | 235614A8 | 55 | Male | Caucasian | |
| **122** | Asterand | | 69865 | 248981A7 | 65 | Male | Caucasian | |
| **123** | Asterand | | 67461 | 235607A6 | 56 | Male | Caucasian | |
| **124** | Asterand | | 67502 | 235640A7 | 59 | Male | Caucasian | |
| **125** | Asterand | | 69929 | 263798A7 | 62 | Male | Caucasian | |

FIG. 12 (cont.)

| | | |
|---|---|---|
| Normal control donor | Normal control donor (Status: Ongoing) | |
| Normal control donor | Normal control donor (Status: Ongoing) | |
| Normal control donor | Normal control donor (Status Ongoing) | |
| Normal control donor | Normal control donor (Status: Ongoing) | |
| Normal control donor | Normal control donor (Status: Ongoing) | |
| Normal control donor | Normal control donor (Status: Ongoing) | |
| Normal control donor | Normal control donor (Status: Ongoing) | |
| Normal control donor | Normal control donor (Status: Ongoing) | |
| Normal control donor | Normal control donor (Status: Ongoing) | |
| Normal control donor | Normal control donor (Status: Ongoing) | |

FIG. 12 (cont.)

| | | | | | | | | |
|---|---|---|---|---|---|---|---|---|
| **126** | Asterand | | 69926 | 263785A8 | 65 | Male | Caucasian | |
| **127** | Asterand | | 62916 | 196638A7 | 50 | Male | Caucasian | |
| **128** | Asterand | | 69908 | 263789A8 | 66 | Male | Caucasian | |
| **129** | Asterand | | 69892 | 263771A6 | 64 | Male | Caucasian | |
| **130** | Asterand | | 69896 | 263762A8 | 69 | Male | Caucasian | |
| **131** | Bioreclamation | Stage I | BRH621388 | 84101 | 85 | Male | | PSA: 0.1,<br>Gleason score: 7 & 8 |
| **132** | Bioreclamation | Stage I | BRH621384 | 71119 | 47 | Male | | PSA: 2.6,<br>Gleason score: 6 |
| **133** | Bioreclamation | Stage I | BRH621385 | 71299 | 66 | Male | | Gleason score: 7 |
| **134** | Bioreclamation | Stage I | BRH621386 | 73599 | 57 | Male | | Gleason score: 7 |
| **135** | Bioreclamation | Stage I | BRH621387 | 100989 | 80 | Male | | Gleason score: 7 |

FIG. 12 (cont.)

| | | |
|---|---|---|
| Normal control donor | Normal control donor (Status: Ongoing) | |
| Normal control donor | Normal control donor (Status: Ongoing) | |
| Normal control donor | Normal control donor (Status: Ongoing) | |
| Normal control donor | Normal control donor (Status: Ongoing) | |
| Normal control donor | Normal control donor (Status: Ongoing) | |
| | | Uroxatrol, Vesicare, Atenolol, Furosemide, KlorCon, ASA, Calcium chew |
| | | Lipitor |
| | | Levothyroxine, Metformin, Glimepiride, Avapro, Atenolol, Chlorathalidone, Proscar, Flomax |
| | | Aspirin, Carvediol, Lipitor, Losartan, Januvia |
| | | Casodex, Lupron |

FIG. 12 (cont.)

| | | | | | | | | |
|---|---|---|---|---|---|---|---|---|
| **136** | Asterand | Stage II | 64938 | 220537A6 | 65 | Male | Caucasian | PSA: 0.32(ng/ml) |
| **137** | Asterand | Stage II | 64960 | 222331A8 | 55 | Male | Caucasian | PSA: 4.5(ng/ml), Gleason score: 6(3+3=6) |
| **138** | Asterand | Stage II | 67709 | 248842A6 | 56 | Male | Caucasian | PSA: 5.34(ng/ml), Gleason score: 7(3+4=7) |
| **139** | Asterand | Stage II | 65594 | 220578A8 | 59 | Male | Caucasian | PSA: 7.5(ng/ml), Gleason score: 5(3+2=5) |
| **140** | Asterand | Stage II | 65451 | 224670A8 | 73 | Male | Caucasian | PSA: 15.7(ng/dl), Gleason score: 6(3+3=6) |
| **141** | Asterand | Stage III | 64030 | 217315A8 | 56 | Male | Caucasian | PSA: 2.8(ng/ml), Gleason score: 9(4+5=9) |

FIG. 12 (cont.)

| | | |
|---|---|---|
| Adenocarcinoma of the prostate gland | Hypertension (Status: Ongoing), Adenocarcinoma of the prostate gland (Status: New) | Enalapril |
| Adenocarcinoma of the prostate gland | Adenocarcinoma of the prostate gland (Status: New) | Multivitamin, Cod liver oil, Flonase |
| Adenocarcinoma of the prostate gland | Hypercholesterolemia (Status:), Depression (Status:), Anxiety (Status:), Gout (Status:), Borderline diabetes (Status:), Gastroesophageal reflux disease (Status:), Adenocarcinoma of the prostate gland (Status: New) | Crestor, Uloric, Tamsulosin, Amitiza, Nexium, Ambien, Xanax, Celexa |
| Adenocarcinoma of the prostate gland | Adenocarcinoma of the prostate gland (Status:New) | |
| Adenocarcinoma of the prostate gland | Hypertension(Status:Ongoing), Adenocarcinoma of the prostate gland (Status:New) | |
| Adenocarcinoma of the prostate gland | Pericarditis (Status:Past), Petite mal seizures (Status: Past), Increased cholesterol (Status: Ongoing), Adenocarcinoma of the prostate gland (Status:New) | Allegra-D, Zocor, Lexapro, Ambien, Viagra, Multivitamin, Tylenol pm |

FIG. 12 (cont.)

| | | | | | | | | |
|---|---|---|---|---|---|---|---|---|
| **142** | Asterand | Stage III | 66588 | 238745A8 | 68 | Male | Caucasian | PSA: 4.44(ng/ml), Gleason score: 8(4+4=8) |
| **143** | Asterand | Stage III | 63718 | 217346A8 | 56 | Male | Caucasian | PSA: 5.6(ng/ml), Gleason score: 6(3+3=6) |
| **144** | Asterand | Stage III | 63191 | 190121A8 | 59 | Male | Caucasian | PSA: 15.5(mmol/L), Gleason score: 7(3+4=7) |
| **145** | Asterand | Stage III | 66517 | 238792A8 | 62 | Male | Caucasian | PSA: 24.72(ng/ml), Gleason score: 9(4+5=9) |
| **146** | Asterand | Stage IV | 66533 | 241880A8 | 76 | Male | African American | PSA: 1.31(ng/ml) |

FIG. 12 (cont.)

| | | |
|---|---|---|
| Adenocarcinoma of the prostate gland | Sleep apnea (Status: Ongoing), Osteoarthritis (Status: Ongoing), Type 2 diabetes (Status: Ongoing), Gastroesophageal reflux disease (Status: Ongoing), Adenocarcinoma of the prostate gland (Status: New) | Alprazolam, Tramadol hcl, Loratadine, Lisinopril, Simvastatin, Metformin HCl, Ranitidine, Fenobirate, Glipizide, Actos |
| Adenocarcinoma of the prostate gland | Osteoarthritis of the neck (Status: Ongoing), Hypertension (Status: Ongoing), Adenocarcinoma of the prostate gland (Status: New) | Green vibrance, Diovan, Aspirin, Excedrin |
| Adenocarcinoma of the prostate gland | Hypertension (Status:Ongoing), Adenocarcinoma of the prostate gland (Status:New) | Gibomet, Enalapril |
| Acinar cell adenocarcinoma of the prost | Hypertension (Status: Ongoing), Hypercholesterolemia (Status: New), Glaucoma (Status: Ongoing), Acinar cell adenocarcinoma of the prostate Gland (Status: New) | Simvastatin, Amlodipine, Lisinopril, Latanoprost |
| | Cancer of the prostate - stage 4 (Status: Ongoing) | |

FIG. 12 (cont.)

| | | | | | | | | |
|---|---|---|---|---|---|---|---|---|
| **147** | Asterand | Stage IV | 70060 | 262110A8 | 50 | Male | Hispanic | PSA: 3.36(ng/mL), Gleason : 9(4+5=9) |
| **148** | Asterand | Stage IV | 66534 | 241895A8 | 80 | Male | Caucasian | PSA: 15.52(ng/ml) |
| **149** | Asterand | Stage IV | 68411 | 196648A8 | 64 | Male | Caucasian | PSA: 30(ng/dl), Gleason score:6(3+3=6) |
| **150** | Asterand | Stage IV | 66950 | 245729A8 | 86 | Male | Caucasian | PSA: 66.49(ng/ml) |

FIG. 12 (cont.)

| | | |
|---|---|---|
| Adenocarcinoma of the prostate gland | Diverticulosis (Status: Ongoing), Bilateral inguinal hernia (Status: Ongoing), Depression (Status: Ongoing), Hematospermia (Status: Past), Gastroesophageal reflux disease (Status: Ongoing), Degenerative joint disease (Status: Ongoing), Adenocarcinoma of the prostate (Status: Ongoing), Metastatic neoplasm, adenocarcinoma of the bone marrow (Status: Ongoing) | Bicalutamide, Aredia, Lupron, Zometa, Paxil, Xqeva, Ketaconazole, Hydrocortisone, Prednisone, Taxotere, Oxycodone, Fentanyl transdermal patch |
| | Cancer of the prostate - stage 4 (Status: Ongoing) | |
| Adenocarcinoma of the prostate gland | Adenocarcinoma of the prostate gland (Status:New) | Avodart |
| Prostate cancer Stage 4 | Chronic obstructive pulmonary disease (Status: Ongoing), Cancer of the prostate - Stage 4 (Status: Ongoing), Degenerative disc disease (Status: Ongoing), Cataract (Status: Past), Cataract (Status: Past) | |

1. FLNa

2. KRT19

KRT19 Levels in Human Prostate Cancer Serum Set 2

Bars represent median with interquartile range

FIG. 17

| | CA vs. Others | | CA vs. BPH | | High Gleason vs. Low | | High Gleason vs. Others | | Super High Gleason vs. Others | |
|---|---|---|---|---|---|---|---|---|---|---|
| | Biomarker | AUC | Biomarker | AUC | Biomarker | AUC | Biomarker | AUC | Biomarker | AUC |
| **Individual** | PSA | 0.569 | PSA | 0.564 | PSA | 0.619 | PSA | 0.631 | PSA | 0.67 |
| | Age | 0.62 | Age | 0.621 | Age | 0.622 | Age | 0.662 | Age | 0.7 |
| | FLNA | 0.574 | FLNA | 0.696 | FLNA | 0.515 | FLNA | 0.56 | FLNA | 0.542 |
| | FLNB | 0.51 | FLNB | 0.516 | FLNB | 0.528 | FLNB | 0.515 | FLNB | 0.515 |
| | Krt19 | 0.519 | Krt19 | 0.618 | Krt19 | 0.573 | Krt19 | 0.567 | Krt19 | 0.574 |
| | P2-1 | 0.55 | P2-1 | 0.636 | P2-1 | 0.527 | P2-1 | 0.551 | P2-1 | 0.528 |
| | P2-2 | 0.502 | P2-2 | 0.582 | P2-2 | 0.528 | P2-2 | 0.552 | P2-2 | 0.53 |
| | P3-1 | 0.51 | P3-1 | 0.524 | P3-1 | 0.547 | P3-1 | 0.529 | P3-1 | 0.5 |
| | P4-2 | 0.522 | P4-2 | 0.595 | P4-2 | 0.551 | P4-2 | 0.555 | P4-2 | 0.578 |
| **Two Combined (top)** | Age & FLNB | 0.63 | FLNA & Krt19 | 0.717 | Age & PSA | 0.659 | Age & PSA | 0.696 | Age & PSA | 0.765 |
| **Three Combined (top)** | Age & FLNB & PSA | 0.635 | FLNA & Krt19 & Age | 0.735 | PSA & Age & FLNB | 0.685 | PSA & Age & FLNB | 0.717 | PSA & Age & FLNB | 0.804 |
| **Four Combined (top)** | Age & FLNA & P2-1 & P2-2 | 0.637 | FLNA & Krt19& P2-1 & Age | 0.746 | PSA & Age & FLNB & P3-1 | 0.693 | PSA & Age & FLNB & P3-1 | 0.723 | PSA & Age & FLNB & P2-2 | 0.81 |
| | | | FLNA & Krt19 & Age & P4-2 | 0.746 | | | | | | |
| **Five Combined (top)** | Age & FLNA & PSA & P2-2 & P2-1 | 0.644 | FLNA & Krt19 & Age & P2-1 & P3-1 | 0.764 | PSA & Age & FLNB & P3-1 & Krt19 | 0.694 | No Improvement | | PSA & Age & FLNB & P2-2 & P2-1 | 0.811 |

FIG. 18

PCA vs. Else: Sensitivity match PSA; cutoff=0.4455

```
> title(main=list(paste("PSA&Age&FLNA&FLNB&P2-1&P4-2:PCA vs.  Else;
AUC=",round(1r1$auc,3), sep=""), cex=1))
> mod1
call: glm(formula = as.factor(PCA) ~ PSA + Age + FLNA +FLNB + p21+
     P42, family = binominal ("probit"), data = data)
Coefficients:
(Intercept)        PSA        Age       FLNA       FLNB        P21        P42
  -1.875729   0.031445   0.024374  -0.001906   0.211370   0.144692  -0.067658
Degrees of Freedom: 294 Total (i.e. Null);  288 Residual
Null Deviance:        408.5
Residual Deviance:    389.9    AIC: 403.9
```

PSA&Age&FLNA& FLNB&P2-1&P4-2: PCA vs. Else; AUC=0.637

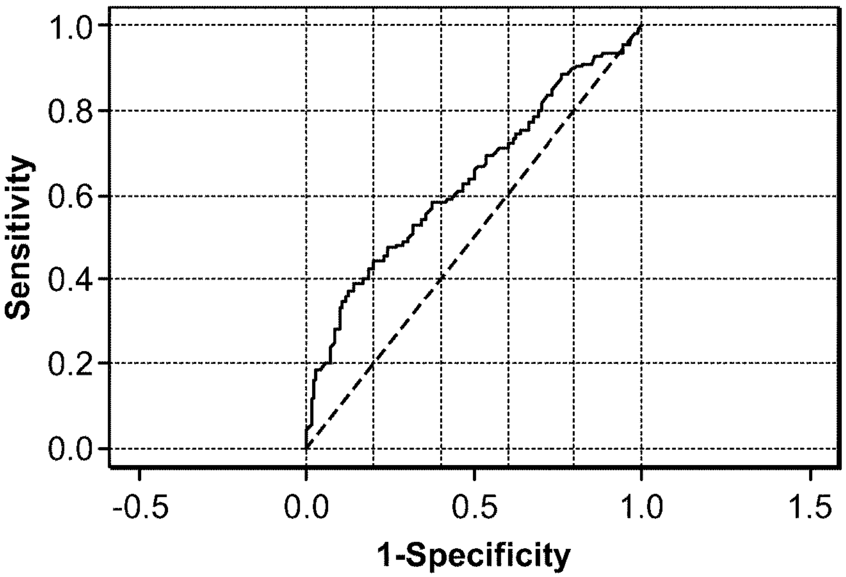

```
> ConfusionMatrix(data$prediction, data$PCA, positive="1")
confusion Matrix and Statistics
          Reference
Prediction   0   1
         0  48  35
         1  94 118
               Accuracy : 0.5627
                 95% CI : (0.504, 0.6201)
    No Information Rate : 0.5186
    P-Value [ACC > NIR] : 0.07244

                  Kappa : 0.1109
 Mcnemar's Test P-Value : 3.28e-07

            Sensitivity : 0.7712
            Specificity : 0.3380
         Pos Pred Value : 0.5566
         Neg Pred Value : 0.5783
             Prevalence : 0.5186
         Detection Rate : 0.4000
   Detection Prevalence : 0.7186
      Balanced Accuracy : 0.5546
       'Positive' class : 1
```

FIG. 20 Accuracy Analysis

Confusion Matrix and Statistics

| Prediction | Reference 0 | Reference 1 |
|---|---|---|
| 0 | 29 | 12 |
| 1 | 52 | 65 |

Accuracy : 0.5949
95% CI : (0.514, 0.6722)
No Information Rate : 0.5127
P-Value [ACC > NIR] : 0.02304

Kappa : 0.1996
Mcnemar's Test P-Value : 1.088e-06

Sensitivity : 0.8442
Specificity : 0.3580
Pos Pred Value : 0.5556
Neg Pred Value : 0.7073
Prevalence : 0.4873
Detection Rate : 0.4114
Detection Prevalence : 0.7405
Balanced Accuracy : 0.6011

'Positive' class : 1

Relative risk

Exposed group

Number with positive (bad) outcome: a= 65
Number with negative (good) outcome: b= 52

Control group

Number with positive (bad) outcome: c= 12
Number with negative (good) outcome: d= 29

Test

Results

| | |
|---|---|
| Relative risk | 1.8981 |
| 95 % CI | 1.1482 to 3.1380 |
| z statistic | 2.499 |
| | P = 0.0125 |

Odds ratio

Cases with positive (bad) outcome

Number in exposed group: a= 65
Number in control group: c= 12

Cases with negative (good) outcome

Number in exposed group: b= 52
Number in control group: d= 29

Test

Results

| | |
|---|---|
| Odds ratio | 3.0208 |
| 95 % CI | 1.4054 to 6.4933 |
| z statistic | 2.832 |
| | P = 0.0046 |

FIG. 21

Super High Gleason vs. Else: Sensitivity > =0.95; cutoff = 0.01997

```
>mod1
call: glm(formula = as.factor(PCA) ~ PSA + Age + FLNB +P42, family = binominal ("probit"),
    data = data)
Coefficients:
(Intercept)      PSA       Age      FLNB       P42
  -3.21767   0.05097   0.03302  -0.31903  -0.10216
Degrees of Freedom: 294 Total (i.e. Null);  290 Residual
Null Deviance:       130
Residual Deviance:   107.9   AIC: 117.9
```

PSA & Age & FLNB & P4-2: Super High Gleason vs. Else; AUC=0.81

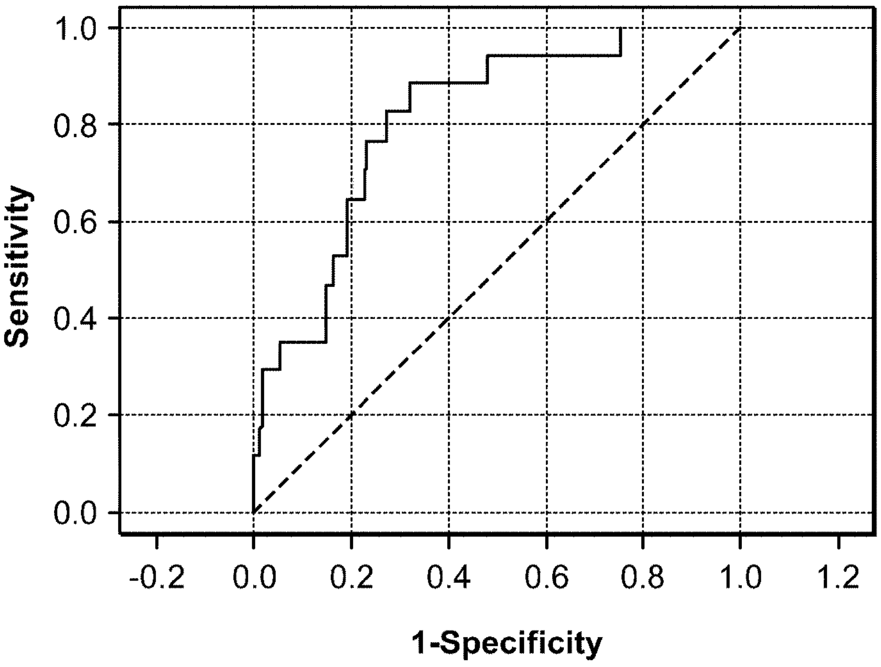

```
> confusionMatrix(data$prediction,
data$PCA, positive="1")
          Reference
Confusion Matrix and Statistics
Prediction   0   1
         0  69   0
         1 209  17
               Accuracy : 0.2917
                 95% CI : (0.2403, 0.347)
    No Information Rate : 0.9424
    P-Value [ACC > NIR] : 1

                  Kappa : 0.0367
 Mcnemar's Test P-Value : <2e-16

            Sensitivity : 1.00000
            Specificity : 0.24820
         Pos Pred Value : 0.07522
         Neg Pred Value : 1.00000
             Prevalence : 0.05763
         Detection Rate : 0.05763
   Detection Prevalence : 0.76610
      Balanced Accuracy : 0.62410

       'Positive' class : 1
```

FIG. 23

Confusion Matrix and Statistics

| Prediction | Reference 0 | Reference 1 |
|---|---|---|
| 0 | 39 | 2 |
| 1 | 112 | 6 |

Accuracy : 0.283
95% CI : (0.2145, 0.3598)
No Information Rate : 0.9497
P-Value [ACC > NIR] : 1

Kappa : 0.0011
Mcnemar's Test P-Value : <2e-16

Sensitivity : 0.75000
Specificity : 0.25828
Pos Pred Value : 0.05085
Neg Pred Value : 0.95122
Prevalence : 0.05031
Detection Rate : 0.03774
Detection Prevalence : 0.74214
Balanced Accuracy : 0.50414

'Positive' class : 1

Relative risk

Exposed group

Number with positive (bad) outcome: a= 6
Number with negative (good) outcome: b= 112

Control group

Number with positive (bad) outcome: c= 2
Number with negative (good) outcome: d= 39

Test

Results

| | |
|---|---|
| Relative risk | 1.0424 |
| 95 % CI | 0.2190 to 4.9624 |
| z statistic | 0.052 |
| | P = 0.9584 |

Odds ratio

Cases with positive (bad) outcome

Number in exposed group: a= 6
Number in control group: c= 2

Cases with negative (good) outcome

Number in exposed group: b= 112
Number in control group: d= 39

Test

Results

| | |
|---|---|
| Odds ratio | 1.0446 |
| 95 % CI | 0.2024 to 5.3923 |
| z statistic | 0.052 |
| | P = 0.9584 |

FIG. 24

High Gleason vs. Else: Sensitivity > =0.8; cutoff = 0.1603

```
>mod1
call: glm(formula = as.factor(PCA) ~ PSA + Age + FLNB +P42, family = binominal ("probit"),
    data = data)
Coefficients:
(Intercept)          PSA        Age       FLNB        P42
  -2.05002       0.04659    0.02420    0.33548   -0.10820

Degrees of Freedom: 294 Total (i.e. Null);  290 Residual
Null Deviance:          295.2
Residual Deviance:      268    AIC: 278
```

PSA & Age & FLNB & P4-2: High Gleason vs. Else; AUC=0.72

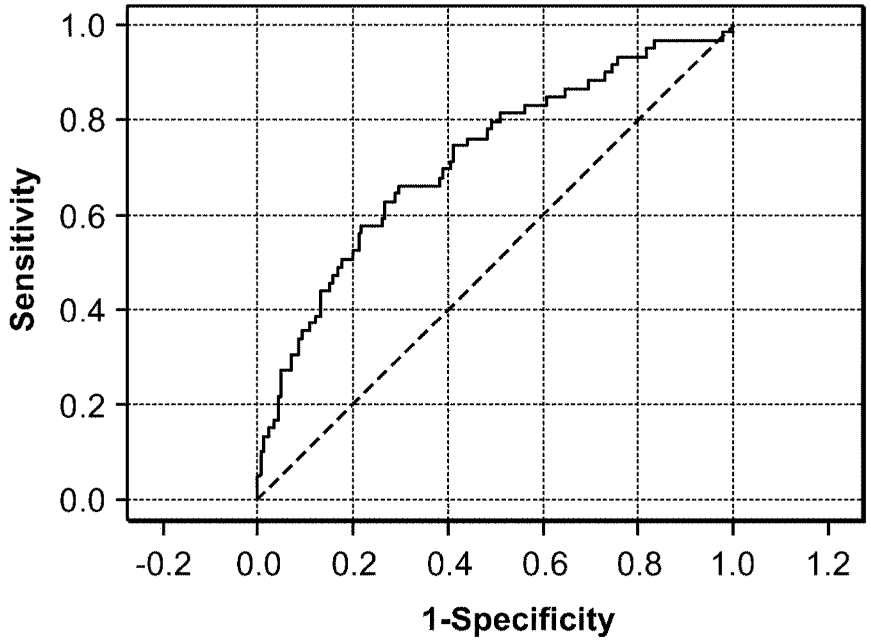

```
> confusionMatrix(data$prediction,
data$PCA, positive="1")
Confusion Matrix and Statistics
           Reference
Prediction   0   1
         0 116  11
         1 120  48
               Accuracy : 0.5559
                 95% CI : (0.4972, 0.6135)
    No Information Rate : 0.8
    P-Value [ACC > NIR] : 1

                  Kappa : 0.1802
 Mcnemar's Test P-Value : <2e-16
            Sensitivity : 0.8136
            Specificity : 0.4915
         Pos Pred Value : 0.2857
         Neg Pred Value : 0.9134
             Prevalence : 0.2000
         Detection Rate : 0.1627
   Detection Prevalence : 0.5695
      Balanced Accuracy : 0.6525
       'Positive' class : 1
```

FIG. 26 Accuracy Analysis

Confusion Matrix and Statistics

| Prediction | Reference 0 | Reference 1 |
|---|---|---|
| 0 | 66 | 9 |
| 1 | 63 | 21 |

Accuracy : 0.5472
95% CI : (0.4664, 0.6261)
No Information Rate : 0.8113
P-Value [ACC > NIR] : 1

Kappa : 0.1252
Mcnemar's Test P-Value : 4.208e-10

Sensitivity : 0.7000
Specificity : 0.5116
Pos Pred Value : 0.2500
Neg Pred Value : 0.8800
Prevalence : 0.1887
Detection Rate : 0.1321
Detection Prevalence : 0.5283
Balanced Accuracy : 0.6058

'Positive' class : 1

Relative risk

Exposed group

Number with positive (bad) outcome: a= 21
Number with negative (good) outcome: b= 63

Control group

Number with positive (bad) outcome: c= 9
Number with negative (good) outcome: d= 66

Test

Results

| | |
|---|---|
| Relative risk | 2.0833 |
| 95 % CI | 1.0180 to 4.2635 |
| z statistic | 2.009 |
| | P = 0.0446 |

Odds ratio

Cases with positive (bad) outcome

Number in exposed group: a= 21
Number in control group: c= 9

Cases with negative (good) outcome

Number in exposed group: b= 63
Number in control group: d= 66

Test

Results

| | |
|---|---|
| Odds ratio | 2.4444 |
| 95 % CI | 1.0408 to 5.7409 |
| z statistic | 2.052 |
| | P = 0.0402 |

FIG. 27

PCA vs. BPH: Sensitivity > =0.8; cutoff = 0.8758

```
>mod1
call: glm(formula = as.factor(PCA) ~ Age + FLNA + KRT19 + P21, family = binominal ("probit"),
    data = data)
Coefficients:
(Intercept)        Age        FLNA      KRT19        P21
  3.339085    0.017895   -0.003951  -0.076261  -0.566652

Degrees of Freedom: 195 Total (i.e. Null);  191 Residual
Null Deviance:       141.7
Residual Deviance:   127.6    AIC: 137.6
```

Age & FLNA & KRT-19 & P2-1 vs. BPH; AUC=0.746

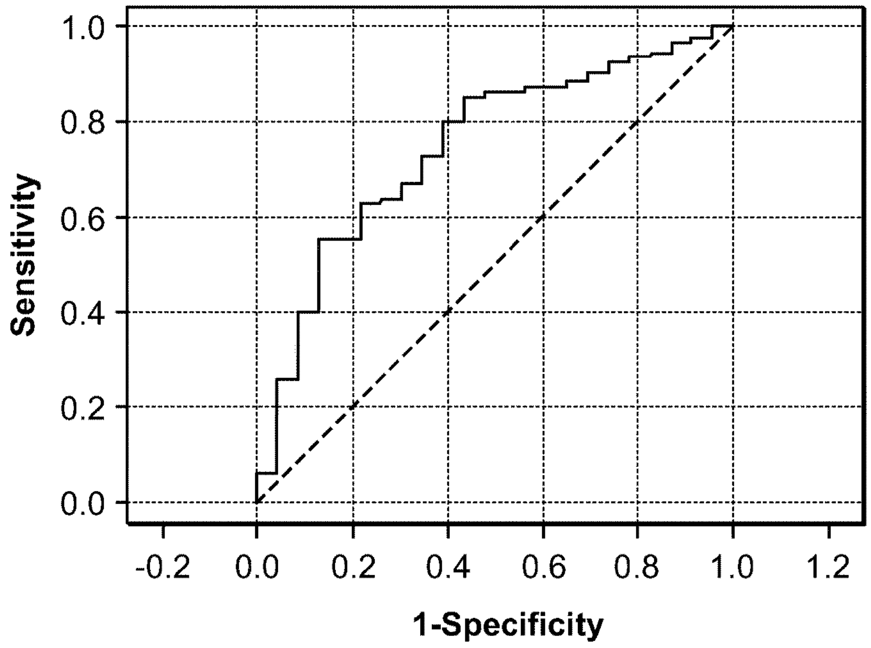

```
> confusionMatrix(data$prediction,
data$PCA, positive="1")
 Confusion Matrix and Statistics
          Reference
 Prediction   0    1
          0  14   34
          1   9  139
               Accuracy : 0.7806
                 95% CI : (0.7161, 0.8364)
    No Information Rate : 0.8827
    P-Value [ACC > NIR] : 0.9999829

                  Kappa : 0.2802
 Mcnemar's Test P-Value : 0.0002522

            Sensitivity : 0.8035
            Specificity : 0.6087
         Pos Pred Value : 0.9392
         Neg Pred Value : 0.2917
             Prevalence : 0.8827
         Detection Rate : 0.7092
   Detection Prevalence : 0.7551
      Balanced Accuracy : 0.7061
       'Positive' class : 1
```

FIG. 29 Accuracy Analysis

Confusion Matrix and Statistics

| Prediction \ Reference | 0 | 1 |
|---|---|---|
| 0 | 4 | 26 |
| 1 | 7 | 55 |

Accuracy : 0.6413
95% CI : (0.5346, 0.7387)
No Information Rate : 0.8804
P-Value [ACC > NIR] : 1.000000

Kappa : 0.0244
Mcnemar's Test P-Value : 0.001728

Sensitivity : 0.6790
Specificity : 0.3636
Pos Pred Value : 0.8871
Neg Pred Value : 0.1333
Prevalence : 0.8804
Detection Rate : 0.5978
Detection Prevalence : 0.6739
Balanced Accuracy : 0.5213

'Positive' class : 1

Relative risk

Exposed group

Number with positive (bad) outcome: a= 55
Number with negative (good) outcome: b= 7

Control group

Number with positive (bad) outcome: c= 26
Number with negative (good) outcome: d= 4

Test

Results

| | |
|---|---|
| Relative risk | 1.0236 |
| 95 % CI | 0.8669 to 1.2085 |
| z statistic | 0.275 |
| | P = 0.7834 |

Odds ratio

Cases with positive (bad) outcome

Number in exposed group: a= 55
Number in control group: c= 26

Cases with negative (good) outcome

Number in exposed group: b= 7
Number in control group: d= 4

Test

Results

| | |
|---|---|
| Odds ratio | 1.2088 |
| 95 % CI | 0.3248 to 4.4983 |
| z statistic | 0.283 |
| | P = 0.7773 |

FIG. 30 FLNA, FLNB, and KRT19 are expressed by prostate cancer cells
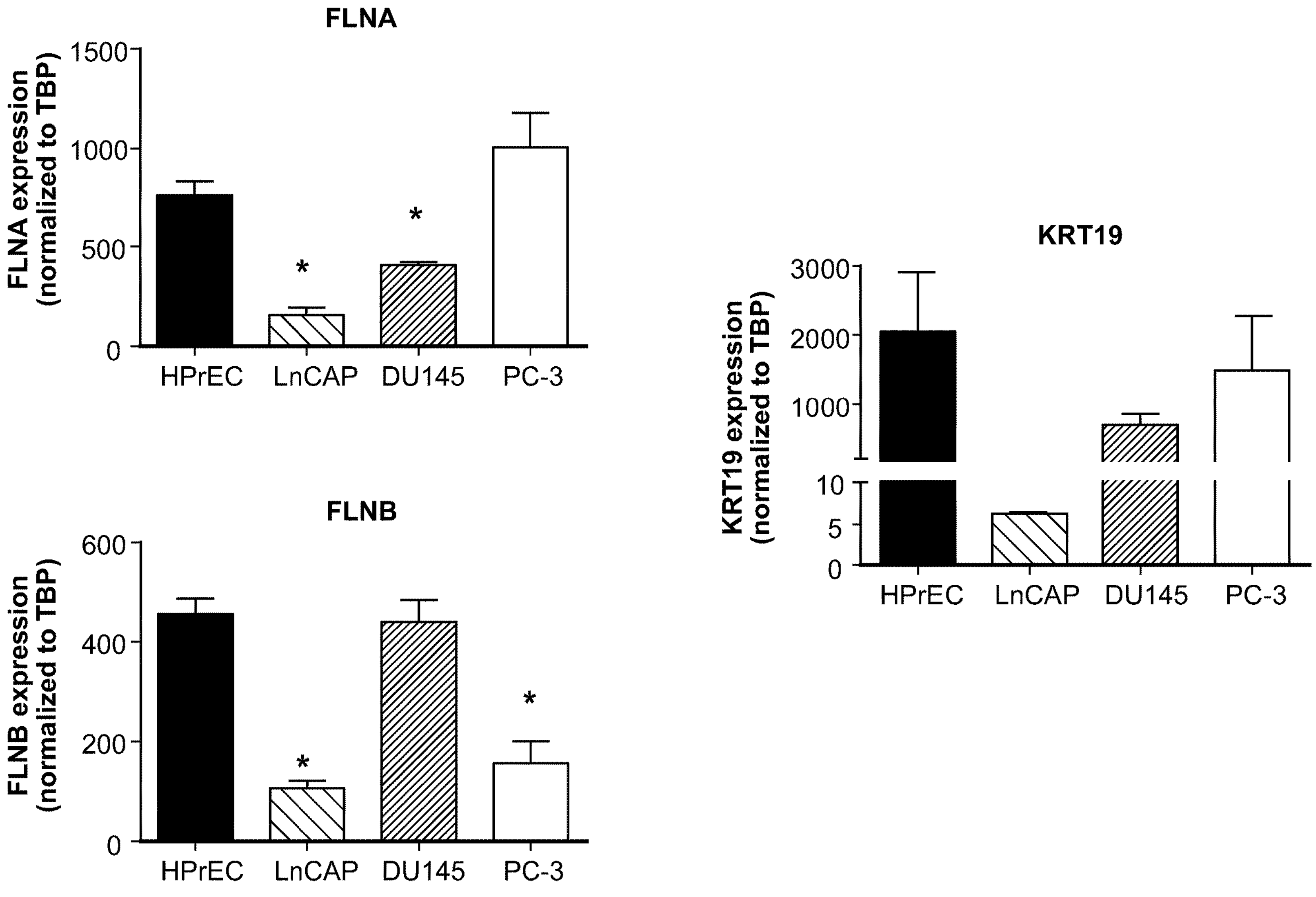

FLNA, FLNB, and KRT19 are expressed by prostate cancer cells

FLNA, FLNB, and KRT19 are secreted from prostate cancer cells

Transcriptional regulation of FLNA, FLNB, and KRT19 expression differs from PSA: Hypoxia (1% oxygen).

Transcriptional regulation of FLNA, FLNB, and KRT19 expression differs from PSA: TNFα (10 ng/mL)

Transcriptional regulation of FLNA, FLNB, and KRT19 expression differs from PSA: R1881 (1 nM)

FLNA and FLNB are detected in human plasma and have predictive power in identifying prostate cancer patients

SEQUENCE LISTING

```
<160> NUMBER OF SEQ ID NOS: 49

<210> SEQ ID NO 1
<211> LENGTH: 520
<212> TYPE: PRT
<213> ORGANISM: Homo Sapiens

<400> SEQUENCE: 1

Met Ile Ala Arg Gln Gln Cys Val Arg Gly Gly Pro Arg Gly Phe Ser
1               5                   10                  15

Cys Gly Ser Ala Ile Val Gly Gly Gly Lys Arg Gly Ala Phe Ser Ser
            20                  25                  30

Val Ser Met Ser Gly Gly Ala Gly Arg Cys Ser Ser Gly Gly Phe Gly
        35                  40                  45

Ser Arg Ser Leu Tyr Asn Leu Arg Gly Asn Lys Ser Ile Ser Met Ser
    50                  55                  60

Val Ala Gly Ser Arg Gln Gly Ala Cys Phe Gly Gly Ala Gly Gly Phe
65                  70                  75                  80

Gly Thr Gly Gly Phe Gly Gly Gly Phe Gly Gly Ser Phe Ser Gly Lys
                85                  90                  95

Gly Gly Pro Gly Phe Pro Val Cys Pro Ala Gly Gly Ile Gln Glu Val
            100                 105                 110

Thr Ile Asn Gln Ser Leu Leu Thr Pro Leu His Val Glu Ile Asp Pro
        115                 120                 125

Glu Ile Gln Lys Val Arg Thr Glu Glu Arg Glu Gln Ile Lys Leu Leu
    130                 135                 140

Asn Asn Lys Phe Ala Ser Phe Ile Asp Lys Val Gln Phe Leu Glu Gln
145                 150                 155                 160

Gln Asn Lys Val Leu Glu Thr Lys Trp Asn Leu Leu Gln Gln Gln Thr
                165                 170                 175

Thr Thr Thr Ser Ser Lys Asn Leu Glu Pro Leu Phe Glu Thr Tyr Leu
            180                 185                 190

Ser Val Leu Arg Lys Gln Leu Asp Thr Leu Gly Asn Asp Lys Gly Arg
        195                 200                 205

Leu Gln Ser Glu Leu Lys Thr Met Gln Asp Ser Val Glu Asp Phe Lys
    210                 215                 220

Thr Lys Tyr Glu Glu Glu Ile Asn Lys Arg Thr Ala Ala Glu Asn Asp
225                 230                 235                 240
```

-continued

```
Phe Val Val Leu Lys Lys Asp Val Asp Ala Ala Tyr Leu Asn Lys Val
                245                 250                 255

Glu Leu Glu Ala Lys Val Asp Ser Leu Asn Asp Glu Ile Asn Phe Leu
            260                 265                 270

Lys Val Leu Tyr Asp Ala Glu Leu Ser Gln Met Gln Thr His Val Ser
        275                 280                 285

Asp Thr Ser Val Val Leu Ser Met Asp Asn Asn Arg Asn Leu Asp Leu
    290                 295                 300

Asp Ser Ile Ile Ala Glu Val Arg Ala Gln Tyr Glu Glu Ile Ala Gln
305                 310                 315                 320

Arg Ser Lys Ala Glu Ala Glu Ala Leu Tyr Gln Thr Lys Val Gln Gln
                325                 330                 335

Leu Gln Ile Ser Val Asp Gln His Gly Asp Asn Leu Lys Asn Thr Lys
            340                 345                 350

Ser Glu Ile Ala Glu Leu Asn Arg Met Ile Gln Arg Leu Arg Ala Glu
        355                 360                 365

Ile Glu Asn Ile Lys Lys Gln Cys Gln Thr Leu Gln Val Ser Val Ala
    370                 375                 380

Asp Ala Glu Gln Arg Gly Glu Asn Ala Leu Lys Asp Ala His Ser Lys
385                 390                 395                 400

Arg Val Glu Leu Glu Ala Ala Leu Gln Gln Ala Lys Glu Glu Leu Ala
                405                 410                 415

Arg Met Leu Arg Glu Tyr Gln Glu Leu Met Ser Val Lys Leu Ala Leu
            420                 425                 430

Asp Ile Glu Ile Ala Thr Tyr Arg Lys Leu Leu Glu Gly Glu Glu Tyr
        435                 440                 445

Arg Met Ser Gly Glu Cys Gln Ser Ala Val Ser Ile Ser Val Val Ser
    450                 455                 460

Gly Ser Thr Ser Thr Gly Gly Ile Ser Gly Gly Leu Gly Ser Gly Ser
465                 470                 475                 480

Gly Phe Gly Leu Ser Ser Gly Phe Gly Ser Gly Ser Gly Ser Gly Phe
                485                 490                 495

Gly Phe Gly Gly Ser Val Ser Gly Ser Ser Ser Ser Lys Ile Ile Ser
            500                 505                 510

Thr Thr Thr Leu Asn Lys Arg Arg
        515                 520
```

<210> SEQ ID NO 2
<211> LENGTH: 2147
<212> TYPE: DNA
<213> ORGANISM: Homo sapiens

<400> SEQUENCE: 2

```
actcaccggc ctgggccctg tcacttctct gatagctccc agctcgctct ctgcagccat     60

gattgccaga cagcagtgtg tccgaggcgg gccccggggc ttcagctgtg gctcggccat    120

tgtaggcggt ggcaagagag gtgccttcag ctcagtctcc atgtctggag gtgctggccg    180

atgctcttct gggggatttg gcagcagaag cctctacaac ctcaggggga acaaaagcat    240

ctccatgagt gtggctgggt cacgacaagg tgcctgcttt gggggtgctg gaggctttgg    300

cactggtggc tttggtggtg gatttggggg ctccttcagt ggtaagggtg gccctggctt    360

ccccgtctgc cccgctgggg gaattcagga ggtcaccatc aaccagagct tgctcacccc    420

cctccacgtg gagattgacc ctgagatcca gaaagtccgg acggaagagc gcgaacagat    480

caagctcctc aacaacaagt ttgcctcctt catcgacaag gtgcagttct tagagcaaca    540
```

```
gaataaggtc ctggagacca aatggaacct gctccagcag cagacgacca ccacctccag    600

caaaaacctt gagcccctct ttgagaccta cctcagtgtc ctgaggaagc agctagatac    660

cttgggcaat gacaaagggc gcctgcagtc tgagctgaag accatgcagg acagcgtgga    720

ggacttcaag actaagtatg aagaggagat caacaaacgc acagcagccg agaatgactt    780

tgtggtccta aagaaggacg tggatgctgc ctacctgaac aaggtggagt tggaggccaa    840

ggtggacagt cttaatgacg agatcaactt cctgaaggtc ctctatgatg cggagctgtc    900

ccagatgcag acccatgtca gcgacacgtc cgtggtcctt tccatggaca acaaccgcaa    960

cctggacctg gacagcatta ttgccgaggt ccgtgcccag tacgaggaga ttgcccagag   1020

gagcaaggct gaggctgaag ccctgtacca gaccaaggtc cagcagctcc agatctcggt   1080

tgaccaacat ggtgacaacc tgaagaacac caagagtgaa attgcagagc tcaacaggat   1140

gatccagagg ctgcgggcag agatcgagaa catcaagaag cagtgccaga ctcttcaggt   1200

atccgtggct gatgcagagc agcgaggtga gaatgccctt aaagatgccc acagcaagcg   1260

cgtagagctg gaggctgccc tgcagcaggc caaggaggag ctggcacgaa tgctgcgtga   1320

gtaccaggag ctcatgagtg tgaagctggc cttggacatc gagatcgcca cctaccgcaa   1380

actgctggag ggcgaggagt acagaatgtc tggagaatgc cagagtgccg tgagcatctc   1440

tgtggtcagc ggtagcacca gcactggagg catcagcgga ggattaggaa gtggctccgg   1500

gtttggcctg agtagtggct ttggctccgg ctctggaagt ggctttgggt ttggtggcag   1560

tgtctctggc agttccagca gcaagatcat ctctaccacc accctgaaca agagacgata   1620

gaggagacga ggtccctgca gctcactgtg tccagctggg cccagcactg gtgtctctgt   1680

gcttccttca cttcacctcc atcctctgtc tctggggctc atcttactag tatcccctcc   1740

actatcccat gggctctctc tgccccagga tgatcttctg tgctgggaca gggactctgc   1800

ctcttggagt ttggtagcta cttcttgatt tgggcctggt gacccacctg gaatgggaag   1860

gatgtcagct gacctctcac ctcccatgga cagagaagaa aatgaccagg agtgtcatct   1920

ccagaattat tggggtcaca tatgtccctt cccagtccaa tgccatctcc cactagatcc   1980

tgtattatcc atctacatca gaaccaaact acttctccaa cacccggcag cacttggccc   2040

tgcaagctta ggatgagaac cacttagtgt cccattctac tcctctcatt ccctcttatc   2100

catctgcagg tgaatcttca ataaaatgct tttgtcattc attctga                2147
```

```
<210> SEQ ID NO 3
<211> LENGTH: 469
<212> TYPE: PRT
<213> ORGANISM: Homo sapiens

<400> SEQUENCE: 3

Met Ser Ile His Phe Ser Ser Pro Val Phe Thr Ser Arg Ser Ala Ala
1               5                   10                  15

Phe Ser Gly Arg Gly Ala Gln Val Arg Leu Ser Ser Ala Arg Pro Gly
            20                  25                  30

Gly Leu Gly Ser Ser Ser Leu Tyr Gly Leu Gly Ala Ser Arg Pro Arg
        35                  40                  45

Val Ala Val Arg Ser Ala Tyr Gly Gly Pro Val Gly Ala Gly Ile Arg
    50                  55                  60

Glu Val Thr Ile Asn Gln Ser Leu Leu Ala Pro Leu Arg Leu Asp Ala
65                  70                  75                  80

Asp Pro Ser Leu Gln Arg Val Arg Gln Glu Glu Ser Glu Gln Ile Lys
```

-continued

```
                85                  90                  95

Thr Leu Asn Asn Lys Phe Ala Ser Phe Ile Asp Lys Val Arg Phe Leu
            100                 105                 110

Glu Gln Gln Asn Lys Leu Leu Glu Thr Lys Trp Thr Leu Leu Gln Glu
        115                 120                 125

Gln Lys Ser Ala Lys Ser Ser Arg Leu Pro Asp Ile Phe Glu Ala Gln
    130                 135                 140

Ile Ala Gly Leu Arg Gly Gln Leu Glu Ala Leu Gln Val Asp Gly Gly
145                 150                 155                 160

Arg Leu Glu Ala Glu Leu Arg Ser Met Gln Asp Val Val Glu Asp Phe
                165                 170                 175

Lys Asn Lys Tyr Glu Asp Glu Ile Asn His Arg Thr Ala Ala Glu Asn
            180                 185                 190

Glu Phe Val Val Leu Lys Lys Asp Val Asp Ala Ala Tyr Met Ser Lys
        195                 200                 205

Val Glu Leu Glu Ala Lys Val Asp Ala Leu Asn Asp Glu Ile Asn Phe
    210                 215                 220

Leu Arg Thr Leu Asn Glu Thr Glu Leu Thr Glu Leu Gln Ser Gln Ile
225                 230                 235                 240

Ser Asp Thr Ser Val Val Leu Ser Met Asp Asn Ser Arg Ser Leu Asp
                245                 250                 255

Leu Asp Gly Ile Ile Ala Glu Val Lys Ala Gln Tyr Glu Glu Met Ala
            260                 265                 270

Lys Cys Ser Arg Ala Glu Ala Glu Ala Trp Tyr Gln Thr Lys Phe Glu
        275                 280                 285

Thr Leu Gln Ala Gln Ala Gly Lys His Gly Asp Asp Leu Arg Asn Thr
    290                 295                 300

Arg Asn Glu Ile Ser Glu Met Asn Arg Ala Ile Gln Arg Leu Gln Ala
305                 310                 315                 320

Glu Ile Asp Asn Ile Lys Asn Gln Arg Ala Lys Leu Glu Ala Ala Ile
                325                 330                 335

Ala Glu Ala Glu Glu Arg Gly Glu Leu Ala Leu Lys Asp Ala Arg Ala
            340                 345                 350

Lys Gln Glu Glu Leu Glu Ala Ala Leu Gln Arg Gly Lys Gln Asp Met
        355                 360                 365

Ala Arg Gln Leu Arg Glu Tyr Gln Glu Leu Met Ser Val Lys Leu Ala
    370                 375                 380

Leu Asp Ile Glu Ile Ala Thr Tyr Arg Lys Leu Leu Glu Gly Glu Glu
385                 390                 395                 400

Ser Arg Leu Ala Gly Asp Gly Val Gly Ala Val Asn Ile Ser Val Met
                405                 410                 415

Asn Ser Thr Gly Gly Ser Ser Ser Gly Gly Gly Ile Gly Leu Thr Leu
            420                 425                 430

Gly Gly Thr Met Gly Ser Asn Ala Leu Ser Phe Ser Ser Ser Ala Gly
        435                 440                 445

Pro Gly Leu Leu Lys Ala Tyr Ser Ile Arg Thr Ala Ser Ala Ser Arg
    450                 455                 460

Arg Ser Ala Arg Asp
465
```

<210> SEQ ID NO 4
<211> LENGTH: 1753
<212> TYPE: DNA
<213> ORGANISM: Homo sapiens

<400> SEQUENCE: 4
cagccccgcc cctacctgtg gaagcccagc cgcccgctcc cgcggataaa aggcgcggag 60
tgtccccgag gtcagcgagt gcgcgctcct cctcgcccgc cgctaggtcc atcccggccc 120
agccaccatg tccatccact tcagctcccc ggtattcacc tcgcgctcag ccgccttctc 180
gggccgcggc gcccaggtgc gcctgagctc cgctcgcccc ggcggccttg gcagcagcag 240
cctctacggc ctcggcgcct cacggccgcg cgtggccgtg cgctctgcct atgggggccc 300
ggtgggcgcc ggcatccgcg aggtcaccat taaccagagc ctgctggccc cgctgcggct 360
ggacgccgac ccctccctcc agcgggtgcg ccaggaggag agcgagcaga tcaagaccct 420
caacaacaag tttgcctcct tcatcgacaa ggtgcggttt ctggagcagc agaacaagct 480
gctggagacc aagtggacgc tgctgcagga gcagaagtcg gccaagagca gccgcctccc 540
agacatcttt gaggcccaga ttgctggcct tcggggtcag cttgaggcac tgcaggtgga 600
tgggggccgc ctggaggcgg agctgcggag catgcaggat gtggtggagg acttcaagaa 660
taagtacgaa gatgaaatta accaccgcac agctgctgag aatgagtttg tggtgctgaa 720
gaaggatgtg gatgctgcct acatgagcaa ggtggagctg gaggccaagg tggatgccct 780
gaatgatgag atcaacttcc tcaggaccct caatgagacg gagttgacag agctgcagtc 840
ccagatctcc gacacatctg tggtgctgtc catggacaac agtcgctccc tggacctgga 900
cggcatcatc gctgaggtca aggcgcagta tgaggagatg gccaaatgca gccgggctga 960
ggctgaagcc tggtaccaga ccaagtttga gaccctccag gcccaggctg ggaagcatgg 1020
ggacgacctc cggaataccc ggaatgagat ttcagagatg aaccgggcca tccagaggct 1080
gcaggctgag atcgacaaca tcaagaacca gcgtgccaag ttggaggccg ccattgccga 1140
ggctgaggag cgtggggagc tggcgctcaa ggatgctcgt gccaagcagg aggagctgga 1200
agccgccctg cagcggggca agcaggatat ggcacggcag ctgcgtgagt accaggaact 1260
catgagcgtg aagctggccc tggacatcga gatcgccacc taccgcaagc tgctggaggg 1320
cgaggagagc cggttggctg gagatggagt gggagccgtg aatatctctg tgatgaattc 1380
cactggtggc agtagcagtg gcggtggcat tgggctgacc ctcgggggaa ccatgggcag 1440
caatgccctg agcttctcca gcagtgcggg tcctgggctc ctgaaggctt attccatccg 1500
gaccgcatcc gccagtcgca ggagtgcccg cgactgagcc gcctcccacc actccactcc 1560
tccagccacc acccacaatc acaagaagat tcccacccct gcctcccatg cctggtccca 1620
agacagtgag acagtctgga aagtgatgtc agaatagctt ccaataaagc agcctcattc 1680
tgaggcctga gtgatccacg tgaaaaaaaa aaaaaaaaaa aaaaaaaaaa aaaaaaaaaa 1740
aaaaaaaaaa aaa 1753

<210> SEQ ID NO 5
<211> LENGTH: 511
<212> TYPE: PRT
<213> ORGANISM: Homo sapiens

<400> SEQUENCE: 5

Met Asn Gly Val Ser Trp Ser Gln Asp Leu Gln Glu Gly Ile Ser Ala
1               5                   10                  15

Trp Phe Gly Pro Pro Ala Ser Thr Pro Ala Ser Thr Met Ser Ile Arg
            20                  25                  30

Val Thr Gln Lys Ser Tyr Lys Val Ser Thr Ser Gly Pro Arg Ala Phe
        35                  40                  45

```
Ser Ser Arg Ser Tyr Thr Ser Gly Pro Gly Ser Arg Ile Ser Ser Ser
    50                  55                  60

Ser Phe Ser Arg Val Gly Ser Ser Asn Phe Arg Gly Gly Leu Gly Gly
65                  70                  75                  80

Gly Tyr Gly Gly Ala Ser Gly Met Gly Gly Ile Thr Ala Val Thr Val
                85                  90                  95

Asn Gln Ser Leu Leu Ser Pro Leu Val Leu Glu Val Asp Pro Asn Ile
            100                 105                 110

Gln Ala Val Arg Thr Gln Glu Lys Glu Gln Ile Lys Thr Leu Asn Asn
        115                 120                 125

Lys Phe Ala Ser Phe Ile Asp Lys Val Arg Phe Leu Glu Gln Gln Asn
    130                 135                 140

Lys Met Leu Glu Thr Lys Trp Ser Leu Leu Gln Gln Gln Lys Thr Ala
145                 150                 155                 160

Arg Ser Asn Met Asp Asn Met Phe Glu Ser Tyr Ile Asn Asn Leu Arg
                165                 170                 175

Arg Gln Leu Glu Thr Leu Gly Gln Glu Lys Leu Lys Leu Glu Ala Glu
            180                 185                 190

Leu Gly Asn Met Gln Gly Leu Val Glu Asp Phe Lys Asn Lys Tyr Glu
        195                 200                 205

Asp Glu Ile Asn Lys Arg Thr Glu Met Glu Asn Glu Phe Val Leu Ile
    210                 215                 220

Lys Lys Asp Val Asp Glu Ala Tyr Met Asn Lys Val Glu Leu Glu Ser
225                 230                 235                 240

Arg Leu Glu Gly Leu Thr Asp Glu Ile Asn Phe Leu Arg Gln Leu Tyr
                245                 250                 255

Glu Glu Glu Ile Arg Glu Leu Gln Ser Gln Ile Ser Asp Thr Ser Val
            260                 265                 270

Val Leu Ser Met Asp Asn Ser Arg Ser Leu Asp Met Asp Ser Ile Ile
        275                 280                 285

Ala Glu Val Lys Ala Gln Tyr Glu Asp Ile Ala Asn Arg Ser Arg Ala
    290                 295                 300

Glu Ala Glu Ser Met Tyr Gln Ile Lys Tyr Glu Glu Leu Gln Ser Leu
305                 310                 315                 320

Ala Gly Lys His Gly Asp Asp Leu Arg Arg Thr Lys Thr Glu Ile Ser
                325                 330                 335

Glu Met Asn Arg Asn Ile Ser Arg Leu Gln Ala Glu Ile Glu Gly Leu
            340                 345                 350

Lys Gly Gln Arg Ala Ser Leu Glu Ala Ala Ile Ala Asp Ala Glu Gln
        355                 360                 365

Arg Gly Glu Leu Ala Ile Lys Asp Ala Asn Ala Lys Leu Ser Glu Leu
    370                 375                 380

Glu Ala Ala Leu Gln Arg Ala Lys Gln Asp Met Ala Arg Gln Leu Arg
385                 390                 395                 400

Glu Tyr Gln Glu Leu Met Asn Val Lys Leu Ala Leu Asp Ile Glu Ile
                405                 410                 415

Ala Thr Tyr Arg Lys Leu Leu Glu Gly Glu Glu Ser Arg Leu Glu Ser
            420                 425                 430

Gly Met Gln Asn Met Ser Ile His Thr Lys Thr Thr Ser Gly Tyr Ala
        435                 440                 445

Gly Gly Leu Ser Ser Ala Tyr Gly Gly Leu Thr Ser Pro Gly Leu Ser
    450                 455                 460
```

-continued

```
Tyr Ser Leu Gly Ser Ser Phe Gly Ser Gly Ala Gly Ser Ser Ser Phe
465                 470                 475                 480

Ser Arg Thr Ser Ser Ser Arg Ala Val Val Val Lys Lys Ile Glu Thr
                485                 490                 495

Arg Asp Gly Lys Leu Val Ser Glu Ser Ser Asp Val Leu Pro Lys
            500                 505                 510


<210> SEQ ID NO 6
<211> LENGTH: 1807
<212> TYPE: DNA
<213> ORGANISM: Homo sapiens

<400> SEQUENCE: 6

attcagcaaa tgtttgcgga atgaatgggg tgagctggag ccaggacctg caggaaggga      60

tctccgcctg gttcggcccg cctgcctcca ctcctgcctc taccatgtcc atcagggtga     120

cccagaagtc ctacaaggtg tccacctctg gcccccgggc cttcagcagc cgctcctaca     180

cgagtgggcc cggttcccgc atcagctcct cgagcttctc ccgagtgggc agcagcaact     240

ttcgcggtgg cctgggcggc ggctatggtg ggccagcggg catgggaggc atcaccgcag     300

ttacggtcaa ccagagcctg ctgagccccc ttgtcctgga ggtggacccc aacatccagg     360

ccgtgcgcac ccaggagaag gagcagatca agaccctcaa caacaagttt gcctccttca     420

tagacaaggt acggttcctg gagcagcaga acaagatgct ggagaccaag tggagcctcc     480

tgcagcagca gaagacggct cgaagcaaca tggacaacat gttcgagagc tacatcaaca     540

accttaggcg gcagctggag actctgggcc aggagaagct gaagctggag gcggagcttg     600

gcaacatgca ggggctggtg gaggacttca agaacaagta tgaggatgag atcaataagc     660

gtacagagat ggagaacgaa tttgtcctca tcaagaagga tgtggatgaa gcttacatga     720

acaaggtaga gctggagtct cgcctggaag ggctgaccga cgagatcaac ttcctcaggc     780

agctatatga agaggagatc cgggagctgc agtcccagat ctcggacaca tctgtggtgc     840

tgtccatgga caacagccgc tccctggaca tggacagcat cattgctgag gtcaaggcac     900

agtacgagga tattgccaac cgcagccggg ctgaggctga gagcatgtac cagatcaagt     960

atgaggagct gcagagcctg gctgggaagc acggggatga cctgcggcgc acaaagactg    1020

agatctctga gatgaaccgg aacatcagcc ggctccaggc tgagattgag ggcctcaaag    1080

gccagagggc ttccctggag gccgccattg cagatgccga gcagcgtgga gagctggcca    1140

ttaaggatgc caacgccaag ttgtccgagc tggaggccgc cctgcagcgg gccaagcagg    1200

acatggcgcg gcagctgcgt gagtaccagg agctgatgaa cgtcaagctg gccctggaca    1260

tcgagatcgc cacctacagg aagctgctgg agggcgagga gagccggctg gagtctggga    1320

tgcagaacat gagtattcat acgaagacca ccagcggcta tgcaggtggt ctgagctcgg    1380

cctatggggg cctcacaagc cccggcctca gctacagcct gggctccagc tttggctctg    1440

gcgcgggctc cagctccttc agccgcacca gctcctccag ggccgtggtt gtgaagaaga    1500

tcgagacacg tgatgggaag ctggtgtctg agtcctctga cgtcctgccc aagtgaacag    1560

ctgcggcagc ccctcccagc ctacccctcc tgcgctgccc cagagcctgg gaaggaggcc    1620

gctatgcagg gtagcactgg gaacaggaga cccacctgag gctcagccct agccctcagc    1680

ccacctgggg agtttactac ctggggaccc cccttgccca tgcctccagc tacaaaacaa    1740

ttcaattgct ttttttttt ggtccaaaat aaaacctcag ctagctctgc caatgtcaaa    1800

aaaaaaa                                                              1807
```

<210> SEQ ID NO 7
<211> LENGTH: 483
<212> TYPE: PRT
<213> ORGANISM: Homo sapiens

<400> SEQUENCE: 7

```
Met Ser Ile Arg Val Thr Gln Lys Ser Tyr Lys Val Ser Thr Ser Gly
1               5                   10                  15

Pro Arg Ala Phe Ser Ser Arg Ser Tyr Thr Ser Gly Pro Gly Ser Arg
            20                  25                  30

Ile Ser Ser Ser Ser Phe Ser Arg Val Gly Ser Ser Asn Phe Arg Gly
        35                  40                  45

Gly Leu Gly Gly Gly Tyr Gly Gly Ala Ser Gly Met Gly Gly Ile Thr
    50                  55                  60

Ala Val Thr Val Asn Gln Ser Leu Leu Ser Pro Leu Val Leu Glu Val
65                  70                  75                  80

Asp Pro Asn Ile Gln Ala Val Arg Thr Gln Glu Lys Glu Gln Ile Lys
                85                  90                  95

Thr Leu Asn Asn Lys Phe Ala Ser Phe Ile Asp Lys Val Arg Phe Leu
            100                 105                 110

Glu Gln Gln Asn Lys Met Leu Glu Thr Lys Trp Ser Leu Leu Gln Gln
        115                 120                 125

Gln Lys Thr Ala Arg Ser Asn Met Asp Asn Met Phe Glu Ser Tyr Ile
    130                 135                 140

Asn Asn Leu Arg Arg Gln Leu Glu Thr Leu Gly Gln Glu Lys Leu Lys
145                 150                 155                 160

Leu Glu Ala Glu Leu Gly Asn Met Gln Gly Leu Val Glu Asp Phe Lys
                165                 170                 175

Asn Lys Tyr Glu Asp Glu Ile Asn Lys Arg Thr Glu Met Glu Asn Glu
            180                 185                 190

Phe Val Leu Ile Lys Lys Asp Val Asp Glu Ala Tyr Met Asn Lys Val
        195                 200                 205

Glu Leu Glu Ser Arg Leu Glu Gly Leu Thr Asp Glu Ile Asn Phe Leu
    210                 215                 220

Arg Gln Leu Tyr Glu Glu Glu Ile Arg Glu Leu Gln Ser Gln Ile Ser
225                 230                 235                 240

Asp Thr Ser Val Val Leu Ser Met Asp Asn Ser Arg Ser Leu Asp Met
                245                 250                 255

Asp Ser Ile Ile Ala Glu Val Lys Ala Gln Tyr Glu Asp Ile Ala Asn
            260                 265                 270

Arg Ser Arg Ala Glu Ala Glu Ser Met Tyr Gln Ile Lys Tyr Glu Glu
        275                 280                 285

Leu Gln Ser Leu Ala Gly Lys His Gly Asp Asp Leu Arg Arg Thr Lys
    290                 295                 300

Thr Glu Ile Ser Glu Met Asn Arg Asn Ile Ser Arg Leu Gln Ala Glu
305                 310                 315                 320

Ile Glu Gly Leu Lys Gly Gln Arg Ala Ser Leu Glu Ala Ala Ile Ala
                325                 330                 335

Asp Ala Glu Gln Arg Gly Glu Leu Ala Ile Lys Asp Ala Asn Ala Lys
            340                 345                 350

Leu Ser Glu Leu Glu Ala Ala Leu Gln Arg Ala Lys Gln Asp Met Ala
        355                 360                 365

Arg Gln Leu Arg Glu Tyr Gln Glu Leu Met Asn Val Lys Leu Ala Leu
    370                 375                 380
```

```
Asp Ile Glu Ile Ala Thr Tyr Arg Lys Leu Leu Glu Gly Glu Glu Ser
385                 390                 395                 400

Arg Leu Glu Ser Gly Met Gln Asn Met Ser Ile His Thr Lys Thr Thr
                405                 410                 415

Ser Gly Tyr Ala Gly Gly Leu Ser Ser Ala Tyr Gly Gly Leu Thr Ser
            420                 425                 430

Pro Gly Leu Ser Tyr Ser Leu Gly Ser Ser Phe Gly Ser Gly Ala Gly
        435                 440                 445

Ser Ser Ser Phe Ser Arg Thr Ser Ser Ser Arg Ala Val Val Val Lys
    450                 455                 460

Lys Ile Glu Thr Arg Asp Gly Lys Leu Val Ser Glu Ser Ser Asp Val
465                 470                 475                 480

Leu Pro Lys


<210> SEQ ID NO 8
<211> LENGTH: 1901
<212> TYPE: DNA
<213> ORGANISM: Homo sapiens

<400> SEQUENCE: 8

acaggccttt ccttacctcc ctccatgctg tccacttcct ctgtaaagct ctcaaccctg     60

tccccttccc cctctctcct gggaaagagc cctcccatgc ctagctgctg ctcttaggga    120

ccctgtggct aggtgcgcgg atggaaatcc aggatctccg cctggttcgg cccgcctgcc    180

tccactcctg cctctaccat gtccatcagg gtgacccaga agtcctacaa ggtgtccacc    240

tctggccccc gggccttcag cagccgctcc tacacgagtg ggcccggttc ccgcatcagc    300

tcctcgagct tctcccgagt gggcagcagc aactttcgcg gtggcctggg cggcggctat    360

ggtggggcca gcggcatggg aggcatcacc gcagttacgg tcaaccagag cctgctgagc    420

ccccttgtcc tggaggtgga ccccaacatc caggccgtgc gcacccagga gaaggagcag    480

atcaagaccc tcaacaacaa gtttgcctcc ttcatagaca aggtacggtt cctggagcag    540

cagaacaaga tgctggagac caagtggagc ctcctgcagc agcagaagac ggctcgaagc    600

aacatggaca acatgttcga gagctacatc aacaacctta ggcggcagct ggagactctg    660

ggccaggaga agctgaagct ggaggcggag cttggcaaca tgcaggggct ggtggaggac    720

ttcaagaaca agtatgagga tgagatcaat aagcgtacag agatggagaa cgaatttgtc    780

ctcatcaaga aggatgtgga tgaagcttac atgaacaagg tagagctgga gtctcgcctg    840

gaagggctga ccgacgagat caacttcctc aggcagctat atgaagagga gatccgggag    900

ctgcagtccc agatctcgga cacatctgtg gtgctgtcca tggacaacag ccgctccctg    960

gacatggaca gcatcattgc tgaggtcaag gcacagtacg aggatattgc caaccgcagc   1020

cgggctgagg ctgagagcat gtaccagatc aagtatgagg agctgcagag cctggctggg   1080

aagcacgggg atgacctgcg gcgcacaaag actgagatct ctgagatgaa ccggaacatc   1140

agccggctcc aggctgagat tgagggcctc aaaggccaga gggcttccct ggaggccgcc   1200

attgcagatg ccgagcagcg tggagagctg gccattaagg atgccaacgc caagttgtcc   1260

gagctggagg ccgccctgca gcgggccaag caggacatgg cgcggcagct gcgtgagtac   1320

caggagctga tgaacgtcaa gctggccctg gacatcgaga tcgccaccta caggaagctg   1380

ctggagggcg aggagagccg gctggagtct gggatgcaga acatgagtat tcatacgaag   1440

accaccagcg gctatgcagg tggtctgagc tcggcctatg gggcctcac aagccccggc   1500
```

-continued

```
ctcagctaca gcctgggctc cagctttggc tctggcgcgg gctccagctc cttcagccgc   1560

accagctcct ccagggccgt ggttgtgaag aagatcgaga cacgtgatgg gaagctggtg   1620

tctgagtcct ctgacgtcct gcccaagtga acagctgcgg cagcccctcc cagcctaccc   1680

ctcctgcgct gccccagagc ctgggaagga ggccgctatg cagggtagca ctgggaacag   1740

gagacccacc tgaggctcag ccctagccct cagcccacct ggggagttta ctacctgggg   1800

acccccttg cccatgcctc cagctacaaa acaattcaat tgcttttttt ttttggtcca   1860

aaataaaacc tcagctagct ctgccaatgt caaaaaaaaa a                        1901
```

<210> SEQ ID NO 9
<211> LENGTH: 456
<212> TYPE: PRT
<213> ORGANISM: Homo sapiens

<400> SEQUENCE: 9

```
Met Thr Thr Thr Phe Leu Gln Thr Ser Ser Ser Thr Phe Gly Gly Gly
1               5                   10                  15

Ser Thr Arg Gly Gly Ser Leu Leu Ala Gly Gly Gly Gly Phe Gly Gly
            20                  25                  30

Gly Ser Leu Ser Gly Gly Gly Gly Ser Arg Ser Ile Ser Ala Ser Ser
        35                  40                  45

Ala Arg Phe Val Ser Ser Gly Ser Gly Gly Gly Tyr Gly Gly Gly Met
    50                  55                  60

Arg Val Cys Gly Phe Gly Gly Gly Ala Gly Ser Val Phe Gly Gly Gly
65                  70                  75                  80

Phe Gly Gly Gly Val Gly Gly Gly Phe Gly Gly Gly Phe Gly Gly Gly
                85                  90                  95

Asp Gly Gly Leu Leu Ser Gly Asn Glu Lys Ile Thr Met Gln Asn Leu
            100                 105                 110

Asn Asp Arg Leu Ala Ser Tyr Leu Asp Lys Val Arg Ala Leu Glu Glu
        115                 120                 125

Ala Asn Ala Asp Leu Glu Val Lys Ile His Asp Trp Tyr Gln Lys Gln
    130                 135                 140

Thr Pro Thr Ser Pro Glu Cys Asp Tyr Ser Gln Tyr Phe Lys Thr Ile
145                 150                 155                 160

Glu Glu Leu Arg Asp Lys Ile Met Ala Thr Thr Ile Asp Asn Ser Arg
                165                 170                 175

Val Ile Leu Glu Ile Asp Asn Ala Arg Leu Ala Ala Asp Asp Phe Arg
            180                 185                 190

Leu Lys Tyr Glu Asn Glu Leu Ala Leu Arg Gln Gly Val Glu Ala Asp
        195                 200                 205

Ile Asn Gly Leu Arg Arg Val Leu Asp Glu Leu Thr Leu Ala Arg Thr
    210                 215                 220

Asp Leu Glu Met Gln Ile Glu Gly Leu Asn Glu Glu Leu Ala Tyr Leu
225                 230                 235                 240

Lys Lys Asn His Glu Glu Glu Met Lys Glu Phe Ser Ser Gln Leu Ala
                245                 250                 255

Gly Gln Val Asn Val Glu Met Asp Ala Ala Pro Gly Val Asp Leu Thr
            260                 265                 270

Arg Val Leu Ala Glu Met Arg Glu Gln Tyr Glu Ala Met Ala Glu Lys
        275                 280                 285

Asn Arg Arg Asp Val Glu Ala Trp Phe Phe Ser Lys Thr Glu Glu Leu
    290                 295                 300
```

-continued

```
Asn Lys Glu Val Ala Ser Asn Thr Glu Met Ile Gln Thr Ser Lys Thr
305                 310                 315                 320

Glu Ile Thr Asp Leu Arg Arg Thr Met Gln Glu Leu Glu Ile Glu Leu
                325                 330                 335

Gln Ser Gln Leu Ser Met Lys Ala Gly Leu Glu Asn Ser Leu Ala Glu
            340                 345                 350

Thr Glu Cys Arg Tyr Ala Thr Gln Leu Gln Gln Ile Gln Gly Leu Ile
        355                 360                 365

Gly Gly Leu Glu Ala Gln Leu Ser Glu Leu Arg Cys Glu Met Glu Ala
    370                 375                 380

Gln Asn Gln Glu Tyr Lys Met Leu Leu Asp Ile Lys Thr Arg Leu Glu
385                 390                 395                 400

Gln Glu Ile Ala Thr Tyr Arg Ser Leu Leu Glu Gly Gln Asp Ala Lys
                405                 410                 415

Met Ala Gly Ile Gly Ile Arg Glu Ala Ser Ser Gly Gly Gly Gly Ser
            420                 425                 430

Ser Ser Asn Phe His Ile Asn Val Glu Glu Ser Val Asp Gly Gln Val
        435                 440                 445

Val Ser Ser His Lys Arg Glu Ile
    450                 455


<210> SEQ ID NO 10
<211> LENGTH: 1861
<212> TYPE: DNA
<213> ORGANISM: Homo sapiens

<400> SEQUENCE: 10

cactcaaggt gtgcaggcag ctgtgtttgt caggaaggca gaaggagttg gctttgcttt     60

aggggaggag acgaggtccc acaacaccct ctgaagggta tataaggagc cccagcgtgc    120

agcctggcct ggtacctcct gccagcatct cttgggtttg ctgagaactc acgggctcca    180

gctacctggc catgaccacc acatttctgc aaacttcttc ctccaccttt gggggtggct    240

caacccgagg gggttccctc ctggctgggg gaggtggctt tggtgggggg agtctctctg    300

ggggaggtgg aagccgaagt atctcagctt cttctgctag gtttgtctct tcagggtcag    360

gaggaggata tgggggtggc atgagggtct gtggctttgg tggaggggct ggtagtgttt    420

tcggtggagg ctttggaggg ggcgttggtg gggttttgg tggtggcttt ggtggtggcg    480

atggtggtct cctctctggc aatgagaaaa ttaccatgca gaacctcaat gaccgcctgg    540

cctcctacct ggacaaggta cgtgccctgg aggaggccaa tgctgacctg gaggtgaaga    600

tccatgactg gtaccagaag cagaccccaa ccagcccaga atgcgactac agccaatact    660

tcaagaccat tgaagagctc cgggacaaga tcatggccac caccatcgac aactcccggg    720

tcatcctgga gatcgacaat gccaggctgg ctgcggacga cttcaggctc aagtatgaga    780

atgagctggc cctgcgccag ggcgttgagg ctgacatcaa cggcttgcgc cgagtcctgg    840

atgagctgac cctggccagg actgacctgg agatgcagat cgagggcctg aatgaggagc    900

tagcctacct gaagaagaac cacgaagagg agatgaagga gttcagcagc cagctggccg    960

gccaggtcaa tgtggagatg gacgcagcac cgggtgtgga cctgacccgt gtgctggcag   1020

agatgaggga gcagtacgag gccatggcgg agaagaaccg ccgggatgtc gaggcctggt   1080

tcttcagcaa gactgaggag ctgaacaaag aggtggcctc caacacagaa atgatccaga   1140

ccagcaagac ggagatcaca gacctgagac gcacgatgca ggagctggag atcgagctgc   1200

agtcccagct cagcatgaaa gctgggctgg agaactcact ggccgagaca gagtgccgct   1260
```

atgccacgca gctgcagcag atccaggggc tcattggtgg cctggaggcc cagctgagtg 1320
agctccgatg cgagatggag gctcagaacc aggagtacaa gatgctgctt gacataaaga 1380
cacggctgga gcaggagatc gctacttacc gcagcctgct cgagggccag gatgccaaga 1440
tggctggcat tggcatcagg gaagcctctt caggaggtgg tggtagcagc agcaatttcc 1500
acatcaatgt agaagagtca gtggatggac aggtggtttc ttcccacaag agagaaatct 1560
aagtgtctat tgcaggagaa acgtcccttg ccactcccca ctctcatcag gccaagtgga 1620
ggactggcca gagggcctgc acatgcaaac tccagtccct gccttcagag agctgaaaag 1680
ggtccctcgg tcttttattt cagggctttg catgcgctct attcccctc tgcctctccc 1740 caccttcttt ggagcaagga gatgcagctg tattgtgtaa caagctcatt tgtacagtgt 1800
ctgttcatgt aataaagaat tacttttcct tttgcaaata aaaaaaaaaa aaaaaaaaaa 1860
a 1861

<210> SEQ ID NO 11
<211> LENGTH: 430
<212> TYPE: PRT
<213> ORGANISM: Homo sapiens

<400> SEQUENCE: 11

```
Met Ser Phe Thr Thr Arg Ser Thr Phe Ser Thr Asn Tyr Arg Ser Leu
1               5                   10                  15

Gly Ser Val Gln Ala Pro Ser Tyr Gly Ala Arg Pro Val Ser Ser Ala
            20                  25                  30

Ala Ser Val Tyr Ala Gly Ala Gly Gly Ser Gly Ser Arg Ile Ser Val
        35                  40                  45

Ser Arg Ser Thr Ser Phe Arg Gly Gly Met Gly Ser Gly Gly Leu Ala
    50                  55                  60

Thr Gly Ile Ala Gly Gly Leu Ala Gly Met Gly Gly Ile Gln Asn Glu
65                  70                  75                  80

Lys Glu Thr Met Gln Ser Leu Asn Asp Arg Leu Ala Ser Tyr Leu Asp
                85                  90                  95

Arg Val Arg Ser Leu Glu Thr Glu Asn Arg Arg Leu Glu Ser Lys Ile
            100                 105                 110

Arg Glu His Leu Glu Lys Lys Gly Pro Gln Val Arg Asp Trp Ser His
        115                 120                 125

Tyr Phe Lys Ile Ile Glu Asp Leu Arg Ala Gln Ile Phe Ala Asn Thr
    130                 135                 140

Val Asp Asn Ala Arg Ile Val Leu Gln Ile Asp Asn Ala Arg Leu Ala
145                 150                 155                 160

Ala Asp Asp Phe Arg Val Lys Tyr Glu Thr Glu Leu Ala Met Arg Gln
                165                 170                 175

Ser Val Glu Asn Asp Ile His Gly Leu Arg Lys Val Ile Asp Asp Thr
            180                 185                 190

Asn Ile Thr Arg Leu Gln Leu Glu Thr Glu Ile Glu Ala Leu Lys Glu
        195                 200                 205

Glu Leu Leu Phe Met Lys Lys Asn His Glu Glu Glu Val Lys Gly Leu
    210                 215                 220

Gln Ala Gln Ile Ala Ser Ser Gly Leu Thr Val Glu Val Asp Ala Pro
225                 230                 235                 240

Lys Ser Gln Asp Leu Ala Lys Ile Met Ala Asp Ile Arg Ala Gln Tyr
                245                 250                 255
```

-continued

```
Asp Glu Leu Ala Arg Lys Asn Arg Glu Glu Leu Asp Lys Tyr Trp Ser
            260                 265                 270

Gln Gln Ile Glu Glu Ser Thr Thr Val Val Thr Thr Gln Ser Ala Glu
        275                 280                 285

Val Gly Ala Ala Glu Thr Thr Leu Thr Glu Leu Arg Arg Thr Val Gln
    290                 295                 300

Ser Leu Glu Ile Asp Leu Asp Ser Met Arg Asn Leu Lys Ala Ser Leu
305                 310                 315                 320

Glu Asn Ser Leu Arg Glu Val Glu Ala Arg Tyr Ala Leu Gln Met Glu
                325                 330                 335

Gln Leu Asn Gly Ile Leu Leu His Leu Glu Ser Glu Leu Ala Gln Thr
            340                 345                 350

Arg Ala Glu Gly Gln Arg Gln Ala Gln Glu Tyr Glu Ala Leu Leu Asn
        355                 360                 365

Ile Lys Val Lys Leu Glu Ala Glu Ile Ala Thr Tyr Arg Arg Leu Leu
    370                 375                 380

Glu Asp Gly Glu Asp Phe Asn Leu Gly Asp Ala Leu Asp Ser Ser Asn
385                 390                 395                 400

Ser Met Gln Thr Ile Gln Lys Thr Thr Thr Arg Arg Ile Val Asp Gly
                405                 410                 415

Lys Val Val Ser Glu Thr Asn Asp Thr Lys Val Leu Arg His
            420                 425                 430


<210> SEQ ID NO 12
<211> LENGTH: 1485
<212> TYPE: DNA
<213> ORGANISM: Homo sapiens

<400> SEQUENCE: 12

tccggggcgg gggcggggcc tcactctgcg atataactcg ggtcgcgcgg ctcgcgcagg      60

ccgccaccgt cgtccgcaaa gcctgagtcc tgtcctttct ctctccccgg acagcatgag     120

cttcaccact cgctccacct tctccaccaa ctaccggtcc ctgggctctg tccaggcgcc     180

cagctacggc gcccggccgg tcagcagcgc ggccagcgtc tatgcaggcg ctgggggctc     240

tggttcccgg atctccgtgt cccgctccac cagcttcagg ggcggcatgg ggtccggggg     300

cctggccacc gggatagccg gggtctggc aggaatggga ggcatccaga acgagaagga     360

gaccatgcaa agcctgaacg accgcctggc ctcttacctg gacagagtga ggagcctgga     420

gaccgagaac cggaggctgg agagcaaaat ccgggagcac ttggagaaga agggacccca     480

ggtcagagac tggagccatt acttcaagat catcgaggac ctgagggctc agatcttcgc     540

aaatactgtg gacaatgccc gcatcgttct gcagattgac aatgcccgtc ttgctgctga     600

tgactttaga gtcaagtatg agacagagct ggccatgcgc cagtctgtgg agaacgacat     660

ccatgggctc cgcaaggtca ttgatgacac caatatcaca cgactgcagc tggagacaga     720

gatcgaggct ctcaaggagg agctgctctt catgaagaag aaccacgaag aggaagtaaa     780

aggcctacaa gcccagattg ccagctctgg gttgaccgtg gaggtagatg cccccaaatc     840

tcaggacctc gccaagatca tggcagacat ccgggcccaa tatgacgagc tggctcggaa     900

gaaccgagag gagctagaca agtactggtc tcagcagatt gaggagagca ccacagtggt     960

caccacacag tctgctgagg ttggagctgc tgagacgacg ctcacagagc tgagacgtac    1020

agtccagtcc ttggagatcg acctggactc catgagaaat ctgaaggcca gcttggagaa    1080

cagcctgagg gaggtggagg cccgctacgc cctacagatg gagcagctca acgggatcct    1140
```

-continued

```
gctgcacctt gagtcagagc tggcacagac ccgggcagag ggacagcgcc aggcccagga   1200

gtatgaggcc ctgctgaaca tcaaggtcaa gctggaggct gagatcgcca cctaccgccg   1260

cctgctggaa gatggcgagg actttaatct tggtgatgcc ttggacagca gcaactccat   1320

gcaaaccatc caaaagacca ccacccgccg gatagtggat ggcaaagtgg tgtctgagac   1380

caatgacacc aaagttctga ggcattaagc cagcagaagc agggtaccct tggggagca   1440

ggaggccaat aaaaagttca gagttcaaaa aaaaaaaaaa aaaaa                   1485


<210> SEQ ID NO 13
<211> LENGTH: 430
<212> TYPE: PRT
<213> ORGANISM: Homo sapiens

<400> SEQUENCE: 13

Met Ser Phe Thr Thr Arg Ser Thr Phe Ser Thr Asn Tyr Arg Ser Leu
1               5                   10                  15

Gly Ser Val Gln Ala Pro Ser Tyr Gly Ala Arg Pro Val Ser Ser Ala
            20                  25                  30

Ala Ser Val Tyr Ala Gly Ala Gly Gly Ser Gly Ser Arg Ile Ser Val
        35                  40                  45

Ser Arg Ser Thr Ser Phe Arg Gly Gly Met Gly Ser Gly Gly Leu Ala
    50                  55                  60

Thr Gly Ile Ala Gly Gly Leu Ala Gly Met Gly Gly Ile Gln Asn Glu
65                  70                  75                  80

Lys Glu Thr Met Gln Ser Leu Asn Asp Arg Leu Ala Ser Tyr Leu Asp
                85                  90                  95

Arg Val Arg Ser Leu Glu Thr Glu Asn Arg Arg Leu Glu Ser Lys Ile
            100                 105                 110

Arg Glu His Leu Glu Lys Lys Gly Pro Gln Val Arg Asp Trp Ser His
        115                 120                 125

Tyr Phe Lys Ile Ile Glu Asp Leu Arg Ala Gln Ile Phe Ala Asn Thr
    130                 135                 140

Val Asp Asn Ala Arg Ile Val Leu Gln Ile Asp Asn Ala Arg Leu Ala
145                 150                 155                 160

Ala Asp Asp Phe Arg Val Lys Tyr Glu Thr Glu Leu Ala Met Arg Gln
                165                 170                 175

Ser Val Glu Asn Asp Ile His Gly Leu Arg Lys Val Ile Asp Asp Thr
            180                 185                 190

Asn Ile Thr Arg Leu Gln Leu Glu Thr Glu Ile Glu Ala Leu Lys Glu
        195                 200                 205

Glu Leu Leu Phe Met Lys Lys Asn His Glu Glu Glu Val Lys Gly Leu
    210                 215                 220

Gln Ala Gln Ile Ala Ser Ser Gly Leu Thr Val Glu Val Asp Ala Pro
225                 230                 235                 240

Lys Ser Gln Asp Leu Ala Lys Ile Met Ala Asp Ile Arg Ala Gln Tyr
                245                 250                 255

Asp Glu Leu Ala Arg Lys Asn Arg Glu Glu Leu Asp Lys Tyr Trp Ser
            260                 265                 270

Gln Gln Ile Glu Glu Ser Thr Thr Val Val Thr Thr Gln Ser Ala Glu
        275                 280                 285

Val Gly Ala Ala Glu Thr Thr Leu Thr Glu Leu Arg Arg Thr Val Gln
    290                 295                 300

Ser Leu Glu Ile Asp Leu Asp Ser Met Arg Asn Leu Lys Ala Ser Leu
305                 310                 315                 320
```

```
Glu Asn Ser Leu Arg Glu Val Glu Ala Arg Tyr Ala Leu Gln Met Glu
                325                 330                 335

Gln Leu Asn Gly Ile Leu Leu His Leu Glu Ser Glu Leu Ala Gln Thr
            340                 345                 350

Arg Ala Glu Gly Gln Arg Gln Ala Gln Glu Tyr Glu Ala Leu Leu Asn
        355                 360                 365

Ile Lys Val Lys Leu Glu Ala Glu Ile Ala Thr Tyr Arg Arg Leu Leu
    370                 375                 380

Glu Asp Gly Glu Asp Phe Asn Leu Gly Asp Ala Leu Asp Ser Ser Asn
385                 390                 395                 400

Ser Met Gln Thr Ile Gln Lys Thr Thr Thr Arg Arg Ile Val Asp Gly
                405                 410                 415

Lys Val Val Ser Glu Thr Asn Asp Thr Lys Val Leu Arg His
            420                 425                 430


<210> SEQ ID NO 14
<211> LENGTH: 1439
<212> TYPE: DNA
<213> ORGANISM: Homo sapiens

<400> SEQUENCE: 14

gcagcctcga gggccaacaa cacctgctgt ccgtgtccat gcccggttgg ccaccccgtt     60

tctgggggca tgagcttcac cactcgctcc accttctcca ccaactaccg gtccctgggc    120

tctgtccagg cgcccagcta cggcgcccgg ccggtcagca gcgcggccag cgtctatgca    180

ggcgctgggg gctctggttc ccggatctcc gtgtcccgct ccaccagctt caggggcggc    240

atggggtccg gggcctggc caccgggata gccgggggtc tggcaggaat gggaggcatc    300

cagaacgaga aggagaccat gcaaagcctg aacgaccgcc tggcctctta cctggacaga    360

gtgaggagcc tggagaccga gaaccggagg ctggagagca aaatccggga gcacttggag    420

aagaagggac cccaggtcag agactggagc cattacttca agatcatcga ggacctgagg    480

gctcagatct tcgcaaatac tgtggacaat gcccgcatcg ttctgcagat tgacaatgcc    540

cgtcttgctg ctgatgactt tagagtcaag tatgagacag agctggccat gcgccagtct    600

gtggagaacg acatccatgg gctccgcaag gtcattgatg acaccaatat cacacgactg    660

cagctggaga cagagatcga ggctctcaag gaggagctgc tcttcatgaa gaagaaccac    720

gaagaggaag taaaaggcct acaagcccag attgccagct ctgggttgac cgtggaggta    780

gatgccccca aatctcagga cctcgccaag atcatggcag acatccgggc ccaatatgac    840

gagctggctc ggaagaaccg agaggagcta gacaagtact ggtctcagca gattgaggag    900

agcaccacag tggtcaccac acagtctgct gaggttggag ctgctgagac gacgctcaca    960

gagctgagac gtacagtcca gtccttggag atcgacctgg actccatgag aaatctgaag   1020

gccagcttgg agaacagcct gagggaggtg gaggcccgct acgccctaca gatggagcag   1080

ctcaacggga tcctgctgca ccttgagtca gagctggcac agacccgggc agagggacag   1140

cgccaggccc aggagtatga ggccctgctg aacatcaagg tcaagctgga ggctgagatc   1200

gccacctacc gccgcctgct ggaagatggc gaggacttta atcttggtga tgccttggac   1260

agcagcaact ccatgcaaac catccaaaag accaccaccc gccggatagt ggatggcaaa   1320

gtggtgtctg agaccaatga caccaaagtt ctgaggcatt aagccagcag aagcagggta   1380

ccctttgggg agcaggaggc caataaaaag ttcagagttc aaaaaaaaaa aaaaaaaaa    1439
```

<210> SEQ ID NO 15
<211> LENGTH: 400
<212> TYPE: PRT
<213> ORGANISM: Homo sapiens

<400> SEQUENCE: 15

```
Met Thr Ser Tyr Ser Tyr Arg Gln Ser Ser Ala Thr Ser Ser Phe Gly
1               5                   10                  15

Gly Leu Gly Gly Gly Ser Val Arg Phe Gly Pro Gly Val Ala Phe Arg
            20                  25                  30

Ala Pro Ser Ile His Gly Gly Ser Gly Gly Arg Gly Val Ser Val Ser
        35                  40                  45

Ser Ala Arg Phe Val Ser Ser Ser Ser Ser Gly Ala Tyr Gly Gly Gly
    50                  55                  60

Tyr Gly Gly Val Leu Thr Ala Ser Asp Gly Leu Leu Ala Gly Asn Glu
65                  70                  75                  80

Lys Leu Thr Met Gln Asn Leu Asn Asp Arg Leu Ala Ser Tyr Leu Asp
                85                  90                  95

Lys Val Arg Ala Leu Glu Ala Ala Asn Gly Glu Leu Glu Val Lys Ile
            100                 105                 110

Arg Asp Trp Tyr Gln Lys Gln Gly Pro Gly Pro Ser Arg Asp Tyr Ser
        115                 120                 125

His Tyr Tyr Thr Thr Ile Gln Asp Leu Arg Asp Lys Ile Leu Gly Ala
    130                 135                 140

Thr Ile Glu Asn Ser Arg Ile Val Leu Gln Ile Asp Asn Ala Arg Leu
145                 150                 155                 160

Ala Ala Asp Asp Phe Arg Thr Lys Phe Glu Thr Glu Gln Ala Leu Arg
                165                 170                 175

Met Ser Val Glu Ala Asp Ile Asn Gly Leu Arg Arg Val Leu Asp Glu
            180                 185                 190

Leu Thr Leu Ala Arg Thr Asp Leu Glu Met Gln Ile Glu Gly Leu Lys
        195                 200                 205

Glu Glu Leu Ala Tyr Leu Lys Lys Asn His Glu Glu Glu Ile Ser Thr
    210                 215                 220

Leu Arg Gly Gln Val Gly Gly Gln Val Ser Val Glu Val Asp Ser Ala
225                 230                 235                 240

Pro Gly Thr Asp Leu Ala Lys Ile Leu Ser Asp Met Arg Ser Gln Tyr
                245                 250                 255

Glu Val Met Ala Glu Gln Asn Arg Lys Asp Ala Glu Ala Trp Phe Thr
            260                 265                 270

Ser Arg Thr Glu Glu Leu Asn Arg Glu Val Ala Gly His Thr Glu Gln
        275                 280                 285

Leu Gln Met Ser Arg Ser Glu Val Thr Asp Leu Arg Arg Thr Leu Gln
    290                 295                 300

Gly Leu Glu Ile Glu Leu Gln Ser Gln Leu Ser Met Lys Ala Ala Leu
305                 310                 315                 320

Glu Asp Thr Leu Ala Glu Thr Glu Ala Arg Phe Gly Ala Gln Leu Ala
                325                 330                 335

His Ile Gln Ala Leu Ile Ser Gly Ile Glu Ala Gln Leu Gly Asp Val
            340                 345                 350

Arg Ala Asp Ser Glu Arg Gln Asn Gln Glu Tyr Gln Arg Leu Met Asp
        355                 360                 365

Ile Lys Ser Arg Leu Glu Gln Glu Ile Ala Thr Tyr Arg Ser Leu Leu
    370                 375                 380
```

Glu Gly Gln Glu Asp His Tyr Asn Asn Leu Ser Ala Ser Lys Val Leu
385 390 395 400

<210> SEQ ID NO 16
<211> LENGTH: 1490
<212> TYPE: DNA
<213> ORGANISM: Homo sapiens

<400> SEQUENCE: 16
agatatccgc ccctgacacc attcctccct tccccccctcc accggccgcg ggcataaaag 60
gcgccaggtg agggcctcgc cgctcctccc gcgaatcgca gcttctgaga ccagggttgc 120
tccgtccgtg ctccgcctcg ccatgacttc ctacagctat cgccagtcgt cggccacgtc 180
gtccttcgga ggcctgggcg gcggctccgt gcgttttggg ccgggggtcg cctttcgcgc 240
gcccagcatt cacgggggct ccggcggccg cggcgtatcc gtgtcctccg cccgctttgt 300
gtcctcgtcc tcctcggggg cctacggcgg cggctacggc ggcgtcctga ccgcgtccga 360
cgggctgctg gcgggcaacg agaagctaac catgcagaac ctcaacgacc gcctggcctc 420
ctacctggac aaggtgcgcg ccctggaggc ggccaacggc gagctagagg tgaagatccg 480
cgactggtac cagaagcagg ggcctgggcc ctcccgcgac tacagccact actacacgac 540
catccaggac ctgcgggaca agattcttgg tgccaccatt gagaactcca ggattgtcct 600
gcagatcgac aatgcccgtc tggctgcaga tgacttccga accaagtttg agacggaaca 660
ggctctgcgc atgagcgtgg aggccgacat caacggcctg cgcagggtgc tggatgagct 720
gaccctggcc aggaccgacc tggagatgca gatcgaaggc ctgaaggaag agctggccta 780
cctgaagaag aaccatgagg aggaaatcag tacgctgagg ggccaagtgg gaggccaggt 840
cagtgtggag gtggattccg ctccgggcac cgatctcgcc aagatcctga gtgacatgcg 900
aagccaatat gaggtcatgg ccgagcagaa ccggaaggat gctgaagcct ggttcaccag 960
ccggactgaa gaattgaacc gggaggtcgc tggccacacg gagcagctcc agatgagcag 1020
gtccgaggtt actgacctgc ggcgcaccct tcagggtctt gagattgagc tgcagtcaca 1080
gctgagcatg aaagctgcct tggaagacac actggcagaa acggaggcgc gctttggagc 1140
ccagctggcg catatccagg cgctgatcag cggtattgaa gcccagctgg gcgatgtgcg 1200
agctgatagt gagcggcaga atcaggagta ccagcggctc atggacatca agtcgcggct 1260
ggagcaggag attgccacct accgcagcct gctcgaggga caggaagatc actacaacaa 1320
tttgtctgcc tccaaggtcc tctgaggcag caggctctgg ggcttctgct gtcctttgga 1380
gggtgtcttc tgggtagagg gatgggaagg aagggaccct tacccccggc tcttctcctg 1440
acctgccaat aaaaatttat ggtccaaggg aaaaaaaaaa aaaaaaaaaa 1490

<210> SEQ ID NO 17
<211> LENGTH: 378
<212> TYPE: PRT
<213> ORGANISM: Homo sapiens

<400> SEQUENCE: 17

Met Asp Ser Val Arg Ser Gly Ala Phe Gly His Leu Phe Arg Pro Asp
1 5 10 15

Asn Phe Ile Phe Gly Gln Ser Gly Ala Gly Asn Asn Trp Ala Lys Gly
20 25 30

His Tyr Thr Glu Gly Ala Glu Leu Val Asp Ser Val Leu Asp Val Val
35 40 45

Arg Lys Glu Cys Glu Asn Cys Asp Cys Leu Gln Gly Phe Gln Leu Thr

```
    50                  55                  60

His Ser Leu Gly Gly Gly Thr Gly Ser Gly Met Gly Thr Leu Leu Ile
65                  70                  75                  80

Ser Lys Val Arg Glu Glu Tyr Pro Asp Arg Ile Met Asn Thr Phe Ser
                85                  90                  95

Val Val Pro Ser Pro Lys Val Ser Asp Thr Val Val Glu Pro Tyr Asn
            100                 105                 110

Ala Thr Leu Ser Ile His Gln Leu Val Glu Asn Thr Asp Glu Thr Tyr
        115                 120                 125

Cys Ile Asp Asn Glu Ala Leu Tyr Asp Ile Cys Phe Arg Thr Leu Lys
    130                 135                 140

Leu Ala Thr Pro Thr Tyr Gly Asp Leu Asn His Leu Val Ser Ala Thr
145                 150                 155                 160

Met Ser Gly Val Thr Thr Ser Leu Arg Phe Pro Gly Gln Leu Asn Ala
                165                 170                 175

Asp Leu Arg Lys Leu Ala Val Asn Met Val Pro Phe Pro Arg Leu His
            180                 185                 190

Phe Phe Met Pro Gly Phe Ala Pro Leu Thr Ala Arg Gly Ser Gln Gln
        195                 200                 205

Tyr Arg Ala Leu Thr Val Pro Glu Leu Thr Gln Gln Met Phe Asp Ala
    210                 215                 220

Lys Asn Met Met Ala Ala Cys Asp Pro Arg His Gly Arg Tyr Leu Thr
225                 230                 235                 240

Val Ala Thr Val Phe Arg Gly Arg Met Ser Met Lys Glu Val Asp Glu
                245                 250                 255

Gln Met Leu Ala Ile Gln Ser Lys Asn Ser Ser Tyr Phe Val Glu Trp
            260                 265                 270

Ile Pro Asn Asn Val Lys Val Ala Val Cys Asp Ile Pro Pro Arg Gly
        275                 280                 285

Leu Lys Met Ser Ser Thr Phe Ile Gly Asn Ser Thr Ala Ile Gln Glu
    290                 295                 300

Leu Phe Lys Arg Ile Ser Glu Gln Phe Thr Ala Met Phe Arg Arg Lys
305                 310                 315                 320

Ala Phe Leu His Trp Tyr Thr Gly Glu Gly Met Asp Glu Met Glu Phe
                325                 330                 335

Thr Glu Ala Glu Ser Asn Met Asn Asp Leu Val Ser Glu Tyr Gln Gln
            340                 345                 350

Tyr Gln Asp Ala Thr Ala Glu Glu Glu Gly Glu Met Tyr Glu Asp Asp
        355                 360                 365

Glu Glu Glu Ser Glu Ala Gln Gly Pro Lys
    370                 375
```

<210> SEQ ID NO 18
<211> LENGTH: 1851
<212> TYPE: DNA
<213> ORGANISM: Homo sapiens

<400> SEQUENCE: 18

```
agacactcac cccggactcc cttgaacagg gacagggagg aaccccaggc agctagaccc      60

cagcagcagc cacacgagca cactgtgggg cagggagggg catctcttga gaacaaaaga     120

tccatttctc gactttccaa actggagagc ttcttgagag aaaagagaga gacaggtaca     180

ggtccacgcc acccacacac agccctgtgc acacagaccg gacacaggcg tccacagttc     240

tgggaagtca tcagtgatga gcatggcatc gaccccagcg gcaactacgt gggcgactcg     300
```

```
gacttgcagc tggagcggat cagcgtctac tacaacgagg cctcttctca caagtacgtg    360
cctcgagcca ttctggtgga cctggaaccc ggaaccatgg acagtgtccg ctcaggggcc    420
tttggacatc tcttcaggcc tgacaatttc atctttggtc agagtggggc cggcaacaac    480
tgggccaagg gtcactacac ggagggggcg gagctggtgg attcggtcct ggatgtggtg    540
cggaaggagt gtgaaaactg cgactgcctg cagggcttcc agctgaccca ctcgctgggg    600
ggcggcacgg gctccggcat gggcacgttg ctcatcagca aggtgcgtga ggagtatccc    660
gaccgcatca tgaacacctt cagcgtcgtg ccctcaccca aggtgtcaga cacggtggtg    720
gagccctaca acgccacgct gtccatccac cagctggtgg agaacacgga tgagacctac    780
tgcatcgaca acgaggcgct ctacgacatc tgcttccgca ccctcaagct ggccacgccc    840
acctacgggg acctcaacca cctggtatcg gccaccatga gcggagtcac cacctccttg    900
cgcttcccgg gccagctcaa cgctgacctg cgcaagctgg ccgtcaacat ggtgcccttc    960
ccgcgcctgc acttcttcat gcccggcttc gcccccctca cagcccgggg cagccagcag   1020
taccgggccc tgaccgtgcc cgagctcacc cagcagatgt tcgatgccaa gaacatgatg   1080
gccgcctgcg acccgcgcca cggccgctac ctgacggtgg ccaccgtgtt ccggggccgc   1140
atgtccatga aggaggtgga cgagcagatg ctggccatcc agagcaagaa cagcagctac   1200
ttcgtggagt ggatccccaa caacgtgaag gtggccgtgt gtgacatccc gccccgcggc   1260
ctcaagatgt cctccacctt catcgggaac agcacggcca tccaggagct gttcaagcgc   1320
atctccgagc agttcacggc catgttccgg cgcaaggcct tcctgcactg gtacacgggc   1380
gagggcatgg acgagatgga gttcaccgag gccgagagca acatgaacga cctggtgtcc   1440
gagtaccagc agtaccagga cgccacggcc gaggaagagg gcgagatgta cgaagacgac   1500
gaggaggagt cggaggccca gggccccaag tgaagctgct cgcagctgga gtgagaggca   1560
ggtggcggcc ggggccgaag ccagcagtgt ctaaaccccc ggagccatct tgctgccgac   1620
accctgcttt cccctcgccc tagggctccc ttgccgccct cctgcagtat ttatggcctc   1680
gtcctcccca cctaggccac gtgtgagctg ctcctgtctc tgtcttattg cagctccagg   1740
cctgacgttt tacggttttg ttttttactg gtttgtgttt atattttcgg ggatacttaa   1800
taaatctatt gctgtcagat acccttaaaa aaaaaaaaaa aaaaaaaaaa a             1851
```

```
<210> SEQ ID NO 19
<211> LENGTH: 450
<212> TYPE: PRT
<213> ORGANISM: Homo sapiens

<400> SEQUENCE: 19

Met Arg Glu Ile Val His Ile Gln Ala Gly Gln Cys Gly Asn Gln Ile
1               5                   10                  15

Gly Ala Lys Phe Trp Glu Val Ile Ser Asp Glu His Gly Ile Asp Pro
            20                  25                  30

Ser Gly Asn Tyr Val Gly Asp Ser Asp Leu Gln Leu Glu Arg Ile Ser
        35                  40                  45

Val Tyr Tyr Asn Glu Ala Ser Ser His Lys Tyr Val Pro Arg Ala Ile
    50                  55                  60

Leu Val Asp Leu Glu Pro Gly Thr Met Asp Ser Val Arg Ser Gly Ala
65                  70                  75                  80

Phe Gly His Leu Phe Arg Pro Asp Asn Phe Ile Phe Gly Gln Ser Gly
                85                  90                  95
```

-continued

```
Ala Gly Asn Asn Trp Ala Lys Gly His Tyr Thr Glu Gly Ala Glu Leu
            100                 105                 110

Val Asp Ser Val Leu Asp Val Val Arg Lys Glu Cys Glu Asn Cys Asp
        115                 120                 125

Cys Leu Gln Gly Phe Gln Leu Thr His Ser Leu Gly Gly Gly Thr Gly
    130                 135                 140

Ser Gly Met Gly Thr Leu Leu Ile Ser Lys Val Arg Glu Glu Tyr Pro
145                 150                 155                 160

Asp Arg Ile Met Asn Thr Phe Ser Val Val Pro Ser Pro Lys Val Ser
                165                 170                 175

Asp Thr Val Val Glu Pro Tyr Asn Ala Thr Leu Ser Ile His Gln Leu
            180                 185                 190

Val Glu Asn Thr Asp Glu Thr Tyr Cys Ile Asp Asn Glu Ala Leu Tyr
        195                 200                 205

Asp Ile Cys Phe Arg Thr Leu Lys Leu Ala Thr Pro Thr Tyr Gly Asp
    210                 215                 220

Leu Asn His Leu Val Ser Ala Thr Met Ser Gly Val Thr Thr Ser Leu
225                 230                 235                 240

Arg Phe Pro Gly Gln Leu Asn Ala Asp Leu Arg Lys Leu Ala Val Asn
                245                 250                 255

Met Val Pro Phe Pro Arg Leu His Phe Phe Met Pro Gly Phe Ala Pro
            260                 265                 270

Leu Thr Ala Arg Gly Ser Gln Gln Tyr Arg Ala Leu Thr Val Pro Glu
        275                 280                 285

Leu Thr Gln Gln Met Phe Asp Ala Lys Asn Met Met Ala Ala Cys Asp
    290                 295                 300

Pro Arg His Gly Arg Tyr Leu Thr Val Ala Thr Val Phe Arg Gly Arg
305                 310                 315                 320

Met Ser Met Lys Glu Val Asp Glu Gln Met Leu Ala Ile Gln Ser Lys
                325                 330                 335

Asn Ser Ser Tyr Phe Val Glu Trp Ile Pro Asn Asn Val Lys Val Ala
            340                 345                 350

Val Cys Asp Ile Pro Pro Arg Gly Leu Lys Met Ser Ser Thr Phe Ile
        355                 360                 365

Gly Asn Ser Thr Ala Ile Gln Glu Leu Phe Lys Arg Ile Ser Glu Gln
    370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ala Glu Glu
            420                 425                 430

Glu Gly Glu Met Tyr Glu Asp Asp Glu Glu Glu Ser Glu Ala Gln Gly
        435                 440                 445

Pro Lys
    450
```

<210> SEQ ID NO 20
<211> LENGTH: 1794
<212> TYPE: DNA
<213> ORGANISM: Homo sapiens

<400> SEQUENCE: 20

```
gacatcagcc gatgcgaagg gcggggccgc ggctataaga gcgcgcggcc gcggtccccg      60
```

-continued

```
accctcagca gccagcccgg cccgcccgcg cccgtccgca gccgcccgcc agacgcgccc    120
agtatgaggg agatcgtgca catccaggcc ggccagtgcg gcaaccagat cggggccaag    180
ttctgggaag tcatcagtga tgagcatggc atcgacccca gcggcaacta cgtgggcgac    240
tcggacttgc agctggagcg gatcagcgtc tactacaacg aggcctcttc tcacaagtac    300
gtgcctcgag ccattctggt ggacctggaa cccggaacca tggacagtgt ccgctcaggg    360
gcctttggac atctcttcag gcctgacaat ttcatctttg gtcagagtgg ggccggcaac    420
aactgggcca agggtcacta cacggagggg gcggagctgg tggattcggt cctggatgtg    480
gtgcggaagg agtgtgaaaa ctgcgactgc ctgcagggct tccagctgac ccactcgctg    540
gggggcggca cgggctccgg catgggcacg ttgctcatca gcaaggtgcg tgaggagtat    600
cccgaccgca tcatgaacac cttcagcgtc gtgccctcac ccaaggtgtc agacacggtg    660
gtggagccct acaacgccac gctgtccatc caccagctgg tggagaacac ggatgagacc    720
tactgcatcg acaacgaggc gctctacgac atctgcttcc gcaccctcaa gctggccacg    780
cccacctacg gggacctcaa ccacctggta tcggccacca tgagcggagt caccacctcc    840
ttgcgcttcc cgggccagct caacgctgac ctgcgcaagc tggccgtcaa catggtgccc    900
ttcccgcgcc tgcacttctt catgcccggc ttcgcccccc tcacagcccg gggcagccag    960
cagtaccggg ccctgaccgt gcccgagctc acccagcaga tgttcgatgc caagaacatg   1020
atggccgcct gcgacccgcg ccacggccgc tacctgacgg tggccaccgt gttccggggc   1080
cgcatgtcca tgaaggaggt ggacgagcag atgctggcca tccagagcaa gaacagcagc   1140
tacttcgtgg agtggatccc caacaacgtg aaggtggccg tgtgtgacat cccgccccgc   1200
ggcctcaaga tgtcctccac cttcatcggg aacagcacgg ccatccagga gctgttcaag   1260
cgcatctccg agcagttcac ggccatgttc cggcgcaagg ccttcctgca ctggtacacg   1320
ggcgagggca tggacgagat ggagttcacc gaggccgaga gcaacatgaa cgacctggtg   1380
tccgagtacc agcagtacca ggacgccacg gccgaggaag agggcgagat gtacgaagac   1440
gacgaggagg agtcggaggc ccagggcccc aagtgaagct gctcgcagct ggagtgagag   1500
gcaggtggcg gccggggccg aagccagcag tgtctaaacc cccggagcca tcttgctgcc   1560
gacaccctgc tttcccctcg ccctagggct cccttgccgc cctcctgcag tatttatggc   1620
ctcgtcctcc ccacctaggc cacgtgtgag ctgctcctgt ctctgtctta ttgcagctcc   1680
aggcctgacg ttttacggtt ttgtttttta ctggtttgtg tttatatttt cggggatact   1740
taataaatct attgctgtca gataccctta aaaaaaaaaa aaaaaaaaaa aaaa         1794
```

<210> SEQ ID NO 21
<211> LENGTH: 170856
<212> TYPE: DNA
<213> ORGANISM: Homo sapiens

<400> SEQUENCE: 21

```
gagttagacc caggttcaag tccagctttg tccagtcatt accagctgac caatagcaaa     60
tcttatcact taatcactaa tgaggggaac aagcattcaa atatagtcat gtgtacataa    120
tgacatttct gtcaacaaca gacagcacaa cacattactg ttgtgtttgt ggtgatgctg    180
gtgtaatcat aaccttctgt gctgcagtcc agtaaaaata tagcacaggc cgggggcggt    240
ggctcacact tgtggagggc cacctccaca agttgcagtg agctgagatc gcaccactgc    300
actccagcct gggcaacaag agtgaaactc catctcaaaa aaataaaaca aacaaacaaa    360
caaacaaaca aacacttttt attgcctggg tgtggtggct cacgcctgta atcccagcac    420
```

-continued

```
tttgggaggc tgaggcagga ggattgcttg agcccaggaa ttttagacca gcctgggcaa    480
catggcgaaa ccctgtctct acaaaaaata caaaaattag ctgggcatgg tggtgcgccc    540
ctatagtccc agctactcag gaggctgaag tgggaagata acctgagccc agggaggtcg    600
ataataaaat tttaaaaatt tttagtagag atgggatttc accgtgttgg accaggctga    660
tctcgaactc ctggcctcag gtgatctgtg cacctcgacc tcccaaagtg ctgggattac    720
aagcgtgagc cactgtgccc agccaacata cttgtttatt atcaaatatt atatactgta    780
cataattgta tgttttatat atgtatgtat gtgtgtgtgt gtatatatat atatatatat    840
atatatattt tttttttttt tttagacaga gtcttgctct gtcacccagg ctggagtgca    900
acggcaccat cttagctcac tgcaacctct gcctcctggg ttcaaaccat tctcccgcct    960
cagcctccca agtagctgag attacaggca ctcgccatca tgccccacta attttttttg   1020
tatttttgta gagatggggt tccaccgtgt tggccaggct ggtctcgaac tcctgacctc   1080
aggtgatccg cctacctcag cctcccaaag tgctgggatt agaggcgtaa cccaccgtgc   1140
ctggccaata aaaagtttta aatacagaaa aaagcttaca gaataaggat ttaaagaaag   1200
aaagaatttt tgtacagctt ataatgtgtt tgtgttttaa gctgttatta caaaagccaa   1260
aaagtcaaag aattaaaaaa tatataaaat taaaaaatta cagtaagcta aggttaattt   1320
ctttttattt tttctttttt cttttttttt tttttttgag acggagtctc actctattgg   1380
caggttggag tgcagtggcg cgatctcggc tcactgtaac ctccacctcc cggattcaag   1440
caactctcct gcctcagcct tccgagtagc tgggactaca ggtgcgtgcc accccaccca   1500
gctagttttt gtattttcag tagagacagg gtttcaccac gttggccagg atggtcttga   1560
tctcttgacc tcgtgatcca cccgcctcag cctcctaaag tgctgggatt acaggggtga   1620
gccaccgtgc ccggcctcta aggttaattt cttattgcag aagaaaaaga ttaaaaaaat   1680
aaacttagta tagcctcagt gtacagtgtt tataaagtct acagtagtgc acagtaatgt   1740
cctaggcctt cacagtcacg taccactcac tcactgactc acccagagca aattccagtg   1800
ctgcaagctc cattcatggc aagtgcccat acaggtagac tatttttatc tttttattta   1860
tttatttagt tagttaattt ttgagatgga gtctctctct gtcttccagg ctggagcgca   1920
gtggtgcgat cttggctcac tgtaacctct gcctcctggg ttcaagcaat tctcctaccc   1980
aagcctcccg agtagctggg attacaggcg cctgccacca tgcctggcta atttttgtat   2040
ttttagtaga gaccgagttt tgccatgttg gtcaggctgg tctcgaactc ctgatctcaa   2100
gtgatccacc cgccttggcc tcccaaagag ctgggattac aggtgtgagc caccacgccc   2160
cgcccaattt tatcttttat atcgtatttt tattataccc ttttaatgtt tagattcaca   2220
aatacttatt gtaacaattg cctacagtat caatatagta acttgctgta caggtttgta   2280
gcccaggggc aacaggtgat cccctctaac ctggatgtgt ggtcgcctgt accatctagg   2340
tctgtgtgaa cacactctct ggtgttccta tcatgacaaa atcctctagc attcctgttg   2400
ttaagcaaca catgagtgta gttactgagt ccctattgtg agccagggcc gggtaatata   2460
ttctctcccc caggctgttg tgaccatttc cagtgagtca gttcatctgt ctgaacaaag   2520
cactctggca ttgattgtat gcaaataacc tgttacagaa tggttctacc cataaactgg   2580
ctggcctctt ttgagcaacc ctcaaagttg caagcccttg ccctctgtcc tggtcaacct   2640
ctcttcctca gaagcttgcc tgctctgaac tcctctccca aaccgggtta ggagcccctt   2700
ctctggtatc agggcaccct gtgcctctct tacagacttg cattatggtt ctaactgtgc   2760
```

-continued

```
tgtgtggcct gggcaagccg ctcaaccact cggttatttc ttcttttttt ttttttgaga   2820
cagagtttca ctgttattgc ccaggctgga gtgcaatctt ggctcaccac aacctctgcc   2880
tcctgggttc aagcgattct cctgcctcag cctcccaagt agctgggatt acaggcatgc   2940
gccaccacgc ccagctaatt ttttgtattt ttagtagagc tagggttttt tcatgttggt   3000
caggctggtc tcgaactcct gacctcaggt gatctgccca ccttggcctc ccaaggtgct   3060
gggattacag gtgtgagcca ctgcacccga cttgaaagaa attgctttgc actgtgcttg   3120
gcacagagga acagcaggtg ttcattcaat gcttgctgtt gtaattattc aggcttttat   3180
caacagaggg ctggcctgag actctgccat atctcagaac ctagcacaga acctggatga   3240
gtacagagta agtgctcaat gtatgctgtg gtaggcagag taatagcccc caaagacgtt   3300
cacatcctaa ctctcaggac ctgtgaacat tcccttaaat ggcaaagggg aattaaggtt   3360
gcaaacagga ttagggttct taatcggctg attttaaaat agggagatca tgttggacta   3420
accagctggc ccaatgtcat cttaagagtc cttaaaaggg ccaggtgtgg ggaggttgaa   3480
gctgcaggga gccgagattg agtcatagca ctccagtttg ggagacggag tgagacaaaa   3540
aaaaggctgg gcaaggtggc tcatgcctgt aatcccatca ctttgggagg cagaggctgg   3600
tggatcgctt gaggtcagga gttcaagacc agcctggcca acatggtgaa agcccgtctc   3660
tattaaaaat acaaaaatta gcggagcgtg gtggcgggtg cctgtaatcc cagccactca   3720
ggaggttgag gcaagagaat tgcttgaacc caggaggagg aggttgcagt gagccgagat   3780
tgcaccactg gactctagcc tgggcaacgg agtaagactc catcgcagga aaaaaaaaaa   3840
aaaggaagat gtgcctatgg agagaggact gtctgaggtc tgagagactc cacctgacat   3900
tgcaggcttg cttttctgtt tttttttttt tttttttttt ttttgagacg gagttttgct   3960
ctgtcgccca ggctggagtg caatggcacc atctcagctc actgtaacct ctgcctccca   4020
ggttcaagcg attctcctat ctcagccttc ccagtagctg ggattacagg tacgcgccac   4080
cacacctggc taatttttgt attttaagta gagatggggt tttaccatgt tggccaggct   4140
ggtctcgaac tcctgacctc aggtgatcca cccaccttgg cctcccaaag tgctgggatt   4200
acaggtgtga gccattgtgc ccagcccatt gcaggctttc acagagaaaa ggggcaggag   4260
tcaggcgcgc aggcagcttc tggaagttag aaaacacaag gaaacagatt cttccctaca   4320
gcctccagaa gggaatgcat cctgccaaca ctttgttttt agctcagcaa gacctgtgtg   4380
ggccatcgaa cctacagaac tgaaggataa tacatttgtg ggtgtgtgtt ttcaaagaca   4440
ctaagttttg gtaacttgtt acagcagtaa ctggaaacta agacatgcaa caagccttat   4500
tgttcatttt taccaccact actgggctgt tggttatggt ggaattacac ttttctcttc   4560
cattaggctg tgtgaactcc ttgaggttgt gcaatacgtt tgtctgattt actactggtt   4620
agcaggctct gagaagaatg gctggtacac aggcggagct caataaaagc ccttactgaa   4680
ttttattcaa tctatatgtg gatgaagacc tccgccccgc gcgcccctcc cgcaagtccc   4740
actgaggccc gacccattct gtccggctcc cagccccccgc gggtcccccc accccggggc   4800
tgaccgggtg attcaggcag ccctacatcc tgctggggtg gtgggcttcg agcgcgggtc   4860
ccaggacgca gtggggcgca gtgcctgcgg caggcggcag gaggcgagcg tggcccagga   4920
actcccgcgg gagggtcggg acggggcggg gcttgggggc ggggcggctc agcgcgcagg   4980
cgcggggcca ggcgcctcgc gcggccaggg gcgggcggcc gcagagcagc accggccgtg   5040
gctccggtag cagcaagttc gaaccccgct cccgctccgc ttcggttctc gctccttcgg   5100
cccttgggcc tccaaacacc agtccccggc agctcgttgc gcattgcgct ctccccgcca   5160
```

-continued

```
ccaggatgcc ggtaaccgag aaggatctag ctgaggacgc gccttggaag aagatccagc   5220
agaacacgtt cacacgctgg tgcaacgagc acctcaagtg cgtgaacaaa cgcatcggca   5280
acctgcagac cgacctgagc gacgggctgc ggctcatcgc gctgctcgag gtgctcagcc   5340
agaagcgcat gtaccgcaag taccatcagc ggcccacctt tcgccagatg cagctcgaga   5400
atgtgtccgt ggcgctcgag ttcctggacc gtgagagcat caagctcgtg tccatcggtg   5460
agttctctgg ccgggcccag gcgcccactg tggtgccgac ccgcccccgc gcgtgcaccc   5520
ctgcggaggg cgaggatttc ccgcagcgcg cccccacctc ggagataagg gggagtcgtc   5580
cccaggggtg ggttataggg ggcctagacc ccctccccgg tgtcttcccc tgggatggga   5640
cctgttgtga tcgctccccg ccatccgccc cagcagtgca cctttggctg gctaagggtt   5700
gagggtttgg gctggggtca caggaggaga ggtggagttg ttgcatttct ctacacctgg   5760
ggcgccccta tgggagctag gggactagaa accctcgttc gctgtccccg ggggcgggcc   5820
ctagggtcag atgctccgcg gagtgctctc cctgctgcgc ccaggttggt gctctcagag   5880
gcagctgaat gggcgttggc tcggaggccg ggccgtgaga cctgaggagg aaccgttctc   5940
tgcgcctggg gcctccctgc ccaggtggag acagagacct ggtaccttcc cctgccgtcg   6000
ctggaatggg tgtgggcccc gaggttgcaa gggtaggcgc gggtgtgtgt cctcgctctc   6060
tctgctccca gctcagctct ggccgcgcgc cgcaggttga acccactcct tgctgccgaa   6120
gttataattt agagatggtg gtggtaacag taattgctgt cttgtaggga gcccaactag   6180
cgtccactgt gtaccgtcag ccttctaagt tatctccgtc cctacgcatc ctgccatctg   6240
gggtgaggct agacccattt tacagataag gggtccgga gggttaattg acctgtccaa   6300
ggtcagcaag tagggcccag ctgagaactg aaggaagtgg gcaacagtta gaaggaggct   6360
ttgttttcct ctcctctccc aaacctacac cagggtcttc ctgaaaggag ggagggaatt   6420
ggtgtctctt gctggactgg gccttctggt ctggggagga agaataagga tgaagtctcc   6480
cttgtggtct gagatagttg gaggcttccc agagggccac aaggctactg atagtgtggg   6540
ctgtgatggt aggggctgtg atgtgtgtgt gcatgtgggc gtttgtgcag agaacgtgtg   6600
tacacacata gcatgtgtgt atagcatgtg catatgcaaa gagtttgcat gtacacggaa   6660
tgtatgcaga gaatgtgtat ccacctacac gtgtgtatgg gtgtgtgtat gtgtgtgtgt   6720
gtatgtgggt gggtgggtgt gggttggggc agaggagggt tctgggtctg gatctcttcc   6780
taaggagaac cagggactgg ccctggcctg tgatttgggt ctcttcctga ggaaaccagg   6840
tcactatagt gaccctagtg acaggaagaa agggagatgg gtgtggctgc caggactttc   6900
tccagtggaa aagggattcc ctctaggctg agcctcccct gggccttagg gcctcaccct   6960
tcccttcccc cacacctgtc ctggcaggta aggctgcttc ctgcttcctg ggcccagatg   7020
gcagccgcac cacccagctg atctccagca gccctccccc tccccaaggg tggcttccct   7080
gcagaagaat ctgcatggca cgctgttgtc ttctttctgg ggtccatctc ctgtactggg   7140
gagggagaac ctcagaatct cctggaattc tttaccattc agaaaccagc ctcccctctg   7200
aagaatccca aggcccagct gggctcaatt tggatctgtt ctttgtttta aaaatgtgta   7260
tttatttaat taactgaata aagaaactta aagtaaacca gaagtatcca aatacgacat   7320
gaaatctcta aaacaacaac aaaaccaaac caaaccgcag cactagcaaa tcacagactg   7380
cctgatctac ccactgttta cagaggcagc agctacttcc agcactgtct ctcatcagtg   7440
cccggggctg tgggtctcat tctagatttt gtctacattt ttttacatgg ttctcctgat   7500
```

tccctgctcc ccctccccac caccgccccg cctggagatg gagccttgct ctgtctccag 7560
gctggagtac aatggtgcca tctctgctca ctgcaacctc cacctcccgg gttcaagcga 7620
ttcttctgcc tcagcctcct gagtagctag aattacaggc acatgccacc acgcccggct 7680
aatttttgta ttcttagtag agatggggtt tcaccatgtt ggccaggctg gtctcgaact 7740
cttgacctca tgatatgccc gcctcggcct cccaagtgcg gggttacag ccctgagcca 7800
ccgcgcccag cccggtcctc cttttatttt cgaatccact caggccctag ctactcccat 7860
tgtcccgacg ttccagggtt agttagcttc ccttcctctg tgctgggcct gtgggctgtt 7920
ggcagcttct tcctgttcct accacaactt gcattctatt tttttccttt ttaatgattt 7980
cttggatcat attccccaga gtgacattcc tgggttaaag ggtgtgacca catttatgac 8040
ttgtatcatt ggctgcctaa ttgctctccc gagagatctt gcaacaaaca ggttttccag 8100
cctctggaga ccacagagag ccctggcaag tgccaggact gctgtgggga taaagcagga 8160
ggcttcttcc ctaagctctt gaggctgttg tgggtaatgg tccttcatcc ttcaaggcaa 8220
agttacctcc agcttggact aaggttcata tattcactgc ttaggttgtg ttacattgtg 8280
ctgacaatga cactagcttc aatttggggg cacctactgg gtgttaagtg tgttctgttg 8340
atcaccccat tgaattttca tgctaatcat tgattgacag caactactgc cctatctcta 8400
atgatctgct tctgcaagtc acttagagag ttcagggctt aacactgtcc tgggcatgtg 8460
ttgcttagaa aatggcgcct gttaattaaa taaggtgctg tctaataatt atctcaaaag 8520
taatgccagg gctggatgcc gtggctcacg cctgtaatcc cagcacttta ggaggccaag 8580
gtgggtggat cacctgaggt caggagttcg agaccagcct ggacaacatg gtgaaaccct 8640
agctctacta aaaatacaaa aattagctgg gcatggtggt gcacacctgt agtcccagct 8700
actcgggagg ctgaggcagg agaattgctt gaacccggga ggtggaggtt gcagtgagcc 8760
gaggtctttg tgtaactgca ctccagcctg ggagagcgag actctgactc aaaaaaaaaa 8820
aaaaaaaaaa aagtcatgcc cgaatggttt gcacaccgaa gggacgttca aaattagggg 8880
agaacagcct ggttgtttgt ttctgtttgg ttgatcatac tcttgccatg gttagtatta 8940
ttatctttat ttaaagatgg gaaacaggag tgaagccact tgtggaggtg acccagctag 9000
ctagtaaatg gtgtctgaaa cccaggtctg cccagctgtt gaattggagc cttaactgac 9060
ttgccttcca gtttcagaga tgagtaaaat acagcttttc tctccacatc agagggtccc 9120
tgcaacacta ggtttgcaag tcttaggtgt tagggtggtg gctggatacc cacactctga 9180
acctctgacc ttggacaaaa tagggatgtc agggccttcc atgattggca ggatgaatcc 9240
tctgggctgt gatgaaggtc tcacaagttg agagtcagcc gggaattaag tgggatcagt 9300
ttgcctcttg tgttttcctc attgtgtttt ggttggttgg ttgagatttc ctactaccca 9360
atggatgatg ttttattcca tcgtcaggga aggtatcatt gaatgaatac agggttttgt 9420
atgctttgga taagaccaga cagttgtgga gtcattagaa ttgtgtacat gcctccagct 9480
ctgagatagg tggtgtttca acagctgcca gaggactctg gcttttctgc ctagaattca 9540
ctgaaagaca accctggcta ttgattcaca tttgtggttc attgtaaggt aggcccctag 9600
gcgccatcca aaagttgaaa atttccttac gtttcttgtt atgtgatggg cagttcatag 9660
tgaggactca gtgtctttaa ttccagctgt ttgccaggag ttggcagttt tatttacttg 9720
tttttccaaa aacctttctg acatggggca gtccagccag ctgggaggaa aaggggtctc 9780
tcagcccaag aatgatgatc aaggcctaga agtttgggtg gtgtgttttg ttttgggcct 9840
ttagagaaag gaattgtttc cttttcagag gatgtggtct aaccctaaag tttacttgac 9900

```
tgacttaaac caggccagcg ccagagcagg cagggtgcgt gttcccaaga cttcgggtca   9960
ctaggcagct tccagggtgg tgggtcactg gtccagtcag ctccttttcc ttcctctccc  10020
ttttgtgcta ctactaccaa aataatttcc aaataacctt aagttctgct ctttcttgca  10080
tgtctagcag atgccagcat gtcttttggg tagtacagag agtgcttaaa aagtagcaaa  10140
gttggccgga cgtggtggct catgcctgta atcccagcac cctgggaggc caaggtgggt  10200
ggatcacctg aggtctggag tttgagacca gcctgaccaa catggagaaa ccccatctct  10260
actaaaaata caaaattaga tggccgtggt ggtgcatgcc tgtaatccca gctacgtggg  10320
aggctgaggc aggacaatag cttgaatcca agggcagagg ctgtgttgag ctgagatcat  10380
gccattgcac tccagcttgg gcaacaggag caaaactcca tctcaaaaaa aagtagcaaa  10440
gtagcatgct ttgtcagaat tattaataac aagttgtggg ccatgtacaa ggtggcacat  10500
tagcattcaa tgtcacttgt gtagtagtta agagcaagga ttcttggttc aaatcccact  10560
tgccactaag tagctattag aaacttctgt gccttggttt ccttatcact aaaatgggga  10620
taataactac cttcttaaaa ggctgttata aagattaaac aagttaataa tttttaaagt  10680
gcttggcaca gtttatggta catagtaagt gctctgtgaa tgcctgttaa ttaaataagg  10740
cactgtttaa taatctcaaa agtcatgccg gaaaggtttg cacactgaaa gggcatttga  10800
aatcagcgcg ctctggggag aacagcttgg ttggctaagg ttgatcctac ttgctaaaat  10860
acggctatgg actgcctaga gggtgtcacc tccttgaaag gggctgcccc ctgctatgtt  10920
atggctgcct ccagggccca ttcacaccag ctttgtttcc aagctggaca gggagctcca  10980
ggcgtctggt cattccagcc tcccacccct ttcaggaatc tctgggccaa atcacttcca  11040
gatggtggtt gggcctctgt ggagttctcc cagcaacggc ggagccagca tgccagtcgg  11100
cagccgcctt cgttcttgga gagtctgagc taaaggaggg ctttgatttg gagccaaatt  11160
gtgtctcttg ggtcctggtt ttgtgctgtg aggcaggtac catggagtgg gctgctggct  11220
tagttgagga tggctgccct gctccttagg ggagcagata cccagggcct ggagccttta  11280
ggccctgcct ccagtagctc catggtcagg gtgccagtca ccttgcgttt tctttttctt  11340
tttttttgag atggagtctt gctctgtcgc ccaggttgga gtgcagtggc gtgatctcgg  11400
ctcactgcaa cctctgtctc ccggggtcaa gcaattctcc tgcctcagcc tcctgagtag  11460
ctgggattac aggcgtgcgc cactatgtct ggctaatttt tgtattttta gtagagatgg  11520
ggtttcacct tgttggtcag gctggtctcg aactcccaac ctcgtgatcc acctgcctcg  11580
gcctcccaaa gtgctgggat tacaggcgtg agccaccgga cccagccaac tttgctacat  11640
cagtttccag gtagcatatc ctaggcaaaa ctggatgtag cctagtgatt cagggcctcg  11700
gtctgaagct agactgtctg gattctaatc cgcactctgc ctgataccag ctgtgcaact  11760
ctagtccact gctttaacct ttctgtgcct gcttccctgt ctataaaatg caagagcaaa  11820
atagttgcta tcttagagtt gctgggagca ttatatttga tgaggttaag ttatagcaca  11880
gtgttgtcat tatcactatg aatattgtgc ttttggaccc aagtccagga ctttgtcttg  11940
tcttctgtct attctctggc cagtccagat atttttggaa tcctattgct gtcatctggt  12000
gtgttagctg ttccctttct ccaagttcag aacgtctgat gaagatgtct cccaagatcc  12060
tttcttcctt tcctcattca acaaatatat gaaagcccat ctctgaacca ggccctgtgc  12120
tgggtgctag gacaacagga atgagaggat catgtccttt gcttgcctca gatactgctc  12180
agaggagaag agacaagcaa gcagggagag ccatgcagag gagagctgct caaaccttca  12240
```

-continued

```
ggcccatgct catcacctgg ggactttgtt aaaaatgcag gtctgattga gtaggtgctg  12300
gggtgtaggc tgggattctg cgtttccagt cagcttcaga tcctgctgtc tgtgcaccgt  12360
gctgtaagta gcaaggatct aggtgccaag ccctctgaaa aggaggagca cctgccccta  12420
ggctgggtat gggtaatcta gaaggttccc tggaggaagg gacctttcag ctaagaccta  12480
aagcgtgact agaattaggc aggcaaacag acatttacac aggagcagac gagtgtgtca  12540
gtttagaggt cttgatgctc aggtcagagg ggcagtggag gggtgggcag ggctggttta  12600
ccaagggctt tctgaaactg gaggctgcct atggggtatg ctccttgagt ttgtttgttt  12660
gttttttttt ttgagttgga gtttcaatct tgtttcctag gctggagtgc agtacagtgg  12720
catgatctcg gctcactgca gcctccatct cccgggttca agagattctc ctgcctgagc  12780
ctcccaagta gctggaatta taggcatgtg cacacctggc taattttgta tttttagtag  12840
atatggtgtt tcaccatgtt ggtcaggctg gcctcgaact cctgacctca ggtgatccac  12900
ccacctagcc tcccaaagtg ctgggattac aggcgtgagc cacggcatcc agccccttgt  12960
ttagtgtagg gtagtaaacc cagccaaaag gggtcgttta tctcaggggt ctcacctgtt  13020
gctccagtca ttcctattag cagaaagttt tgtatgtgcc ccttcctcat atatatatat  13080
atttatatat gtatttatat atatttataa gttataaaca tactctactg tcaatttgta  13140
tattaaatat tagtaaatct tagtttcttt ttagatgaca aatccaaata taaaatctgt  13200
tttttttcctg gctctaacgg attatcttat gtccccttgg ggtggacata cctcttttgg  13260
aggctcccgt gaaggtttgt gtttctacat ttagtttttt tcttttttcc atattcttgt  13320
tattctgctt ttaattttca tctttgagta ttctaaatta aggagctgga tctgtaattg  13380
taacaccttc ccccaacaat aagtttaact aatgaaaata ttcaatggaa tgagccattt  13440
taatctaaat ggggctattt cctgctttta taatgattac agttgctttt catgacattc  13500
tactagaagc catcttacat tactgttgta aatctagtta ttcattaaac gggcacagta  13560
atccctaaat tggctcaggt tattgtataa taaacaacaa tactttcttc ttcaggagct  13620
tgagaagtga tcttgtattt ttaaggtgcc taactaactt ttcatgggaa actgagtcca  13680
tgtactggga agaaagcttt ttggggaaaa tgattagaaa accaaatggg tctctttatg  13740
actgaagtga tgaaccagca ggtgagagta ggtatagatg gtacagagga cggaattact  13800
gggtatttta atcaggccca cttagtatca caatttatta ttctattcta tttttattat  13860
tattttttga gatggagttt cgctcttgtc atccaggctg gagtgcagtg gcgctatctc  13920
agctcactgc aacctccgcc tcccgggttc aagagattct cctgcctcag cctcccaagt  13980
agctgggatt acaggcatgc gccatcacac ctggataatt tttttgcatt tttagtagag  14040
atgaggtttc tccatgttgg tcaggctggt ctcgaactcc cgatctcagg tgatccgccc  14100
gctttggcct ctcaaagtgc tgggattgca ggtgtgagcc atcgcgcctg gccagtgtca  14160
ggatttattc tgtgggaggg gaggaggaca aagaaaaata ctgagctatg tttgaagctc  14220
ctgccctcta agagccttag agcagctgac ttaaatgtgt tcctttgata aactgtagat  14280
ggttgttgta actcttctgc aaactgttta tttttaaaaa caatttgatg agattttact  14340
tatgcccatt gtttgagtac agcatttacc aaagaacaat tttggccaga tcccatgcag  14400
tagaatgccc ttggccaaaa ttttcttgta ctataagcaa agaagcagtt tggtttttca  14460
cttaggcaag actgcctatc agactgagtt attgtgacag agccgctgac tctctccctt  14520
tccccattat caaaatctgg cttttctaag cagcgcatgt aaaaagcttg gcaaggagga  14580
cccttgtcct cctacatatt attctttggc tcttcttggt accaagaata catacaaata  14640
```

-continued atgctggctg tgtactgaat gttgaggtgt gcactgttga ggatattcat cctctaatat 14700
aacatctagt atttctcaca ccttccgtct gctgagcatt ggtctatctt acttatacta 14760
cttctaatcc tcgtgaactc tgcaaaacta gtggctttac atctatgaga aaagaaaaga 14820
acttttatcg gaagaaggtg agtcctttta aagtatcagg cctggaaaga cattaaatga 14880
gacagcgaac acatcctgct accctctttg agctatgtat tcattgactt tttttttttt 14940
tttttttttt ttttgaggca gagttttgct ttgtcaccag gctggagtgt agtggtgcaa 15000
tcttggctca ctgcaacctc tgcctccggg gttcaagtga ttctcatgcc acagcctcct 15060
gagtagctgg gattacaggc gcctgccacc ttgcctggct agttttggta tttttatttt 15120
tatttattta ttttaagaca gggtctcact ctgtcaccca ggctggagta cagtggcgcg 15180
atcttggctc actgcaacct ctgcctcccg ggttccagcg attctcctgc ctcaacctct 15240
ccagtagctg ggattacagg cgccttggca ccacagccag ttaatttttt gtatttttag 15300
tagaaacggg gtttcagcat gttggccagg ctggtctcga actcccaacc tcaggtaatc 15360
cgcctgcttt ggcctcccaa agtgctggga ttacgagtgt gagccattgt gccccgccta 15420
tgtattcatt tcttaaaatt ggttgctggc taggtgtggt ggtacatgcc tgtcctataa 15480
tcacagcact ttggaaggcc ggtgctggag gatctattga ggccaggagt ttaagaccag 15540
cctgggtgag atcacatctc tacaaaaaaa aaaaaaaaaa aaaaaattat ctggatgcag 15600
tggcacaagc ctacatagtt gtagctgctt gggaggctga gttgggagga tagcttgagc 15660
ccaggagttt gagtctgcag tgagctatga ttgcgtcact gcactctagc ctgggcgaca 15720
gagtgagacc cgtttctaaa acaaagaaat tgctattgtc acaattagtt ataaattaat 15780
ctaataatgc tgcacgcagt accataatcc acaccctata gcttaacgat ggatggccaa 15840
ccactaatca atgctatttc tgtacgccaa tgagaattcc tgacaaaaaa ctttgtatca 15900
gccccactcc ctgtctgtcc cctcttttgc ttttaaaaac ctgcttgtaa caaaggccaa 15960
acagagctca tatccaaggt tacttgggcc tgagtctttc aggcagctgt cttcactttg 16020
gctcaagtaa actctttaat agtttaaatt ttaagcctct gcctctttct tttaggttga 16080
catctgtttc cattttacag atgagaaaac tgaggctcag ctctgcctca ctttacaggt 16140
caggcttaat ccctaatccc tgcctgcatc atgctgtaaa ggacttttgt gtcaaaactg 16200
agtttcacac tctgtaaagt aaaatagata tattgtagtg agagggtgta gaagagactg 16260
ttttctgctt ctgtggattt tttttcttcc tgttttgctt tgctccaaac tttactcatt 16320
tgcgcttgat tcatgtgaaa ctgaaatttc cttctacaga acaaaacttt ttgggggcta 16380
cttaccatat cttttcccac accgtggagc tctgactggg accttttcca gtttttggag 16440
acattgctcc agttctttcc ctgcctttgg tttccagggg gcagtaatgt caccgcaggt 16500
gtggacagta gggaccagct aaaggttgct ttggaggagg tgggcagggc ttttgtttgt 16560
gaggtctaga aaccagaggt gaggaaggag gtgtccctgg aactccccct ggctgcaggg 16620
ctcacagcac acaccatgac accacagggg tgtgtgtgtg tgtgtgtgtg tgtgtgtgtg 16680
tgtgtgtgtg tgtgtgttga ggggagtgtt gttgagagcc aactatgcca ggagatcctt 16740
ggtgacagcg gacataggca cagctatgct ctgtcaggaa tgagttcacc cacacccttt 16800
tcttctgcta ccttgtttaa ctggtgggag ggtgtgctgg gttgtgtttg ctggtgagcc 16860
cagcaactgc acccttcttt ccaggcctag cacccagcct ttatcagtct catggccctg 16920
gcacaagtgg gcagcctgct tccaatccaa gcaggcagct ttccgctcat ctgcaggtag 16980

```
cctcgtgctg tggcagcaca aagttgtgtg agccagagct gaacttgtga tccccacggg  17040
catctcctga ggcgcacctc tcctgagaga gaaagctggt ccgtccagcc cattcagggc  17100
tcagcctccc cagccgtcgc agggctggct tgctgaaagg tctgggtgtt aacacagcac  17160
tcctgttctc tctctctgaa ggccctttat gctggcatga attccttttc tcatagagat  17220
ctgaaagctc ttttgactaa atgggtcacc tttctgagta ttttcataag gctgtcagcc  17280
tttaccatgc cagacaagtt ttctggaatt tcctttccag aaaaaaaaaa aaaaaaggct  17340
actaaagagg ttggagttat ttggaacaca gggtggaatt ctggcattcg aactataggg  17400
aaacgggtgg ggatttgtgg caggcactat gtaaatttgc cgcaagccca taaattcaga  17460
ctttaagatg aaagatggca agcagcagtc agctttcctt caacaggcag gaacggtgct  17520
accttccgcc tgtgctgagt gtgactgagg gagaggcagg cctcctaggg aggccggggc  17580
aggaaaggtt tcttggtggc taaaatagga tttctcagtt tcccccgtgt cccaagaaaa  17640
taagttctta tcatgcttgt accacacttc ttgtgcgtat caccctggtt tccctgcacc  17700
tccttgaagt ggtttatcag attccaggga cacaagaatg gtttggcatc tacagcctat  17760
tgtgggagca ggggcccggc ctggtgcttc ttgcccagga acaaactgat tgttcccttg  17820
gtgtggggta aagcaggcca gagtatggga ccaggccctg cctcccaggg gacctgaggt  17880
gcaaggtctt tgagctgaga ccctaaaagg cctttgtgag tctgtagtgc tatcagttga  17940
gcagagttca gggttctgtt tacaagattc cctctcagca gaggcaggga ggggtacctg  18000
ctggaagacc aggaatgtgc tgctgctggg atgggggccc tcggtggagc ttctagccat  18060
ctggaggcag aacccagaat gtgttctgag tgaggcgcct tggcagagtt ggcttgaaag  18120
cacctaggca gtggcttgtc acattcctta tctccaccaa aggaggcaag ctagcacctg  18180
ggggatggct ctcccatcag ggagtccttt acaggatgtg atccaggtgt cacattacac  18240
ttcctgcagg tgtgcacctc ttacctaatt gtctctccta tcccttttc tcagcactat  18300
tgtctgacat ccatggggag tcacacccaa agttgggcat gaggtcctct cctgggcacc  18360
caacaccttg ttttttttgtt tttgtttttt ttggagatag agtcttgctc tgtcacccag  18420
gctagagtgc agtggtgcca tcacagctcg ctgcagcctc gacctccttg gctcaagcga  18480
tcctcccacc tcagcctccc acgtagtcag aattacaggc acacacacca acactgctgg  18540
ctaattttgt attttttgta gattcggttt gctatgttgc ccaggctggt cttgaactcc  18600
tgggctcaag cgatctgcct gcctcagcct cccaaagtgt ggggattaca ggcatgagcc  18660
acctcacttg gccacactgc cctcttactg agccgtattg gtgttctaaa tggccttctt  18720
actctcccac gggtcatcag tgctccaggg gcaggcgctg tgtctcttgt ttacctctgt  18780
ggctctgacc ttggcactta ataggaattt aataaataac ttgttaaata aacagtctct  18840
agtataatag cttgagtatt aagactggta cattgactta tttgcaattc agaaaatgca  18900
aaacagtggt tctttgctgc ctttagtgaa gtgggaatta tatgtagtag acaactgggt  18960
ctggggtccc agtggaacac ttcgtttttg gactgtgatg ctgaacttaa agaactcagc  19020
agttcatgtt cattctctgg acatctgtga tttgcttcaa caactgttag agaacaaggc  19080
cttttccagg tgaagctcag aaaatgaatt taataggaaa ttactgaaag tcacaatcat  19140
agtaacagtt tcattagtta cagtgaatat agagagagcc catacaaagt accaggcatt  19200
gtgataaacg cttcttacta atagctatac aaaacatcat tgcaattctg agaagtagtt  19260
attgttgtaa ttcccgttat gcagatgaga aaactgaggc acacccagat tggccagtga  19320
gtgtgtggtt attactcaga ttcttgtctg agattttaat cttcatattt tactgctttc  19380
```

ccaaggaaag ccatcagctc agcaagtctt tgaaatttgc ttcttttttt tttttgaga 19440
cagagtcttg ctgtgtctcc caggctggag tacagtggcg caatcttggc tcactgcaac 19500
ctccgcctcc tgggttcaag cgattctctt gcctcagcct cccgagtagc tgggaatata 19560
gttgcatgcc accacacctg gctattttgt atttttagta gagacggggt ttcaccatgt 19620
tggccagcct ggtcctgaac tcctgatctc gagatccacc tgcctcggcc tcctaaagtg 19680
ctgggatcag gcttgagcca ccgaactcgg cctttttttt ttttttttt gaaatgatgt 19740
ctccttttgt tgcccaaact gcagtcttgg ctcactgcaa cttctgcctc ctgggttcaa 19800
gtgattctcc tgcctcagcc tcccgagtag ctgggactac aggcacgtgc caccatgccc 19860
agctaatttt tgtattttta tagagacagg ctaagcttgt cttgaactcc tgacctcaag 19920
tgatccacct acctggccct cccaaagtgc tgggattaca ggagtgagcc cctgtgccca 19980
gcctgaaatt caattctaat aaatttttat tggagcatta aaaagttaca tctgtagttg 20040
ttactctttg caaaaaattg caagaacaca gaaaaatata aagaaaaaaa tcacctgtga 20100
agaattttaa tgaatctttt tctactttta ggggatttg cttacagctg ccttttaatc 20160
agaataggga agaaagagat tcctttctca ggaaaaaagt gactgtggac tggaaatgct 20220
ttgtgaaata attttggtca tactgatggt tataacaaga ttcgtcttca attgagttat 20280
tgctgagctt tgtccaacat taaaatgaaa ggtctcattt gagtctcatt gtggtttgca 20340
agtctccctt ggtctagaaa tatgtttggt caaccacggc atggaggtgt tccagccact 20400
ttctgtctct taaaagtttt taggacctac ttttattggg actgccaggg tctcttaata 20460
atagttatta tacttggtaa ctattgtgac cttgtctcat aggcagccca gcatagaaac 20520
tcatttagct tttagttgct cagctccatt agctgtttaa acatgtttca gatgtgagcc 20580
tgacaatgta cttgggcagc ttggttcacc cttgactgcc tgggaacttt gagaagtctg 20640
aaaattatat gtagccctaa ggtcttcatg gtattgtttt tttggaggca ccatttccca 20700
atagccctga ggacaccagg cccatgaagc catcctgtct cagccaggag gcagaggaga 20760
tggaatggaa accacttctg gatacagatc cagccacttc cggagtgctt cagagcatgg 20820
gtcagataga ccttgctgct ttctagctgg cagacttggg gaaggttgtt tgacctctct 20880
gagtttgtgt cccagactat agcagtaccc ccttactggc gttatcgaag ataaaatgat 20940
ataatcctga taaatcactt gacccagtcc ttggaggtgg tggtgggggc tggggtaagt 21000
gccccatgaa tggtggtcat catgctcccc accaacctcc tttctctctt ctcctttccc 21060
gtctttcaca cccctaattc ctggacctgg gggtggtctc tccagactag atgaagaagc 21120
aatctaatta tctaggaagg tgaaaggtgg ttgggaatac tcccagaaat aggccaaaga 21180
taccgcctcc tacctaacag actcttttta gaagaagagg caacctgggt ttttggataa 21240
ctgttgagta ggaaccatca tgagtggcat ttctgcattt ctggtcttct ggccaagcct 21300
cctttttttt tttttttttt tttttttta accttgagac agtcttgctt tgttgccagg 21360
ctggattgca atggtgcagt cttggctcac tgcaacctcc atctcccagg ttcaagcgat 21420
tctcctgcct cagcctcctg agtagctggt actacaggtg ccgccactat gcccagctaa 21480
tttttgtatt tttagtaggg acggggtttc atcatattgg ccaggatggt ctcaatctct 21540
tgacctcata ctctgcccgc ctcggcctcc caaagtgcca gaattacaag cgtgagccac 21600
tgagcccagc cttccttttt tttttttttt tttaagtagc tccattgccc tccctcaccc 21660
tttcttttgt ctcctgtaat gtccttccct tccatttctt ttttttcttt tttcttttct 21720

-continued

```
tctttctttc tttcttttttt tttttttga gataggatct cattctgtgg caaaggctgg  21780
agtgtagtgg cacattcacg gctcattgca gcctcgacct ccaggactca ggtgatcctc  21840
acatctcagc ctcccgagta gctgggacca caggcacaca ccaccacacc cggctaattt  21900
ttgcattttt tgtagaggta gtgttttgcc atgtttccca ggctggtctt gagctcctgg  21960
gctcaagtga tactccctcc tcagcctccc aaattgctga gattacaggc ataagcctct  22020
gcacctggcc ttccctctca tttttttttc tttcctggtt ttgcctgtcc cagaccaccc  22080
tcttggaaag atgctctccc agcagcggca gtaaggtcct ggtcttgtgt ttgctcctgg  22140
gcctgagtct tggctttgct gctttgtagc tagctggctg acaccaggga gctgcttccc  22200
tccaggagcc tgtcgtccat atgctgaatg tgatccttaa atgctctgtc ttacaggggc  22260
cagacattgt ggctcatgca cttcaggggg ctgaggcgtg cagatcactt gaggccagga  22320
gtttgagacc agcctggcca acatggcgaa accctgtctc tactaaaaat acaaaaatta  22380
gccggaggtg gtagtgtgtg cctttaattc cagctacttg gaaggctgag gcaggaaaat  22440
cgctagaacc tgggaggcgg aggttgcagt gagccgagat catgccactg cactccagcc  22500
tgatcaacag agcgagattg tctcaaacaa acaaacaaaa aatgttctgc cttacagagt  22560
tcttaggtat aaaagagaag gtgcctctaa agctcttggc accgtgcctg gcttatagta  22620
agtgcttggt aaacgtcagc tgctgctgtt gtggtgttag tatcagcatt gttgctgtga  22680
gaccctgcac ttcccactta gccttggaaa aataagtctt cacgttaatg ccatgggcta  22740
ccgcttctct tttcagggct tcttggagga gggtggagat ggagagacag gtgggggact  22800
gccagggtta catcctccat gaggctgagg ctgtgctgac tgccttgtgt gctttcaacc  22860
tggagtaaag ggtggctgtg ccagctgctc ccatcccccca ggagtctgac tcgtccctgc  22920
cttggccctg ggcagcactt tccctcctag ctctttggca tctggggtca tggtggggct  22980
gcctgccatc tgtcaaaatt tttgctgccc tgggtgtggt ggtaaacccc cgcactatcc  23040
aacttggtgt catggagctg gcgacaatat ttttacagtg gttagtgctt ggaaactgga  23100
cttctgggtt atgccctgta caaacagcat caaagtcgct gggctagggt gacagaggag  23160
gctgccaaca gggaattctg tggctcctgg gacaggaatg gatatgggag gttgggggcc  23220
agtattttcg gttctcttga ggagttggcg agtattagtc tttgccctga tggatagaag  23280
gaatctgtct gtgtcttgca tgaaccgtgt acttcccccca gttactcctt ggacaccagc  23340
tgcctgctgt tcataattgg gccagatttc taatactgca gcgctaccaa atgtcagttt  23400
taggccatct ctggtgtagc cagggaacgc ccaacacctt tcccaaaggt agaatttgtg  23460
tgggttttac ttcactgagt gactaatgca gatctttatg ttttaatgat gggaagaaat  23520
tcgtcagcct gggtactttt tccatgtgat ggggcaaaaa tttaaaacac ttgcacaacg  23580
gcttttgttt ctccagctac taaaggtgac tgtcatttag gcattatcag tatgatcagc  23640
tgatgttaac ccactcccct tctggagacc cgtttctgtt tctgggaaag gtgtaggaca  23700
tgctggattt ggcaagattg caggtcccag gcagatgtcc ggacttagac tctggctctt  23760
tttttttttt ccagacaggg tctccctctg tcacccagtc tggagtgcag tggcgcgatc  23820
tcggctcacc acaacctccg cctcccaggt tcaagggatt ctcctgcctc agccccctga  23880
gtagctggga ttacaggcgt gcaccactat gcccagctaa ttcttttttt ttttttgaga  23940
tagaggctca ctgtcaccca ggttggagtg cggtggcccg gtccgcctgc ctcagcctcc  24000
caaagtgtta ggattacagg tgtgagccac cgtgcctggc ctcagctaac ttttgtattt  24060
ttagtatcaa cgaggtttca ccatgttggc caggctggct ttgaattcct ggcctcaatt  24120
```

gatctgccca cctcggcctc ccaaagtgct gggattacag gcatgagcca ccgcgcctgg 24180
cccagaccct ggctcttact cctaggtcta cctctaccat cactggggcc ctcgcctgaa 24240
ccttttgccc catctataaa atgggagaac tagactaggt ctgtgtcccc caagcttcaa 24300
tcatttgtaa aggaaccacc tttactattt tgccatatcc cacggctgtc tctatttcat 24360
ttttcactta atattatttt cccctgcagt tgactcactt gtaaaacaaa tgtatttgaa 24420
aaggagactt tgtgtcacta taataacgga aaaacagcgt cactaggtaa atggaaggta 24480
accataaata aaccccaaac agttattaaa ttccagccag cactgttgcc tgttcacaac 24540
atgaggcata ctctcttttg gttaaaaagg gaaattagca agagatggag aggtgttgaa 24600
ggtaacctag cactacattg agccttttcc ttgacctgct caggaggatt gagaaagaac 24660
taggagaact gggaagagaa taacgtcttt ttgtgatgca aagtgcctga gtgtgaccaa 24720
gagctcagag tagtaatgta tagatgcttt gtttggatac ttatgcagcc attaccatgt 24780
gccaggggtg tagaggggct aggagtatag aggggattgg gacttgttca ctgacttctg 24840
gttgcttgtg gtctagtagt ggggaggtgg tcatagaata ttgaatacaa acgaagatcg 24900
aacaggctgc aggggtttaa taggaaaatc acaggactaa attctgtcat gtgtacatgg 24960
ggtctacaaa taagagttgt ttagaatttt ttttaattta aatttcccat gaaatataaa 25020
tctatttcat tccagaatga ttctagagaa gctctaaata cattaaagtt gtgttggctg 25080
ggtgcagtgg ctcatgcctg taatcccagc actttgggag gctgaggctg gagaatcact 25140
tgtggccagg agtttgagac cagcctgggc aacatgggag accttatctc taccaaaaaa 25200
aatttttttt tcttttcttt tttttttttt tgagacaaag tttcgctctt gttgcccagg 25260
ctagagtgca atggcatgat ctcagctcac tgcaacctcc gcctccctgg ttcaagcaat 25320
tctcctgcct cagcctccca agtagctggg attacaggca tgtaccacca cacccagcta 25380
attttgtatt ttttttagtg gaggtgggat ttcaccatgt cgatcaggct ggtcttgaac 25440
tcctgacctc aggtgatcca cccatctcag tctcacaaag tgttgggatt acaggcgata 25500
gccactgcac ctggccaaaa acattttaat aaattagctg ggtatggtgg tatgtgcctg 25560
taatcctagc tacttgggag gctggggcag gaggatccct tgagcccagg aattccaagc 25620
tgcagtgaac tataatcagg tcactgcact gaagccggag tgacagagtg agaccttgtc 25680
tcttaaaata aatttgtgtc attgtttgtt gtttttatgg tgttatgaca atgatccatc 25740
ttaacccttt atgtagtggt aactaacttt ctcttttcct aaaagctgat ttgagtttta 25800
ggttctcttg gagtctgtga caattgtaaa tagataagat ataacaaaat ggcctgaaat 25860
actcttgcaa cactcatatt tccccccctca gattagcatg ttctatactc tctgcaaagc 25920
aagatataca ccagaattag gcctctaaaa agcctcatac tgctaatctc tgggaatgaa 25980
tggtgttctt tgggataatg ggatatgaag ctcagtctga tttttctgtt ctgctggtag 26040
cttagggccc cctttcttct gttgggtttt ttgggagaag ggaagttgtg attaagaatg 26100
agaattcttt tttttttttt ttgtctcaag agtcttgctc tgtcgcccag gctggagtgc 26160
aatggctcga tctcggctca ctgcagtctt cacctcctgg tgtcaagcga ttctcctgcc 26220
ttagcctcca agtagctggg aatacaggca cctgccacca tgcctggcta attttttgta 26280
tttttagtaa agatggggtt tcaccatgtt ggccaggctg gtctcgaact actgacccca 26340
tgatcccaac ccccccgacc tccccggcct cccaaagtgc tgggattata ggggggagcc 26400
actgcgtcca gccaagaatg agaatttggg agtcaggcac ctctgggatt gaatctggaa 26460
ttgactgagt gtacatgctt tctctgaggc ctccgtcctc actgctctca tctataaact 26520
gggaataatc atagtttcta tctgaaacag tgggtgtgaa gatttaacga gctaaattgt 26580
aaagtgcctg agacatggga agaagtcagg atgtgctaat gggtaatctt acacttcccc 26640
aatggaaagg gccaggttta tattactcta ggctggtagt aagcgaggca aaggagatat 26700
caggtttcag ctttgttaga acatgctaat ggcaccagga cactcagaag agatacagag 26760
tttgagacaa atggcaccat gagccctgag acattgtgta tggggtgaat cggatagcaa 26820
gaatagactt caaggaggga agtagggcag ttagaatcct ttcagctgca aggaactgaa 26880
aactggctca catagaagga aaatgattgg ctcatgtcag caagcctaga tgcagagcaa 26940
gttatgggtt tcagggatcc agcatctaaa tgatgtcatc aagaacccaa gtttttttggg 27000
tctctgctct gttggtttct ttcatcctaa agctggttct cctgtggttt accatagtag 27060
agttcctgtg agaactccac tctgaccaat caggccttcc cagagccagg gatggatgga 27120
gtcgcttctt ttgaggccca tgggtcctat ctggagggga tggatccaga ctcctatcag 27180
gaatctagga ggggccgggc acggtggctc atgcctgtaa tcccagcact tcataatgcc 27240
aaggtggaca gatcacttga ggccaggagt tccagatcag cctggccagt atggtgaaac 27300
cccatctcta ctaaaaatac aaaaattagc taggcgtggt agcaggcgcc tgttgtccca 27360
gctactcggg tggctgaggt gggaggatca cttgagcctg ggcacagagg ttgcggtgag 27420
gttgtggtga gctgtggttg cgctgctgcc ctccagcctg ggcaacagag tgagaccctg 27480
tctcaaaaac aacaacaaca aaatcttatg taccccataa atatatacac ctactgtgta 27540
tccacaaaag ttaaaaatta gaaaaggcaa attgcagaga tttccatatg ctatgatacc 27600
gtttatatga agttttacat atgtcataaa aatacagata acctttaggg gaatgatcat 27660
taccaaactt ttggataacg gtttctgggg atgggcagag agggctatac agtcatgaag 27720
aggtgtatag gggctttcaa ctctttgtag tgttttattt cttcagtccc atggtggtta 27780
tatgattctt cactcccctt tttttgtgtg gaatattttt cttataaaaa gtgtgtcttt 27840
tatttattta tttatctttt tcacatggag tctcactctg tcgcccaggc tggagtgcag 27900
tgttgcgatc tcggctcact gcaagctccg cctcccgggt tcgcgccatt ctcctgcctc 27960
agcctcccga gtagctggga ctacaggcgc ccgccaccac gcctggctaa tttttttgtat 28020
ttttagcaga gacggggttt cactgtgtta gccaggatgg tctcaatctg ctgaccttgt 28080
gatctgcctg cctcggcctc ccaaagtgct aggggattac agacgtgagc caccgtgccc 28140
tgcctttttt tttttttttt ttttttttta aaggcagagt cttgccctgt tggccaggct 28200
gcagtgcagt ggcctgataa tggctcactg cagcttccac ctcccaggct caagcaatcc 28260
tcccacctca gcctcctgag tagctgggac tacaggtatg tgccaccaag cctggctaat 28320
ttttccattt ttaaaggttt tgccatgttg cccaggctgg tctcgaaccc ctgggttcaa 28380
gccatcctcc caccttggcc tcccaaattg ctgggactat agacgtgaac cactgcaccc 28440
ccatccaaaa gtgtcatttt aatgctgaca tactgcatta ctaagcttga ccaggggaag 28500
agaaaaaaaa ataccttgtg tttattattt tgtttgtttg tttgtttgag acagggtctt 28560
gctctttctc ccaggctaga gtgcagtggc atgaacatgg ctcactgcag cctccacttc 28620
ccagggtcaa gccatcctcc cacttcagcc tcccaagtag ctgggattac aggtgtgtgc 28680
caccacacct gactaatttt tcttttttttc tttttttgta tttttggtag agacagggtt 28740
gcccaggctg gtcttgaact cctgagctca agcaatcctc tcttcagcct cccaaagtgc 28800
tgggattaca agtatgagcc actgtgcccg gcctgtttgt ttgttttaaa gacaagtttg 28860
ggcccagttt ataagaaaag aaaacagacc atccttaggg tgtcaggatg atattttgac 28920
aaaggcattc atgcttagca ggatttctct ccccctaccc ccacccccaag tgttgaaacg 28980
gctgagctaa ttaccttaga atgtaaggct tcctctgttg cttgtgaacg tggcagactt 29040
gggattctca gagacagagg gcttcagaag cttgcctctg ggagcgtcca gtcaatagct 29100
ttttgtctga gcagaaggag atattgctca aggtaccatc tcaagggact gctgaatcag 29160
ttgcattgtc tctaaaagta ggtaaaagtc tagagtaggg ctggttcaac agtggaatga 29220
gtgttaagag agagttgcat tctaagaaca cctttacact gtggccaaat tcaagcaggt 29280
ccattttgtg gtttggtggt ccccatctag tgggatgtgg tctggtatcc caggcacctg 29340
catatatgag ctcagatggg tttaattttt gaaaaactgc tttattggct gggtgtggta 29400
gctcatgcct gtaatcccaa cattttggga ggccaaggca ggaggatctc ttgagcctgg 29460
gaattcagga ccagcctggg caacattgag agatccccat ctctactccc ttccccgcca 29520
aaaaaaagct aggtgtagtg acatgcacct gtggtcccag ctactcagga ggctgaggtg 29580
ggaggattgc ttgagcccgg gaagtcaaga ctgcagtgag ctgagattgc atgactgcac 29640
tccagcctgg gcaaaagagt gagacattgt ctcaatctcc ccacccctgc caagaaaacc 29700
caaaaaatat tgaggtataa ttgttataca atgaagaaca cattttgatt agcttataca 29760
cacactcctg tgtacacatg tacactcaca catcaggaaa ccatcaccat aatcaagaca 29820
gcgaacctcc ctatccagcc ccagaagttt ccttgtgcct ctttgtaatt cttgcctttt 29880
atctctccat gtcttccaca cccatgctca agcattcact gatctgcttt ctgtcattat 29940
cagtcagttt tcatctttta gccttttata taaatggaat catatagtat gctgttttgt 30000
ttttttttga gacaagagtc tcactctgtt acccaggctg gagtgcagtg gtgcgacctc 30060
ggctcactac aacctccatc tccccagatt taagtgattc tcctgcccta gcttcccgag 30120
tagcagggat tacaggcaca tgctatcatg cctagctaat ttttgtattt ttagtaaaga 30180
tggggattca ccatgttggc caggctggtc ccgaactcct gacctcaggt gatcacccgc 30240
cttggcctcc caaagtgcta ggatcacagg catgagccac tacgccctgc cagtatgtac 30300
tctttttgtc tggcttcttc tagcatagtt attctgaaat tcatccttgt tgcatgtgtc 30360
aatagtccta ttccttttta ttgctgagta gtagtccatt gtatggatat actacatttt 30420
gtttatacat ccttctgttg ataacatttg ggtggtttct tatttattta tttatttttg 30480
agacggagtc tcactctgtt gaacaggctg gagtgcagtg gtgtgatctt ggctcactgc 30540
aacctccacc tcccgggttc aagcaattct cctgcctcag ccttctgagt agctgggatt 30600
acaggcattt gccaccacac ctggctaatt tttgtatttt tagtagagac ggggtttcac 30660
catgttggtc atgctggtct cgaactcctg accttaggcg atccgctcac ctctgcctcc 30720
caaagtgcag ggattatagg tgtgagccac cacgcctggc cgggtggttt ctaaataaag 30780
ctatcatgaa catcttttac tactctttgt atggatgtat atttctattt ttctgagtgg 30840
aatgttagga tcatacatca taggtgtacg tttaactgtt caagaaactg ccaaactgtt 30900
tcccaaagtg gttgtattgt tttacatttc cacgagcagt gtttgagagc tccagttctt 30960
gcacatccta gccacaaaaa ggttctgttt tttaaagaca attttttttt tttttgaga 31020
gtttcgccct agtcgcccag gctggagtgc agtggtaagc gaatccctgc tacaggccag 31080
agactgttct cagttggttt ttacaccaag tatcgcactt cattctaaca ctccaccatt 31140
ttacaaatga ggaaaccgag gcactgagag gtttagtaac ttgtggcaca gccaggaagc 31200

-continued agtagagaaa gactttgaat ataaatgtat ccattaggat gtatatggtt ccaagtcatg 31260
ggaaacctac ctaatcctgg tttatccaaa aagggagctc attggctctc gtaactgaaa 31320
agtcaagggg taggcaggca gttggacctg gaagtctcca gggcatcaga gagccttggc 31380
tctgcttctc tgattctgtt gtctctccac agacgggtgg gtgtagcagt cccaggcccg 31440
cagccacacc ccacacctcc cagaggaaga aggcgggccc tgatcccagc agtcccagga 31500
aagccctgag gttcactgtg attggaccag cctatgtcac ctgctcacat ctcagcccac 31560
cactggcaag ggtgtttgac tcttgggaat gactcttggg actggcttgt cctagatcac 31620
atgttctacc tgaaattggg gacattgcag aggattggtg gagtggacct caaggaggtg 31680
tttcacgtgg cttcctgtgt cactaggttg ccatttattc tttagaaagc ccctttgttt 31740
gatgaaaccc tggtgtcaca ggctgtgtga cttagggtaa tccccttgtc cacatctgtg 31800
aagtgagatt acctcttcac ctcacaggca gatcaaacag gaaaacaaaa acaaaaccaa 31860
acccaaaata cacgtaaatt gcagagtgct tgaggtttct tttaagctgt ctatgtaatt 31920
aaaagctgtt acttagactt ggatatgaaa taaaatctga cttcaaattt aagtggtgta 31980
atttccatgc ctcttaaaat atcaggtaac ttcatttgtg agcctcagtc tgtagacttg 32040
agggatttcc atctgaagag ggggcagaat ggtggtttag ggaacgcaac atgtacccca 32100
cccccaactt ttttaagagg aagagttgaa agaaataatg aatgtgtgag aaataagggg 32160
tttgattgcc ttccagggtc catgttgaag gagaggaaaa tgtagctcaa ccacagtgac 32220
tctccccaat taaaaactaa aaaaagatcc gtggttatag ggcttggact tcggacaagc 32280
cagcagcctc agtcattgtg agtgtgattc cagattggaa ggttctgcta ggaggaaagt 32340
ggaagttttg agaattccta gttggacaga atgcctcttg atcacggcct tagctaaagg 32400
agaccactct ttgctggatg gatcagtcag ctacgtgtga agtttggctc agtacaacat 32460
tctcggcctg gggcggcagc atgggaaaga tttttattgg aattaacttt ctacagagat 32520
gtactttcaa atgagaccat ccttctctca ctggtgagct cacccgggct cttattccac 32580
aaagcttaat tgttttggac ccatacattt aaactcctta attaattgac tcaagactta 32640
ggacagattt gcttttcttt ataatgactc catggctgta aatgctgctg attcagatga 32700
aagaggaccc tagagcacag aatgagaagg acgtggactc aggatacctg tttctttatt 32760
ctgactgtgc tcttcgtcag ctctggggct ttggacccca gttttgtaac cacctaacga 32820
gttcaccttg cctgctgcct agacggagct gatttatcaa gacagaggaa ttgcaatgga 32880
gaaagagtaa gtcacccaga gccagctgtg tgggaggcta gaattttatt gttactgaaa 32940
tcagtctccc gagcatttgg gatcagagtt tttaaagata attcggcagg taggggctca 33000
ggaagtgggg agtgctgatt ggtcaagttg gagatggagt cacagggggt cgaagtgacg 33060
ttttcttgct gtcttctgtt cctgggtggg atggcagaac tggttgagcc agattaccgc 33120
tctgggaggt gtcagctgat ccatggagtg cagggtctgc aaactatctc aagcactgat 33180
gttaagtttt acagtagtga tgttatctcc agaagcaatt tgtggaggtt cagactcttg 33240
cagtttctga cccctaaacc ttaatttcta atcttgtagc taatttgtta gtcctacaaa 33300
ggcagactgc tcccaaggca agaagagggt ctttttggga aagggctatt agcagttttt 33360
tttcagagtg aaaccataaa ctaaattcat tcccaaggtt agtttggcct atgcccagga 33420
atgaacaagg acagcctaaa ggttagaagc aagatggagt cggttaggtc tgacctcttt 33480
cactgtctat aatttttgca aaggcagttt cagtttctca cctgtaaacg ttgaagactg 33540
agccagaatc agggtcatca aatagcaccc cggctatact ttcttctctt catgacaaac 33600
attgctggtc agttgatatg atgttctttc ccactgggcc cagacttgac attagagtct 33660
ttttttttt ttttttttt tttttgagac agtctcgctc tatcaccctg gctggagtgc 33720
agtggcacca tctcagctca ctgcaacctc cgtctccaga gttcaagcaa ttctcctgcc 33780
tcagcctctc aggtagctgg gattacagga gtgcaccacc acacccagca gatttttgta 33840
tttttagtag agacggggtt tcgccatgtt ggccaggctt gtctggaact cctgacctca 33900
ggccatccgc tcgctttggc ctcccaaagt gctaggatta taggcgtaag ccaccacgcc 33960
tggccgacat cagagtcatt ttagcctgca atgcaagttg tcctcagtgg gctgctagca 34020
ttggcttcaa ccttcatatc agccagctaa agccccttgt aatgaatggg gaggttcctt 34080
caccccttgcc tcccgctgcc tcctcttgac cactcatttt ttttcttgta gttcaggaac 34140
caattcagat gatttccctc gtgaagtcct ctcgaaagcc cccaggtaga attattcatt 34200
ttttcccttg cattcccaca gcactgtgca cacaaattag aatccttgta aaatggccat 34260
gattctgttt atgaccctgg ccctccacca gaccagcctc tctgccctct ggctttttta 34320
gatcactggc atggtttctg cctactccag gtgccagtat tattttgtga atgttttttt 34380
tcttcatatc tactcatctt tatactactt tactcgtaaa aggaaactag agaacatgat 34440
cttaaatgaa aaccacgatc acttgccaga aagaacaggt aactaggctt tgaaaaaata 34500
agttagagga gatagcataa gaaaaaatta aaaaataaat aaaatcaatg aaaacaacgt 34560
gttactaaat tcttgaaaag ttttttgaag actttgagcc tgaggcctgt tcttattgtt 34620
tgtttgtttg tttgtttgtt tgtttttatg acagagtttc gctcttgttg cccaggctag 34680
agtgcaatgg catgatctcg gctcattgca gcatttgcct cctgtgttca agcgattctc 34740
ctgcctcagc ctcccgagta gctgggatta caggtgcccg ccaccatgcc cagctaattt 34800
ttgtatttta gtagagatgg gtttttgcca tgttggccag gctggtctcg aactcctgac 34860
ctcaggtgat ccacctgcct tggcctccca aagtgtgggg attacaggcg tgagccacca 34920
tgctcggcct gttcttattg ttaaaaagag agatttgtgt gaaagctgct gacgtctttt 34980
tggcaccaag tcaagactga gttagttctt gtcagaatct gattgtttgt gaattgatgg 35040
ctttttttt tttcctgagt tgggggtctc gctctgttgc ccaggctgga gtacgaccac 35100
tataacctca aattgctggg ctcaagcaat ccttccgcct cagctgccca agtagctggg 35160
actactaggc atgctccacc atgcccagtt aattaatttt ttttttttt tgagagacag 35220
ggtctcacta tgttccccag gctggtctca aattcctggc ctcaagtgat ctcctgcctc 35280
agcctcccaa agctctggga ttacaggagc gagccactgt gcctggccgg attttaaagt 35340
tctgcccatg cacctcctta gctctggcag ttactacttg caggcatctc ctttgtctgc 35400
cctgcccctt gttaggaaag gctgtgctga ctgtcagctg gcacccagtg catagaagag 35460
atagttctct gtagatgatg ttgaacaatg tggtactata atcccaacct gttgtatctt 35520
tgtttactct caaaagcaac aattgggctg ggcatggtgg ctcatgcctg taatcgcagc 35580
actttgggag gctaaggtgg gagggttgct tgaagttagt tcctttttt ttttttttt 35640
aaaaaaaaga caagatctcg ctctgtcacc ccggctggaa tgcagtggca tgatcatagc 35700
tcactgcagc cttgaccacg tgggctcaag gaatgaacca ttgtgccagg agttcaacac 35760
cagcctggat aacatagcga gaccctgtct ctacaggaaa aaaaaaaaaa aagaagaatt 35820
gcataagtat catcagaact gttgaatgga aaatcagact ttgtgggttt ggtttgttaa 35880
ttacttctcg ttggattaga atttgatagg taaaaaaaaa aaaaaaggtg tagaaaagtg 35940
attccagtct tgagcaaatt tttaatggaa aacggtgtct tggttctctg ttcactacaa 36000
cttgtatcta agggaaagcc tagtgatgca gacatttcat ttcgtgatgg gaaaactgat 36060
gcccagaggt tcacagctga ccaggggcta gtctgactgg ggggatctag gtcaccaccc 36120
cccttgcctt gttttcccag ctagtgcatt tcctactaga cttgactcta ctgtaattca 36180
agttgctgag tagcaaacaa gaactacaat gactagaagg aacagaacta gctttttttgt 36240 gctctgaaag tggaaactta ttgagggttc ttttcctccc agagaatgca gaagtgccct 36300
gatttgcttt tggaaggaca ccattcactt tattgcctct tttcattgtt gcccagaata 36360
tcaccatgat ttattcatgg gtggtgggga gggtagcact agtgtatgct cccagcaaag 36420
aggaacatct cacgttgtga agagatgcgc aaaactaagc cagggcaggg tgtggtggct 36480
catgcctgta atcccagcac tttgggaagc tgaggtgggc agatcacctg aggtcaagag 36540
ttgaagacca ccctggccaa catggtgaaa ctctgtctgt actaaaaata caaaaattag 36600
ctgggtctga ttgcaggtgc ctctaattgc agctacttgg gaggctgagg caggagaatt 36660
tcttgaacct gggaggcaga ggttgcagtg agctgagact gtgccgttgt actctagcct 36720
gggcaacaag agccatctca aaaaaagaag caagccagat ctttggggtg ctgtgacggc 36780
aaatccccca gcgctggcct ctcaggttct cttgcgggat tagtgtttgt tgaataataa 36840
gcaatacacc ctgacccagc gagccaaagc aaacaggaca gtaactgaaa ctgcagggga 36900
gtgtgagtaa acagttacct tctaccctca tggagctggc ctctggccag caacatgata 36960
gctgtttgca tcttactctt atggagccat tggccctctc attaaggtgg gggcagcttc 37020
tggtccatgc ctgcaagtcc tcatgggagt gggtacctga cagggtgtaa agggtaggtc 37080
tgaggacatg gtttcttttt tttattgttg ttgagatgga atcctgctct tgtcacacag 37140
tctggagtgc agtggcctga tctcggctca ctgcaacctc cgtctcactg gttcaagcga 37200
ttctcctgcc taagcctcct gagtagctgg gactataggc gcatcctgcc atgcctggct 37260
aagttttgta tttttagtag agacggggtt tcaccacgtt ggccaggctg gtctcgaact 37320
cctgacctca ggtgatccac ccacctcagc ctcccaaagt gctgggatta caggcgtgag 37380
ccaccgtccc cagccaacat ggtttcttta aaatatactc cccgctccat cccattcatg 37440
tgtgggagtt gagctgcatc tgggtttttc ttttctcttt ttctgtaaat ctttattgta 37500 tttttttgg atcatagaat ggatacatgt ttcttaaagt ttgatcatta tagaaactta 37560
attagactat tatttgagtg ctaaccatag tgagtgagtg cttactgtgt gctaggtggc 37620
tttttatgcc tcatgtcact tacatgaggt ctgaggaacg gtgttaatcc cgttttgcag 37680
ctgaggaaac tgaggctaca tttacggtca cctagctggc aagcaagtgg ctgagcctgg 37740
agcagcagca gatctgggga actccacaaa ccagatttct gtgtggtatc cctgtggaca 37800
caaggattta acttgattct ttttgctttc agtatcactt tatgatatta caatgagctt 37860
gcagtattta ttttcagaag aaaagccaga ttattcccat ttatgagaga agcagccagg 37920
tgggcaggga tttccagcgc tgaaccagcc agtgtgtgca ttgtctcttc ccgctgagcg 37980
gccctggtgt gctgggttag tctgtgagcc acaggaaatg ttgtcagggc ctctgggctt 38040
ttggatgtca gcaggccttc agtggtgagg aggttgtggc tggactcaga ggactccttg 38100
cttttgctga acgaccctcc ccaccaacca ccaccaccac caccagtggg actagcccat 38160
gagctgtaag ccaacctttt ccttcctaac ttaattttcc aaagaatagt aacttaccca 38220
ccaccactgc agtcactggg ccgggaagac aagcactctt gccttgaatc catgccttga 38280
gccagtagcc ttgacccagg gtaaagcagt tatgtgcttg ggtcacctgg gtcatgtttt 38340

-continued

```
tgaaattgcc tcaagcctac cttacaaatc cttcctggaa ccctgcttgg cttttctttg  38400
tgggcttccc ttaggaggga agcttcccga gcagcttgtc ttgactgtag ccagctgggt  38460
ggtcccagcc acagaattta actgtcaaac agcaccagaa gggttcctca tccagctgtc  38520
ttgccccaag tgccctcttt gctttctttt tagagagttc tgagactcat tagagagttt  38580
agagatttta gcattcttga agttctttct gtggtcagtt tggtgaacca cttcatttct  38640
aaagtttctc agttgacccc attcttcccc agctttgcat tctccatgaa gccacctgtg  38700
tttggtgtgt atgggttttc tgcaacctag gttgaacaag tcctctagaa tcctgaacaa  38760
ttggtgattc atgctggcct ggtttttcta attggcctgg aaatgtggct gtagtggaca  38820
caagtggact tggcctcctc tttgatgcgg gtaaacttta gatttgcatt agctctgttt  38880
gattagagga tcttactggt tttgttgtt atttatttac cttttaggag ctttagtctc  38940
tgtaggtttt tttttttttt tttttaaagt ccgggtctta ctctgtcacc caggctaggg  39000
tgcagtggca tgatcacagc tcactgcagc ccccaccttc ctgggctcag gtgatcctgc  39060
caccttagtt tcctgagtag ctgggactac aggcatgtgc caccatgccc agcaaattta  39120
tttctacttt ttgaaaacag ggtctcactt tgtcacccag gccagaatgc agtagcacga  39180
tcatggctca ctgcagtctc aacctcccag gcttaaggga ttctcccacc tcagcctccc  39240
aagtagctgg gaggctactt ggcatgcatc acaaggccca gctaatttgt gtttttttctt  39300
gtagaggcgg ggtttgcca tgttgcccag gctggtctcg aactcctggg gtcaagttat  39360
actctctcct ttgcctccag ccatgagccg ttcgttgcgc ctgggctagt cattatagat  39420
ttatcccttc tttcatctca tgctacaaaa gcagttcttg tatttttacc cgacttgtga  39480
ttttctactg ggaatgtttg tttgtgatgg ttagcagggt gctgagaggg aattaatccc  39540
aggaggccca atattgggcc atgtcgtgct gttgagcaca gtcatttgac acctataact  39600
tctcatcaat tcttctgata gactgaggag gaattgggaa atttcctaga gttttgtctg  39660
cattattggg ttgttttgag aacataaacc ttaaactcta gctatgtaaa ctggataagt  39720
cattttggta atttggcatt cctttttttt tttttttttt tttttgagac agagtttcac  39780
tctgttgccc gggggaatga tctctgctca ctgcaacctc tgcctcccag gttcaagcaa  39840
ttcttctgcc tcagcctccc aagtagttgg gactacaggc acactccacc gtgtccggct  39900
aatttttgta tttttaatag agacaggatt tcatcatgtt gaccaggctg gtaatttggc  39960
attcttttga gtacaagtga gagaaactca cttgagctgg cttaagtgaa aaaattcttt  40020
gtcaggagag ttttgtgaat ttctgtttag tggcaagttg tagaaaccac ttgaaactgc  40080
ttaaaggcaa aagagggagc cacttgtccc agtaactgag acatcccaga gccgactgcc  40140
cccaagcatt acttggtccc aagtttcaaa cgggtcttca gggtttgatc tctctcctca  40200
tctccagtct gcttcattca ttttggctct atgtggtggc agaagggctt ctggcatctc  40260
tggaccttta tgcctcccag gtccaaaccc agccagaaag gagagtgaga gtgctgagtg  40320
caaaactctc ctatagctcc tatacaagtc caggatttgc tattagactc cttgaattat  40380
gtgcccagct ctgagccaat ggctgtgctt aggaggctcc tgtctcatgc acccacccca  40440
gtactgggca tcagaaacaa ccagtgatcc ctataatgaa ccacgggttc acagacttaa  40500
gtgtaatcct gcagcagggc ctcaggaaga cttgaaaccc aaaatcagaa agccatggtt  40560
tcttgtcttc ctggtgtctg ttttgtccct tccctctgta gaggagtcct gctatcactg  40620
caggcaacgg ggctgccctg cagctcctgc tgtttacatt tcactcggtg tagccatagg  40680
```

-continued

```
cagagacctc agggagaacc tgattcggct tggattgagt caggttccac cccagtccag  40740
tcagttgtgg actgagaggt gatgaggctg ggccctttaa gacaaatctg ggtgggtgga  40800
gtctgtgctt aatgaagttg tgatgttagc tgatggccca gaagggactg gtaggtgcct  40860
ctcattgtct ggttgggaag cattctctta agtccaagat gatgataaat agtattaggc  40920
caggtgccgt gtcatgcctc tatacccagc actttgagag gccaaggtgg gaggatcgct  40980
tgagcccaga agttcaaagc cagagtgggc aacataaaga gaccctgtct ctacaaaaaa  41040
caaacaaaca aacaaaccaa aaaaacccca caacaattag ccaggcatga tggcgcacac  41100
cagtagtccc agctactcag gaggctgagg tgggaggatt gcttgagcct ggcgggtcga  41160
ggttgcagca agctgtgatc acacctctgc gctccagcct gggtgacaga gtgagaccct  41220
gtctcaaaaa gtaaaaaatt caaataaata aacaaataat atcaagggcc tctctcccaa  41280
gctaggaaga tatcagctga agctctagcc cagctacgtg gatggctgct tcctgcctgg  41340
aagcgatgcc cagatcagca ccttgggacc cccctgaact tgcctctgct ccagtgtggg  41400
cccttccttc ctgcagagga gacagcactg tctgagaggc atgaatgaga atttcctcct  41460
tctaggccca agtcagcatg actcgaggat ggctttgact ggaaaaactg aatcaaagag  41520
tgtgctacag ccaaggattt ccccaaacac taatcagtgc tgattacttc cagggtattg  41580
cctttggctc tgtggagttt tgtccactgt ggctgcaatg tctggcttct gctgcccaga  41640
agatgagaaa tgagtttgta gggatgagcc tgggtgaagg gatgtgcccc ctcaccatcc  41700
tgacctctat taggtgtaaa agaccctgat tgccaaattc ataggtcatg ggttggctct  41760
gcctccagca ttaacacttg gggtggagt tggggaatca tagtattact tgcataaatg  41820
gaatcctaaa agtttgttgg gacagtttca taaaaatcct caccatgatc agtttgaaaa  41880
tgacgttccc ttcacatgtt tgtcttctga actgagttgc aatgctgagt atgagtttga  41940
gagtcccaag accatctaaa gcaagcctgt ccaacccaca gactgcaggc tgtaggcagc  42000
ccaggacagc tctgaatgcg ccccaacaca aattcgtaaa ctttcttaaa acattatgag  42060
atcctttcgc atttgttttt taaagctcat cagctatcat tagtgttagt gtatcttatg  42120
tggccaagac aattcttctt cttccagtgt ggcccaggga agccaagaga ttggacaccc  42180
ccgatttaaa ggaagtaact caattttgtg aacctgaaac ttgatcttgg atgaaccaaa  42240
tgaaatttta tgattctctt aagctcacga aagttcaata actgtgctgt gtaaaataga  42300
ggtaaaagac ttgagttgga ccaggaatgg ttgctcatgc ctgtaatccc agcactctgg  42360
gaggctgagg cgggtgcatc acttgaagtc aggagttcaa gaccagcccg gccaacatgg  42420
tgaaaccctg tttctactaa aaatataaaa attagccggg cgtggtagtg tacgcctgta  42480
gtcttagctt cttgggaggc tgaggcagga taatcccttg aacccaggag gtggaggttg  42540
cagtgagcaa gatcatacca ctgcactaca gcctgggcta cagagcgaga ctccgtctcc  42600
aaaaaaaaaa aaaaaaaaaa aaaaagactt gagttggttc taatagaata ccttggagaa  42660
cctcaagatg ccttctggtc cagccaggtt tacagattgg aagatattct gttaatcaga  42720
atctcagaga gggacaggcc ctgatcaagg taacacagtg agttgtggta gctgggctgg  42780
gctagaacct gggcctcctt ggttccaggt cacagggacc aagggatttg gcttgtctta  42840
gtcctacttg taactacaat actgccttct gctaggaaga ataagagctt gcaggctaga  42900
ggaatttata ggaattttct ttctttaaaa aaatcccccc aaaaccagct ttactgagat  42960
ataactcaca caccataaaa ttcacccttt taaagtatgc aatttttagt atattcacag  43020
aattatgcaa ctatcatcac tataatttta gaattgtttt tttttttttg gagacggagt  43080
```

cttactcttg cccaggctgg agtgcagtgg tgcagtcttg gctcactgca acctccatct 43140
cccaggttca agcgattctc cttcctcagc cttccgagta gctgggatta taggtgcatg 43200
ccaccacacc caactaattt ttgtattttt agtagacatg ggtttcacc attttggtca 43260
ggctggtctc aaactccgcc tgccttggcc tcccaaagtg ttgggattac aggtgtgagc 43320
cactgtgcct ggccaatttt agaatatttt tattgcctca gaagaacccc tgtatccatt 43380
agcagtcact ctccctttcc cttccccaac caggcccaat aaaccactaa tctactctgt 43440
ctctatggat ctgtccattc agaacatttc atatggtaaa atcatacacg tgttctggtg 43500
ttactgactt ctttcactta gcagaatgtt ttcaaggttc agccatgtta tgtctgtact 43560
ttattctttt ttacggccaa gtgttggaat gtgtaggatt tgaattttca aataaagctt 43620
taaagttttc agatttattt ttactttgcc tggtgtgttt tttcctggaa agccaacttc 43680
tacatttgga gattaaaaga caaactttct caaactccct gtacctaagt ggttgctgct 43740
tttcttaaat gttttgacac caaagagaaa aattggtttc tggaagaaag tgtgtttttct 43800
tttattgcca agaaaattag tgcatgttaa ttaatataga tgctcaggac ccagagttgt 43860
aatgaacttt tttcttatat ttattttcta gatgtttgac ttattttaac agttttcatt 43920
ttagcaataa tgtttccttc ccactcccaa atttattgga aaccctcaat caaccctatt 43980
tatttattta ttttagagat gggatctcac tatgttgtcc aggctggtct ggaaaccctc 44040
actcttatag atagtatgaa agaagattat agccaactct tatataacct tccccagagc 44100
ctccaattgt taatgttttg ccatatttgc ttgctctatc acttgctcta aagatgcata 44160
tcacacactt tttttttttt taatttattt ttgagacaga gtctggctct gtcgcccagg 44220
ctgtagtgca gtggcatgat cttggcttac tgcatcctct gcctcctggg ttcaagcgat 44280
tctcctgcct tagtctcctg agtagctggg attacaggca cgggccacca tgcccagcta 44340
atttttgtat ttttagtaga gatggggttg gccaagctgg tcgtgaacta ttgacctcaa 44400
gtgatcctcc tgcctcagcc tcccaaagtg ctaggattac aggagtgagc caccatgcct 44460
ggccacatgc gtgtttttta ttgaatcatt tgaaagtact cagctcgtat catgaccctt 44520
cacccccaca tactccaaca agcatctcta agaaaaagga cattctccta accacagtgt 44580
ctctgcattc ccaggacatt cttctaacca cagcgtcact gcatacccaa gaggttagca 44640
ccgatacagt aataacatct tgtgtaaaac ttcccaaaat gctcccaagt gtcctttatg 44700
acagtttaaa aaaaaatggc attttttggg atccaggaac caattaacga ttactcaatt 44760
gaatttggtt tcaaagtcac atacctcaac ttttccttta atcaagaaca gcccccctgc 44820
cttttacaca tttttttgtc tttcgtgacc gtgtcatttt tgaagaaatc aggcccgttg 44880
tcttgtagaa ctggtgtttc tcaagtgtgc ttgggagggt cttggtaaaa tgcacattct 44940
gattctggag aacagggtgg agcctgggaa tctgcatttc cagccagcat cccggtgatg 45000
ccagtgcagc tggtcttcgg ctgtagaatg ttccacattc taggtctgtc tgtttccttg 45060
tgattaaatt caagttgaat atttttggct agggcacttc ctgaggtcat aggtacttcc 45120
cactgcctca cagcacaggc tcacaatctc agtttgtcct gttacttcgt ggtgctaagt 45180
gtggtcacct gcttcaagtg gtgtccgcct gctctctgtt gaaacaatac ctttctccta 45240
gtataatgat taggtaacct gtgattgtaa ttggtaagta atctttgaga ctacatgaat 45300
atcctgttcc ccagcagttt tcactcattg gtgaactgtt ttgggaaaaa taatagcatc 45360
ttacagttat aataccctgc tggtaacaca tggctcttac ataatcagca gttaattgtt 45420

```
tgtatgtgtg ttaattttta tttttaaaat gtaactagtg actggtaact ctcatttgta  45480
ttttaaacat tggcttttac agcttctcag tacatttcac tctgtgtatg tttttggtag  45540
agcatttgtt gtcctgtata atggtttagg aaatcctata ggccaaatga agggctggag  45600
actcacctgt gttcccacca ctgtgtttca ctgtgtattg ccagagaaaa tacagttaaa  45660
tttgaatttc agatagacaa tgaataactt tttagtataa gtatgttcca agtgtggcag  45720
acagctctca caagttacaa gtcgttgcgt aggacatacc tatgctaaac gatttgatgt  45780
ttatctaaat taatatgtaa ctgatatctt gtatttttat ttgtacgatc ttccaagccc  45840
acgtcccacc gccttctcgg ggatggccac catttgtgtt tgctgcctgg tggtgtttgc  45900
agctgcgaga agggccttgg aggaggagca aagtgtagtg gtatctccgt gctgtggcct  45960
tgggcactgg ggtgggggtt agatgagtaa ttagctgaat atgacctcac ccatgaagaa  46020
tgtgcccttg ctaggtatta gcagaggttt aggctccagg gagccattgt cagaagcttg  46080
tcagtgatgt catcagctgg aagggccagc tttcaggcct caggaaaaag cttgaaagtc  46140
agggctccag ttttggtaat aaatgggaat ggagtttcac aggtagggtg tggaggaatt  46200
tattgtgaca ggaagcctga tggagcctct tgcctgtgtg cagcccccag ccaggtttct  46260
gagttctgat gaactaccag aaacttccac cacggcctgt gattacactg ttggcccaat  46320
gccctggaaa aattggcttg ctctcgggga acactccagg agctgcaaag gggggtgtcag  46380
gactgttgtg cagctcccct taaattgggg aggaggggtg gctgatgtgg aaactgttca  46440
ttagactgct cagggtagtg tgagaaaacg tgtaatctgt gggcatctac ccctagctgc  46500
ccctctgatc tcacccacta ctgtgggagg accccgtgga tgggggcaga ggagggtctt  46560
ctggatttag acactcacaa aacttccttt taccttgttc attggaagaa atagaaaatg  46620
cctttttttt tttttttttc tttttttttg agacagagtc tcgctctgtt gacaggctgg  46680
agtgcagtgg catgatcttg gctcaccgca acctctgcct cccgggttct aacaattctc  46740
ctgcctcagc ctctggagta gctgggacta cagccacgtg ccaccacacc cagctaattt  46800
ttgtattttt agtacagacg gggtttcacc atgttggcca ggacggtctt gagctcttga  46860
cctcgttatc cacccgcctc ggcctcccaa agtgctggga ttacaggcgt gagccaccat  46920
gcctggtctc tttttcattt ttaaagggta atttgctgtg caggagtggg ctctcagacc  46980
agaagtgggg acctgaatga aatcaaggac tgagtatggt aactacagcc atttaatttt  47040
atttgaagtc tcccgtaaaa tgttctggaa aaaacagggg ttccagggct gggtgggcag  47100
tttcaatcat ggactggatt ttgtggttca gatttctctg ggcctgttgg aggttcccct  47160
taagcaatta cccaaggcag ttctgcccag ctgaagtact gattacctgc acactatacc  47220
agtgaggact catgggtgag cagatgggag gcactgagct tgattctgaa accctggcct  47280
ccatcccacc tgacattcaa tgtcagatta gaatttggaa gaccctaagt ctccagattg  47340
gtgcactggg tagctcctga aatggggtgg ctgagacagg tcctctgtgc cccctttccac  47400
agcttcctct ggggcccttc tgctcactgg catgtgcttc tgggcaaata ggcctctccc  47460
agcatttgtt ttggctctgt gaaatggggt aatatttgtt cctattgcgg gtgaagcgct  47520
gctgttggga tgctcaggta actcactccg tgggtagctg atattgcctg ggcaagtggc  47580
attttagagg aaatctgtgc catcaaaaga gttggacctg atcacacttt tgcttttgaa  47640
tatgctttgt cccagcctgg ccattcgtca cttgggaccc cctgagtctc tctgacccca  47700
ctgtaaaatg gatatgccat ggagttgtcc caggaatcaa gggcaggtcc tctccagtga  47760
gtgatgggct tgcctctcac ttctctaaca cccttctgct tccttgtgta agatttcact  47820
```

attagtggct attctctttt acagaagaaa aagggagacg catgcctctt ccagttcact 47880
gttcaccatt gcagcatatt tattccaagg gactggccga atcatccctt tctttgttag 47940
aatgtggttt tgttgccttg agacaagtgg cccgcatgtc tgcactgaag gaggctttgc 48000
gcaatagcct tgggcacctc cggttctgca agcatgtaca gtacttgctc tcctttccct 48060
ttctttgtat actttttctg gtctgctacg tgtccatctg catgtggata aagggtcgtc 48120
gtcttgagta gtgattttgc tgtgatgtga ttcctgtgag gtctagttgc acacagtgat 48180
tccgaaggta gacccagctg gaaagctttt aaattgctga tactccagcc ccactcccca 48240
agagatgctg attttgtttt gttttgggga gggcagtttt tttgggtttt ttttttaagc 48300
tttttgatgt gtagccaggg ttgagactga agtgattttt gtgagtaacg gagaagtgtt 48360
aaggcttgag aagttggaag agccatgctt gagataggac caaggtcata tccccggcat 48420
tagcacagag caaccctgac ctgttggaga gttgggctgg atggatgcgg tcaggggaga 48480
gactcgcttt attttattta tttagagata cagtttcact cttgtcaccc aggctggagt 48540
gtaatggcac gatctcggct cactgcaacc tctgcctcct gggttcaagt gattctcgtg 48600
cctcagcctc ctgagtggct gggactccag gcacgcgccg ccacaccctg ctagtttttg 48660
tgtttttact agagacaggg tttcaccatt gttggccagg ctggtcttga actcctgacc 48720
tcaggtgatc cgcccacctc ggcctaccaa agtgctggga ttatgggtgt gagccactgt 48780
gcccagcctc gactcgcttt attatatcca cacttggaat acaattcgga ttgattgtag 48840
tggggcattt tataattagg aaaaattaat caggaaaaat cactccatgt agattagtac 48900
caccatatga ggggacaaga atttcttcag attaggaact tcttccaaca ggactgacag 48960
ggtccaaaac tactcttgga tccagcttta agatggaccc agcccactgt tgagtcccct 49020
ctgaggtctt ctctctgtgg atggatttga ttgttaacaa tggctgagtc atgtggcacc 49080
cagcccggtg agtaagacag ctgagtaaga ggggaaacag ggcctttggt cagaaaaacc 49140
agactgactt cagtcttatc tgtttagaga agccccagaa gctgcaaaaa ttgcagcttc 49200
cagactttag tgtgccgtgg tcatgacatc ggtgtggatg gcaggttgtc atctgagcag 49260
tcagggtggc agcacacagc ttgcgggctg gctgatggcc gaggtgtgtg aactgacctg 49320
ccccaagtga cttcagtgct gggcacagca taggagcagt actaatgata tggacagtat 49380
gctcagagga cgttagggag cacagctttg tgtaaagggc atgccctgcc ctgtccggat 49440
ttaaagcagc tatagcactg aaaccccatg gtcaccctcg catttctaca cttctgcctg 49500
tgccaagtct agtttgtgtg cctcctccat tttgtgtgta catgggggta tttttttctg 49560
ctaggcaact gctatttatg cctctcagta ctgtacttag tgtgtaccat tcctgcaagg 49620
tatagacatt gtcagcccat tttacagatg aggaaaatgg agtttttgag agggtgagat 49680
cattcagtgg cagaatggaa tgttaaccca ggtagtctaa cctctctgct gtagatctga 49740
tgtccatttg aactttagac ttcccatctg tgtctacagt ctagccctta aaaaatgtga 49800
taaacaggtt tttaggtaag tctgttaatt tcagaaagac attattatta ttttttagaa 49860
agttagagct tatgttaggg ctcagtctat cctcctgcct cagctgcctg aatagctggg 49920
actgcaggca catgccacca tgcctggtta atttctgtgg tatacatcat tgattactga 49980
gaagtcacag tccgttgtta aataactgag ctattcatag ccaaatcatt tttaaaaaca 50040
caaatataag caaaaacaaa acatttattt atttatttat tgagacggag tctcgctgtc 50100
acccgggctg gagtgcagtg gcgctatctc agctcactgc aacctctgcc tcctgggttc 50160
aagtgattct tctgcttcag cctccccagt agctgggact acagacaccc actaccatgc 50220
ccggctaatt ttttttttat ttttagtaga gacagggttt cactgtgtta gtcaggatgg 50280
tctttatctc ctgaccttgt gatctgcccg cctcggcctc ccaaagtgct gggattacag 50340
acgtgagcca ctgtacctgg cccaaacatg tggttttttt aaatgaaagt gtgttcattt 50400
tacaaacagt gcattcttac taattttaca ggccctgtgc tagggacatg gcctcgtctt 50460
ccgctatctt agagtgaaga agtaaagaca gagaaagtgt tcacaagttg ctgcacaagt 50520
ctcattgcag tgcctcccag aggcgcgaag agcaacacct ttcacctggg ctgtcctaga 50580
aggcccgtgg cagggtgggg ttggtgaaca ctggggctta agggggtgaa ttcagaagac 50640
aaaggacctt ctgggcaaag aagggcccag tagtgggaag tgcaggagtg tgagagtgcc 50700
tggaattgcc cactcactgg ctctggagct tggtgctgag tgcttgggaa gtgttgggag 50760
gatcagttat attgctggct gggttctaaa gaacctccaa agtttacata aaagttacct 50820
ttgatttgac tgttctaccc tccagtcacg tggctaaatt aattaaatca aatttaaaat 50880
taagctcagc cataccaagt atatccagtg ttcaataggt acatgtggct tgtggctgat 50940
gcactggaca gtgtacatat aaaacatttc catcgttgca gaaacttcta ttgaacagca 51000
gttgtattag tccgttctca acactgctgt gaagaaatac ctgagactgg gtaatttata 51060
aaggaaagag gtttaattga ttcccagttc cacagggctg gggaagtctc gggaaactta 51120
caatcatggc agaaggggaa gcaaacatgt ccttcttcac atggaggccg cagcaaggag 51180
aagtgcagag agaagagggg gaaaagcccc ttataaaacc atcagatctt gtgagaacag 51240
cagcatgggg gtaaccattc ccctgattca attacctccc accaggtccc tccaatgacc 51300
tgtggggatt atgggaacta caatttaaga tgagatttgg gtggggacat agccaagcca 51360
catcagtgtt gttacacacc acagtggtgc tgtggtgtgt aggtgggaaa actatggcat 51420
gggggccata tctggtcctc tgcctatttt tataaagttt tattggaaca taggccacac 51480
tcatttattt atgtactgtc tatggatgct ttcacactgc aacaatagat ccaaatagtt 51540
gcaaagagac tgtgtggccc acaaaaccta aatatttact atccaggcca ggcatggtgg 51600
ctcatgcctg taattccagc actttgggag gttgaggtgg gcagatccct tgaggtcagg 51660
agttcaagac catcctagcc aacatggtga aatcctgtct ctaccaaaaa tacaaaaatt 51720
agctaggctt ggtggtgctt gcctgtaatc ccagctactt gggtgtcgag acacgagaat 51780
tgcttgaacc cagaaggcag aggttgcagt gagctgggat catgccactg tactccagcc 51840
tgggtgacag agtgagattc tgtctctcaa aaaaaaaaaa cttactcttt ggccctttat 51900
ggaaagtttg ctgacctctt ctgtagatgg tagggtacgg tagaaggtgt tcaagccagg 51960
agtaacatga atgattgtat ttatggccta agaggataac tcgtggtggt gggcgggcca 52020
tatttgtgga gagacccatt ttcagtgact tccaagagtc tgcgtgagag atgactgagg 52080
tcttgccctg gcaggaatgg ttccattaat ctgtgtctca tttgacaaat gaggaactac 52140
aaatgggaac agtttaagat gagatttggg tggggacaca gccaaaccac atcagtggtg 52200
ctaatagaca gtggtgctgt ggtgtgtagt agggaaaact atggcctgtg ggccaaattt 52260
tgaagtcctt ttacttttttg gttctaaaaa ttattaattg tagccagagt tgttaactta 52320
atatgtcttg gacccttgg gctctctgaa gactgtactc tttctttcca cttaataata 52380
tacatggaat tgcaaaggaa accaatgata ttgaaataga tatcagaaat aaaattttta 52440
gatatagcaa taaatgcaca tctgtattaa aatgtgtaat aacaagatct aacagtgagt 52500
ctaagaacta ctataattat catgtagcaa tggcataaag gatagtttgt gctatctaaa 52560
acagtcaatg acaggagaaa atctgatttc tttggtgata aaacgacagg tgctgctaat 52620
acacctgtgt tttatggtct tcgtttgtaa tgaaaagaaa tgccattaat aaattttatt 52680
tatttattta tttatttatt tatttatttt tttttttttt gaggtggagt ctcactctgt 52740
cgcccaggct gaagtgcagt ggcatgatct cggctcacta ctacctcctc ctcctgggtt 52800
caagggattc ttctgcctca ggctcctgag tagctgggat tacaggcgcc caccaccatg 52860
ccaagctaat ttttgtattt ttaatagagg tgggggtttc accatgttga ccaggctagt 52920
ctcgaactcc tgaccttgtg atctgcctac ctcgggctcc caaagtcctg ggattacagg 52980
tgtgagccac cgcacccggc cagatgctgg gatgtttttt aagaccttag accctaagcc 53040
tatcatatca aatacaatga aacacaccca cttttcacac tttaaaaaaa gtgtgttggt 53100
gtttattgct gtaaaatagt ttgaaacttt ttaaaaaaag ttttggtctt gctcatactt 53160
gtgttttaaa aaagtatttg gctatgacta actcagttat gtatttattt atttattttt 53220
gagacggagt ctcgctttgt tgcccaggct ggagtgcagt ggcatgacct cggctcactg 53280
cagtcgccgc ctcctgggtt caagcctcag cctctcgagt agctagaatt acaggcgtgc 53340
tccaccatac ccagctaatt tttgtatttt tagtagagat ggggttttac catattggtc 53400
aggatagtct tgatctcctg acctcctgat ctgcctgcct cggcctccca aagtgctggg 53460
attacaggcg tgagccacca cgccctgtga ctaactcagt tatttaacaa ttgactgtaa 53520
tttctcagca atcagtgtat acttggaaat tcttgggatg tgagaaaact aacctataac 53580
tcattttctt ttttctttga ggtgaggtct ctctttgtta cccaggctgg cgtgcagtgg 53640
catgaacagg gctcactgca gccttgacct cctgggctca atcctcccac ctcagtctcc 53700
tgagtagctg ggactactgg cacgtgccac catgcctggt taatttttgt attttctgta 53760
gaaatggggt ctcactgtgt tgcccaggct gatcctgaac tcctgagctc aagcaatcca 53820
cccactttgg cctcccaaca taccgggatt acaggcatga atgagccacc atgcctggcc 53880
tgcaacttct ataaatagca aagttagtaa ttagtgaaga tgatggtttg caagcactga 53940
attatacttc tattaatttc atttcctttc aattttctaa tgttttgtgc ccaatctgtc 54000
ctgtctgcct ctacctagct ttagaagtgt tttgttggtt cctgagatgg agctgtgcct 54060
gaagggtatg aggttaccct ctgggttcag cggggagatt tgggaagagt tttgatttgt 54120
aggccagtaa aggggcctga cattagatga tggctgctgg gctagggaac aacttagagg 54180
cagctaacag gattcaggga gagtggattt ggtgggagag agtagtctag gatgaatcca 54240
attgggtttt tatgagtagt ttggtagttg gttgactggg tgggtggtcc cttggtaatt 54300
atttgttgat tagtggttgt tgggttaggt tggttacact tacattatag tcgatggaat 54360
ctcagatttg gatctaatac cacatgtaag tcgagtggat ttttttttga gacagagttt 54420
tgctcttgtt gctcaggctg gagtgcagtg gaacagtctc agctcaccac aacctccgcc 54480
tcccaggttc aagcgattct cctacctcag cctcccgagt agctgggatt acaggcatgc 54540
gccaccacgc cgggctaatt ttgtattttt aagagttggg ggtttcacca tattggtcag 54600
gctggtctcg aactcccgac ctcaggtgat ccgcctgcct tggcctccta aagtgctggc 54660
attacagggg tgagccactg tgcctggcca gttgagtgga ttttttttagc actcaagctt 54720
cgtggctcat tgctattatt gtgcatgtga gcgttttatc tttcagtagc attagggatg 54780
ctacttggat gtgttttagt tattacagaa atagttttta ctaactttta ctaagttatc 54840
tttcctctcc tgtgtaggaa gtttagagtg aagcggcagt tggctggagg ttctgaaggt 54900

-continued

```
ttccccctttt cacataattt gatgttccag ttgcccacat caggacgact ccctctcttt  54960
ctactgatgt aagcagtggg ccaaattatg gggctccatc cctgcatctt cctacttgtc  55020
taaatcttcg tcacagacaa catattgctc taaaggaaac ctagaaagga ggagaagctg  55080
gttttcgccc aaattcctca aaatcatcgc ctgttgttta agaattacag tttgcactgg  55140
aacaataaga tgttccttaa tgtggttttt aagtgagttg gttgtcgcct gaatttcata  55200
aacactggct aaggattgtg caaaagggtg tgcttccctt tagcatcctt aattagggac  55260
agcgttttga aaactgcttt ttattgtcct ttatctgcaa aacttcttga atccaaatag  55320
cgagattctc atttcttaat cactgccaca gaaagttgta gattagagaa agctccaatt  55380
ccttatttcc tgtcttcctt tctttctgtg tgtttattgc ctgtgtctca tcctcactcc  55440
tgccagtttt atagaatgta acctcccagc ctctgggaat gtttgggaga cttgttcata  55500
gaggatctga agagcagttt aaagtggact tacccaaact atcttctgga gaacattagt  55560
ctctttggag ataaaatttt taaacatccg ctagtccaat agtgttggca aattccctgt  55620
gacactgtag ccctctcttt gagattgtca atgtacgttg gcatgttaaa ggctctgaga  55680
agtcctgcag cagttaaaaa attgtttagt ctagtgtgcc cccagttgtt tggccactga  55740
aacccccttt tctggaaaaa ccagctaaca tctggtagtc ttttctaaga ggtggtactg  55800
aagatgatac tcatgttaca catttaaaaa ttctaacatg tgtttttcat gtgtttataa  55860
aatgcaacta atgtatcaaa cctgtgattt ccaggacata attacttaag ctaaggaaaa  55920
aagaaaacat gagtgaagga aaaactttag taaataggcc aggtggtaag aggagagagc  55980
cttgtctgtg agtgtggtct agggggatgc tggacctagc ttttcagagc taggttcagg  56040
cagagctgct ctgagatgta gacactgcag ctggggttct tgttgagccg ggaagcagct  56100
tctgactaag gtgcagactg tttagatgag ctggtcataa agagccctga ctgtggactg  56160
cgtctccagc cacggcagca gctggtggat ggggtgatgc cttggatatt tatcgtgtgt  56220
ttcttgcctg gcctgccctt ggacagtgcg cctcaggaat gttagaatgt gttcccccctt  56280
tagcagcaaa gccgatctgc tgtgtacttg ttctgtttat cttactgcca cgaccgttta  56340
tcacgggcca gagttcaggg gcacactgat aaatctcttt taggaggatg atgtaaccct  56400
cagcattttc cccctacttg gttctgagtt tttaaagctt ttgtaacacc atcatgtcct  56460
tgtttgggca tcttcctgtg tactcccgtt tgggtctcca gggtgaaata gccaacagtg  56520
gattctggag tcatggcctg ggttcaaatt cctgctctgc tgcttatcaa ctctgacttt  56580
gggtttaatt gacctattca ttatttttct taatctggaa aatggagcca acagcagttc  56640
ctcataaagc agctgtaagg attcaggggg gtaactgcac agggccaagc cctcaggttt  56700
cacctctcac tgggaggtcg gacctctgca taatggacaa gctctcctag ggtgcaagtg  56760
aacgggggcg caagggagtt aggaaggtgg gtgtttttttg tttttgtttt ttggtggctt  56820
gaaaaacatg cccaaggctg ggtgtggtgg ctcatgcctg taattccagc actttggaag  56880
gcagaggcgg gagcattgtt tgagcccggg agtttgagat cagcctgggc aacatggtga  56940
gaccctgtct ctcttttttt tttttttttt ttgagatgga gtctcgctct gttgcccaga  57000
ctggagtgca gtggcgcaat ctcagctcac tgcaaccttc acccccaggt tcaagtgatt  57060
ctcctgcctc agcctcccaa gtagctggga ttacaggcgt gtgccattgt gcccagctaa  57120
tttttgtgct tttagtagag atggggtttt gtcatgttgg ccaggctggt ctcgaactcc  57180
tgatcacagg tgacccatcc accttggcct cccaaagtgc taggattata ggcgtgagct  57240
actgtgcctg gctgacccaa aaaattagct gggcgtggtg gcacacaccc ctgtagtccc  57300
```

agctacttgt gaggctgggg caggaggatt gcttgaggcc agcctgggca acagagcaag 57360
accttgtctc aaaaaaaaaa aaaaaaaaaa aaaaaaaaaa gaaagaaaga aaagaaaaga 57420
aaagaaaaga aaaacatgcc caaaggcaac caaatgactc catcttttgc aatgtaatct 57480
tcaacatcga ctcctctggc aagctgtttg gaaatggcaa agtccatctc ctgaggctgg 57540
gagattgctt gtccaggacg ggtgtgtctg gtgaggaatg gaaggcattt ggatggccac 57600
tgagaaagct gagccaagga gcatcagaaa gacaatcagg caaacccaca gagtctccag 57660
gtattccttt gctgataggt aacattgcac tagcgattta aacaaacagg tgaaaggcca 57720
ttgccctacc accccacctc acctctattc cttgctgctc tttccagaag caactgcatg 57780
gtctgggaac agttttttgt cttgtcaaga gacagtctgt acatagatga attcaattat 57840
attacttctg tagtaccctg tactcaaatt tgaacctgtc atacacattg cttttatcat 57900
ttcataatac ctgttgattt tcccacgtta gtacctatag atcctgacaa gcaattttgt 57960
taagatgaag agttcttcat atgtattgta ctatgtttct ttttttgatg atgtatgtca 58020
agatttatta taaaagtaac agatgggtag ggcatggtgg ctcattcctg tgatcccagc 58080
actttgggag accgagatgg gaggattgct tgagcccggg agtttaagac aagcctggga 58140
aacctggcga aatcctgtct ctacaaaaat tacgaaaatt agccaggcat ggtggtgact 58200
gtcccagcta cttgggaccc aaatgtccca gatactcagg aagctgagtc gggagcctga 58260
tcctcagagg tcgaggttgc agtgagccgt gattgcacca ctgcactcca gcctaggtga 58320
cagagtgaga ccctgtctcc ccctggcctc caaaaaaaaa aaaaaaagta acatatgtag 58380
tttaaatttt aaaaattaaa tttttggggg ggctgggtgt ggtggctcat gcctgtaatc 58440
ccagcacttt gggaggccaa ggtgggcaga tcacctgaga tcaggagttc aagaccagcc 58500
tggccaacat ggtgaaaccc tgtctctaga aaaacacaaa aattagctgg gcatgatggg 58560
gggcgcctgt aatcccagct acttgggagg ctgaggtggg agaatcgctt gaacctggga 58620
ggcggaggtt gcagtaagcc gaaatcatgc cactgcactc cagcctgggt gacagagcga 58680
gactccatta aaaaataaaa ataaaaaatc aagcaatgca gaataaataa caacaataaa 58740
atgaaagccc atcttccacc atcagcttct tagttttctt cctagaagga gccagtgagg 58800
acagtttggt gtttatgctt ccagatcttt ctgttcagat gcagtcatga cttctgaaaa 58860
acaggattgt acaattcata cttttctaca aattatcccc ttcccttaat acatcataga 58920
agcctattca tattggaaca aacaaacatt tcttattctt ttcacagcac cctgttttcc 58980
tcttgcttga atgtaaagtt tatttaacca cttactgtca gggaggcatt tgttttcagt 59040
tctccctccc tccccccacc agttgtcttg taatgaactg ctttaatggc taaagatcac 59100
tttaatatca aaacctcccc cacctcccat tagaaaaaga aatcatgtta gggaacttca 59160
aattgaattt acggaccttg tgtttaattt tctatcagca gtggccccag cctggcccct 59220
gcagactgcc ccggaatctg tgggaggagt tggggtggcc tgcagactag agcacactgc 59280
cagttcattc agcagctcac cgagcaagaa acatcttgat tctatcagcc ttaatgctgt 59340
gtcccattag ggacccagct cttgtggtca ttagcagatg gaatgctcat ctgtgctaga 59400
aggcggaatt ctagggcatt cggctctgag cagtcttgaa ccagaattga atggcttgaa 59460
tccttttcac aatgccaacg gggaggcacc cttagctccc aaacttgtgt gtgttataat 59520
actatggtag taataacagt ggttgtagta gcccccgtga atttgatggg acagtcgtca 59580
ggcagtgctg cttgcttgct ttactccatc gtatcaccgc agcctgatga ggcgagggag 59640

-continued

```
ttacgactct cattttgcag gtgaggacac tgagcacagg gaatcgaccc actcatggtc  59700
acacagcttg ccaagtcgct gtgcttggga ggtgaaccag gcttctctga cgccccagca  59760
ggacgtctga acttctagct gccccatcac taactgactt aatgcccctg actcctgggt  59820
gacttggcca ccagttactt cagccagcga cctgcccttt ctttgagtgg gttccaccca  59880
tccctgcacc atgcctttta ctttggatgt tggtggcatg gaattccacc cgtaagaagg  59940
aggtcggtcc ctgggctgag agagtttgca gagagctctg ttgggattgg gtgggacgtg  60000
tgtttggagg cctcctcaca taattgtggg ctgaaaggtc cagatttggg gatataaagt  60060
tgagccgtca gctgagctaa agacagggca cagggaggag ccatccagaa agtgtcagtg  60120
taggtaaagc aggcagagtt ccccctatct gtcctctgag ggcctccttt cttgtggttt  60180
cctccctttt ctgtggtgat ggtcagagcc agcggttata aattatttgg aattttcctc  60240
agcttggttc ctactcaaga ctttaaatta ggagttttgt tccctttat gacttcacaa  60300
tctttgggca ggctgccatc tctacagcag gctaatatga gttgtaactt gaggtgagtt  60360
acaggggaaa aatggaagct gatttctccc cttttaaacc aaggaagcca ccttgatctg  60420
actttgtaac aaagctcaac ttttgtaagt ttgcaattaa aggataaata cctatcctat  60480
ttattattat tattaacttt ttattataaa aggggaaaaa actcccagga aacatagcct  60540
aatatgaggg acaaaaagcc aaaaggtttt ttttttcttc ctttaaaagg tcctcaatgt  60600
cttgccctgt ggagacacca gttttcatta taataacgcc attatctctt tgtagagtca  60660
tttcaagcca atttaacttt ctcatttaaa agtataattg gtattcagca cagagctggg  60720
agctcagtag gcagttagaa aatatgtgta tattttttga gacgaagttt cactcttgtc  60780
acctaggctg gagtgcagtg gtgcgatctt ggcttactgc aacctccacc tcccgggttc  60840
aagcaattct cctgcctcag cctcccaaat agctggaact acaggcactc accaccacgc  60900
ccaactaatt ttcgtatttt tagtagagat ggggtttcac catggctggt ctcaaactcc  60960
tgagtttcgc caggctggtt tcaaactcct gatttcaggt gatctacctg ccttggcctc  61020
ctaaagtgct ggcattatag gcatgagcca cagcacctgg ctggcagtta ggaaatattt  61080
attgaatatg agaaaagaaa aatagagcaa attgaatctt caagtagtat gtgagtaact  61140
ctaattcctg ttttctggaa aacacacagg ctgataggtt tgggtaaata agagcagagc  61200
tgcatcttct ctcaagttcc ctgattccct caaggagtta cctgagaata gctctgtgcc  61260
aagcagtgcg gcatgcatag gggacctctt gaatggaggg acagtccatt atcattagaa  61320
tccccagttc cagccaggtg cagtggctca tgcctgtaat cccagcactt tgagaggcca  61380
atgtgggcag attgcttgag ttcaggagtt caagactagc ctgggcaaca tggcaaaacc  61440
ttgtctcccc ccgccacaca cacaccacac agacacacag acacacacac actggctagg  61500
cgtggtggca ggtgtctgta gtcccagcta cttagaaagc tgaggtagga ggattgcttg  61560
agacttggag gtcgatactg cagtgagctg tgatcgtgcc actgcactcc agcttgggtg  61620
acagagcaag accccggacc ctgtctcaaa aaaaaaattc cccagttctc agggtgtggt  61680
agaggccgag tcagtcatgg ctgagacaag gggactgtgc tctgtgtgct tctgtgccct  61740
gtgtttatat ggttcatacg ctgcctgtcc accatgtttt tcccgagagc ctcggcagcg  61800
caggcatcat gggaatgact gagtcaggtg gaaattcaga ggccctgccc tggtgggcag  61860
agaagcctgg cttacctccc aagcacagca tgtgtgtgga tcacttctgt gcactgtctc  61920
ctcatctcca aaatgggagt cataactgaa ctcacctcat caagttgtta tgagatgatg  61980
tagattcagc gaagtagcaa gagtaggagt ttgggctttg ataacagaga gaagtgagtt  62040
```

tccatctaga ttctccccct gtgtcacttt tggcagttgg cttcacctct gtgggcctct 62100
gttatgtcat ctgtaaaatg ggattaaccc taaaagccac cctcacaggg tcattgtgag 62160
gattgcacaa ggtgatgcaa gtggcacagg gtctggccca ggagaggggg ctggaagaga 62220
gcgagctgcc attgtatttt ggttgctgtg gatctaagga gaagagatgt ttaggagtct 62280
ttccctggca tggttcctcc tgccttcacc catcactctt ttcctcgagg gattccctgt 62340
ggggtgcaca gccccagggt gggccagact gagctcacag gagcatgggc tgtgtttcag 62400
gtgaggtggc ctcaccacat gacaaactga gctggagtca aagggtcacg aggacctcca 62460
ttcacagcca gcatttatta tttcagctgg aaatgtttgc cgagcagttg tagctggaag 62520
ctgtgagcga gacacagact gccatcaggc tgaggcctcc agagctcatg ctgggcttta 62580
acctgagcct cttgggggct gggctctgag ctcctccact tctgctcatg cccaggcgtc 62640
cttgggggcc ttgaactgtc agttgtccag gagaactgtg tggcagcaac agaatgagtt 62700
tgtatagcaa cctgttgctt tgaggtttaa aacttagttt agaacgcaat tgctttgacc 62760
attttggagt gtctatactt tttttcttct tctttaagtt ttcttttttc ttttttttctt 62820 ttttttttt ttgagacaga gtttttgctct tgttgcccag tggcaacaag agtgcaatgg 62880
cgaaatctcg gctcaccaca acctctacct cctgggttca agctattctc ctgcctcggc 62940
cttctgagta gctgggatta caggcgcccg ccaccatgcc tgaccaattt ttgtattttt 63000
agtagagacg ggtttcaccg tgttcaccag gctggtctcg aactcctgac ctcaggtgat 63060
tcatctgcct tggcctccca aaatgctggg attacaggca taagccatca agccctgctt 63120
ttttgtttcc cttcttcgac ctttctaaca agaggttgga atcctcgttt tgacttttaa 63180
aggatttccc agtgctagaa agtggtaaga tagttactgt atcctaggcc ctttagcaga 63240
cctgtctcat tgatcattta tttagtccag tgtggctttg ttgttggata ttaagtaatt 63300
ctcaaaattt taccttttca aaagtggcat tgaaaataaa ggcattgggt gatgaaaatg 63360
gaacttttaa atacagtgat tcctgttaac cagaaatagg gtgtttggga taatttatga 63420
agcagtacac catcatagat actatgagct gaaagttcac caaactctct atcccaaaat 63480
aacaataagg tatttatgaa gtgattcgtt ccaactattt gaggcaaaaa ttgtccagca 63540
agtgagagag aacagaagga atagttggca aaatagggaa tttgaagtct gaggttatgc 63600
ataaggaatg tgttatgggc ctatagtaga aatctcaaat cagggattag ggaatgttta 63660
ctcagttctg ttgcagagaa atcctggcca cgactccccc atgccatgcc cagggcaggc 63720
attgctaatc ttcactgcct ccattctcca tgccctgttc acggaagaca tttctaatgc 63780
attttagcag tcttttttttt ttttgctgaa tccagatgtg gcctcagaat ccttctcaac 63840
acagtgtact agcaccactt ggtgctcctg atctactgta tcatctcttg aaaaactact 63900
aacatgaaaa gacctgccaa gtcaacttta tattaactga acccttgaca cagtgatgga 63960
taaaaattaa ttcaaacagc ttctttgtga tctttgagta gttcatgagc aagaaagaga 64020
attggaaatc cagccaactt cggcccccctt gtctacttgt attttactgt ggtttatgtt 64080
ttctcttacc aattgagata ggcccatgag acttctggtc ttccaaagcc cagaacatcc 64140
ccacattata gtttaaccac tgtaacaaag aggttttttt tgtttgtttt tttgtttttt 64200
ttttgttttt tttttgggac agaatctcgc tctgtcgccc aggctggagt gcagtggcat 64260
gatcttggct cactgcaagc tccgcctccc aggttcacgc cattctcctg cctcagcctc 64320
ctgagtagct ggggttacag gcgcccacca tcacgcccgg ctaatttttt gcattttta 64380

-continued atagagacgg ggtgtctgga tctctgacct cgtgatccgc ccacctccgc ctcccaaagt 64440
gctgggatta caggcgtgag ccaccacgcc tggccagagg ttttcttaaa aacaataaca 64500
acaaaaacag ttgtggaaag catgtagagt gtgggttttt tcggtcttca ggttggcagg 64560
gcatctgata ctgggaccca ggttccttcc ctcaccttgc tgtgcctctc ctagtgcagg 64620
ccaaagccag gtgactgcgc tgtctgggct cctggctggc aatcggggaa agagtgcatg 64680
gagcaggcat gcccactgtt caggtcctga agccgtggct catttcatat catttgttgc 64740
ttatttgaaa gacaggcaca gcactgactt ccaggggagg ctgactgacc atctaggtgg 64800
aagttgcatg cctgggaggg agaaggggac aaaggccaca gataggcatc agttatcagg 64860
gccttaagtc tgccttgttg gcatgcagcc ttttattgga tcaaggccct ggagaaaagc 64920
cctgagcagg aggagataag ccagcttggt ccccttcatc ctacccaggg gcctctgggg 64980
tacctgagcc aaagtgcaca gttcattggc tgtgtggatg gaagggatat gggacttgaa 65040
aatgggacac tggtcctggg cagctgaccg acatggtcct ccttaacctg ctgtctgggg 65100
agatgggttg catctggcta ggttttgact gaggaactga ggagagctgt cagctgtccc 65160
cgctttggtt cagaatgccc ttttgtttgg acagctgaag cctacaattc agccatggtt 65220
tgtttgggct cagaaaacag gcaaggatgg agagaaactg caaagctgac ctgggctgtc 65280
agtgggcacc aggtcctgct ggcctggggt ctggatgcag gagatctgag ctcttcaatg 65340
tggggtggtc ttgcagcagc tcttcacagg ctgctgctgc tgctgctgta ggctcaccca 65400
agcagccaag acggacagga tctattctag ttttgtgcag agttggatat agaagaggca 65460
ttagagggag aggggatggg gaaggagttc caggccaggt gagcatgggg cacagtaaac 65520
tgggatgtta aggaggggcc agtttgtgac cagcctgggc aacatggcgg aaccctgtct 65580
ctataaaaaa ttaaattagc caggtgggtg gcatgtgcct gtagtcctag ctacccagga 65640
ggctgaggtg gaaggatcgc ttgagcccag gaggcggatg ttgcagtgag cagagattgt 65700
accattgtat tctagcctgg atgaccgaga ccctgtcttt aaaaaaaaaa aaaaaggagg 65760
ggccagaccc ctgacccata tgtgctgctc ttttctttca gggaggtctg ataaaatatc 65820
agtagttcaa ttcttttttt tttttttttt ttttttctga gatggagtct tgctctgttg 65880
cccaggctgg agtgcaatgg agtgatttcg gctcactgag acctccgtct cccaggttca 65940
agtgattctt gtgcctcagc ctcccaagta gctgggatta caaggtgccc accgccatgc 66000
ctggctgatt tttgtatttt tagtagcgac agggtttcac catattgtcc aggctggtct 66060
cgaactcgtg acctcaggag gtcctcctgc ctcagcctcc caaagtgctg ggattatagg 66120
cgtgagccac catgcccggc ccatagttca gttctttagg tggttcttgg tgctgcatat 66180
gagatctctg caagaaggac acgtctgagc cgggtggttt agaagaccag catggcccaa 66240
gaccctcaga gcaacaccaa gaaccaccta aaattctttc tcagacgtgt ccttcttgca 66300
gagatctcac gtgccccagg ttcgctgcag cgttaggggt cagcctccct ttggagcagg 66360
agagcagggg ccttggaggt ggcagtcatg gccctcctaa ttaattgctt ggctcagaga 66420
agtgacaaat tgaacatttc aaccacctgt taattcacaa ggtacttctt ttcatttctt 66480
gctgcttgca caaaacactt ggagtatggc ttgtggatgt ctggccctag ggaagagtgt 66540
ttggcacata gcaggtactt aagtattagg aaaatgagga tggaggggag ggagggaaca 66600
ttattaagcg gccaactgtg agacaggcat tgtgcttgac tctttctttc tttttttttt 66660 ttttttgag acagagtctc tttctgtcac ccaggctgga gtgcagtggt gtgatctcgg 66720
atcactgcaa ccgcgcctcc tgggttcaag tgattttcgt gcctcagcct cccaagtagc 66780
tgggattaca ggcgcctgcc attatgccct gctaatttta tttttagtgg agacagggtt 66840
tcaccatgtt ggccaggctg gtctcgaact cctgacctca gtgatctgcc tgcctcggcc 66900
tcccaaagtg ccaggattac aggcgtgagc cactgtgccc ggccgacact tggcattctc 66960
taacctacct actccttata acagccctgg gaagtagttg accatggcca tttctatttg 67020
gtagatgagg aaaaataagg ttcagagatg gattgttcaa accgatgtat ctagtcaagc 67080
tactggttcc cgagcctgtg tttgcaaccc ctctaccatg tagcctctcc gggtggtaga 67140
gatgaggggg cagagtgcac agtgcatggc atcctgttcc ccagatggcc aagtcttagt 67200
gcgagtgtgt gtggccttgg taacttgtgt caagcacaca ccccatctct ctctctctct 67260
cttttttttt ttttttttga aacggagtct cactcggtca cccaggctgg agtgcagtgg 67320
tgctatcttg gctcactgca acctctgcct cctgggttca ggcgattctc ttgcctcagc 67380
ctcccgagta gctgggacta caggcacatg ccaccacgcc cagcaaattt ttagaagaga 67440
ctgggtttca ccatgttggc caggatggtc ttgaactcct gacctcgtga tctgccctcc 67500
ttggcctccc aaagtgctag gattacaggc tctcttgctc tctctctctc ttgttttttt 67560
ttttttgaga cagagtctta ctttgttgcc cagcttggag tgcagtggcg tgatcatggt 67620
tcactgcagc ctcgatctcc tggctcaagc aatcctcctg cctcagcctc tcaagtacta 67680
gttggtacta atgggcatgc accactacac ctgactaatt ttttttatta tttgtaggga 67740
cagggtgtcc ctatgttgcc caggctctgg tcttgaactc ctgggctcga gctatcctcc 67800
tgtctcagct tcccatagtg ctgggattac agagatgaac cgcctggcct acacacccct 67860
atctctcctc gattcttttt tttttttttt tttttttgag acagagtctc cctctgtctc 67920
ccaggctgga gtgcagtggg gtgatcttgg ctcactgtag cctatggctc ccaggttcaa 67980
gcgattcttg tgcttcagcc acccaagtag ctgggattac aggcacacac caccatgccc 68040
agctaatttt tgtattttga gtagagacag ggtttcaccg tgttagccag gctggcctcg 68100
aactcctgac cccaagtgat cctcctgcct cggcctccca aagtgttgag attataggtg 68160
tgagccacca tgcctggcct ctccttgatt cttacagtca ctttgttggc tgtttctgac 68220
tcagcagcta cctgcattgt ggccaaagga tgacctattc cttctcagga gggcaaaaat 68280
gtggaatagt gtctgtccat gcctctcctc atgggctacc acctctgcca ccgtggttaa 68340
tcagtaacaa ccaggagaga agctgctgga actgacctct gggaactccc tggatggttt 68400
ggtgcaggaa tgtagtaggc atacacgtgg ttgcgtggat ctgggccctc ctgatgtgag 68460
tagagaggta aaaggccacc atctccttga cctctgggga actcatccac aaagaagatg 68520
tttccaagat gcttctgaag attgcctaaa aatagccggt ttccaccccc gtgaatgcat 68580
ccattctaga atgctccttc accaggacca gagaactgat ttacagaagt gacatgaaaa 68640
cattccatcc cagaatttgc agtagctcaa attaagtttc tagctattaa aaagaaaaga 68700
aaacaaaact aaacaaaaca cacccaccct gctcacttag aagcaacact gagtaatttt 68760
aagtagttcg agaaaatgta tgtggtttga gggtcagggt tgtccagagc caagaccagt 68820
tatgtgggaa ttgttattgg ctggatttgg ggaggagaaa cccatggccc aattccaacc 68880
cactgaaatc taagcagatt ctaggtggtt aggcggacct ggtaggcgtt ggtttatttt 68940
attcccgaaa aaggccctgg agcaagtctt cacatggaat cctgctgaaa ggcttccggc 69000
tcatctggcc ttttcctcct cttaaggttc tgctccatgt tttaccctcg gcgtaaacat 69060
tgcagagcac gttcagatct gaaaagtgtc tcatctacgt gatggtcaga cgttgttgac 69120

```
cctgtgatgc tgtgtaacat ttcattttcg aggcttgggg agtctcctat ttcatgtgga  69180
tgggaacctg gaggtctttg ggcaagtcgc catctttttta ttgttccaag agtttggtga  69240
agcgtttgaa ccttcacctg tcaaaatcag ttttggaatg agaactgctc tctctctagt  69300
ccttataata gcagaaggaa ggtatcattt atcccaatga gaccataaag ggggctttcc  69360
cgtgtggaca cccaccttga attcaattgg aaacagaaat tctgggcatt gtattttttg  69420
taaatttggc tcagacttca actggatcat atttcccccca aaatcttttc gaaaaagact  69480
tgtgtctcat tcctttagac tagcatgtgt aagctgggta aaaatagagc aagccgattt  69540
catgttaatg atttcatgtt aggtttgtga atcaaatctg caagtctgct tttgaaaagc  69600
atttaacata taacttggga aagtttgagt tttgcagact aatgcctgtg gccggatgag  69660
acttcatagc tccatccaat ccctcctggt gcaagagatc aatgccttga gggtgcctgg  69720
ccaccaccat taccctgaca gtatacccac tatttattta tttatttatt tatttattta  69780
cttatttatt gtttaccctt ttgaagattg ctcttctccc tttaacttaa aggaattggc  69840
atggaaactt gtttgatctg gaatttctga taatcagtag gtagtaactc cgtaatcaat  69900
agcacttcaa aacaacaacc aaataacagg ataactaatc caaaaaattc agtcatggtc  69960
aaggacttcc agctcaggaa atgtctggtc ccgtggggtg gattccttgg ataaccaagt  70020
tccgtgcagg gcctggagtt ttatgcagac cattgctcct tgattgacca caggacctca  70080
aaaggagggc tggcttcatg accacatgac ccgtgtgctc agaagggccc tgtacttggt  70140
ttattgctct gctgttgctg tcttgaagtt cttaattttt tttttttttt tggcactggg  70200
gagttgcagt ttcaaacaac acttattcat tgtctcacag tttctgtggg ccaggagtcc  70260
agccatggct taagaccagg tcctctgctc cgggtctcac gagactacaa ggaaggtgcc  70320
atctagggtg tgttttcatc tgaatgccta actaaggaaa aatccacttc attcaggttc  70380
attcaggttt ttaaaagaat ccatttctgt gtgattgtcc cactgacagg tcccagcttt  70440
ttactagctg ttgcttggag gctaacctca ggttttacag gctacgctca tatctctgcc  70500
atgaggcctt ctgcataggc aattcataac acaggtgcct gtttcctcac agccagcaag  70560
agaatctgtc tcctgtctgc taaagtggag tttcatgcat cgtaatatgg tcatgggagt  70620
aatagcccgt cacctctgcc atttttctgt tggttagaat aaaggcacag gttttcccca  70680
cactcaggaa gaacccatga tataaaggct ttcagtaaag gagacgacaa acagaatatg  70740
gaatgatcag aattactctt atgacccaga ccaagaacat cagcattacc tacgaattta  70800
ttggaaattc aaattctcct gtttcacccc aggcctgtta aatcagaaac tttaaaagcg  70860
agcccagcat tctgtggttt aacagatcct tcaggtgatt ctgacacctg ctgaattttg  70920
agaaccactg gtctagaggc aggcaggtct tgctccccta ggagttaagt ttgatgtatc  70980
ttctggtaat actgagaaat gagctgggaa atggttccaa aatcagatta tcctccccag  71040
gattaacaag actcatactt gcaaaagaga gtgaagaaga gaaactaaaa aaagcaagag  71100
gctgtgtgtg aagctagatt caaacagtta aagacagcaa cacatggcaa aggatgggaa  71160
tttgaggaag tgggtagtga aagcaattct tgagctaaat tacaagaaaa cacggtgaat  71220
ttgtatctgt ttcctatatt tagggggctg gcttaaacgt tagtgataca tttggggagt  71280
agaaaatgga tgttggtgtg aagttcttaa gttttggaca aggaaccctg tattttcatt  71340
tttctctgag ccccatgaat tatgtagaca gtcctgcttc gaagttatta tttatacaat  71400
tcattataga gaaagtcctt gggaacctta actttgagtg aggattgctt gagttagttt  71460
ttcttaccag ccactccatg atactctttg ttttttccag gttagatgat cgagttttat  71520
```

tatgactgaa tctgcacctg caaaattaat tctgattaat taatttaata attaaattct 71580
gatgatttct ctctgatggt ttgggtgtgg gctcttaaag agggtctttt tttgcaagag 71640
gatataacaa taatcaggtt aattaaaaaa ataaggctct caccctttca tttttgagtg 71700
gcatgccatg caccccttat cagcatgtga gtatgctttt catgtggtcg tggttgggtt 71760
tcattaagtg taatttggca tgtgttcaac cagcattcag gtggctcttg gtgggtggct 71820
ggggagacac caagatgcag atagctcagt cactcctcaa caagcggctt agttctggaa 71880
tgaggtggga ggccaaggaa ctcacacata aatgctggtg ggagtgaagt gccaccagct 71940
gtagaatctg gtgtcagaat gatgagccag gagttatccc acaggaggat gggtgaaggt 72000
cttcccatca aagggataga gaacatgtga agaggtccag gggctcaggg caagatgtag 72060
tccaggaaca aggagtcttt gagcctgcag tatggtgggt ggaagtggca agagtggaaa 72120
gcggattgga tggggtttat gtaggttctg aggtgctgtg tatgtttaag gagctgattg 72180
tgtgcagcgg gaaccctggt gaatttggaa gcacagaggc acctgacgag aaagatggtt 72240
ctggggttat gtgaacagtg attcggcttc aaggctatca aagacaaaaa tgtttattgg 72300
gagggtatag aaaagggttt gccaaaagag ttaggtaggg atagaattga cacattgtgg 72360
aaactatacc cagagtttaa gaggtggagt ccaggatagt gcccatgttt gtagcttggg 72420
gtcctggtag aatgggagct ggctatggag tatctttgtt ggagagtggg tatagggaaa 72480
cggagagaga gagaaagttg cagggggtgc gggagatgga tagctgcaga gaaggcaagg 72540
gcagggaaag tggaaacaaa tggcagtgag actcctggaa ggtgctggcc aggggcatgg 72600
catggcatgt tctgttaagc aaggaaagga ctagaaaggg gccatgattt tggctgggca 72660
cttatcctcc tcacaacagg acgcatttgt gtcatggctt actcttaaga atgactgacg 72720
tgtcagaata gcaaatatga aaatgattga taacacctag cattggtgag atttgcaggg 72780
ataactagct ggcctcttaa atctatagat aggaatgtaa acagaaacaa actttttata 72840
gggaaaagat atctaggaca taatgattaa tgaaaagaaa aaaattccta cctatcgaaa 72900
aacgtgaatt caggcagcaa acacacatgc atgtatacac atacacacgt gcacacacgc 72960
atacacacac aatctggtag gctgtatact accagtttag caggttgtta cctctgggat 73020
gcagtcactc ctttttgttg tgtatatttg tgaaatgatt tctttcaatt tttgagacag 73080
ggtctcactc tgttgcccag gctggagtgc agtggcgtga cgtcagctct ctgcaacttt 73140
cacttcccgg gctcaagcga tcctccaacc tcagtctcct gagtagctgg gactacagga 73200
gtgagccacc atgctcggct aatttttttt ttttttttgg gtagagaggg agtttgccca 73260
tgttgcccag gctggtcttg aactcctaag ctcaaagcaa tcctcctgcc tcggcctccc 73320
aaaagtgctg ggttacagg agtgtgccac tgcacctggc cattattatg gaaaatttta 73380
ggcgtataca aaagtagaga cagtggtgtc ttacatgctc atgaacccat gatccagtga 73440
catccgttaa tggcattttg gaatcatatt tcatctgttt ttgtcctcaa atgttttgaa 73500
gcaaatttca gcattacatc atttcactct taaatatctc agtatggttc tctaatagtt 73560
gaagactcca tttacattta tataaggagc ataatttaca cttgtgtaac ccaaaggaat 73620
gaccaagcct gtgcttctct ccccagatag caaagccatt gtggatggga acctgaagct 73680
catcttgggt ctggtgtgga cgctgatcct ccactactcc atctccatgc ccgtgtggga 73740
ggatgaaggg gatgatgatg ccaagaagca gacgccaaag cagaggctgc tggggtggat 73800
tcagaacaag atcccctact tgcccatcac caactttaac cagaactggc aagacggcaa 73860

-continued agccctggga gccctggtag acagctgtgc tccaggtaag tggccagggc tgcctaaacc 73920
atctgtccag gatgggggtg tgtgggtccc aaacattctg gttttcaacg ggaatgctat 73980
ctttgctttg attagcgtat ttctccaggt cttagcccat tataagccca ttataaggaa 74040
actaaaactg gctctgtgta cccttccaag ggcagatttt ctaggtatat ccatagacat 74100
gtttgagcat caagttgagt cttttatcca aattccaatg aaggagttgg tgcttagaag 74160
caagacttgg gtttaggttc cagactccaa aatcctgtgt cttcccacat tggtgctcag 74220
tttctcattg gatttggaga aacatttggt cctattaggt ggcttggcat gaaaatctga 74280
aaacttccat ggagtggaaa gtacccattt ttattaacca ctggtttgac tatatatggc 74340
attctccacc cttttctttc tgtgttgctg tgaaatagca tttggtcagg atccagttgg 74400
agccttttcc acccttgatg ggctgctcat ttcttagtgg ttgagtgtat atgaaggttg 74460
taattattcc cactggaggg tttagattga tgggtagagt ttgctggtac acactcagta 74520
gaaagaccag agtcagagtt tacacacacc ccctaaagtt gattttaata aaaaaaaaag 74580
gtattaatca tattttccat ttactgtgta ttctgtattt actgggcaca ttagtattta 74640
gttagttagt ggttcttgac atactcaaag cagaactagt gtcagttggg taggggaggg 74700
ctgaaggcct cattcttact tgagagccta taagttggtg tcatccagga aaaattcaaa 74760
gtgcagcatt aattgatttc ctaatatcct cttctttact tccatttaag gacacatttt 74820
aggatacctc tttccaattt aaacctggga gtttttactc tagtccttta cctcatgtgc 74880
ttacaaaggc ttttaagata attctaggtt tgtgcctttg agcaagtgga tttttgaatc 74940
acacaggatg ctattctaga ctttttagat atatccagga atagagtaaa aaataaaatc 75000
cctcctgcat aaaggcacca ggctttttcc aagctttgtt tattttttaa caccacttct 75060
tcaaggaatg gataatcccc atcttcatgc aagaacatag cacccggagg agaagtctca 75120
gtaatggagg atagtttaca ccctggcaca ctcatacctg tgatactttt tgcctattaa 75180
atatatgatt tgctcagatt ttaggaaaaa atcattctct gaactaaaag aaaaaatggg 75240
gttagtttag gcacatggtt tcctttaatc tctttggtca gctaatgcta aaagaatctt 75300
ttgtgttctg ttaacaggtc tgtgcccaga ctgggaatcc tgggacccgc agaagcctgt 75360
ggataatgca cgagaagcca tgcagcaggc agatgactgg ctgggtgtcc cacaggtatg 75420
cacaagtgtg ccaggtcctg tgaggctgcc cccacccact agcttgttct gtggatgcct 75480
tcccgggtca ggcagcccga ccttcttggc attgagactt cagagagcat tgcctgtgat 75540
gctctctcat cttcctcagt ttacccataa taatagtagg ttctcattga ctcaggtgct 75600
tatagatctt agtgtgttgg tttaatgtag atcatccaga aattttcatg tcactcttct 75660
ttgtcacaca ctggcaaatt ttctagtatt tcttctctaa atattttgaa gactaccttt 75720
aaaccccaga ctacaaatat ggaccctaac tattaggttg agccataaga aattgatagt 75780
atttgaccat ttttcaatct acattttaaa aggtaatttt aatccaatag cttaagaaaa 75840
gtcacaggac ttaaaatttt tttttttttt tgagatggag tctcgctttg tcgcccaggc 75900
tggagtgcag tggtgtgatc tccactcact gcaacctctg cctcccgggt tcaagcaatt 75960
ctcctgcctc agcctcctga gtagctggga ttataggtgc gcaccaccac acctggctaa 76020
tttttgtatt tttagtagag acagggtttt accatgttgg tcaggctagt ctcgaactcc 76080
tgacctcgtg atctgcccgc ctcagcctcc caaagtgctg ggattacagg cgtgagccac 76140
tgtgcctggc cgacttaaaa cttttaaaaa catgtaagcc aggataatcc accattaatg 76200
gaaactgtgg aagaatctct atcacccata atcctatcac aggaatataa caagagaact 76260
cagaaatcaa ataagtcttg gataccatct acagtagtca cattgcttag ttgaagtctg 76320
atcttcctag ctgggaggaa aaccagtgtt ttctttccag aaactccctc taacagttag 76380
gcaccatgag tcccgtgtcc aaaggctagc cagggaagat tgcaggtagc cagtgccatg 76440
ggactgatgg cgtcactata ggctgcattg aggtctgagt tcagtgtatt ttgtaacagg 76500
gtcccttgga aggtagaaca acatgcctgt ttctttggtt tggttttgga gtcatgtctc 76560
tcctacatgg ctcattggtt tcttggctcg tccaccctca ggaagtggtg tggtgtgttt 76620
ttcatctccg cttaaaccta aaccgtctcc tttttacgtt cacgtgatgt tggcatgggt 76680
gaagttgttg aaggagctgc tgggaagaaa tgccaaatcg acacacatcc tactttttat 76740
ggaatgtatt gaaggcgact gttcaaaccc aagtagctct tttgttcctg caggctaatg 76800
gtcagaatgt tttctggtgc tttttatcac atggggaggg aagttggaca catctgttgt 76860
tcattgcaca tggttaacct ggtccatgag acagagcctc tgttcatctg aggaagtgtg 76920
atttacctcc ttagcaccat tactggaggc agggaggact ctgcaagctg tttagggctg 76980
ggtcagatga tggtactgaa actgaggtgg tggcaccttc agggaagtca cctgtccagg 77040
atgggtctag tcttgctcct aagctgaata tcaagagaag ttcacccatt ccctattttt 77100 ttttttttt tttgagatgg agtcttgctc tgtcacatag gctggagtgc agtggcacga 77160
tctcagctca ctgcaacctc cgcctcctag gtacaagcga ttctcctgtc tcagcctccc 77220
gagtagctgg gactgcaggt gtatgccacc atgcctggct aattttgtat ttttagtaga 77280
aatggggttt caccatgttg gccaggcttg tcttgaactc ctgacctcgt gatccaccca 77340
cctcggcctc ccaaagtgct gggattacag gtgtgagcta ctgcgtctgg cctttttttt 77400 tttttaaag agacagcgtc ttactcctct gttacccagg ctggagtgca gtggcatgat 77460
ctcggttcac tgaaacctcc acctgctggg ttcaagccat cctcctgcct cagcctccct 77520
agtagctggg attacaggtg tctgccacca cactgggcta atttttgtat ttttagtaga 77580
gactgggttt taccatgttg gccaggcttg tctcgaactc ctgacctcaa gtgatttctc 77640
ttgtcttggc ctcctaaagt gatgggatta cagtcatgag ctaccacgcc tggcttccct 77700 attttttaa tggctcctaa tatattgaga tcacatatct aatatttaca tgttatttct 77760
tttttattta cctttttaa ttagtagagt taatacagat acagaccatg agtatacaag 77820
caaaggaaaa agctggttaa cctgtgcact tttttgtaac atgctctaat cccatgtgtg 77880
cttgtttctt cattttcctg ccttgctata gcttatcctt ttatcatttt tgaaattttg 77940
accagaggag taaatggact tttggggaat ggggaggaca atgaactttt ggaagttaca 78000
tgcagaattt tttggagagg ggcccctagc tttcaaaggg gtctgcaatt tctcaaaaat 78060
ggttaaaaac actgatattg gtgtgttggt ttaaagtaat ttcacttaat tgagaagctg 78120
actcagtttc ttaatatttg tagtgcttgg tttaagaggc atttgcaaac acttcaatag 78180
ttgcaaagtg atgtgttctg ggtgttcatc caccatgtca ttatcctagg tcatcactcc 78240
tgaagaaatc attcacccgg atgtggacga gcactcagtt atgacttacc tgtcccagtt 78300
ccccaaagcc aagctcaagc cgggggctcc tctcaaaccc aaactcaacc cgaagaaagc 78360
cagggcctat ggcagaggtg agtgctggtc ctctggtgtt gtattggaga catgtcctct 78420
ggtgttggag atgatttcat ggcttcaaga gtgatgttct tagaatcaaa aatagatagg 78480
tgtaatcctc aaagagaccc caagcctcct ttgtaacaca ttttatgact gttttattct 78540
gccttgtttt tctaaggctt taagaaatgt ttctgcttag atggaaaggg caagtttgct 78600
gcttggtgat tttagtgcag tagcccattg ctcccatttt tcagaagagg aatcgcgggg 78660
tagggagtcg ggggagtttg gtcttgcccc agatcaccac agtcagtgat gggggtgggc 78720
catctggctg ctgattcatt tctccttctg ttacactaag cctgcctcag atttccagcc 78780
ggagtgggag ctattgttaa cccctggcag atacttcctt gctaagacat cctgtttatg 78840
actgcgaggc agctgcggaa caccgttttg ctcagaacat tatagtgggt agaagccatt 78900
tcaaggcatt tggtgttgtg attggcacct gacttcaagc acactagctt tgtgaagaga 78960
acagttacat ggctgcaaag tgtggtttct ggtgaagatc aacatggcca gatacaactt 79020
aatgcctttt ctatgggggga ggggaaggag tgcattttat ttctcatttt tcataattaa 79080
gaaaatatcg gccgggtgtg atggttcatg cctataatct cagcactttg agaggccgag 79140
gcgggcagat cacctgaggt caggagttgg agaccagcct ggccaacatg gtgaaaccct 79200
gtctctacaa aaaatacaaa aattagccag gcatggtggc gggtgcctgt aatcccagct 79260
attcaggagg ctgaggcagg agaatcgctt gaacccagga ggcagaggtt gcatcgagcc 79320
gagatcttgc cactgcactc cagcctgggt gacagagtgc gtgagcctcc gtctcaaaaa 79380
aaaaaaacga gaaagaaaat gttatcccag tgggataata gttatacaca cagtattctg 79440
tatatcttct cccagaattg acagttgtta ccattctagc ttaatagttt tctcttgccc 79500
tttgtgtgtg tttgcatatg tgttcatgtg tatgattgct gaattatttg aaaataagtt 79560
gcaagcatgg tgacagttct gtcctcagta catcactaag cttctcctaa gaataggata 79620
tcctctagca taaccacagt attcattgcc acatgtaaga aaattaacaa tagtttcata 79680
taatctaata ttcagtttgt tgtagaattt ctctattgtc ctaagattat cttttatagt 79740
tgttgctgtt ttacaaacta agatctgatt aaggttcact tactacattt gtttgttatt 79800
tctctttaga ctcttttcat gctaaataat ttccccaaac tttttttttt tttttttaa 79860
atgacactga ctttctgaat agttaagggc atgtgtcttg taggatgttc cttccctaca 79920
aatgttccct ttgaataaag tattttcctg cttggtatca gcttagtctt tttttttttt 79980
tttttttttg agagtcttgc tctgtcgccc aggctggagt gcagtggcac gatctcagct 80040
cactgcaacc tctgcctcct gggttcaagc gatcctcctg cctcagcctc ccgagtagct 80100
gggattacag gcatccacca ccatgcctgg ctaatttttg tatttttagt agagatgggg 80160
tttcaccatg ttggccaggc tggtctccaa ctcctggcct caggtgatct gcccggctcg 80220
gcctcccaat ccgcttattc ttaagacgac acatggctag ggcagtgatg ctgaccacgt 80280
gctgttctca cctcagtggt cgagtcttct catctgactt tttgggcatg atttagaccg 80340
gcagatagtt ctggaacaaa ccccttacca tttgaggttc cgtttgcagt gggttgtgag 80400
gtgtgtgaga catcacttgt gttatgtagg gactagggac ttcaaagccc tcctcccatt 80460
cacagtcact tgaaggctgg catgtcctca ctttctttaa aagtgctttc tttggccggg 80520
cttggtggct cacacctgta atcctagcac tttggaggct gaggcaggca gatcacaagg 80580
tcagaagatt gagaccatcc tggctaacaa ggtgaaaccc catctctact aaaaatacaa 80640
aaattagctt ggcgtggtgg tacaagcctg tagtcccagc tactcgggag gctgaggcag 80700
gagaattgct tgaacctggg aggcggaggt tgcagtgagc cgagatcgcg ccactgcact 80760
ccagcctggg tgacagaacg agactctgtc tcaaaaaaaa aaaaaaaaaa gtgctttctt 80820
taaggcatac cacaggtggt ggctggaatg aggaatctct gactttaaag gttatgcttc 80880
cttaatgaca aaacagttgc aaacaaccaa ttaaatcctt tgtcaaccag attggtcaaa 80940
tggactgaat ctaatcaagg catagtgtat gtttgtaata accttatcac tggccatccg 81000
gcttccctgt tgttaatgtg agacggtttc ctttcacggt gctattttct agaaaatgat 81060
cacttgttat ggttcaggaa tgtggctggt cattgccatt tccttcatct gcctcttagc 81120
aagtgtggtg cacttgtaga ggaaacacac ccttttaaaa aaaaattttt ttttatatgt 81180
gtgctttttg catttttta attgtgggaa aatatccata acataaaatt cactatttta 81240
accattttta agtgtggcat taagtgtatt cacgttgttg tgcaaccgcc actgctatcc 81300
atctccagaa ctttttcaac ttcccaaact gaaactccat actcattaaa caatagcgcc 81360
ccattctccc ctctcctctg ctcctggtaa cctttattct actccctgtc tctatgaatt 81420
tgcttattct agggacctcc tagaagtgaa atcatatgct gtctgttagg tacctcctag 81480
aagtggaatc atacgctgtc tgttaggtac ctcctagaag tagaatcata tgctgtcttt 81540
ttttctctgg cttacttcat ttgtcatatg ttttcagggt tcaccatgtt gtagcatgtg 81600
ttagaatttc attccttttt aaggctgaat aatattcctt tgtacgtgta tatcacattt 81660
tgcttataca ttcgtctgct gatagacatt tgggttgtta cattcttttg gctattgtga 81720
ataatgctgc tatgaaaaca tgggtgtaca agtgctgttt gagaccctgc tttcaattct 81780
tttagggata tacccagaag tggaattggt ggatcatatg gtaattctat atgcagctta 81840
tttttcagga ggaagtggcc tcactctgct ttttaaagta ggagacaaaa tggtcatatt 81900
aggtgacagg gtcacaaggc cacatgggtg gggctgtgag atatgtccct gtcatgtggt 81960
tagatgaaag ccggggtcag ttttggtctt ctctgtgtga ccacattgct tcatttctgc 82020
cacctgagcc caggaagaga gaccgtttca tcttctagtt tctaaaagat ttgaaagtgt 82080
tgttttattt tttatttcct gattgtttaa tagatgccag ttgccagcca gttagcattt 82140
gttgatccat tcactgagtc ccaccttgct tagttctagt gggttgaaag gagagagggc 82200
tggggtgagg tggacctcca gccacaaaca gatctttgtg gtgggcttcc ttgcagggtt 82260
agctatgtga aaagcattcg tccatgagct aatcagaaat ctttgtaaaa atctagttct 82320
ctatgaagca tttactgtag agcaatcctt aagcaccctt ctatctgagt aatcagaggg 82380
gtaccagttg tctcctttca tggtaagcaa agctccgcag aagtttacag agttggggtg 82440
tggttcaact ttctaaccag ccatggttag ccacgggtga ccaacccaag cccagacctt 82500
tgacaagctg cagagtacgt tgtttcttag gctgctggag tcacacgaag tggaactttt 82560
agtattttag gtgcatgttt atttacttac ttatttttgt tgttgtcgtt ttcagataga 82620
gtctcactct ctctctctgt gtgtggagtg tcgtgatgcc atcacggcta actgcagcct 82680
tgaccttctg ggctcaagtg attctccctc ctcagcttcc ctagtagttc ggaccacagg 82740
tgtgcaccac catgtccagc tttttttttt tttaatattt tagtttgaga ccagcctggc 82800
catgttgccc aggctggtct caaaatcctg agctcaagca atccccctgc cttggccccc 82860
tcaaagtgct gggattacag gcatgagcca ccatgcttgg ctattaggtg tatgtttaaa 82920
tccatttgct tatatcagtt acataacctg agtgttatgt aaatcttaag caaaagaaaa 82980
atatatgaaa taaaaattga aactcacttc ccaactgcca atctcattcc tgccttcaaa 83040
gtttcaggta tttatttcta gcctttttc tatgctgagt taaactgtgt atcttctttg 83100
ctttgcattt cttactgagc agtgtgggaa ggctaccttt taaaatttat ttgtagttct 83160
ttataatttt tacctttctt tttaggcaga aagattatct tattatataa cagtctacgg 83220
ccatttttc ttaaactaaa ttattgggaa atgaatagaa atccagagta tagtaacaaa 83280
tgacctagtg tctttaacag attggtagct aggaaaagga agtggtggag agacagccgg 83340

```
agattaaatg agacttaaga gacttagcaa ccatttgtaa tatgtgacct tatttggatc    83400
ctattcaaac taatggttaa aaaaattcat gatagctggg catggtggct cacgcctgta    83460
atcccagtac tttgggaggc tgaggtgggt ggatcacgag gtcaggagat cgagaccatc    83520
ctggccaacg tggtgaaacc cccttttacca aaaatacaaa aattagctgg gcatggcggc    83580
atgtgcctgt agtcccagct acttgggagg ctgaggcagg aaaatcgctt gaacctggga    83640
ggtggaggtt gcagtgaacc gagatggcgc cactgcactc caggctggcg acagagctag    83700
actctgtctc aaacaaacaa acaaacaaat aaaaattcat gataaagcag cagctcaagg    83760
tgctgtaaga aattcatgat atttataaga taattgaaaa tttgaacact gaatatttga    83820
cattaaggaa ttattttttt ttatatggta tcgatattgt gggtactttg caagtatctt    83880
ttaaggatac atagtgattg tggataaaaa atctgaggtc taggatttgt gtcaaaataa    83940
tacaggaagg ggaggtggcg ggagtgaagg tgaaacaaga ccagctgtga gttgatagtt    84000
gttgaagctg ggtacaggag gtccactgtg cagtgctctc tacatctgtg tttgtaattc    84060
tttttttttt ttgagacgga gtctcactct gtcgcccagg ctggagtgca gtggcatgat    84120
ctcggcccac tgcaacctct gctgcccggg ttcaagcgtt ctcctgcctc agcctgccaa    84180
gtagctggga ttacaggcgc ccaccaccac acccggctaa ttttgtagtt ttagtagaga    84240
tggggtttca ccatcttggc caggctggtc ttgaactcct gacctcgtga tccacctgcc    84300
tcggcctccc gaagtgttgg gattacaggt gtgagccact gcgcccagcc ttttttttga    84360
gacagagttt cgctcttgtt gcccaggctg gagtgcaatg gcacgatctc ggctcactgc    84420
aacctctgcc tcctggattc aagtaattct cctgcctcag cctcccaagt agctgggatt    84480
acaggcatgc accaccacac cccgccaatt ttgtattttt agtagagaca aggttacacc    84540
atgttggtca ggctggtctt gaactgctga ccttgggtga tctgcccacc ttggcctcga    84600
aagtgctgag attacaggtg tgaaccacgg cgcccagcct tttttttttt tttttttttt    84660
tgctgaagtt tcacttctgt ttcacaggtt ggagtgcaat ggtatgatct tggctcgctg    84720
caaccccgc ctctgcctcc tgggttcaag ggattctcct gcctcagcct cccgagtagc    84780
tgagattata ggcatctacc atcacacctg gctaattttt gtattttttag tagagacgga    84840
gtttcaccat gttggccagg ctggtctcga actcctgacc tcaggtaatc cacctgcctt    84900
ggcctcccaa attgctggaa ttacaggtgt gagccactgt gtccagccta gtttggaatt    84960
cttcataata aaaagctttt taaaaaggta atatttggac ttctgctcct gggaagatgg    85020
aataggactt ttcctaattc tttcttctaa ctacaactaa aaccctggg ctatacataa    85080
ggaaaacaca gggagcctct gaaaaaggat gaggcagacc aaccagggat cttgggactc    85140
gaggaatgac acagtactga gttccttggg tttactttgc tttatatatc ccagacttgg    85200
agccaaagaa agaagctgac aacctgaaaa tgccagtggg cacaaacaca gaaagtgcca    85260
acaaaagctc ccctgtccag ccagaagacc aggaaagggc agcccagtga ggcagaaaac    85320
ttaaagagtc actgctctac tccaggtcca caccatagaa aaaactatgc agccccacac    85380
ttacacccgc agaggtgaat ggggagccta ggctttgaca acagtctagc aataaggaag    85440
ccactctccg gggccatgga ggagcagtaa tgaggcactc ctacttcctc cagccagaac    85500
tcccaccttc acgcaccagt aatgagcccc ccaatcttga gcatcagtcg aggttgaatg    85560
gagagcctag acttcttccc ccactgttag taacaaggtg tgtacccttc cctcccctgc    85620
cacagtggta tcataaaatg ccagctacaa cagaacattt acagaagacc cagagtctca    85680
ttacatgata ccccaaatat ccagtttcaa aaaaaaaaag aaatcacttg tcataccaag    85740
```

aaccaggaag atctcaaact gaatgaaaaa gacagttgat gccaacactg aggtgataga 85800
gatgttagaa tcctatgaca aaaattttaa agcagccatt aaaaaaggct tcagtagcca 85860
ggcgtggtgg ctcactttgg gaggcttgta atcccaggac tttgggaggc cgaggcgggc 85920
agatcacctg aggtcaggaa ttcgatacca gcctgaccaa ccttatgaaa cccagtctct 85980
actaaaaata caaaaaatta gccaggtgag gtggtgggca cctgtaatcc cagctactcg 86040
ggaggctgag gcaggagaat cgcttgaaac tgggaggtgg aggttgcagt gagctgaggt 86100
catgccgttg ccctccagcc tgggcaagaa gagtgagact ccatctcaaa aaaaaaaaaa 86160
aaggcttcgg taggcagtta agaacaatca tgaaaaaaat gaaaaaatta aaaatctcaa 86220
caaagaaata caatgtccca gcaaaataat aataaaaatt taggagataa aaagaaccaa 86280
atggacattt tagaattgga aattgcagta actgaaataa aaacttattg gataagcgca 86340
atagcagggt ggaaggacag agaaaagaat ccttcaactg gacaacaatt ggttgttttg 86400
ttctgaggtg gagttttgct cttgtcaccc aggctagagt acagtggagt gatcttggct 86460
tactgcaacc tctgcctcct gggttcaagc tattctcctg cctcagcctc cctagtagct 86520
gggcttacag gtgcccacca ccacttctgg ctaatttttt tatttttagt agagacgtag 86580
tttcaccctg ttggcctggc tggtcttgaa ctcctgacct taggtgatcc acctcggtaa 86640
tccaccttag gtgatccaaa gtgctgggat tacaggtgtg agccactgga cccggcctct 86700
gtaagctttt ttctgtgttt aaaacttttc atttttgtac ttttaaaact tttttttttt 86760
tttaaacaca cacattagtc tagacttaca cagggtcagg atcatcatta tcactatctt 86820
ccacctccaa atcctgtccc actgtcccac tggtaggtcg tcaagagcag taatgtgtgg 86880
aaccgccgtc tcctataata acaatgcctt cttctagaat atttcctgaa ggacttgctt 86940
gaggctgctt tacagttaac ttaattttta aatagaagat gcccactcta aaatataatg 87000
ataaaaagta tagcatatta aatacataaa ccagtagcat tgtcatttat catcaagtat 87060
tatgtattga acataattgt ctgtgctata tatgtttcta tggccggtag cccagtgggt 87120
ttgtttatac cagcatcatc acaaatacat gagtaatgcg atgcgttact gtgacgtcag 87180
taggcaacag gaatttttttg gctctattta taatcttacg ggaccatcat tgtatgtgtg 87240
gactattttt gactgaaact tcattattta gcaaatgact atattagcaa ataaaattga 87300
gctgtatata atgaagaagt atgcattata accaagtggg gtttattgca gggatgcaag 87360
gcctcgttca ctattagaaa atcagtcaac agcctggctc ggtggctcac gcctgtaatc 87420
ccagcacttt gggaggccga ggtgggcgat gggcggatca tgaggtcagg agatcaagac 87480
catcctggct aacacggtga aaccctgtct ctactaaaaa tacaaaaaat tagctgggcg 87540
tggtggtggg tgcctgtagt cccagctact cgggaggctg aggcaggaga atggcatgaa 87600
cccgggaggc agagcttgca gtgagccaag attgtgccac cgcactgtag cctgggcgac 87660
agagcgagac tccgtctcaa aaaaaaaaaa aaaaagtcaa atagtaaaga taccacctct 87720
cctcaaattg tcattcaggt ttgatgcaat tgctgtcaaa atcccagcaa gagtttttgc 87780
agatagcaag attattattt taaaacctat atgaaaaggc aaaggaatta aagtagcaaa 87840
aacaattttg agaaagaagt acaacatgga ggaatcagcc ttcctgattt caagacttgc 87900
tgtatagcta cagaagtcca gattttgtag tattggtcaa aggatagaca ttatagatca 87960
gtgaaacaga attgcagccc cacacaaata tgcacaactg attattgaca aaggtgcaaa 88020
gataagtcat tgggggaaaa aaccttttcg gcacatggtg gcagagaaat tgaacatccc 88080

-continued

```
taggcaaaac aaaacaaaag caaaccccaa accaaaaaac aaaaaaccca tataactata  88140
aaactttgag aaaaaaacat agaagagaat ctttgagatc tagagctagg caaatagttc  88200
tcagatttga caccaaaaac atgatccatt aaaaaaaaat aagttggatt tcatcaaaat  88260
taaaaacttt ttaatgtttt aagaaggatg gtctgtctca aagactcaac atggtacatg  88320
gtggttggcc tttatgtgct gttgagggtt ttcctgcatt gaagggtgca ctcctgggtc  88380
acctactgtc ctgcaagaca agctgtctta gccctcacac tataaaagcc acccggacac  88440
cgtctcaaac agaactcaaa atgttgctga gactgggatc tgggggctgg attttacttt  88500
tacaaacaat ttaaaacttt ttacagttaa gaggatgaat atacaggcta aagactggga  88560
gaaaaaattt gcaaaccata tgtccaacag aacactagta tctagaacat gtagaaagaa  88620
ctctcaagtc ttagtcgtta aaaaacagac aaacatttaa ccaaacaacc caataagaaa  88680
atgggcaaaa gacataaaca gtttctgctg aagagaacgt ccatatgaca aaaaaacaca  88740
tcgaaatttg ttcagtatca ttaaccatga gaaaaatgcg aattaatcct agtacacact  88800
atcagaacgg ctaaaataaa aaatattaat actgataaca ctaaatgcag aacggatgga  88860
gagaaactga atctggatca ctcactcata cattgctggt gggaatgtaa aatggtgtag  88920
ctactttgga acactgtttg gtagtttctt aataaagaaa taggctgggc acagtgactc  88980
ccttctgtaa tcccagcact ttgggaggct gaggctggag gatcacttga gcccaggagt  89040
ttgagaccag cctgggcaac atagggagat tgcatctcta caaataattt ttaaaaatta  89100
tacaggtgtg gtggtatgca cctgtggtcc cagctactca ggagattgag gcaggaggat  89160
tgcctgagcc tgggaggtcg aggttgcagt gagccgtaat tgtgccactg tgctccagcc  89220
tgggctacag agtgagactt ggtctcaaaa caaaaacaaa aacaaaacct caaaaaacag  89280
tacatgcaac taccatatgg cccaacaatt gcactccttg gcatttatcc cagaggaatg  89340
aaaacttact gtatatgaga gccactgttt ttccttctat agtctcacag ctaaagaaaa  89400
aaaacttttc tcatcttctc tactactcct ctcagtattt cgcttccggt caccaaaatc  89460
tatggatttc tgtcccccat actgacaagt tctccaattt tatgtggaca acaagtaggt  89520
gtcctataat caattccctt caattctgac actatctacc tgaagttagt gcagacgcca  89580
ttaagggctc ggtccctcaa aactgcccct gacttcagag gccagtcaga agtggtgggt  89640
cctcaggtaa cccacagctt ctgtccaggt ttgctacaaa tcagaaggtc ccattacccc  89700
ttcctcatgt tatgttattt gctagagtgg ctcacagaac tcagggaaac acttaccttt  89760
agcagttgtg tagtgaagga tatgatagag gatacagatg atgccccaga tgaagaggtg  89820
cacggggcaa agtttagagg cgttttgaac acaggagcgt ctgtccccat gaagttgggg  89880
tgggccatcc tcttggcaca tggatgtgtt caccaaccca gaagctctct aaactccata  89940
cttcagggat gtggaggcta agtcacgtag gcgtgattga cattaactga gactacagtt  90000
cctctccctt ccctgtagga tggggagtgg ggccgaaagt tctaagcttc tgatcatgac  90060
ttggtctttc tgttgattag ccacatcttg aaagctatcc gggagcccac taagagttgc  90120
ctgattagaa cagaagatgc tcttgtcacc aaggacattc caaggggttt aggaactctg  90180
gaaccagggg cagagaccta tatatataat ttcttactat tttatactta tgttcacaca  90240
cacacacaca cacacacaca cccctatgca cagatgttta cagcagcttt attggtaaga  90300
gacaactaga aacaacccag atgttcttca gtgggcgaat ggttaaactg tggtacatct  90360
ataccatgga atattagcta ctcagcaata aaaaggaaaa aaaccattga cagaagcaac  90420
aacctgggtg aacctgtaga caattatatg tagtgaaaaa ggccactcct aaaaggttac  90480
```

atagttatga ttccattgat gtgacgttac cgaaataata aaattacagt gtggagaacg 90540
ggttagtggt tatcagggct aaggagagtg tgggtgtggt tatgcaaggg cagcaggagg 90600
gctccctgtg ctaaagggaa tgttctctat tttgattgta tcaacgtcaa taccctggtt 90660
gtgagattga gtcatagctt tttaccgtgt taccactggg gaaactattt tgagatggag 90720
tcatgctctg ccgcctagga tgcgatctgg gctcactgca acctccacct ccctggttca 90780
agcaattctc ctgcctcagc ctcccaagta gctgggatta caggcatgtg ccaccacgtt 90840
gtatttttag tagagacagg gtttcaccat gttggccagg ctggtcttga acgcctgact 90900
tcaggtgatc cacctgcctc agcctcccaa agtgctggga ttacaggcat gagccaccgc 90960
tcccagcaag ggcattgttt cttacaccta caggtaaaat ctgtctcgat gaatttgctc 91020
gatcatctta aaataaaaag gttaattaaa aaaatgattg aatataattt ttaaaaatgt 91080
caggcaatac aataaatgct gtttaatgag aaataagctt cgctcctccc tgctgtgttg 91140
cttccatcaa ggcaagctct gctactactt attaaccaca ttatttccac aattttatat 91200
agactcctga ctgaggttct ctgaatatca aaattggata ttacttcaat aacatgggca 91260
aaattaaggc tttcgacctg cctgattttc cttgtcaagg cagtttgtcc ccatttccca 91320
catgggatct gcagggctgg gtcccatctc tcagttccct gaaagagatg cagtgggcga 91380
tggctcatga cacaccctcg cctggcttct aacatgtctg tgtaaacctg tggcaggaat 91440
cgagcccact ggaaacatgg tgaagcagcc agccaagttc actgtggaca ccatcagcgc 91500
cgggcaagga gacgtgatgg tgtttgttga ggacccagaa gggaacaaag aggaggtatg 91560
ttggaggatg ctgcctctcc tttccagcac ctcatggagc ttttggggct tgtaatgcgg 91620
ccagggactg tgcctccatt ttcatttcag ctcacaacca aaagtgtttt ttaccaaaag 91680
gatactgagg cttatagctg ttaaagtaac ctgcccaaga ggtgagcctt gaaatcaaat 91740
ttaaattgat tgccagggac acagtgttta atgaaataaa ggatactttg gatttagcaa 91800
aggtgccttg tcagttgagg tttatgtatg tatttattta tttatttatt tatttattga 91860
gacagagttt cactcctgtt gcccgggttg gagtgcagtg gcacaatctt ggctcacggc 91920
aacattcacc tactgggttc aggcgattct cctgcctcag cccggctaat ttttgtaacc 91980
caagtaactg ggattacagg gacctgccac cacgcctggc taatttttgt atttttagta 92040
gagacagggt ttcaccacat tggccaggct ggtcttgaac tcctgacctc aggtgatcca 92100
cctgcctctg cctcccaaac tgctgggatt acaggtgtga gccaccgtgc ccagcctcag 92160
ttgaggtttt atatactgat ggccagaata ataagagtct tgccctgctc tcttcccaca 92220
ttggccattc tttggttcct ccctcagagc ctttgcacat gctgttcttt ctgtcactta 92280
ttttcgtagg accatatttt attcttggca tttagcataa tttgcaattc taagtttaca 92340
gatggatggt ccatttcccc caccggggca gggattgtat ctgacttgct catgttttat 92400
ttttagtacc taacactggg ccctgcattt cataagcttt caatgaacta ttgagtggat 92460
aaaggtttaa gtttcttgct tcatattctc tcttacctag agagtgccag cctgacactg 92520
gacactggag agtcctgact ctgttatgcc tctgtgctgc atggttttgt ttctgtgact 92580
tcaagcagtt tctctctagg ggcgttgtgc aagagggaca ggagctcgcc agcaccttca 92640
gtgtttccga cctggcagct cctgcagaac ccctgctgac acagcatgct ccttactcac 92700
acccggcacc ttttctaact gttgcccacc ttccctccta ggcacaagtg acccctgaca 92760
gtgacaagaa caagacatac tctgtggagt atctgcccaa ggtcaccggg ctacacaaag 92820

-continued taagatgaag cagcatggct gtggcttggg ctgctctggg gctaggagaa gaaagatagc 92880
ccaggaagaa gagtgttttt cttaagtgaa tttctgattt tcctttctga ttatagaagg 92940
atctatgctc atgatagaaa attggaatca ctaggattcc ctctactagc taggatgagt 93000
tgtttgcaat gtcgtaagat ttttccaact ccatctaggt aactaatggt tgcagctgtg 93060
tgtctggagt gtagatgctg tggtgactac actatagatg ggttctttgt ccttgattct 93120
ttttttggag acagggtctt gctctgtcac ccaagctgga gtgcagtggt gtggtctcag 93180
ctcactgcaa cccccgcctc ctgggctcaa gcgatcctct cacctcagcc tcccaagtag 93240
gtgggattat aggcacccac aaccactccc agctaatttt tgcattttta gtagagacca 93300
ggtttcacca ggtcacctag actgttcttg aactcctgac ctcaaactat cctcctgcct 93360
cagcctccca aagtgctggg attatagaca tgagccacca caccctgctg gctctttgtc 93420
cttaatgctt tcttaagaac tctccttgga ggtgctctgg aggagctgtc agcattgaag 93480
gctgaggatg gagtagttca gctgaatata gtagagggaa atggccctct cagcacctgg 93540
agaaatgata gggattgagg cctcaggctc tttgtcttgg cagcctttcg agttctgttt 93600
gagatgacat ccaggtgacc tatagggcaa gggctgagag agcctgtctt gcaggagagt 93660
ggggtgaccc aggagtacac ttttcattgg aagaaagccc tcaacagcac ataaaggcca 93720
atcccatcat gtacctgccc agactttgga atacagactg tactcaccac cttgggcttt 93780
agtgaattca cctggaatga tggccttagc gttctcttag actcttagac tatgatgcat 93840
ttggagtaaa tgctcttgaa gggagcattt ataatgtaat taattaattc cagtcaagta 93900
taggttcaca tgaaacccaa cccaattacc ccccaaaaat ttcagagatg agaacagtga 93960
ctcaagtttt agatggaaat cattctactt tgtcccaaat ccatgtatct aagaatgatt 94020
ttcgtccctt gaaaaaacag tttggctgtg gatttgaaat cctggaactg catattttat 94080
tctgagggat agtggcccat tcagcccccg aaaggactca atgtccagag attgaaatgt 94140
gtttgtttcc tattaaagag actaagtgta tataaggtca gcatttttat tttgctaaag 94200
gtgtgatgtc ccagacccag ctgtatggct gaaggggcca ggtgggagtc ccattcaggc 94260
tgttaaactt ggttccaggg ctccttattc tagacacctt gtgtgtgcca tcatgggagg 94320
gtaggagagg tgatcatcaa tgtatgtggc ttgatgtcag tcttgctggg cacagagaag 94380
tgattatgta tttctcacct atctgtcacc tataggtcac agtcctcttt gcaggacagc 94440
acatctccaa gagcccattt gaagtgagtg ttgacaaggc ccagggagat gccagtaaag 94500
tcactgcaaa aggtccaggg ttggaagctg tagggaacat cgccaataag cccacctact 94560
ttgacatcta tacggcaggt aacgtgcctc tcctccatgg atctgacctt tgcgctttct 94620
tccagaggct gaaatataat cctcggggac ttgaaggcct gaccttttgt cttttaaatc 94680
aaataaataa tcacaaagac aatttttttca aatgtgttat attagatttt tcaaaaccag 94740
cttttcttct ctaaaatact caggcttcac ttgaataaga catacttctt gaattgttgg 94800
cttcttttcc atgtagtaaa tagaaaatgc agaagaagga aacattcaac cataaaccct 94860
tcaaccccta gaaaatagtt gttaacatct tggtgtggac ctctctgagg gcctgtctcc 94920
tgtttacttg ttttgttgtt gttgttgggg gaacagagaa tcactctatt gcccagactg 94980
gagtgcagtg gcgtgatctt ggctcaacgc aacctccgcc tcctgggttc aagcgattct 95040
catacatcag cctctcaagt agctgggatt acaggcgtgc gccaccatgc ttggctaatt 95100
tttgtatttt ttttagtaga gacggatttc accatgttgg ccaggctggt ctcgaaatcc 95160
tgacctcaag tgatctaccc acctcggcct ctcgaagtgc tgggattaca agcatgagcc 95220
accacactgg tcctgtttgc attttgcact cagcagcagt gagctttcag agagggtgac 95280
ttgggctcat ggaatgcttg ctttcttgta ggagctggtg tgggtgacat tggtgtggag 95340
gtggaagatc cccaggggaa gaacaccgtg gagttgctcg tggaagacaa aggaaaccag 95400
gtgtatcgat gtgtgtacaa acccatgcag cctggccctc acgtggtcaa gatcttcttt 95460
gctggggaca ctattcctaa gagtcccttc gttgtgcagg ttggggaagg tgagtgctgg 95520
gctgctggcc acatgtgctt ctcataggga agctgactgc acagctgggc agggaggcca 95580
ggaaaacagt cagggcccaa cattgacctt atgcctatcc cttttctgcc agggctactt 95640
cagcagtaag tggcttactt tgtcctcaat atattaatat taatatcttc tatgagccac 95700
gcagagacct aaatgctttg cttatattaa ctcatttact tctctccaaa acacatgtac 95760
aggagagtaa ttatcctcat ggagggaggt gggactgagg cagtgggagg actcggtagc 95820
ataactgaag ttagcagcag caacatgggc cctgcagcct ccattgcttg gcctttactg 95880
gcccaggcac ttaccatgac tgcatctaat cattgcacca gcctgtgtgt tgcaggtgct 95940
attattatcc ctagcttgca ggtggagatg ctgaggctta gatagcgtta ggtatcagta 96000
ctacaaggca tcagcagggc tagaaccaca gactctgttg gccttaccct taactactct 96060
gctaaactcc ctctggcgct gggggtacgc atttttctca aatgttagac tctctccctc 96120
tgactttgtt gcccctttttt ttctgttttg ttttgttttg ttttgttttc caactgtact 96180
accttttcta acccacactt gcctttccct gttctgtcct ctgaatctgc gtctgcagac 96240
gtggcttcct cttccgaatc ctacctctgg gccagcctgg accctgaagc tgttggcttc 96300
ctagttgaga ccactgggcc agaggcctct tgcttggtaa gggctggttg ggtgggactt 96360
ccttgccagt tctttgtgct gcttgtgaat gttagctggg cccgtgttct gtgtgatttt 96420
aggaaactct gtgcaggtgt tattattaca gcctgtccag ccggaaccca aacccactgt 96480
ctaattgcct ttaaacacat ctagggcttt tttagatggt gaaggagctg gtggtgccct 96540
tcagactcta gccccattta atgtttatat gaactcagca attactcttt tgatgttgag 96600
actgttgcac atgttcataa tttccatgag tgtgtgtgtg tttcttaaga cacattaaag 96660
ccctccgagg aagtcctgtc attgtattgt gactgacttc tggtatgacc aacttttctc 96720
cccttgacaa agaaaaaaca ggcaaaaaaa attctaacat attcctaagc aaagctcttt 96780
tttacataag agagcatttt gaatagcttt cctaattcta ctattgtttt ccaacctttc 96840
ctcactcgtg gacttccttt ttcttttctg gcctgtacat cctatactat ttagcattta 96900
atgaataacc tttttctttt aatttactaa catcctctct cccacctaaa tgattttaca 96960
tatgtaaaaa aaaaatatat atatatttgc aggggcgcgg tgggaaggat acagggtctc 97020
actctgtctt ttgggctgga gtgcagtggt accatcatgg ctcacttgta gcctcgacct 97080
cccaggctca aatgatcctc ccacttcagc ctcttgagta gctaagactg tagatgtgcg 97140
ccaccatgcc tggttacatt ttttaccctt tttttttctt tttctttttc tttttttttt 97200
tgttttgttt tgttttgaga cagagtctca ctctctcacc catgctggag tgtggtggtg 97260
tgatcttggc tcactgcagc ttctgcttcc ctggttcaag tgattcttgc ctcagccacc 97320
tgagtagctg ggactacagg tgcacaccac cacgcctggc taagtttttt tgtactttta 97380
gcagacacag ggtttcacta tgttggccag gctggtctcg aactcctgat gtcaagtgat 97440
ccacctgcct cggcctccca aaatgctggg tttacaggca taagccacca tgcctgacct 97500
aatttttcttt ttttttgtag aggtggggtc tcactctgtt gtccagactg gtcttaaacc 97560

-continued

```
cctggactca agcaatctcc ccgcctcagc ctcccaaagt gctgggttta cagatgtaaa  97620
ttattttatg ttaaaagaaa ctttatatca ctttcacaat ggaaaaccaa agtcacttgc  97680
cataaagtgc caccgtaagc ttatgttcat ccataaacca tctaaaatca tctctaactc  97740
caagggtatg tgtatgactc tttgggaagc agttgtttgc caaatagcca gctaaggcca  97800
ttgcaggaag gaggaaccag aggaggaatt accttccgtc tgtggagtag agtcccgtct  97860
tctggagtct gtgaccttcc tgtatagaga tttgtcaaat tttcagtgtt agatttggaa  97920
aggaaaagcc acttaataac atgacatttt ccccactagt ctcccgtttc tatttactga  97980
aaaggttgtc cgtgctgggc agaagattta ttctagggca taaaggtatc ttttatcaac  98040
ctctagatac catggaacag tagttctgtg gacatttcaa gtaaggcata ttggaagcta  98100
tcttcgccct taacttttag acttacaact ctaggttttc aagctagacc cggaaatgaa  98160
atcagcaatg gtgtttactg ctaattattg cctttatagc cacccacatt ctgaaggcct  98220
tgtaacagac agcacgaaaa gattggtctg cctcagccaa ggtggggctg aactggtctc  98280
tttccaagct gtgttggttg tttttgcctg gttgttcagg cggaagacaa caacatttag  98340
acacttaaaa atggctgacc caggttttgg aacccagaca ggcattttca agtactgcat  98400
tttccaagaa gacttgaaaa agtccagtct atccaattac tgagcccttg agtatggcag  98460
tgaggtttga ataatgtcca gcactcggcc ttaactccct ttcacaaatg aaaggttaaa  98520
tgctggaagc aggagcacag catggatttg ctgtgctctc ctgttttctt tgccaaagtc  98580
acttttctcc agtccttctg tggtgtcact ggacaaagtt atattgtgtc tgtatttgct  98640
agcctggtgt gctccctgag tgggacccct ggtcttgggc aactactgca tactatttgt  98700
gcaaagcaaa tattttcttg gcgggtggct ccaggttacc ttggctttca cgactctgac  98760
taaagaatga aagattgaat tgatgtcaaa actgtgcttg cagcctgcaa tccaaatgcc  98820
tgccgggcca gtggccgagg cctacaaccc aaaggcgtcc gtatccggga gaccacagat  98880
ttcaaggttg acaccaaagc tgcaggaagt ggggagctcg gtgtaaccat gaagggtcct  98940
agtaagtgtt cctttgtttc tctatctcag gtgtggtttt ggctaacttt gcagccatgg  99000
catatggatt tcatcccacg gccagttgtc ctcaataatc ccagaaggct atgtcaagga  99060
tttgaggcta tctgggctcc ttggggaaga cggcagtgat tgattagtaa tgtctgccct  99120
ggatgcggcc agtgggtggc ttgacagctt tacattacat caagacttct gggagtagaa  99180
aaagcagtga tgtaaaggag ttggggaaat gctgctgttg gaacaagtgg ctcatttttt  99240
attttagaca tctgggctca gagaggaagg ctcttgccta aggtcataca gcgtttgtaa  99300
tcatctgagc tggaattcaa gcacagtctc caaagccagt gattttccca ctacaggtta  99360
cattttatag agtatgaaat tatgtcaagt acttaattac tatgatcagt gcttatagaa  99420
ggagaataaa attccctaag attaagtttt ctttgtagat aaatgccatt tgtggaggta  99480
caggttaaac cctgcaaccc attctctctc cctcttttgg ggaaggagac agcagatgtg  99540
gggatgggtg tcttcacttt tttcgttgga acagagaagc atttcagcac ttctagtctc  99600
gggtgtagca gcctttggtg gttttactcc catgcctgtg gaatcttgag cttcctgtac  99660
caggattgct cttaccttct gtgttcccaa caggctgggg caggagcatt ctgagctcca  99720
gaaagttaat atttgacttc acagcaccag gctttgggtc aggctgtgcc ctgagggtag  99780
ccgaggttct agactgccca gacctggagt caagctgctt ggggactgtc ttccctccca  99840
gattattcca acaggagcca aggagggtgt gtgtgtgtgt gtgtgtgtgt gtgtgcacgc  99900
gcgtgcatgc ctctgcgtat gtgtgcgtac gtgtgtgttt tctcctgacc ttgaatactt  99960
```

-continued gcttgactca acggctttcc tggccaaacc tcagggctca acacaaaaca agttcctgcc 100020
tgatggctgg gtttggagtt tgcagcgtca catctaaaac ctgtcctctt gcagatagcg 100080
tctgaggact ttcttgcttt tgttgtccag ctttagatgg aaaagtatac gctggaacac 100140
tgaacctaaa actcatacca aatacttcta aaggtttact tcttccccag tttttgtggg 100200
ggactaggaa gggtagctat gattattggg aaatactgaa atgtgactgg atttatcttt 100260
atgcaggccc agggagttca ggacctcagg gcccctcgta gccaagcaag atttctaaag 100320
ccaattagct gggaaatcct ccatttcctc ataccttgaa gcagagatgg ctgtgttttt 100380
agctttgaaa taatctccca ggctttgagg ggagaggtcc catactctgg ggcagcccac 100440
ttggttttta tgtatggttt atgttttgtt cagtgtggct gcctctctgt tcttgtcctt 100500
ttgattctca ttttgggcct aggattgtgt tggaaagatt atctccttcc ttcccacaga 100560
gggtctggag gagctggtga agcagaaaga ctttctggat ggggtctacg cattcgagta 100620
ttaccccagc accccgggga gatacagcat tgccatcaca tggggggggac accacattcc 100680
aaagaggtga ggctcctgct gcagaggggt cttctctgga gggtgctcgg cccagggcgg 100740
actcatgggt agttgcttcc cgggctgcag gagggaaaga gatctgcttt gttgaaaact 100800
ttttttttt ttttttcgga gcagcacaga catttggcct gttctcaaaa gcagcagaaa 100860
gttgctgtgg ttttagctga cttgctttaa atcaaatgct ggtggttagg ggctggtggg 100920
aggcagggga ggcagaagga gcagttagag caaatgggct gtgtgtctag atgcccgcat 100980
ataaactgag attctctttt tcaatgaact cctttgttca tgaatgccac ggggcagaat 101040
ctgctgtggt ttacattaag accgtctacg tgagtgctgt caggggccaa gggacgcagt 101100
ctacagcttt gccttgtggg cattgcactt gcccctctgc gttctgtgtt ttccagctcc 101160
cctggaggtg caactttaaa ctccgaataa attcagttag ccttgagaaa tatttgggca 101220
ttattgggtt ccgaatacct accacgcttt tttttttaag cctcccatgc caaggttaca 101280
gcacattcat tcatgtatga gataaagccc attcaaccaa gttttctggt tatagcataa 101340
gcaggatata gtgtgtggac tctctcactt tccagggtca tagtctgggg aggcctgcac 101400
acaaaggtaa agggccagga ggctggtgca aagcagcgtg gcttgagtgc caacccagtg 101460
gccacctgag ctcccagaag cagtcacatt acattatatt gttgacataa cagtagctat 101520
gggtgagagg cctgcaggag gaagggcttg gctgcagttt gggatgccag atgaaaggat 101580
caggcaagtg gaaagaatgt gcaaaggaac tgcagcttat ggctatagtg acaccttact 101640
ttactcttct ttgatgcttc ttctattcct ttccctgtag ccccttttgaa gttcaagttg 101700
gccctgaagc gggtatgcag aaagtccgtg cttggggccc tgggctccat ggtgggattg 101760
tcgggcggtc agcggacttc gtggtagaat ccattggctc tgaagtgggg tctctgggta 101820
agtggacaca gctgaccagc atcttctgga ggactgagga ttacagggct tccgggctgt 101880
gtcaggctgg atgttggggc cttgcctagc ctcaatacct ttagcttcct ggcctcctgg 101940
ccaccctaag ccatctctgc gtgctgctgt acatttgcag ttgcctctga taccagcatt 102000
gattcattca ggagaccttg agggcagaaa ccttatgtgg gtattgtgcc taaaacaatg 102060
cttggaacgt agtaaacact tagcaaatag tgttgactga cctttatagt ttagatgaat 102120
gaatgaatga attttgctga aatttggatt tggaagataa atatttcctt tggagcacag 102180
ctgaagtata ttttaaatac atgtctaatg tatatatgat cattttatat caggagtcag 102240
ccagcttttt ctataaaagg ccagatggca aatattttcc acctgtgggc cttatggtct 102300

-continued ctgtcacagt tatttgactc tgccgttgta gcctgaaagc agctatagga atacgtaaac 102360
aaacgtgtgt ggccatgttc cagtaaaact ttatttgcaa aagtaagcaa tgggccagat 102420
gtggccttca gactgtcgtt tagcaacccg ttttaggtaa tagcaataag caaaagagaa 102480
aaataagaaa tcacatttaa ttttcccttc tagagagatg atatgaatcg tcttgtatat 102540
tcttagtcta gagataatat taagtctttt agtgtatcct tctagacttt tttctctata 102600
tatgcatgca aatattgatt tggtacagaa aatatcttag acaagtcttt atatctttat 102660
gcgtaaatat agggtatgcc ttcattttcc atagcttcca tggaattcca ttgtatggct 102720
ctatccattg tcaggctctt cagttatttc cagggttttg ctataaaaac agtgctgact 102780
gtgtatcctt ggtaattgcc ttcagataaa aacccagaag tggatttggt ggtgctaaga 102840
gtgggtgttg gttcaaggct tttgccacat gttgccacat ctccaacaga agggtttgct 102900
ggttggactt cccctgttgg atgatgataa aatacatata atgtatttaa tactatatat 102960
atatatatat atatatatcc tcctggcctc aagtgatcca cctgcctcgg ccctcccaaa 103020
gtgctgggat gacaggtgtg agccaccaca cccagcccag gcctacattt gaaaaaaaaa 103080
aaatatatat atattttcca ccccttccat ctctactgaa gacttaatga gcttggtttt 103140
ggaagaaagg gatacaaaca gatttcaatc ttctggccaa cacttggctt ttagggaggc 103200
agcgggaatg agctgtcgta acatagaata ggtgctttcc accatataac cagggagacc 103260
cttccacctc cacccccctag ggtttgccat tgaaggcccc tctcaggcaa agattgagta 103320
caacgaccag aatgatggat cgtgtgatgt caaatactgg cccaaggagc ctggcgaata 103380
tgctgttcac atcatgtgtg acgacgaaga catcaaggac agcccgtaca tggccttcat 103440
ccacccagcc acgggaggct acaaccctga tctggtgaat cagctgctgt gcttctgtct 103500
tcttgtccct ggcccctggt tcctcacccc catgcccgaa gttgccttaa gcagcatgtt 103560
gagagatggc agagaggaat catttggatt ttaggaagga aacaggcctg catttgtttg 103620
tttgtttgtt tgtttgtttg tttgttttga gacagactct tgctctgtcg cccaggctgg 103680
ggtacggtgg catgatcaca gctcactgga acctctgcct cctgggttca agtgattctc 103740
gtgccttagc ctcccaagta gctggaacta caggcatgtg ccaccacagc tggctaatct 103800
ttgtattgtt tagtagagat ggggtttcac catgttggcc aggctggtct cgaactcctg 103860
gcctcaagtg atccacccgc ctcggccctc ccaaagtgct gggattacag gtgtgagcct 103920
ccacacccag cccaggccta catttgaatc ctggtagtag cacttagcac ttttatagtg 103980
ttgggcaagt aacttaccta tctgactctt ggtgtcttcc tctataagac aggaatgata 104040
gtagtctctg cttctagaga gcttctagga tgattcagga ggtggcatgc ataaagaccg 104100
cctttggctt atgcctggcc catgcaggga gctccataag ctgttatttt cttgcaactc 104160
cggggatcat atgtcagtct tacagccatt ttctatagtt attatttcaa ggtgctccat 104220
agataaagga tttttttttc ctagttccgt gtctcttaag ttggagcaat gtttccaaga 104280
gtgtcctctc aaacccttag caggctgata agcatcaagt ctgagccagc ctggctgaca 104340
gggagttggc cccagaggcc acgtgtgcta ctgttggccc acacgggcag ctgtccatag 104400
gctgatgtca gtctgggctg gtagctaccc cgttttggcc aaatgatatt cctttgccct 104460
ctagggcaaa tgttgtccgt ggtaaagatt ctgagtcccc tcaaagtggg aacgttgaaa 104520
ctgggcatga ctagaggtct ctgccccagt tgttagaagt tctttaggtc aactcagaat 104580
aaggcaggga gcatgggtta gtttgggcat ggttttagaa caggggtttc caatattttg 104640
ccttccctgg gccacactgg aaggagaaga attgtcttgg gccacacata aaatactaat 104700
gatagccgat gaacaaaaac aaaaacaaaa aaaaaattgc aaaaaatttt ataacatttt 104760
aagaaagttt acaaatttgt gttgggctgc attcaaagcc atcctgggcc gcatgcgggc 104820
ttcaggccgt gggttggatt tgtttagaga gttttctccc ttatgaggga gagacatttg 104880
tttttaagtt acaacctact ttagcacttt acttcccata accaacctct tatgtggata 104940
ctgtaaaacc agacacaggt cattttgttc ttcccccacc ccctggttac ctgtctttgt 105000
ataagggttt agttggggca ttacacagaa agagacttac tatctgcctt tgcttcaggt 105060
tcgagcatac gggccaggtt tggagaaatc tggatgcatt gtcaacaacc tggccgagtt 105120
cactgtggat cctaaggatg ctggaaaagc tcccttaaag atatttgctc aggtaaattt 105180
cagggggcca cctgtgcagg taattgtcag gtaacaagat ctgaccacgt aatggcaagt 105240
tgctgagtcc atctgatctt cagtttcctc atctgcaccg tggaaatgat aagaagatta 105300
tcttataggg ttatgtgagg gttcagtgag actaccatgt agagtactgg gctttaaaaa 105360
aatcagcttt ctgatttata ttctgtggaa atgaggcttg tttgtttcag gttattctat 105420
aatgtctttt ggtgtggctg aagctgctga ggccatgggg ggagatttgt aaacaaggat 105480
ttaaaaagta tgtttattta atctaattga atttggccaa aggacttaaa tgcaggaatt 105540
gagtggccaa agctttgttt ttgggtcact tgctcttaat aactaaaaat aaataaatgc 105600
atgtcatatt ttgtcactgg ttgtcaccgt gttgtgaaaa tatggcacat tgtagttggt 105660
ccatgaagtt ttgttgtata agcaagtggt gacttggctg tcttgggagg ccacagtgac 105720
cctgtctgat agagacagtg tgagggccac ctctggtcct agctctggct tttttgcagg 105780
atggggaagg ccaacgcatt gacatccaga tgaagaaccg gatggacggc acatatgcat 105840
gctcatacac cccggtgaag gccatcaagc acaccattgc tgtggtctgg ggaggcgtga 105900
acatcccgca cagcccctac agggtaggtt gtgaggcaga atcctggctg ttttatggaa 105960
atgcctggtc atacaccagg tctgggatcc atgcctgaca gccaaggcag acatatggaa 106020
ggaacccatc cctggtgggc cttgaatgat ggaggggccc gaagggcaga gtgctccagc 106080
ctgctcagaa gaactatttc taacaatgtt ttttaatagt attttactgg gtccaagtgg 106140
aggagaactt gatgaccttc tccatgtctt ctctaggtca acatcgggca aggtagccat 106200
cctcagaagg tcaaagtgtt tgggccaggt gtggagagaa gtggtctgaa ggcaaatgaa 106260
cctacacact tcacggtgga ctgtactgag gctggggaag gtgagaaagg gctttgttca 106320
acccagtgat cattgctccg tggggaaggc agttcttttc ataacgtttc aatgcctttt 106380
gaactaggaa gtagtccatc tgaataggta atcatctact gagcctctga gtcattcctt 106440
agtgatatct ttgctaatcc atcatccctt tccccaaatc cttactcttt ctcaggtttc 106500
ttactagaaa cttcccaatt gctttttgag ggtgttaacc tgagctggaa gagattgcac 106560
aggacatgct gtttcttgta agctggtgct aataagctgg tctgttccag gtgatgtcag 106620
tgttggcatt aagtgtgatg cccgggtgtt aagtgaagat gaggaagacg tggattttga 106680
cattattcac aatgccaatg atacgttcac agtcaaatat gtgcctcctg ctgctgggcg 106740
atacactatc aaagttctct ttgcatctca ggtacgtggt ggggcctggg aggagatggg 106800
tggagtaggc ctggattctc tttggccact tgtgtgcatg tctcatctac tttttggtgt 106860
tttgttagta ttattatttt tgagatggag tctcactctt tcacccaagc tagagtgcag 106920
tggtgtgatc ttggctcact gcaacctctg cctcccaggt tcaagtgatc ctcccacctc 106980
agcctcccaa gtagctgggg actacaggct cataccacca cccagctaat ttttttttaa 107040
tttgttttta tttttttatt ttttttttga gatggagttt tgctcttgtt gcccaagctg 107100
gagtgcaatg gcatgatctt ggctcactgc aacctctgcc tcccgggttc aagtgattct 107160
cctgcctcag cctcccaagt agctgggatt acaggccacc acgcctggct aatttttttg 107220
tatttttata gaaatggggt ttcaccatgt tagccaggct ggtctcaaac ttctgacctc 107280
agatgatacg cctgccttgg cctcccaaag tgctgggatt ctaggtgtga gccaccgtgc 107340
ctggccactc agctaattgt tttgcatttt tagtagagac ggttgcccag actgctctcg 107400
agctcctgac ctcaggccca cctggcctcc caaagtgttg ggattatagg catgagccac 107460
cacatttggc ctcctttttg gtgttttact gacagggaag ttgtcttgag aacactgctc 107520
aatcgttttc tctctggctc cttacaacca agaaggaaaa aaaatttacc cagagctaaa 107580
ttattaccac tttctaacaa aagtgaggca gtgtgttcag tggttaaaag caggggtctg 107640
gagagagact agtttgtaat aaattttcat caatattttg gttgaaatgc agttagcttc 107700
tagatatgtt ctactttgat gcctttgaag caatgactgt ggtctccacc cttaaatttt 107760
tatagagaga ggtgatttga agtttcaggt atgcaatagt gaagataggg tgagcaggat 107820
cctgaaagag agaattttga aatcctaggg attaaaatta accttacata aaaatggaaa 107880
tcttagtaga atgttctgtg cctaaaggta gtggtcttga catccattta acctcttctg 107940
cctttattcc aatagtctgc aacattcttt ttgaagaatt ataatcattc tgtctctgat 108000
cacttcttgc atttccccag accttagctc tcagctgtcc ctggaggaca tttccttccc 108060
ccagccccat gtattattgt cgtttttggt tttattcttg ttggcatttt tcatcctgag 108120
tactcaacat tcagtattaa aggctcaaag tcctcgggtt tgtttgtgac atcagggatc 108180
caggcattag agagtgacct gttatagaag gccctttccc aatgctgggc ccttttggct 108240
tatcttaccc ttctgtttac ctgtggtaat agaagtctgc tcaccactcg ctaagtcaga 108300
gtgatgctaa ggttcaccct ttgttgaagg ctccctgagc tctggctgtt gcttcagggg 108360
ctttcctact aagactgtgt ctctgctaca ggaaatcccc gccagccctt tcagagtcaa 108420
agttgaccct tcccacgatg ccagcaaagt gaaggcagaa ggcccagggc tcagcaaagc 108480
aggtaagatg gcacgtctag gttgtcctgg gcccctctgc cagccggtgg cactgggcgt 108540
gtttcatcca cggccttgag gaacttcatc tccaccaaca ccaacaccaa gctggcaggt 108600
tttctgtgca gctctgatgc agcagtggct ggccaggccc gttgctggct gtcataatag 108660
acctggtgct gttgaacctg tctgacgggt tctcaaagtg aaactactcc agctggtctg 108720
tctcctcact tcacagtata tctttccagg tgtggaaaat gggaaaccga cccacttcac 108780
tgtctacacc aagggggctg ggaaagcccc gctcaacgtg cagttcaaca gccctcttcc 108840
tggcgatgca gtgaaggatt tggatatcat cgataattat gactactctc acacggttaa 108900
atatacaccc acccaacagg tagggtcctt ctcccctctg ctcccctggc ccccagccag 108960
gccccttct atgcagtcgg tgctgggtca ctgtggacac caaggggtgt gagaggtgct 109020
ctgccaaagt gctccctgat gggaggcagc tcctggcact ttgaacccct ctgggagcac 109080
ctataggaag cccaatgggt tctatcaggt gaactgcaga attccccaaa agcaagcagg 109140
aagctggtcc catatctcca cctttggttt gcattttatc agagaaatgc tcagttcttg 109200
atattcaggc cctaatatct atctttctgt tacacatgtg cacacatgtg cacacacaca 109260
cacatacaca cacacacgtg cattccctcg cggcctcacc agctgccttt tagtcttttc 109320
attaattacc cacagaaaaa gagctgctac acctttgtgt ttccttcctg gtccttttag 109380
cttagtttac ccttttttatg aggtgttgga atgaggtctt ttctcaaaga gccagttcag 109440
cctttcgtcc ctaaggccca gcacactatt tagggcagca aattattccc ctttacaaaa 109500
tgcaggattt cacatgtgat cttaccatct aggctggctt actctgatta tttcaggcca 109560
taagggcctt aaaactgcct ctctgtacaa gttaatgttt atttgtttaa aaacattaaa 109620
aaaaatttgt atcgtggtaa aatacacata acacaaaatt taccgtctta accattttta 109680
agtgtatagt tcattagtgt taagtgcatt cattatgtcg tgcacccatc accaccatcc 109740
atctccataa ttctttacat cttgtaaaac tgaagccctg tatccattat atttgtttaa 109800
aattttgttt cgcttcatgt tcacacctct ggggtctgga gagcagacat cctggcagaa 109860
aagtctggat tttaatactt aagcctagtg ttcgaagtgg ttgttccaag cctctgagat 109920
tcctttattc ttaagggaaa tgatcctgct gtgtttgaaa tgccatttgt aggagaagaa 109980
gggcaacgct ttctgcagaa gcactgctca gaagccttgc tcccgtctgg gtcctctcag 110040
cgaggagcag tcaagagtca agtggggaag aaagaggatt atagtgagga aggggtcatg 110100
gtgtaactgt cccctgagtt tgggggctgc actcccttgg agatggaatc cttactgtga 110160
gaacatccct gcagtgggag ggattccctg ggcgaaggga ttctgtgtgt cgtgttataa 110220
atgtggcccc ttacatccag gcttgctgct gtttgtgctt tcttccccaa atttttattt 110280
ttatttattt attttttaga caaaagtctt gctctgttgc ccaagctgga gtgcagtggc 110340
atgatctcag ctcactgcaa cctctgcctc ccaggttcaa gcgattctcc tgcctcagcc 110400
tcccgagcag gtgggattac aggcacatgc caccacacct ggctaatttt tgtatttttg 110460
gtagagacgg ggtttcgcca tgttggccag gctggtctcc aactcctggg ctgaggcaat 110520
cctttcacct cagcctccaa acctgcggat attacaggca tgagccactg cgcctgacct 110580
cagtatttgt ctttttgtga ctgatttatt tttcttccta tatgtcctcc atgttgtagc 110640
acgtgtcaga acttcattcc ttttcgaggc tgcattccac tgtatgtata tatgttttgc 110700
ttctctcttc gtctgttttt tgtttgtttt ttcttgagac tcgctctgtt cctcaagctg 110760
gagtggcact gtctcggctc actgcaacct ctgtctcctg ggttcaagtg attgtcctgc 110820
ctcagcctac cgagtagctg gaagtacagg cacgtgccac catgcccagc taatttttgt 110880
atttttagta tagatgtttc accatgttgg ccaaggtttc accatggggt ttcaccatgt 110940
tggccaggcc ggtcttgaat tcctgatctc aggtgatctg cccacctcag cctccgaaag 111000
tgctgggatt ataggcatga gccaccgcgc ccggccatct tcatttgttg aagaacattt 111060
gggttgcttc cgtcttttgt ctgttgtgaa taatgctggg tgtacaaata tctctttgag 111120
tctctgcatt taattcttgt gattataaac ccgaaatgga attgctggat catatggaaa 111180
tctcttttta atttttttgag aaactactat actgtattcc acagtggctg cactacttta 111240
cagtcctgcc aacagcatgc aagggtcctg gtttctccac atccttgcta acatttgttt 111300
tttttctgtt ttttttttt gttgttgttg ttgttgttga tagtgaccat cctgttgagt 111360
gtaagatggt gtcttattgt ggttttgatt tgcattttcc taatgattag tgatgctgat 111420
catcttttca tgtgcttatt ggtcctttgc atattttctt tggagaatta tctacttgcc 111480
catttttata tcaaccttct taattttatg ttgagtttta ggaattctcc atgtattctg 111540
gatattagtt ccttatcaga taaatgattt gcaaatatat tctctcactc cttggtttgc 111600
cttttcacgc cgttaacagt tctcgtgtgc aggttataaa cgcggcttct tatctccaga 111660
cttgctcttc ctgtgcttta aaataaaaaa tccaaaacaa aacattcatt attagtaatg 111720
ataaaactaa cacttttata gatagagcat tcttttctca tcaggccact caatagtaag 111780

-continued taggtaatta ttttcctgct gatggttctg agggttggtg ggagccttac tactgggtgc 111840
accacgctga atcttctttg ttgccaaatt ctccatattc tttaggagaa agcaccagaa 111900
agccatagct gtctgcgtac aatgactggg atcacaaggc catgacgtct tctaaaaaca 111960
ttttgtgact tctgctttat tctatgtcta tatgcctttt agtgttttgg ctgagccgtt 112020
agaaagtaag ttgcagatat caggacaggg tcagggtttg acctgcatcc ttggaaagga 112080
ctgcagaacc cagtacccca gacgtcccct gctgctggtt gaggcagaag tggagattag 112140
gagcctaggt ccggttttgt cccctttgaa gtaatgctgg agtgggaggc tccttacttc 112200
agagtcaccc caaggtcaca ttcatccagt tctctgatag cagcaggttt gagaactgct 112260
gccatgctga gtactcactt agggctttgt gtccggatgc tcccaggatg cattcaagga 112320
gccgggtggg ccttggtggc ggtcgttgcc accaagtggc aacatccaag ctgcttgaag 112380
ccacccacaa ccccacaacc aagagaagag aagaccaaag tcctcaggta aatcacaagt 112440
gtgaatgact tgcagggtgg cactggggtc cttcttgttg tttgttgctt ggagctgggt 112500
ttattgtttc attatttggg caacttgcaa ttctgcctat ttttctatgg caaagaacac 112560
attaaatctc tccttagatt gaatttcctt cccaccccca cccccagcac agagcctggc 112620
cctataagtg ctctgtgtgg attaatggct gtgagtgagc gaataaatga catggcgcct 112680
ggattcacaa gcggagatgg cctaagaacg ttgtaatctg gtagaggagt gatgccaaca 112740
cctcctcatt ctcctttgaa ctctgttttc tgaagagcag ctaaaagctc aagactgggc 112800
taaggaagtg tgcccttgga tgtggttaag agacctgggt cagcccagaa agccaccccc 112860
tgacacgggg gagggagcat actttgaggg ctgacaccca caggcacacc ttctcatggt 112920
agttttaggg tataacaggc tggaaatccc cagaaaggtg gctgcttggg catgggtgtg 112980
tcctggcctg gtgtgggcgc ttccccctca gaacacaggc tgtgccacgt ggggagccga 113040
ggtcctgcct gagtaaccca ggtccctgat tgctggtttt gctccctgac acctgcaggc 113100
ctgccactcc acctcgcaaa gtccctgagt gacagcttgc aggtgcttgc ctgcctgggg 113160
tggatgagtg atgtggatgg ctgtaggatc ctgtgagtcc cttgaggatg caaaagtaga 113220
gcgcgttttg ccttagagga atggacttgt tggcttgggg cttgaggacc ctcccagagg 113280
tcaaagactc ggttttatag aagggaagtg atttccctga ggactttggt cttctcttct 113340
cttggttgtg ggtggcttca agcagcttaa atttctcacc gcacgttccc ctgcgcagag 113400
cagtttgaga agctggtggc aatgtctcca ttacgtgctg tgctgggagc cactaggatt 113460
ggggaccact ccatgtagta ctctggcacc tttagaaatc cctgtgagct cacagaccct 113520
cacagagtaa cagcttctac cttgaaatgt tcttaacgtg gtggtcctgg ctgctcctgg 113580
agggccctaa aagggatggt gctgagggtg gctctctcag tcccatcctc ttctgagctg 113640
tctggtcagt gtcttgtgta tgtatatttt gaagaataag attcaggttt cagaagcatg 113700
tagaggagag tgaaactgtc ttgcagcctg cgaagtcgtg gcgaaatgca ctggccatca 113760
ctacccagac atccctcact tcatagccct gttggggaat aaacacagtc cattccttag 113820
ttggggcctc aggggacact ttaaaatgct gtaggcattg taggtgtaaa tctccgagat 113880
tttttccctc ccccttctta ggttatttaa ggtacagttc attttctatc tgagtttttg 113940
ttttgttttt gactggtaac aagagcatac tttcttttat gggatgggtg ggcttaactg 114000
gaagagggtt tttccctctc ttttttagca cttcagagaa gaggccagaa aactttatgc 114060
gggtgaggga ggaggtatcc ccaagacctc tggttagcct gaggtctgct tagtgagccc 114120
ctgaattgtt aggggctgtg gggaaacgga agctcgggaa gagttggcac gttgggaatg 114180
ccacgttggc tgaagtagcg agtcagtcct gccttaaaca gtacaaaaag gagacctttc 114240
ctgccccttg gctggctccc agctctgttg aatttgacct gtacacattt taccaggaaa 114300
tgttgttcac atgaggcagg gggccaattg gttttgtgtg cagtgcttaa aaatgctgga 114360
aaattaatcc tctcttcatt gatgcaacca gttttttttt ttttttcttg gcctttaccc 114420
ccttccttat tacaaaagga atgtgacaaa atatacatag gccaaatgct acaccctttt 114480
aacacttgat cagcaacagc tttcagcagg gcctgcattc cagcaaggct gctggattct 114540
tggggggaac tcgtctctcc ctcacacttt cctgttacat tatgcctggc cgattgtggt 114600
gaaggggatc ttgatctact gagacagcca tgagatttct tggagcctcg atttggaggg 114660
agggaacttg gccaaccatg gagagaagaa gccggctgtg tgccagcctg gaaccggcga 114720
gaggagagaa atggcgcaca catggctatc gcgtgccacc cggccacccg tgagggtgcc 114780
tgccaatcct gcaagcacca tctgccttca cacttgcaat tttattttct ttcacatgga 114840
aatggaagtt cagatattgt gcgatggtct tagcacaggt ctaggtgaac tcttgcaaat 114900
ccctgttgca gcctgggggc ctcaaactga ttcctaggac agaaatggtt ctgtttggtg 114960
agtggcccca ggcccagctg cactggctgg cactgggtat gatgatgggg aggtggtgtg 115020
gcagagcagc taggacacag atttgggggc catgggtatg aggcccagct cgcaccctta 115080
ccaaggtgtg tgacttgggg cacgttcctt taccagtctg agccacagtt tcctctcctg 115140
aaaaaatgag atgacagtag gaactacccc ttaggactgt tttgatcttg aattgaggaa 115200
atgcataaaa gcacatagca tggtgcttgg tgtgtagaaa atgctcatta agttgcttct 115260
gttattatta gctgctctta tttgatctaa tttttctgtt attcttgcct tgtggtcaaa 115320
agctagaaga aatagatcta agatactttc tacattgatt ggaatcaagt ctcccctgtc 115380
cgtgagaaga atgagggatc ttgaggggat tttaaatgcc aagttagctt tttggtaccc 115440
aaaggtaaac tgagttttct ctcttgttcc agggcaacat gcaggttctg gtgacttacg 115500
gtggcgatcc catccctaaa agccctttca ctgtgggtgt tgctgcaccg ctggatctga 115560
gcaagataaa actcaatggg ctggaaaaca gtaagtgcct gaatggagag cagatgggtt 115620
gttgatgacc ccccaacgtg gctgctggtt agattttctt caaaaggtga aatttgcaga 115680
gaagcaaatt ctatgttaag agactttgca gttgcacaga ctttggttcg aattaaggcc 115740
gtggtgtgaa gtaactgtga ctgtgtctgc cccttagcca caccgagact cagctttctc 115800
atttgtacag tggggggtgg tcggcgggga gaggttgaga acacccatgg gaatattttg 115860
aaaattatat gagctaatgg ttcagaggct ggcacgtagt cagccccctg gcattgcagt 115920
aggaagtttt cattaaaaag agaatttggg ctatgttgct ttctgatgag tttctaactg 115980
tgccagctat ccttggcaac tgaatccgca ctaaggttgc gagtcaagca taaatgccaa 116040
atccctggca ctcagaagtc actaccacca cacctctgcc ccatcccaat gttcctttag 116100
cttgttaggg attttactag tataagctca tttcgcttat tttcaatttt ctgattattt 116160
tttagtaggg aaaatttcaa acagaaaagg aaagagaata gtataacatg aacactgatg 116220
tacttatcac tcagcttcag atgtgcaaca catgctcata aaatgatttt tttatacaag 116280
taaaaatata tccatttttc atctaaaaaa cattacagtt aagggataat tccactttaa 116340
ccctcacctc tccttctccc tagggttaac caaagttttc aattcagttt ctgttcttcc 116400
agatcttctc tctgcatcta tacatataga tgtgcctgtg gaacacattt ggctgtattt 116460
attttgcatt aaagttgccc tgctgtataa acctacttct tcggcctgcc ttccaacagt 116520

-continued gcatctcggg aatcattcac tcctacatct tttccgtctg tgtttactgc tgagtggctc 116580
cagactggat gtacctcagg gctcacattc acctggtttc aggcttactg aggcagggct 116640
gagtgcatac ccccaggacg gggcctcctg tattcacctg tgagggtttc tccagagtac 116700
cactagcagt gccattagtg agcatcttcc ttcactcgtg acccaagtgc acaagttgca 116760
agcaaggcca gctcccagtt gcagagatcc aaagtgagag ctcactgttg gcttttgtgg 116820
ctggagcagc cagctctgag tgtgtaaacg tccactgccc aaccctgtca tgtgtcccct 116880
tgtcactcct ttccccaaga cactgagagc tttgactcca gaacaggaaa agcagggtgc 116940
caattaggaa agcctctttt ccggtgggaa gtagcgatcc gggacctcct tgcctgtggt 117000
tcggcagtgt ccatcttgcc aggccctatg ttccttcaga gtcaaggttc tctgggttgt 117060
ggcaggggcc ctgtgttccc agtgcttttg ttttgggtaa agtcctttcc ctgttcttgt 117120
ctaatctaac acttgggctt cctgcagccc tgctttgcag agaccttttg gaaaccatca 117180
cggtacagtc agttctcagc acttgcttca atcggctcgc atttggcagc tctgtgactt 117240
ctgctttctt gagggggagg ggtgcctata agatggagtt ggctgccaag aattagtaaa 117300
taaaacattg acttatgagg gtgtttggat atcaagttaa caccaaaagt aagtaaataa 117360
gagacgacag tgtcagatta caactttctg gtcagcaaag attgtggggt caggtaaatt 117420
tcactttgag tcccagcttg gcaggctgct gcatatgtca ccctggacaa gttacttaac 117480
ctctctgagc atcagtttcc ccatctgtga aagccattgg ttaataataa ataccccata 117540
ggattgtggt gaaaattaag acaataacct atttgtgctt ggcatataaa atgcattcag 117600
taaatgatag ccgttattgc tgtcatcact aattgattat tgtgccgaca cttgttgtta 117660
ctgaggctga gatgctgatg atacttactc agctttgctg cttgtcctct gcagcagctg 117720
ttgcttacag tggaggctga gataagtccc cgtgtccaaa gaaccattgc ttctgtgctc 117780
tggattgttc ctgctgctga aaagggtcag ctcttcacct cagcttgtgt ttcttttcca 117840
ggggtggaag ttgggaagga tcaggagttc accgttgata ccaggggggc aggaggccag 117900
gggaagctgg acgtgacaat cctcagcccc tctcggaagg tcgtgccatg cctagtgaca 117960
cctgtgacag gccgggagaa cagcacggcc aagttcatcc ctcgggagga ggggctgtat 118020
gctgtagacg tgacctacga tggacaccct gtgcccggga gcccctacac agtggaggcc 118080
tcgctgccac cagatcccag caaggtcagc ctttgctttt gtcccagaac ttgtctcatt 118140
gctgtcaaac atgacaccat agtccttctc tggttcttcc tggcaaagac cttctgaaaa 118200
tcgttttgtg atgaaagtta gcacaattca ctgtgaaagg tcccctgggt aggtgggtca 118260
caaccctgct cctcctcttg ctctctgact acaagacttt ggtgaggggc tccctgtccc 118320
agagtcttct ttcttcgctt gttagcataa tcacagtcct cactacaaag ccagcctgta 118380
aggggtaggt gagttagcaa acgtggaggc ctctgcccag cacccagctc acagacggag 118440
ctcaccctcc agaagctaga atcatgtaat ataaaaatac attattctgg ccaggcgcgg 118500
tggctcatgc ctgtaatccc agcactttgg gaggccgagg cgggcggatc atgaggtcag 118560
gagatcaaga ccatcctggc taccacggtg aaaccccgtc tccactaaaa atacaaaaaa 118620
ttagctgggc atggtggcgg gcacctgtag tcccagctac tcgggaggct gaggcaggag 118680
aatggtgtga acctgggagg cggagcttgc agtgagctga gatcacacca ctgcactcca 118740
gcctgggcga cagagcaaga ctccgtctca aaaaaaaaaa aaaaaaaacc acaaaaaaaa 118800
acattattct tggctgggcg cagcggctca cgcctgtaat cactgcactt tgggaggcca 118860
aggtggatgg ataacttgag gtcaggagtt tgagaccaac ctggccaaca tggtgaaacc 118920
ccatctctac taaaaataca aagattagct gggtgtggtg acgcatgcct gtaatcccag 118980
ctactcggga ggctgaggtg ggataatcgc ttgaacctgg gaggcagagg ttgcagtgag 119040
ctgagattgt gccactgcac tccagcctgg gcaacagagt gagattccgt cccctccaaa 119100
aaaaaaaaaa aaagttcatc gtcatttctt catagtaacc ctgactcaag gggttttgga 119160
agatttccag tggtctcaat ggtgtgaatc ctatgaaggt gtcttatttg ttgaattaga 119220
ggtgaaagcc tccttcctca ctcttttta gaaacagttt agttttatta ttatgcagaa 119280
tttgttgagc aaattgcaac agcccaagcc acagctagct ccacaagagc ccttccatga 119340
gccctcaacc tgggatctcg tgtatctttg ttggaatgga cattaggttt ccaagtccag 119400
gcctgtgatt tagaagggtc aggttgggta ggagagagga gagtcttgga ggggctgctc 119460
catgggggtc acacctctct cctgtgggtt ttcgctggtg attgagttct gaggcatttg 119520
ctgcattgac tgttgtagct ttaactcgtg tgcacgtgtg acacataaag ccccaagaga 119580
agggctgcct ggctcagatg cacttccatg ctgattatat gcatgggtgt tgaaagcagt 119640
gctggctgag cagcgatccc agtgcagttt gactttattc tttgctcaaa taggtgaagg 119700
cccacggtcc cggcctcgaa ggtggtctcg tgggcaagcc tgccgagttc accatcgata 119760
ccaaaggagc tggtactgga ggtctgggct taacggtgga aggtccgtgc gaggccaaaa 119820
tcgagtgctc cgacaatggt gatgggacct gctccgtctc ttaccttccc acaaaacccg 119880
gggagtactt cgtcaacatc ctctttgaag aagtccacat acctgggtct cccttcaaag 119940
ctgacattga aatgcccttt gacccctcta aagtcgtggc atcggggcca ggtctcgagc 120000
acgggaaggt gggtgaagct ggcctcctta gcgtcgactg ctcggaagcg ggaccggggg 120060
ccctgggcct ggaagctgtc tcggactcgg gaacaaaagc cgaagtcagt attcagaaca 120120
acaaagatgg cacctacgcg gtgacctacg tgcccctgac ggccggcatg tacacgttga 120180
ccatgaagta tggtggcgaa ctcgtgccac acttccccgc ccgggtcaag gtggagcccg 120240
ccgtggacac cagcaggatc aaagtctttg gaccaggaat agaagggaaa ggtgggtttc 120300
atttaaaaaa aaaaaaaaaa aaaaaaagac aagctgggac ttaagggcta cctgaaactt 120360
ggagctgcaa actcagccac ctgcaggagc caggtgacat ataaggcggt gctcacctgt 120420
tccctctgcc tcggggagta gttggggggc cctggtgaag gttaagcaca ttgcatttct 120480
ggggaccgtg ctactcaacc cctgttttct gtttctccat ggggaacagg acctagcatt 120540
gtcagcagaa tctctagttt tttggcaaag gcagaaatct tgatttttct ctggaaactc 120600
aacatacaac atgttggcat ttaattggaa aaaagtttaa aatgtagtgt tgtctaacac 120660
ctgcatgcca cacagcaggt tagtcttcaa cctttaacct gtcctcgagc ccggtgtgag 120720
cagtcgtgtt gtcacttagc cgtggctact ctagaaaggc cttctttggg atggaggggg 120780
ttaatattct tgatttgaga gttagaaaaa ccagttttcc agttactgaa attggacttc 120840
atgtgtcctg aagtgccaag aaccttggtt ctggggtttg cttttgggtc tggggtactg 120900
gtggcagtgt tagctatgtg cttgctctgc agatgtgttc cgggaagcta ccaccgactt 120960
tacagttgac tctcggccgc tgacccaggt tgggggtgac cacatcaagg cccacattgc 121020
caacccctca ggggcctcca ccgagtgctt tgtcacagac aatgcggatg ggacctacca 121080
ggtggaatac acaccctttg agaaaggtga gccgccctgt cctcggactg gaccctcgtt 121140
cagagctgcc cttggtcatt gcctcctggt ggctggtact gatgcctgcc ccatgtgcta 121200
ggcctgtctc agcagggcca cgtgcagagt gacagagtgg aagtcagcgt ccgctgcagt 121260

-continued cacctgccca ctcagtgcct ggcttgctgg ccttgtgtaa taggtgggct gggtttagcc 121320
tcagtctcac ctcagcaagt tatggggtaa tgtcatgatg ttgctcattt gtgccatttt 121380
tctttgcgta tgaatttctt tcttcttgag tattaggaat tataaaaaat ttcaataaat 121440
agaaaaccat aaagaaaaaa aagtgccatg tatatctcca ctacctggag atcggaagcc 121500
tgcgatattc tgatatagat attttcagtc ttcttgtgga tgcctgtttc ttctgtttca 121560
cgggtttcgc tttttctttt ggttaatggc tggatggtgt tttcccgaat gagagtagtc 121620
tgtttaggat gactgacttg aatatttgct tggttggggt ggagtggctt atgtgactgc 121680
agatagacgg tttgtattat ttaaaagtca gatcatacct acattactgt gggattgttt 121740
tgttttgttt tgaaacagga tgtcactctg ttgcccaggc tggagtgcag tggtgtgatc 121800
acggctcact gcaggctcaa cctcctgggc tcaaatgatc ctcctgcctc agccccctga 121860
gtagctggaa ctgcaggtgt gcaccaccac actcagctaa tttttgtatt ttttgtagag 121920
atggggtctc gccatgttgc ccaggctggt cttgaactcc tggactcaag tgatctaccc 121980
acctcggcct cccaaagtgc tgggattata ggtgtaagcc actgccccca gccacattac 122040
tgtgttttta acccccttttt ccaaataaca tagtatagca tgcagacttc gatgctagat 122100
gaaactctga agtagagaat catttttcac aaatagggga tttgtatgca aatatgcgtt 122160
tctgtttgtt gttttgagca ggtctccatg tagtggaggt gacatatgat gacgtgccta 122220
tcccaaacag tcccttcaag gtggctgtca ctgaaggctg ccagccatct agggtgcaag 122280
cccaaggacc tggattgaaa gaggccttta ccaacaagcc caatgtcttc accgtggtta 122340
ccaggtaggc aaggccctac atttggtgtc ttgagtctca cttttgtggc tagattctac 122400
ctatgtgtca tggtttccta acttttgata agatgaattt ttattttttat aacatgtatt 122460 tccttctgta gagacttatg ttacatagaa agaccaagca tacctaaaaa acataccaaa 122520
gcacttgata atggtcatga aactatttag caaaccagga gtcaatcaag ctctataact 122580
tgataatgta aaaatttgta gccaaccttg taagtatttt tattaaagtt ggttgcaagg 122640
catatgcctg cgttgtactt gcagtcctag ccagtgcaat tagataagaa aaataggctg 122700
ggtgtggcgg ctcacacctg taatctcagc acttcaggtg gccgagacgg gacaattgct 122760
tgaggccagg agtttgagac cagcctggcc aacatggcaa aaccccatcc ctacaagaaa 122820
tataaaaatt agctgggctt ggtagtacac gcctgtaatc ccagctacta cttgggaggc 122880
tgaggcatgt gaattgcttg aacccaagag acataggttg cagtgagccg agaccgcgcc 122940
actgcactcc agcctgggca atggagtgag actctgtctc aggaaaaaga aaaataaatg 123000
aagcataagc attgaaaatg aggggtcaga gtgtctttac ttacattata ctaatgtgaa 123060
attccctatg tgagaggtgt agtaattgag ttggggtggc tacgtggaat agtttataaa 123120
gggaatttgc atgaattttg gcaataagca gaccagcata aataaatggt gcacatttca 123180
ctttcttttc cactctttcc agaggcgcag gaattggtgg gcttggcata actgttgagg 123240
gaccatcaga gtcgaagata aattgcagag acaacaagga tggcagctgc agtgctgagt 123300
acattccttt cgcaccgggg gattacgatg ttaatatcac atatggagga gcccacatcc 123360
ccggtgagct attcctcaga gaggacccca gagaataatt gattttgcag gaaaatgggt 123420
ttgattttgg ttatctctct gagtggggaa aacaatctga tatttgtaat agctgcaaaa 123480
ggagagtttt tcttagggct acatctccaa gattatctca actcccagta gaaccggtaa 123540
catggcaaaa agcatcggct tagaattttg actggaaaca gttgtgcgtg tgttggagga 123600
cctagttctt gattcagggg aaagctggtt ctttacaaag ttgaaaatca cagtggctca 123660
cacctgtaat ccccaaactt tgggaggcca aggcatgcag attgcttcag gtcaggagtt 123720
tgagaccagc ccaggcaaca tggggaatcc ccatctttac aagaaataca aaacttagct 123780
gagtgtgatg gtgcgtgcct gtaatcctag ctatgtgggg tgggggctgt gatgggacga 123840
tgtctgagat gggagcctgg gaggttgagt gagctgagat tgcgccactg cgctccagct 123900
tgggtgacag aggaagaccc tgtctcaaaa aaaaaaaaaa agaaaaagaa agaaaatttc 123960
taccttattt tgtgcttggc tccttattca tgtgtcttgg tttctttttt ttcactgaca 124020
atactagtag ctgatcaaga tatgcagatt caaattcttt cttttgtatt tagtgatgtc 124080
atgtgtaatc actgtgaaac acggtttctc aactccggca ctatgacact ttgggctaga 124140
tgattctttg tggtgtgggg ctgtcctgtt cattgtagac ttttgtcagc atccctgccc 124200
tgtacctgct agatgcccat agcagacttc tccttcccca ttcttatttg tggcaaccaa 124260
aaatgtctcc atatcttgcc agatgtctta agggacaaaa tcacttcagc ctgaaccact 124320
gctgtaaaga ttcaaacaat aaataaatat atgacttaag tagtgaaaga ccctcctcca 124380
tttgttttgg ggggaggact ctccataggt tctagttatc tactcaaatg attgtcaccc 124440
ccacacattt tatttattta tttcaatagc tttggggtac aagtcgtttg tggttacatg 124500
gatgaattct atagtggtga attctgagac cacctccccc gcccccattt ctaaaagggc 124560
aggcaagtgt gtggtgtgga cagaagaccg agggctgggg ctgttctggg ccacttatgc 124620
cttgtcttag gtgtggtgtg aagagggcaa agccccaccc caggacccca ggagcagaaa 124680
gagcctcagc ggggtcttgt tcttctttct ctgggtcacg ctgagagggg aagggcaggt 124740
tgaggggccc actgctgggt tctgggttaa ctctcaggca gctggagtgt ccactgacca 124800
cacgctttcc tgattccatt cctgcttccc ccttaccaca tggaaatgtg cacacacact 124860
cacactcact ctctctcaca ctgatcagaa agtattgaca ttcaactcag actgattcta 124920
ctcagatact catttaagcc tcaagtcatt taaaacaaca tgtttctcct caaacttgtg 124980
cttgcggctc attcaatata gatttaaaaa attcctataa tcactagtct aggggacttc 125040
agctgtgggc aagacaaagt tcctgccctc agggagctta ctgtctaggg cttttacaac 125100
taaaacttgt gatgactgct atgaagaatg agaatggggc tcggtgacag aattcagagc 125160
tacgggcttg ttttggagtt ttgtaacact tgcgttagga gagagttggg cacaggaaac 125220
gggtagaagg ctgctcccag gaggggtgat gtggctccga cctggcaggc aacagtggag 125280
atgaacatct cctgtggcaa tgaaactttt tgactatggg gaaaggctgg tgagtgccac 125340
cagcttccga atccccctta cagaaagggg tcagagtttg tcccctgtgg ccgacctgtg 125400
agcttaaagc aaatggtcgt ctttgagcat aacaacagaa agacactcat ttgtggtttt 125460
cccatcaggt gtggatggtg ccttttttatg tttcaggctc tctgttgcct cccagagagc 125520
caaatgccgg cttttccaga accccagaac tttcccaggc agagatattt agtgaagtgt 125580
tggttggttt tctaagcatc aggcttctta gctaaggcaa cctatggggg tactgccggg 125640
aaacagtcgg ctacctgcca ccttctaatt tgctttcatg gtaattctgg gtgcttaaat 125700
attagcctag tttttcctgg cctggttaaa aacccggagt ggagttattt ttaacaacgt 125760
gtcctgtctt acccgtaatg gcatgttgat ttcctgtggt aggccagctg tggttggttg 125820
gtggcggctc cctagaccac tggattgact ggggttcaga gtgcatgagg aagaagatct 125880
ggcatgaggg aatggtgaca tgtgtctggg catggaacag gggagtggcg gataatgctt 125940
ggggtctgcc atcttggaca gtttatctta cccgggtttg ttggtttttg gctactctca 126000
tgctgagctc agacaacttc tagtggaggc tctgacttaa agattggcct cagaggtagt 126060
cccttgccat cagctgttga cattgaaatc ctcaactgtc actctctaaa gtaaagcccc 126120
cttttgttcc tctcacccca gtgtggaggc ctgtgcttgt ttgccagggc cagccattta 126180
tttcacgtag ctaaagacct ggatgccgtt gaaacccagc tgttgttaga aagccaggga 126240
ctcaattctt tgtgtgtctt ggctgtctac catctctaat tctacaaagt ataaattctc 126300
tgggatgcaa agcagagatc cctcagcttt cacggcagtc attaactttg ccagatacca 126360
tggggagcac caggactccc atgcgaggca gaggtgcacg tagccccttg gtgatgggcg 126420
tggtagcctg aggcatgctg ccgttcgctg gatggggagg tccccctcca cagtggagtc 126480
catgagtgtc cttggcctag cccttgtttc tctgtttagc acttctctag caaatcacta 126540
tctcctctcc tcgactcctc tgtgcttcat ctttaaaact gacaccctca aggagtcaga 126600
ggccctcagg gtcccccggg gggtcagcca tgtagcagga gctcagctta cactcaggaa 126660
gacggcaagg cttcaccagg tggccgagtg accgagaagg ctgagtgtgg tcagaaggtg 126720
ccagctgcat tggagggaga ggagtctggg ggacacacag gagccatgtg tgggggacag 126780
ggctggatgt gggctgcagg gcctgcccat ctctctccgt tctgttgttc caccacttgg 126840
cttcctcctt cagttgctcc agcagcctgt ctcctccctc gcctctaggc tcctgcatgt 126900
gctgaggcct ctctacttga agcacctctc tgtctgctcc ctcttgtgcc gcaactgaga 126960
tgttactgga aagctttctc tggtctcccg cagaccaggt taattgcctc ctgagtgctc 127020
caccttccac accccaaata tgttatgtag gatgttagag tgacttgctt gcctcatcct 127080
tctcctgcag ttgtgggttc ctggggggtg ttaaccgctc aggatccagc acgtggcaca 127140
acatctgcac gtagtaggtg ttctgtgaga atggttgaca acaatgagta ggcacatgag 127200
cagtgcacac agtgaggcag ggggagctga ccgaggcctg catggccgag gtcccggggg 127260
agcagcagtg ctattctggg tgtgcacaag gtggtctcca attcccagct tgtgctcaga 127320
atcccacaac ctctcttcca ggcagcccct tcagggttcc tgtgaaggat gttgtggacc 127380
ccagcaaggt caagattgcc ggccccgggc tgggctcagg cgtccgagcc cgtgtcctgc 127440
agtccttcac ggtggacagc agcaaggctg gcctggctcc gctggaagtg agggttctgg 127500
gcccacgagg taagtgtgca ccctgccttc ctgcagacat tcatctgccc caggcagggg 127560
cagctgtaac ccagagcaga tgctttgctt ttgagtttgc tcatgagctt aaaattaaat 127620
taaaaaaaat tattgtttca tttctagtta aacagtagaa attcctgctt acaagtaagc 127680
aggcttgtta tttctccagt gatctgtccc cccatttaat aatatggcta tcaatttctt 127740
agaggaagca gcagtatttg ggctgtcata tgtaatatgg tggcgactgt ttcattatgt 127800
gtttcagcat ttgtgagggg gtgggttgct ctggatgtgg cagatggtgg ggtttggagg 127860
tgataactca ttgagatatc ttggtgtcca tgtggtacat accagaacct ctgggaatgc 127920
caggcacatg atgcacgtga tacgtggctt tgtcattgtc ttagttcccc agagagagag 127980
tgtgtcttgg ggaatgggct ttgttggcaa tttggcctgc cttgttggca gcttggaact 128040
tgggtttggt aaggctagcg ggccatatag ggacaaagcc ctgaagtgca ttggaacttg 128100
cctttttgga taagtgacca tgtttcctcc tccagcactt aaaatgtgcc tttctcccac 128160
atagaggaca gtgtgcctaa tttcttacgt aatctggatt ttcctcgcca atgatatgtt 128220
cttggattca cagaagtggc aaatggggtt ttccctcttt gaagaggaac cttctccttc 128280
atggggttca gcaggaggtt ttatcttttg aagctcaggg cagaaatggt ttgggggaaa 128340
ttaggtcatg ggtctgggat cagattctgt gaagttactg agcttcagga cctgcatgtg 128400

-continued tttgtgtgca tgtatgtgtc cctgtgtatg tgtgaatgag agagggagaa aaagaagaaa 128460
gagaagcttt acttggatat ctgcctctat tatgaaggac tctcaagtaa cagccttttg 128520 atttagctg acgacacgga ttcccagtca tggcgcagcc ccttgaaagc cctttcagag 128580
ttctttaaag gtgacccgaa gggtgacttt aataagacag gtttgcattt tcccatggct 128640
gctgaattat gtaacccaaa tgcttcttgc tggcctcact tctaaaattg cttacacctg 128700
cctcatctgc tttgcttaat gagcatgcca tcctttgatt aacctaccct ggagttgacc 128760
catccttgac tgtcacgttg gaagctggga tctggactct gcaacccaac gcgtgccttg 128820
attatgtttt agcataatct ctaacatctc cacaggcttc accttgaggg tccccttgcc 128880
ccatgagatt ggcaccctca cctgccctgc acctatgccc cagcatgctg gtaccacagt 128940
gttctttgct caaaggtggc cacaagtctt gactagccag cccattggtt aatttttgct 129000
cttcacaatt ctggactctt tggcagtgtc tcagctgtag agtaaaattg ccacatccta 129060
agcgtgccta accagcttga aaggttatat tgtgtcttca acacacatca tccacataca 129120
ccctccagca gcaagcacag gcagtctcct taattatact ctagggcaga ctgagtgtat 129180
tttagccaac aaaaagctaa aggtgtctct cggggtcatt tctgcaacca tgaattgggg 129240
atcctgtgat ttttttcagg cctgtgatta tggttgctgg ccttttttgtt actcatcagt 129300 ggaaaccaat agctcttggg gatggatgtg gtcctatttc agactcagcc aagggtggag 129360
taaaggtgag gccaggcagc tccttaaacc tctcatctct gtcctcaggc ttggtggagc 129420
cagtgaacgt ggtggacaat ggagatggca cacacacagt aacctacacc ccatctcagg 129480
agggacctta catggtctca gttaaatatg ctgatgaaga gattcctcgc aggtaagctc 129540
catccatctg cccatccatt cctccatcag tctatctgtc cacccatcca ttcctccatc 129600
agtccatcca cccatccgtt cctccatcat tccatccatc cactcatcca ttcctccatc 129660
agtccatcca tccacccatc cattcctcca tcagtccatc catccatcca ttctttcatc 129720
attccatcca tccacccatc cattcctcca tcagtccgtc tacccattca tagaggcagc 129780
aagtattaca tagaacctgc aacttgtcac cacacactag ccttgatatt tgtggctccc 129840
gctctctcac tcccccagtt cctttcagac atctttagtt taaaggtgag ctgaaattaa 129900
gaagttggaa atcctaacca cgtgtggtgg gattcgcctg taatcccagc tacttgggag 129960
actgagatga gaggatcact tgagcccaag agtttgaggc cagcctgggc aacatagacc 130020
ctcccctgac atctctggaa aaaaaaaaaa aaaaaaaaaa aaaaaagcaa tagtagtaga 130080
caatcattga tgaaataaat aatttattag tttattagag gcttcctttt ggtgttttgg 130140
tgaacctgca agtagtttc tgattgggac aggacaaagg tctttacttc agggtttgct 130200
tgataaaagc atttccaaaa ggttttacat agaaaccttg ttccttgttg atattaatac 130260
aaaaaaaaat gttacataag ctcttcacct cttggaacaa tctctaaggg ttttcttttc 130320
tttttttaaa aaatcatgcc ccttaagatg aaaaactttc acccatatcc cctaacacat 130380
attttatata gagataagca tattagctct atgtagaaat atgtaattta taaattacat 130440
ttgtatattg ctttactaat ataccatgta ccatatgaag catactatag aataattata 130500
gatacagaat atagaataag atgagatata aatattaaaa ctgaagttcc agtattctct 130560
ttccatttgg tgaccatgat cttagcataa caaaagtggg gtaaatgtgt ttaaccctgt 130620
gtttcccaaa ctaatttgtg aactcttcct ccccaaacta cttgtatccc ttggaacaga 130680
ggtccccaac ccttggagcg tggactggtg tgggtgcacg gcatgttagg aattgggccg 130740
cacggtggtg ggtgagccat cattactgcc tgagccctgc ctcctgtcag atcagcagct 130800
gcattagatt ctcataggag tgcgaaccct attgtgaact gcacatgaga aggatctaga 130860
ttgcacactc cttgtgagaa tctaactagt gcctgatgat ctgaggtgga acagttttat 130920
cctgaaagca ttcccccacc aggccccctg gtcttctacg aaaccagtcc ctagtgccaa 130980
aaaggttggg gaccgctgcc ttggaacaca ctcaggacaa aaccagtctg tcatatgatg 131040
gttactacct catagttgta aatttctgct agacttaggc accttgacta actcactgtc 131100
ttatctgctg tagaaatccc cttttccatc ccactcttat gtgtaagaaa agtcagatgc 131160
agctgggttg acatgtatct ttattgacta gggtgtgtgt gtgtgtgtct atcaagtccc 131220
ttcaaggtca aggtccttcc cacatatgat gccagcaaag tgactgccag tggccccggc 131280
cttagttcct atggtgtgcc tgccagtcta cctgtggact ttgcaattga tgcccgagat 131340
gccggggaag gcctgcttgc tgttcaaata acggtaactt ggagttattt tctgagccaa 131400
accttaatcc taagacttaa tttctgggcc agatttaaga acaagggttt caataaccga 131460
tttctgactc aatgcaagtt gtttgttaga ttttcccacc aaagagtcag taaatgtgca 131520
gaagcagaag cagctcacct gagagatttg agggtgtagc tccaagaacc actttttggt 131580
gaattttcat gtttttttac tacatctatt cctatgtttt tatttttatt tttttaaag 131640 atggggtttc accatgttgc ccaatctggt cttgaactct cttgggttca agcagtctgc 131700
ctgcctcaac ctcccaaagt gctgggattg cagacatgag acactgtgcc cgtcccctat 131760
gtttttattt ttaaatgttt taaattactc tttggttcat ttaagactaa gttatgctgc 131820
atatcacagt aaaccttaaa ataagagtgg ctgaaataaa tgagattatt ctctcttgtt 131880
aaggaacccc aggctaagcc acctgggtgc cctgcagctc accaaggaag tcagctccat 131940
ctctctgctc ctctacctag catgtggctt ctgtccttaa ggtctcctcc tggaccataa 132000
ggctgccagt gctctggcca tcacatccac atggcaggcc agaaggagga agaaagaagg 132060
gaaaaagggg tcctcccagc tcagtgggct ctcttaagca gccctgccaa aagtccatca 132120
tagacttcca ttcccttctg atttgttggg ggttggtcac aattcacatt acctagtggc 132180
aaggatgcta ggaagtggat tcccatcttc tgggagcggt gcacctagct aagagttatg 132240
gtcctgttaa taaagagaaa agggagactg gatgtggtgg tgtgtgagca gaagcctctg 132300
cctcctcccc tccctacatt tcagaggatt tcgagctaaa acactcttgg ttcacctgac 132360
aacaaaatta ctaaaaattg gccatgtctg tcatggtgtt aaagggatct gtgaccctct 132420
actctcccta ccaaaaaaca aaacaaaact agattgtatt aagccatcaa ttctgtctgt 132480
ttccactaga ggcactaatt ggaaaatatg tcagggtttt ccatgaatgt tttctacatc 132540
ttgacaacat cctaaatagc atttctctat gatccacagg accaagaagg aaaacccaaa 132600
agagccattg tccatgacaa taaagatggc acgtatgctg tcacctacat ccccgacaag 132660
actgggcgct atatgattgg agtcacctac gggggtgacg acatcccact ttctccttat 132720
cgcatccgag ccacacagac gggtgatgcc agcaagtgcc tggccacggg tgagtacagg 132780
gcatctcaag gtcaggggca caggctttgc aatcagaaag ccgggccgta gcccttctct 132840
gtgacttaca agctacatga tctgggcacg ttgctcaacc tcactgaact tcagtttgac 132900
atagattgaa gctctttgtt tttatttgga gaacatttag atccaagaag ctcttctaag 132960
gaacagagac tgttttacag ggttactgca aagattagat gaggtcaggc atgaaaaatg 133020
cttagcacag tgctaggtac atgataacta ttattatatg cttttgaaat gttgagaacc 133080
caactctgat ggcggctccc atgaaaagca gcacatttct gccttttatg agtagatagt 133140
tactcaggat tcattcaaga gcatttcagg tcagcattag agaaacacat ttaaggatct 133200
aggttttttt catcatgcat atgtaaacct ctcaggaatt ctccatgaat atttgagcat 133260
cacagtttct ttggtttctt tctttttttt tcccctcctt tttccttcag tttctaagac 133320
acaactattg actgtcacag gccattcttt tttttttttt tttttttttt gagatggagt 133380
cttgctctgt tgcccaggct ggagtgcagt gacgcaatct cagctcactg cagcctcagc 133440
ctcctgagta gctgggacca caggtgccca cgaccatgcc cggctaagtt ttgtattttt 133500
agtggattca gggtttcacc ataattggcc aggctggtct cgaactcctg gcctcaagtg 133560
atctgccctc ctcagcctcc caaagtgctg ggattacagg tgtgagcacc acgcctggcc 133620
ggcctttcag tttttaagaa cagcccttgg gcagctcagt gctgctgctc aagcagattt 133680
taaaacacga atccccatct ctaaaatgag acagatttac ttctttttaa ataagaagac 133740
taaacacagg accacccttg atgtgttctg tttctctctt agcccatctt tttttgaatg 133800
gagaaaatct gggctttcac ggcaaggttg tgaattgctc agcgtggccc tttttggctc 133860
acccatggca aaaaatggaa aaattttgga atgcaggcca atccaccacc tcctaggtct 133920
atgcagctgc cagcgacaac cagatcatct ttactaattg atggcatgtt aacgttggat 133980
ggggacttcc cccttgcctt gcaggcccta tttcctcccc cagcttgggc agaagcctga 134040
gctgaatact tgccttttgg ccacacctct gggtctgtca ttcagggtct tccacagatt 134100
gactccagtc ttctcttcca ctcctccctg aacaaactgt tcttgccacc ctccctatta 134160
ctcctacgca cttggctcat atctaccaat gtgcttttag ttcatgcttt tctgcatttc 134220
ctgatatgtg gatcctgtgt aaaggggcgc cagaaatcaa gagagagact ggtcactggg 134280
gagaggttgc aagtctccct tagctaacag cacccatcct tcagggttca gccatgtttc 134340
ctttctttag gaagcccttt gtcagtgcgg caaccctggg atataaattc ttagaacctt 134400
tgcctagata tgctgccaga cacttctctg aggaacagtt tgttattttt tctgtaactt 134460
agttcctctt cagcatttcc actgcagttg gaaatgtcgt tcttggtgcc tggccctgtt 134520
aacatcttga gagcagggac tgtgtcttgc ccacctttat gtgtacctgg cacttaagaa 134580
aatgcccaat atgtttgcta ttgaaagtca accttcattg ccataccttt aaatgctggc 134640
aaacccaggc taacctttag tcaacactca gagcttacag atgctcctta tttagtaagt 134700
aattgatgac gtaacccttt gagcaacacc tgatcagggg atctttggga tatccctctg 134760
aatggcagca gttggaggcc taacatttac aggcacagac aacatggatg ggtatgattt 134820
gttcttgggc ctccaggatg tgtgtccata cttccattct cttcccctga actcttctcc 134880
aggtcctgga atcgcctcca ctgtgaaaac tggcgaagaa gtaggctttg tggttgatgc 134940
caagactgcc gggaagggta aagtgacctg cacggttctg accccagatg gcactgaggc 135000
cgaggccgat gtcattgaga atgaagatgg aacctatgac atcttctaca cagctgccaa 135060
gccgggcaca tatgtgatct atgtgcgctt cggtggtgtt gatattccta acagcccctt 135120
cactgtcatg gtaaggaaaa ttccttctcc cgagcatgct gttattggtg gaaactgtaa 135180
cagctgccgt ttgttgaacc ctgactagga tatcctcttc accttttttt tcctttggaa 135240
aaaaatttgt taagcagtca tgaccttgta gagtcccaga gtaatctcta gaaactcaga 135300
gacccttttgg ctgtaagggt ttttagggaa tcttactggc caccaaggtg tctatcataa 135360
taagggactt gggcaatatc ctggcctaag cccaggcatt ttgaaagata actcctcaga 135420
aaaacacacc tttatgaaaa tgtttctaca taaaacatga caggttttta accggccagc 135480

-continued tcttccttct tccatcttca tggccattct ccatggctgg aggagagagc ttcctgatgc 135540
tgttttgttt ggagacttga ctctgaaatc ccaggactca aagtacctcc acttgtgttt 135600
tggaaagatt cacactttat gtatgagggg gaaatacctc gtcttttgca gctaggaaca 135660
tctggaataa aaggaggaaa ccattatgca aacacctggg ttagtgaatg accaaggtct 135720
ttcattttca gttgtgagtt acttatagat cttcctctgt ttatttattt ttattattac 135780
ataatagatc ttcttctgaa tattcttcaa ccaggaaaag ggttagaaac cttggggaca 135840
ttacctcatt gaaccctcaa aaccaagcat cgttggcttt tttacaaatg aagcatgctt 135900
ggtctagaca gacaccaaat accatgctgt catcctcact ggtgtccttt gatactgtgg 135960
tcagcagccg cacttgacca caaggtttat aggcccttaa tgacctggcc ttgtgcacag 136020
ccgacaaagc accttctaat tatttcattt tgtgcagcaa tggagaggtg catgaagact 136080
ccattccaaa ctccaaagct cagggacttt cttccgaaca gtctatactc tgttgtagta 136140
ttattccctt ccatcgacgt ctgtttatct gtaaacagca tgccagagat ctggaggctc 136200
ttttatgtct caagtatgta aatgtaaaca cttgtcaact tttgacattg ttcatttaag 136260
agtgtttttc tcctgtagga agaaagaaat acagctggga agttgatgtc cttattcaca 136320
gagaagggta ccagttgtag ttttcagaat ctgtttttag cccatagtgg gttttatctg 136380
gttggttaga attaggtgga aggagggaag agcagccaag cactgagcag tggtcatggg 136440
cctgctggtg caatgatttg ggggtaagag aagaccatat tgggaaggtc tacgtgagaa 136500
agtcagagta aaaaaattga ggaccctttt tgcagaagtg gaggcttcca aactcagtaa 136560
taagtgtctt ctagcccctg aatacacaca aagcaagaat actttgtgtt tacccactgc 136620
cccctgacca ctgctgaagg cagaaaggga cgatcaccta cagtacctgg tttgggtctt 136680
tattctctca ttccagggag agaaccttaa ctagatggac tgactgactg ttcattggct 136740
ttggttgggt agattccctg cttccctcta taagtttgac gccaaaaaag gacaccgacc 136800
agcactgcag tcatagcaaa tgtctcaagg agacccacag ggtggtttct tcaaatacac 136860
tactcacaca cagcacatgg agtcatggac aaacagctta actgcccatt gcctttgaga 136920
agtcctggac caaaggccat agctcagcca ttgaaagatc ttccttctga ctgatatgtc 136980
cctgcatagc tccaacctgt gcaggcagag gatagggctg ttccaaatgt cgctcacaga 137040
gctgcctttg cctttctgca gatcccaaga tacacacaaa gcagttaaca tgggtaaata 137100
ggccttcctc tgtaggagag ggcttctgat tcttattctt tcttatggcg gaagagggtg 137160
ttgagagggg ttcccttgct gttggttctg ttgaatcagg agcattaaat ctttttgtt 137220
ttttttgag acagaatctc actctgtcac ccaggctgga gtacagtggt gcaatctcag 137280
ctctctgcaa cctccacctc ctgggtttaa gcgattctcc tgcctcagcc tcccgagtag 137340
ctgggattat aggcacctgc caccacgcct ggctattttt tgtatattta gtagagatgg 137400
ggtttcacca tgttggccag gctggtaact cctgacctcc agtgatccac ctgccttggc 137460
ctcccaaagt gctgggatta ccggcatgag ccactgcgcc cagccatgag cattaaagct 137520
aagatttgtt gaaaatgaat ttataaaaaa ctttagaaac attaactgct gagcatggtg 137580
gctcatgcct gaaatctcag cagtttggga ggccaaggtg agagggttgc tggatcccag 137640
gagtttaaga ccagcctggg caatacagtg agaccccatc tctaccaaaa aaaaaaaata 137700
ataattagcc tggtgtggtg gtgcacgcct ctagtcccaa ctgctcagga ggctgaggtg 137760
ggaggatcac ctgggcccag aaggttgagg ctgtagtaag ctgagattgc gccactgcac 137820
tccagcctgg atgacagagc aaaactctgc ctcaaaaaaa attaaataat taaccacagt 137880
agacatttat caagtaaaaa aagaactttt tcctgattct gtgctgcaga gatgccttgt 137940
gttagttttt acctacttac acttcacaca cctcactttc atgcctgggg tcacaccgta 138000
catactgctt tcgcaccttg cttccttccc tcaatgtgtc ataggtaccc ttacatattg 138060
attcattgga cctgactgcc atgttccact ggacagactc accagaattt atttgaccaa 138120
atcccttcca gatggacatt gggttgcttt agttttgcac gaccacagac agcaccagtc 138180
aaggtcctta cacacatcaa ttaactatgg agtctcccgc cagcttaggt ctgcgtgcta 138240
caagtggggt tgtgggctca cagggcatgc gcatctgaca gttgaagaga ggacaccaac 138300
tgccttccaa aagggcagta agaaagtgtc cttcgctaga gtgagtggct cactgcagtt 138360
caagatggag cagtggggga agcagctctg tggtggtagt ctactgagtg tatccttcca 138420
gtatggttcc caactaatct ccatttgcca ctgaccaggc cacagatggg gaagtcacag 138480
ccgtggagga ggcaccggta aatgcatgtc cccctggatt caggccctgg gtacaatttt 138540
ggtttttcc tttttgtgtt tctgtgttta ctcagccttc atttcagaaa atctgccatc 138600
tgcttctggg attgcttaag ccctgtgggt gtcctggtca ttggtgtgcc cctcactgat 138660
cagcccatca cgatgatccc tgcttttct gtaataagat cacctttgcg tcaccatccg 138720
tgctccacga atcgccagcc gtcgtgtctg tgatcacgct cggtgcagtt tgtctctgtg 138780
tttaaagaga aagacagaca gctgtctgca gccctcctgc tgcctctcaa agccgccact 138840
tgcacattca gtttctgttc aggggaaag ccacccactg ctactctctg ccacttaaaa 138900
tgcaccttct tttccaggcc acaagcaact aaacctttcc agatggagcc tcttgggact 138960
catagacatt gctgtctctc acttttccac tttcccgtgg gtgctgctgg gaattttaca 139020
aacagactcc cgagtgattg ctaacagttg gtcagcatga cctctccagt ccctcaggtt 139080
ctaccctggg tctggagcca cttagacaaa gcccatacca caatgggcag ccgcattccc 139140
aaatcccggc ctcactggct tgtagaattc ccagcagctc taacccctgt agcttcacca 139200
gctcccgctg ttgtctgctt tacccagtga ccactgcctt ctgtttttag gtgaccgaag 139260
aggcctatgt cccagtgagt gacatgaacg gcctgggatt taagcctttt gacctggtca 139320
ttccgtttgc tgtcaggaaa ggagaaatca ctggtaagca cttgccataa aggccgtctc 139380
attctcactt gctctcacga gcttcccaga atggtgctgg ggaggtgtgt ccactgtccc 139440
ccagacccag gctccttaac ccagggtcac gagttcttgg tctccggtgt tgggccgtgg 139500
gctcctgaaa ctacagaata tgccacgtgt gtgtttctct gaagaagtgg ctcactgaca 139560
acttgcatta ctttcttgag cagtcccatg attctctcta ggttaaaaac tgctgtgttt 139620
agatacctca tgactgtcgg gttcttgttt gccccttttt cctgccttct cttatttgac 139680
ttttccagat gtgactttga cactgagtct gtcatacagg agttcctttc tcccctcagc 139740
ctcttttcaa tggcccactt ctctttggtt tgatgctcta tgtatccagc tggtttcatg 139800
gtgttctcaa gtcctttctg agcttgattt tgccagttgt agaaaactct ttaagagttg 139860
tctgctatat tttgtggaag ccaaatggaa ctggaaaaaa aaaaaagaaa agagcaaatg 139920
gtctctccca ttgtgggact tgaatgtttt aggcagcaac gaatgttctt gggtctggaa 139980
acctttattt tgaatacatc tgtgccttgg gctctgcttc tctggggaag gttgctggtg 140040
ggcttcattg ccccgtctct ctgtgctcca taggagaggt ccacatgcct tctgggaaga 140100
cagccacacc tgagattgtg gacaacaagg acggcacggt cactgttaga tatgccccca 140160
ctgaggtcgg gctccatgag atgcacatca aatacatggg cagccacatc cctggtaagc 140220
tgagtcagca ggcccagcag ggctccacca ttcaggggca tccgggcagc ctgcagacac 140280
tcctcagccg ctttgcaggg agcagctctc ggcagcaggc tggagaatgc agcgttggta 140340
cccctgtgaa accaaacagt ctgggaccct agcaggtcca gctgatttct ggaagggatg 140400
atgtagctca gtgtcttggg tcacagtgca ggcctttggg tctgtggttg tttatctttg 140460
tcactacgct gagtgtggcc agaggtcaag ctgggagaaa aatgggaggc atggtgaggg 140520
actttccagc ctggcctgca gagccctgtg tgggctggag gcttggggcc aggtcagagg 140580
tggaagaaga ggaccagcag ccctggaaga agaggaccag cagccctcta caagggaagc 140640
cagcccaggt ttcatgggtc accaaccagc acagtgtcac cagttcattc tttctttttg 140700
tagttgtatt tgtttttttaa tttagtattt tgaataggta acacattctc atggttcaaa 140760
aataaaaatg atacgaagaa agttttcctt cctacccctc tccttgaact agactatcat 140820
aaattttttt atgttcgatt tcagagtttc agggttttat tttttatttt tttgtggaga 140880
tagggtctca ctgtgttgca cagattggtc tcaaactcct gtcctcaagc agacctcccg 140940
cctttgtctc ctaaagtgtt gggataacag gcatgagccg ccacgcctgg ccaatttcag 141000
agtattttta agactctcca tgcaaacgga aatacagata tataagagag tgtcttccca 141060
gccttccctc atgtggacga accattacat atttgaccat ttccctattg gagggcattt 141120
tggttcttcc tgccctcgct gtccccagtg ttgctgcgca aatcgacttt tcccctagtc 141180
acctcacact cacaaagatg tatctgtgag atttagttac cagaggaggc aatgctaggg 141240
ccccagtgca ggcatctatg attttgacag atcttgccaa attgcccttc agaggggctg 141300
ttgcagttca cacgccctct ggccatggag aagagcacct tcttttccac aaaatttgcc 141360
agtagaatat ggtatcaaat ttttggagct ttgccagtct gatggttgga aagaaacaga 141420
atctcagcgt tgctttattt gtatttctct tgtgaatgag accacacaac tttccctatg 141480
tctatttgta tttcttttc tgtgaactga acatttggat ccacggcctg tttttctatt 141540
tggttattgg cctttgtcat atagtttcta agagcaatgt aaacattgga gagattagcc 141600
ctttgtggta ggagttgcaa atgtttctct gagattggca tttactttag ttgtctgtat 141660
gtaatattgg tttaaagcaa aaatgtatta tctgcttcta tttaaatatt ctaaagcggc 141720
agatggagag agaggaaaaa atgtctttct cacatctgcc atccacttcc actgctggtg 141780
tgagttgtgt atcttttcag atgtttctct ctgtatctac aaacatacat ataattttat 141840
tctattttgt ttttaaagga atagcataat ggtattcata gtttatagca acttgctttt 141900
tttcttttta atgcatcata ttatggataa tttctcaagt cagtaaacat gggtcttcct 141960
cactcttttt aatggcccat gagtagatca gcatttattt aaccggtccc ctgttgtgaa 142020
cacttaggtc ttttcctgat gtgcacccga acactgcaga aatgaaagtg cttacatagg 142080
gctaggagtc ggggtgggca gagaagacca ctgtggggtt gattccttac aggttgaatg 142140
gcatgggcaa atggccttcc aaaagccctt tccacttacc ttccctctgg ccatgggtcc 142200
tttcaccacc cagtgcaaaa gtttcttcct tatttgtcag gttgggctgg taccttacct 142260
tagccccctt cctcatctgg agcagcttcc aggattgttt ttcttatgtt gtgattgaag 142320
gaataatact gcgtagaccc tctctgatgt cctaggatgg cgggggatgg gaggtgcatg 142380
tgcatctcct tctgtctctt catgcctctg cttaggaggc gccagacctg tagagaggtg 142440
gacgtcaaga tgccagttgt ccagggtctt cgttcacccc ttaatgagca ccaattttgt 142500
ttgtgtcctt cgtaaaccca gagagcccac tccagttcta cgtgaactac cccaacagtg 142560
gaagtgtttc tgcatacggt ccaggcctcg tgtatggagt ggccaacaaa actgccacct 142620
tcaccatcgt cacagaggat gcaggagaag gtactgtgtg gtttacgtgt ttatacgcct 142680
ccagctgtcc atttggaggg tgaagtggac acggttccag ggtggctttt aaaagtgaga 142740
caatcgaatg gtagtatttg tcttgtcttt tctctcgtgt aaatctgttt cttctttaga 142800
gccgcttcgt cttctaccca gacagacatt tttgaagtcc tttgtgttct aactgaaatc 142860
agattcatgc tatgaaatac tttatgtgac ttgtctggaa tttaagtgtg ttttggttgg 142920
tgatgttttt gttcttgttg cacatgtatc cacaagacca catgacttac tgagtggctc 142980
tttttgataa agctgtgtgc ccattcccgt ggtattcatg gataatccca aatctgtggt 143040
tctaatggga tttccgtgat ggcagccagt gcctgatggg cagggacaat ccacctctgc 143100
cctccaccac ccaccgtctc ctatgtgtaa ttgatgtaca cggctccttc cttttctcat 143160
cccatgcatc ctgagagtag agagagctcc agggttactt gcagtgaaga actcagatgt 143220
ttggggtttc ttctcagtgg gtgtttttac tgcgtggact gcttcattct gacagatgtc 143280
cctttgccca cagctcacgt ggagtgcgtc aatccattgt ccccagcatc agggctgccc 143340
tggatgagtt gttaaaagga aactcttaaa acaaggcaac tctctcccta acacccctgc 143400
atccctgttc ccacttgtag gtggtctgga cttggctatt gagggcccct caaaagcaga 143460
aatcagctgc attgacaata aagatgggac atgcacagtg acctacctgc cgactctgcc 143520
aggcgactac agcattctgg tcaagtacaa tgacaagcac atccctggca gccccttcac 143580
agccaagatc acaggtaggg ttgtctggct tctggggtct tcctcgtggg aagtatggct 143640
gcctctgact gccaccctcc ttatcagacc cctggcagca ggctagacgt ctctttgagt 143700
ttaggtttca cagagacttg ttgaggagga gcaggggatg gaatgcaatt ttggattagc 143760
taaatccttc tcttgctgat aatccaggaa aatgcgagag ctagtatttg gagcacactt 143820
ttattgtgcc agtgtgactc tagggtgcaa agagaaagct ctcagatgga gtgttcgaat 143880
catacttact gcaatagtgc atgaagtgca tgagcttaga catgcccttc agcgtcacta 143940
ctaggtaaat tttctgctat cccttttaca gatgggaaaa ctgaggcttg gcaaggtagt 144000
ggtgtagcca agttcacata taggtaaaca gatccaggtt atcaaattcc aaagcccatg 144060
ctcctcacct tgctgtgttc aggttatgct ttcagtgggt tataaggaag atgcacaagg 144120
cagatcctgt ttccccaccg tatttagacc tgtctgtgaa gcagccagta gtactgtgtg 144180
gaatgtggtc attgtttacc tagaaatgcc cacagccatg ccaggcaggt atgaggtgcc 144240
ttcaactaac aaaaattcct atattttatt ttatttttga gacagagtct cactctatca 144300
cccaggctgg agttttagtg gcatgatctc ggctcactgt gacctctacc tcctgggttc 144360
aagcgattct cctgcctcag cctcctgaat agctgggatt acagcaccca ccaccacacc 144420
cagcttattt ttgtattttt aatagagatg aagtttcacc atgttggaca ggctggtctt 144480
gaactcctga cctcaagtga ttcgtctgcc tcagcctctc aaagtgttgg gattaggcac 144540
ctggcccaaa gattccttta aaatgtggtc catgaggact caagtctcta ggtcctgcca 144600
gcttcttgtc tttgctgcaa gcaggcatga atcccatcat tcttcattgg ttgggtctac 144660
tcagtgttca aggctcattt ttttttcact taactttgtg taattagttc ttgcgtgttc 144720
atccgtgaac agcatatggc atggcagctc tgtgaagcca gggtaaccac atgtaacggg 144780
agtccttttt gggggatgtt tcccagatga cagcaggcgg tgctcccagg tgaagttggg 144840
ctcagccgct gacttcctgc tcgacatcag tgagactgac ctcagcagcc tgacggccag 144900
cattaaggcc ccatctggcc gagacgagcc ctgtctcctg aagaggctgc ccaacaacca 144960

-continued cattggtgag ctaggctacc cttcctggct ggagccagga catcttgggt gggagatggg 145020
gactcttgca gtcctttctt gggaatgggt agcacaatgg agtgtgatgt gataaacctg 145080
ctgggtcaca cgcacgataa atgcccaagc gtatttgtgc attgtgatat cgacactctg 145140
gattgttggg tgtcaggaaa gaggacatat ttctatttct gagagtgtgt ctctctcctg 145200
cttcctctcc gccatcccct tacaagcccc aatctgtgtt ctggtccagg catctccttc 145260
atcccccggg aagtgggcga acatctggtc agcatcaaga aaaatggcaa ccatgtggcc 145320
aacagccccg tgtctatcat ggtggtccag tcggagattg gtgacgcccg ccgagccaaa 145380
gtctatggcc gcggcctgtc agaaggccgg actttcgaga tgtctgactt catcgtggac 145440
acaagggatg caggtctgtg tggtcccagg ggagaggccc agagcttgtg ggaaccgact 145500
tattttgctg aggcagcgtc atcttttcat cctaccaact ccttttcctt tctgagcatc 145560
cttcaagcta taggtccttc tgcctgcatt gtcttttatg cctcatgacc attggcaaaa 145620
atgggattgt ctttgttttt tagatgatga aactgaggct tgcaaggttt agagcccccct 145680 ctgcactagg atctgaaccc agagccacaa cacctcgcaa acccctgttt tcttatctgc 145740
tctcccaccc ttgttctcag cttcccagcg tctctccaag caaagaatgt tgggttgatt 145800
ggccaagacc atggtcatct gagcagagct tttgtggaaa tgaagcatct ctttctgttt 145860
tctctttgag atggtttgag ttagattgtg tctcttccaa gcttgccaca ccccagtgcc 145920
tccagtcatc tgctttcttg aaggatggcc acgctggtga attctagaca aattctaacc 145980
cggggagagg gctggagaat ttctggtcct ggttgggaga tactccctgt taaaccttcg 146040
gatatgctga cctagctgag gtagccaggg gctatttaaa aattcaaaat ctcagatctg 146100
gctgtggata aacccccaag gtggtacgtg cagtacttgg aggcgtgagg gcagaaggtc 146160
ctccccagca gtttgtacgg gacacatcat ctatgggata ttagtaaata tccttaagga 146220
aaggcttctg tggtcaaaac caggttcagc aggttatttc actatggggc ttctcaggac 146280
gcttaaccta ctcatccccc tctgggcttt gcaaacgagg ccgccattgc tttctttctg 146340
ctatgtagaa atagattgag gcgtaagggt cggatgtcct ttctccattc atcaggctcc 146400
ctcttcctga ggagctgctg tcagaacagc ctggggctgc tgtgttgcag gttatggtgg 146460
catatccttg gcggtggaag gccccagcaa agtggacatc cagacggagg acctggaaga 146520
tggcacctgc aaagtctcct acttccctac cgtgcctggg gtttatatcg tctccaccaa 146580
attcgctgac gagcacgtgc ctggtatgtg cattccattc ccctccaggt gggatgcttg 146640
ggttttctgt aaatgctgtg ccttggcctc tggcctgctc acaggagcct tcttgggtct 146700
tgcagggagc ccatttaccg tgaagatcag tggggaggga agagtcaaag agagcatcac 146760
ccgcaccagt cgggccccgt ccgtggccac tgtcgggagc atttgtgacc tgaacctgaa 146820
aatcccaggt gggcgtcggg gactagtagg gtggggaagc cttggctcca gccttcaggg 146880
cagtgggtgc ctttgggaac caagtttagg catggcccag aacacagtat ccaagtcggc 146940
tgtgctgacc ttttcatttc acttcatttc attatgttct tctatgttta ttttcacaga 147000
gtctcatcca agaaaaacaa atgtttacct tgctaccttt ttcctcttcc aaataaaaat 147060
agctttattg tgtcacatgg gggaaacgta gatatgcttt tagattttta gattaactat 147120
ctgtcaaata gaatcatgtc agtgaaagaa ctggccctgc cgatgccagg gtctggaagt 147180
atttaagagg tggcagccca gcggcatcct tctagtattt ctctttcatt cctgaaatta 147240
gaacgagggc tgtgctgcag aactcgctgg gccacatcta gccctttggt ggtgaattgt 147300
tcttcttggg ccccgattag ccagtcaaca ggtcacacag tctgtctgaa atgtgttcca 147360
agttctttct ataaagaatc cttccagagg gaagccactg tgagtgaaaa ttttgaggct 147420
cctctgccca gaagttggca tgtcctgtgg aattgcacaa attctacaga gaagggaaat 147480
ctaaatcgtc ttcagatgga gcttgtgttg cgagctctgg agagggggtt gtctttctac 147540
actgcatctc ccatccttcc taacgagtca cggagctgtc gactccgcct tcttggcttt 147600
agttaacagg ttcttcttgt gtagtcacat caacgtcggg tcacatggga atgtggtaaa 147660
gcctcattac tgtagagttc agacatgatc acttaaaaag agctttattg ggccgggcgc 147720
ggtggcttac tcctataatc ccagcacttt ggggggccga ggcaggcaga tcacctgagg 147780
tcaggagttc gagaccagcc tggctaacat ggcaaaaccc tatctcttct aaaaatacaa 147840
aaataagcag ggcgtggtgg cgggcacctg taatcccacc tactcaggag gctgaggcac 147900
aagaattgcg taaacctggg aggtggaggt tgcagtgagc tgaaattgca ccgctgcact 147960
ccagcctggg caacaaagtg agactccttc tcaaaaaaaa aaaaaaaaaa aaaaaagagc 148020
tgtactgatc gtttgtagtc ataaacagtt cgtgtgcctc aaggtggggg gaggaagtgt 148080
cacctcccag agagagcttg gttcacattt taggtacaga gttggaccct ggctgcccca 148140
tcctcatagc cacgtctgct cactttccag tcacattggt gtactcatcc actgtttttg 148200
tgggcatctt cccacctcaa aaaatagaca tccacatcat ctctttcatg accctgataa 148260
aatgccattt cattcaatgg aactattggt gatagaaaaa gagagattcc atttcatgtc 148320
tagatgcatc aaccttcgtt actcatctct gtgcctcagc tcccatcatc agggctgctg 148380
tgacatttgc caccctgtgc tcaggctgtg ggctggatgc ccaggagtgg gctgggctgg 148440
tgcatttcag atgctgccat gccttggcag accgccctcc acatttctcc atactccccc 148500
accagcactg gggctgtctc tccttctcac tttggccaac ctgatggaaa aacatggcat 148560
tcagtgttca gtttcatatc ttcgattact agtgatatgt gtactgtgtt ttcttttcat 148620
ttgctttaca tttctcattt ggcaaaattt ctgtgctctg cttatttctt gaggaactag 148680
caagtatctg cagtgtggac gtttaccctt tctcttaagt ctcttccagc tcttggccat 148740
tttgttattc ttttagttac ttagtaccag atgactctgg gtgaggctcg attttccact 148800
cattacccaa atgatcctct cggagatccc ctcctcctta atggaggaca gctcactaac 148860
ttcagatgtc ctccggaccc aggttttgcg gggcatcttt gtcagtttgg gctgctgtag 148920
caaaatcaca tgaactaggt ggcaaccaac agaaatgtat gcctcacagt tgtggaggct 148980
ggaagtccaa gatcaggtgc cagcatggcc agattgtggt gagggcctcc ttccaggctg 149040
caaaccgaca gcgtcccctt gtatcctcac atgctggaga acggagggag ccagctgtct 149100
gggactctta caaggccact gaccccatca cagggtcgct ccactttcat gaccttatct 149160
aatcctaatt gcctcctcaa ggcccatgat aatcccatca cattgttggg ggtagggttt 149220
caatatttga attttggagg gacacaaaca ttcagttcat tacatgggtg accctctttt 149280
caacctccct tccctttcct gtcctcaggg gtcagagtca tgaactgctc tgcccagatc 149340
ctgtggggct ggagggtgca gtttcatact ggctctaggt gatggcagtg ctccgtgccc 149400
cgcatgcggc cgcctggcct caccacggca gtgcaggcac agtcgttggc atgacgtgag 149460
cagctcacgg agagtgatgt ggtcttgcgt cctagcactg gtgacccgag acattgcttt 149520
tctgaaagtg tggcccctgg tctttggttt gctcaaagct ttgctcacgc atggtttccc 149580
ctctgccatt gggacttaca tatgttcacc tttttctcta actttgtctt gttgcctaaa 149640
agaaatgcca aagcttcttg acggtaaagg atgatggctc ttgttttcta cccttaccta 149700
tctgtggaaa ggagcccgtc tgtgcatgat ggatgaccac gtcacctttg gcaaaaagtc 149760
tcagtgcccc cagcatgggt ggcctgaagg gccctgccca ctccatgctg gccacagaag 149820
ggcaggcacc cagcctgaag ggaaggaagc ctgggcacct cacgtccacc gggctgcaca 149880
caccttgctc tcggctgctt gccctgcatg tcctgccctg tctcaggccc ttgccctaac 149940
cctcttctct cccccaacct ccctccctct ttcagaaatc aacagcagtg atatgtcggc 150000
ccacgtcacc agcccctctg gccgtgtgac tgaggcagag attgtgccca tggggaagaa 150060
ctcacactgc gtccggtttg tgccccagga gatgggcgtg cacacggtca gcgtcaagta 150120
ccgtgggcag cacgtcaccg gcagcccctt ccagttcacc gtggggccac ttggtgaagg 150180
aggcgcccac aaggtgcggg caggaggccc tggcctggag agaggagaag cgggagtccc 150240
aggtgagcat tgcgggcagg attttcactt gggaagaata gagttgagcc caggcagtgt 150300
gggcacccac atactttttt gccccatttg aaagagaaga cttctgatag gtggcattaa 150360
gggcattatt taaaacaagg catcatgact aagtctggca cagtttgtaa ctaagctttg 150420
ctcacttacg taaagccaaa caggtttctt actgggagcc tccttggagc ccgtatctta 150480
ttagtgtgca cctgagtctc taattgggga gcagagtaat acggtttcca gagcatcttt 150540
cagggctgat gttctgtgga acatactaga aagctacaaa actgactgta agcatccttt 150600
cctgtggttg ccgctggtgg gaagatctgt agggaaaaaa tggaacattc tcatctttct 150660
ctggcttggt taaggtgtat tcattttttta aattttttat ttaatatctt tttctctctt 150720
gtttgttaga gatggggtcc cactatcttg ctcagactgg tcttgaactc ctgggctcaa 150780
gtgatcctcc tgccttggcc tcctaaagtg ctgggattat aggcatgagc cactgtgcct 150840
ggccggttaa gatgtattca gggctgggcg tggtggctca cacctgtaac tctagcactt 150900
tgcaaggccg aggcaggcag actgcctgag ctcaggagtt caagaccagc ctgggcaaca 150960
cggtgaaacc ccatctttac taaaatataa aagaaattag ctgggcatgg cggcatgagc 151020
ctgtagtctc agctactcgg gaggctgaga caggagaatt gcttgaacac aggagatgga 151080
gcttgcagtg agctgagatt gcaccactgc actccagcct gggcagcaga gcaagactcc 151140
gtctcaaaaa aaaaaaaaaa aagacatgtc ttcagaggac tccagatgtc ctgtgaattt 151200
agttatcact agtgatgctt aggaaacttc agcaatggac cttggacctt gcttgggttc 151260
tgcttggggt tggagaaaga ggaaagggct agcaacagac gaaacctagc actgcaggtt 151320
tgaacaagga tggaagaggg acaggggctc tgtggggctc agtcactaac caggtttctc 151380
tttgctctca gctgagttca gcatttggac ccgggaagca ggcgctggag gcctctccat 151440
cgctgttgag ggccccagta aggccgagat tacattcgat gaccataaaa atgggtcgtg 151500
cggtgtatct tatattgccc aagagcctgg tatgtattca gggttcacaa gaggacattt 151560
tccttgtttg aacatgatta ggttgcaagg aacagaaatc catcaagttt gctgaagtca 151620
atgaggaatc tatgtgtatg ggcacatggg acagcctcct agaaatccag ttgcaagata 151680
catggccaga cctcttaagg gtgggaacgc ttgttctggt tgccttttgc ctttctccat 151740
tagcctctct gcttcttgct ttcattcaat tgctccattc tttccaccaa ccagcctctg 151800
tctgcccacc catggctacc ctggctggct gccccagaag agtggccttg gcatctgagc 151860
tccctctagc aggagctctt aaccttttgt gtgccattga ctcttgccat ctggcgaagc 151920
ctatggggac tgttcttggg ataatgtttt aaagcacata aaatgaaata tgtcacatta 151980
taaaagaaat cattgatatt atagtacagt taccaaaatc ttacaagaac aaatatgcaa 152040
catagaaaca tgcatatctt cgttaataca ttaaatcata agatttggtg acagtatatt 152100

-continued aactgtcatc aaagtgacaa agtaataagt gaaaatgata cgtcaaaata actgtaaaat 152160
gacataaaaa tatatgattt ttaatggtga tgtaagtcat atgtacttat aatgtgctgt 152220
gatttcttgt caacatttct gaagaaagga aatggtaaat ttcagttaga gaatggtgaa 152280
aattaaaacg taattttttc cccattgaag tccatggatc tgctgaattc aatacaggcc 152340
atttggggac cctgtgagcc ccggttaaga gtccctggcc ttacccccact aaggaaatca 152400 tatcggccca gcctcagcca ggcgactccc actcaaccaa tcagctgtgg ccattgagga 152460
gggctgggtc tctctgaagg cattttagcc cttggtgaga agcaagagtc cactctgggt 152520
ccagagtctc tgaaatgatg ggactttcct gtcctcatag gtaactacga ggtgtccatc 152580
aagttcaatg atgagcacat cccggaaagc ccctacctgg tgccggtcat cgcaccctcc 152640
gacgacgccc gccgcctcac tgttatgagc cttcaggtga gatgcaagga agcatccatc 152700
tccttggccg caggccacca gtgagacccc tggactcctg aggctgcttc aatgtcccct 152760
taggtgctga ggccccttt cacattttga ccacagatgt cacccagtca ctggggagct 152820
ttcctgtggc agagtcaact ccccatacac ttagggcgga tgacacttgg ggcgagcaaa 152880
aacagagcca cagtcaacaa cacaccttaa tgtttgggga cacgtttgtt tttaaaggtt 152940
tatttaagag aaacaaagga agcctgttca taactggtta agggataaca agggctttca 153000
aaacaaaacc aacacaaaaa taacagtgca gtgatgtttt agcctgctgt tgttggctgc 153060
ctttcttcaa gaaagtcagt tgcaacttac tgtgattcat taataagtgt gcagggaact 153120
atattaagag ctttatcagt gttacctcag taaatccttg caatagcctg acaagtaggt 153180
tctcttgacc ccattttaat gatggaaaaa cagagataca aggaggtttt gtccactggg 153240
aaccagctag tatgaggcag aacaggcaca gtgtggctcc agaacctgta tttttgtttg 153300
tttgttgttg ttgttgaggc agagtctcgc tctgtcaccc aggctggagt gcagtggcat 153360
gatctcggct cactgaaacc tctgcctccc aggttcaagt gattcttctg cctcagcctc 153420
ctgagtagct gagactccag gcacgcgcca tcacacccgg ctaatttttg gatttttcgt 153480
agagatgggg ttgcaccatg ttggccaggc tggtctcaaa ctcctgacct gaggtgatcc 153540
accccactca acctcccaaa gtgctgggat tacagacgtg agccactgtg cctggccaga 153600
acctgtgccc ttaacggcaa cctctctaac ccccacctga tgttgtggca cacggttgca 153660
tagtccatcc cattaggata ccaggagatg caacattttt cctcgtccta aacaggtcac 153720
ttaattcaag gttgtactag caccttcagc caaactaaga accatcgggg atgcctctgg 153780
gtttttgccc aggacactga aaaataatta ggtgtctgaa ctgggagtag caattaagtt 153840
gtgaaataac atcgaaatcc caaagtatga tttctgggta agagtttcta aatagccttg 153900
agctgccccc agttcttgaa aatattggat tcattaaaat ccaatctgat gtctaagatt 153960
ggtgatatca ttggctttag ttccatacac ttggtttaca tttgagattc taatcttact 154020
ctgaggggaa ctgggatacc tccagttgtt ccaaacatta gtctttcatt tagagacgta 154080
aacagaaccc aaaccagact cagtccacac attgaagcgg cctcatccgg agaataccaa 154140
gggtactaac tggttactgt ggtgtagatg tttttcttgt gtttcattta aaggcttctt 154200
aacagaagtg tcttttgtgg ccaacttaac taaaacctac ggagggagat aaacccagca 154260
cttattgagg gcaggagctg ccctcatgca tctcgaagat ttctttcaaa tctgccgagg 154320
catttatctc cctcttgagg atttagcggc aagcggattc aggtaatgta aatgattctg 154380
tctaaaagga gctggtttgg aaaaatcccc tccaggaaac ttctgtagag tgctctcgtc 154440

-continued

```
atagctgggt cataaatgtt tcagtaagtg cacagcaggc tgtttcttaa gcttttgtaa 154500
ccagctgctg ccgcaggaga agtgtgttca tcagcatcgc cccctgttct tcccgggtca 154560
tttgatgccg agtgatatgt aaattattga tcagagattt tgcggaggcc cacgcaagca 154620
acatctggtg ctggttagca aagagaggca tgtatcgttt tgtcttgctt ttgagacttt 154680
ttaggaaatt ggagtaggct ggcacttggg gtgggggtgg gatgggagtg atctggtgat 154740
caaagaccct ctaattctgt gttctgtcct ccctcctcag tctatatccc ctagggcagc 154800
acagtccaat agtaggttct gcagtgatca aaatgcttca agtctatgct atgcagcatg 154860
atagccacta accatatgtg actattgaac atctgaaatg tggccagagg aaccaaggag 154920
ctggatgttt agttttattt aagtgcatta agttgaaata tatgtatata tggcctcgtg 154980
gctggtgact accaaattag ccagtgcagc tttaggacct tgccatgaag atgtggttct 155040
tgggccagtt cttggacctc agcatcacct gagaacttca gtcccagacc cactggaaaa 155100
gaatctgtat tttaataaga tccccagatg gtttgcttac acattaagtg tgagccatgc 155160
tgcttcagag ttattgcctg aggagtggct gtccgaccaa gtctaaatca aaattactga 155220
cttgtaaaat gctgctgttc aggattggct agtcttaaaa tatctcaaat gttgttgctc 155280
agctttgttc ttaaccatct gaacttctaa tcccctcctc ccagaagagg agatagtttc 155340
caagacaaag tatggggagt gaaactgatc cagggaagag caaaagctat gtctttctat 155400
ggcttcttgt ggggatacaa cctctaaatg catattaata tttaataata agctgacgtt 155460
ttcgagcctc tctgtgtatg ggctaggccc tgtgataaat gttttgcatg cacagcttca 155520
tttgatcttt atagtagccc tcgagataga tcgttattat gcccatttta cagatgagga 155580
aactgagact cgaagaggtt tggcacccta gatatatagc taggaaatgg taggaaatcc 155640
agatccagct gattcttaac tgctatggag tactgccttc tttgcacacg tagcccttta 155700
taatatgttc ctccaggtct gcccttgaga taacaaacag cataacataa aactgtgttc 155760
gtgttcgtga gtgcatgact ttgttagctg cagtatcctc ttaaaagagg acactttttt 155820
gacctggaac atactgggtt ttctggcctg catgggcatt attttggatg ctgagatgat 155880
agtccttttg accaggatgt ctcaagtatc caagcccaga aatcatctct tctaggctga 155940
atcaagatgg tttgcataag agaccatgca gatgcacgtc tctgctatct tacattaaaa 156000
atgcagaatg gctcacctgc cctttgttgt catatgttat atagaaaaac ctatttgcat 156060
gagaactgtc acccacagtt ttgggtaggg tcagtgtgtg ccactgagca ggaacgccga 156120
gggccataac ctgtctgatg tattaaattc tcaggaatcg ggattaaaag ttaaccagcc 156180
agcatccttt gctataaggt tgaatggcgc aaaaggcaag attgatgcaa aggtgcacag 156240
cccctctgga gccgtggagg agtgccacgt gtctgagctg gagccaggtg agcaggaggc 156300
ctgctggggg gtcccagcac cagcactttc cagcagaatg ttcctgtaaa tgtgtgtccc 156360
aagggagggc tgatcagttt cattactgcc agtgagcctc tgaattccct ttgctgttgc 156420
cagatattgt ttataaatta gggtttaaac atgtgccagg gatagggaga ccctttatgc 156480
taggagagaa tgctcattct ttctttcttt tttaaacaaa tgctgggctg ggtacagtgc 156540
cttaacctga gaggtcaagg ctgcagtgag ctatgatgca gtgagctatg attgtgccac 156600
tgaactccag cctgggtgac agagtgagac cctgtctcca gaaaaaaaac aaaaaaacaa 156660
aaaaacacat acacacaaca caaaaacaaa tgcttctttg ttttctgtta gtttttcaga 156720
ttccttttgc atgacattca tcataatttt tctttcatat tgtaacaaca tcttacagat 156780
ttttattcat tgaccttatg gcacgagtaa gcatattttg atctcacttt actctaaagg 156840
```

aaaagtaggt taatgttctg taaatttaaa aaagaaaatc tgggtctcta ggccctaatg 156900
tcctaagatt tttcttgctt ggtgccttgg tatatggaat tctctgattt aatcaacttt 156960
aaagagacag tgttaccggt gaacataata aatttattaa gtgtcagaaa cttgaaggaa 157020
ggtataaggc tcaaagagtt gctcaaagtt tagtgaaggc ctggccaaaa agcagatgat 157080
gaccccaaat gatcactagt accacaggag aactgtgaag caaatggtaa agatggtcag 157140
agcaggagag agaaatagtt tctgcctcgg tgagttcagg agggcttctc agaggaggtg 157200
acatttgatg tgggccttga tgtatgagga ggagacctat gattactgcc ttatagggca 157260
tttgttgtgt gcctggctgt atttgtatag tgtagttgga aatctaggct ctgaccaggc 157320
atggtggctc acacctgtaa tctcagcact ttgggaggat cagttgagcc caggagtttg 157380
ggaccaacct gggtaacata gtgagacccc ttctctacaa aaaaaagtaa aaaaaaaatt 157440
agccaggcat ggtggcacac acctgtagtc tacttgtggg ggatgaggtg ggaggattgc 157500
ttatgtccag gaggtcgaga ctgctgtgag ctgtgatcat gccattgcac tccagcctgg 157560
gtaacacagc aagaccctgt ctcaaaaaga aagaaaaagg aatgtaggct ctgtgtgaac 157620
atttagatct atgtttccta gtaggcagaa aggcagtggg gagcctcagg aggaacaagt 157680
gtaaaggatg gggtcagatc ctggttttag tctgaaaggc caagtggcaa gctggtgctc 157740
ccagagtggt ccatttgagg aagcagtggc actggaaatg gagaggaggg acttgaggcc 157800
agagatctat ggtggctata gagagtgaga gagagaatcc attccaaaat gttccacgta 157860
gcttagtgat tgggtcggaa gatgacagtg cagttatcag aactagggcc agccaggcag 157920
agggtgggtg aggattggtc agggccttaa agggtttaat attttacttt gaggggtttt 157980
gaaggatccc caatacccaa atggagatgt ttactagatc actgtgaggt ttggtggcct 158040
cagccccaac agtccctcac tgggtaccct ccctcttctc ttaaagccaa tgtgcttcag 158100
gggaagctaa ctccacccca gacaggattt gaacccctac agatgtatga gatcattagc 158160
atgacacagt tactattgat tgcaaattac agaataccca gctcaagcca actcacacaa 158220
taaaggggcc cagtaagttg cataactaga aagttcaaga catccaagac aggtttcagc 158280
aatttgattt ggtcattgag ctgcgccctg caaggcgtca aatatttctg ctgttctgct 158340
ttgtgggcct ggttctggcc ttcctcttgg tggcaggatg gccttcctct tggtggcagg 158400
atggctgcag cagcaccaga tgtcccacct tcacgccaca tcaattaaga gagacaccct 158460
ctcaggattc ttagaagtcg agagcctcct ttcccagaag tctccagcac gtctgccttc 158520
ccctctcact gacctggaca catgcccact gctgagtcat ttcctgtggc taaagaaatg 158580
ccatgtgctc attgactaag gcttagtgaa gaaggatttt tccctgatcc actcagggac 158640
cacacctgga catggcggtg gagccagctt cccctacaac acattggctt taagggaggc 158700
ggatggggac tgttggagga tgttcagtgc caaaggacgt agggtgcaca gcttcatgga 158760
ggtgcacctc tgtggagacg tccagaggca gggagaagag ctttggggaa cacaaattct 158820
gagagggatg aagagtacta ggcaccaggg agagaccgag agactacctg gagaggtagg 158880
aggagaacag gctctgcacc ctgggcagga gggcttcaag gaggaagcgg cagtcaggtg 158940
gtgcacaatg ggtagatgtt ctaggtgccc acttcagtta acagattacc ttgctacatg 159000
ctgtgaccca aacgcacagc cacaaacctg ccctgtgggg gcagttccta gctttgagct 159060
taattaagga gcattaatgc cagttggaac cgtttttttt ccccttcaag tggccaaata 159120
gagaaacata gaagaagtga ggttttcttt tttcccttca tatatattcc tttttatttc 159180

-continued ttgttatgcc ttcccaaaac agagacattg aacagtagtt agaatggcca tctcccaatg 159240
tttaaaaaca aactgaactc cccaatgggt gaacaaagta aagagtagta acctggagtt 159300
cagctgagta agccgctgcg gagccttaag tggtgaggtc ttccaatttc agagtgctgt 159360
gtcttcaact tgtatcatca ttttagtgga aaaacataat ttaattttgg tgaaatgaga 159420
ttcatctcgt gacaggatta gtaacagcat tcacagaatt tcacactgaa gaagtgaggt 159480
tttctaaaga aaggaagtgt tcttctgagg caggggtcag agtcttgtcc tgtgtttata 159540
ggatttgcaa tgtggatgcg tttcccttgg ggctgatgag ggatacccag gggtctgtc 159600 tggttctgaa atccaggatg ctgagtgcca ggctccctgt agaactgttg attttaaatg 159660
ggccatctca gcttggcctc catcctttat cctcactgaa ctcaggggtg tccatttgct 159720
tgatttcacc ctgtgccttt gctcattctc ctagataagt atgctgttcg cttcatccct 159780
catgagaatg gtgtccacac catcgatgtc aagttcaatg ggagccacgt ggttggaagc 159840
cccttcaaag tgcgcgttgg ggagcctgga caagcgggga accctgccct ggtgtccgcc 159900
tatggcacgg gactcgaagg gggcaccaca ggtaacccac tcttctgctt cttgaagcct 159960
taactgaacc agctccaggg accaagccag atggaaatcc tcaagcccca tgaaagcttt 160020
ttacacgtac tccccgtgga aactggggtc atgcacactt cggaggcgct tgctgtccaa 160080
agctgttttg ggagttgcgg tttgacccac gataaatcca gagtgagagc tcgatggccg 160140
tgttatcaca cctcattact gttagttgtg attcagattc cttcctctgc caagtttctt 160200
gactttcaga acaggatgct gatagtcagg gaacacagca cagtgtcatt aattttgagg 160260
gtttctttgc ctgcacagaa ttcatgatgc gtccaagtgg gctcctaccc gtctgttctt 160320
tcatggtacc aggctcccag aaatgcactg aagcagcaat aagacctgtc ccagcctatc 160380
tcctcctctt tttactctca gatcttaatg gaggaggaga aaagactgaa atgttcaaag 160440
aattctgaag ctttttagac ccgttacaat ttacttttat tctttgccac agatgggaca 160500
tgtttgatta tgaaagatac aggcagtgaa gaagtaaata aagtgagact cactccatct 160560
tctctcctcc tcccccacct gggtctggaa gcaaacggct ctgggaaggg aggaccttca 160620
ccctgtctgt catctcattg tctgtcttca ttcttggttg ctgggttggt tagctaattg 160680
gttcattaga caagcagaca cagagttttg cttttgtctt acagaaagaa tcttactgta 160740
tccactgtgt ggtatagctt gtgtttttgc tttgacatct taaagatctt tccatgtcag 160800
aacagatctt cccctccttt tcctggctgt agtgagaatt cctgctgtga atcgcagtta 160860
tttgaacagg tggcatcggg tggtgcgcag tgagtgcgtc actgttatgg aggctgccag 160920
ggtggagagt cagtccttag tctttgcagg ggaagtgcgc agtgtggact cactggggca 160980
tgtttgcatt tggtgttact ttggaccctc ttgggaaagc agtatgtcct ggtttcttga 161040
gtctcttgtg tgtgtacccc caccccgcat aaggagagtg ggatggagca gacttgcctc 161100
ccaggggtga ggggtgagtg gctgcatggt tgcctggcat ccagccctag gagcaagtga 161160
cctgtgtggc caaggggccc tctccgggtg caggagtgac tggtgggctg gcaggctgcc 161220
cgggactctg gccaaagcag tggcctcagc aaagccaccc acaggggtgg tgtgagtgct 161280
gccagactcc ccaggcaaat ccagcccggc tccacgctga actctgggcc tgcggcttgc 161340
cttttgtgaa aggcatggta tcattttacc gtaagtgatg tccattttac agatgtggaa 161400
agtgagatgc agaggttgag tcactcccca aacaacactc ccccaaaaag cagtcagctg 161460
ggaggaggca gaaccaggaa tcagtctaca tccgtgacct cagagcctat gcgctgaacc 161520
cccgagcttg gccccctctc taagtggctg gctcacccag aggcagtgac tgcatcccca 161580
gcccactttg gggatgtcct aaaccaggac ccctgtcctc ccagccactc aggagtactt 161640
tccaggcagc agtgctggca cttgggccct gacaaggtac tcacctttga gggcccaggt 161700
ggggtcctct cggcacttgg agcgcgtggc aggcttcagg ccaggcctca cagcagctgc 161760
tggggtctcc cacactggcc aggaagcatc tcaccctcct gctggctcat gccgctgtgc 161820
ctgggccctc tcccatttcc ttttggctgt tcgcacacct ttttgggagc ttgggtttca 161880
ggctgtgctc tgcaagtgct ggacgctgct gagagaagga gttgctcttg cagggaagct 161940
cctagccagg aggggagagg tacagaaccg cctgcttcaa accctgtgta aatattgctc 162000
ttgtcacagg gaaggcgcct tgtttttcca gccctcctgc tcccaagcct ttccctaaat 162060
atccattctg agattacaca gctgcagtgt gcatggaatg aaaaggtatc tgtgcttggc 162120
cgccagagcg cccagtatcc tgaccttctg aacaaagcaa acctccctct gtttttaatg 162180
ggtgagtttg ctgtatctct tggctcaagc tttaaatggt ccattctgta gattttggag 162240
taggggaatg tggagaattt ggggcgggac cctgctggag gcggcttgag aggctgggag 162300
atagaccagg gagctccaga ttctttggag ccgctgagca attttcctaa tgaaatggtc 162360
caggaacccc agtgtgctcg gggtatacca gaagggcctc cttccttaac tgccttgaag 162420
aacaagcagt gctgcgttta acatgcatta aactcacagg aactgagctg gacatatttg 162480
agggggtggg ggaagaccgc cacgcccaga gatgttttgt ggtgtcagat acaggttata 162540
gctagaggca gtggtgagag acttctgctt gtggattttt ttccttccat cttctctcag 162600
gtaagtgctt tagctccaag ttggacagac tttatgttta aatcccagtt ctgctggtcc 162660
ccagctgtgt gactccagat gaattatctg acttcactgt gcctctgctt cctttcctgt 162720
aaaacaggat taataacagg acccacctaa taggcttgtt tggagctgta gaggaggtaa 162780
cagccaagta gtagctcttg tcccataacc cctgctttct cttttcccac ctcgtcttcc 162840
ctgccctttt gggccctcac agtcaagatg aactgatttt tggttggtca aaatattgca 162900
ttagggccaa atgggtgcgg tggctcatgc ctgtaatcaa agcactttgg aaggccaagg 162960
cagaaagatt gtttgaggcc aagagtttga gaccagcctg ggtgacatag taaaactcca 163020
tctctaccaa aaaaaaaaat ttttaaagac gaacttagga atgaaacagc ttgttaaaaa 163080
atggtggaac tttcccctgc agccacatca tttcaacttc actttaaaaa tatctttttg 163140
gcctggcaca gtggctcaca cctgtaatcc cagcactttg ggaggtggag gtgggaggat 163200
cacttgagcc taggagtttg agaccagccc aggcaacaca gcaaaacccc atctctacaa 163260
aaaaatttaa aaattagcca ggcgtggtgg tgcatgcctg aagtcccagc tactttggag 163320
gctgaggcag gaggatggct tgagcctgga agattgacgc tgtggtgagc tgtgatcatg 163380
ccaccgtact ccagcctggg caacagagga agactttatc taaaaaaaaa aatattagta 163440
ataaggccgg gtgcgttggc tcatgcctgt aatcctagca ctttgggaga ccaaggtggg 163500
cagatcactt gaggtcagga gctcaagacc agcctggcca acatggtgag accccatctc 163560
tactaaagaa atacaaaaat tagctgggca tggtggcgag tgcctgtaat cccagctaat 163620
caggaagctg aagcaggaga atcgcttgaa cctgggaggc ggaggttgca ataagccaag 163680
atcatggtac tgcactccag cctgggcaac agagcgagac tctatctcaa tcaatcaatc 163740
aataaaatat ctttccttat catcacctta cagctgcttc ctggatggac acactgtctc 163800
cttgttgctc acctcccgct tcttccctac gtagccccag gcctcagagc tgctgcttga 163860
ggggcttctt ggctgcacag attagatacc atgatgaggt tgagatagtg ttgggggtgg 163920
accttggggc aggagcctca agagcttcca ggaacagctg ggttgtgttt gagagttgca 163980
cgatagcagc tcttttgttt ttattgatat ccagaacaat aattctttct ctggactagg 164040
agctataatt aaaccaaaat atttcccagc tggggcagtg tctagggctc tggcagaagc 164100
atagccctgc atggggatgc tatgccaggc atgccccata gagggcactg tagcaggcat 164160
gcgccagacc tgatgactga aggaggctct ccctgggcca gctaagttgt ctcagggctg 164220
cagttagggg atctgaggca gctccactgc ccatccaggg gtcaagagat gagcctggca 164280
ccagagccat gcagacatgg ttcaaacccg gctctaccac tttctggttg tgtagcgtga 164340
ctggccccct ccctgagccg cagagtcatt tgtgaagcag gaatcacgga aaggattcca 164400
taccacatgc gtaaatggtg ctgtgcacag gacctggagc cggagtgggg tacgcatgcc 164460
ccgtcagcgg gagctgctgt tctgttcctg tgcttgttgc tggaattcac ggcaaagtgg 164520
gtgggctggc aggtcacagt ggctgcaccc ggtctgcagc acagtgcctg gggtgagggc 164580
tgaggaggaa gggaggagat gcttggcctc cctggcttct ccaagtctac ccggagaaga 164640
aaggacagtc agaggggccc acgcctcccc cacacccctg gagggagagc tggactctgg 164700
tggctgaagc agcacttcag gctcacagtg tgactcaggc ttcttgccct cagccacaat 164760
ggctcatgcc cagaggagag aacagggtgt ccaggctgtt ggtgcttgtg ggcgaaatgt 164820
cagccatgct cctcctgcct tggcctagaa aagggagccc ccaccccgca gggcctgagg 164880
ttctctctgc cagaagttca gagctagtgc cagtgggttc ccatgccacc agggtgagcc 164940
ctctgtaagg ggatctatgt gtgtccctca ccacggcctc agtgctccca ggaaagccct 165000
ccaagtcatc aacacagcat tttctattcc tttctcccag gtatccagtc ggaattcttt 165060
attaacacca cccgagcagg tccagggaca ttatccgtca ccatcgaagg cccatccaag 165120
gttaaaatgg attgccagga aacacctgaa gggtacaaag tcatgtacac ccccatggct 165180
cctggtaact acctgatcag cgtcaaatac ggtgggccca accacatcgt gggcagtccc 165240
ttcaaggcca aggtgacagg taacgaacaa ccaccttcgg agttactctc ccttcctggg 165300
gagctggttg tgtcagatca atcatagtgg aaactatgga tggttttaga tgtgttaaag 165360
ctactttgaa ctttgaatgt cagtaaatag tatgagatgt cagagggcag tgtttgaaac 165420
ttacaaaagt ccacagagtg gagccgtgca gaagttgaga aagcatgtta ggatgttagg 165480
tggttttcta tctctaacag gaaagaatac atattgaaat cttacgtatt tgtttagatc 165540
agggtctgaa aaatcccctg atttctaatt ttcacttgaa aaataatcaa aaagttttcc 165600
tatacttata aaaatgtgtc tcctccaaaa cactggaaaa aataccaaac tatgaaaacc 165660
acttcacagc caccacccaa ggtaaccacc ataaacactg tagtaaatcc cttccacacg 165720
tcatgattca ctgttacata aagaatgtag gttcatcgca ggaaaattag aaaattcaga 165780
tagaaaaatc atcctttctc atccacagaa tcatttttg atatttcatt atatgtcatc 165840
ccaaactttt acactgctta tacatagact attttatgtc aatagaaaga tgtgaattcc 165900
acaggcacat ctttggtggg tagggggtgg ggggattggg agggtccttg gccttgtcag 165960
ccaaggccag actcatccat ttgcccagaa agccagatcc tagttgtatg ggggtgggat 166020
cctaggggtt tagaagacat tatgggtgtg agatacaggt gtggtggctt ttgtgttggg 166080
gtgcgcgggc tctcctgggg ttactgtgta gggtactcgc ctgtcctctg gctgagagac 166140
ccctcttgat ctggccattc atgcctgtcc ccctccctcc tgtatcttag gccagcgtct 166200
agttagccct ggctcagcca acgagacctc atccatcctg gtggagtcag tgaccaggtc 166260
gtctacagag acctgctata gcgccattcc caaggcatcc tcggacgcca gcaaggtgac 166320
ctctaagggg gcagggctct caaaggcctt tgtgggccag aagagttcct tcctggtgga 166380
ctgcagcaaa gctggtaggt gtctgggcct tttcaagggt ggggtggggc aggggcaggc 166440
tgggcaccct gggtacactg gccttccctg ctgaggtctc ctgcagtgcc cacccccatg 166500
taggccagcc gtttgcaagt aaccatcgtc atgaccctgt tctcctgcac ttaatatttt 166560
taaatgattt ccttctcttt tgccttttga acttgggtat ttatttgggt ttcaagggtc 166620
ggttgcctgg gttctggcat ccagtacacc tgggctggaa acctagtacc gccacttcat 166680
tcattcattc gtttgttcta aaacttattt agccatgtga ccttggaaag ttattaaatc 166740
tctttccaaa agtcagtttc ctcttctcgg aagtaccttc cttaaggtgc ttgtgagagt 166800
aaacaagaag attctcatag ccaacactta gaatagccct tactgtgtgc taggttttga 166860
cacccataac tcttaaacct cacaactagt tcgtgaggta tgtgctgttc tcattccctg 166920
tttacagatg gggaagctga gctagggaga ggtgagattc cagtccaagg tcacccaggt 166980
agcaagtggc agggcaggga ttcgaaccca caccgtcagg ctctatgagc ctctgcttgt 167040
aattgccacg ctctcccacc tcttaggggc cccagcatta tcgtggaagc accttacctt 167100
tggctctcat atttcctctt cttcctgtgc ctgtcctgat gcatccgggt ggagtaacca 167160
ccttttgcct cctaggctcc aacatgctgc tgatcggggt ccatgggccc accacccccct 167220
gcgaggaggt ctccatgaag catgtaggca accagcaata caacgtcaca tacgtcgtca 167280
aggagagggg cgattatgtg ctggctgtga agtgggggga ggaacacatc cctggcagcc 167340
cttttcatgt cacagtgcct taaaacagtt ttctcaaatc ctggagagag ttcttgtggt 167400
tgcttttgtt gcttgtttgt aattcatttt atacaaagcc ctccagcctg tttgtggggc 167460
tgaaacccca tccctaaaat attgctgttg taaaatgcct tcagaaataa gtcctagact 167520
ggactcttga gggacatatt ggagaatctt aagaaatgca agcttgttca gggggctgag 167580
aagatcctga gtacactagg tgcaaaccag aactcttggt ggaacagacc agccactgca 167640
gcagacagac caggaacaca atgagactga catttcaaaa aaacaaaact ggctagcctg 167700
agctgctggt tcactcttca gcatttatga aacaaggcta ggggaagatg ggcagagaaa 167760
aaggggacac ctagtttggt tgtcatttgg caaaggagat gacttaaaat ccgcttaatc 167820
tcttccagtg tccgtgttaa tgtatttggc tattagatca ctagcactgc tttaccgctc 167880
ctcatcgcca acacccccat gctctgtggc cttcttacac ttctcagagg gcagagtggc 167940
agccgggcac cctacagaaa ctcagagggc agagtggcag ccaggcccac atgtctctca 168000
agtacctgtc ccctcgctct ggtgattatt tcttgcagaa tcaccacacg agaccatccc 168060
ggcagtcatg gttttgcttt agttttccaa gtccgtttca gtcccttcct tggtctgaag 168120
aaattctgca gtggcgagca gtttcccact tgccaaagat cccttttaac caacactagc 168180
ccttgttttt aacacacgct ccagcccttc atcagcctgg gcagtcttac caaaatgttt 168240
aaagtgatct cagaggggcc catggattaa cgccctcatc ccaaggtccg tcccatgaca 168300
taacactcca cacccgcccc agccaacttc atgggtcact ttttctggaa aataatgatc 168360
tgtacagaca ggacagaatg aaactcctgc gggtctttgg cctgaaagtt gggaatggtt 168420
gggggagaga agggcagcag cttattggtg gtcttttcac cattggcaga aacagtgaga 168480
gctgtgtggt gcagaaatcc agaaatgagg tgtagggaat tttgcctgcc ttcctgcaga 168540
cctgagctgg ctttggaatg aggttaaagt gtcagggacg ttgcctgagc ccaaatgtgt 168600
agtgtggtct gggcaggcag acctttaggt tttgctgctt agtcctgagg aagtggccac 168660

-continued tcttgtggca ggtgtagtat ctggggcgag tgttgggggt aaaagcccac cctacagaaa 168720
gtggaacagc ccggagcctg atgtgaaagg accacgggtg ttgtaagctg ggacacggaa 168780
gccaaactgg aatcaaacgc cgactgtaaa ttgtatctta taacttatta aataaaacat 168840
ttgctccgta aagttgcctt ggtgttcttg gatgatgtcg cttctgaata aattgtttaa 168900
tcctaggagt tcaacaccct cagcctgggt aacagcaaga cccagcctct acaaaaaatt 168960
aaaaaattag ccagcatggt gatgcatgcc tgcagtccca gctactcagg aggcggaggc 169020
aggaggattg cttgagcctg agaggccaag gttgcagtga gctgtgtttg caaccctgca 169080
ctctagcctg ggcaacagag caagacagtg taacacacac acacacacac acacacacac 169140
acacacacac acaggcacat cgttggagcc ccagatcagc tctcccaacc ccttaaggga 169200
cacaaaacta gcaacttgtt ttgacaatga acctgggctc cttttgtggg ggtggggtgg 169260
ggctggtaaa caagctgtca cctgtcaccc tgctgtgctt attgttgctg ctgcctctgt 169320
ttctcttttt tttttttttt taattttcct tttttgagac agagtctcac tctgttgccc 169380
aggctggagt gcagtggcag gatctctgct cactgcagcc tccgcctccc aggttcaagt 169440
gattcttctg cctcagcttc ccaagtagct gggactacag gcgtgcacca ccatgcctgg 169500
ctaatttttg tctttttagt agagatgtgg tttcgccgtg ttggccaggc tggtcttgaa 169560
ctcctgacct caagtgatcc gccctgcctt ggtcttccaa agtgctgtat tacaggcgtc 169620
aaccactgcg actggcctgt ttctcctttt tctagaagag cttttgattg ctgaatgctt 169680
acgaggtacc tagcacccct cctccgcccc cacctcctcc tcctctgtct ccgcctcctc 169740
cccaccccac agcagtgata ccgctttaca gatggcacta ccacctcagg tgctgcaatg 169800
acatgtttgc agatgcaaag ctcacttggg ggaagaccct aggcccctgc cttcttgacc 169860
ccagggtgct agctctaccc cctggtgata ccgctgtgga aacaggagtc cccagatagg 169920
ccccggcagg tgccacggtg atgggaaatc acggctgggc ccccagccct ccagatgggg 169980
gttgggggtg gagagaaaag cagggaaggg agactggatt cttctgacac ctggctgtca 170040
attgggatca attgtttgcc tctgagagga gggaggaaga gagtggagga aaggtcctct 170100
cctcccggag ggagcagcct tatctgtggc ctgcaccagg aagcactgct tcctggactc 170160
ctatctgaga aggtccgtgg gcttcgggat tctgcagtgg cgggcagttc ccccacttgc 170220
caaagagtcc attcaggctc tgcccggtgg ggtctggccg ggccacagta tcatgctagt 170280
ttgcccacag aggagcacag ggcgcagcca ttggtctctc cactgtgaag cctggcggct 170340
ttctgttggg ggaggcagca tttgtaaatt aacagcatgg gctttggtgt caggcacccc 170400
agagcttcaa cgctggctct gccgttcatt agctgtgtgg ccctggggaa gtcgccttgc 170460
ctcacctctc tgggtggtcg tgaggatcaa ataagagccc acagggagct gtaaggaaca 170520
attccctgcc agagtctcag ccactgctgt ctgtgaccaa cacctgctgg aagtgatgtt 170580
cctggcagaa ggccgccccc tggctgcttg ttggcatctg gggctacact tggttgtccc 170640
ctgcatggga gcgatggtga tgttaccctg gggtaaattt ccccactaga agccactgcc 170700
tcctgttaca tcaaagacat cccagggtgg gatgcacctc tttatcagtc aatggctagg 170760
accacagggc aacccttacc tgcacctggg cttggctgct atggaaacca gctgtttgtg 170820
caaatacctt gaaaactttg aaacttgacc ccggac 170856

<210> SEQ ID NO 22
<211> LENGTH: 2633
<212> TYPE: PRT
<213> ORGANISM: Homo sapiens

<400> SEQUENCE: 22

Met Pro Val Thr Glu Lys Asp Leu Ala Glu Asp Ala Pro Trp Lys Lys
1 5 10 15

Ile Gln Gln Asn Thr Phe Thr Arg Trp Cys Asn Glu His Leu Lys Cys
20 25 30

Val Asn Lys Arg Ile Gly Asn Leu Gln Thr Asp Leu Ser Asp Gly Leu
35 40 45

Arg Leu Ile Ala Leu Leu Glu Val Leu Ser Gln Lys Arg Met Tyr Arg
50 55 60

Lys Tyr His Gln Arg Pro Thr Phe Arg Gln Met Gln Leu Glu Asn Val
65 70 75 80

Ser Val Ala Leu Glu Phe Leu Asp Arg Glu Ser Ile Lys Leu Val Ser
85 90 95

Ile Asp Ser Lys Ala Ile Val Asp Gly Asn Leu Lys Leu Ile Leu Gly
100 105 110

Leu Val Trp Thr Leu Ile Leu His Tyr Ser Ile Ser Met Pro Val Trp
115 120 125

Glu Asp Glu Gly Asp Asp Asp Ala Lys Lys Gln Thr Pro Lys Gln Arg
130 135 140

Leu Leu Gly Trp Ile Gln Asn Lys Ile Pro Tyr Leu Pro Ile Thr Asn
145 150 155 160

Phe Asn Gln Asn Trp Gln Asp Gly Lys Ala Leu Gly Ala Leu Val Asp
165 170 175

Ser Cys Ala Pro Gly Leu Cys Pro Asp Trp Glu Ser Trp Asp Pro Gln
180 185 190

Lys Pro Val Asp Asn Ala Arg Glu Ala Met Gln Gln Ala Asp Asp Trp
195 200 205

Leu Gly Val Pro Gln Val Ile Thr Pro Glu Glu Ile Ile His Pro Asp
210 215 220

Val Asp Glu His Ser Val Met Thr Tyr Leu Ser Gln Phe Pro Lys Ala
225 230 235 240

Lys Leu Lys Pro Gly Ala Pro Leu Lys Pro Lys Leu Asn Pro Lys Lys
245 250 255

Ala Arg Ala Tyr Gly Arg Gly Ile Glu Pro Thr Gly Asn Met Val Lys
260 265 270

Gln Pro Ala Lys Phe Thr Val Asp Thr Ile Ser Ala Gly Gln Gly Asp
275 280 285

Val Met Val Phe Val Glu Asp Pro Glu Gly Asn Lys Glu Glu Ala Gln
290 295 300

Val Thr Pro Asp Ser Asp Lys Asn Lys Thr Tyr Ser Val Glu Tyr Leu
305 310 315 320

Pro Lys Val Thr Gly Leu His Lys Val Thr Val Leu Phe Ala Gly Gln
325 330 335

His Ile Ser Lys Ser Pro Phe Glu Val Ser Val Asp Lys Ala Gln Gly
340 345 350

Asp Ala Ser Lys Val Thr Ala Lys Gly Pro Gly Leu Glu Ala Val Gly
355 360 365

Asn Ile Ala Asn Lys Pro Thr Tyr Phe Asp Ile Tyr Thr Ala Gly Ala
370 375 380

Gly Val Gly Asp Ile Gly Val Glu Val Glu Asp Pro Gln Gly Lys Asn
385 390 395 400

Thr Val Glu Leu Leu Val Glu Asp Lys Gly Asn Gln Val Tyr Arg Cys

-continued

```
                405                 410                 415

Val Tyr Lys Pro Met Gln Pro Gly Pro His Val Val Lys Ile Phe Phe
            420                 425                 430

Ala Gly Asp Thr Ile Pro Lys Ser Pro Phe Val Val Gln Val Gly Glu
        435                 440                 445

Ala Cys Asn Pro Asn Ala Cys Arg Ala Ser Gly Arg Gly Leu Gln Pro
    450                 455                 460

Lys Gly Val Arg Ile Arg Glu Thr Thr Asp Phe Lys Val Asp Thr Lys
465                 470                 475                 480

Ala Ala Gly Ser Gly Glu Leu Gly Val Thr Met Lys Gly Pro Lys Gly
                485                 490                 495

Leu Glu Glu Leu Val Lys Gln Lys Asp Phe Leu Asp Gly Val Tyr Ala
            500                 505                 510

Phe Glu Tyr Tyr Pro Ser Thr Pro Gly Arg Tyr Ser Ile Ala Ile Thr
        515                 520                 525

Trp Gly Gly His His Ile Pro Lys Ser Pro Phe Glu Val Gln Val Gly
    530                 535                 540

Pro Glu Ala Gly Met Gln Lys Val Arg Ala Trp Gly Pro Gly Leu His
545                 550                 555                 560

Gly Gly Ile Val Gly Arg Ser Ala Asp Phe Val Val Glu Ser Ile Gly
                565                 570                 575

Ser Glu Val Gly Ser Leu Gly Phe Ala Ile Glu Gly Pro Ser Gln Ala
            580                 585                 590

Lys Ile Glu Tyr Asn Asp Gln Asn Asp Gly Ser Cys Asp Val Lys Tyr
        595                 600                 605

Trp Pro Lys Glu Pro Gly Glu Tyr Ala Val His Ile Met Cys Asp Asp
    610                 615                 620

Glu Asp Ile Lys Asp Ser Pro Tyr Met Ala Phe Ile His Pro Ala Thr
625                 630                 635                 640

Gly Gly Tyr Asn Pro Asp Leu Val Arg Ala Tyr Gly Pro Gly Leu Glu
                645                 650                 655

Lys Ser Gly Cys Ile Val Asn Asn Leu Ala Glu Phe Thr Val Asp Pro
            660                 665                 670

Lys Asp Ala Gly Lys Ala Pro Leu Lys Ile Phe Ala Gln Asp Gly Glu
        675                 680                 685

Gly Gln Arg Ile Asp Ile Gln Met Lys Asn Arg Met Asp Gly Thr Tyr
    690                 695                 700

Ala Cys Ser Tyr Thr Pro Val Lys Ala Ile Lys His Thr Ile Ala Val
705                 710                 715                 720

Val Trp Gly Gly Val Asn Ile Pro His Ser Pro Tyr Arg Val Asn Ile
                725                 730                 735

Gly Gln Gly Ser His Pro Gln Lys Val Lys Val Phe Gly Pro Gly Val
            740                 745                 750

Glu Arg Ser Gly Leu Lys Ala Asn Glu Pro Thr His Phe Thr Val Asp
        755                 760                 765

Cys Thr Glu Ala Gly Glu Gly Asp Val Ser Val Gly Ile Lys Cys Asp
    770                 775                 780

Ala Arg Val Leu Ser Glu Asp Glu Glu Asp Val Asp Phe Asp Ile Ile
785                 790                 795                 800

His Asn Ala Asn Asp Thr Phe Thr Val Lys Tyr Val Pro Pro Ala Ala
                805                 810                 815

Gly Arg Tyr Thr Ile Lys Val Leu Phe Ala Ser Gln Glu Ile Pro Ala
            820                 825                 830
```

Ser Pro Phe Arg Val Lys Val Asp Pro Ser His Asp Ala Ser Lys Val
835 840 845

Lys Ala Glu Gly Pro Gly Leu Ser Lys Ala Gly Val Glu Asn Gly Lys
850 855 860

Pro Thr His Phe Thr Val Tyr Thr Lys Gly Ala Gly Lys Ala Pro Leu
865 870 875 880

Asn Val Gln Phe Asn Ser Pro Leu Pro Gly Asp Ala Val Lys Asp Leu
885 890 895

Asp Ile Ile Asp Asn Tyr Asp Tyr Ser His Thr Val Lys Tyr Thr Pro
900 905 910

Thr Gln Gln Gly Asn Met Gln Val Leu Val Thr Tyr Gly Gly Asp Pro
915 920 925

Ile Pro Lys Ser Pro Phe Thr Val Gly Val Ala Ala Pro Leu Asp Leu
930 935 940

Ser Lys Ile Lys Leu Asn Gly Leu Glu Asn Arg Val Glu Val Gly Lys
945 950 955 960

Asp Gln Glu Phe Thr Val Asp Thr Arg Gly Ala Gly Gly Gln Gly Lys
965 970 975

Leu Asp Val Thr Ile Leu Ser Pro Ser Arg Lys Val Val Pro Cys Leu
980 985 990

Val Thr Pro Val Thr Gly Arg Glu Asn Ser Thr Ala Lys Phe Ile Pro
995 1000 1005

Arg Glu Glu Gly Leu Tyr Ala Val Asp Val Thr Tyr Asp Gly His
1010 1015 1020

Pro Val Pro Gly Ser Pro Tyr Thr Val Glu Ala Ser Leu Pro Pro
1025 1030 1035

Asp Pro Ser Lys Val Lys Ala His Gly Pro Gly Leu Glu Gly Gly
1040 1045 1050

Leu Val Gly Lys Pro Ala Glu Phe Thr Ile Asp Thr Lys Gly Ala
1055 1060 1065

Gly Thr Gly Gly Leu Gly Leu Thr Val Glu Gly Pro Cys Glu Ala
1070 1075 1080

Lys Ile Glu Cys Ser Asp Asn Gly Asp Gly Thr Cys Ser Val Ser
1085 1090 1095

Tyr Leu Pro Thr Lys Pro Gly Glu Tyr Phe Val Asn Ile Leu Phe
1100 1105 1110

Glu Glu Val His Ile Pro Gly Ser Pro Phe Lys Ala Asp Ile Glu
1115 1120 1125

Met Pro Phe Asp Pro Ser Lys Val Val Ala Ser Gly Pro Gly Leu
1130 1135 1140

Glu His Gly Lys Val Gly Glu Ala Gly Leu Leu Ser Val Asp Cys
1145 1150 1155

Ser Glu Ala Gly Pro Gly Ala Leu Gly Leu Glu Ala Val Ser Asp
1160 1165 1170

Ser Gly Thr Lys Ala Glu Val Ser Ile Gln Asn Asn Lys Asp Gly
1175 1180 1185

Thr Tyr Ala Val Thr Tyr Val Pro Leu Thr Ala Gly Met Tyr Thr
1190 1195 1200

Leu Thr Met Lys Tyr Gly Gly Glu Leu Val Pro His Phe Pro Ala
1205 1210 1215

Arg Val Lys Val Glu Pro Ala Val Asp Thr Ser Arg Ile Lys Val
1220 1225 1230

-continued

```
Phe Gly  Pro Gly Ile Glu Gly  Lys Asp Val Phe Arg  Glu Ala Thr
    1235                 1240                 1245

Thr Asp  Phe Thr Val Asp Ser  Arg Pro Leu Thr Gln  Val Gly Gly
    1250                 1255                 1260

Asp His  Ile Lys Ala His Ile  Ala Asn Pro Ser Gly  Ala Ser Thr
    1265                 1270                 1275

Glu Cys  Phe Val Thr Asp Asn  Ala Asp Gly Thr Tyr  Gln Val Glu
    1280                 1285                 1290

Tyr Thr  Pro Phe Glu Lys Gly  Leu His Val Val Glu  Val Thr Tyr
    1295                 1300                 1305

Asp Asp  Val Pro Ile Pro Asn  Ser Pro Phe Lys Val  Ala Val Thr
    1310                 1315                 1320

Glu Gly  Cys Gln Pro Ser Arg  Val Gln Ala Gln Gly  Pro Gly Leu
    1325                 1330                 1335

Lys Glu  Ala Phe Thr Asn Lys  Pro Asn Val Phe Thr  Val Val Thr
    1340                 1345                 1350

Arg Gly  Ala Gly Ile Gly Gly  Leu Gly Ile Thr Val  Glu Gly Pro
    1355                 1360                 1365

Ser Glu  Ser Lys Ile Asn Cys  Arg Asp Asn Lys Asp  Gly Ser Cys
    1370                 1375                 1380

Ser Ala  Glu Tyr Ile Pro Phe  Ala Pro Gly Asp Tyr  Asp Val Asn
    1385                 1390                 1395

Ile Thr  Tyr Gly Gly Ala His  Ile Pro Gly Ser Pro  Phe Arg Val
    1400                 1405                 1410

Pro Val  Lys Asp Val Val Asp  Pro Ser Lys Val Lys  Ile Ala Gly
    1415                 1420                 1425

Pro Gly  Leu Gly Ser Gly Val  Arg Ala Arg Val Leu  Gln Ser Phe
    1430                 1435                 1440

Thr Val  Asp Ser Ser Lys Ala  Gly Leu Ala Pro Leu  Glu Val Arg
    1445                 1450                 1455

Val Leu  Gly Pro Arg Ala Asp  Asp Thr Asp Ser Gln  Ser Trp Arg
    1460                 1465                 1470

Ser Pro  Leu Lys Ala Leu Ser  Glu Phe Phe Lys Gly  Asp Pro Lys
    1475                 1480                 1485

Gly Asp  Phe Asn Lys Thr Gly  Leu Val Glu Pro Val  Asn Val Val
    1490                 1495                 1500

Asp Asn  Gly Asp Gly Thr His  Thr Val Thr Tyr Thr  Pro Ser Gln
    1505                 1510                 1515

Glu Gly  Pro Tyr Met Val Ser  Val Lys Tyr Ala Asp  Glu Glu Ile
    1520                 1525                 1530

Pro Arg  Ser Pro Phe Lys Val  Lys Val Leu Pro Thr  Tyr Asp Ala
    1535                 1540                 1545

Ser Lys  Val Thr Ala Ser Gly  Pro Gly Leu Ser Ser  Tyr Gly Val
    1550                 1555                 1560

Pro Ala  Ser Leu Pro Val Asp  Phe Ala Ile Asp Ala  Arg Asp Ala
    1565                 1570                 1575

Gly Glu  Gly Leu Leu Ala Val  Gln Ile Thr Asp Gln  Glu Gly Lys
    1580                 1585                 1590

Pro Lys  Arg Ala Ile Val His  Asp Asn Lys Asp Gly  Thr Tyr Ala
    1595                 1600                 1605

Val Thr  Tyr Ile Pro Asp Lys  Thr Gly Arg Tyr Met  Ile Gly Val
    1610                 1615                 1620

Thr Tyr  Gly Gly Asp Asp Ile  Pro Leu Ser Pro Tyr  Arg Ile Arg
```

```
    1625                1630                1635

Ala Thr Gln Thr Gly Asp Ala Ser Lys Cys Leu Ala Thr Gly Pro
    1640                1645                1650

Gly Ile Ala Ser Thr Val Lys Thr Gly Glu Glu Val Gly Phe Val
    1655                1660                1665

Val Asp Ala Lys Thr Ala Gly Lys Gly Lys Val Thr Cys Thr Val
    1670                1675                1680

Leu Thr Pro Asp Gly Thr Glu Ala Glu Ala Asp Val Ile Glu Asn
    1685                1690                1695

Glu Asp Gly Thr Tyr Asp Ile Phe Tyr Thr Ala Ala Lys Pro Gly
    1700                1705                1710

Thr Tyr Val Ile Tyr Val Arg Phe Gly Gly Val Asp Ile Pro Asn
    1715                1720                1725

Ser Pro Phe Thr Val Met Ala Thr Asp Gly Glu Val Thr Ala Val
    1730                1735                1740

Glu Glu Ala Pro Val Asn Ala Cys Pro Pro Gly Phe Arg Pro Trp
    1745                1750                1755

Val Thr Glu Glu Ala Tyr Val Pro Val Ser Asp Met Asn Gly Leu
    1760                1765                1770

Gly Phe Lys Pro Phe Asp Leu Val Ile Pro Phe Ala Val Arg Lys
    1775                1780                1785

Gly Glu Ile Thr Gly Glu Val His Met Pro Ser Gly Lys Thr Ala
    1790                1795                1800

Thr Pro Glu Ile Val Asp Asn Lys Asp Gly Thr Val Thr Val Arg
    1805                1810                1815

Tyr Ala Pro Thr Glu Val Gly Leu His Glu Met His Ile Lys Tyr
    1820                1825                1830

Met Gly Ser His Ile Pro Glu Ser Pro Leu Gln Phe Tyr Val Asn
    1835                1840                1845

Tyr Pro Asn Ser Gly Ser Val Ser Ala Tyr Gly Pro Gly Leu Val
    1850                1855                1860

Tyr Gly Val Ala Asn Lys Thr Ala Thr Phe Thr Ile Val Thr Glu
    1865                1870                1875

Asp Ala Gly Glu Gly Gly Leu Asp Leu Ala Ile Glu Gly Pro Ser
    1880                1885                1890

Lys Ala Glu Ile Ser Cys Ile Asp Asn Lys Asp Gly Thr Cys Thr
    1895                1900                1905

Val Thr Tyr Leu Pro Thr Leu Pro Gly Asp Tyr Ser Ile Leu Val
    1910                1915                1920

Lys Tyr Asn Asp Lys His Ile Pro Gly Ser Pro Phe Thr Ala Lys
    1925                1930                1935

Ile Thr Asp Asp Ser Arg Arg Cys Ser Gln Val Lys Leu Gly Ser
    1940                1945                1950

Ala Ala Asp Phe Leu Leu Asp Ile Ser Glu Thr Asp Leu Ser Ser
    1955                1960                1965

Leu Thr Ala Ser Ile Lys Ala Pro Ser Gly Arg Asp Glu Pro Cys
    1970                1975                1980

Leu Leu Lys Arg Leu Pro Asn Asn His Ile Gly Ile Ser Phe Ile
    1985                1990                1995

Pro Arg Glu Val Gly Glu His Leu Val Ser Ile Lys Lys Asn Gly
    2000                2005                2010

Asn His Val Ala Asn Ser Pro Val Ser Ile Met Val Val Gln Ser
    2015                2020                2025
```

-continued

```
Glu Ile  Gly Asp Ala Arg Arg  Ala Lys Val Tyr Gly  Arg Gly Leu
    2030                 2035                 2040

Ser Glu  Gly Arg Thr Phe Glu  Met Ser Asp Phe Ile  Val Asp Thr
    2045                 2050                 2055

Arg Asp  Ala Gly Tyr Gly Gly  Ile Ser Leu Ala Val  Glu Gly Pro
    2060                 2065                 2070

Ser Lys  Val Asp Ile Gln Thr  Glu Asp Leu Glu Asp  Gly Thr Cys
    2075                 2080                 2085

Lys Val  Ser Tyr Phe Pro Thr  Val Pro Gly Val Tyr  Ile Val Ser
    2090                 2095                 2100

Thr Lys  Phe Ala Asp Glu His  Val Pro Gly Ser Pro  Phe Thr Val
    2105                 2110                 2115

Lys Ile  Ser Gly Glu Gly Arg  Val Lys Glu Ser Ile  Thr Arg Thr
    2120                 2125                 2130

Ser Arg  Ala Pro Ser Val Ala  Thr Val Gly Ser Ile  Cys Asp Leu
    2135                 2140                 2145

Asn Leu  Lys Ile Pro Glu Ile  Asn Ser Ser Asp Met  Ser Ala His
    2150                 2155                 2160

Val Thr  Ser Pro Ser Gly Arg  Val Thr Glu Ala Glu  Ile Val Pro
    2165                 2170                 2175

Met Gly  Lys Asn Ser His Cys  Val Arg Phe Val Pro  Gln Glu Met
    2180                 2185                 2190

Gly Val  His Thr Val Ser Val  Lys Tyr Arg Gly Gln  His Val Thr
    2195                 2200                 2205

Gly Ser  Pro Phe Gln Phe Thr  Val Gly Pro Leu Gly  Glu Gly Gly
    2210                 2215                 2220

Ala His  Lys Val Arg Ala Gly  Gly Pro Gly Leu Glu  Arg Gly Glu
    2225                 2230                 2235

Ala Gly  Val Pro Ala Glu Phe  Ser Ile Trp Thr Arg  Glu Ala Gly
    2240                 2245                 2250

Ala Gly  Gly Leu Ser Ile Ala  Val Glu Gly Pro Ser  Lys Ala Glu
    2255                 2260                 2265

Ile Thr  Phe Asp Asp His Lys  Asn Gly Ser Cys Gly  Val Ser Tyr
    2270                 2275                 2280

Ile Ala  Gln Glu Pro Gly Asn  Tyr Glu Val Ser Ile  Lys Phe Asn
    2285                 2290                 2295

Asp Glu  His Ile Pro Glu Ser  Pro Tyr Leu Val Pro  Val Ile Ala
    2300                 2305                 2310

Pro Ser  Asp Asp Ala Arg Arg  Leu Thr Val Met Ser  Leu Gln Glu
    2315                 2320                 2325

Ser Gly  Leu Lys Val Asn Gln  Pro Ala Ser Phe Ala  Ile Arg Leu
    2330                 2335                 2340

Asn Gly  Ala Lys Gly Lys Ile  Asp Ala Lys Val His  Ser Pro Ser
    2345                 2350                 2355

Gly Ala  Val Glu Glu Cys His  Val Ser Glu Leu Glu  Pro Asp Lys
    2360                 2365                 2370

Tyr Ala  Val Arg Phe Ile Pro  His Glu Asn Gly Val  His Thr Ile
    2375                 2380                 2385

Asp Val  Lys Phe Asn Gly Ser  His Val Val Gly Ser  Pro Phe Lys
    2390                 2395                 2400

Val Arg  Val Gly Glu Pro Gly  Gln Ala Gly Asn Pro  Ala Leu Val
    2405                 2410                 2415
```

-continued

```
Ser Ala  Tyr Gly Thr Gly Leu  Glu Gly Gly Thr Thr  Gly Ile Gln
    2420                 2425                 2430

Ser Glu  Phe Phe Ile Asn Thr  Thr Arg Ala Gly Pro  Gly Thr Leu
    2435                 2440                 2445

Ser Val  Thr Ile Glu Gly Pro  Ser Lys Val Lys Met  Asp Cys Gln
    2450                 2455                 2460

Glu Thr  Pro Glu Gly Tyr Lys  Val Met Tyr Thr Pro  Met Ala Pro
    2465                 2470                 2475

Gly Asn  Tyr Leu Ile Ser Val  Lys Tyr Gly Gly Pro  Asn His Ile
    2480                 2485                 2490

Val Gly  Ser Pro Phe Lys Ala  Lys Val Thr Gly Gln  Arg Leu Val
    2495                 2500                 2505

Ser Pro  Gly Ser Ala Asn Glu  Thr Ser Ser Ile Leu  Val Glu Ser
    2510                 2515                 2520

Val Thr  Arg Ser Ser Thr Glu  Thr Cys Tyr Ser Ala  Ile Pro Lys
    2525                 2530                 2535

Ala Ser  Ser Asp Ala Ser Lys  Val Thr Ser Lys Gly  Ala Gly Leu
    2540                 2545                 2550

Ser Lys  Ala Phe Val Gly Gln  Lys Ser Ser Phe Leu  Val Asp Cys
    2555                 2560                 2565

Ser Lys  Ala Gly Ser Asn Met  Leu Leu Ile Gly Val  His Gly Pro
    2570                 2575                 2580

Thr Thr  Pro Cys Glu Glu Val  Ser Met Lys His Val  Gly Asn Gln
    2585                 2590                 2595

Gln Tyr  Asn Val Thr Tyr Val  Val Lys Glu Arg Gly  Asp Tyr Val
    2600                 2605                 2610

Leu Ala  Val Lys Trp Gly Glu  Glu His Ile Pro Gly  Ser Pro Phe
    2615                 2620                 2625

His Val  Thr Val Pro
    2630
```

<210> SEQ ID NO 23
<211> LENGTH: 9560
<212> TYPE: DNA
<213> ORGANISM: Homo sapiens

<400> SEQUENCE: 23

```
gcggccaggg gcgggcggcc gcagagcagc accggccgtg gctccggtag cagcaagttc     60

gaaccccgct cccgctccgc ttcggttctc gctccttcgg cccttgggcc tccaaacacc    120

agtccccggc agctcgttgc gcattgcgct ctccccgcca ccaggatgcc ggtaaccgag    180

aaggatctag ctgaggacgc gccttggaag aagatccagc agaacacgtt cacacgctgg    240

tgcaacgagc acctcaagtg cgtgaacaaa cgcatcggca acctgcagac cgacctgagc    300

gacgggctgc ggctcatcgc gctgctcgag gtgctcagcc agaagcgcat gtaccgcaag    360

taccatcagc ggcccacctt tcgccagatg cagctcgaga atgtgtccgt ggcgctcgag    420

ttcctggacc gtgagagcat caagctcgtg tccatcgata gcaaagccat tgtggatggg    480

aacctgaagc tcatcttggg tctggtgtgg acgctgatcc tccactactc catctccatg    540

cccgtgtggg aggatgaagg ggatgatgat gccaagaagc agacgccaaa gcagaggctg    600

ctggggtgga ttcagaacaa gatcccctac ttgcccatca ccaactttaa ccagaactgg    660

caagacggca aagccctggg agccctggta gacagctgtg ctccaggtct gtgcccagac    720

tgggaatcct gggacccgca gaagcctgtg gataatgcac gagaagccat gcagcaggca    780
```

-continued

```
gatgactggc tgggtgtccc acaggtcatc actcctgaag aaatcattca cccggatgtg    840
gacgagcact cagttatgac ttacctgtcc cagttcccca aagccaagct caagccgggg    900
gctcctctca aacccaaact caacccgaag aaagccaggg cctatggcag aggaatcgag    960
cccactggaa acatggtgaa gcagccagcc aagttcactg tggacaccat cagcgccggg   1020
caaggagacg tgatggtgtt tgttgaggac ccagaaggga acaaagagga ggcacaagtg   1080
acccctgaca gtgacaagaa caagacatac tctgtggagt atctgcccaa ggtcaccggg   1140
ctacacaaag tcacagtcct ctttgcagga cagcacatct ccaagagccc atttgaagtg   1200
agtgttgaca aggcccaggg agatgccagt aaagtcactg caaaaggtcc agggttggaa   1260
gctgtaggga acatcgccaa taagcccacc tactttgaca tctatacggc aggagctggt   1320
gtgggtgaca ttggtgtgga ggtggaagat ccccagggga agaacaccgt ggagttgctc   1380
gtggaagaca aaggaaacca ggtgtatcga tgtgtgtaca aacccatgca gcctggccct   1440
cacgtggtca agatcttctt tgctggggac actattccta agagtccctt cgttgtgcag   1500
gttggggaag cctgcaatcc aaatgcctgc cgggccagtg gccgaggcct acaacccaaa   1560
ggcgtccgta tccgggagac cacagatttc aaggttgaca ccaaagctgc aggaagtggg   1620
gagctcggtg taaccatgaa gggtcctaag ggtctggagg agctggtgaa gcagaaagac   1680
tttctggatg gggtctacgc attcgagtat taccccagca ccccggggag atacagcatt   1740
gccatcacat ggggggggaca ccacattcca aagagcccct ttgaagttca agttggccct   1800
gaagcgggta tgcagaaagt ccgtgcttgg ggccctgggc tccatggtgg gattgtcggg   1860
cggtcagcgg acttcgtggt agaatccatt ggctctgaag tggggtctct ggggtttgcc   1920
attgaaggcc cctctcaggc aaagattgag tacaacgacc agaatgatgg atcgtgtgat   1980
gtcaaatact ggcccaagga gcctggcgaa tatgctgttc acatcatgtg tgacgacgaa   2040
gacatcaagg acagcccgta catggccttc atccacccag ccacgggagg ctacaaccct   2100
gatctggttc gagcatacgg gccaggtttg gagaaatctg gatgcattgt caacaacctg   2160
gccgagttca ctgtggatcc taaggatgct ggaaaagctc ccttaaagat atttgctcag   2220
gatggggaag gccaacgcat tgacatccag atgaagaacc ggatggacgg cacatatgca   2280
tgctcataca ccccggtgaa ggccatcaag cacaccattg ctgtggtctg gggaggcgtg   2340
aacatcccgc acagccccta cagggtcaac atcgggcaag gtagccatcc tcagaaggtc   2400
aaagtgtttg ggccaggtgt ggagagaagt ggtctgaagg caaatgaacc tacacacttc   2460
acggtggact gtactgaggc tggggaaggt gatgtcagtg ttggcattaa gtgtgatgcc   2520
cgggtgttaa gtgaagatga ggaagacgtg gattttgaca ttattcacaa tgccaatgat   2580
acgttcacag tcaaatatgt gcctcctgct gctgggcgat acactatcaa agttctcttt   2640
gcatctcagg aaatccccgc cagccctttc agagtcaaag ttgacccttc ccacgatgcc   2700
agcaaagtga aggcagaagg cccagggctc agcaaagcag gtgtggaaaa tgggaaaccg   2760
acccacttca ctgtctacac caagggggct gggaaagccc cgctcaacgt gcagttcaac   2820
agccctcttc ctggcgatgc agtgaaggat ttggatatca tcgataatta tgactactct   2880
cacacggtta aatatacacc cacccaacag ggcaacatgc aggttctggt gacttacggt   2940
ggcgatccca tccctaaaag ccctttcact gtgggtgttg ctgcaccgct ggatctgagc   3000
aagataaaac tcaatgggct ggaaaacagg gtggaagttg ggaaggatca ggagttcacc   3060
gttgatacca ggggggcagg aggccagggg aagctggacg tgacaatcct cagcccctct   3120
cggaaggtcg tgccatgcct agtgacacct gtgacaggcc gggagaacag cacggccaag   3180
```

-continued

```
ttcatccctc gggaggaggg gctgtatgct gtagacgtga cctacgatgg acaccctgtg   3240
cccgggagcc cctacacagt ggaggcctcg ctgccaccag atcccagcaa ggtgaaggcc   3300
cacggtcccg gcctcgaagg tggtctcgtg ggcaagcctg ccgagttcac catcgatacc   3360
aaaggagctg gtactggagg tctgggctta acggtggaag gtccgtgcga ggccaaaatc   3420
gagtgctccg acaatggtga tgggacctgc tccgtctctt accttcccac aaaacccggg   3480
gagtacttcg tcaacatcct ctttgaagaa gtccacatac ctgggtctcc cttcaaagct   3540
gacattgaaa tgccctttga cccctctaaa gtcgtggcat cggggccagg tctcgagcac   3600
gggaaggtgg gtgaagctgg cctccttagc gtcgactgct cggaagcggg accgggggcc   3660
ctgggcctgg aagctgtctc ggactcggga acaaaagccg aagtcagtat tcagaacaac   3720
aaagatggca cctacgcggt gacctacgtg cccctgacgg ccggcatgta cacgttgacc   3780
atgaagtatg gtggcgaact cgtgccacac ttccccgccc gggtcaaggt ggagcccgcc   3840
gtggacacca gcaggatcaa agtctttgga ccaggaatag aagggaaaga tgtgttccgg   3900
gaagctacca ccgactttac agttgactct cggccgctga cccaggttgg gggtgaccac   3960
atcaaggccc acattgccaa cccctcaggg gcctccaccg agtgctttgt cacagacaat   4020
gcggatggga cctaccaggt ggaatacaca ccctttgaga aaggtctcca tgtagtggag   4080
gtgacatatg atgacgtgcc tatcccaaac agtcccttca aggtggctgt cactgaaggc   4140
tgccagccat ctagggtgca agcccaagga cctggattga aagaggcctt taccaacaag   4200
cccaatgtct tcaccgtggt taccagaggc gcaggaattg gtgggcttgg cataactgtt   4260
gagggaccat cagagtcgaa gataaattgc agagacaaca aggatggcag ctgcagtgct   4320
gagtacattc ctttcgcacc gggggattac gatgttaata tcacatatgg aggagcccac   4380
atccccggca gccccttcag ggttcctgtg aaggatgttg tggaccccag caaggtcaag   4440
attgccggcc ccgggctggg ctcaggcgtc cgagcccgtg tcctgcagtc cttcacggtg   4500
gacagcagca aggctggcct ggctccgctg gaagtgaggg ttctgggccc acgagctgac   4560
gacacggatt cccagtcatg gcgcagcccc ttgaaagccc tttcagagtt ctttaaaggt   4620
gacccgaagg gtgactttaa taagacaggc ttggtggagc cagtgaacgt ggtggacaat   4680
ggagatggca cacacacagt aacctacacc ccatctcagg agggacctta catggtctca   4740
gttaaatatg ctgatgaaga gattcctcgc agtcccttca aggtcaaggt ccttcccaca   4800
tatgatgcca gcaaagtgac tgccagtggc cccggcctta gttcctatgg tgtgcctgcc   4860
agtctacctg tggactttgc aattgatgcc cgagatgccg gggaaggcct gcttgctgtt   4920
caaataacgg accaagaagg aaaacccaaa agagccattg tccatgacaa taaagatggc   4980
acgtatgctg tcacctacat ccccgacaag actgggcgct atatgattgg agtcacctac   5040
gggggtgacg acatcccact ttctccttat cgcatccgag ccacacagac gggtgatgcc   5100
agcaagtgcc tggccacggg tcctggaatc gcctccactg tgaaaactgg cgaagaagta   5160
ggctttgtgg ttgatgccaa gactgccggg aagggtaaag tgacctgcac ggttctgacc   5220
ccagatggca ctgaggccga ggccgatgtc attgagaatg aagatggaac ctatgacatc   5280
ttctacacag ctgccaagcc gggcacatat gtgatctatg tgcgcttcgg tggtgttgat   5340
attcctaaca gccccttcac tgtcatggcc acagatgggg aagtcacagc cgtggaggag   5400
gcaccggtaa atgcatgtcc ccctggattc aggccctggg tgaccgaaga ggcctatgtc   5460
ccagtgagtg acatgaacgg cctgggattt aagccttttg acctggtcat tccgtttgct   5520
```

-continued

```
gtcaggaaag gagaaatcac tggagaggtc cacatgcctt ctgggaagac agccacacct   5580
gagattgtgg acaacaagga cggcacggtc actgttagat atgcccccac tgaggtcggg   5640
ctccatgaga tgcacatcaa atacatgggc agccacatcc ctgagagccc actccagttc   5700
tacgtgaact accccaacag tggaagtgtt tctgcatacg gtccaggcct cgtgtatgga   5760
gtggccaaca aaactgccac cttcaccatc gtcacagagg atgcaggaga aggtggtctg   5820
gacttggcta ttgagggccc ctcaaaagca gaaatcagct gcattgacaa taaagatggg   5880
acatgcacag tgacctacct gccgactctg ccaggcgact acagcattct ggtcaagtac   5940
aatgacaagc acatccctgg cagcccctte acagccaaga tcacagatga cagcaggcgg   6000
tgctcccagg tgaagttggg ctcagccgct gacttcctgc tcgacatcag tgagactgac   6060
ctcagcagcc tgacggccag cattaaggcc ccatctggcc gagacgagcc ctgtctcctg   6120
aagaggctgc ccaacaacca cattggcatc tccttcatcc cccgggaagt gggcgaacat   6180
ctggtcagca tcaagaaaaa tggcaaccat gtggccaaca gccccgtgtc tatcatggtg   6240
gtccagtcgg agattggtga cgcccgccga gccaaagtct atggccgcgg cctgtcagaa   6300
ggccggactt tcgagatgtc tgacttcatc gtggacacaa gggatgcagg ttatggtggc   6360
atatccttgg cggtggaagg ccccagcaaa gtggacatcc agacggagga cctggaagat   6420
ggcacctgca aagtctccta cttccctacc gtgcctgggg tttatatcgt ctccaccaaa   6480
ttcgctgacg agcacgtgcc tgggagccca tttaccgtga agatcagtgg ggagggaaga   6540
gtcaaagaga gcatcacccg caccagtcgg gccccgtccg tggccactgt cgggagcatt   6600
tgtgacctga acctgaaaat cccagaaatc aacagcagtg atatgtcggc ccacgtcacc   6660
agcccctctg gccgtgtgac tgaggcagag attgtgccca tggggaagaa ctcacactgc   6720
gtccggtttg tgccccagga gatgggcgtg cacacggtca gcgtcaagta ccgtgggcag   6780
cacgtcaccg gcagcccctt ccagttcacc gtggggccac ttggtgaagg aggcgcccac   6840
aaggtgcggg caggaggccc tggcctggag agaggagaag cgggagtccc agctgagttc   6900
agcatttgga cccgggaagc aggcgctgga ggcctctcca tcgctgttga gggccccagt   6960
aaggccgaga ttacattcga tgaccataaa aatgggtcgt gcggtgtatc ttatattgcc   7020
caagagcctg gtaactacga ggtgtccatc aagttcaatg atgagcacat cccggaaagc   7080
ccctacctgg tgccggtcat cgcaccctcc gacgacgccc gccgcctcac tgttatgagc   7140
cttcaggaat cgggattaaa agttaaccag ccagcatcct ttgctataag gttgaatggc   7200
gcaaaaggca agattgatgc aaaggtgcac agcccctctg gagccgtgga ggagtgccac   7260
gtgtctgagc tggagccaga taagtatgct gttcgcttca tccctcatga gaatggtgtc   7320
cacaccatcg atgtcaagtt caatgggagc cacgtggttg gaagcccctt caaagtgcgc   7380
gttggggagc ctggacaagc ggggaaccct gccctggtgt ccgcctatgg cacgggactc   7440
gaagggggca ccacaggtat ccagtcggaa ttctttatta acaccacccg agcaggtcca   7500
gggacattat ccgtcaccat cgaaggccca tccaaggtta aaatggattg ccaggaaaca   7560
cctgaagggt acaaagtcat gtacaccccc atggctcctg gtaactacct gatcagcgtc   7620
aaatacggtg ggcccaacca catcgtgggc agtcccttca aggccaaggt gacaggccag   7680
cgtctagtta gccctggctc agccaacgag acctcatcca tcctggtgga gtcagtgacc   7740
aggtcgtcta cagagacctg ctatagcgcc attcccaagg catcctcgga cgccagcaag   7800
gtgacctcta agggggcagg gctctcaaag gcctttgtgg gccagaagag ttccttcctg   7860
gtggactgca gcaaagctgg ctccaacatg ctgctgatcg ggtccatggg gcccaccacc   7920
```

```
ccctgcgagg aggtctccat gaagcatgta ggcaaccagc aatacaacgt cacatacgtc   7980

gtcaaggaga ggggcgatta tgtgctggct gtgaagtggg gggaggaaca catccctggc   8040

agcccttttc atgtcacagt gccttaaaac agttttctca aatcctggag agagttcttg   8100

tggttgcttt tgttgcttgt ttgtaattca ttttatacaa agccctccag cctgtttgtg   8160

gggctgaaac cccatcccta aaatattgct gttgtaaaat gccttcagaa ataagtccta   8220

gactggactc ttgagggaca tattggagaa tcttaagaaa tgcaagcttg ttcagggggc   8280

tgagaagatc ctgagtacac taggtgcaaa ccagaactct tggtggaaca gaccagccac   8340

tgcagcagac agaccaggaa cacaatgaga ctgacatttc aaaaaaacaa aactggctag   8400

cctgagctgc tggttcactc ttcagcattt atgaaacaag gctaggggaa gatgggcaga   8460

gaaaaagggg acacctagtt tggttgtcat ttggcaaagg agatgactta aaatccgctt   8520

aatctcttcc agtgtccgtg ttaatgtatt tggctattag atcactagca ctgctttacc   8580

gctcctcatc gccaacaccc ccatgctctg tggccttctt acacttctca gagggcagag   8640

tggcagccgg gcaccctaca gaaactcaga gggcagagtg gcagccaggc ccacatgtct   8700

ctcaagtacc tgtcccctcg ctctggtgat tatttcttgc agaatcacca cacgagacca   8760

tcccggcagt catggttttg ctttagtttt ccaagtccgt ttcagtccct tccttggtct   8820

gaagaaattc tgcagtggcg agcagtttcc cacttgccaa agatcccttt taaccaacac   8880

tagcccttgt ttttaacaca cgctccagcc cttcatcagc ctgggcagtc ttaccaaaat   8940

gtttaaagtg atctcagagg ggcccatgga ttaacgccct catcccaagg tccgtcccat   9000

gacataacac tccacacccg ccccagccaa cttcatgggt cactttttct ggaaaataat   9060

gatctgtaca gacaggacag aatgaaactc ctgcgggtct ttggcctgaa agttgggaat   9120

ggttggggga gagaagggca gcagcttatt ggtggtcttt tcaccattgg cagaaacagt   9180

gagagctgtg tggtgcagaa atccagaaat gaggtgtagg gaattttgcc tgccttcctg   9240

cagacctgag ctggctttgg aatgaggtta aagtgtcagg gacgttgcct gagcccaaat   9300

gtgtagtgtg gtctgggcag gcagaccttt aggttttgct gcttagtcct gaggaagtgg   9360

ccactcttgt ggcaggtgta gtatctgggg cgagtgttgg gggtaaaagc ccaccctaca   9420

gaaagtggaa cagcccggag cctgatgtga aaggaccacg ggtgttgtaa gctgggacac   9480

ggaagccaaa ctggaatcaa acgccgactg taaattgtat cttataactt attaaataaa   9540

acatttgctc cgtaaagttg                                               9560
```

<210> SEQ ID NO 24
<211> LENGTH: 2591
<212> TYPE: PRT
<213> ORGANISM: Homo sapiens

<400> SEQUENCE: 24

```
Met Pro Val Thr Glu Lys Asp Leu Ala Glu Asp Ala Pro Trp Lys Lys
1               5                   10                  15

Ile Gln Gln Asn Thr Phe Thr Arg Trp Cys Asn Glu His Leu Lys Cys
            20                  25                  30

Val Asn Lys Arg Ile Gly Asn Leu Gln Thr Asp Leu Ser Asp Gly Leu
        35                  40                  45

Arg Leu Ile Ala Leu Leu Glu Val Leu Ser Gln Lys Arg Met Tyr Arg
    50                  55                  60

Lys Tyr His Gln Arg Pro Thr Phe Arg Gln Met Gln Leu Glu Asn Val
65                  70                  75                  80
```

```
Ser Val Ala Leu Glu Phe Leu Asp Arg Glu Ser Ile Lys Leu Val Ser
                85                  90                  95

Ile Asp Ser Lys Ala Ile Val Asp Gly Asn Leu Lys Leu Ile Leu Gly
            100                 105                 110

Leu Val Trp Thr Leu Ile Leu His Tyr Ser Ile Ser Met Pro Val Trp
        115                 120                 125

Glu Asp Glu Gly Asp Asp Asp Ala Lys Lys Gln Thr Pro Lys Gln Arg
    130                 135                 140

Leu Leu Gly Trp Ile Gln Asn Lys Ile Pro Tyr Leu Pro Ile Thr Asn
145                 150                 155                 160

Phe Asn Gln Asn Trp Gln Asp Gly Lys Ala Leu Gly Ala Leu Val Asp
                165                 170                 175

Ser Cys Ala Pro Gly Leu Cys Pro Asp Trp Glu Ser Trp Asp Pro Gln
            180                 185                 190

Lys Pro Val Asp Asn Ala Arg Glu Ala Met Gln Gln Ala Asp Asp Trp
        195                 200                 205

Leu Gly Val Pro Gln Val Ile Thr Pro Glu Glu Ile Ile His Pro Asp
    210                 215                 220

Val Asp Glu His Ser Val Met Thr Tyr Leu Ser Gln Phe Pro Lys Ala
225                 230                 235                 240

Lys Leu Lys Pro Gly Ala Pro Leu Lys Pro Lys Leu Asn Pro Lys Lys
                245                 250                 255

Ala Arg Ala Tyr Gly Arg Gly Ile Glu Pro Thr Gly Asn Met Val Lys
            260                 265                 270

Gln Pro Ala Lys Phe Thr Val Asp Thr Ile Ser Ala Gly Gln Gly Asp
        275                 280                 285

Val Met Val Phe Val Glu Asp Pro Glu Gly Asn Lys Glu Glu Ala Gln
    290                 295                 300

Val Thr Pro Asp Ser Asp Lys Asn Lys Thr Tyr Ser Val Glu Tyr Leu
305                 310                 315                 320

Pro Lys Val Thr Gly Leu His Lys Val Thr Val Leu Phe Ala Gly Gln
                325                 330                 335

His Ile Ser Lys Ser Pro Phe Glu Val Ser Val Asp Lys Ala Gln Gly
            340                 345                 350

Asp Ala Ser Lys Val Thr Ala Lys Gly Pro Gly Leu Glu Ala Val Gly
        355                 360                 365

Asn Ile Ala Asn Lys Pro Thr Tyr Phe Asp Ile Tyr Thr Ala Gly Ala
    370                 375                 380

Gly Val Gly Asp Ile Gly Val Glu Val Glu Asp Pro Gln Gly Lys Asn
385                 390                 395                 400

Thr Val Glu Leu Leu Val Glu Asp Lys Gly Asn Gln Val Tyr Arg Cys
                405                 410                 415

Val Tyr Lys Pro Met Gln Pro Gly Pro His Val Val Lys Ile Phe Phe
            420                 425                 430

Ala Gly Asp Thr Ile Pro Lys Ser Pro Phe Val Val Gln Val Gly Glu
        435                 440                 445

Ala Cys Asn Pro Asn Ala Cys Arg Ala Ser Gly Arg Gly Leu Gln Pro
    450                 455                 460

Lys Gly Val Arg Ile Arg Glu Thr Thr Asp Phe Lys Val Asp Thr Lys
465                 470                 475                 480

Ala Ala Gly Ser Gly Glu Leu Gly Val Thr Met Lys Gly Pro Lys Gly
                485                 490                 495
```

-continued

```
Leu Glu Glu Leu Val Lys Gln Lys Asp Phe Leu Asp Gly Val Tyr Ala
            500                 505                 510

Phe Glu Tyr Tyr Pro Ser Thr Pro Gly Arg Tyr Ser Ile Ala Ile Thr
        515                 520                 525

Trp Gly Gly His His Ile Pro Lys Ser Pro Phe Glu Val Gln Val Gly
    530                 535                 540

Pro Glu Ala Gly Met Gln Lys Val Arg Ala Trp Gly Pro Gly Leu His
545                 550                 555                 560

Gly Gly Ile Val Gly Arg Ser Ala Asp Phe Val Val Glu Ser Ile Gly
                565                 570                 575

Ser Glu Val Gly Ser Leu Gly Phe Ala Ile Glu Gly Pro Ser Gln Ala
            580                 585                 590

Lys Ile Glu Tyr Asn Asp Gln Asn Asp Gly Ser Cys Asp Val Lys Tyr
        595                 600                 605

Trp Pro Lys Glu Pro Gly Glu Tyr Ala Val His Ile Met Cys Asp Asp
    610                 615                 620

Glu Asp Ile Lys Asp Ser Pro Tyr Met Ala Phe Ile His Pro Ala Thr
625                 630                 635                 640

Gly Gly Tyr Asn Pro Asp Leu Val Arg Ala Tyr Gly Pro Gly Leu Glu
                645                 650                 655

Lys Ser Gly Cys Ile Val Asn Asn Leu Ala Glu Phe Thr Val Asp Pro
            660                 665                 670

Lys Asp Ala Gly Lys Ala Pro Leu Lys Ile Phe Ala Gln Asp Gly Glu
        675                 680                 685

Gly Gln Arg Ile Asp Ile Gln Met Lys Asn Arg Met Asp Gly Thr Tyr
    690                 695                 700

Ala Cys Ser Tyr Thr Pro Val Lys Ala Ile Lys His Thr Ile Ala Val
705                 710                 715                 720

Val Trp Gly Gly Val Asn Ile Pro His Ser Pro Tyr Arg Val Asn Ile
                725                 730                 735

Gly Gln Gly Ser His Pro Gln Lys Val Lys Val Phe Gly Pro Gly Val
            740                 745                 750

Glu Arg Ser Gly Leu Lys Ala Asn Glu Pro Thr His Phe Thr Val Asp
        755                 760                 765

Cys Thr Glu Ala Gly Glu Gly Asp Val Ser Val Gly Ile Lys Cys Asp
    770                 775                 780

Ala Arg Val Leu Ser Glu Asp Glu Glu Asp Val Asp Phe Asp Ile Ile
785                 790                 795                 800

His Asn Ala Asn Asp Thr Phe Thr Val Lys Tyr Val Pro Pro Ala Ala
                805                 810                 815

Gly Arg Tyr Thr Ile Lys Val Leu Phe Ala Ser Gln Glu Ile Pro Ala
            820                 825                 830

Ser Pro Phe Arg Val Lys Val Asp Pro Ser His Asp Ala Ser Lys Val
        835                 840                 845

Lys Ala Glu Gly Pro Gly Leu Ser Lys Ala Gly Val Glu Asn Gly Lys
    850                 855                 860

Pro Thr His Phe Thr Val Tyr Thr Lys Gly Ala Gly Lys Ala Pro Leu
865                 870                 875                 880

Asn Val Gln Phe Asn Ser Pro Leu Pro Gly Asp Ala Val Lys Asp Leu
                885                 890                 895

Asp Ile Ile Asp Asn Tyr Asp Tyr Ser His Thr Val Lys Tyr Thr Pro
            900                 905                 910

Thr Gln Gln Gly Asn Met Gln Val Leu Val Thr Tyr Gly Gly Asp Pro
```

-continued

```
        915                 920                 925

Ile Pro Lys Ser Pro Phe Thr Val Gly Val Ala Ala Pro Leu Asp Leu
    930                 935                 940

Ser Lys Ile Lys Leu Asn Gly Leu Glu Asn Arg Val Glu Val Gly Lys
945                 950                 955                 960

Asp Gln Glu Phe Thr Val Asp Thr Arg Gly Ala Gly Gly Gln Gly Lys
                965                 970                 975

Leu Asp Val Thr Ile Leu Ser Pro Ser Arg Lys Val Val Pro Cys Leu
            980                 985                 990

Val Thr Pro Val Thr Gly Arg Glu  Asn Ser Thr Ala Lys  Phe Ile Pro
        995                 1000                 1005

Arg Glu  Glu Gly Leu Tyr Ala  Val Asp Val Thr Tyr  Asp Gly His
    1010                 1015                 1020

Pro Val  Pro Gly Ser Pro Tyr  Thr Val Glu Ala Ser  Leu Pro Pro
    1025                 1030                 1035

Asp Pro  Ser Lys Val Lys Ala  His Gly Pro Gly Leu  Glu Gly Gly
    1040                 1045                 1050

Leu Val  Gly Lys Pro Ala Glu  Phe Thr Ile Asp Thr  Lys Gly Ala
    1055                 1060                 1065

Gly Thr  Gly Gly Leu Gly Leu  Thr Val Glu Gly Pro  Cys Glu Ala
    1070                 1075                 1080

Lys Ile  Glu Cys Ser Asp Asn  Gly Asp Gly Thr Cys  Ser Val Ser
    1085                 1090                 1095

Tyr Leu  Pro Thr Lys Pro Gly  Glu Tyr Phe Val Asn  Ile Leu Phe
    1100                 1105                 1110

Glu Glu  Val His Ile Pro Gly  Ser Pro Phe Lys Ala  Asp Ile Glu
    1115                 1120                 1125

Met Pro  Phe Asp Pro Ser Lys  Val Val Ala Ser Gly  Pro Gly Leu
    1130                 1135                 1140

Glu His  Gly Lys Val Gly Glu  Ala Gly Leu Leu Ser  Val Asp Cys
    1145                 1150                 1155

Ser Glu  Ala Gly Pro Gly Ala  Leu Gly Leu Glu Ala  Val Ser Asp
    1160                 1165                 1170

Ser Gly  Thr Lys Ala Glu Val  Ser Ile Gln Asn Asn  Lys Asp Gly
    1175                 1180                 1185

Thr Tyr  Ala Val Thr Tyr Val  Pro Leu Thr Ala Gly  Met Tyr Thr
    1190                 1195                 1200

Leu Thr  Met Lys Tyr Gly Gly  Glu Leu Val Pro His  Phe Pro Ala
    1205                 1210                 1215

Arg Val  Lys Val Glu Pro Ala  Val Asp Thr Ser Arg  Ile Lys Val
    1220                 1225                 1230

Phe Gly  Pro Gly Ile Glu Gly  Lys Asp Val Phe Arg  Glu Ala Thr
    1235                 1240                 1245

Thr Asp  Phe Thr Val Asp Ser  Arg Pro Leu Thr Gln  Val Gly Gly
    1250                 1255                 1260

Asp His  Ile Lys Ala His Ile  Ala Asn Pro Ser Gly  Ala Ser Thr
    1265                 1270                 1275

Glu Cys  Phe Val Thr Asp Asn  Ala Asp Gly Thr Tyr  Gln Val Glu
    1280                 1285                 1290

Tyr Thr  Pro Phe Glu Lys Gly  Leu His Val Val Glu  Val Thr Tyr
    1295                 1300                 1305

Asp Asp  Val Pro Ile Pro Asn  Ser Pro Phe Lys Val  Ala Val Thr
    1310                 1315                 1320
```

```
Glu Gly  Cys Gln Pro Ser Arg  Val Gln Ala Gln Gly  Pro Gly Leu
    1325                 1330                 1335

Lys Glu  Ala Phe Thr Asn Lys  Pro Asn Val Phe Thr  Val Val Thr
    1340                 1345                 1350

Arg Gly  Ala Gly Ile Gly Gly  Leu Gly Ile Thr Val  Glu Gly Pro
    1355                 1360                 1365

Ser Glu  Ser Lys Ile Asn Cys  Arg Asp Asn Lys Asp  Gly Ser Cys
    1370                 1375                 1380

Ser Ala  Glu Tyr Ile Pro Phe  Ala Pro Gly Asp Tyr  Asp Val Asn
    1385                 1390                 1395

Ile Thr  Tyr Gly Gly Ala His  Ile Pro Gly Ser Pro  Phe Arg Val
    1400                 1405                 1410

Pro Val  Lys Asp Val Val Asp  Pro Ser Lys Val Lys  Ile Ala Gly
    1415                 1420                 1425

Pro Gly  Leu Gly Ser Gly Val  Arg Ala Arg Val Leu  Gln Ser Phe
    1430                 1435                 1440

Thr Val  Asp Ser Ser Lys Ala  Gly Leu Ala Pro Leu  Glu Val Arg
    1445                 1450                 1455

Val Leu  Gly Pro Arg Gly Leu  Val Glu Pro Val Asn  Val Val Asp
    1460                 1465                 1470

Asn Gly  Asp Gly Thr His Thr  Val Thr Tyr Thr Pro  Ser Gln Glu
    1475                 1480                 1485

Gly Pro  Tyr Met Val Ser Val  Lys Tyr Ala Asp Glu  Glu Ile Pro
    1490                 1495                 1500

Arg Ser  Pro Phe Lys Val Lys  Val Leu Pro Thr Tyr  Asp Ala Ser
    1505                 1510                 1515

Lys Val  Thr Ala Ser Gly Pro  Gly Leu Ser Ser Tyr  Gly Val Pro
    1520                 1525                 1530

Ala Ser  Leu Pro Val Asp Phe  Ala Ile Asp Ala Arg  Asp Ala Gly
    1535                 1540                 1545

Glu Gly  Leu Leu Ala Val Gln  Ile Thr Asp Gln Glu  Gly Lys Pro
    1550                 1555                 1560

Lys Arg  Ala Ile Val His Asp  Asn Lys Asp Gly Thr  Tyr Ala Val
    1565                 1570                 1575

Thr Tyr  Ile Pro Asp Lys Thr  Gly Arg Tyr Met Ile  Gly Val Thr
    1580                 1585                 1590

Tyr Gly  Gly Asp Asp Ile Pro  Leu Ser Pro Tyr Arg  Ile Arg Ala
    1595                 1600                 1605

Thr Gln  Thr Gly Asp Ala Ser  Lys Cys Leu Ala Thr  Gly Pro Gly
    1610                 1615                 1620

Ile Ala  Ser Thr Val Lys Thr  Gly Glu Glu Val Gly  Phe Val Val
    1625                 1630                 1635

Asp Ala  Lys Thr Ala Gly Lys  Gly Lys Val Thr Cys  Thr Val Leu
    1640                 1645                 1650

Thr Pro  Asp Gly Thr Glu Ala  Glu Ala Asp Val Ile  Glu Asn Glu
    1655                 1660                 1665

Asp Gly  Thr Tyr Asp Ile Phe  Tyr Thr Ala Ala Lys  Pro Gly Thr
    1670                 1675                 1680

Tyr Val  Ile Tyr Val Arg Phe  Gly Gly Val Asp Ile  Pro Asn Ser
    1685                 1690                 1695

Pro Phe  Thr Val Met Ala Thr  Asp Gly Glu Val Thr  Ala Val Glu
    1700                 1705                 1710
```

-continued

```
Glu Ala  Pro Val Thr Glu Glu  Ala Tyr Val Pro Val  Ser Asp Met
    1715                 1720                 1725

Asn Gly  Leu Gly Phe Lys Pro  Phe Asp Leu Val Ile  Pro Phe Ala
    1730                 1735                 1740

Val Arg  Lys Gly Glu Ile Thr  Gly Glu Val His Met  Pro Ser Gly
    1745                 1750                 1755

Lys Thr  Ala Thr Pro Glu Ile  Val Asp Asn Lys Asp  Gly Thr Val
    1760                 1765                 1770

Thr Val  Arg Tyr Ala Pro Thr  Glu Val Gly Leu His  Glu Met His
    1775                 1780                 1785

Ile Lys  Tyr Met Gly Ser His  Ile Pro Glu Ser Pro  Leu Gln Phe
    1790                 1795                 1800

Tyr Val  Asn Tyr Pro Asn Ser  Gly Ser Val Ser Ala  Tyr Gly Pro
    1805                 1810                 1815

Gly Leu  Val Tyr Gly Val Ala  Asn Lys Thr Ala Thr  Phe Thr Ile
    1820                 1825                 1830

Val Thr  Glu Asp Ala Gly Glu  Gly Gly Leu Asp Leu  Ala Ile Glu
    1835                 1840                 1845

Gly Pro  Ser Lys Ala Glu Ile  Ser Cys Ile Asp Asn  Lys Asp Gly
    1850                 1855                 1860

Thr Cys  Thr Val Thr Tyr Leu  Pro Thr Leu Pro Gly  Asp Tyr Ser
    1865                 1870                 1875

Ile Leu  Val Lys Tyr Asn Asp  Lys His Ile Pro Gly  Ser Pro Phe
    1880                 1885                 1890

Thr Ala  Lys Ile Thr Asp Asp  Ser Arg Arg Cys Ser  Gln Val Lys
    1895                 1900                 1905

Leu Gly  Ser Ala Ala Asp Phe  Leu Leu Asp Ile Ser  Glu Thr Asp
    1910                 1915                 1920

Leu Ser  Ser Leu Thr Ala Ser  Ile Lys Ala Pro Ser  Gly Arg Asp
    1925                 1930                 1935

Glu Pro  Cys Leu Leu Lys Arg  Leu Pro Asn Asn His  Ile Gly Ile
    1940                 1945                 1950

Ser Phe  Ile Pro Arg Glu Val  Gly Glu His Leu Val  Ser Ile Lys
    1955                 1960                 1965

Lys Asn  Gly Asn His Val Ala  Asn Ser Pro Val Ser  Ile Met Val
    1970                 1975                 1980

Val Gln  Ser Glu Ile Gly Asp  Ala Arg Arg Ala Lys  Val Tyr Gly
    1985                 1990                 1995

Arg Gly  Leu Ser Glu Gly Arg  Thr Phe Glu Met Ser  Asp Phe Ile
    2000                 2005                 2010

Val Asp  Thr Arg Asp Ala Gly  Tyr Gly Gly Ile Ser  Leu Ala Val
    2015                 2020                 2025

Glu Gly  Pro Ser Lys Val Asp  Ile Gln Thr Glu Asp  Leu Glu Asp
    2030                 2035                 2040

Gly Thr  Cys Lys Val Ser Tyr  Phe Pro Thr Val Pro  Gly Val Tyr
    2045                 2050                 2055

Ile Val  Ser Thr Lys Phe Ala  Asp Glu His Val Pro  Gly Ser Pro
    2060                 2065                 2070

Phe Thr  Val Lys Ile Ser Gly  Glu Gly Arg Val Lys  Glu Ser Ile
    2075                 2080                 2085

Thr Arg  Thr Ser Arg Ala Pro  Ser Val Ala Thr Val  Gly Ser Ile
    2090                 2095                 2100

Cys Asp  Leu Asn Leu Lys Ile  Pro Glu Ile Asn Ser  Ser Asp Met
```

2105 2110 2115

Ser Ala His Val Thr Ser Pro Ser Gly Arg Val Thr Glu Ala Glu
2120 2125 2130

Ile Val Pro Met Gly Lys Asn Ser His Cys Val Arg Phe Val Pro
2135 2140 2145

Gln Glu Met Gly Val His Thr Val Ser Val Lys Tyr Arg Gly Gln
2150 2155 2160

His Val Thr Gly Ser Pro Phe Gln Phe Thr Val Gly Pro Leu Gly
2165 2170 2175

Glu Gly Gly Ala His Lys Val Arg Ala Gly Gly Pro Gly Leu Glu
2180 2185 2190

Arg Gly Glu Ala Gly Val Pro Ala Glu Phe Ser Ile Trp Thr Arg
2195 2200 2205

Glu Ala Gly Ala Gly Gly Leu Ser Ile Ala Val Glu Gly Pro Ser
2210 2215 2220

Lys Ala Glu Ile Thr Phe Asp Asp His Lys Asn Gly Ser Cys Gly
2225 2230 2235

Val Ser Tyr Ile Ala Gln Glu Pro Gly Asn Tyr Glu Val Ser Ile
2240 2245 2250

Lys Phe Asn Asp Glu His Ile Pro Glu Ser Pro Tyr Leu Val Pro
2255 2260 2265

Val Ile Ala Pro Ser Asp Asp Ala Arg Arg Leu Thr Val Met Ser
2270 2275 2280

Leu Gln Glu Ser Gly Leu Lys Val Asn Gln Pro Ala Ser Phe Ala
2285 2290 2295

Ile Arg Leu Asn Gly Ala Lys Gly Lys Ile Asp Ala Lys Val His
2300 2305 2310

Ser Pro Ser Gly Ala Val Glu Glu Cys His Val Ser Glu Leu Glu
2315 2320 2325

Pro Asp Lys Tyr Ala Val Arg Phe Ile Pro His Glu Asn Gly Val
2330 2335 2340

His Thr Ile Asp Val Lys Phe Asn Gly Ser His Val Val Gly Ser
2345 2350 2355

Pro Phe Lys Val Arg Val Gly Glu Pro Gly Gln Ala Gly Asn Pro
2360 2365 2370

Ala Leu Val Ser Ala Tyr Gly Thr Gly Leu Glu Gly Gly Thr Thr
2375 2380 2385

Gly Ile Gln Ser Glu Phe Phe Ile Asn Thr Thr Arg Ala Gly Pro
2390 2395 2400

Gly Thr Leu Ser Val Thr Ile Glu Gly Pro Ser Lys Val Lys Met
2405 2410 2415

Asp Cys Gln Glu Thr Pro Glu Gly Tyr Lys Val Met Tyr Thr Pro
2420 2425 2430

Met Ala Pro Gly Asn Tyr Leu Ile Ser Val Lys Tyr Gly Gly Pro
2435 2440 2445

Asn His Ile Val Gly Ser Pro Phe Lys Ala Lys Val Thr Gly Gln
2450 2455 2460

Arg Leu Val Ser Pro Gly Ser Ala Asn Glu Thr Ser Ser Ile Leu
2465 2470 2475

Val Glu Ser Val Thr Arg Ser Ser Thr Glu Thr Cys Tyr Ser Ala
2480 2485 2490

Ile Pro Lys Ala Ser Ser Asp Ala Ser Lys Val Thr Ser Lys Gly
2495 2500 2505

```
Ala Gly  Leu Ser Lys Ala Phe  Val Gly Gln Lys Ser  Ser Phe Leu
    2510                 2515                 2520

Val Asp  Cys Ser Lys Ala Gly  Ser Asn Met Leu Leu  Ile Gly Val
    2525                 2530                 2535

His Gly  Pro Thr Thr Pro Cys  Glu Glu Val Ser Met  Lys His Val
    2540                 2545                 2550

Gly Asn  Gln Gln Tyr Asn Val  Thr Tyr Val Val Lys  Glu Arg Gly
    2555                 2560                 2565

Asp Tyr  Val Leu Ala Val Lys  Trp Gly Glu Glu His  Ile Pro Gly
    2570                 2575                 2580

Ser Pro  Phe His Val Thr Val  Pro
    2585                 2590
```

<210> SEQ ID NO 25
<211> LENGTH: 9434
<212> TYPE: DNA
<213> ORGANISM: Homo sapiens

<400> SEQUENCE: 25

```
gcggccaggg gcgggcggcc gcagagcagc accggccgtg gctccggtag cagcaagttc     60
gaaccccgct cccgctccgc ttcggttctc gctccttcgg cccttgggcc tccaaacacc    120
agtccccggc agctcgttgc gcattgcgct ctccccgcca ccaggatgcc ggtaaccgag    180
aaggatctag ctgaggacgc gccttggaag aagatccagc agaacacgtt cacacgctgg    240
tgcaacgagc acctcaagtg cgtgaacaaa cgcatcggca acctgcagac cgacctgagc    300
gacgggctgc ggctcatcgc gctgctcgag gtgctcagcc agaagcgcat gtaccgcaag    360
taccatcagc ggcccacctt tcgccagatg cagctcgaga atgtgtccgt ggcgctcgag    420
ttcctggacc gtgagagcat caagctcgtg tccatcgata gcaaagccat tgtggatggg    480
aacctgaagc tcatcttggg tctggtgtgg acgctgatcc tccactactc catctccatg    540
cccgtgtggg aggatgaagg ggatgatgat gccaagaagc agacgccaaa gcagaggctg    600
ctggggtgga ttcagaacaa gatcccctac ttgcccatca ccaactttaa ccagaactgg    660
caagacggca aagccctggg agccctggta gacagctgtg ctccaggtct gtgcccagac    720
tgggaatcct gggacccgca gaagcctgtg gataatgcac gagaagccat gcagcaggca    780
gatgactggc tgggtgtccc acaggtcatc actcctgaag aaatcattca cccggatgtg    840
gacgagcact cagttatgac ttacctgtcc cagttcccca aagccaagct caagccgggg    900
gctcctctca aacccaaact caacccgaag aaagccaggg cctatggcag aggaatcgag    960
cccactggaa acatggtgaa gcagccagcc aagttcactg tggacaccat cagcgccggg   1020
caaggagacg tgatggtgtt tgttgaggac ccagaaggga acaaagagga ggcacaagtg   1080
acccctgaca gtgacaagaa caagacatac tctgtggagt atctgcccaa ggtcaccggg   1140
ctacacaaag tcacagtcct ctttgcagga cagcacatct ccaagagccc atttgaagtg   1200
agtgttgaca aggcccaggg agatgccagt aaagtcactg caaaaggtcc agggttggaa   1260
gctgtaggga acatcgccaa taagcccacc tactttgaca tctatacggc aggagctggt   1320
gtgggtgaca ttggtgtgga ggtggaagat ccccagggga agaacaccgt ggagttgctc   1380
gtggaagaca aaggaaacca ggtgtatcga tgtgtgtaca aacccatgca gcctggccct   1440
cacgtggtca agatcttctt tgctggggac actattccta agagtccctt cgttgtgcag   1500
gttggggaag cctgcaatcc aaatgcctgc cgggccagtg gccgaggcct acaacccaaa   1560
```

-continued

```
ggcgtccgta tccgggagac cacagatttc aaggttgaca ccaaagctgc aggaagtggg   1620
gagctcggtg taaccatgaa gggtcctaag ggtctggagg agctggtgaa gcagaaagac   1680
tttctggatg gggtctacgc attcgagtat taccccagca ccccggggag atacagcatt   1740
gccatcacat gggggggaca ccacattcca aagagcccct ttgaagttca agttggccct   1800
gaagcgggta tgcagaaagt ccgtgcttgg ggccctgggc tccatggtgg gattgtcggg   1860
cggtcagcgg acttcgtggt agaatccatt ggctctgaag tggggtctct ggggtttgcc   1920
attgaaggcc cctctcaggc aaagattgag tacaacgacc agaatgatgg atcgtgtgat   1980
gtcaaatact ggcccaagga gcctggcgaa tatgctgttc acatcatgtg tgacgacgaa   2040
gacatcaagg acagcccgta catggccttc atccacccag ccacgggagg ctacaaccct   2100
gatctggttc gagcatacgg gccaggtttg gagaaatctg gatgcattgt caacaacctg   2160
gccgagttca ctgtggatcc taaggatgct ggaaaagctc ccttaaagat atttgctcag   2220
gatggggaag gccaacgcat tgacatccag atgaagaacc ggatggacgg cacatatgca   2280
tgctcataca ccccggtgaa ggccatcaag cacaccattg ctgtggtctg ggaggcgtg    2340
aacatcccgc acagccccta cagggtcaac atcgggcaag gtagccatcc tcagaaggtc   2400
aaagtgtttg ggccaggtgt ggagagaagt ggtctgaagg caaatgaacc tacacacttc   2460
acggtggact gtactgaggc tggggaaggt gatgtcagtg ttggcattaa gtgtgatgcc   2520
cgggtgttaa gtgaagatga ggaagacgtg gattttgaca ttattcacaa tgccaatgat   2580
acgttcacag tcaaatatgt gcctcctgct gctgggcgat acactatcaa agttctcttt   2640
gcatctcagg aaatccccgc cagccctttc agagtcaaag ttgacccttc ccacgatgcc   2700
agcaaagtga aggcagaagg cccagggctc agcaaagcag gtgtggaaaa tgggaaaccg   2760
acccacttca ctgtctacac caagggggct gggaaagccc cgctcaacgt gcagttcaac   2820
agccctcttc ctggcgatgc agtgaaggat ttggatatca tcgataatta tgactactct   2880
cacacggtta aatatacacc cacccaacag ggcaacatgc aggttctggt gacttacggt   2940
ggcgatccca tccctaaaag ccctttcact gtgggtgttg ctgcaccgct ggatctgagc   3000
aagataaaac tcaatgggct ggaaaacagg gtggaagttg ggaaggatca ggagttcacc   3060
gttgatacca ggggggcagg aggccagggg aagctggacg tgacaatcct cagcccctct   3120
cggaaggtcg tgccatgcct agtgacacct gtgacaggcc gggagaacag cacggccaag   3180
ttcatccctc gggaggaggg gctgtatgct gtagacgtga cctacgatgg acaccctgtg   3240
cccgggagcc cctacacagt ggaggcctcg ctgccaccag atcccagcaa ggtgaaggcc   3300
cacggtcccg gcctcgaagg tggtctcgtg ggcaagcctg ccgagttcac catcgatacc   3360
aaaggagctg gtactggagg tctgggctta acggtggaag gtccgtgcga ggccaaaatc   3420
gagtgctccg acaatggtga tgggacctgc tccgtctctt accttcccac aaaacccggg   3480
gagtacttcg tcaacatcct ctttgaagaa gtccacatac ctgggtctcc cttcaaagct   3540
gacattgaaa tgccctttga cccctctaaa gtcgtggcat cggggccagg tctcgagcac   3600
gggaaggtgg gtgaagctgg cctccttagc gtcgactgct cggaagcggg accgggggcc   3660
ctgggcctgg aagctgtctc ggactcggga acaaaagccg aagtcagtat tcagaacaac   3720
aaagatggca cctacgcggt gacctacgtg cccctgacgg ccggcatgta cacgttgacc   3780
atgaagtatg gtggcgaact cgtgccacac ttccccgccc gggtcaaggt ggagcccgcc   3840
gtggacacca gcaggatcaa agtctttgga ccaggaatag aagggaaaga tgtgttccgg   3900
gaagctacca ccgactttac agttgactct cggccgctga cccaggttgg gggtgaccac   3960
```

atcaaggccc acattgccaa cccctcaggg gcctccaccg agtgctttgt cacagacaat 4020
gcggatggga cctaccaggt ggaatacaca ccctttgaga aaggtctcca tgtagtggag 4080
gtgacatatg atgacgtgcc tatcccaaac agtcccttca aggtggctgt cactgaaggc 4140
tgccagccat ctagggtgca agcccaagga cctggattga aagaggcctt taccaacaag 4200
cccaatgtct tcaccgtggt taccagaggc gcaggaattg gtgggcttgg cataactgtt 4260
gagggaccat cagagtcgaa gataaattgc agagacaaca aggatggcag ctgcagtgct 4320
gagtacattc ctttcgcacc gggggattac gatgttaata tcacatatgg aggagcccac 4380
atccccggca gccccttcag ggttcctgtg aaggatgttg tggaccccag caaggtcaag 4440
attgccggcc ccgggctggg ctcaggcgtc cgagcccgtg tcctgcagtc cttcacggtg 4500
gacagcagca aggctggcct ggctccgctg gaagtgaggg ttctgggccc acgaggcttg 4560
gtggagccag tgaacgtggt ggacaatgga gatggcacac acacagtaac ctacacccca 4620
tctcaggagg gaccttacat ggtctcagtt aaatatgctg atgaagagat tcctcgcagt 4680
cccttcaagg tcaaggtcct tcccacatat gatgccagca aagtgactgc cagtggcccc 4740
ggccttagtt cctatggtgt gcctgccagt ctacctgtgg actttgcaat tgatgcccga 4800
gatgccgggg aaggcctgct tgctgttcaa ataacggacc aagaaggaaa acccaaaaga 4860
gccattgtcc atgacaataa agatggcacg tatgctgtca cctacatccc cgacaagact 4920
gggcgctata tgattggagt cacctacggg ggtgacgaca tcccactttc tccttatcgc 4980
atccgagcca cacagacggg tgatgccagc aagtgcctgg ccacgggtcc tggaatcgcc 5040
tccactgtga aaactggcga agaagtaggc tttgtggttg atgccaagac tgccgggaag 5100
ggtaaagtga cctgcacggt tctgacccca gatggcactg aggccgaggc cgatgtcatt 5160
gagaatgaag atggaaccta tgacatcttc tacacagctg ccaagccggg cacatatgtg 5220
atctatgtgc gcttcggtgg tgttgatatt cctaacagcc ccttcactgt catggccaca 5280
gatggggaag tcacagccgt ggaggaggca ccggtgaccg aagaggccta tgtcccagtg 5340
agtgacatga acggcctggg atttaagcct tttgacctgg tcattccgtt tgctgtcagg 5400
aaaggagaaa tcactggaga ggtccacatg ccttctggga agacagccac acctgagatt 5460
gtggacaaca aggacggcac ggtcactgtt agatatgccc ccactgaggt cgggctccat 5520
gagatgcaca tcaaatacat gggcagccac atccctgaga gcccactcca gttctacgtg 5580
aactacccca acagtggaag tgtttctgca tacggtccag gcctcgtgta tggagtggcc 5640
aacaaaactg ccaccttcac catcgtcaca gaggatgcag gagaaggtgg tctggacttg 5700
gctattgagg gcccctcaaa agcagaaatc agctgcattg acaataaaga tgggacatgc 5760
acagtgacct acctgccgac tctgccaggc gactacagca ttctggtcaa gtacaatgac 5820
aagcacatcc ctggcagccc cttcacagcc aagatcacag atgacagcag gcggtgctcc 5880
caggtgaagt tgggctcagc cgctgacttc ctgctcgaca tcagtgagac tgacctcagc 5940
agcctgacgg ccagcattaa ggccccatct ggccgagacg agccctgtct cctgaagagg 6000
ctgcccaaca accacattgg catctccttc atcccccggg aagtgggcga acatctggtc 6060
agcatcaaga aaaatggcaa ccatgtggcc aacagccccg tgtctatcat ggtggtccag 6120
tcggagattg gtgacgcccg ccgagccaaa gtctatggcc gcggcctgtc agaaggccgg 6180
actttcgaga tgtctgactt catcgtggac acaagggatg caggttatgg tggcatatcc 6240
ttggcggtgg aaggccccag caaagtggac atccagacgg aggacctgga agatggcacc 6300

-continued

```
tgcaaagtct cctacttccc taccgtgcct ggggtttata tcgtctccac caaattcgct   6360
gacgagcacg tgcctgggag cccatttacc gtgaagatca gtggggaggg aagagtcaaa   6420
gagagcatca cccgcaccag tcgggccccg tccgtggcca ctgtcgggag catttgtgac   6480
ctgaacctga aaatcccaga aatcaacagc agtgatatgt cggcccacgt caccagcccc   6540
tctggccgtg tgactgaggc agagattgtg cccatgggga agaactcaca ctgcgtccgg   6600
tttgtgcccc aggagatggg cgtgcacacg gtcagcgtca agtaccgtgg gcagcacgtc   6660
accggcagcc ccttccagtt caccgtgggg ccacttggtg aaggaggcgc ccacaaggtg   6720
cgggcaggag gccctggcct ggagagagga gaagcgggag tcccagctga gttcagcatt   6780
tggacccggg aagcaggcgc tggaggcctc tccatcgctg ttgagggccc cagtaaggcc   6840
gagattacat tcgatgacca taaaaatggg tcgtgcggtg tatcttatat tgcccaagag   6900
cctggtaact acgaggtgtc catcaagttc aatgatgagc acatcccgga aagcccctac   6960
ctggtgccgg tcatcgcacc ctccgacgac gcccgccgcc tcactgttat gagccttcag   7020
gaatcgggat taaaagttaa ccagccagca tcctttgcta taaggttgaa tggcgcaaaa   7080
ggcaagattg atgcaaaggt gcacagcccc tctggagccg tggaggagtg ccacgtgtct   7140
gagctggagc cagataagta tgctgttcgc ttcatccctc atgagaatgg tgtccacacc   7200
atcgatgtca agttcaatgg gagccacgtg gttggaagcc ccttcaaagt gcgcgttggg   7260
gagcctggac aagcggggaa ccctgccctg gtgtccgcct atggcacggg actcgaaggg   7320
ggcaccacag gtatccagtc ggaattcttt attaacacca cccgagcagg tccagggaca   7380
ttatccgtca ccatcgaagg cccatccaag gttaaaatgg attgccagga aacacctgaa   7440
gggtacaaag tcatgtacac ccccatggct cctggtaact acctgatcag cgtcaaatac   7500
ggtgggccca accacatcgt gggcagtccc ttcaaggcca aggtgacagg ccagcgtcta   7560
gttagccctg gctcagccaa cgagacctca tccatcctgg tggagtcagt gaccaggtcg   7620
tctacagaga cctgctatag cgccattccc aaggcatcct cggacgccag caaggtgacc   7680
tctaaggggg cagggctctc aaaggccttt gtgggccaga agagttcctt cctggtggac   7740
tgcagcaaag ctggctccaa catgctgctg atcggggtcc atgggcccac cacccccctgc   7800
gaggaggtct ccatgaagca tgtaggcaac cagcaataca acgtcacata cgtcgtcaag   7860
gagaggggcg attatgtgct ggctgtgaag tggggggagg aacacatccc tggcagccct   7920
tttcatgtca cagtgcctta aaacagtttt ctcaaatcct ggagagagtt cttgtggttg   7980
cttttgttgc ttgtttgtaa ttcattttat acaaagccct ccagcctgtt tgtggggctg   8040
aaaccccatc cctaaaatat tgctgttgta aaatgccttc agaaataagt cctagactgg   8100
actcttgagg gacatattgg agaatcttaa gaaatgcaag cttgttcagg gggctgagaa   8160
gatcctgagt acactaggtg caaaccagaa ctcttggtgg aacagaccag ccactgcagc   8220
agacagacca ggaacacaat gagactgaca tttcaaaaaa acaaaactgg ctagcctgag   8280
ctgctggttc actcttcagc atttatgaaa caaggctagg ggaagatggg cagagaaaaa   8340
ggggacacct agtttggttg tcatttggca aaggagatga cttaaaatcc gcttaatctc   8400
ttccagtgtc cgtgttaatg tatttggcta ttagatcact agcactgctt taccgctcct   8460
catcgccaac acccccatgc tctgtggcct tcttacactt ctcagagggc agagtggcag   8520
ccgggcaccc tacagaaact cagagggcag agtggcagcc aggcccacat gtctctcaag   8580
tacctgtccc ctcgctctgg tgattatttc ttgcagaatc accacacgag accatcccgg   8640
cagtcatggt tttgctttag ttttccaagt ccgtttcagt cccttccttg gtctgaagaa   8700
```

attctgcagt ggcgagcagt ttcccacttg ccaaagatcc cttttaacca acactagccc 8760
ttgtttttaa cacacgctcc agcccttcat cagcctgggc agtcttacca aaatgtttaa 8820
agtgatctca gaggggccca tggattaacg ccctcatccc aaggtccgtc ccatgacata 8880
acactccaca cccgccccag ccaacttcat gggtcacttt ttctggaaaa taatgatctg 8940
tacagacagg acagaatgaa actcctgcgg gtctttggcc tgaaagttgg gaatggttgg 9000
gggagagaag ggcagcagct tattggtggt cttttcacca ttggcagaaa cagtgagagc 9060
tgtgtggtgc agaaatccag aaatgaggtg tagggaattt tgcctgcctt cctgcagacc 9120
tgagctggct ttggaatgag gttaaagtgt cagggacgtt gcctgagccc aaatgtgtag 9180
tgtggtctgg gcaggcagac ctttaggttt tgctgcttag tcctgaggaa gtggccactc 9240
ttgtggcagg tgtagtatct ggggcgagtg ttgggggtaa aagcccaccc tacagaaagt 9300
ggaacagccc ggagcctgat gtgaaaggac cacgggtgtt gtaagctggg acacggaagc 9360
caaactggaa tcaaacgccg actgtaaatt gtatcttata acttattaaa taaaacattt 9420
gctccgtaaa gttg 9434

<210> SEQ ID NO 26
<211> LENGTH: 2578
<212> TYPE: PRT
<213> ORGANISM: Homo sapiens

<400> SEQUENCE: 26

Met Pro Val Thr Glu Lys Asp Leu Ala Glu Asp Ala Pro Trp Lys Lys
1               5                   10                  15

Ile Gln Gln Asn Thr Phe Thr Arg Trp Cys Asn Glu His Leu Lys Cys
            20                  25                  30

Val Asn Lys Arg Ile Gly Asn Leu Gln Thr Asp Leu Ser Asp Gly Leu
        35                  40                  45

Arg Leu Ile Ala Leu Leu Glu Val Leu Ser Gln Lys Arg Met Tyr Arg
    50                  55                  60

Lys Tyr His Gln Arg Pro Thr Phe Arg Gln Met Gln Leu Glu Asn Val
65                  70                  75                  80

Ser Val Ala Leu Glu Phe Leu Asp Arg Glu Ser Ile Lys Leu Val Ser
                85                  90                  95

Ile Asp Ser Lys Ala Ile Val Asp Gly Asn Leu Lys Leu Ile Leu Gly
            100                 105                 110

Leu Val Trp Thr Leu Ile Leu His Tyr Ser Ile Ser Met Pro Val Trp
        115                 120                 125

Glu Asp Glu Gly Asp Asp Asp Ala Lys Lys Gln Thr Pro Lys Gln Arg
    130                 135                 140

Leu Leu Gly Trp Ile Gln Asn Lys Ile Pro Tyr Leu Pro Ile Thr Asn
145                 150                 155                 160

Phe Asn Gln Asn Trp Gln Asp Gly Lys Ala Leu Gly Ala Leu Val Asp
                165                 170                 175

Ser Cys Ala Pro Gly Leu Cys Pro Asp Trp Glu Ser Trp Asp Pro Gln
            180                 185                 190

Lys Pro Val Asp Asn Ala Arg Glu Ala Met Gln Gln Ala Asp Asp Trp
        195                 200                 205

Leu Gly Val Pro Gln Val Ile Thr Pro Glu Glu Ile Ile His Pro Asp
    210                 215                 220

Val Asp Glu His Ser Val Met Thr Tyr Leu Ser Gln Phe Pro Lys Ala
225                 230                 235                 240

-continued

```
Lys Leu Lys Pro Gly Ala Pro Leu Lys Pro Lys Leu Asn Pro Lys Lys
                245                 250                 255

Ala Arg Ala Tyr Gly Arg Gly Ile Glu Pro Thr Gly Asn Met Val Lys
            260                 265                 270

Gln Pro Ala Lys Phe Thr Val Asp Thr Ile Ser Ala Gly Gln Gly Asp
        275                 280                 285

Val Met Val Phe Val Glu Asp Pro Glu Gly Asn Lys Glu Glu Ala Gln
    290                 295                 300

Val Thr Pro Asp Ser Asp Lys Asn Lys Thr Tyr Ser Val Glu Tyr Leu
305                 310                 315                 320

Pro Lys Val Thr Gly Leu His Lys Val Thr Val Leu Phe Ala Gly Gln
                325                 330                 335

His Ile Ser Lys Ser Pro Phe Glu Val Ser Val Asp Lys Ala Gln Gly
            340                 345                 350

Asp Ala Ser Lys Val Thr Ala Lys Gly Pro Gly Leu Glu Ala Val Gly
        355                 360                 365

Asn Ile Ala Asn Lys Pro Thr Tyr Phe Asp Ile Tyr Thr Ala Gly Ala
    370                 375                 380

Gly Val Gly Asp Ile Gly Val Glu Val Glu Asp Pro Gln Gly Lys Asn
385                 390                 395                 400

Thr Val Glu Leu Leu Val Glu Asp Lys Gly Asn Gln Val Tyr Arg Cys
                405                 410                 415

Val Tyr Lys Pro Met Gln Pro Gly Pro His Val Val Lys Ile Phe Phe
            420                 425                 430

Ala Gly Asp Thr Ile Pro Lys Ser Pro Phe Val Val Gln Val Gly Glu
        435                 440                 445

Ala Cys Asn Pro Asn Ala Cys Arg Ala Ser Gly Arg Gly Leu Gln Pro
    450                 455                 460

Lys Gly Val Arg Ile Arg Glu Thr Thr Asp Phe Lys Val Asp Thr Lys
465                 470                 475                 480

Ala Ala Gly Ser Gly Glu Leu Gly Val Thr Met Lys Gly Pro Lys Gly
                485                 490                 495

Leu Glu Glu Leu Val Lys Gln Lys Asp Phe Leu Asp Gly Val Tyr Ala
            500                 505                 510

Phe Glu Tyr Tyr Pro Ser Thr Pro Gly Arg Tyr Ser Ile Ala Ile Thr
        515                 520                 525

Trp Gly Gly His His Ile Pro Lys Ser Pro Phe Glu Val Gln Val Gly
    530                 535                 540

Pro Glu Ala Gly Met Gln Lys Val Arg Ala Trp Gly Pro Gly Leu His
545                 550                 555                 560

Gly Gly Ile Val Gly Arg Ser Ala Asp Phe Val Val Glu Ser Ile Gly
                565                 570                 575

Ser Glu Val Gly Ser Leu Gly Phe Ala Ile Glu Gly Pro Ser Gln Ala
            580                 585                 590

Lys Ile Glu Tyr Asn Asp Gln Asn Asp Gly Ser Cys Asp Val Lys Tyr
        595                 600                 605

Trp Pro Lys Glu Pro Gly Glu Tyr Ala Val His Ile Met Cys Asp Asp
    610                 615                 620

Glu Asp Ile Lys Asp Ser Pro Tyr Met Ala Phe Ile His Pro Ala Thr
625                 630                 635                 640

Gly Gly Tyr Asn Pro Asp Leu Val Arg Ala Tyr Gly Pro Gly Leu Glu
                645                 650                 655
```

Lys Ser Gly Cys Ile Val Asn Asn Leu Ala Glu Phe Thr Val Asp Pro
660 665 670

Lys Asp Ala Gly Lys Ala Pro Leu Lys Ile Phe Ala Gln Asp Gly Glu
675 680 685

Gly Gln Arg Ile Asp Ile Gln Met Lys Asn Arg Met Asp Gly Thr Tyr
690 695 700

Ala Cys Ser Tyr Thr Pro Val Lys Ala Ile Lys His Thr Ile Ala Val
705 710 715 720

Val Trp Gly Gly Val Asn Ile Pro His Ser Pro Tyr Arg Val Asn Ile
725 730 735

Gly Gln Gly Ser His Pro Gln Lys Val Lys Val Phe Gly Pro Gly Val
740 745 750

Glu Arg Ser Gly Leu Lys Ala Asn Glu Pro Thr His Phe Thr Val Asp
755 760 765

Cys Thr Glu Ala Gly Glu Gly Asp Val Ser Val Gly Ile Lys Cys Asp
770 775 780

Ala Arg Val Leu Ser Glu Asp Glu Glu Asp Val Asp Phe Asp Ile Ile
785 790 795 800

His Asn Ala Asn Asp Thr Phe Thr Val Lys Tyr Val Pro Pro Ala Ala
805 810 815

Gly Arg Tyr Thr Ile Lys Val Leu Phe Ala Ser Gln Glu Ile Pro Ala
820 825 830

Ser Pro Phe Arg Val Lys Val Asp Pro Ser His Asp Ala Ser Lys Val
835 840 845

Lys Ala Glu Gly Pro Gly Leu Ser Lys Ala Gly Val Glu Asn Gly Lys
850 855 860

Pro Thr His Phe Thr Val Tyr Thr Lys Gly Ala Gly Lys Ala Pro Leu
865 870 875 880

Asn Val Gln Phe Asn Ser Pro Leu Pro Gly Asp Ala Val Lys Asp Leu
885 890 895

Asp Ile Ile Asp Asn Tyr Asp Tyr Ser His Thr Val Lys Tyr Thr Pro
900 905 910

Thr Gln Gln Gly Asn Met Gln Val Leu Val Thr Tyr Gly Gly Asp Pro
915 920 925

Ile Pro Lys Ser Pro Phe Thr Val Gly Val Ala Ala Pro Leu Asp Leu
930 935 940

Ser Lys Ile Lys Leu Asn Gly Leu Glu Asn Arg Val Glu Val Gly Lys
945 950 955 960

Asp Gln Glu Phe Thr Val Asp Thr Arg Gly Ala Gly Gly Gln Gly Lys
965 970 975

Leu Asp Val Thr Ile Leu Ser Pro Ser Arg Lys Val Val Pro Cys Leu
980 985 990

Val Thr Pro Val Thr Gly Arg Glu Asn Ser Thr Ala Lys Phe Ile Pro
995 1000 1005

Arg Glu Glu Gly Leu Tyr Ala Val Asp Val Thr Tyr Asp Gly His
1010 1015 1020

Pro Val Pro Gly Ser Pro Tyr Thr Val Glu Ala Ser Leu Pro Pro
1025 1030 1035

Asp Pro Ser Lys Val Lys Ala His Gly Pro Gly Leu Glu Gly Gly
1040 1045 1050

Leu Val Gly Lys Pro Ala Glu Phe Thr Ile Asp Thr Lys Gly Ala
1055 1060 1065

Gly Thr Gly Gly Leu Gly Leu Thr Val Glu Gly Pro Cys Glu Ala

```
    1070                1075                1080

Lys Ile  Glu Cys Ser Asp Asn  Gly Asp Gly Thr Cys  Ser Val Ser
    1085                1090                1095

Tyr Leu  Pro Thr Lys Pro Gly  Glu Tyr Phe Val Asn  Ile Leu Phe
    1100                1105                1110

Glu Glu  Val His Ile Pro Gly  Ser Pro Phe Lys Ala  Asp Ile Glu
    1115                1120                1125

Met Pro  Phe Asp Pro Ser Lys  Val Val Ala Ser Gly  Pro Gly Leu
    1130                1135                1140

Glu His  Gly Lys Val Gly Glu  Ala Gly Leu Leu Ser  Val Asp Cys
    1145                1150                1155

Ser Glu  Ala Gly Pro Gly Ala  Leu Gly Leu Glu Ala  Val Ser Asp
    1160                1165                1170

Ser Gly  Thr Lys Ala Glu Val  Ser Ile Gln Asn Asn  Lys Asp Gly
    1175                1180                1185

Thr Tyr  Ala Val Thr Tyr Val  Pro Leu Thr Ala Gly  Met Tyr Thr
    1190                1195                1200

Leu Thr  Met Lys Tyr Gly Gly  Glu Leu Val Pro His  Phe Pro Ala
    1205                1210                1215

Arg Val  Lys Val Glu Pro Ala  Val Asp Thr Ser Arg  Ile Lys Val
    1220                1225                1230

Phe Gly  Pro Gly Ile Glu Gly  Lys Asp Val Phe Arg  Glu Ala Thr
    1235                1240                1245

Thr Asp  Phe Thr Val Asp Ser  Arg Pro Leu Thr Gln  Val Gly Gly
    1250                1255                1260

Asp His  Ile Lys Ala His Ile  Ala Asn Pro Ser Gly  Ala Ser Thr
    1265                1270                1275

Glu Cys  Phe Val Thr Asp Asn  Ala Asp Gly Thr Tyr  Gln Val Glu
    1280                1285                1290

Tyr Thr  Pro Phe Glu Lys Gly  Leu His Val Val Glu  Val Thr Tyr
    1295                1300                1305

Asp Asp  Val Pro Ile Pro Asn  Ser Pro Phe Lys Val  Ala Val Thr
    1310                1315                1320

Glu Gly  Cys Gln Pro Ser Arg  Val Gln Ala Gln Gly  Pro Gly Leu
    1325                1330                1335

Lys Glu  Ala Phe Thr Asn Lys  Pro Asn Val Phe Thr  Val Val Thr
    1340                1345                1350

Arg Gly  Ala Gly Ile Gly Gly  Leu Gly Ile Thr Val  Glu Gly Pro
    1355                1360                1365

Ser Glu  Ser Lys Ile Asn Cys  Arg Asp Asn Lys Asp  Gly Ser Cys
    1370                1375                1380

Ser Ala  Glu Tyr Ile Pro Phe  Ala Pro Gly Asp Tyr  Asp Val Asn
    1385                1390                1395

Ile Thr  Tyr Gly Gly Ala His  Ile Pro Gly Ser Pro  Phe Arg Val
    1400                1405                1410

Pro Val  Lys Asp Val Val Asp  Pro Ser Lys Val Lys  Ile Ala Gly
    1415                1420                1425

Pro Gly  Leu Gly Ser Gly Val  Arg Ala Arg Val Leu  Gln Ser Phe
    1430                1435                1440

Thr Val  Asp Ser Ser Lys Ala  Gly Leu Ala Pro Leu  Glu Val Arg
    1445                1450                1455

Val Leu  Gly Pro Arg Gly Leu  Val Glu Pro Val Asn  Val Val Asp
    1460                1465                1470
```

Asn Gly Asp Gly Thr His Thr Val Thr Tyr Thr Pro Ser Gln Glu
1475 1480 1485

Gly Pro Tyr Met Val Ser Val Lys Tyr Ala Asp Glu Glu Ile Pro
1490 1495 1500

Arg Ser Pro Phe Lys Val Lys Val Leu Pro Thr Tyr Asp Ala Ser
1505 1510 1515

Lys Val Thr Ala Ser Gly Pro Gly Leu Ser Ser Tyr Gly Val Pro
1520 1525 1530

Ala Ser Leu Pro Val Asp Phe Ala Ile Asp Ala Arg Asp Ala Gly
1535 1540 1545

Glu Gly Leu Leu Ala Val Gln Ile Thr Asp Gln Glu Gly Lys Pro
1550 1555 1560

Lys Arg Ala Ile Val His Asp Asn Lys Asp Gly Thr Tyr Ala Val
1565 1570 1575

Thr Tyr Ile Pro Asp Lys Thr Gly Arg Tyr Met Ile Gly Val Thr
1580 1585 1590

Tyr Gly Gly Asp Asp Ile Pro Leu Ser Pro Tyr Arg Ile Arg Ala
1595 1600 1605

Thr Gln Thr Gly Asp Ala Ser Lys Cys Leu Ala Thr Gly Pro Gly
1610 1615 1620

Ile Ala Ser Thr Val Lys Thr Gly Glu Glu Val Gly Phe Val Val
1625 1630 1635

Asp Ala Lys Thr Ala Gly Lys Gly Lys Val Thr Cys Thr Val Leu
1640 1645 1650

Thr Pro Asp Gly Thr Glu Ala Glu Ala Asp Val Ile Glu Asn Glu
1655 1660 1665

Asp Gly Thr Tyr Asp Ile Phe Tyr Thr Ala Ala Lys Pro Gly Thr
1670 1675 1680

Tyr Val Ile Tyr Val Arg Phe Gly Gly Val Asp Ile Pro Asn Ser
1685 1690 1695

Pro Phe Thr Val Met Val Thr Glu Glu Ala Tyr Val Pro Val Ser
1700 1705 1710

Asp Met Asn Gly Leu Gly Phe Lys Pro Phe Asp Leu Val Ile Pro
1715 1720 1725

Phe Ala Val Arg Lys Gly Glu Ile Thr Gly Glu Val His Met Pro
1730 1735 1740

Ser Gly Lys Thr Ala Thr Pro Glu Ile Val Asp Asn Lys Asp Gly
1745 1750 1755

Thr Val Thr Val Arg Tyr Ala Pro Thr Glu Val Gly Leu His Glu
1760 1765 1770

Met His Ile Lys Tyr Met Gly Ser His Ile Pro Glu Ser Pro Leu
1775 1780 1785

Gln Phe Tyr Val Asn Tyr Pro Asn Ser Gly Ser Val Ser Ala Tyr
1790 1795 1800

Gly Pro Gly Leu Val Tyr Gly Val Ala Asn Lys Thr Ala Thr Phe
1805 1810 1815

Thr Ile Val Thr Glu Asp Ala Gly Glu Gly Gly Leu Asp Leu Ala
1820 1825 1830

Ile Glu Gly Pro Ser Lys Ala Glu Ile Ser Cys Ile Asp Asn Lys
1835 1840 1845

Asp Gly Thr Cys Thr Val Thr Tyr Leu Pro Thr Leu Pro Gly Asp
1850 1855 1860

```
Tyr Ser  Ile Leu Val Lys Tyr  Asn Asp Lys His Ile  Pro Gly Ser
    1865                 1870                 1875

Pro Phe  Thr Ala Lys Ile Thr  Asp Asp Ser Arg Arg  Cys Ser Gln
    1880                 1885                 1890

Val Lys  Leu Gly Ser Ala Ala  Asp Phe Leu Leu Asp  Ile Ser Glu
    1895                 1900                 1905

Thr Asp  Leu Ser Ser Leu Thr  Ala Ser Ile Lys Ala  Pro Ser Gly
    1910                 1915                 1920

Arg Asp  Glu Pro Cys Leu Leu  Lys Arg Leu Pro Asn  Asn His Ile
    1925                 1930                 1935

Gly Ile  Ser Phe Ile Pro Arg  Glu Val Gly Glu His  Leu Val Ser
    1940                 1945                 1950

Ile Lys  Lys Asn Gly Asn His  Val Ala Asn Ser Pro  Val Ser Ile
    1955                 1960                 1965

Met Val  Val Gln Ser Glu Ile  Gly Asp Ala Arg Arg  Ala Lys Val
    1970                 1975                 1980

Tyr Gly  Arg Gly Leu Ser Glu  Gly Arg Thr Phe Glu  Met Ser Asp
    1985                 1990                 1995

Phe Ile  Val Asp Thr Arg Asp  Ala Gly Tyr Gly Gly  Ile Ser Leu
    2000                 2005                 2010

Ala Val  Glu Gly Pro Ser Lys  Val Asp Ile Gln Thr  Glu Asp Leu
    2015                 2020                 2025

Glu Asp  Gly Thr Cys Lys Val  Ser Tyr Phe Pro Thr  Val Pro Gly
    2030                 2035                 2040

Val Tyr  Ile Val Ser Thr Lys  Phe Ala Asp Glu His  Val Pro Gly
    2045                 2050                 2055

Ser Pro  Phe Thr Val Lys Ile  Ser Gly Glu Gly Arg  Val Lys Glu
    2060                 2065                 2070

Ser Ile  Thr Arg Thr Ser Arg  Ala Pro Ser Val Ala  Thr Val Gly
    2075                 2080                 2085

Ser Ile  Cys Asp Leu Asn Leu  Lys Ile Pro Glu Ile  Asn Ser Ser
    2090                 2095                 2100

Asp Met  Ser Ala His Val Thr  Ser Pro Ser Gly Arg  Val Thr Glu
    2105                 2110                 2115

Ala Glu  Ile Val Pro Met Gly  Lys Asn Ser His Cys  Val Arg Phe
    2120                 2125                 2130

Val Pro  Gln Glu Met Gly Val  His Thr Val Ser Val  Lys Tyr Arg
    2135                 2140                 2145

Gly Gln  His Val Thr Gly Ser  Pro Phe Gln Phe Thr  Val Gly Pro
    2150                 2155                 2160

Leu Gly  Glu Gly Gly Ala His  Lys Val Arg Ala Gly  Gly Pro Gly
    2165                 2170                 2175

Leu Glu  Arg Gly Glu Ala Gly  Val Pro Ala Glu Phe  Ser Ile Trp
    2180                 2185                 2190

Thr Arg  Glu Ala Gly Ala Gly  Gly Leu Ser Ile Ala  Val Glu Gly
    2195                 2200                 2205

Pro Ser  Lys Ala Glu Ile Thr  Phe Asp Asp His Lys  Asn Gly Ser
    2210                 2215                 2220

Cys Gly  Val Ser Tyr Ile Ala  Gln Glu Pro Gly Asn  Tyr Glu Val
    2225                 2230                 2235

Ser Ile  Lys Phe Asn Asp Glu  His Ile Pro Glu Ser  Pro Tyr Leu
    2240                 2245                 2250

Val Pro  Val Ile Ala Pro Ser  Asp Asp Ala Arg Arg  Leu Thr Val
```

-continued

```
    2255                2260                2265

Met Ser  Leu Gln Glu Ser Gly  Leu Lys Val Asn Gln  Pro Ala Ser
    2270                2275                2280

Phe Ala  Ile Arg Leu Asn Gly  Ala Lys Gly Lys Ile  Asp Ala Lys
    2285                2290                2295

Val His  Ser Pro Ser Gly Ala  Val Glu Glu Cys His  Val Ser Glu
    2300                2305                2310

Leu Glu  Pro Asp Lys Tyr Ala  Val Arg Phe Ile Pro  His Glu Asn
    2315                2320                2325

Gly Val  His Thr Ile Asp Val  Lys Phe Asn Gly Ser  His Val Val
    2330                2335                2340

Gly Ser  Pro Phe Lys Val Arg  Val Gly Glu Pro Gly  Gln Ala Gly
    2345                2350                2355

Asn Pro  Ala Leu Val Ser Ala  Tyr Gly Thr Gly Leu  Glu Gly Gly
    2360                2365                2370

Thr Thr  Gly Ile Gln Ser Glu  Phe Phe Ile Asn Thr  Thr Arg Ala
    2375                2380                2385

Gly Pro  Gly Thr Leu Ser Val  Thr Ile Glu Gly Pro  Ser Lys Val
    2390                2395                2400

Lys Met  Asp Cys Gln Glu Thr  Pro Glu Gly Tyr Lys  Val Met Tyr
    2405                2410                2415

Thr Pro  Met Ala Pro Gly Asn  Tyr Leu Ile Ser Val  Lys Tyr Gly
    2420                2425                2430

Gly Pro  Asn His Ile Val Gly  Ser Pro Phe Lys Ala  Lys Val Thr
    2435                2440                2445

Gly Gln  Arg Leu Val Ser Pro  Gly Ser Ala Asn Glu  Thr Ser Ser
    2450                2455                2460

Ile Leu  Val Glu Ser Val Thr  Arg Ser Ser Thr Glu  Thr Cys Tyr
    2465                2470                2475

Ser Ala  Ile Pro Lys Ala Ser  Ser Asp Ala Ser Lys  Val Thr Ser
    2480                2485                2490

Lys Gly  Ala Gly Leu Ser Lys  Ala Phe Val Gly Gln  Lys Ser Ser
    2495                2500                2505

Phe Leu  Val Asp Cys Ser Lys  Ala Gly Ser Asn Met  Leu Leu Ile
    2510                2515                2520

Gly Val  His Gly Pro Thr Thr  Pro Cys Glu Glu Val  Ser Met Lys
    2525                2530                2535

His Val  Gly Asn Gln Gln Tyr  Asn Val Thr Tyr Val  Val Lys Glu
    2540                2545                2550

Arg Gly  Asp Tyr Val Leu Ala  Val Lys Trp Gly Glu  Glu His Ile
    2555                2560                2565

Pro Gly  Ser Pro Phe His Val  Thr Val Pro
    2570                2575


<210> SEQ ID NO 27
<211> LENGTH: 9395
<212> TYPE: DNA
<213> ORGANISM: Homo sapiens

<400> SEQUENCE: 27

gcggccaggg gcgggcggcc gcagagcagc accggccgtg gctccggtag cagcaagttc      60

gaaccccgct cccgctccgc ttcggttctc gctccttcgg cccttgggcc tccaaacacc     120

agtccccggc agctcgttgc gcattgcgct ctccccgcca ccaggatgcc ggtaaccgag     180
```

-continued

```
aaggatctag ctgaggacgc gccttggaag aagatccagc agaacacgtt cacacgctgg    240
tgcaacgagc acctcaagtg cgtgaacaaa cgcatcggca acctgcagac cgacctgagc    300
gacgggctgc ggctcatcgc gctgctcgag gtgctcagcc agaagcgcat gtaccgcaag    360
taccatcagc ggcccacctt tcgccagatg cagctcgaga atgtgtccgt ggcgctcgag    420
ttcctggacc gtgagagcat caagctcgtg tccatcgata gcaaagccat tgtggatggg    480
aacctgaagc tcatcttggg tctggtgtgg acgctgatcc tccactactc catctccatg    540
cccgtgtggg aggatgaagg ggatgatgat gccaagaagc agacgccaaa gcagaggctg    600
ctggggtgga ttcagaacaa gatcccctac ttgcccatca ccaactttaa ccagaactgg    660
caagacggca aagccctggg agccctggta gacagctgtg ctccaggtct gtgcccagac    720
tgggaatcct gggacccgca gaagcctgtg gataatgcac gagaagccat gcagcaggca    780
gatgactggc tgggtgtccc acaggtcatc actcctgaag aaatcattca cccggatgtg    840
gacgagcact cagttatgac ttacctgtcc cagttcccca aagccaagct caagccgggg    900
gctcctctca aacccaaact caacccgaag aaagccaggg cctatggcag aggaatcgag    960
cccactggaa acatggtgaa gcagccagcc aagttcactg tggacaccat cagcgccggg   1020
caaggagacg tgatggtgtt tgttgaggac ccagaaggga acaaagagga ggcacaagtg   1080
acccctgaca gtgacaagaa caagacatac tctgtggagt atctgcccaa ggtcaccggg   1140
ctacacaaag tcacagtcct ctttgcagga cagcacatct ccaagagccc atttgaagtg   1200
agtgttgaca aggcccaggg agatgccagt aaagtcactg caaaaggtcc agggttggaa   1260
gctgtaggga acatcgccaa taagcccacc tactttgaca tctatacggc aggagctggt   1320
gtgggtgaca ttggtgtgga ggtggaagat ccccagggga agaacaccgt ggagttgctc   1380
gtggaagaca aaggaaacca ggtgtatcga tgtgtgtaca aacccatgca gcctggccct   1440
cacgtggtca agatcttctt tgctggggac actattccta agagtccctt cgttgtgcag   1500
gttggggaag cctgcaatcc aaatgcctgc cgggccagtg gccgaggcct acaacccaaa   1560
ggcgtccgta tccgggagac cacagatttc aaggttgaca ccaaagctgc aggaagtggg   1620
gagctcggtg taaccatgaa gggtcctaag ggtctggagg agctggtgaa gcagaaagac   1680
tttctggatg gggtctacgc attcgagtat taccccagca ccccggggag atacagcatt   1740
gccatcacat ggggggggaca ccacattcca aagagcccct ttgaagttca agttggccct   1800
gaagcgggta tgcagaaagt ccgtgcttgg ggccctgggc tccatggtgg gattgtcggg   1860
cggtcagcgg acttcgtggt agaatccatt ggctctgaag tggggtctct ggggtttgcc   1920
attgaaggcc cctctcaggc aaagattgag tacaacgacc agaatgatgg atcgtgtgat   1980
gtcaaatact ggcccaagga gcctggcgaa tatgctgttc acatcatgtg tgacgacgaa   2040
gacatcaagg acagcccgta catggccttc atccacccag ccacgggagg ctacaaccct   2100
gatctggttc gagcatacgg gccaggtttg gagaaatctg gatgcattgt caacaacctg   2160
gccgagttca ctgtggatcc taaggatgct ggaaaagctc ccttaaagat atttgctcag   2220
gatggggaag gccaacgcat tgacatccag atgaagaacc ggatggacgg cacatatgca   2280
tgctcataca ccccggtgaa ggccatcaag cacaccattg ctgtggtctg gggaggcgtg   2340
aacatcccgc acagccccta cagggtcaac atcgggcaag gtagccatcc tcagaaggtc   2400
aaagtgtttg ggccaggtgt ggagagaagt ggtctgaagg caaatgaacc tacacacttc   2460
acggtggact gtactgaggc tggggaaggt gatgtcagtg ttggcattaa gtgtgatgcc   2520
cgggtgttaa gtgaagatga ggaagacgtg gattttgaca ttattcacaa tgccaatgat   2580
```

acgttcacag tcaaatatgt gcctcctgct gctgggcgat acactatcaa agttctcttt 2640
gcatctcagg aaatccccgc cagccctttc agagtcaaag ttgacccttc ccacgatgcc 2700
agcaaagtga aggcagaagg cccagggctc agcaaagcag gtgtggaaaa tgggaaaccg 2760
acccacttca ctgtctacac caaggggct gggaaagccc cgctcaacgt gcagttcaac 2820
agccctcttc ctggcgatgc agtgaaggat ttggatatca tcgataatta tgactactct 2880
cacacggtta aatatacacc cacccaacag ggcaacatgc aggttctggt gacttacggt 2940
ggcgatccca tccctaaaag ccctttcact gtgggtgttg ctgcaccgct ggatctgagc 3000
aagataaaac tcaatgggct ggaaaacagg gtggaagttg ggaaggatca ggagttcacc 3060
gttgatacca ggggggcagg aggccagggg aagctggacg tgacaatcct cagcccctct 3120
cggaaggtcg tgccatgcct agtgacacct gtgacaggcc gggagaacag cacggccaag 3180
ttcatccctc gggaggaggg gctgtatgct gtagacgtga cctacgatgg acaccctgtg 3240
cccgggagcc cctacacagt ggaggcctcg ctgccaccag atcccagcaa ggtgaaggcc 3300
cacggtcccg gcctcgaagg tggtctcgtg ggcaagcctg ccgagttcac catcgatacc 3360
aaaggagctg gtactggagg tctgggctta acggtggaag gtccgtgcga ggccaaaatc 3420
gagtgctccg acaatggtga tgggacctgc tccgtctctt accttcccac aaaacccggg 3480
gagtacttcg tcaacatcct ctttgaagaa gtccacatac ctgggtctcc cttcaaagct 3540
gacattgaaa tgccctttga cccctctaaa gtcgtggcat cggggccagg tctcgagcac 3600
gggaaggtgg gtgaagctgg cctccttagc gtcgactgct cggaagcggg accgggggcc 3660
ctgggcctgg aagctgtctc ggactcggga acaaaagccg aagtcagtat tcagaacaac 3720
aaagatggca cctacgcggt gacctacgtg cccctgacgg ccggcatgta cacgttgacc 3780
atgaagtatg gtggcgaact cgtgccacac ttccccgccc gggtcaaggt ggagcccgcc 3840
gtggacacca gcaggatcaa agtctttgga ccaggaatag aagggaaaga tgtgttccgg 3900
gaagctacca ccgactttac agttgactct cggccgctga cccaggttgg gggtgaccac 3960
atcaaggccc acattgccaa cccctcaggg gcctccaccg agtgctttgt cacagacaat 4020
gcggatggga cctaccaggt ggaatacaca ccctttgaga aaggtctcca tgtagtggag 4080
gtgacatatg atgacgtgcc tatcccaaac agtcccttca aggtggctgt cactgaaggc 4140
tgccagccat ctagggtgca agcccaagga cctggattga aagaggcctt taccaacaag 4200
cccaatgtct tcaccgtggt taccagaggc gcaggaattg gtgggcttgg cataactgtt 4260
gagggaccat cagagtcgaa gataaattgc agagacaaca aggatggcag ctgcagtgct 4320
gagtacattc ctttcgcacc gggggattac gatgttaata tcacatatgg aggagcccac 4380
atccccggca gccccttcag ggttcctgtg aaggatgttg tggaccccag caaggtcaag 4440
attgccggcc ccgggctggg ctcaggcgtc cgagcccgtg tcctgcagtc cttcacggtg 4500
gacagcagca aggctggcct ggctccgctg gaagtgaggg ttctgggccc acgaggcttg 4560
gtggagccag tgaacgtggt ggacaatgga gatggcacac acacagtaac ctacacccca 4620
tctcaggagg gaccttacat ggtctcagtt aaatatgctg atgaagagat tcctcgcagt 4680
cccttcaagg tcaaggtcct tcccacatat gatgccagca aagtgactgc cagtggcccc 4740
ggccttagtt cctatggtgt gcctgccagt ctacctgtgg actttgcaat tgatgcccga 4800
gatgccgggg aaggcctgct tgctgttcaa ataacggacc aagaaggaaa acccaaaaga 4860
gccattgtcc atgacaataa agatggcacg tatgctgtca cctacatccc cgacaagact 4920

-continued

```
gggcgctata tgattggagt cacctacggg ggtgacgaca tcccactttc tccttatcgc   4980
atccgagcca cacagacggg tgatgccagc aagtgcctgg ccacgggtcc tggaatcgcc   5040
tccactgtga aaactggcga agaagtaggc tttgtggttg atgccaagac tgccgggaag   5100
ggtaaagtga cctgcacggt tctgacccca gatggcactg aggccgaggc cgatgtcatt   5160
gagaatgaag atggaaccta tgacatcttc tacacagctg ccaagccggg cacatatgtg   5220
atctatgtgc gcttcggtgg tgttgatatt cctaacagcc ccttcactgt catggtgacc   5280
gaagaggcct atgtcccagt gagtgacatg aacggcctgg gatttaagcc ttttgacctg   5340
gtcattccgt ttgctgtcag gaaaggagaa atcactggag aggtccacat gccttctggg   5400
aagacagcca cacctgagat tgtggacaac aaggacggca cggtcactgt tagatatgcc   5460
cccactgagg tcgggctcca tgagatgcac atcaaataca tgggcagcca catccctgag   5520
agcccactcc agttctacgt gaactacccc aacagtggaa gtgtttctgc atacggtcca   5580
ggcctcgtgt atggagtggc caacaaaact gccaccttca ccatcgtcac agaggatgca   5640
ggagaaggtg gtctggactt ggctattgag ggcccctcaa aagcagaaat cagctgcatt   5700
gacaataaag atgggacatg cacagtgacc tacctgccga ctctgccagg cgactacagc   5760
attctggtca agtacaatga caagcacatc cctggcagcc ccttcacagc caagatcaca   5820
gatgacagca ggcggtgctc ccaggtgaag ttgggctcag ccgctgactt cctgctcgac   5880
atcagtgaga ctgacctcag cagcctgacg gccagcatta aggccccatc tggccgagac   5940
gagccctgtc tcctgaagag gctgcccaac aaccacattg gcatctcctt catcccccgg   6000
gaagtgggcg aacatctggt cagcatcaag aaaaatggca accatgtggc caacagcccc   6060
gtgtctatca tggtggtcca gtcggagatt ggtgacgccc gccgagccaa agtctatggc   6120
cgcggcctgt cagaaggccg gactttcgag atgtctgact tcatcgtgga cacaagggat   6180
gcaggttatg gtggcatatc cttggcggtg gaaggcccca gcaaagtgga catccagacg   6240
gaggacctgg aagatggcac ctgcaaagtc tcctacttcc ctaccgtgcc tggggtttat   6300
atcgtctcca ccaaattcgc tgacgagcac gtgcctggga gcccatttac cgtgaagatc   6360
agtggggagg gaagagtcaa agagagcatc acccgcacca gtcgggcccc gtccgtggcc   6420
actgtcggga gcatttgtga cctgaacctg aaaatcccag aaatcaacag cagtgatatg   6480
tcggcccacg tcaccagccc ctctggccgt gtgactgagg cagagattgt gcccatgggg   6540
aagaactcac actgcgtccg gtttgtgccc caggagatgg gcgtgcacac ggtcagcgtc   6600
aagtaccgtg ggcagcacgt caccggcagc ccctttccagt tcaccgtggg gccacttggt   6660
gaaggaggcg cccacaaggt gcgggcagga ggccctggcc tggagagagg agaagcggga   6720
gtcccagctg agttcagcat ttggacccgg gaagcaggcg ctggaggcct ctccatcgct   6780
gttgagggcc ccagtaaggc cgagattaca ttcgatgacc ataaaaatgg gtcgtgcggt   6840
gtatcttata ttgcccaaga gcctggtaac tacgaggtgt ccatcaagtt caatgatgag   6900
cacatcccgg aaagccccta cctggtgccg gtcatcgcac cctccgacga cgcccgccgc   6960
ctcactgtta tgagccttca ggaatcggga ttaaaagtta accagccagc atcctttgct   7020
ataaggttga atggcgcaaa aggcaagatt gatgcaaagg tgcacagccc ctctggagcc   7080
gtggaggagt gccacgtgtc tgagctggag ccagataagt atgctgttcg cttcatccct   7140
catgagaatg gtgtccacac catcgatgtc aagttcaatg ggagccacgt ggttggaagc   7200
cccttcaaag tgcgcgttgg ggagcctgga caagcgggga accctgccct ggtgtccgcc   7260
tatggcacgg gactcgaagg gggcaccaca ggtatccagt cggaattctt tattaacacc   7320
```

```
acccgagcag gtccagggac attatccgtc accatcgaag gcccatccaa ggttaaaatg    7380

gattgccagg aaacacctga agggtacaaa gtcatgtaca cccccatggc tcctggtaac    7440

tacctgatca gcgtcaaata cggtgggccc aaccacatcg tgggcagtcc cttcaaggcc    7500

aaggtgacag gccagcgtct agttagccct ggctcagcca acgagacctc atccatcctg    7560

gtggagtcag tgaccaggtc gtctacagag acctgctata gcgccattcc caaggcatcc    7620

tcggacgcca gcaaggtgac ctctaagggg gcagggctct caaaggcctt tgtgggccag    7680

aagagttcct tcctggtgga ctgcagcaaa gctggctcca acatgctgct gatcggggtc    7740

catgggccca ccaccccctg cgaggaggtc tccatgaagc atgtaggcaa ccagcaatac    7800

aacgtcacat acgtcgtcaa ggagaggggc gattatgtgc tggctgtgaa gtgggggag     7860

gaacacatcc ctggcagccc ttttcatgtc acagtgcctt aaaacagttt tctcaaatcc    7920

tggagagagt tcttgtggtt gcttttgttg cttgtttgta attcatttta tacaaagccc    7980

tccagcctgt ttgtggggct gaaaccccat ccctaaaata ttgctgttgt aaaatgcctt    8040

cagaaataag tcctagactg gactcttgag ggacatattg gagaatctta agaaatgcaa    8100

gcttgttcag ggggctgaga agatcctgag tacactaggt gcaaaccaga actcttggtg    8160

gaacagacca gccactgcag cagacagacc aggaacacaa tgagactgac atttcaaaaa    8220

aacaaaactg gctagcctga gctgctggtt cactcttcag catttatgaa acaaggctag    8280

gggaagatgg gcagagaaaa aggggacacc tagtttggtt gtcatttggc aaaggagatg    8340

acttaaaatc cgcttaatct cttccagtgt ccgtgttaat gtatttggct attagatcac    8400

tagcactgct ttaccgctcc tcatcgccaa cacccccatg ctctgtggcc ttcttacact    8460

tctcagaggg cagagtggca gccgggcacc ctacagaaac tcagagggca gagtggcagc    8520

caggcccaca tgtctctcaa gtacctgtcc cctcgctctg gtgattattt cttgcagaat    8580

caccacacga gaccatcccg gcagtcatgg ttttgcttta gttttccaag tccgtttcag    8640

tcccttcctt ggtctgaaga aattctgcag tggcgagcag tttcccactt gccaaagatc    8700

ccttttaacc aacactagcc cttgttttta acacacgctc cagcccttca tcagcctggg    8760

cagtcttacc aaaatgttta aagtgatctc agaggggccc atggattaac gccctcatcc    8820

caaggtccgt cccatgacat aacactccac acccgcccca gccaacttca tgggtcactt    8880

tttctggaaa ataatgatct gtacagacag gacagaatga aactcctgcg ggtctttggc    8940

ctgaaagttg ggaatggttg ggggagagaa gggcagcagc ttattggtgg tcttttcacc    9000

attggcagaa acagtgagag ctgtgtggtg cagaaatcca gaaatgaggt gtagggaatt    9060

ttgcctgcct tcctgcagac ctgagctggc tttggaatga ggttaaagtg tcagggacgt    9120

tgcctgagcc caaatgtgta gtgtggtctg gcaggcagaa cctttaggtt ttgctgctta    9180

gtcctgagga agtggccact cttgtggcag gtgtagtatc tggggcgagt gttggggta    9240

aaagcccacc ctacagaaag tggaacagcc cggagcctga tgtgaaagga ccacgggtgt    9300

tgtaagctgg gacacggaag ccaaactgga atcaaacgcc gactgtaaat tgtatcttat    9360

aacttattaa ataaaacatt tgctccgtaa agttg                               9395
```

<210> SEQ ID NO 28
<211> LENGTH: 2602
<212> TYPE: PRT
<213> ORGANISM: Homo sapiens

<400> SEQUENCE: 28

-continued

```
Met Pro Val Thr Glu Lys Asp Leu Ala Glu Asp Ala Pro Trp Lys Lys
1               5                   10                  15

Ile Gln Gln Asn Thr Phe Thr Arg Trp Cys Asn Glu His Leu Lys Cys
            20                  25                  30

Val Asn Lys Arg Ile Gly Asn Leu Gln Thr Asp Leu Ser Asp Gly Leu
        35                  40                  45

Arg Leu Ile Ala Leu Leu Glu Val Leu Ser Gln Lys Arg Met Tyr Arg
    50                  55                  60

Lys Tyr His Gln Arg Pro Thr Phe Arg Gln Met Gln Leu Glu Asn Val
65                  70                  75                  80

Ser Val Ala Leu Glu Phe Leu Asp Arg Glu Ser Ile Lys Leu Val Ser
                85                  90                  95

Ile Asp Ser Lys Ala Ile Val Asp Gly Asn Leu Lys Leu Ile Leu Gly
            100                 105                 110

Leu Val Trp Thr Leu Ile Leu His Tyr Ser Ile Ser Met Pro Val Trp
        115                 120                 125

Glu Asp Glu Gly Asp Asp Asp Ala Lys Lys Gln Thr Pro Lys Gln Arg
    130                 135                 140

Leu Leu Gly Trp Ile Gln Asn Lys Ile Pro Tyr Leu Pro Ile Thr Asn
145                 150                 155                 160

Phe Asn Gln Asn Trp Gln Asp Gly Lys Ala Leu Gly Ala Leu Val Asp
                165                 170                 175

Ser Cys Ala Pro Gly Leu Cys Pro Asp Trp Glu Ser Trp Asp Pro Gln
            180                 185                 190

Lys Pro Val Asp Asn Ala Arg Glu Ala Met Gln Gln Ala Asp Asp Trp
        195                 200                 205

Leu Gly Val Pro Gln Val Ile Thr Pro Glu Glu Ile Ile His Pro Asp
    210                 215                 220

Val Asp Glu His Ser Val Met Thr Tyr Leu Ser Gln Phe Pro Lys Ala
225                 230                 235                 240

Lys Leu Lys Pro Gly Ala Pro Leu Lys Pro Lys Leu Asn Pro Lys Lys
                245                 250                 255

Ala Arg Ala Tyr Gly Arg Gly Ile Glu Pro Thr Gly Asn Met Val Lys
            260                 265                 270

Gln Pro Ala Lys Phe Thr Val Asp Thr Ile Ser Ala Gly Gln Gly Asp
        275                 280                 285

Val Met Val Phe Val Glu Asp Pro Glu Gly Asn Lys Glu Glu Ala Gln
    290                 295                 300

Val Thr Pro Asp Ser Asp Lys Asn Lys Thr Tyr Ser Val Glu Tyr Leu
305                 310                 315                 320

Pro Lys Val Thr Gly Leu His Lys Val Thr Val Leu Phe Ala Gly Gln
                325                 330                 335

His Ile Ser Lys Ser Pro Phe Glu Val Ser Val Asp Lys Ala Gln Gly
            340                 345                 350

Asp Ala Ser Lys Val Thr Ala Lys Gly Pro Gly Leu Glu Ala Val Gly
        355                 360                 365

Asn Ile Ala Asn Lys Pro Thr Tyr Phe Asp Ile Tyr Thr Ala Gly Ala
    370                 375                 380

Gly Val Gly Asp Ile Gly Val Glu Val Glu Asp Pro Gln Gly Lys Asn
385                 390                 395                 400

Thr Val Glu Leu Leu Val Glu Asp Lys Gly Asn Gln Val Tyr Arg Cys
                405                 410                 415

Val Tyr Lys Pro Met Gln Pro Gly Pro His Val Val Lys Ile Phe Phe
```

```
            420                 425                 430

Ala Gly Asp Thr Ile Pro Lys Ser Pro Phe Val Val Gln Val Gly Glu
        435                 440                 445

Ala Cys Asn Pro Asn Ala Cys Arg Ala Ser Gly Arg Gly Leu Gln Pro
    450                 455                 460

Lys Gly Val Arg Ile Arg Glu Thr Thr Asp Phe Lys Val Asp Thr Lys
465                 470                 475                 480

Ala Ala Gly Ser Gly Glu Leu Gly Val Thr Met Lys Gly Pro Lys Gly
                485                 490                 495

Leu Glu Glu Leu Val Lys Gln Lys Asp Phe Leu Asp Gly Val Tyr Ala
            500                 505                 510

Phe Glu Tyr Tyr Pro Ser Thr Pro Gly Arg Tyr Ser Ile Ala Ile Thr
        515                 520                 525

Trp Gly Gly His His Ile Pro Lys Ser Pro Phe Glu Val Gln Val Gly
    530                 535                 540

Pro Glu Ala Gly Met Gln Lys Val Arg Ala Trp Gly Pro Gly Leu His
545                 550                 555                 560

Gly Gly Ile Val Gly Arg Ser Ala Asp Phe Val Val Glu Ser Ile Gly
                565                 570                 575

Ser Glu Val Gly Ser Leu Gly Phe Ala Ile Glu Gly Pro Ser Gln Ala
            580                 585                 590

Lys Ile Glu Tyr Asn Asp Gln Asn Asp Gly Ser Cys Asp Val Lys Tyr
        595                 600                 605

Trp Pro Lys Glu Pro Gly Glu Tyr Ala Val His Ile Met Cys Asp Asp
    610                 615                 620

Glu Asp Ile Lys Asp Ser Pro Tyr Met Ala Phe Ile His Pro Ala Thr
625                 630                 635                 640

Gly Gly Tyr Asn Pro Asp Leu Val Arg Ala Tyr Gly Pro Gly Leu Glu
                645                 650                 655

Lys Ser Gly Cys Ile Val Asn Asn Leu Ala Glu Phe Thr Val Asp Pro
            660                 665                 670

Lys Asp Ala Gly Lys Ala Pro Leu Lys Ile Phe Ala Gln Asp Gly Glu
        675                 680                 685

Gly Gln Arg Ile Asp Ile Gln Met Lys Asn Arg Met Asp Gly Thr Tyr
    690                 695                 700

Ala Cys Ser Tyr Thr Pro Val Lys Ala Ile Lys His Thr Ile Ala Val
705                 710                 715                 720

Val Trp Gly Gly Val Asn Ile Pro His Ser Pro Tyr Arg Val Asn Ile
                725                 730                 735

Gly Gln Gly Ser His Pro Gln Lys Val Lys Val Phe Gly Pro Gly Val
            740                 745                 750

Glu Arg Ser Gly Leu Lys Ala Asn Glu Pro Thr His Phe Thr Val Asp
        755                 760                 765

Cys Thr Glu Ala Gly Glu Gly Asp Val Ser Val Gly Ile Lys Cys Asp
    770                 775                 780

Ala Arg Val Leu Ser Glu Asp Glu Glu Asp Val Asp Phe Asp Ile Ile
785                 790                 795                 800

His Asn Ala Asn Asp Thr Phe Thr Val Lys Tyr Val Pro Pro Ala Ala
                805                 810                 815

Gly Arg Tyr Thr Ile Lys Val Leu Phe Ala Ser Gln Glu Ile Pro Ala
            820                 825                 830

Ser Pro Phe Arg Val Lys Val Asp Pro Ser His Asp Ala Ser Lys Val
        835                 840                 845
```

-continued

```
Lys Ala Glu Gly Pro Gly Leu Ser Lys Ala Gly Val Glu Asn Gly Lys
    850                 855                 860

Pro Thr His Phe Thr Val Tyr Thr Lys Gly Ala Gly Lys Ala Pro Leu
865                 870                 875                 880

Asn Val Gln Phe Asn Ser Pro Leu Pro Gly Asp Ala Val Lys Asp Leu
                885                 890                 895

Asp Ile Ile Asp Asn Tyr Asp Tyr Ser His Thr Val Lys Tyr Thr Pro
            900                 905                 910

Thr Gln Gln Gly Asn Met Gln Val Leu Val Thr Tyr Gly Gly Asp Pro
        915                 920                 925

Ile Pro Lys Ser Pro Phe Thr Val Gly Val Ala Ala Pro Leu Asp Leu
    930                 935                 940

Ser Lys Ile Lys Leu Asn Gly Leu Glu Asn Arg Val Glu Val Gly Lys
945                 950                 955                 960

Asp Gln Glu Phe Thr Val Asp Thr Arg Gly Ala Gly Gly Gln Gly Lys
                965                 970                 975

Leu Asp Val Thr Ile Leu Ser Pro Ser Arg Lys Val Val Pro Cys Leu
            980                 985                 990

Val Thr Pro Val Thr Gly Arg Glu  Asn Ser Thr Ala Lys  Phe Ile Pro
        995                 1000                1005

Arg Glu  Glu Gly Leu Tyr Ala  Val Asp Val Thr Tyr  Asp Gly His
    1010                1015                1020

Pro Val  Pro Gly Ser Pro Tyr  Thr Val Glu Ala Ser  Leu Pro Pro
    1025                1030                1035

Asp Pro  Ser Lys Val Lys Ala  His Gly Pro Gly Leu  Glu Gly Gly
    1040                1045                1050

Leu Val  Gly Lys Pro Ala Glu  Phe Thr Ile Asp Thr  Lys Gly Ala
    1055                1060                1065

Gly Thr  Gly Gly Leu Gly Leu  Thr Val Glu Gly Pro  Cys Glu Ala
    1070                1075                1080

Lys Ile  Glu Cys Ser Asp Asn  Gly Asp Gly Thr Cys  Ser Val Ser
    1085                1090                1095

Tyr Leu  Pro Thr Lys Pro Gly  Glu Tyr Phe Val Asn  Ile Leu Phe
    1100                1105                1110

Glu Glu  Val His Ile Pro Gly  Ser Pro Phe Lys Ala  Asp Ile Glu
    1115                1120                1125

Met Pro  Phe Asp Pro Ser Lys  Val Val Ala Ser Gly  Pro Gly Leu
    1130                1135                1140

Glu His  Gly Lys Val Gly Glu  Ala Gly Leu Leu Ser  Val Asp Cys
    1145                1150                1155

Ser Glu  Ala Gly Pro Gly Ala  Leu Gly Leu Glu Ala  Val Ser Asp
    1160                1165                1170

Ser Gly  Thr Lys Ala Glu Val  Ser Ile Gln Asn Asn  Lys Asp Gly
    1175                1180                1185

Thr Tyr  Ala Val Thr Tyr Val  Pro Leu Thr Ala Gly  Met Tyr Thr
    1190                1195                1200

Leu Thr  Met Lys Tyr Gly Gly  Glu Leu Val Pro His  Phe Pro Ala
    1205                1210                1215

Arg Val  Lys Val Glu Pro Ala  Val Asp Thr Ser Arg  Ile Lys Val
    1220                1225                1230

Phe Gly  Pro Gly Ile Glu Gly  Lys Asp Val Phe Arg  Glu Ala Thr
    1235                1240                1245
```

Thr Asp Phe Thr Val Asp Ser Arg Pro Leu Thr Gln Val Gly Gly
1250 1255 1260

Asp His Ile Lys Ala His Ile Ala Asn Pro Ser Gly Ala Ser Thr
1265 1270 1275

Glu Cys Phe Val Thr Asp Asn Ala Asp Gly Thr Tyr Gln Val Glu
1280 1285 1290

Tyr Thr Pro Phe Glu Lys Gly Leu His Val Val Glu Val Thr Tyr
1295 1300 1305

Asp Asp Val Pro Ile Pro Asn Ser Pro Phe Lys Val Ala Val Thr
1310 1315 1320

Glu Gly Cys Gln Pro Ser Arg Val Gln Ala Gln Gly Pro Gly Leu
1325 1330 1335

Lys Glu Ala Phe Thr Asn Lys Pro Asn Val Phe Thr Val Val Thr
1340 1345 1350

Arg Gly Ala Gly Ile Gly Gly Leu Gly Ile Thr Val Glu Gly Pro
1355 1360 1365

Ser Glu Ser Lys Ile Asn Cys Arg Asp Asn Lys Asp Gly Ser Cys
1370 1375 1380

Ser Ala Glu Tyr Ile Pro Phe Ala Pro Gly Asp Tyr Asp Val Asn
1385 1390 1395

Ile Thr Tyr Gly Gly Ala His Ile Pro Gly Ser Pro Phe Arg Val
1400 1405 1410

Pro Val Lys Asp Val Val Asp Pro Ser Lys Val Lys Ile Ala Gly
1415 1420 1425

Pro Gly Leu Gly Ser Gly Val Arg Ala Arg Val Leu Gln Ser Phe
1430 1435 1440

Thr Val Asp Ser Ser Lys Ala Gly Leu Ala Pro Leu Glu Val Arg
1445 1450 1455

Val Leu Gly Pro Arg Gly Leu Val Glu Pro Val Asn Val Val Asp
1460 1465 1470

Asn Gly Asp Gly Thr His Thr Val Thr Tyr Thr Pro Ser Gln Glu
1475 1480 1485

Gly Pro Tyr Met Val Ser Val Lys Tyr Ala Asp Glu Glu Ile Pro
1490 1495 1500

Arg Ser Pro Phe Lys Val Lys Val Leu Pro Thr Tyr Asp Ala Ser
1505 1510 1515

Lys Val Thr Ala Ser Gly Pro Gly Leu Ser Ser Tyr Gly Val Pro
1520 1525 1530

Ala Ser Leu Pro Val Asp Phe Ala Ile Asp Ala Arg Asp Ala Gly
1535 1540 1545

Glu Gly Leu Leu Ala Val Gln Ile Thr Asp Gln Glu Gly Lys Pro
1550 1555 1560

Lys Arg Ala Ile Val His Asp Asn Lys Asp Gly Thr Tyr Ala Val
1565 1570 1575

Thr Tyr Ile Pro Asp Lys Thr Gly Arg Tyr Met Ile Gly Val Thr
1580 1585 1590

Tyr Gly Gly Asp Asp Ile Pro Leu Ser Pro Tyr Arg Ile Arg Ala
1595 1600 1605

Thr Gln Thr Gly Asp Ala Ser Lys Cys Leu Ala Thr Gly Pro Gly
1610 1615 1620

Ile Ala Ser Thr Val Lys Thr Gly Glu Glu Val Gly Phe Val Val
1625 1630 1635

Asp Ala Lys Thr Ala Gly Lys Gly Lys Val Thr Cys Thr Val Leu

```
    1640                1645                1650

Thr Pro  Asp Gly Thr Glu Ala  Glu Ala Asp Val Ile  Glu Asn Glu
    1655                1660                1665

Asp Gly  Thr Tyr Asp Ile Phe  Tyr Thr Ala Ala Lys  Pro Gly Thr
    1670                1675                1680

Tyr Val  Ile Tyr Val Arg Phe  Gly Gly Val Asp Ile  Pro Asn Ser
    1685                1690                1695

Pro Phe  Thr Val Met Ala Thr  Asp Gly Glu Val Thr  Ala Val Glu
    1700                1705                1710

Glu Ala  Pro Val Asn Ala Cys  Pro Pro Gly Phe Arg  Pro Trp Val
    1715                1720                1725

Thr Glu  Glu Ala Tyr Val Pro  Val Ser Asp Met Asn  Gly Leu Gly
    1730                1735                1740

Phe Lys  Pro Phe Asp Leu Val  Ile Pro Phe Ala Val  Arg Lys Gly
    1745                1750                1755

Glu Ile  Thr Gly Glu Val His  Met Pro Ser Gly Lys  Thr Ala Thr
    1760                1765                1770

Pro Glu  Ile Val Asp Asn Lys  Asp Gly Thr Val Thr  Val Arg Tyr
    1775                1780                1785

Ala Pro  Thr Glu Val Gly Leu  His Glu Met His Ile  Lys Tyr Met
    1790                1795                1800

Gly Ser  His Ile Pro Glu Ser  Pro Leu Gln Phe Tyr  Val Asn Tyr
    1805                1810                1815

Pro Asn  Ser Gly Ser Val Ser  Ala Tyr Gly Pro Gly  Leu Val Tyr
    1820                1825                1830

Gly Val  Ala Asn Lys Thr Ala  Thr Phe Thr Ile Val  Thr Glu Asp
    1835                1840                1845

Ala Gly  Glu Gly Gly Leu Asp  Leu Ala Ile Glu Gly  Pro Ser Lys
    1850                1855                1860

Ala Glu  Ile Ser Cys Ile Asp  Asn Lys Asp Gly Thr  Cys Thr Val
    1865                1870                1875

Thr Tyr  Leu Pro Thr Leu Pro  Gly Asp Tyr Ser Ile  Leu Val Lys
    1880                1885                1890

Tyr Asn  Asp Lys His Ile Pro  Gly Ser Pro Phe Thr  Ala Lys Ile
    1895                1900                1905

Thr Asp  Asp Ser Arg Arg Cys  Ser Gln Val Lys Leu  Gly Ser Ala
    1910                1915                1920

Ala Asp  Phe Leu Leu Asp Ile  Ser Glu Thr Asp Leu  Ser Ser Leu
    1925                1930                1935

Thr Ala  Ser Ile Lys Ala Pro  Ser Gly Arg Asp Glu  Pro Cys Leu
    1940                1945                1950

Leu Lys  Arg Leu Pro Asn Asn  His Ile Gly Ile Ser  Phe Ile Pro
    1955                1960                1965

Arg Glu  Val Gly Glu His Leu  Val Ser Ile Lys Lys  Asn Gly Asn
    1970                1975                1980

His Val  Ala Asn Ser Pro Val  Ser Ile Met Val Val  Gln Ser Glu
    1985                1990                1995

Ile Gly  Asp Ala Arg Arg Ala  Lys Val Tyr Gly Arg  Gly Leu Ser
    2000                2005                2010

Glu Gly  Arg Thr Phe Glu Met  Ser Asp Phe Ile Val  Asp Thr Arg
    2015                2020                2025

Asp Ala  Gly Tyr Gly Gly Ile  Ser Leu Ala Val Glu  Gly Pro Ser
    2030                2035                2040
```

```
Lys Val  Asp Ile Gln Thr Glu  Asp Leu Glu Asp Gly  Thr Cys Lys
    2045                 2050                 2055

Val Ser  Tyr Phe Pro Thr Val  Pro Gly Val Tyr Ile  Val Ser Thr
    2060                 2065                 2070

Lys Phe  Ala Asp Glu His Val  Pro Gly Ser Pro Phe  Thr Val Lys
    2075                 2080                 2085

Ile Ser  Gly Glu Gly Arg Val  Lys Glu Ser Ile Thr  Arg Thr Ser
    2090                 2095                 2100

Arg Ala  Pro Ser Val Ala Thr  Val Gly Ser Ile Cys  Asp Leu Asn
    2105                 2110                 2115

Leu Lys  Ile Pro Glu Ile Asn  Ser Ser Asp Met Ser  Ala His Val
    2120                 2125                 2130

Thr Ser  Pro Ser Gly Arg Val  Thr Glu Ala Glu Ile  Val Pro Met
    2135                 2140                 2145

Gly Lys  Asn Ser His Cys Val  Arg Phe Val Pro Gln  Glu Met Gly
    2150                 2155                 2160

Val His  Thr Val Ser Val Lys  Tyr Arg Gly Gln His  Val Thr Gly
    2165                 2170                 2175

Ser Pro  Phe Gln Phe Thr Val  Gly Pro Leu Gly Glu  Gly Gly Ala
    2180                 2185                 2190

His Lys  Val Arg Ala Gly Gly  Pro Gly Leu Glu Arg  Gly Glu Ala
    2195                 2200                 2205

Gly Val  Pro Ala Glu Phe Ser  Ile Trp Thr Arg Glu  Ala Gly Ala
    2210                 2215                 2220

Gly Gly  Leu Ser Ile Ala Val  Glu Gly Pro Ser Lys  Ala Glu Ile
    2225                 2230                 2235

Thr Phe  Asp Asp His Lys Asn  Gly Ser Cys Gly Val  Ser Tyr Ile
    2240                 2245                 2250

Ala Gln  Glu Pro Gly Asn Tyr  Glu Val Ser Ile Lys  Phe Asn Asp
    2255                 2260                 2265

Glu His  Ile Pro Glu Ser Pro  Tyr Leu Val Pro Val  Ile Ala Pro
    2270                 2275                 2280

Ser Asp  Asp Ala Arg Arg Leu  Thr Val Met Ser Leu  Gln Glu Ser
    2285                 2290                 2295

Gly Leu  Lys Val Asn Gln Pro  Ala Ser Phe Ala Ile  Arg Leu Asn
    2300                 2305                 2310

Gly Ala  Lys Gly Lys Ile Asp  Ala Lys Val His Ser  Pro Ser Gly
    2315                 2320                 2325

Ala Val  Glu Glu Cys His Val  Ser Glu Leu Glu Pro  Asp Lys Tyr
    2330                 2335                 2340

Ala Val  Arg Phe Ile Pro His  Glu Asn Gly Val His  Thr Ile Asp
    2345                 2350                 2355

Val Lys  Phe Asn Gly Ser His  Val Val Gly Ser Pro  Phe Lys Val
    2360                 2365                 2370

Arg Val  Gly Glu Pro Gly Gln  Ala Gly Asn Pro Ala  Leu Val Ser
    2375                 2380                 2385

Ala Tyr  Gly Thr Gly Leu Glu  Gly Gly Thr Thr Gly  Ile Gln Ser
    2390                 2395                 2400

Glu Phe  Phe Ile Asn Thr Thr  Arg Ala Gly Pro Gly  Thr Leu Ser
    2405                 2410                 2415

Val Thr  Ile Glu Gly Pro Ser  Lys Val Lys Met Asp  Cys Gln Glu
    2420                 2425                 2430
```

```
Thr Pro  Glu Gly Tyr Lys Val  Met Tyr Thr Pro Met  Ala Pro Gly
    2435                 2440                 2445

Asn Tyr  Leu Ile Ser Val Lys  Tyr Gly Gly Pro Asn  His Ile Val
    2450                 2455                 2460

Gly Ser  Pro Phe Lys Ala Lys  Val Thr Gly Gln Arg  Leu Val Ser
    2465                 2470                 2475

Pro Gly  Ser Ala Asn Glu Thr  Ser Ser Ile Leu Val  Glu Ser Val
    2480                 2485                 2490

Thr Arg  Ser Ser Thr Glu Thr  Cys Tyr Ser Ala Ile  Pro Lys Ala
    2495                 2500                 2505

Ser Ser  Asp Ala Ser Lys Val  Thr Ser Lys Gly Ala  Gly Leu Ser
    2510                 2515                 2520

Lys Ala  Phe Val Gly Gln Lys  Ser Ser Phe Leu Val  Asp Cys Ser
    2525                 2530                 2535

Lys Ala  Gly Ser Asn Met Leu  Leu Ile Gly Val His  Gly Pro Thr
    2540                 2545                 2550

Thr Pro  Cys Glu Glu Val Ser  Met Lys His Val Gly  Asn Gln Gln
    2555                 2560                 2565

Tyr Asn  Val Thr Tyr Val Val  Lys Glu Arg Gly Asp  Tyr Val Leu
    2570                 2575                 2580

Ala Val  Lys Trp Gly Glu Glu  His Ile Pro Gly Ser  Pro Phe His
    2585                 2590                 2595

Val Thr  Val Pro
    2600


<210> SEQ ID NO 29
<211> LENGTH: 9467
<212> TYPE: DNA
<213> ORGANISM: Homo sapiens

<400> SEQUENCE: 29

gcggccaggg gcgggcggcc gcagagcagc accggccgtg gctccggtag cagcaagttc     60

gaaccccgct cccgctccgc ttcggttctc gctccttcgg cccttgggcc tccaaacacc    120

agtccccggc agctcgttgc gcattgcgct ctccccgcca ccaggatgcc ggtaaccgag    180

aaggatctag ctgaggacgc gccttggaag aagatccagc agaacacgtt cacacgctgg    240

tgcaacgagc acctcaagtg cgtgaacaaa cgcatcggca acctgcagac cgacctgagc    300

gacgggctgc ggctcatcgc gctgctcgag gtgctcagcc agaagcgcat gtaccgcaag    360

taccatcagc ggcccacctt tcgccagatg cagctcgaga atgtgtccgt ggcgctcgag    420

ttcctggacc gtgagagcat caagctcgtg tccatcgata gcaaagccat tgtggatggg    480

aacctgaagc tcatcttggg tctggtgtgg acgctgatcc tccactactc catctccatg    540

cccgtgtggg aggatgaagg ggatgatgat gccaagaagc agacgccaaa gcagaggctg    600

ctggggtgga ttcagaacaa gatcccctac ttgcccatca ccaactttaa ccagaactgg    660

caagacggca aagccctggg agccctggta gacagctgtg ctccaggtct gtgcccagac    720

tgggaatcct gggacccgca gaagcctgtg gataatgcac gagaagccat gcagcaggca    780

gatgactggc tgggtgtccc acaggtcatc actcctgaag aaatcattca cccggatgtg    840

gacgagcact cagttatgac ttacctgtcc cagttcccca aagccaagct caagccgggg    900

gctcctctca aacccaaact caacccgaag aaagccaggg cctatggcag aggaatcgag    960

cccactggaa acatggtgaa gcagccagcc aagttcactg tggacaccat cagcgccggg   1020

caaggagacg tgatggtgtt tgttgaggac ccagaaggga acaaagagga ggcacaagtg   1080
```

```
accccctgaca gtgacaagaa caagacatac tctgtggagt atctgcccaa ggtcaccggg   1140
ctacacaaag tcacagtcct ctttgcagga cagcacatct ccaagagccc atttgaagtg   1200
agtgttgaca aggcccaggg agatgccagt aaagtcactg caaaaggtcc agggttggaa   1260
gctgtaggga acatcgccaa taagcccacc tactttgaca tctatacggc aggagctggt   1320
gtgggtgaca ttggtgtgga ggtggaagat ccccagggga agaacaccgt ggagttgctc   1380
gtggaagaca aaggaaacca ggtgtatcga tgtgtgtaca aacccatgca gcctggccct   1440
cacgtggtca agatcttctt tgctggggac actattccta agagtccctt cgttgtgcag   1500
gttggggaag cctgcaatcc aaatgcctgc cgggccagtg gccgaggcct acaacccaaa   1560
ggcgtccgta tccgggagac cacagatttc aaggttgaca ccaaagctgc aggaagtggg   1620
gagctcggtg taaccatgaa gggtcctaag ggtctggagg agctggtgaa gcagaaagac   1680
tttctggatg gggtctacgc attcgagtat taccccagca ccccggggag atacagcatt   1740
gccatcacat ggggggggaca ccacattcca aagagcccct ttgaagttca agttggccct   1800
gaagcgggta tgcagaaagt ccgtgcttgg ggccctgggc tccatggtgg gattgtcggg   1860
cggtcagcgg acttcgtggt agaatccatt ggctctgaag tggggtctct ggggtttgcc   1920
attgaaggcc cctctcaggc aaagattgag tacaacgacc agaatgatgg atcgtgtgat   1980
gtcaaatact ggcccaagga gcctggcgaa tatgctgttc acatcatgtg tgacgacgaa   2040
gacatcaagg acagcccgta catggccttc atccacccag ccacgggagg ctacaaccct   2100
gatctggttc gagcatacgg gccaggtttg gagaaatctg gatgcattgt caacaacctg   2160
gccgagttca ctgtggatcc taaggatgct ggaaaagctc ccttaaagat atttgctcag   2220
gatggggaag gccaacgcat tgacatccag atgaagaacc ggatggacgg cacatatgca   2280
tgctcataca ccccggtgaa ggccatcaag cacaccattg ctgtggtctg ggaggcgtg   2340
aacatcccgc acagccccta cagggtcaac atcgggcaag gtagccatcc tcagaaggtc   2400
aaagtgtttg ggccaggtgt ggagagaagt ggtctgaagg caaatgaacc tacacacttc   2460
acggtggact gtactgaggc tggggaaggt gatgtcagtg ttggcattaa gtgtgatgcc   2520
cgggtgttaa gtgaagatga ggaagacgtg gattttgaca ttattcacaa tgccaatgat   2580
acgttcacag tcaaatatgt gcctcctgct gctgggcgat acactatcaa agttctcttt   2640
gcatctcagg aaatccccgc cagccctttc agagtcaaag ttgacccttc ccacgatgcc   2700
agcaaagtga aggcagaagg cccagggctc agcaaagcag gtgtggaaaa tgggaaaccg   2760
acccacttca ctgtctacac caagggggct gggaaagccc cgctcaacgt gcagttcaac   2820
agccctcttc ctggcgatgc agtgaaggat ttggatatca tcgataatta tgactactct   2880
cacacggtta aatatacacc cacccaacag ggcaacatgc aggttctggt gacttacggt   2940
ggcgatccca tccctaaaag ccctttcact gtgggtgttg ctgcaccgct ggatctgagc   3000
aagataaaac tcaatgggct ggaaaacagg gtggaagttg ggaaggatca ggagttcacc   3060
gttgatacca ggggggcagg aggccagggg aagctggacg tgacaatcct cagcccctct   3120
cggaaggtcg tgccatgcct agtgacacct gtgacaggcc gggagaacag cacggccaag   3180
ttcatccctc gggaggaggg gctgtatgct gtagacgtga cctacgatgg acaccctgtg   3240
cccgggagcc cctacacagt ggaggcctcg ctgccaccag atcccagcaa ggtgaaggcc   3300
cacggtcccg gcctcgaagg tggtctcgtg ggcaagcctg ccgagttcac catcgatacc   3360
aaaggagctg gtactggagg tctgggctta acggtggaag gtccgtgcga ggccaaaatc   3420
```

-continued gagtgctccg acaatggtga tgggacctgc tccgtctctt accttcccac aaaacccggg 3480
gagtacttcg tcaacatcct ctttgaagaa gtccacatac ctgggtctcc cttcaaagct 3540
gacattgaaa tgccctttga cccctctaaa gtcgtggcat cggggccagg tctcgagcac 3600
gggaaggtgg gtgaagctgg cctccttagc gtcgactgct cggaagcggg accgggggcc 3660
ctgggcctgg aagctgtctc ggactcggga acaaaagccg aagtcagtat tcagaacaac 3720
aaagatggca cctacgcggt gacctacgtg cccctgacgg ccggcatgta cacgttgacc 3780
atgaagtatg gtggcgaact cgtgccacac ttccccgccc gggtcaaggt ggagcccgcc 3840
gtggacacca gcaggatcaa agtctttgga ccaggaatag aagggaaaga tgtgttccgg 3900
gaagctacca ccgactttac agttgactct cggccgctga cccaggttgg gggtgaccac 3960
atcaaggccc acattgccaa cccctcaggg gcctccaccg agtgctttgt cacagacaat 4020
gcggatggga cctaccaggt ggaatacaca ccctttgaga aaggtctcca tgtagtggag 4080
gtgacatatg atgacgtgcc tatcccaaac agtcccttca aggtggctgt cactgaaggc 4140
tgccagccat ctagggtgca agcccaagga cctggattga aagaggcctt taccaacaag 4200
cccaatgtct tcaccgtggt taccagaggc gcaggaattg gtgggcttgg cataactgtt 4260
gagggaccat cagagtcgaa gataaattgc agagacaaca aggatggcag ctgcagtgct 4320
gagtacattc ctttcgcacc gggggattac gatgttaata tcacatatgg aggagcccac 4380
atccccggca gccccttcag ggttcctgtg aaggatgttg tggaccccag caaggtcaag 4440
attgccggcc ccgggctggg ctcaggcgtc cgagcccgtg tcctgcagtc cttcacggtg 4500
gacagcagca aggctggcct ggctccgctg gaagtgaggg ttctgggccc acgaggcttg 4560
gtggagccag tgaacgtggt ggacaatgga gatggcacac acacagtaac ctacacccca 4620
tctcaggagg gaccttacat ggtctcagtt aaatatgctg atgaagagat tcctcgcagt 4680
cccttcaagg tcaaggtcct tcccacatat gatgccagca aagtgactgc cagtggcccc 4740
ggccttagtt cctatggtgt gcctgccagt ctacctgtgg actttgcaat tgatgcccga 4800
gatgccgggg aaggcctgct tgctgttcaa ataacggacc aagaaggaaa acccaaaaga 4860
gccattgtcc atgacaataa agatggcacg tatgctgtca cctacatccc cgacaagact 4920
gggcgctata tgattggagt cacctacggg ggtgacgaca tcccactttc tccttatcgc 4980
atccgagcca cacagacggg tgatgccagc aagtgcctgg ccacgggtcc tggaatcgcc 5040
tccactgtga aaactggcga agaagtaggc tttgtggttg atgccaagac tgccgggaag 5100
ggtaaagtga cctgcacggt tctgacccca gatggcactg aggccgaggc cgatgtcatt 5160
gagaatgaag atggaaccta tgacatcttc tacacagctg ccaagccggg cacatatgtg 5220
atctatgtgc gcttcggtgg tgttgatatt cctaacagcc ccttcactgt catggccaca 5280
gatggggaag tcacagccgt ggaggaggca ccggtaaatg catgtccccc tggattcagg 5340
ccctgggtga ccgaagaggc ctatgtccca gtgagtgaca tgaacggcct gggatttaag 5400
ccttttgacc tggtcattcc gtttgctgtc aggaaaggag aaatcactgg agaggtccac 5460
atgccttctg ggaagacagc cacacctgag attgtggaca acaaggacgg cacggtcact 5520
gttagatatg cccccactga ggtcgggctc catgagatgc acatcaaata catgggcagc 5580
cacatccctg agagcccact ccagttctac gtgaactacc ccaacagtgg aagtgtttct 5640
gcatacggtc caggcctcgt gtatggagtg gccaacaaaa ctgccacctt caccatcgtc 5700
acagaggatg caggagaagg tggtctggac ttggctattg agggcccctc aaaagcagaa 5760
atcagctgca ttgacaataa agatgggaca tgcacagtga cctacctgcc gactctgcca 5820

```
ggcgactaca gcattctggt caagtacaat gacaagcaca tccctggcag ccccttcaca   5880
gccaagatca cagatgacag caggcggtgc tcccaggtga agttgggctc agccgctgac   5940
ttcctgctcg acatcagtga gactgacctc agcagcctga cggccagcat taaggcccca   6000
tctggccgag acgagccctg tctcctgaag aggctgccca acaaccacat tggcatctcc   6060
ttcatccccc gggaagtggg cgaacatctg gtcagcatca agaaaaatgg caaccatgtg   6120
gccaacagcc ccgtgtctat catggtggtc cagtcggaga ttggtgacgc ccgccgagcc   6180
aaagtctatg gccgcggcct gtcagaaggc cggactttcg agatgtctga cttcatcgtg   6240
gacacaaggg atgcaggtta tggtggcata tccttggcgg tggaaggccc cagcaaagtg   6300
gacatccaga cggaggacct ggaagatggc acctgcaaag tctcctactt ccctaccgtg   6360
cctggggttt atatcgtctc caccaaattc gctgacgagc acgtgcctgg gagcccattt   6420
accgtgaaga tcagtgggga gggaagagtc aaagagagca tcacccgcac cagtcgggcc   6480
ccgtccgtgg ccactgtcgg gagcatttgt gacctgaacc tgaaaatccc agaaatcaac   6540
agcagtgata tgtcggccca cgtcaccagc ccctctggcc gtgtgactga ggcagagatt   6600
gtgcccatgg ggaagaactc acactgcgtc cggtttgtgc cccaggagat gggcgtgcac   6660
acggtcagcg tcaagtaccg tggcagcac gtcaccggca gccccttcca gttcaccgtg   6720
gggccacttg gtgaaggagg cgcccacaag gtgcgggcag gaggccctgg cctggagaga   6780
ggagaagcgg gagtcccagc tgagttcagc atttggaccc gggaagcagg cgctggaggc   6840
ctctccatcg ctgttgaggg ccccagtaag gccgagatta cattcgatga ccataaaaat   6900
gggtcgtgcg gtgtatctta tattgcccaa gagcctggta actacgaggt gtccatcaag   6960
ttcaatgatg agcacatccc ggaaagcccc tacctggtgc cggtcatcgc accctccgac   7020
gacgcccgcc gcctcactgt tatgagcctt caggaatcgg gattaaaagt taaccagcca   7080
gcatcctttg ctataaggtt gaatggcgca aaaggcaaga ttgatgcaaa ggtgcacagc   7140
ccctctggag ccgtggagga gtgccacgtg tctgagctgg agccagataa gtatgctgtt   7200
cgcttcatcc ctcatgagaa tggtgtccac accatcgatg tcaagttcaa tgggagccac   7260
gtggttggaa gccccttcaa agtgcgcgtt ggggagcctg gacaagcggg gaaccctgcc   7320
ctggtgtccg cctatggcac gggactcgaa gggggcacca caggtatcca gtcggaattc   7380
tttattaaca ccacccgagc aggtccaggg acattatccg tcaccatcga aggcccatcc   7440
aaggttaaaa tggattgcca ggaaacacct gaagggtaca aagtcatgta cacccccatg   7500
gctcctggta actacctgat cagcgtcaaa tacggtgggc ccaaccacat cgtgggcagt   7560
cccttcaagg ccaaggtgac aggccagcgt ctagttagcc ctggctcagc caacgagacc   7620
tcatccatcc tggtggagtc agtgaccagg tcgtctacag agacctgcta tagcgccatt   7680
cccaaggcat cctcggacgc cagcaaggtg acctctaagg gggcagggct ctcaaaggcc   7740
tttgtgggcc agaagagttc cttcctggtg gactgcagca aagctggctc caacatgctg   7800
ctgatcgggg tccatgggcc caccaccccc tgcgaggagg tctccatgaa gcatgtaggc   7860
aaccagcaat acaacgtcac atacgtcgtc aaggagaggg gcgattatgt gctggctgtg   7920
aagtgggggg aggaacacat ccctggcagc ccttttcatg tcacagtgcc ttaaaacagt   7980
tttctcaaat cctggagaga gttcttgtgg ttgcttttgt tgcttgtttg taattcattt   8040
tatacaaagc cctccagcct gtttgtgggg ctgaaacccc atccctaaaa tattgctgtt   8100
gtaaaatgcc ttcagaaata agtcctagac tggactcttg agggacatat tggagaatct   8160
```

```
taagaaatgc aagcttgttc agggggctga gaagatcctg agtacactag gtgcaaacca   8220

gaactcttgg tggaacagac cagccactgc agcagacaga ccaggaacac aatgagactg   8280

acatttcaaa aaaacaaaac tggctagcct gagctgctgg ttcactcttc agcatttatg   8340

aaacaaggct aggggaagat gggcagagaa aaaggggaca cctagtttgg ttgtcatttg   8400

gcaaaggaga tgacttaaaa tccgcttaat ctcttccagt gtccgtgtta atgtatttgg   8460

ctattagatc actagcactg ctttaccgct cctcatcgcc aacacccccca tgctctgtgg   8520

ccttcttaca cttctcagag ggcagagtgg cagccgggca ccctacagaa actcagaggg   8580

cagagtggca gccaggccca catgtctctc aagtacctgt cccctcgctc tggtgattat   8640

ttcttgcaga atcaccacac gagaccatcc cggcagtcat ggttttgctt tagttttcca   8700

agtccgtttc agtcccttcc ttggtctgaa gaaattctgc agtggcgagc agtttcccac   8760

ttgccaaaga tccctttttaa ccaacactag cccttgtttt taacacacgc tccagccctt   8820

catcagcctg ggcagtctta ccaaaatgtt taaagtgatc tcagaggggc ccatggatta   8880

acgccctcat cccaaggtcc gtcccatgac ataacactcc acacccgccc cagccaactt   8940

catgggtcac tttttctgga aaataatgat ctgtacagac aggacagaat gaaactcctg   9000

cgggtctttg gcctgaaagt tggggaatggt tgggggagag aagggcagca gcttattggt   9060

ggtcttttca ccattggcag aaacagtgag agctgtgtgg tgcagaaatc cagaaatgag   9120

gtgtagggaa ttttgcctgc cttcctgcag acctgagctg gctttggaat gaggttaaag   9180

tgtcagggac gttgcctgag cccaaatgtg tagtgtggtc tgggcaggca gacctttagg   9240

ttttgctgct tagtcctgag gaagtggcca ctcttgtggc aggtgtagta tctggggcga   9300

gtgttggggg taaaagccca ccctacagaa agtggaacag cccggagcct gatgtgaaag   9360

gaccacgggt gttgtaagct gggacacgga agccaaactg gaatcaaacg ccgactgtaa   9420

attgtatctt ataacttatt aaataaaaca tttgctccgt aaagttg                 9467
```

<210> SEQ ID NO 30
<211> LENGTH: 193
<212> TYPE: PRT
<213> ORGANISM: Homo sapiens

<400> SEQUENCE: 30

```
Met Val Ala Pro Lys Ser His Thr Asp Asp Trp Ala Pro Gly Pro Phe
1               5                   10                  15

Ser Ser Lys Pro Gln Arg Ser Gln Leu Gln Ile Phe Ser Ser Val Leu
            20                  25                  30

Gln Thr Ser Leu Leu Phe Leu Leu Met Gly Leu Arg Ala Ser Gly Lys
        35                  40                  45

Asp Ser Ala Pro Thr Val Val Ser Gly Ile Leu Gly Gly Ser Val Thr
    50                  55                  60

Leu Pro Leu Asn Ile Ser Val Asp Thr Glu Ile Glu Asn Val Ile Trp
65                  70                  75                  80

Ile Gly Pro Lys Asn Ala Leu Ala Phe Ala Arg Pro Lys Glu Asn Val
                85                  90                  95

Thr Ile Met Val Lys Ser Tyr Leu Gly Arg Leu Asp Ile Thr Lys Trp
            100                 105                 110

Ser Tyr Ser Leu Cys Ile Ser Asn Leu Thr Leu Asn Asp Ala Gly Ser
        115                 120                 125

Tyr Lys Ala Gln Ile Asn Gln Arg Asn Phe Glu Val Thr Thr Glu Glu
    130                 135                 140
```

-continued

```
Glu Phe Thr Leu Phe Val Tyr Ala Pro Phe Ile Glu Lys Leu Ser Val
145                 150                 155                 160

His Val Ile Glu Gly Asp His Arg Thr Leu Leu Glu Gly Ser Gly Leu
                165                 170                 175

Glu Ser Ile Ile Ser Thr Leu Ala Glu Pro Arg Val Ser Val Arg Glu
            180                 185                 190

Gly
```

<210> SEQ ID NO 31
<211> LENGTH: 1525
<212> TYPE: DNA
<213> ORGANISM: Homo sapiens

<400> SEQUENCE: 31

```
acatacacat acacatgcac acacacactc atatacacat gcagaagctg tgacacgtgc     60
ggaagctgtg gtaagtgcat cctccttcag tctcagttct gaaaatagat catcatggtg    120
gcaccaaaga gtcacacaga tgactgggct cctgggcctt tctccagtaa gccacagagg    180
agtcagctgc aaatattctc ttctgttcta cagacctctc tcctcttcct gctcatggga    240
ctaagagcct ctggaaagga ctcagcccca acagtggtgt cagggatcct agggggttcc    300
gtgactctcc ccctaaacat ctcagtagac acagagattg agaacgtcat ctggattggt    360
cccaaaaatg ctcttgcttt cgcacgtccc aaagaaaatg taaccattat ggtcaaaagc    420
tacctgggcc gactagacat caccaagtgg agttactccc tgtgcatcag caatctgact    480
ctgaatgatg caggatccta caaagcccag ataaaccaaa ggaattttga agtcaccact    540
gaggaggaat tcaccctgtt cgtctatgca ccatttattg aaaagttgtc cgtccacgtc    600
atcgagggtg accaccgcac actcctggag ggcagcggcc tggagtccat catcagcacc    660
ctggctgagc cacgtgtgag cgtgcgggag ggctaggccc tcgcccccac ctgccactgg    720
agaccgctcc gccatcccca cctcaccgcc gcgcagcaga gctggaaggg tcctgccgat    780
gggaccctgc caggcccagt gccactgccc cccgaggctg ctagacgtgg gcgttaggcg    840
tgtcccaccc acccgccgcc tcccatggca cgtcgggaac accggagccg ccaacttgga    900
gactcctggt ctgtgaagag ccgctgacgc ccgcaggaac cgggctgggc cttgtgtgcc    960
agtggggttt gtgcttggtc tttctccgct tggatttgct tatttattgc attgctggta   1020
gagactccca agcctgtcca ccctgcaaag actcctcggg cagcatgcgg gtcccgcaca   1080
ctgcacccat ttcctggatg tcccctgcag gcgcgggagg ccatccgggc ctgctggctg   1140
cggccccctc tcagccaggc ctggctcagc ccactgcgtg ggaggtcacc ggccactccc   1200
cgaggagctg ggatccccgg gatgcaggcc cacagtgcgg ggctgcaccc atgatgcgga   1260
gctggcctcc aaccctgcgg gccgcgccag gcaccaactc agtgtttgtc agtgtttgtt   1320
tttccaagaa atggttcaaa ttgctgctca gatttttaaa tttactgtag ctgccagtgt   1380
acacgtgtgg accccatttt atttttacac caatttggtg aaaatgctgc tttcctcagc   1440
ctccccacaa ttaaactgca catggtctct aaaaaaataa aaataaataa ataaataaat   1500
aaataaaaag tatcttttct cccca                                         1525
```

<210> SEQ ID NO 32
<211> LENGTH: 641
<212> TYPE: PRT
<213> ORGANISM: Homo sapiens

<400> SEQUENCE: 32

Met Val Ala Pro Lys Ser His Thr Asp Asp Trp Ala Pro Gly Pro Phe
1               5                   10                  15

Ser Ser Lys Pro Gln Arg Ser Gln Leu Gln Ile Phe Ser Ser Val Leu
            20                  25                  30

Gln Thr Ser Leu Leu Phe Leu Leu Met Gly Leu Arg Ala Ser Gly Lys
        35                  40                  45

Asp Ser Ala Pro Thr Val Val Ser Gly Ile Leu Gly Gly Ser Val Thr
    50                  55                  60

Leu Pro Leu Asn Ile Ser Val Asp Thr Glu Ile Glu Asn Val Ile Trp
65                  70                  75                  80

Ile Gly Pro Lys Asn Ala Leu Ala Phe Ala Arg Pro Lys Glu Asn Val
                85                  90                  95

Thr Ile Met Val Lys Ser Tyr Leu Gly Arg Leu Asp Ile Thr Lys Trp
            100                 105                 110

Ser Tyr Ser Leu Cys Ile Ser Asn Leu Thr Leu Asn Asp Ala Gly Ser
        115                 120                 125

Tyr Lys Ala Gln Ile Asn Gln Arg Asn Phe Glu Val Thr Thr Glu Glu
    130                 135                 140

Glu Phe Thr Leu Phe Val Tyr Glu Gln Leu Gln Glu Pro Gln Val Thr
145                 150                 155                 160

Met Lys Ser Val Lys Val Ser Glu Asn Phe Ser Cys Asn Ile Thr Leu
                165                 170                 175

Met Cys Ser Val Lys Gly Ala Glu Lys Ser Val Leu Tyr Ser Trp Thr
            180                 185                 190

Pro Arg Glu Pro His Ala Ser Glu Ser Asn Gly Gly Ser Ile Leu Thr
        195                 200                 205

Val Ser Arg Thr Pro Cys Asp Pro Asp Leu Pro Tyr Ile Cys Thr Ala
    210                 215                 220

Gln Asn Pro Val Ser Gln Arg Ser Ser Leu Pro Val His Val Gly Gln
225                 230                 235                 240

Phe Cys Thr Asp Pro Gly Ala Ser Arg Gly Gly Thr Thr Gly Glu Thr
                245                 250                 255

Val Val Gly Val Leu Gly Glu Pro Val Thr Leu Pro Leu Ala Leu Pro
            260                 265                 270

Ala Cys Arg Asp Thr Glu Lys Val Val Trp Leu Phe Asn Thr Ser Ile
        275                 280                 285

Ile Ser Lys Glu Arg Glu Glu Ala Ala Thr Ala Asp Pro Leu Ile Lys
    290                 295                 300

Ser Arg Asp Pro Tyr Lys Asn Arg Val Trp Val Ser Ser Gln Asp Cys
305                 310                 315                 320

Ser Leu Lys Ile Ser Gln Leu Lys Ile Glu Asp Ala Gly Pro Tyr His
                325                 330                 335

Ala Tyr Val Cys Ser Glu Ala Ser Ser Val Thr Ser Met Thr His Val
            340                 345                 350

Thr Leu Leu Ile Tyr Arg Arg Leu Arg Lys Pro Lys Ile Thr Trp Ser
        355                 360                 365

Leu Arg His Ser Glu Asp Gly Ile Cys Arg Ile Ser Leu Thr Cys Ser
    370                 375                 380

Val Glu Asp Gly Gly Asn Thr Val Met Tyr Thr Trp Thr Pro Leu Gln
385                 390                 395                 400

Lys Glu Ala Val Val Ser Gln Gly Glu Ser His Leu Asn Val Ser Trp
                405                 410                 415

Arg Ser Ser Glu Asn His Pro Asn Leu Thr Cys Thr Ala Ser Asn Pro

```
            420                 425                 430

Val Ser Arg Ser Ser His Gln Phe Leu Ser Glu Asn Ile Cys Ser Gly
        435                 440                 445

Pro Glu Arg Asn Thr Lys Leu Trp Ile Gly Leu Phe Leu Met Val Cys
    450                 455                 460

Leu Leu Cys Val Gly Ile Phe Ser Trp Cys Ile Trp Lys Arg Lys Gly
465                 470                 475                 480

Arg Cys Ser Val Pro Ala Phe Cys Ser Ser Gln Ala Glu Ala Pro Ala
                485                 490                 495

Asp Thr Pro Gly Tyr Glu Lys Leu Asp Thr Pro Leu Arg Pro Ala Arg
            500                 505                 510

Gln Gln Pro Thr Pro Thr Ser Asp Ser Ser Ser Asp Ser Asn Leu Thr
        515                 520                 525

Thr Glu Glu Asp Glu Asp Arg Pro Glu Val His Lys Pro Ile Ser Gly
    530                 535                 540

Arg Tyr Glu Val Phe Asp Gln Val Thr Gln Glu Gly Ala Gly His Asp
545                 550                 555                 560

Pro Ala Pro Glu Gly Gln Ala Asp Tyr Asp Pro Val Thr Pro Tyr Val
                565                 570                 575

Thr Glu Val Glu Ser Val Val Gly Glu Asn Thr Met Tyr Ala Gln Val
            580                 585                 590

Phe Asn Leu Gln Gly Lys Thr Pro Val Ser Gln Lys Glu Glu Ser Ser
        595                 600                 605

Ala Thr Ile Tyr Cys Ser Ile Arg Lys Pro Gln Val Val Pro Pro Pro
    610                 615                 620

Gln Gln Asn Asp Leu Glu Ile Pro Glu Ser Pro Thr Tyr Glu Asn Phe
625                 630                 635                 640

Thr


<210> SEQ ID NO 33
<211> LENGTH: 2508
<212> TYPE: DNA
<213> ORGANISM: Homo sapiens

<400> SEQUENCE: 33

acatacacat acacatgcac acacacactc atatacacat gcagaagctg tgacacgtgc      60

ggaagctgtg gtaagtgcat cctccttcag tctcagttct gaaaatagat catcatggtg     120

gcaccaaaga gtcacacaga tgactgggct cctgggcctt tctccagtaa gccacagagg     180

agtcagctgc aaatattctc ttctgttcta cagacctctc tcctcttcct gctcatggga     240

ctaagagcct ctggaaagga ctcagcccca acagtggtgt cagggatcct agggggttcc     300

gtgactctcc ccctaaacat ctcagtagac acagagattg agaacgtcat ctggattggt     360

cccaaaaatg ctcttgcttt cgcacgtccc aaagaaaatg taaccattat ggtcaaaagc     420

tacctgggcc gactagacat caccaagtgg agttactccc tgtgcatcag caatctgact     480

ctgaatgatg caggatccta caaagcccag ataaaccaaa ggaattttga agtcaccact     540

gaggaggaat tcaccctgtt cgtctatgag cagctgcagg agccccaagt caccatgaag     600

tctgtgaagg tgtctgagaa cttctcctgt aacatcactc taatgtgctc cgtgaagggg     660

gcagagaaaa gtgttctgta cagctggacc ccaagggaac cccatgcttc tgagtccaat     720

ggaggctcca ttcttaccgt ctcccgaaca ccatgtgacc cagacctgcc atacatctgc     780

acagcccaga accccgtcag ccagagaagc tccctccctg tccatgttgg gcagttctgt     840
```

```
acagatccag gagcctccag aggaggaaca acgggggaga ctgtggtagg ggtcctggga    900
gagccagtca ccctgccact tgcactccca gcctgccggg acacagagaa ggttgtctgg    960
ttgtttaaca catccatcat tagcaaagag agggaagaag cagcaacggc agatccactc   1020
attaaatcca gggatcctta caagaacagg gtgtgggtct ccagccagga ctgctccctg   1080
aagatcagcc agctgaagat agaggacgcc ggcccctacc atgcctacgt gtgctcagag   1140
gcctccagcg tcaccagcat gacacatgtc accctgctca tctaccgcag gctgaggaag   1200
cccaaaatca cgtggagcct caggcacagt gaggatggca tctgcaggat cagcctgacc   1260
tgctccgtgg aggacggggg aaacactgtc atgtacacat ggaccccgct gcagaaggaa   1320
gctgttgtgt cccaagggga atcacacctc aatgtctcat ggagaagcag tgaaaatcac   1380
cccaacctca catgcacagc cagcaaccct gtcagcagga gttcccacca gtttctttct   1440
gagaacatct gttcaggacc tgagagaaac acaaagcttt ggattgggtt gttcctgatg   1500
gtttgccttc tgtgcgttgg gatcttcagc tggtgcattt ggaagcgaaa aggacggtgt   1560
tcagtcccag ccttctgttc cagccaagct gaggccccag cggatacacc aggatatgag   1620
aagctggaca ctcccctcag gcctgccagg caacagccta cacccacctc agacagcagc   1680
tctgacagca acctcacaac tgaggaggat gaggacaggc ctgaggtgca caagcccatc   1740
agtggaagat atgaggtatt tgaccaggtc actcaggagg gcgctggaca tgacccagcc   1800
cctgagggcc aagcagacta tgatcccgtc actccatatg tcacggaagt tgagtctgtg   1860
gttggagaga acaccatgta tgcacaagtg ttcaacttac agggaaagac cccagtttct   1920
cagaaggaag agagctcagc cacaatctac tgctccatac ggaaacctca ggtggtgcca   1980
ccaccacaac agaatgatct tgagattcct gaaagtccta cctatgaaaa tttcacctga   2040
aaggaaaagc agctgctgcc tctctcctgg gaccgtgggg ttggaaagtc agctggacct   2100
catggggcct ggggctcaca gacagaagca cctcagaatt tccttcagtg cctcagagat   2160
gcctggatgt ggcccctccc cctccttctc acccttaagg actcccaaac ccattaatag   2220
ttcagacaca ggctccttct tggagcctat gggcttcaga tgtctttgcc ccatttgtca   2280
cctcgcacac ttatagcgtt tcctcctcga aattctacca agactggtca aatgttgctg   2340
aggggcctgg accagctgtc ctttacacca ccttctcaac actgctgaaa agaacccaag   2400
agaattgtca cacatgacac aagatgtaca taatatcatg ctcactgcag tgttatttaa   2460
aataaaaggc aggaaataaa aaaaaaaaaa aaaaaaaaaa aaaaaaaa                2508
```

<210> SEQ ID NO 34
<211> LENGTH: 565
<212> TYPE: PRT
<213> ORGANISM: Homo sapiens

<400> SEQUENCE: 34

```
Met Val Ala Pro Lys Ser His Thr Asp Asp Trp Ala Pro Gly Pro Phe
1               5                   10                  15

Ser Ser Lys Pro Gln Arg Ser Gln Leu Gln Ile Phe Ser Ser Val Leu
            20                  25                  30

Gln Thr Ser Leu Leu Phe Leu Leu Met Gly Leu Arg Ala Ser Gly Lys
        35                  40                  45

Asp Ser Ala Pro Thr Val Val Ser Gly Ile Leu Gly Gly Ser Val Thr
    50                  55                  60

Leu Pro Leu Asn Ile Ser Val Asp Thr Glu Ile Glu Asn Val Ile Trp
65                  70                  75                  80
```

```
Ile Gly Pro Lys Asn Ala Leu Ala Phe Ala Arg Pro Lys Glu Asn Val
                85                  90                  95

Thr Ile Met Val Lys Ser Tyr Leu Gly Arg Leu Asp Ile Thr Lys Trp
            100                 105                 110

Ser Tyr Ser Leu Cys Ile Ser Asn Leu Thr Leu Asn Asp Ala Gly Ser
        115                 120                 125

Tyr Lys Ala Gln Ile Asn Gln Arg Asn Phe Glu Val Thr Thr Glu Glu
    130                 135                 140

Glu Phe Thr Leu Phe Val Tyr Glu Gln Leu Gln Glu Pro Gln Val Thr
145                 150                 155                 160

Met Lys Ser Val Lys Val Ser Glu Asn Phe Ser Cys Asn Ile Thr Leu
                165                 170                 175

Met Cys Ser Val Lys Gly Ala Glu Lys Ser Val Leu Tyr Ser Trp Thr
            180                 185                 190

Pro Arg Glu Pro His Ala Ser Glu Ser Asn Gly Gly Ser Ile Leu Thr
        195                 200                 205

Val Ser Arg Thr Pro Cys Asp Pro Asp Leu Pro Tyr Ile Cys Thr Ala
    210                 215                 220

Gln Asn Pro Val Ser Gln Arg Ser Ser Leu Pro Val His Val Gly Gln
225                 230                 235                 240

Phe Cys Thr Asp Pro Gly Ala Ser Arg Gly Gly Thr Thr Gly Glu Thr
                245                 250                 255

Val Val Gly Val Leu Gly Glu Pro Val Thr Leu Pro Leu Ala Leu Pro
            260                 265                 270

Ala Cys Arg Asp Thr Glu Lys Val Val Trp Leu Phe Asn Thr Ser Ile
        275                 280                 285

Ile Ser Lys Glu Arg Glu Glu Ala Ala Thr Ala Asp Pro Leu Ile Lys
    290                 295                 300

Ser Arg Asp Pro Tyr Lys Asn Arg Val Trp Val Ser Ser Gln Asp Cys
305                 310                 315                 320

Ser Leu Lys Ile Ser Gln Leu Lys Ile Glu Asp Ala Gly Pro Tyr His
                325                 330                 335

Ala Tyr Val Cys Ser Glu Ala Ser Ser Val Thr Ser Met Thr His Val
            340                 345                 350

Thr Leu Leu Ile Tyr Arg Pro Glu Arg Asn Thr Lys Leu Trp Ile Gly
        355                 360                 365

Leu Phe Leu Met Val Cys Leu Leu Cys Val Gly Ile Phe Ser Trp Cys
    370                 375                 380

Ile Trp Lys Arg Lys Gly Arg Cys Ser Val Pro Ala Phe Cys Ser Ser
385                 390                 395                 400

Gln Ala Glu Ala Pro Ala Asp Thr Pro Glu Pro Thr Ala Gly His Thr
                405                 410                 415

Leu Tyr Ser Val Leu Ser Gln Gly Tyr Glu Lys Leu Asp Thr Pro Leu
            420                 425                 430

Arg Pro Ala Arg Gln Gln Pro Thr Pro Thr Ser Asp Ser Ser Ser Asp
        435                 440                 445

Ser Asn Leu Thr Thr Glu Glu Asp Glu Asp Arg Pro Glu Val His Lys
    450                 455                 460

Pro Ile Ser Gly Arg Tyr Glu Val Phe Asp Gln Val Thr Gln Glu Gly
465                 470                 475                 480

Ala Gly His Asp Pro Ala Pro Glu Gly Gln Ala Asp Tyr Asp Pro Val
                485                 490                 495

Thr Pro Tyr Val Thr Glu Val Glu Ser Val Val Gly Glu Asn Thr Met
```

-continued

```
            500                 505                 510

Tyr Ala Gln Val Phe Asn Leu Gln Gly Lys Thr Pro Val Ser Gln Lys
        515                 520                 525

Glu Glu Ser Ser Ala Thr Ile Tyr Cys Ser Ile Arg Lys Pro Gln Val
    530                 535                 540

Val Pro Pro Pro Gln Gln Asn Asp Leu Glu Ile Pro Glu Ser Pro Thr
545                 550                 555                 560

Tyr Glu Asn Phe Thr
                565


<210> SEQ ID NO 35
<211> LENGTH: 2280
<212> TYPE: DNA
<213> ORGANISM: Homo sapiens

<400> SEQUENCE: 35

acatacacat acacatgcac acacacactc atatacacat gcagaagctg tgacacgtgc     60

ggaagctgtg gtaagtgcat cctccttcag tctcagttct gaaaatagat catcatggtg    120

gcaccaaaga gtcacacaga tgactgggct cctgggcctt tctccagtaa gccacagagg    180

agtcagctgc aaatattctc ttctgttcta cagacctctc tcctcttcct gctcatggga    240

ctaagagcct ctggaaagga ctcagcccca acagtggtgt cagggatcct agggggttcc    300

gtgactctcc ccctaaacat ctcagtagac acagagattg agaacgtcat ctggattggt    360

cccaaaaatg ctcttgcttt cgcacgtccc aaagaaaatg taaccattat ggtcaaaagc    420

tacctgggcc gactagacat caccaagtgg agttactccc tgtgcatcag caatctgact    480

ctgaatgatg caggatccta caaagcccag ataaaccaaa ggaattttga agtcaccact    540

gaggaggaat tcaccctgtt cgtctatgag cagctgcagg agccccaagt caccatgaag    600

tctgtgaagg tgtctgagaa cttctcctgt aacatcactc taatgtgctc cgtgaagggg    660

gcagagaaaa gtgttctgta cagctggacc ccaagggaac cccatgcttc tgagtccaat    720

ggaggctcca ttcttaccgt ctcccgaaca ccatgtgacc cagacctgcc atacatctgc    780

acagcccaga accccgtcag ccagagaagc tccctccctg tccatgttgg gcagttctgt    840

acagatccag gagcctccag aggaggaaca acgggggaga ctgtggtagg ggtcctggga    900

gagccagtca ccctgccact tgcactccca gcctgccggg acacagagaa ggttgtctgg    960

ttgtttaaca catccatcat tagcaaagag agggaagaag cagcaacggc agatccactc   1020

attaaatcca gggatcctta caagaacagg gtgtgggtct ccagccagga ctgctccctg   1080

aagatcagcc agctgaagat agaggacgcc ggcccctacc atgcctacgt gtgctcagag   1140

gcctccagcg tcaccagcat gacacatgtc accctgctca tctaccgacc tgagagaaac   1200

acaaagcttt ggattgggtt gttcctgatg gtttgccttc tgtgcgttgg gatcttcagc   1260

tggtgcattt ggaagcgaaa aggacggtgt tcagtcccag ccttctgttc cagccaagct   1320

gaggccccag cggatacacc agaacccaca gctggccaca cgctatactc tgtgctctcc   1380

caaggatatg agaagctgga cactcccctc aggcctgcca ggcaacagcc tacacccacc   1440

tcagacagca gctctgacag caacctcaca actgaggagg atgaggacag gcctgaggtg   1500

cacaagccca tcagtggaag atatgaggta tttgaccagg tcactcagga gggcgctgga   1560

catgacccag cccctgaggg ccaagcagac tatgatcccg tcactccata tgtcacggaa   1620

gttgagtctg tggttggaga gaacaccatg tatgcacaag tgttcaactt acagggaaag   1680

accccagttt ctcagaagga agagagctca gccacaatct actgctccat acggaaacct   1740
```

```
caggtggtgc caccaccaca acagaatgat cttgagattc ctgaaagtcc tacctatgaa   1800

aatttcacct gaaaggaaaa gcagctgctg cctctctcct gggaccgtgg ggttggaaag   1860

tcagctggac ctcatggggc ctggggctca cagacagaag cacctcagaa tttccttcag   1920

tgcctcagag atgcctggat gtggcccctc cccctccttc tcacccttaa ggactcccaa   1980

acccattaat agttcagaca caggctcctt cttggagcct atgggcttca gatgtctttg   2040

ccccatttgt cacctcgcac acttatagcg tttcctcctc gaaattctac caagactggt   2100

caaatgttgc tgaggggcct ggaccagctg tcctttacac caccttctca acactgctga   2160

aaagaaccca agagaattgt cacacatgac acaagatgta cataatatca tgctcactgc   2220

agtgttattt aaaataaaag gcaggaaata aaaaaaaaaa aaaaaaaaaa aaaaaaaaaa   2280
```

<210> SEQ ID NO 36
<211> LENGTH: 655
<212> TYPE: PRT
<213> ORGANISM: Homo sapiens

<400> SEQUENCE: 36

```
Met Val Ala Pro Lys Ser His Thr Asp Asp Trp Ala Pro Gly Pro Phe
1               5                   10                  15

Ser Ser Lys Pro Gln Arg Ser Gln Leu Gln Ile Phe Ser Ser Val Leu
            20                  25                  30

Gln Thr Ser Leu Leu Phe Leu Leu Met Gly Leu Arg Ala Ser Gly Lys
        35                  40                  45

Asp Ser Ala Pro Thr Val Val Ser Gly Ile Leu Gly Gly Ser Val Thr
    50                  55                  60

Leu Pro Leu Asn Ile Ser Val Asp Thr Glu Ile Glu Asn Val Ile Trp
65                  70                  75                  80

Ile Gly Pro Lys Asn Ala Leu Ala Phe Ala Arg Pro Lys Glu Asn Val
                85                  90                  95

Thr Ile Met Val Lys Ser Tyr Leu Gly Arg Leu Asp Ile Thr Lys Trp
            100                 105                 110

Ser Tyr Ser Leu Cys Ile Ser Asn Leu Thr Leu Asn Asp Ala Gly Ser
        115                 120                 125

Tyr Lys Ala Gln Ile Asn Gln Arg Asn Phe Glu Val Thr Thr Glu Glu
    130                 135                 140

Glu Phe Thr Leu Phe Val Tyr Glu Gln Leu Gln Glu Pro Gln Val Thr
145                 150                 155                 160

Met Lys Ser Val Lys Val Ser Glu Asn Phe Ser Cys Asn Ile Thr Leu
                165                 170                 175

Met Cys Ser Val Lys Gly Ala Glu Lys Ser Val Leu Tyr Ser Trp Thr
            180                 185                 190

Pro Arg Glu Pro His Ala Ser Glu Ser Asn Gly Gly Ser Ile Leu Thr
        195                 200                 205

Val Ser Arg Thr Pro Cys Asp Pro Asp Leu Pro Tyr Ile Cys Thr Ala
    210                 215                 220

Gln Asn Pro Val Ser Gln Arg Ser Ser Leu Pro Val His Val Gly Gln
225                 230                 235                 240

Phe Cys Thr Asp Pro Gly Ala Ser Arg Gly Gly Thr Thr Gly Glu Thr
                245                 250                 255

Val Val Gly Val Leu Gly Glu Pro Val Thr Leu Pro Leu Ala Leu Pro
            260                 265                 270

Ala Cys Arg Asp Thr Glu Lys Val Val Trp Leu Phe Asn Thr Ser Ile
```

```
        275                 280                 285

Ile Ser Lys Glu Arg Glu Glu Ala Ala Thr Ala Asp Pro Leu Ile Lys
    290                 295                 300

Ser Arg Asp Pro Tyr Lys Asn Arg Val Trp Val Ser Ser Gln Asp Cys
305                 310                 315                 320

Ser Leu Lys Ile Ser Gln Leu Lys Ile Glu Asp Ala Gly Pro Tyr His
                325                 330                 335

Ala Tyr Val Cys Ser Glu Ala Ser Ser Val Thr Ser Met Thr His Val
            340                 345                 350

Thr Leu Leu Ile Tyr Arg Arg Leu Arg Lys Pro Lys Ile Thr Trp Ser
        355                 360                 365

Leu Arg His Ser Glu Asp Gly Ile Cys Arg Ile Ser Leu Thr Cys Ser
    370                 375                 380

Val Glu Asp Gly Gly Asn Thr Val Met Tyr Thr Trp Thr Pro Leu Gln
385                 390                 395                 400

Lys Glu Ala Val Val Ser Gln Gly Glu Ser His Leu Asn Val Ser Trp
                405                 410                 415

Arg Ser Ser Glu Asn His Pro Asn Leu Thr Cys Thr Ala Ser Asn Pro
            420                 425                 430

Val Ser Arg Ser Ser His Gln Phe Leu Ser Glu Asn Ile Cys Ser Gly
        435                 440                 445

Pro Glu Arg Asn Thr Lys Leu Trp Ile Gly Leu Phe Leu Met Val Cys
    450                 455                 460

Leu Leu Cys Val Gly Ile Phe Ser Trp Cys Ile Trp Lys Arg Lys Gly
465                 470                 475                 480

Arg Cys Ser Val Pro Ala Phe Cys Ser Ser Gln Ala Glu Ala Pro Ala
                485                 490                 495

Asp Thr Pro Glu Pro Thr Ala Gly His Thr Leu Tyr Ser Val Leu Ser
            500                 505                 510

Gln Gly Tyr Glu Lys Leu Asp Thr Pro Leu Arg Pro Ala Arg Gln Gln
        515                 520                 525

Pro Thr Pro Thr Ser Asp Ser Ser Ser Asp Ser Asn Leu Thr Thr Glu
    530                 535                 540

Glu Asp Glu Asp Arg Pro Glu Val His Lys Pro Ile Ser Gly Arg Tyr
545                 550                 555                 560

Glu Val Phe Asp Gln Val Thr Gln Glu Gly Ala Gly His Asp Pro Ala
                565                 570                 575

Pro Glu Gly Gln Ala Asp Tyr Asp Pro Val Thr Pro Tyr Val Thr Glu
            580                 585                 590

Val Glu Ser Val Val Gly Glu Asn Thr Met Tyr Ala Gln Val Phe Asn
        595                 600                 605

Leu Gln Gly Lys Thr Pro Val Ser Gln Lys Glu Glu Ser Ser Ala Thr
    610                 615                 620

Ile Tyr Cys Ser Ile Arg Lys Pro Gln Val Val Pro Pro Pro Gln Gln
625                 630                 635                 640

Asn Asp Leu Glu Ile Pro Glu Ser Pro Thr Tyr Glu Asn Phe Thr
                645                 650                 655
```

<210> SEQ ID NO 37
<211> LENGTH: 2550
<212> TYPE: DNA
<213> ORGANISM: Homo sapiens

<400> SEQUENCE: 37

-continued

```
acatacacat acacatgcac acacacactc atatacacat gcagaagctg tgacacgtgc     60
ggaagctgtg gtaagtgcat cctccttcag tctcagttct gaaaatagat catcatggtg    120
gcaccaaaga gtcacacaga tgactgggct cctgggcctt tctccagtaa gccacagagg    180
agtcagctgc aaatattctc ttctgttcta cagacctctc tcctcttcct gctcatggga    240
ctaagagcct ctggaaagga ctcagcccca acagtggtgt cagggatcct agggggttcc    300
gtgactctcc ccctaaacat ctcagtagac acagagattg agaacgtcat ctggattggt    360
cccaaaaatg ctcttgcttt cgcacgtccc aaagaaaatg taaccattat ggtcaaaagc    420
tacctgggcc gactagacat caccaagtgg agttactccc tgtgcatcag caatctgact    480
ctgaatgatg caggatccta caaagcccag ataaaccaaa ggaattttga agtcaccact    540
gaggaggaat tcaccctgtt cgtctatgag cagctgcagg agccccaagt caccatgaag    600
tctgtgaagg tgtctgagaa cttctcctgt aacatcactc taatgtgctc cgtgaagggg    660
gcagagaaaa gtgttctgta cagctggacc ccaagggaac cccatgcttc tgagtccaat    720
ggaggctcca ttcttaccgt ctcccgaaca ccatgtgacc cagacctgcc atacatctgc    780
acagcccaga accccgtcag ccagagaagc tccctccctg tccatgttgg gcagttctgt    840
acagatccag gagcctccag aggaggaaca acgggggaga ctgtggtagg ggtcctggga    900
gagccagtca ccctgccact tgcactccca gcctgccggg acacagagaa ggttgtctgg    960
ttgtttaaca catccatcat tagcaaagag agggaagaag cagcaacggc agatccactc   1020
attaaatcca gggatcctta caagaacagg gtgtgggtct ccagccagga ctgctccctg   1080
aagatcagcc agctgaagat agaggacgcc ggcccctacc atgcctacgt gtgctcagag   1140
gcctccagcg tcaccagcat gacacatgtc accctgctca tctaccgcag gctgaggaag   1200
cccaaaatca cgtggagcct caggcacagt gaggatggca tctgcaggat cagcctgacc   1260
tgctccgtgg aggacggggg aaacactgtc atgtacacat ggaccccgct gcagaaggaa   1320
gctgttgtgt cccaagggga atcacacctc aatgtctcat ggagaagcag tgaaaatcac   1380
cccaacctca catgcacagc cagcaaccct gtcagcagga gttcccacca gtttctttct   1440
gagaacatct gttcaggacc tgagagaaac acaaagcttt ggattgggtt gttcctgatg   1500
gtttgccttc tgtgcgttgg gatcttcagc tggtgcattt ggaagcgaaa aggacggtgt   1560
tcagtcccag ccttctgttc cagccaagct gaggccccag cggatacacc agaacccaca   1620
gctggccaca cgctatactc tgtgctctcc caaggatatg agaagctgga cactcccctc   1680
aggcctgcca ggcaacagcc tacacccacc tcagacagca gctctgacag caacctcaca   1740
actgaggagg atgaggacag gcctgaggtg cacaagccca tcagtggaag atatgaggta   1800
tttgaccagg tcactcagga gggcgctgga catgacccag cccctgaggg ccaagcagac   1860
tatgatcccg tcactccata tgtcacggaa gttgagtctg tggttggaga gaacaccatg   1920
tatgcacaag tgttcaactt acagggaaag accccagttt ctcagaagga agagagctca   1980
gccacaatct actgctccat acggaaacct caggtggtgc caccaccaca acagaatgat   2040
cttgagattc ctgaaagtcc tacctatgaa aatttcacct gaaaggaaaa gcagctgctg   2100
cctctctcct gggaccgtgg ggttggaaag tcagctggac ctcatggggc ctggggctca   2160
cagacagaag cacctcagaa tttccttcag tgcctcagag atgcctggat gtggcccctc   2220
cccctccttc tcacccttaa ggactcccaa acccattaat agttcagaca caggctcctt   2280
cttggagcct atgggcttca gatgtctttg ccccatttgt cacctcgcac acttatagcg   2340
tttcctcctc gaaattctac caagactggt caaatgttgc tgaggggcct ggaccagctg   2400
```

tcctttacac caccttctca acactgctga aaagaaccca agagaattgt cacacatgac 2460
acaagatgta cataatatca tgctcactgc agtgttattt aaaataaaag gcaggaaata 2520
aaaaaaaaaa aaaaaaaaaa aaaaaaaaaa 2550

<210> SEQ ID NO 38
<211> LENGTH: 238
<212> TYPE: PRT
<213> ORGANISM: Homo sapiens

<400> SEQUENCE: 38

Met Trp Val Pro Val Val Phe Leu Thr Leu Ser Val Thr Trp Ile Gly
1 5 10 15

Ala Ala Pro Leu Ile Leu Ser Arg Ile Val Gly Gly Trp Glu Cys Glu
20 25 30

Lys His Ser Gln Pro Trp Gln Val Leu Val Ala Ser Arg Gly Arg Ala
35 40 45

Val Cys Gly Gly Val Leu Val His Pro Gln Trp Val Leu Thr Ala Ala
50 55 60

His Cys Ile Arg Asn Lys Ser Val Ile Leu Leu Gly Arg His Ser Leu
65 70 75 80

Phe His Pro Glu Asp Thr Gly Gln Val Phe Gln Val Ser His Ser Phe
85 90 95

Pro His Pro Leu Tyr Asp Met Ser Leu Leu Lys Asn Arg Phe Leu Arg
100 105 110

Pro Gly Asp Asp Ser Ser His Asp Leu Met Leu Leu Arg Leu Ser Glu
115 120 125

Pro Ala Glu Leu Thr Asp Ala Val Lys Val Met Asp Leu Pro Thr Gln
130 135 140

Glu Pro Ala Leu Gly Thr Thr Cys Tyr Ala Ser Gly Trp Gly Ser Ile
145 150 155 160

Glu Pro Glu Glu Phe Leu Thr Pro Lys Lys Leu Gln Cys Val Asp Leu
165 170 175

His Val Ile Ser Asn Asp Val Cys Ala Gln Val His Pro Gln Lys Val
180 185 190

Thr Lys Phe Met Leu Cys Ala Gly Arg Trp Thr Gly Gly Lys Ser Thr
195 200 205

Cys Ser Trp Val Ile Leu Ile Thr Glu Leu Thr Met Pro Ala Leu Pro
210 215 220

Met Val Leu His Gly Ser Leu Val Pro Trp Arg Gly Gly Val
225 230 235

<210> SEQ ID NO 39
<211> LENGTH: 1906
<212> TYPE: DNA
<213> ORGANISM: Homo sapiens

<400> SEQUENCE: 39
agccccaagc ttaccacctg cacccggaga gctgtgtcac catgtgggtc ccggttgtct 60
tcctcaccct gtccgtgacg tggattggtg ctgcacccct catcctgtct cggattgtgg 120
gaggctggga gtgcgagaag cattcccaac cctggcaggt gcttgtggcc tctcgtggca 180
gggcagtctg cggcggtgtt ctggtgcacc cccagtgggt cctcacagct gcccactgca 240
tcaggaacaa aagcgtgatc ttgctgggtc ggcacagcct gtttcatcct gaagacacag 300
gccaggtatt tcaggtcagc cacagcttcc cacacccgct ctacgatatg agcctcctga 360
agaatcgatt cctcaggcca ggtgatgact ccagccacga cctcatgctg ctccgcctgt 420
cagagcctgc cgagctcacg gatgctgtga aggtcatgga cctgcccacc caggagccag 480
cactggggac cacctgctac gcctcaggct ggggcagcat tgaaccagag gagttcttga 540
ccccaaagaa acttcagtgt gtggacctcc atgttatttc caatgacgtg tgtgcgcaag 600
ttcaccctca gaaggtgacc aagttcatgc tgtgtgctgg acgctggaca gggggcaaaa 660
gcacctgctc gtgggtcatt ctgatcaccg aactgaccat gccagccctg ccgatggtcc 720
tccatggctc cctagtgccc tggagaggag gtgtctagtc agagagtagt cctggaaggt 780
ggcctctgtg aggagccacg gggacagcat cctgcagatg gtcctggccc ttgtcccacc 840
gacctgtcta caaggactgt cctcgtggac cctcccctct gcacaggagc tggaccctga 900
agtcccttcc ccaccggcca ggactggagc ccctacccct ctgttggaat ccctgcccac 960
cttcttctgg aagtcggctc tggagacatt tctctcttct tccaaagctg ggaactgcta 1020
tctgttatct gcctgtccag gtctgaaaga taggattgcc caggcagaaa ctgggactga 1080
cctatctcac tctctccctg cttttaccct tagggtgatt ctgggggccc acttgtctgt 1140
aatggtgtgc ttcaaggtat cacgtcatgg ggcagtgaac catgtgccct gcccgaaagg 1200
ccttccctgt acaccaaggt ggtgcattac cggaagtgga tcaaggacac catcgtggcc 1260
aacccctgag cacccctatc aaccccctat tgtagtaaac ttggaacctt ggaaatgacc 1320
aggccaagac tcaagcctcc ccagttctac tgacctttgt ccttaggtgt gaggtccagg 1380
gttgctagga aaagaaatca gcagacacag gtgtagacca gagtgtttct taaatggtgt 1440
aattttgtcc tctctgtgtc ctggggaata ctggccatgc ctggagacat atcactcaat 1500
ttctctgagg acacagatag gatggggtgt ctgtgttatt tgtggggtac agagatgaaa 1560
gaggggtggg atccacactg agagagtgga gagtgacatg tgctggacac tgtccatgaa 1620
gcactgagca gaagctggag gcacaacgca ccagacactc acagcaagga tggagctgaa 1680
aacataaccc actctgtcct ggaggcactg ggaagcctag agaaggctgt gagccaagga 1740
gggagggtct tcctttggca tgggatgggg atgaagtaag gagagggact ggacccccctg 1800 gaagctgatt cactatgggg ggaggtgtat tgaagtcctc cagacaaccc tcagatttga 1860
tgatttccta gtagaactca cagaaataaa gagctgttat actgtg 1906

<210> SEQ ID NO 40
<211> LENGTH: 218
<212> TYPE: PRT
<213> ORGANISM: Homo sapiens

<400> SEQUENCE: 40

Met Trp Val Pro Val Val Phe Leu Thr Leu Ser Val Thr Trp Ile Gly
1 5 10 15

Ala Ala Pro Leu Ile Leu Ser Arg Ile Val Gly Gly Trp Glu Cys Glu
20 25 30

Lys His Ser Gln Pro Trp Gln Val Leu Val Ala Ser Arg Gly Arg Ala
35 40 45

Val Cys Gly Gly Val Leu Val His Pro Gln Trp Val Leu Thr Ala Ala
50 55 60

His Cys Ile Arg Lys Pro Gly Asp Asp Ser Ser His Asp Leu Met Leu
65 70 75 80

Leu Arg Leu Ser Glu Pro Ala Glu Leu Thr Asp Ala Val Lys Val Met
85 90 95

-continued

```
Asp Leu Pro Thr Gln Glu Pro Ala Leu Gly Thr Thr Cys Tyr Ala Ser
            100                 105                 110

Gly Trp Gly Ser Ile Glu Pro Glu Glu Phe Leu Thr Pro Lys Lys Leu
        115                 120                 125

Gln Cys Val Asp Leu His Val Ile Ser Asn Asp Val Cys Ala Gln Val
    130                 135                 140

His Pro Gln Lys Val Thr Lys Phe Met Leu Cys Ala Gly Arg Trp Thr
145                 150                 155                 160

Gly Gly Lys Ser Thr Cys Ser Gly Asp Ser Gly Gly Pro Leu Val Cys
                165                 170                 175

Asn Gly Val Leu Gln Gly Ile Thr Ser Trp Gly Ser Glu Pro Cys Ala
            180                 185                 190

Leu Pro Glu Arg Pro Ser Leu Tyr Thr Lys Val Val His Tyr Arg Lys
        195                 200                 205

Trp Ile Lys Asp Thr Ile Val Ala Asn Pro
    210                 215


<210> SEQ ID NO 41
<211> LENGTH: 1335
<212> TYPE: DNA
<213> ORGANISM: Homo sapiens

<400> SEQUENCE: 41

agccccaagc ttaccacctg cacccggaga gctgtgtcac catgtgggtc ccggttgtct     60

tcctcaccct gtccgtgacg tggattggtg ctgcacccct catcctgtct cggattgtgg    120

gaggctggga gtgcgagaag cattcccaac cctggcaggt gcttgtggcc tctcgtggca    180

gggcagtctg cggcggtgtt ctggtgcacc cccagtgggt cctcacagct gcccactgca    240

tcaggaagcc aggtgatgac tccagccacg acctcatgct gctccgcctg tcagagcctg    300

ccgagctcac ggatgctgtg aaggtcatgg acctgcccac ccaggagcca gcactgggga    360

ccacctgcta cgcctcaggc tggggcagca ttgaaccaga ggagttcttg accccaaaga    420

aacttcagtg tgtggacctc catgttattt ccaatgacgt gtgtgcgcaa gttcaccctc    480

agaaggtgac caagttcatg ctgtgtgctg gacgctggac agggggcaaa agcacctgct    540

cgggtgattc tgggggccca cttgtctgta atggtgtgct tcaaggtatc acgtcatggg    600

gcagtgaacc atgtgccctg cccgaaaggc cttccctgta caccaaggtg gtgcattacc    660

ggaagtggat caaggacacc atcgtggcca acccctgagc acccctatca accccctatt    720

gtagtaaact tggaaccttg gaaatgacca ggccaagact caagcctccc cagttctact    780

gacctttgtc cttaggtgtg aggtccaggg ttgctaggaa aagaaatcag cagacacagg    840

tgtagaccag agtgtttctt aaatggtgta attttgtcct ctctgtgtcc tggggaatac    900

tggccatgcc tggagacata tcactcaatt tctctgagga cacagatagg atggggtgtc    960

tgtgttattt gtggggtaca gagatgaaag aggggtggga tccacactga gagagtggag   1020

agtgacatgt gctggacact gtccatgaag cactgagcag aagctggagg cacaacgcac   1080

cagacactca cagcaaggat ggagctgaaa acataaccca ctctgtcctg gaggcactgg   1140

gaagcctaga gaaggctgtg agccaaggag ggagggtctt cctttggcat gggatgggga   1200

tgaagtaagg agagggactg gaccccctgg aagctgattc actatggggg gaggtgtatt   1260

gaagtcctcc agacaaccct cagatttgat gatttcctag tagaactcac agaaataaag   1320

agctgttata ctgtg                                                    1335
```

<210> SEQ ID NO 42
<211> LENGTH: 69
<212> TYPE: PRT
<213> ORGANISM: Homo sapiens

<400> SEQUENCE: 42

```
Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Lys
65
```

<210> SEQ ID NO 43
<211> LENGTH: 555
<212> TYPE: DNA
<213> ORGANISM: Homo sapiens

<400> SEQUENCE: 43

```
agccccaagc ttaccacctg cacccggaga gctgtgtcac catgtgggtc ccggttgtct      60

tcctcaccct gtccgtgacg tggattggtg ctgcacccct catcctgtct cggattgtgg     120

gaggctggga gtgcgagaag cattcccaac cctggcaggt gcttgtggcc tctcgtggca     180

gggcagtctg cggcggtgtt ctggtgcacc cccagtgggt cctcacagct gcccactgca     240

tcaggaagtg agtaggggcc tggggtctgg ggagcaggtg tctgtgtccc agaggaataa     300

cagctgggca ttttccccag gataacctct aaggccagcc ttgggactgg gggagagagg     360

gaaagttctg gttcaggtca catggggagg cagggttggg gctggaccac cctccccatg     420

gctgcctggg tctccatctg tgttcctcta tgtctctttg tgtcgctttc attatgtctc     480

ttggtaactg gcttcggttg tgtctctccg tgtgactatt ttgttctctc tctccctctc     540

ttctctgtct tcagt                                                      555
```

<210> SEQ ID NO 44
<211> LENGTH: 261
<212> TYPE: PRT
<213> ORGANISM: Homo sapiens

<400> SEQUENCE: 44

```
Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110
```

-continued

```
Pro Gly Asp Asp Ser Ser His Asp Leu Met Leu Leu Arg Leu Ser Glu
        115                 120                 125

Pro Ala Glu Leu Thr Asp Ala Val Lys Val Met Asp Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
            180                 185                 190

Thr Lys Phe Met Leu Cys Ala Gly Arg Trp Thr Gly Gly Lys Ser Thr
        195                 200                 205

Cys Ser Gly Asp Ser Gly Gly Pro Leu Val Cys Asn Gly Val Leu Gln
    210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
                245                 250                 255

Ile Val Ala Asn Pro
            260


<210> SEQ ID NO 45
<211> LENGTH: 1464
<212> TYPE: DNA
<213> ORGANISM: Homo sapiens

<400> SEQUENCE: 45

agccccaagc ttaccacctg cacccggaga gctgtgtcac catgtgggtc ccggttgtct      60

tcctcaccct gtccgtgacg tggattggtg ctgcacccct catcctgtct cggattgtgg     120

gaggctggga gtgcgagaag cattcccaac cctggcaggt gcttgtggcc tctcgtggca     180

gggcagtctg cggcggtgtt ctggtgcacc cccagtgggt cctcacagct gcccactgca     240

tcaggaacaa aagcgtgatc ttgctgggtc ggcacagcct gtttcatcct gaagacacag     300

gccaggtatt tcaggtcagc cacagcttcc cacacccgct ctacgatatg agcctcctga     360

agaatcgatt cctcaggcca ggtgatgact ccagccacga cctcatgctg ctccgcctgt     420

cagagcctgc cgagctcacg gatgctgtga aggtcatgga cctgcccacc caggagccag     480

cactggggac cacctgctac gcctcaggct ggggcagcat tgaaccagag gagttcttga     540

ccccaaagaa acttcagtgt gtggacctcc atgttatttc caatgacgtg tgtgcgcaag     600

ttcaccctca gaaggtgacc aagttcatgc tgtgtgctgg acgctggaca gggggcaaaa     660

gcacctgctc gggtgattct gggggcccac ttgtctgtaa tggtgtgctt caaggtatca     720

cgtcatgggg cagtgaacca tgtgccctgc ccgaaaggcc ttccctgtac accaaggtgg     780

tgcattaccg gaagtggatc aaggacacca tcgtggccaa cccctgagca cccctatcaa     840

ccccctattg tagtaaactt ggaaccttgg aaatgaccag gccaagactc aagcctcccc     900

agttctactg acctttgtcc ttaggtgtga ggtccagggt tgctaggaaa agaaatcagc     960

agacacaggt gtagaccaga gtgtttctta aatggtgtaa ttttgtcctc tctgtgtcct    1020

ggggaatact ggccatgcct ggagacatat cactcaattt ctctgaggac acagatagga    1080

tggggtgtct gtgttatttg tggggtacag agatgaaaga ggggtgggat ccacactgag    1140

agagtggaga gtgacatgtg ctggacactg tccatgaagc actgagcaga agctggaggc    1200

acaacgcacc agacactcac agcaaggatg gagctgaaaa cataacccac tctgtcctgg    1260
```

aggcactggg aagcctagag aaggctgtga gccaaggagg gagggtcttc ctttggcatg 1320
ggatggggat gaagtaagga gagggactgg accccctgga agctgattca ctatgggggg 1380
aggtgtattg aagtcctcca gacaaccctc agatttgatg atttcctagt agaactcaca 1440
gaaataaaga gctgttatac tgtg 1464

<210> SEQ ID NO 46
<211> LENGTH: 8533
<212> TYPE: DNA
<213> ORGANISM: Homo sapiens

<400> SEQUENCE: 46
attcgcgtgg aggcgcgtcg cgcgcagcgg acgccgacag aatccccgag gcgcctggcg 60
cgggcgcggg cgcgaaggcg atccgggcgc caccccgcgg tcatcggtca ccggtcgctc 120
tcaggaacag cagcgcaacc tctgctccct gcctcgcctc ccgcgcgcct aggtgcctgc 180
gactttaatt aaagggccgt cccctcgccg aggctgcagc accgcccccc cggcttctcg 240
cgcctcaaaa tgagtagctc ccactctcgg gcgggccaga gcgcagcagg cgcggctccg 300
ggcggcggcg tcgacacgcg ggacgccgag atgccggcca ccgagaagga cctggcggag 360
gacgcgccgt ggaagaagat ccagcagaac actttcacgc gctggtgcaa cgagcacctg 420
aagtgcgtga gcaagcgcat cgccaacctg cagacggacc tgagcgacgg gctgcggctt 480
atcgcgctgt tggaggtgct cagccagaag aagatgcacc gcaagcacaa ccagcggccc 540
actttccgcc aaatgcagct tgagaacgtg tcggtggcgc tcgagttcct ggaccgcgag 600
agcatcaaac tggtgtccat cgacagcaag gccatcgtgg acgggaacct gaagctgatc 660
ctgggcctca tctggaccct gatcctgcac tactccatct ccatgcccat gtgggacgag 720
gaggaggatg aggaggccaa gaagcagacc cccaagcaga ggctcctggg ctggatccag 780
aacaagctgc cgcagctgcc catcaccaac ttcagccggg actggcagag cggccgggcc 840
ctgggcgccc tggtggacag ctgtgccccg ggcctgtgtc ctgactggga ctcttgggac 900
gccagcaagc ccgttaccaa tgcgcgagag gccatgcagc aggcggatga ctggctgggc 960
atcccccagg tgatcacccc cgaggagatt gtggacccca acgtggacga gcactctgtc 1020
atgacctacc tgtcccagtt ccccaaggcc aagctgaagc caggggctcc cttgcggccc 1080
aaactgaacc cgaagaaagc ccgtgcctac gggccaggca tcgagcccac aggcaacatg 1140
gtgaagaagc gggcagagtt cactgtggag accagaagtg ctggccaggg agaggtgctg 1200
gtgtacgtgg aggacccggc cggacaccag gaggaggcaa aagtgaccgc caataacgac 1260
aagaaccgca ccttctccgt ctggtacgtc cccgaggtga cggggactca taaggttact 1320
gtgctctttg ctggccagca catcgccaag agccccttcg aggtgtacgt ggataagtca 1380
cagggtgacg ccagcaaagt gacagcccaa ggtcccggcc tggagcccag tggcaacatc 1440
gccaacaaga ccacctactt tgagatcttt acggcaggag ctggcacggg cgaggtcgag 1500
gttgtgatcc aggaccccat gggacagaag ggcacggtag agcctcagct ggaggcccgg 1560
ggcgacagca cataccgctg cagctaccag cccaccatgg agggcgtcca caccgtgcac 1620
gtcacgtttg ccggcgtgcc catccctcgc agcccctaca ctgtcactgt tggccaagcc 1680
tgtaacccga gtgcctgccg ggcggttggc cggggcctcc agcccaaggg tgtgcgggtg 1740
aaggagacag ctgacttcaa ggtgtacaca aagggcgctg gcagtgggga gctgaaggtc 1800
accgtgaagg gccccaaggg agaggagcgc gtgaagcaga aggacctggg ggatggcgtg 1860

-continued

```
tatggcttcg agtattaccc catggtccct ggaacctata tcgtcaccat cacgtggggt   1920
ggtcagaaca tcgggcgcag tcccttcgaa gtgaaggtgg gcaccgagtg tggcaatcag   1980
aaggtacggg cctggggccc tgggctggag ggcggcgtcg ttggcaagtc agcagacttt   2040
gtggtggagg ctatcgggga cgacgtgggc acgctgggct tctcggtgga agggccatcg   2100
caggctaaga tcgaatgtga cgacaagggc gacggctcct gtgatgtgcg ctactggccg   2160
caggaggctg gcgagtatgc cgttcacgtg ctgtgcaaca gcgaagacat ccgcctcagc   2220
cccttcatgg ctgacatccg tgacgcgccc caggacttcc acccagacag ggtgaaggca   2280
cgtgggcctg gattggagaa gacaggtgtg gccgtcaaca agccagcaga gttcacagtg   2340
gatgccaagc acggtggcaa ggccccactt cgggtccaag tccaggacaa tgaaggctgc   2400
cctgtggagg cgttggtcaa ggacaacggc aatggcactt acagctgctc ctacgtgccc   2460
aggaagccgg tgaagcacac agccatggtg tcctggggag gcgtcagcat ccccaacagc   2520
cccttcaggg tgaatgtggg agctggcagc caccccaaca aggtcaaagt atacggcccc   2580
ggagtagcca agacagggct caaggcccac gagcccacct acttcactgt ggactgcgcc   2640
gaggctggcc agggggacgt cagcatcggc atcaagtgtg cccctggagt ggtaggcccc   2700
gccgaagctg acatcgactt cgacatcatc cgcaatgaca atgacacctt cacggtcaag   2760
tacacgcccc ggggggctgg cagctacacc attatggtcc tctttgctga ccaggccacg   2820
cccaccagcc ccatccgagt caaggtggag ccctctcatg acgccagtaa ggtgaaggcc   2880
gagggccctg gcctcagtcg cactggtgtc gagcttggca agcccaccca cttcacagta   2940
aatgccaaag ctgctggcaa aggcaagctg gacgtccagt tctcaggact caccaagggg   3000
gatgcagtgc gagatgtgga catcatcgac caccatgaca acacctacac agtcaagtac   3060
acgcctgtcc agcagggtcc agtaggcgtc aatgtcactt atggaggggga tcccatccct   3120
aagagccctt tctcagtggc agtatctcca agcctggacc tcagcaagat caaggtgtct   3180
ggcctgggag agaaggtgga cgttggcaaa gaccaggagt tcacagtcaa atcaaagggt   3240
gctggtggtc aaggcaaagt ggcatccaag attgtgggcc cctcgggtgc agcggtgccc   3300
tgcaaggtgg agccaggcct gggggctgac aacagtgtgg tgcgcttcct gccccgtgag   3360
gaagggccct atgaggtgga ggtgacctat gacggcgtgc ccgtgcctgg cagcccccttt   3420
cctctggaag ctgtggcccc caccaagcct agcaaggtga aggcgtttgg gccggggctg   3480
cagggaggca gtgcgggctc cccgcccgc ttcaccatcg acaccaaggg cgccggcaca   3540
ggtggcctgg gcctgacggt ggagggcccc tgtgaggcgc agctcgagtg cttggacaat   3600
ggggatggca catgttccgt gtcctacgtg cccaccgagc ccggggacta caacatcaac   3660
atcctcttcg ctgacaccca catccctggc tccccattca aggcccacgt ggttccctgc   3720
tttgacgcat ccaaagtcaa gtgctcaggc cccgggctgg agcgggccac cgctggggag   3780
gtgggccaat tccaagtgga ctgctcgagc gcgggcagcg cggagctgac cattgagatc   3840
tgctcggagg cggggcttcc ggccgaggtg tacatccagg accacggtga tggcacgcac   3900
accattacct acattcccct ctgccccggg gcctacaccg tcaccatcaa gtacggcggc   3960
cagcccgtgc ccaacttccc cagcaagctg caggtggaac ctgcggtgga cacttccggt   4020
gtccagtgct atgggcctgg tattgagggc cagggtgtct tccgtgaggc caccactgag   4080
ttcagtgtgg acgcccgggc tctgacacag accggagggc cgcacgtcaa ggcccgtgtg   4140
gccaacccct caggcaacct gacggagacc tacgttcagg accgtggcga tggcatgtac   4200
aaagtggagt acacgcctta cgaggaggga ctgcactccg tggacgtgac ctatgacggc   4260
```

agtcccgtgc ccagcagccc cttccaggtg cccgtgaccg agggctgcga cccctcccgg 4320
gtgcgtgtcc acgggccagg catccaaagt ggcaccacca acaagcccaa caagttcact 4380
gtggagacca ggggagctgg cacgggcggc ctgggcctgg ctgtagaggg cccctccgag 4440
gccaagatgt cctgcatgga taacaaggac ggcagctgct cggtcgagta catcccttat 4500
gaggctggca cctacagcct caacgtcacc tatggtggcc atcaagtgcc aggcagtcct 4560
ttcaaggtcc ctgtgcatga tgtgacagat gcgtccaagg tcaagtgctc tgggcccggc 4620
ctgagcccag gcatggttcg tgccaacctc cctcagtcct tccaggtgga cacaagcaag 4680
gctggtgtgg ccccattgca ggtcaaagtg caagggccca aaggcctggt ggagccagtg 4740
gacgtggtag acaacgctga tggcacccag accgtcaatt atgtgcccag ccgagaaggg 4800
ccctacagca tctcagtact gtatggagat gaagaggtac cccggagccc cttcaaggtc 4860
aaggtgctgc ctactcatga tgccagcaag gtgaaggcca gtggccccgg gctcaacacc 4920
actggcgtgc ctgccagcct gcccgtggag ttcaccatcg atgcaaagga cgccggggag 4980
ggcctgctgg ctgtccagat cacggatccc gaaggcaagc cgaagaagac acacatccaa 5040
gacaaccatg acggcacgta tacagtggcc tacgtgccag acgtgacagg tcgctacacc 5100
atcctcatca agtacggtgg tgacgagatc cccttctccc cgtaccgcgt gcgtgccgtg 5160
cccaccgggg acgccagcaa gtgcactgtc acaggtgctg gcatcggccc caccattcag 5220
attggggagg agacggtgat cactgtggac actaaggcgg caggcaaagg caaagtgacg 5280
tgcaccgtgt gcacgcctga tggctcagag gtggatgtgg acgtggtgga gaatgaggac 5340
ggcactttcg acatcttcta cacggccccc cagccgggca aatacgtcat ctgtgtgcgc 5400
tttggtggcg agcacgtgcc caacagcccc ttccaagtga cggctctggc tggggaccag 5460
ccctcggtgc agcccccctct acggtctcag cagctggccc cacagtacac ctacgcccag 5520
ggcggccagc agacttgggc cccggagagg cccctggtgg gtgtcaatgg gctggatgtg 5580
accagcctga ggccctttga ccttgtcatc cccttcacca tcaagaaggg cgagatcaca 5640
ggggaggttc ggatgccctc aggcaaggtg gcgcagccca ccatcactga caacaaagac 5700
ggcaccgtga ccgtgcggta tgcacccagc gaggctggcc tgcacgagat ggacatccgc 5760
tatgacaaca tgcacatccc aggaagcccc ttgcagttct atgtggatta cgtcaactgt 5820
ggccatgtca ctgcctatgg gcctggcctc acccatggag tagtgaacaa gcctgccacc 5880
ttcaccgtca acaccaagga tgcaggagag gggggcctgt ctctggccat tgagggcccg 5940
tccaaagcag aaatcagctg cactgacaac caggatggga catgcagcgt gtcctacctg 6000
cctgtgctgc cgggggacta cagcattcta gtcaagtaca atgaacagca cgtcccaggc 6060
agccccttca ctgctcgggt cacaggtgac gactccatgc gtatgtccca cctaaaggtc 6120
ggctctgctg ccgacatccc catcaacatc tcagagacgg atctcagcct gctgacggcc 6180
actgtggtcc cgccctcggg ccgggaggag ccctgtttgc tgaagcggct gcgtaatggc 6240
cacgtgggga tttcattcgt gcccaaggag acgggggagc acctggtgca tgtgaagaaa 6300
aatggccagc acgtggccag cagccccatc ccggtggtga tcagccagtc ggaaattggg 6360
gatgccagtc gtgttcgggt ctctggtcag ggccttcacg aaggccacac ctttgagcct 6420
gcagagttta tcattgatac ccgcgatgca ggctatggtg ggctcagcct gtccattgag 6480
ggccccagca aggtggacat caacacagag gacctggagg acgggacgtg cagggtcacc 6540
tactgcccca cagagccagg caactacatc atcaacatca agtttgccga ccagcacgtg 6600

```
cctggcagcc ccttctctgt gaaggtgaca ggcgagggcc gggtgaaaga gagcatcacc   6660
cgcaggcgtc gggctccttc agtggccaac gttggtagtc attgtgacct cagcctgaaa   6720
atccctgaaa ttagcatcca ggatatgaca gcccaggtga ccagcccatc gggcaagacc   6780
catgaggccg agatcgtgga aggggagaac cacacctact gcatccgctt tgttcccgct   6840
gagatgggca cacacacagt cagcgtgaag tacaagggcc agcacgtgcc tgggagcccc   6900
ttccagttca ccgtggggcc cctaggggaa gggggagccc acaaggtccg agctgggggc   6960
cctggcctgg agagagctga agctggagtg ccagccgaat tcagtatctg gacccgggaa   7020
gctggtgctg gaggcctggc cattgctgtc gagggcccca gcaaggctga gatctctttt   7080
gaggaccgca aggacggctc ctgtggtgtg gcttatgtgg tccaggagcc aggtgactac   7140
gaagtctcag tcaagttcaa cgaggaacac attcccgaca gccccttcgt ggtgcctgtg   7200
gcttctccgt ctggcgacgc ccgccgcctc actgtttcta gccttcagga gtcagggcta   7260
aaggtcaacc agccagcctc ttttgcagtc agcctgaacg gggccaaggg ggcgatcgat   7320
gccaaggtgc acagcccctc aggagccctg gaggagtgct atgtcacaga aattgaccaa   7380
gataagtatg ctgtgcgctt catccctcgg gagaatggcg tttacctgat tgacgtcaag   7440
ttcaacggca cccacatccc tggaagcccc ttcaagatcc gagttgggga gcctgggcat   7500
ggaggggacc caggcttggt gtctgcttac ggagcaggtc tggaaggcgg tgtcacaggg   7560
aacccagctg agttcgtcgt gaacacgagc aatgcgggag ctggtgccct gtcggtgacc   7620
attgacggcc cctccaaggt gaagatggat tgccaggagt gccctgaggg ctaccgcgtc   7680
acctataccc ccatggcacc tggcagctac ctcatctcca tcaagtacgg cggcccctac   7740
cacattgggg gcagcccctt caaggccaaa gtcacaggcc cccgtctcgt cagcaaccac   7800
agcctccacg agacatcatc agtgtttgta gactctctga ccaaggccac ctgtgccccc   7860
cagcatgggg ccccgggtcc tggcctgct  gacgccagca aggtggtggc caagggcctg   7920
gggctgagca aggcctacgt aggccagaag agcagcttca cagtagactg cagcaaagca   7980
ggcaacaaca tgctgctggt gggggttcat ggcccaagga ccccctgcga ggagatcctg   8040
gtgaagcacg tgggcagccg gctctacagc gtgtcctacc tgctcaagga caagggggag   8100
tacacactgg tggtcaaatg gggggacgag cacatcccag gcagccccta ccgcgttgtg   8160
gtgccctgag tctggggccc gtgccagccg gcagccccca agcctgcccc gctacccaag   8220
cagccccgcc ctcttcccct caaccccggc ccaggccgcc ctggccgccc gcctgtcact   8280
gcagccgccc ctgccctgtg ccgtgctgcg ctcacctgcc tccccagcca gccgctgacc   8340
tctcggcttt cacttgggca gagggagcca tttggtggcg ctgcttgtct tctttggttc   8400
tgggaggggt gagggatggg ggtcctgtac acaaccaccc actagttctc ttctccagcc   8460
aagaggaata aagttttgct tccattaaaa aaaaaaaaaa aaaaaaaaaa aaaaaaaaaa   8520
aaaaaaaaaa aaa                                                      8533
```

<210> SEQ ID NO 47
<211> LENGTH: 2639
<212> TYPE: PRT
<213> ORGANISM: Homo sapiens

<400> SEQUENCE: 47

```
Met Ser Ser Ser His Ser Arg Ala Gly Gln Ser Ala Ala Gly Ala Ala
1               5                   10                  15

Pro Gly Gly Gly Val Asp Thr Arg Asp Ala Glu Met Pro Ala Thr Glu
            20                  25                  30
```

-continued

```
Lys Asp Leu Ala Glu Asp Ala Pro Trp Lys Lys Ile Gln Gln Asn Thr
        35                  40                  45

Phe Thr Arg Trp Cys Asn Glu His Leu Lys Cys Val Ser Lys Arg Ile
    50                  55                  60

Ala Asn Leu Gln Thr Asp Leu Ser Asp Gly Leu Arg Leu Ile Ala Leu
65                  70                  75                  80

Leu Glu Val Leu Ser Gln Lys Lys Met His Arg Lys His Asn Gln Arg
                85                  90                  95

Pro Thr Phe Arg Gln Met Gln Leu Glu Asn Val Ser Val Ala Leu Glu
            100                 105                 110

Phe Leu Asp Arg Glu Ser Ile Lys Leu Val Ser Ile Asp Ser Lys Ala
        115                 120                 125

Ile Val Asp Gly Asn Leu Lys Leu Ile Leu Gly Leu Ile Trp Thr Leu
    130                 135                 140

Ile Leu His Tyr Ser Ile Ser Met Pro Met Trp Asp Glu Glu Glu Asp
145                 150                 155                 160

Glu Glu Ala Lys Lys Gln Thr Pro Lys Gln Arg Leu Leu Gly Trp Ile
                165                 170                 175

Gln Asn Lys Leu Pro Gln Leu Pro Ile Thr Asn Phe Ser Arg Asp Trp
            180                 185                 190

Gln Ser Gly Arg Ala Leu Gly Ala Leu Val Asp Ser Cys Ala Pro Gly
        195                 200                 205

Leu Cys Pro Asp Trp Asp Ser Trp Asp Ala Ser Lys Pro Val Thr Asn
    210                 215                 220

Ala Arg Glu Ala Met Gln Gln Ala Asp Asp Trp Leu Gly Ile Pro Gln
225                 230                 235                 240

Val Ile Thr Pro Glu Glu Ile Val Asp Pro Asn Val Asp Glu His Ser
                245                 250                 255

Val Met Thr Tyr Leu Ser Gln Phe Pro Lys Ala Lys Leu Lys Pro Gly
            260                 265                 270

Ala Pro Leu Arg Pro Lys Leu Asn Pro Lys Lys Ala Arg Ala Tyr Gly
        275                 280                 285

Pro Gly Ile Glu Pro Thr Gly Asn Met Val Lys Lys Arg Ala Glu Phe
    290                 295                 300

Thr Val Glu Thr Arg Ser Ala Gly Gln Gly Glu Val Leu Val Tyr Val
305                 310                 315                 320

Glu Asp Pro Ala Gly His Gln Glu Glu Ala Lys Val Thr Ala Asn Asn
                325                 330                 335

Asp Lys Asn Arg Thr Phe Ser Val Trp Tyr Val Pro Glu Val Thr Gly
            340                 345                 350

Thr His Lys Val Thr Val Leu Phe Ala Gly Gln His Ile Ala Lys Ser
        355                 360                 365

Pro Phe Glu Val Tyr Val Asp Lys Ser Gln Gly Asp Ala Ser Lys Val
    370                 375                 380

Thr Ala Gln Gly Pro Gly Leu Glu Pro Ser Gly Asn Ile Ala Asn Lys
385                 390                 395                 400

Thr Thr Tyr Phe Glu Ile Phe Thr Ala Gly Ala Gly Thr Gly Glu Val
                405                 410                 415

Glu Val Val Ile Gln Asp Pro Met Gly Gln Lys Gly Thr Val Glu Pro
            420                 425                 430

Gln Leu Glu Ala Arg Gly Asp Ser Thr Tyr Arg Cys Ser Tyr Gln Pro
        435                 440                 445
```

Thr Met Glu Gly Val His Thr Val His Val Thr Phe Ala Gly Val Pro
450 455 460

Ile Pro Arg Ser Pro Tyr Thr Val Thr Val Gly Gln Ala Cys Asn Pro
465 470 475 480

Ser Ala Cys Arg Ala Val Gly Arg Gly Leu Gln Pro Lys Gly Val Arg
485 490 495

Val Lys Glu Thr Ala Asp Phe Lys Val Tyr Thr Lys Gly Ala Gly Ser
500 505 510

Gly Glu Leu Lys Val Thr Val Lys Gly Pro Lys Gly Glu Glu Arg Val
515 520 525

Lys Gln Lys Asp Leu Gly Asp Gly Val Tyr Gly Phe Glu Tyr Tyr Pro
530 535 540

Met Val Pro Gly Thr Tyr Ile Val Thr Ile Thr Trp Gly Gly Gln Asn
545 550 555 560

Ile Gly Arg Ser Pro Phe Glu Val Lys Val Gly Thr Glu Cys Gly Asn
565 570 575

Gln Lys Val Arg Ala Trp Gly Pro Gly Leu Glu Gly Gly Val Val Gly
580 585 590

Lys Ser Ala Asp Phe Val Val Glu Ala Ile Gly Asp Asp Val Gly Thr
595 600 605

Leu Gly Phe Ser Val Glu Gly Pro Ser Gln Ala Lys Ile Glu Cys Asp
610 615 620

Asp Lys Gly Asp Gly Ser Cys Asp Val Arg Tyr Trp Pro Gln Glu Ala
625 630 635 640

Gly Glu Tyr Ala Val His Val Leu Cys Asn Ser Glu Asp Ile Arg Leu
645 650 655

Ser Pro Phe Met Ala Asp Ile Arg Asp Ala Pro Gln Asp Phe His Pro
660 665 670

Asp Arg Val Lys Ala Arg Gly Pro Gly Leu Glu Lys Thr Gly Val Ala
675 680 685

Val Asn Lys Pro Ala Glu Phe Thr Val Asp Ala Lys His Gly Gly Lys
690 695 700

Ala Pro Leu Arg Val Gln Val Gln Asp Asn Glu Gly Cys Pro Val Glu
705 710 715 720

Ala Leu Val Lys Asp Asn Gly Asn Gly Thr Tyr Ser Cys Ser Tyr Val
725 730 735

Pro Arg Lys Pro Val Lys His Thr Ala Met Val Ser Trp Gly Gly Val
740 745 750

Ser Ile Pro Asn Ser Pro Phe Arg Val Asn Val Gly Ala Gly Ser His
755 760 765

Pro Asn Lys Val Lys Val Tyr Gly Pro Gly Val Ala Lys Thr Gly Leu
770 775 780

Lys Ala His Glu Pro Thr Tyr Phe Thr Val Asp Cys Ala Glu Ala Gly
785 790 795 800

Gln Gly Asp Val Ser Ile Gly Ile Lys Cys Ala Pro Gly Val Val Gly
805 810 815

Pro Ala Glu Ala Asp Ile Asp Phe Asp Ile Ile Arg Asn Asp Asn Asp
820 825 830

Thr Phe Thr Val Lys Tyr Thr Pro Arg Gly Ala Gly Ser Tyr Thr Ile
835 840 845

Met Val Leu Phe Ala Asp Gln Ala Thr Pro Thr Ser Pro Ile Arg Val
850 855 860

Lys Val Glu Pro Ser His Asp Ala Ser Lys Val Lys Ala Glu Gly Pro 865 870 875 880

Gly Leu Ser Arg Thr Gly Val Glu Leu Gly Lys Pro Thr His Phe Thr
885 890 895

Val Asn Ala Lys Ala Ala Gly Lys Gly Lys Leu Asp Val Gln Phe Ser
900 905 910

Gly Leu Thr Lys Gly Asp Ala Val Arg Asp Val Asp Ile Ile Asp His
915 920 925

His Asp Asn Thr Tyr Thr Val Lys Tyr Thr Pro Val Gln Gln Gly Pro
930 935 940

Val Gly Val Asn Val Thr Tyr Gly Gly Asp Pro Ile Pro Lys Ser Pro
945 950 955 960

Phe Ser Val Ala Val Ser Pro Ser Leu Asp Leu Ser Lys Ile Lys Val
965 970 975

Ser Gly Leu Gly Glu Lys Val Asp Val Gly Lys Asp Gln Glu Phe Thr
980 985 990

Val Lys Ser Lys Gly Ala Gly Gly Gln Gly Lys Val Ala Ser Lys Ile
995 1000 1005

Val Gly Pro Ser Gly Ala Ala Val Pro Cys Lys Val Glu Pro Gly
1010 1015 1020

Leu Gly Ala Asp Asn Ser Val Val Arg Phe Leu Pro Arg Glu Glu
1025 1030 1035

Gly Pro Tyr Glu Val Glu Val Thr Tyr Asp Gly Val Pro Val Pro
1040 1045 1050

Gly Ser Pro Phe Pro Leu Glu Ala Val Ala Pro Thr Lys Pro Ser
1055 1060 1065

Lys Val Lys Ala Phe Gly Pro Gly Leu Gln Gly Gly Ser Ala Gly
1070 1075 1080

Ser Pro Ala Arg Phe Thr Ile Asp Thr Lys Gly Ala Gly Thr Gly
1085 1090 1095

Gly Leu Gly Leu Thr Val Glu Gly Pro Cys Glu Ala Gln Leu Glu
1100 1105 1110

Cys Leu Asp Asn Gly Asp Gly Thr Cys Ser Val Ser Tyr Val Pro
1115 1120 1125

Thr Glu Pro Gly Asp Tyr Asn Ile Asn Ile Leu Phe Ala Asp Thr
1130 1135 1140

His Ile Pro Gly Ser Pro Phe Lys Ala His Val Val Pro Cys Phe
1145 1150 1155

Asp Ala Ser Lys Val Lys Cys Ser Gly Pro Gly Leu Glu Arg Ala
1160 1165 1170

Thr Ala Gly Glu Val Gly Gln Phe Gln Val Asp Cys Ser Ser Ala
1175 1180 1185

Gly Ser Ala Glu Leu Thr Ile Glu Ile Cys Ser Glu Ala Gly Leu
1190 1195 1200

Pro Ala Glu Val Tyr Ile Gln Asp His Gly Asp Gly Thr His Thr
1205 1210 1215

Ile Thr Tyr Ile Pro Leu Cys Pro Gly Ala Tyr Thr Val Thr Ile
1220 1225 1230

Lys Tyr Gly Gly Gln Pro Val Pro Asn Phe Pro Ser Lys Leu Gln
1235 1240 1245

Val Glu Pro Ala Val Asp Thr Ser Gly Val Gln Cys Tyr Gly Pro
1250 1255 1260

Gly Ile Glu Gly Gln Gly Val Phe Arg Glu Ala Thr Thr Glu Phe
1265 1270 1275

```
Ser Val  Asp Ala Arg Ala Leu  Thr Gln Thr Gly Gly  Pro His Val
    1280                 1285                 1290

Lys Ala  Arg Val Ala Asn Pro  Ser Gly Asn Leu Thr  Glu Thr Tyr
    1295                 1300                 1305

Val Gln  Asp Arg Gly Asp Gly  Met Tyr Lys Val Glu  Tyr Thr Pro
    1310                 1315                 1320

Tyr Glu  Glu Gly Leu His Ser  Val Asp Val Thr Tyr  Asp Gly Ser
    1325                 1330                 1335

Pro Val  Pro Ser Ser Pro Phe  Gln Val Pro Val Thr  Glu Gly Cys
    1340                 1345                 1350

Asp Pro  Ser Arg Val Arg Val  His Gly Pro Gly Ile  Gln Ser Gly
    1355                 1360                 1365

Thr Thr  Asn Lys Pro Asn Lys  Phe Thr Val Glu Thr  Arg Gly Ala
    1370                 1375                 1380

Gly Thr  Gly Gly Leu Gly Leu  Ala Val Glu Gly Pro  Ser Glu Ala
    1385                 1390                 1395

Lys Met  Ser Cys Met Asp Asn  Lys Asp Gly Ser Cys  Ser Val Glu
    1400                 1405                 1410

Tyr Ile  Pro Tyr Glu Ala Gly  Thr Tyr Ser Leu Asn  Val Thr Tyr
    1415                 1420                 1425

Gly Gly  His Gln Val Pro Gly  Ser Pro Phe Lys Val  Pro Val His
    1430                 1435                 1440

Asp Val  Thr Asp Ala Ser Lys  Val Lys Cys Ser Gly  Pro Gly Leu
    1445                 1450                 1455

Ser Pro  Gly Met Val Arg Ala  Asn Leu Pro Gln Ser  Phe Gln Val
    1460                 1465                 1470

Asp Thr  Ser Lys Ala Gly Val  Ala Pro Leu Gln Val  Lys Val Gln
    1475                 1480                 1485

Gly Pro  Lys Gly Leu Val Glu  Pro Val Asp Val Val  Asp Asn Ala
    1490                 1495                 1500

Asp Gly  Thr Gln Thr Val Asn  Tyr Val Pro Ser Arg  Glu Gly Pro
    1505                 1510                 1515

Tyr Ser  Ile Ser Val Leu Tyr  Gly Asp Glu Glu Val  Pro Arg Ser
    1520                 1525                 1530

Pro Phe  Lys Val Lys Val Leu  Pro Thr His Asp Ala  Ser Lys Val
    1535                 1540                 1545

Lys Ala  Ser Gly Pro Gly Leu  Asn Thr Thr Gly Val  Pro Ala Ser
    1550                 1555                 1560

Leu Pro  Val Glu Phe Thr Ile  Asp Ala Lys Asp Ala  Gly Glu Gly
    1565                 1570                 1575

Leu Leu  Ala Val Gln Ile Thr  Asp Pro Glu Gly Lys  Pro Lys Lys
    1580                 1585                 1590

Thr His  Ile Gln Asp Asn His  Asp Gly Thr Tyr Thr  Val Ala Tyr
    1595                 1600                 1605

Val Pro  Asp Val Thr Gly Arg  Tyr Thr Ile Leu Ile  Lys Tyr Gly
    1610                 1615                 1620

Gly Asp  Glu Ile Pro Phe Ser  Pro Tyr Arg Val Arg  Ala Val Pro
    1625                 1630                 1635

Thr Gly  Asp Ala Ser Lys Cys  Thr Val Thr Gly Ala  Gly Ile Gly
    1640                 1645                 1650

Pro Thr  Ile Gln Ile Gly Glu  Glu Thr Val Ile Thr  Val Asp Thr
    1655                 1660                 1665
```

```
Lys Ala Ala Gly Lys Gly Lys Val Thr Cys Thr Val Cys Thr Pro
    1670                1675                1680

Asp Gly Ser Glu Val Asp Val Asp Val Val Glu Asn Glu Asp Gly
    1685                1690                1695

Thr Phe Asp Ile Phe Tyr Thr Ala Pro Gln Pro Gly Lys Tyr Val
    1700                1705                1710

Ile Cys Val Arg Phe Gly Gly Glu His Val Pro Asn Ser Pro Phe
    1715                1720                1725

Gln Val Thr Ala Leu Ala Gly Asp Gln Pro Ser Val Gln Pro Pro
    1730                1735                1740

Leu Arg Ser Gln Gln Leu Ala Pro Gln Tyr Thr Tyr Ala Gln Gly
    1745                1750                1755

Gly Gln Gln Thr Trp Ala Pro Glu Arg Pro Leu Val Gly Val Asn
    1760                1765                1770

Gly Leu Asp Val Thr Ser Leu Arg Pro Phe Asp Leu Val Ile Pro
    1775                1780                1785

Phe Thr Ile Lys Lys Gly Glu Ile Thr Gly Glu Val Arg Met Pro
    1790                1795                1800

Ser Gly Lys Val Ala Gln Pro Thr Ile Thr Asp Asn Lys Asp Gly
    1805                1810                1815

Thr Val Thr Val Arg Tyr Ala Pro Ser Glu Ala Gly Leu His Glu
    1820                1825                1830

Met Asp Ile Arg Tyr Asp Asn Met His Ile Pro Gly Ser Pro Leu
    1835                1840                1845

Gln Phe Tyr Val Asp Tyr Val Asn Cys Gly His Val Thr Ala Tyr
    1850                1855                1860

Gly Pro Gly Leu Thr His Gly Val Val Asn Lys Pro Ala Thr Phe
    1865                1870                1875

Thr Val Asn Thr Lys Asp Ala Gly Glu Gly Gly Leu Ser Leu Ala
    1880                1885                1890

Ile Glu Gly Pro Ser Lys Ala Glu Ile Ser Cys Thr Asp Asn Gln
    1895                1900                1905

Asp Gly Thr Cys Ser Val Ser Tyr Leu Pro Val Leu Pro Gly Asp
    1910                1915                1920

Tyr Ser Ile Leu Val Lys Tyr Asn Glu Gln His Val Pro Gly Ser
    1925                1930                1935

Pro Phe Thr Ala Arg Val Thr Gly Asp Asp Ser Met Arg Met Ser
    1940                1945                1950

His Leu Lys Val Gly Ser Ala Ala Asp Ile Pro Ile Asn Ile Ser
    1955                1960                1965

Glu Thr Asp Leu Ser Leu Leu Thr Ala Thr Val Val Pro Pro Ser
    1970                1975                1980

Gly Arg Glu Glu Pro Cys Leu Leu Lys Arg Leu Arg Asn Gly His
    1985                1990                1995

Val Gly Ile Ser Phe Val Pro Lys Glu Thr Gly Glu His Leu Val
    2000                2005                2010

His Val Lys Lys Asn Gly Gln His Val Ala Ser Ser Pro Ile Pro
    2015                2020                2025

Val Val Ile Ser Gln Ser Glu Ile Gly Asp Ala Ser Arg Val Arg
    2030                2035                2040

Val Ser Gly Gln Gly Leu His Glu Gly His Thr Phe Glu Pro Ala
    2045                2050                2055

Glu Phe Ile Ile Asp Thr Arg Asp Ala Gly Tyr Gly Gly Leu Ser
```

```
    2060                2065                2070

Leu Ser  Ile Glu Gly Pro Ser  Lys Val Asp Ile Asn  Thr Glu Asp
    2075                2080                2085

Leu Glu  Asp Gly Thr Cys Arg  Val Thr Tyr Cys Pro  Thr Glu Pro
    2090                2095                2100

Gly Asn  Tyr Ile Ile Asn Ile  Lys Phe Ala Asp Gln  His Val Pro
    2105                2110                2115

Gly Ser  Pro Phe Ser Val Lys  Val Thr Gly Glu Gly  Arg Val Lys
    2120                2125                2130

Glu Ser  Ile Thr Arg Arg Arg  Arg Ala Pro Ser Val  Ala Asn Val
    2135                2140                2145

Gly Ser  His Cys Asp Leu Ser  Leu Lys Ile Pro Glu  Ile Ser Ile
    2150                2155                2160

Gln Asp  Met Thr Ala Gln Val  Thr Ser Pro Ser Gly  Lys Thr His
    2165                2170                2175

Glu Ala  Glu Ile Val Glu Gly  Glu Asn His Thr Tyr  Cys Ile Arg
    2180                2185                2190

Phe Val  Pro Ala Glu Met Gly  Thr His Thr Val Ser  Val Lys Tyr
    2195                2200                2205

Lys Gly  Gln His Val Pro Gly  Ser Pro Phe Gln Phe  Thr Val Gly
    2210                2215                2220

Pro Leu  Gly Glu Gly Gly Ala  His Lys Val Arg Ala  Gly Gly Pro
    2225                2230                2235

Gly Leu  Glu Arg Ala Glu Ala  Gly Val Pro Ala Glu  Phe Ser Ile
    2240                2245                2250

Trp Thr  Arg Glu Ala Gly Ala  Gly Gly Leu Ala Ile  Ala Val Glu
    2255                2260                2265

Gly Pro  Ser Lys Ala Glu Ile  Ser Phe Glu Asp Arg  Lys Asp Gly
    2270                2275                2280

Ser Cys  Gly Val Ala Tyr Val  Val Gln Glu Pro Gly  Asp Tyr Glu
    2285                2290                2295

Val Ser  Val Lys Phe Asn Glu  Glu His Ile Pro Asp  Ser Pro Phe
    2300                2305                2310

Val Val  Pro Val Ala Ser Pro  Ser Gly Asp Ala Arg  Arg Leu Thr
    2315                2320                2325

Val Ser  Ser Leu Gln Glu Ser  Gly Leu Lys Val Asn  Gln Pro Ala
    2330                2335                2340

Ser Phe  Ala Val Ser Leu Asn  Gly Ala Lys Gly Ala  Ile Asp Ala
    2345                2350                2355

Lys Val  His Ser Pro Ser Gly  Ala Leu Glu Glu Cys  Tyr Val Thr
    2360                2365                2370

Glu Ile  Asp Gln Asp Lys Tyr  Ala Val Arg Phe Ile  Pro Arg Glu
    2375                2380                2385

Asn Gly  Val Tyr Leu Ile Asp  Val Lys Phe Asn Gly  Thr His Ile
    2390                2395                2400

Pro Gly  Ser Pro Phe Lys Ile  Arg Val Gly Glu Pro  Gly His Gly
    2405                2410                2415

Gly Asp  Pro Gly Leu Val Ser  Ala Tyr Gly Ala Gly  Leu Glu Gly
    2420                2425                2430

Gly Val  Thr Gly Asn Pro Ala  Glu Phe Val Val Asn  Thr Ser Asn
    2435                2440                2445

Ala Gly  Ala Gly Ala Leu Ser  Val Thr Ile Asp Gly  Pro Ser Lys
    2450                2455                2460
```

Val Lys Met Asp Cys Gln Glu Cys Pro Glu Gly Tyr Arg Val Thr
2465 2470 2475

Tyr Thr Pro Met Ala Pro Gly Ser Tyr Leu Ile Ser Ile Lys Tyr
2480 2485 2490

Gly Gly Pro Tyr His Ile Gly Gly Ser Pro Phe Lys Ala Lys Val
2495 2500 2505

Thr Gly Pro Arg Leu Val Ser Asn His Ser Leu His Glu Thr Ser
2510 2515 2520

Ser Val Phe Val Asp Ser Leu Thr Lys Ala Thr Cys Ala Pro Gln
2525 2530 2535

His Gly Ala Pro Gly Pro Gly Pro Ala Asp Ala Ser Lys Val Val
2540 2545 2550

Ala Lys Gly Leu Gly Leu Ser Lys Ala Tyr Val Gly Gln Lys Ser
2555 2560 2565

Ser Phe Thr Val Asp Cys Ser Lys Ala Gly Asn Asn Met Leu Leu
2570 2575 2580

Val Gly Val His Gly Pro Arg Thr Pro Cys Glu Glu Ile Leu Val
2585 2590 2595

Lys His Val Gly Ser Arg Leu Tyr Ser Val Ser Tyr Leu Leu Lys
2600 2605 2610

Asp Lys Gly Glu Tyr Thr Leu Val Val Lys Trp Gly Asp Glu His
2615 2620 2625

Ile Pro Gly Ser Pro Tyr Arg Val Val Val Pro
2630 2635

<210> SEQ ID NO 48
<211> LENGTH: 8557
<212> TYPE: DNA
<213> ORGANISM: Homo sapiens

<400> SEQUENCE: 48
attcgcgtgg aggcgcgtcg cgcgcagcgg acgccgacag aatccccgag gcgcctggcg 60
cgggcgcggg cgcgaaggcg atccgggcgc caccccgcgg tcatcggtca ccggtcgctc 120
tcaggaacag cagcgcaacc tctgctccct gcctcgcctc ccgcgcgcct aggtgcctgc 180
gactttaatt aaagggccgt cccctcgccg aggctgcagc accgcccccc cggcttctcg 240
cgcctcaaaa tgagtagctc ccactctcgg gcgggccaga gcgcagcagg cgcggctccg 300
ggcggcggcg tcgacacgcg ggacgccgag atgccggcca ccgagaagga cctggcggag 360
gacgcgccgt ggaagaagat ccagcagaac actttcacgc gctggtgcaa cgagcacctg 420
aagtgcgtga gcaagcgcat cgccaacctg cagacggacc tgagcgacgg gctgcggctt 480
atcgcgctgt tggaggtgct cagccagaag aagatgcacc gcaagcacaa ccagcggccc 540
actttccgcc aaatgcagct tgagaacgtg tcggtggcgc tcgagttcct ggaccgcgag 600
agcatcaaac tggtgtccat cgacagcaag gccatcgtgg acgggaacct gaagctgatc 660
ctgggcctca tctggaccct gatcctgcac tactccatct ccatgcccat gtgggacgag 720
gaggaggatg aggaggccaa gaagcagacc cccaagcaga ggctcctggg ctggatccag 780
aacaagctgc cgcagctgcc catcaccaac ttcagccggg actggcagag cggccgggcc 840
ctgggcgccc tggtggacag ctgtgccccg ggcctgtgtc ctgactggga ctcttgggac 900
gccagcaagc ccgttaccaa tgcgcgagag gccatgcagc aggcggatga ctggctgggc 960
atcccccagg tgatcacccc cgaggagatt gtggacccca acgtggacga gcactctgtc 1020

```
atgacctacc tgtcccagtt ccccaaggcc aagctgaagc caggggctcc cttgcggccc   1080
aaactgaacc cgaagaaagc ccgtgcctac gggccaggca tcgagcccac aggcaacatg   1140
gtgaagaagc gggcagagtt cactgtggag accagaagtg ctggccaggg agaggtgctg   1200
gtgtacgtgg aggacccggc cggacaccag gaggaggcaa aagtgaccgc caataacgac   1260
aagaaccgca ccttctccgt ctggtacgtc cccgaggtga cggggactca taaggttact   1320
gtgctctttg ctggccagca catcgccaag agccccttcg aggtgtacgt ggataagtca   1380
cagggtgacg ccagcaaagt gacagcccaa ggtcccggcc tggagcccag tggcaacatc   1440
gccaacaaga ccacctactt tgagatcttt acggcaggag ctggcacggg cgaggtcgag   1500
gttgtgatcc aggaccccat gggacagaag ggcacggtag agcctcagct ggaggcccgg   1560
ggcgacagca cataccgctg cagctaccag cccaccatgg agggcgtcca caccgtgcac   1620
gtcacgtttg ccggcgtgcc catccctcgc agcccctaca ctgtcactgt tggccaagcc   1680
tgtaacccga gtgcctgccg ggcggttggc cggggcctcc agcccaaggg tgtgcgggtg   1740
aaggagacag ctgacttcaa ggtgtacaca aagggcgctg gcagtgggga gctgaaggtc   1800
accgtgaagg gccccaaggg agaggagcgc gtgaagcaga aggacctggg ggatggcgtg   1860
tatggcttcg agtattaccc catggtccct ggaacctata tcgtcaccat cacgtggggt   1920
ggtcagaaca tcgggcgcag tcccttcgaa gtgaaggtgg gcaccgagtg tggcaatcag   1980
aaggtacggg cctggggccc tgggctggag ggcggcgtcg ttggcaagtc agcagacttt   2040
gtggtggagg ctatcgggga cgacgtgggc acgctgggct tctcggtgga agggccatcg   2100
caggctaaga tcgaatgtga cgacaagggc gacggctcct gtgatgtgcg ctactggccg   2160
caggaggctg gcgagtatgc cgttcacgtg ctgtgcaaca gcgaagacat ccgcctcagc   2220
cccttcatgg ctgacatccg tgacgcgccc caggacttcc acccagacag ggtgaaggca   2280
cgtgggcctg gattggagaa gacaggtgtg gccgtcaaca agccagcaga gttcacagtg   2340
gatgccaagc acggtggcaa ggccccactt cgggtccaag tccaggacaa tgaaggctgc   2400
cctgtggagg cgttggtcaa ggacaacggc aatggcactt acagctgctc ctacgtgccc   2460
aggaagccgg tgaagcacac agccatggtg tcctggggag gcgtcagcat ccccaacagc   2520
cccttcaggg tgaatgtggg agctggcagc caccccaaca aggtcaaagt atacggcccc   2580
ggagtagcca agacagggct caaggcccac gagcccacct acttcactgt ggactgcgcc   2640
gaggctggcc agggggacgt cagcatcggc atcaagtgtg cccctggagt ggtaggcccc   2700
gccgaagctg acatcgactt cgacatcatc cgcaatgaca atgacacctt cacggtcaag   2760
tacacgcccc ggggggctgg cagctacacc attatggtcc tctttgctga ccaggccacg   2820
cccaccagcc ccatccgagt caaggtggag ccctctcatg acgccagtaa ggtgaaggcc   2880
gagggccctg gcctcagtcg cactggtgtc gagcttggca agcccaccca cttcacagta   2940
aatgccaaag ctgctggcaa aggcaagctg gacgtccagt tctcaggact caccaagggg   3000
gatgcagtgc gagatgtgga catcatcgac caccatgaca acacctacac agtcaagtac   3060
acgcctgtcc agcagggtcc agtaggcgtc aatgtcactt atggagggga tcccatccct   3120
aagagccctt tctcagtggc agtatctcca agcctggacc tcagcaagat caaggtgtct   3180
ggcctgggag agaaggtgga cgttggcaaa gaccaggagt tcacagtcaa atcaaagggt   3240
gctggtggtc aaggcaaagt ggcatccaag attgtgggcc cctcgggtgc agcggtgccc   3300
tgcaaggtgg agccaggcct gggggctgac aacagtgtgg tgcgcttcct gccccgtgag   3360
gaagggccct atgaggtgga ggtgacctat gacggcgtgc ccgtgcctgg cagccccttt   3420
```

cctctggaag ctgtggcccc caccaagcct agcaaggtga aggcgtttgg gccggggctg 3480
cagggaggca gtgcgggctc cccgcccgc ttcaccatcg acaccaaggg cgccggcaca 3540
ggtggcctgg gcctgacggt ggagggcccc tgtgaggcgc agctcgagtg cttggacaat 3600
ggggatggca catgttccgt gtcctacgtg cccaccgagc ccggggacta caacatcaac 3660
atcctcttcg ctgacaccca catccctggc tccccattca aggcccacgt ggttccctgc 3720
tttgacgcat ccaaagtcaa gtgctcaggc cccgggctgg agcgggccac cgctggggag 3780
gtgggccaat tccaagtgga ctgctcgagc gcgggcagcg cggagctgac cattgagatc 3840
tgctcggagg cggggcttcc ggccgaggtg tacatccagg accacggtga tggcacgcac 3900
accattacct acattcccct ctgccccggg gcctacaccg tcaccatcaa gtacggcggc 3960
cagcccgtgc ccaacttccc cagcaagctg caggtggaac ctgcggtgga cacttccggt 4020
gtccagtgct atgggcctgg tattgagggc cagggtgtct tccgtgaggc caccactgag 4080
ttcagtgtgg acgcccgggc tctgacacag accggagggc cgcacgtcaa ggcccgtgtg 4140
gccaacccct caggcaacct gacggagacc tacgttcagg accgtggcga tggcatgtac 4200
aaagtggagt acacgcctta cgaggaggga ctgcactccg tggacgtgac ctatgacggc 4260
agtcccgtgc ccagcagccc cttccaggtg cccgtgaccg agggctgcga cccctcccgg 4320
gtgcgtgtcc acgggccagg catccaaagt ggcaccacca acaagcccaa caagttcact 4380
gtggagacca ggggagctgg cacgggcggc ctgggcctgg ctgtagaggg cccctccgag 4440
gccaagatgt cctgcatgga taacaaggac ggcagctgct cggtcgagta catcccttat 4500
gaggctggca cctacagcct caacgtcacc tatggtggcc atcaagtgcc aggcagtcct 4560
ttcaaggtcc ctgtgcatga tgtgacagat gcgtccaagg tcaagtgctc tgggcccggc 4620
ctgagcccag gcatggttcg tgccaacctc cctcagtcct tccaggtgga cacaagcaag 4680
gctggtgtgg ccccattgca ggtcaaagtg caagggccca aaggcctggt ggagccagtg 4740
gacgtggtag acaacgctga tggcacccag accgtcaatt atgtgcccag ccgagaaggg 4800
ccctacagca tctcagtact gtatggagat gaagaggtac cccggagccc cttcaaggtc 4860
aaggtgctgc ctactcatga tgccagcaag gtgaaggcca gtggccccgg gctcaacacc 4920
actggcgtgc ctgccagcct gcccgtggag ttcaccatcg atgcaaagga cgccggggag 4980
ggcctgctgg ctgtccagat cacggatccc gaaggcaagc cgaagaagac acacatccaa 5040
gacaaccatg acggcacgta tacagtggcc tacgtgccag acgtgacagg tcgctacacc 5100
atcctcatca agtacggtgg tgacgagatc cccttctccc cgtaccgcgt gcgtgccgtg 5160
cccaccgggg acgccagcaa gtgcactgtc acagtgtcaa tcggaggtca cgggctaggt 5220
gctggcatcg gccccaccat tcagattggg gaggagacgg tgatcactgt ggacactaag 5280
gcggcaggca aaggcaaagt gacgtgcacc gtgtgcacgc ctgatggctc agaggtggat 5340
gtggacgtgg tggagaatga ggacggcact ttcgacatct tctacacggc cccccagccg 5400
ggcaaatacg tcatctgtgt gcgctttggt ggcgagcacg tgcccaacag cccttccaa 5460 gtgacggctc tggctgggga ccagccctcg gtgcagcccc ctctacggtc tcagcagctg 5520
gccccacagt acacctacgc ccagggcggc cagcagactt gggccccgga gaggcccctg 5580
gtgggtgtca atgggctgga tgtgaccagc ctgaggccct ttgaccttgt catcccttc 5640 accatcaaga agggcgagat cacaggggag gttcggatgc cctcaggcaa ggtggcgcag 5700
cccaccatca ctgacaacaa agacggcacc gtgaccgtgc ggtatgcacc cagcgaggct 5760

-continued

```
ggcctgcacg agatggacat ccgctatgac aacatgcaca tcccaggaag cccccttgcag   5820
ttctatgtgg attacgtcaa ctgtggccat gtcactgcct atgggcctgg cctcacccat    5880
ggagtagtga acaagcctgc caccttcacc gtcaacacca aggatgcagg agaggggggc    5940
ctgtctctgg ccattgaggg cccgtccaaa gcagaaatca gctgcactga caaccaggat    6000
gggacatgca gcgtgtccta cctgcctgtg ctgccggggg actacagcat tctagtcaag    6060
tacaatgaac agcacgtccc aggcagcccc ttcactgctc gggtcacagg tgacgactcc    6120
atgcgtatgt cccacctaaa ggtcggctct gctgccgaca tccccatcaa catctcagag    6180
acggatctca gcctgctgac ggccactgtg gtcccgccct cgggccggga ggagccctgt    6240
ttgctgaagc ggctgcgtaa tggccacgtg gggatttcat tcgtgcccaa ggagacgggg    6300
gagcacctgg tgcatgtgaa gaaaaatggc cagcacgtgg ccagcagccc catcccggtg    6360
gtgatcagcc agtcggaaat tggggatgcc agtcgtgttc gggtctctgg tcagggcctt    6420
cacgaaggcc acacctttga gcctgcagag tttatcattg atacccgcga tgcaggctat    6480
ggtgggctca gcctgtccat tgagggcccc agcaaggtgg acatcaacac agaggacctg    6540
gaggacggga cgtgcagggt cacctactgc cccacagagc caggcaacta catcatcaac    6600
atcaagtttg ccgaccagca cgtgcctggc agccccttct ctgtgaaggt gacaggcgag    6660
ggccgggtga aagagagcat cacccgcagg cgtcgggctc cttcagtggc caacgttggt    6720
agtcattgtg acctcagcct gaaaatccct gaaattagca tccaggatat gacagcccag    6780
gtgaccagcc catcgggcaa gacccatgag gccgagatcg tggaaggggga gaaccacacc    6840
tactgcatcc gctttgttcc cgctgagatg ggcacacaca cagtcagcgt gaagtacaag    6900
ggccagcacg tgcctgggag ccccttccag ttcaccgtgg ggcccctagg ggaaggggga    6960
gcccacaagg tccgagctgg gggccctggc ctggagagag ctgaagctgg agtgccagcc    7020
gaattcagta tctggacccg ggaagctggt gctggaggcc tggccattgc tgtcgagggc    7080
cccagcaagg ctgagatctc ttttgaggac cgcaaggacg gctcctgtgg tgtggcttat    7140
gtggtccagg agccaggtga ctacgaagtc tcagtcaagt tcaacgagga acacattccc    7200
gacagcccct tcgtggtgcc tgtggcttct ccgtctggcg acgcccgccg cctcactgtt    7260
tctagccttc aggagtcagg gctaaaggtc aaccagccag cctcttttgc agtcagcctg    7320
aacggggcca agggggcgat cgatgccaag gtgcacagcc cctcaggagc cctggaggag    7380
tgctatgtca cagaaattga ccaagataag tatgctgtgc gcttcatccc tcgggagaat    7440
ggcgtttacc tgattgacgt caagttcaac ggcacccaca tccctggaag cccccttcaag   7500
atccgagttg gggagcctgg gcatggaggg gacccaggct tggtgtctgc ttacggagca    7560
ggtctggaag gcggtgtcac agggaaccca gctgagttcg tcgtgaacac gagcaatgcg    7620
ggagctggtg ccctgtcggt gaccattgac ggcccctcca aggtgaagat ggattgccag    7680
gagtgccctg agggctaccg cgtcacctat acccccatgg cacctggcag ctacctcatc    7740
tccatcaagt acggcggccc ctaccacatt gggggcagcc ccttcaaggc caaagtcaca    7800
ggcccccgtc tcgtcagcaa ccacagcctc cacgagacat catcagtgtt tgtagactct    7860
ctgaccaagg ccacctgtgc cccccagcat ggggccccgg gtcctgggcc tgctgacgcc    7920
agcaaggtgg tggccaaggg cctggggctg agcaaggcct acgtaggcca gaagagcagc    7980
ttcacagtag actgcagcaa agcaggcaac aacatgctgc tggtgggggt tcatggccca    8040
aggacccccct gcgaggagat cctggtgaag cacgtgggca gccggctcta cagcgtgtcc   8100
tacctgctca aggacaaggg ggagtacaca ctggtggtca aatgggggga cgagcacatc    8160
```

```
ccaggcagcc cctaccgcgt tgtggtgccc tgagtctggg gcccgtgcca gccggcagcc   8220

cccaagcctg ccccgctacc caagcagccc cgccctcttc ccctcaaccc cggcccaggc   8280

cgccctggcc gcccgcctgt cactgcagcc gcccctgccc tgtgccgtgc tgcgctcacc   8340

tgcctcccca gccagccgct gacctctcgg ctttcacttg ggcagaggga gccatttggt   8400

ggcgctgctt gtcttctttg gttctgggag gggtgaggga tgggggtcct gtacacaacc   8460

acccactagt tctcttctcc agccaagagg aataaagttt tgcttccatt aaaaaaaaaa   8520

aaaaaaaaaa aaaaaaaaaa aaaaaaaaaa aaaaaaa                            8557
```

<210> SEQ ID NO 49
<211> LENGTH: 2647
<212> TYPE: PRT
<213> ORGANISM: Homo sapiens

<400> SEQUENCE: 49

```
Met Ser Ser Ser His Ser Arg Ala Gly Gln Ser Ala Ala Gly Ala Ala
1               5                   10                  15

Pro Gly Gly Gly Val Asp Thr Arg Asp Ala Glu Met Pro Ala Thr Glu
            20                  25                  30

Lys Asp Leu Ala Glu Asp Ala Pro Trp Lys Lys Ile Gln Gln Asn Thr
        35                  40                  45

Phe Thr Arg Trp Cys Asn Glu His Leu Lys Cys Val Ser Lys Arg Ile
    50                  55                  60

Ala Asn Leu Gln Thr Asp Leu Ser Asp Gly Leu Arg Leu Ile Ala Leu
65                  70                  75                  80

Leu Glu Val Leu Ser Gln Lys Lys Met His Arg Lys His Asn Gln Arg
                85                  90                  95

Pro Thr Phe Arg Gln Met Gln Leu Glu Asn Val Ser Val Ala Leu Glu
            100                 105                 110

Phe Leu Asp Arg Glu Ser Ile Lys Leu Val Ser Ile Asp Ser Lys Ala
        115                 120                 125

Ile Val Asp Gly Asn Leu Lys Leu Ile Leu Gly Leu Ile Trp Thr Leu
    130                 135                 140

Ile Leu His Tyr Ser Ile Ser Met Pro Met Trp Asp Glu Glu Glu Asp
145                 150                 155                 160

Glu Glu Ala Lys Lys Gln Thr Pro Lys Gln Arg Leu Leu Gly Trp Ile
                165                 170                 175

Gln Asn Lys Leu Pro Gln Leu Pro Ile Thr Asn Phe Ser Arg Asp Trp
            180                 185                 190

Gln Ser Gly Arg Ala Leu Gly Ala Leu Val Asp Ser Cys Ala Pro Gly
        195                 200                 205

Leu Cys Pro Asp Trp Asp Ser Trp Asp Ala Ser Lys Pro Val Thr Asn
    210                 215                 220

Ala Arg Glu Ala Met Gln Gln Ala Asp Asp Trp Leu Gly Ile Pro Gln
225                 230                 235                 240

Val Ile Thr Pro Glu Glu Ile Val Asp Pro Asn Val Asp Glu His Ser
                245                 250                 255

Val Met Thr Tyr Leu Ser Gln Phe Pro Lys Ala Lys Leu Lys Pro Gly
            260                 265                 270

Ala Pro Leu Arg Pro Lys Leu Asn Pro Lys Lys Ala Arg Ala Tyr Gly
        275                 280                 285

Pro Gly Ile Glu Pro Thr Gly Asn Met Val Lys Lys Arg Ala Glu Phe
    290                 295                 300
```

Thr Val Glu Thr Arg Ser Ala Gly Gln Gly Glu Val Leu Val Tyr Val
305 310 315 320

Glu Asp Pro Ala Gly His Gln Glu Glu Ala Lys Val Thr Ala Asn Asn
325 330 335

Asp Lys Asn Arg Thr Phe Ser Val Trp Tyr Val Pro Glu Val Thr Gly
340 345 350

Thr His Lys Val Thr Val Leu Phe Ala Gly Gln His Ile Ala Lys Ser
355 360 365

Pro Phe Glu Val Tyr Val Asp Lys Ser Gln Gly Asp Ala Ser Lys Val
370 375 380

Thr Ala Gln Gly Pro Gly Leu Glu Pro Ser Gly Asn Ile Ala Asn Lys
385 390 395 400

Thr Thr Tyr Phe Glu Ile Phe Thr Ala Gly Ala Gly Thr Gly Glu Val
405 410 415

Glu Val Val Ile Gln Asp Pro Met Gly Gln Lys Gly Thr Val Glu Pro
420 425 430

Gln Leu Glu Ala Arg Gly Asp Ser Thr Tyr Arg Cys Ser Tyr Gln Pro
435 440 445

Thr Met Glu Gly Val His Thr Val His Val Thr Phe Ala Gly Val Pro
450 455 460

Ile Pro Arg Ser Pro Tyr Thr Val Thr Val Gly Gln Ala Cys Asn Pro
465 470 475 480

Ser Ala Cys Arg Ala Val Gly Arg Gly Leu Gln Pro Lys Gly Val Arg
485 490 495

Val Lys Glu Thr Ala Asp Phe Lys Val Tyr Thr Lys Gly Ala Gly Ser
500 505 510

Gly Glu Leu Lys Val Thr Val Lys Gly Pro Lys Gly Glu Glu Arg Val
515 520 525

Lys Gln Lys Asp Leu Gly Asp Gly Val Tyr Gly Phe Glu Tyr Tyr Pro
530 535 540

Met Val Pro Gly Thr Tyr Ile Val Thr Ile Thr Trp Gly Gly Gln Asn
545 550 555 560

Ile Gly Arg Ser Pro Phe Glu Val Lys Val Gly Thr Glu Cys Gly Asn
565 570 575

Gln Lys Val Arg Ala Trp Gly Pro Gly Leu Glu Gly Gly Val Val Gly
580 585 590

Lys Ser Ala Asp Phe Val Val Glu Ala Ile Gly Asp Asp Val Gly Thr
595 600 605

Leu Gly Phe Ser Val Glu Gly Pro Ser Gln Ala Lys Ile Glu Cys Asp
610 615 620

Asp Lys Gly Asp Gly Ser Cys Asp Val Arg Tyr Trp Pro Gln Glu Ala
625 630 635 640

Gly Glu Tyr Ala Val His Val Leu Cys Asn Ser Glu Asp Ile Arg Leu
645 650 655

Ser Pro Phe Met Ala Asp Ile Arg Asp Ala Pro Gln Asp Phe His Pro
660 665 670

Asp Arg Val Lys Ala Arg Gly Pro Gly Leu Glu Lys Thr Gly Val Ala
675 680 685

Val Asn Lys Pro Ala Glu Phe Thr Val Asp Ala Lys His Gly Gly Lys
690 695 700

Ala Pro Leu Arg Val Gln Val Gln Asp Asn Glu Gly Cys Pro Val Glu
705 710 715 720

-continued

```
Ala Leu Val Lys Asp Asn Gly Asn Gly Thr Tyr Ser Cys Ser Tyr Val
                725                 730                 735

Pro Arg Lys Pro Val Lys His Thr Ala Met Val Ser Trp Gly Gly Val
            740                 745                 750

Ser Ile Pro Asn Ser Pro Phe Arg Val Asn Val Gly Ala Gly Ser His
        755                 760                 765

Pro Asn Lys Val Lys Val Tyr Gly Pro Gly Val Ala Lys Thr Gly Leu
    770                 775                 780

Lys Ala His Glu Pro Thr Tyr Phe Thr Val Asp Cys Ala Glu Ala Gly
785                 790                 795                 800

Gln Gly Asp Val Ser Ile Gly Ile Lys Cys Ala Pro Gly Val Val Gly
                805                 810                 815

Pro Ala Glu Ala Asp Ile Asp Phe Asp Ile Ile Arg Asn Asp Asn Asp
            820                 825                 830

Thr Phe Thr Val Lys Tyr Thr Pro Arg Gly Ala Gly Ser Tyr Thr Ile
        835                 840                 845

Met Val Leu Phe Ala Asp Gln Ala Thr Pro Thr Ser Pro Ile Arg Val
    850                 855                 860

Lys Val Glu Pro Ser His Asp Ala Ser Lys Val Lys Ala Glu Gly Pro
865                 870                 875                 880

Gly Leu Ser Arg Thr Gly Val Glu Leu Gly Lys Pro Thr His Phe Thr
                885                 890                 895

Val Asn Ala Lys Ala Ala Gly Lys Gly Lys Leu Asp Val Gln Phe Ser
            900                 905                 910

Gly Leu Thr Lys Gly Asp Ala Val Arg Asp Val Asp Ile Ile Asp His
        915                 920                 925

His Asp Asn Thr Tyr Thr Val Lys Tyr Thr Pro Val Gln Gln Gly Pro
    930                 935                 940

Val Gly Val Asn Val Thr Tyr Gly Gly Asp Pro Ile Pro Lys Ser Pro
945                 950                 955                 960

Phe Ser Val Ala Val Ser Pro Ser Leu Asp Leu Ser Lys Ile Lys Val
                965                 970                 975

Ser Gly Leu Gly Glu Lys Val Asp Val Gly Lys Asp Gln Glu Phe Thr
            980                 985                 990

Val Lys Ser Lys Gly Ala Gly Gly  Gln Gly Lys Val Ala  Ser Lys Ile
        995                 1000                1005

Val Gly  Pro Ser Gly Ala Ala  Val Pro Cys Lys Val  Glu Pro Gly
    1010                1015                1020

Leu Gly  Ala Asp Asn Ser Val  Val Arg Phe Leu Pro  Arg Glu Glu
    1025                1030                1035

Gly Pro  Tyr Glu Val Glu Val  Thr Tyr Asp Gly Val  Pro Val Pro
    1040                1045                1050

Gly Ser  Pro Phe Pro Leu Glu  Ala Val Ala Pro Thr  Lys Pro Ser
    1055                1060                1065

Lys Val  Lys Ala Phe Gly Pro  Gly Leu Gln Gly Gly  Ser Ala Gly
    1070                1075                1080

Ser Pro  Ala Arg Phe Thr Ile  Asp Thr Lys Gly Ala  Gly Thr Gly
    1085                1090                1095

Gly Leu  Gly Leu Thr Val Glu  Gly Pro Cys Glu Ala  Gln Leu Glu
    1100                1105                1110

Cys Leu  Asp Asn Gly Asp Gly  Thr Cys Ser Val Ser  Tyr Val Pro
    1115                1120                1125

Thr Glu  Pro Gly Asp Tyr Asn  Ile Asn Ile Leu Phe  Ala Asp Thr
```

```
    1130                1135                1140

His Ile  Pro Gly Ser Pro Phe  Lys Ala His Val Val  Pro Cys Phe
    1145                1150                1155

Asp Ala  Ser Lys Val Lys Cys  Ser Gly Pro Gly Leu  Glu Arg Ala
    1160                1165                1170

Thr Ala  Gly Glu Val Gly Gln  Phe Gln Val Asp Cys  Ser Ser Ala
    1175                1180                1185

Gly Ser  Ala Glu Leu Thr Ile  Glu Ile Cys Ser Glu  Ala Gly Leu
    1190                1195                1200

Pro Ala  Glu Val Tyr Ile Gln  Asp His Gly Asp Gly  Thr His Thr
    1205                1210                1215

Ile Thr  Tyr Ile Pro Leu Cys  Pro Gly Ala Tyr Thr  Val Thr Ile
    1220                1225                1230

Lys Tyr  Gly Gly Gln Pro Val  Pro Asn Phe Pro Ser  Lys Leu Gln
    1235                1240                1245

Val Glu  Pro Ala Val Asp Thr  Ser Gly Val Gln Cys  Tyr Gly Pro
    1250                1255                1260

Gly Ile  Glu Gly Gln Gly Val  Phe Arg Glu Ala Thr  Thr Glu Phe
    1265                1270                1275

Ser Val  Asp Ala Arg Ala Leu  Thr Gln Thr Gly Gly  Pro His Val
    1280                1285                1290

Lys Ala  Arg Val Ala Asn Pro  Ser Gly Asn Leu Thr  Glu Thr Tyr
    1295                1300                1305

Val Gln  Asp Arg Gly Asp Gly  Met Tyr Lys Val Glu  Tyr Thr Pro
    1310                1315                1320

Tyr Glu  Glu Gly Leu His Ser  Val Asp Val Thr Tyr  Asp Gly Ser
    1325                1330                1335

Pro Val  Pro Ser Ser Pro Phe  Gln Val Pro Val Thr  Glu Gly Cys
    1340                1345                1350

Asp Pro  Ser Arg Val Arg Val  His Gly Pro Gly Ile  Gln Ser Gly
    1355                1360                1365

Thr Thr  Asn Lys Pro Asn Lys  Phe Thr Val Glu Thr  Arg Gly Ala
    1370                1375                1380

Gly Thr  Gly Gly Leu Gly Leu  Ala Val Glu Gly Pro  Ser Glu Ala
    1385                1390                1395

Lys Met  Ser Cys Met Asp Asn  Lys Asp Gly Ser Cys  Ser Val Glu
    1400                1405                1410

Tyr Ile  Pro Tyr Glu Ala Gly  Thr Tyr Ser Leu Asn  Val Thr Tyr
    1415                1420                1425

Gly Gly  His Gln Val Pro Gly  Ser Pro Phe Lys Val  Pro Val His
    1430                1435                1440

Asp Val  Thr Asp Ala Ser Lys  Val Lys Cys Ser Gly  Pro Gly Leu
    1445                1450                1455

Ser Pro  Gly Met Val Arg Ala  Asn Leu Pro Gln Ser  Phe Gln Val
    1460                1465                1470

Asp Thr  Ser Lys Ala Gly Val  Ala Pro Leu Gln Val  Lys Val Gln
    1475                1480                1485

Gly Pro  Lys Gly Leu Val Glu  Pro Val Asp Val Val  Asp Asn Ala
    1490                1495                1500

Asp Gly  Thr Gln Thr Val Asn  Tyr Val Pro Ser Arg  Glu Gly Pro
    1505                1510                1515

Tyr Ser  Ile Ser Val Leu Tyr  Gly Asp Glu Glu Val  Pro Arg Ser
    1520                1525                1530
```

Pro Phe Lys Val Lys Val Leu Pro Thr His Asp Ala Ser Lys Val
1535 1540 1545

Lys Ala Ser Gly Pro Gly Leu Asn Thr Thr Gly Val Pro Ala Ser
1550 1555 1560

Leu Pro Val Glu Phe Thr Ile Asp Ala Lys Asp Ala Gly Glu Gly
1565 1570 1575

Leu Leu Ala Val Gln Ile Thr Asp Pro Glu Gly Lys Pro Lys Lys
1580 1585 1590

Thr His Ile Gln Asp Asn His Asp Gly Thr Tyr Thr Val Ala Tyr
1595 1600 1605

Val Pro Asp Val Thr Gly Arg Tyr Thr Ile Leu Ile Lys Tyr Gly
1610 1615 1620

Gly Asp Glu Ile Pro Phe Ser Pro Tyr Arg Val Arg Ala Val Pro
1625 1630 1635

Thr Gly Asp Ala Ser Lys Cys Thr Val Thr Val Ser Ile Gly Gly
1640 1645 1650

His Gly Leu Gly Ala Gly Ile Gly Pro Thr Ile Gln Ile Gly Glu
1655 1660 1665

Glu Thr Val Ile Thr Val Asp Thr Lys Ala Ala Gly Lys Gly Lys
1670 1675 1680

Val Thr Cys Thr Val Cys Thr Pro Asp Gly Ser Glu Val Asp Val
1685 1690 1695

Asp Val Val Glu Asn Glu Asp Gly Thr Phe Asp Ile Phe Tyr Thr
1700 1705 1710

Ala Pro Gln Pro Gly Lys Tyr Val Ile Cys Val Arg Phe Gly Gly
1715 1720 1725

Glu His Val Pro Asn Ser Pro Phe Gln Val Thr Ala Leu Ala Gly
1730 1735 1740

Asp Gln Pro Ser Val Gln Pro Pro Leu Arg Ser Gln Gln Leu Ala
1745 1750 1755

Pro Gln Tyr Thr Tyr Ala Gln Gly Gly Gln Gln Thr Trp Ala Pro
1760 1765 1770

Glu Arg Pro Leu Val Gly Val Asn Gly Leu Asp Val Thr Ser Leu
1775 1780 1785

Arg Pro Phe Asp Leu Val Ile Pro Phe Thr Ile Lys Lys Gly Glu
1790 1795 1800

Ile Thr Gly Glu Val Arg Met Pro Ser Gly Lys Val Ala Gln Pro
1805 1810 1815

Thr Ile Thr Asp Asn Lys Asp Gly Thr Val Thr Val Arg Tyr Ala
1820 1825 1830

Pro Ser Glu Ala Gly Leu His Glu Met Asp Ile Arg Tyr Asp Asn
1835 1840 1845

Met His Ile Pro Gly Ser Pro Leu Gln Phe Tyr Val Asp Tyr Val
1850 1855 1860

Asn Cys Gly His Val Thr Ala Tyr Gly Pro Gly Leu Thr His Gly
1865 1870 1875

Val Val Asn Lys Pro Ala Thr Phe Thr Val Asn Thr Lys Asp Ala
1880 1885 1890

Gly Glu Gly Gly Leu Ser Leu Ala Ile Glu Gly Pro Ser Lys Ala
1895 1900 1905

Glu Ile Ser Cys Thr Asp Asn Gln Asp Gly Thr Cys Ser Val Ser
1910 1915 1920

-continued

```
Tyr Leu  Pro Val Leu Pro Gly  Asp Tyr Ser Ile Leu  Val Lys Tyr
    1925                 1930                 1935

Asn Glu  Gln His Val Pro Gly  Ser Pro Phe Thr Ala  Arg Val Thr
    1940                 1945                 1950

Gly Asp  Asp Ser Met Arg Met  Ser His Leu Lys Val  Gly Ser Ala
    1955                 1960                 1965

Ala Asp  Ile Pro Ile Asn Ile  Ser Glu Thr Asp Leu  Ser Leu Leu
    1970                 1975                 1980

Thr Ala  Thr Val Val Pro Pro  Ser Gly Arg Glu Glu  Pro Cys Leu
    1985                 1990                 1995

Leu Lys  Arg Leu Arg Asn Gly  His Val Gly Ile Ser  Phe Val Pro
    2000                 2005                 2010

Lys Glu  Thr Gly Glu His Leu  Val His Val Lys Lys  Asn Gly Gln
    2015                 2020                 2025

His Val  Ala Ser Ser Pro Ile  Pro Val Val Ile Ser  Gln Ser Glu
    2030                 2035                 2040

Ile Gly  Asp Ala Ser Arg Val  Arg Val Ser Gly Gln  Gly Leu His
    2045                 2050                 2055

Glu Gly  His Thr Phe Glu Pro  Ala Glu Phe Ile Ile  Asp Thr Arg
    2060                 2065                 2070

Asp Ala  Gly Tyr Gly Gly Leu  Ser Leu Ser Ile Glu  Gly Pro Ser
    2075                 2080                 2085

Lys Val  Asp Ile Asn Thr Glu  Asp Leu Glu Asp Gly  Thr Cys Arg
    2090                 2095                 2100

Val Thr  Tyr Cys Pro Thr Glu  Pro Gly Asn Tyr Ile  Ile Asn Ile
    2105                 2110                 2115

Lys Phe  Ala Asp Gln His Val  Pro Gly Ser Pro Phe  Ser Val Lys
    2120                 2125                 2130

Val Thr  Gly Glu Gly Arg Val  Lys Glu Ser Ile Thr  Arg Arg Arg
    2135                 2140                 2145

Arg Ala  Pro Ser Val Ala Asn  Val Gly Ser His Cys  Asp Leu Ser
    2150                 2155                 2160

Leu Lys  Ile Pro Glu Ile Ser  Ile Gln Asp Met Thr  Ala Gln Val
    2165                 2170                 2175

Thr Ser  Pro Ser Gly Lys Thr  His Glu Ala Glu Ile  Val Glu Gly
    2180                 2185                 2190

Glu Asn  His Thr Tyr Cys Ile  Arg Phe Val Pro Ala  Glu Met Gly
    2195                 2200                 2205

Thr His  Thr Val Ser Val Lys  Tyr Lys Gly Gln His  Val Pro Gly
    2210                 2215                 2220

Ser Pro  Phe Gln Phe Thr Val  Gly Pro Leu Gly Glu  Gly Gly Ala
    2225                 2230                 2235

His Lys  Val Arg Ala Gly Gly  Pro Gly Leu Glu Arg  Ala Glu Ala
    2240                 2245                 2250

Gly Val  Pro Ala Glu Phe Ser  Ile Trp Thr Arg Glu  Ala Gly Ala
    2255                 2260                 2265

Gly Gly  Leu Ala Ile Ala Val  Glu Gly Pro Ser Lys  Ala Glu Ile
    2270                 2275                 2280

Ser Phe  Glu Asp Arg Lys Asp  Gly Ser Cys Gly Val  Ala Tyr Val
    2285                 2290                 2295

Val Gln  Glu Pro Gly Asp Tyr  Glu Val Ser Val Lys  Phe Asn Glu
    2300                 2305                 2310

Glu His  Ile Pro Asp Ser Pro  Phe Val Val Pro Val  Ala Ser Pro
```

-continued

```
    2315                2320                2325

Ser Gly  Asp Ala Arg Arg Leu  Thr Val Ser Ser Leu  Gln Glu Ser
    2330                2335                2340

Gly Leu  Lys Val Asn Gln Pro  Ala Ser Phe Ala Val  Ser Leu Asn
    2345                2350                2355

Gly Ala  Lys Gly Ala Ile Asp  Ala Lys Val His Ser  Pro Ser Gly
    2360                2365                2370

Ala Leu  Glu Glu Cys Tyr Val  Thr Glu Ile Asp Gln  Asp Lys Tyr
    2375                2380                2385

Ala Val  Arg Phe Ile Pro Arg  Glu Asn Gly Val Tyr  Leu Ile Asp
    2390                2395                2400

Val Lys  Phe Asn Gly Thr His  Ile Pro Gly Ser Pro  Phe Lys Ile
    2405                2410                2415

Arg Val  Gly Glu Pro Gly His  Gly Gly Asp Pro Gly  Leu Val Ser
    2420                2425                2430

Ala Tyr  Gly Ala Gly Leu Glu  Gly Gly Val Thr Gly  Asn Pro Ala
    2435                2440                2445

Glu Phe  Val Val Asn Thr Ser  Asn Ala Gly Ala Gly  Ala Leu Ser
    2450                2455                2460

Val Thr  Ile Asp Gly Pro Ser  Lys Val Lys Met Asp  Cys Gln Glu
    2465                2470                2475

Cys Pro  Glu Gly Tyr Arg Val  Thr Tyr Thr Pro Met  Ala Pro Gly
    2480                2485                2490

Ser Tyr  Leu Ile Ser Ile Lys  Tyr Gly Gly Pro Tyr  His Ile Gly
    2495                2500                2505

Gly Ser  Pro Phe Lys Ala Lys  Val Thr Gly Pro Arg  Leu Val Ser
    2510                2515                2520

Asn His  Ser Leu His Glu Thr  Ser Ser Val Phe Val  Asp Ser Leu
    2525                2530                2535

Thr Lys  Ala Thr Cys Ala Pro  Gln His Gly Ala Pro  Gly Pro Gly
    2540                2545                2550

Pro Ala  Asp Ala Ser Lys Val  Val Ala Lys Gly Leu  Gly Leu Ser
    2555                2560                2565

Lys Ala  Tyr Val Gly Gln Lys  Ser Ser Phe Thr Val  Asp Cys Ser
    2570                2575                2580

Lys Ala  Gly Asn Asn Met Leu  Leu Val Gly Val His  Gly Pro Arg
    2585                2590                2595

Thr Pro  Cys Glu Glu Ile Leu  Val Lys His Val Gly  Ser Arg Leu
    2600                2605                2610

Tyr Ser  Val Ser Tyr Leu Leu  Lys Asp Lys Gly Glu  Tyr Thr Leu
    2615                2620                2625

Val Val  Lys Trp Gly Asp Glu  His Ile Pro Gly Ser  Pro Tyr Arg
    2630                2635                2640

Val Val  Val Pro
    2645
```

USE OF MARKERS INCLUDING FILAMIN A IN THE DIAGNOSIS AND TREATMENT OF PROSTATE CANCER

RELATED APPLICATIONS

This application claims priority to U.S. Provisional Application No. 62/088,931, filed on Dec. 8, 2014; U.S. Provisional Application No. 62/134,956, filed on Mar. 18, 2015; and U.S. Provisional Application No. 62/148,294, filed on Apr. 16, 2015, the entire contents of each of which are expressly incorporated herein by reference.

INCORPORATION BY REFERENCE

All documents cited or referenced herein and all documents cited or referenced in the herein cited documents, together with any manufacturer's instructions, descriptions, product specifications, and product sheets for any products mentioned herein or in any document incorporated by reference herein, are hereby incorporated by reference, and may be employed in the practice of the invention.

BACKGROUND

A. Field of the Invention

The invention generally relates to novel biomarkers and combinations of biomarkers which can be used to detect and monitor prostate cancer. The invention also generally relates to methods for diagnosing, monitoring, and treating prostate cancer involving the detection of biomarkers of the invention.

B. Background of the Invention

Prostate cancer is a leading cause of male cancer-related deaths—second only to lung cancer—and afflicts one out of nine men over the age of 65. According to the American Cancer Society, 241,000 new cases of prostate cancer were reported with about 30,000 prostate cancer-related deaths that same year. Although the disease is typically diagnosed in men over the age of 65, its impact is still significant in that the average life span of a man who dies from prostate cancer is reduced by nearly a decade on average. However, if prostate cancer is discovered early, 90% of the cases may be cured with surgery. Once the tumor spreads outside the area of the prostate gland and forms distant metastases, the disease is more difficult to treat. Therefore, early detection is of critical importance to the success of interventional therapies, and for reducing the mortality rate associated with prostate cancer.

Prostate cancer typically develops in the various tissues of the prostate, a gland in the male reproductive system. Most prostate cancers are slow growing. However, there are also a significant number of cases per year of aggressive prostate cancers, in which the cancer cells may metastasize from the prostate to other parts of the body, particularly to the bones and lymph nodes. Prostate cancer may cause pain, difficulty in urinating, problems during sexual intercourse, or erectile dysfunction. Other symptoms can potentially develop during later stages of the disease.

Currently, prostate cancer is screened using only a limited number of detection means, including the digital rectal exam (DRE) and/or the measurement of the levels of prostate specific antigen (PSA). However, these approaches have an unacceptably high rate of false-positives. Indeed, most men (75%) with an elevated PSA level turn out not to have prostate cancer as determined by subsequent confirmatory prostate biopsies.

As such, the current screening tests are not specific enough to robustly screen for prostate cancer. Each year, based on the results of the DRE and PSA screens, about one million prostate biopsies are performed in the U.S. alone. Only 25% of these biopsies confirm the presence of cancer. PSA is secreted from epithelial cells of the prostate gland and is higher in blood due to increased number of prostate epithelial cells. When prostate cancers develop, PSA levels in the blood can start to climb. In the United States, the FDA has approved the PSA test for annual screening of prostate cancer in men of age 50 and older. PSA levels between 4 and 10 ng/mL are considered to be suspicious and consideration should be given to confirming the abnormal PSA with a repeat test. If indicated, a prostate biopsy is performed to obtain a tissue sample for histopathological analysis. Complications—such as infection, internal bleeding, allergic reactions, impotence, and urinary incontinence—induced by needless biopsies and treatments injure many more men than are potentially helped by early detection of cancers.

Indeed, the U.S. Preventative Services Task Force (USPSTF) estimates that about 90% of diagnosed men are treated and 2 in 1000 men will develop serious cardiovascular events, 1 in 1000 men will develop deep venous thrombosis, 29 in 1000 men will develop erectile dysfunction, 18 in 1000 men will develop urinary incontinence, and 1 in 1000 men will die due to treatment. A large majority of these men would have remained asymptomatic for life if left untreated. As such, most cancers found through PSA tests are not, in fact, dangerous. Nevertheless, given the lack of more effective predictors of prostate cancer, the field takes a more conservative approach in the use of biopsies and treatment, erring on the side of precaution but risking significant harm to otherwise healthy men.

Despite the current drawbacks in prostate cancer detection, the USPSTF estimates that one life will be saved for every 1,000 men screened every 1-4 years over a 10-year period. This overall outlook can be further improved by limiting unnecessary biopsies with the use of improved pre-biopsy screening methods that are associated with fewer false-positive results. With fewer unnecessary biopsies, fewer men will suffer the associated biopsy complications. In addition, fewer complications will also lead to an overall cost reduction to the healthcare system in the management of prostate cancer.

Accordingly, there is an unmet need for improved prostate cancer screening tools that improve the accuracy of prostate cancer detection. Molecular-based biomarkers may address this need.

SUMMARY OF THE INVENTION

In view of the fact that prostate cancer remains a life threatening disease reaching a significant portion of the male population, there remains a need for efficient, accurate, and rapid molecular diagnosis means, particularly which do not suffer from a high proportion of false results. The development of molecular tests for the accurate detection of prostate cancer will also lead to improved management of appropriate therapies, and an overall improved survival rate. Thus, there remains a need to provide an improved diagnostic test for the detection of prostate cancer which is more reliable and accurate than PSA and other current screening tests. The present invention addresses this need by providing the use of a new biomarker, filamin A, either used alone or in combination with other markers, for the accurate and reliable detection of prostate cancer.

The present invention is based, at least in part, on the discovery that filamin A is differentially regulated in prostate cancer cells. In particular, the invention is based on the surprising discovery that filamin A levels are significantly elevated in the serum of patients with prostate cancer. Accordingly, the invention provides methods for diagnosing and/or monitoring (e.g., monitoring of disease progression or treatment) an oncological disease state, e.g., prostate cancer, in a mammal. The invention also provides methods for treating or for adjusting treatment regimens based on diagnostic information relating to the levels of filamin A in the serum of a subject with an oncological disease state, e.g., prostate cancer. The invention further provides panels and kits for practicing the methods of the invention.

Accordingly, in one aspect, the present invention provides a method for diagnosing the presence of prostate cancer in a subject, comprising: (a) detecting the level of filamin A in a biological sample of the subject, and (b) comparing the level of filamin A in the biological sample with a predetermined threshold value, wherein the level filamin A above the predetermined threshold value indicates the presence of prostate cancer in the subject.

In another aspect, the invention provides a method for diagnosing the presence of prostate cancer in a subject, comprising: (a) contacting a biological sample with a reagent that selectively binds to filamin A; (b) allowing a complex to form between the reagent and filamin A; (c) detecting the level of the complex, and (d) comparing the level of the complex with a predetermined threshold value, wherein the level of the complex above the predetermined threshold value indicates the presence of prostate cancer in the subject.

In certain embodiments, the diagnostic method further comprises detecting the level of one or more additional markers of prostate cancer.

The one or more additional markers of prostate cancer can include, but is not limited to, prostate specific antigen (PSA), filamin B, LY9, keratin 4, keratin 7, keratin 8, keratin 15, kertin 18, keratin 19, and tubulin-beta 3. In another embodiment, the one or more additional markers of prostate cancer can include age. Age can be used as a continuous predictive biomarker. For example, increased age is associated with higher risk of having prostate cancer. Lower age is associated with decreased risk of having prostate cancer.

In certain other embodiments, the one or more additional markers can include genes that have been described in the literature as being specifically expressed in the prostate. These genes can include, for example, prostate-specific membrane antigen (PSM) (Fair et al., 1997, Prostate-specific membrane antigen. Prostate 32:140-148), prostate stem cell antigen (PSCA) (Reiter et al., 1998, Prostate stem cell antigen: a cell surface marker overexpressed in prostate cancer. Proc. Natl. Acad. Sci. USA 95:1735-1740), TMPRSS2 (Lin et al., 1999. Prostate-localized and androgen-regulated expression of the membrane-bound serine protease TMPRSS2. Cancer Res. 59:4180-4184), PDEF (Oettgen et al., 2000, PDEF, a novel prostate epithelium-specific ETS transcription factor, interacts with the androgen receptor and activates prostate-specific antigen gene expression. J. Biol. Chem. 275:1216-1225), prostate-specific gene-1 (Herness, 2003. A novel human prostate-specific gene-1 (HPG-1): molecular cloning, sequencing, and its potential involvement in prostate carcinogenesis. Cancer Res. 63:329-336), and even various non-coding RNA's (ncRNA's), like PCA3 (Bussemakers et al., 1999. DD3: a new prostate-specific gene, highly overexpressed in prostate cancer, Cancer Res. 59:5975-5979), PCGEM1 (Srikantan et al., 2000. PCGEM1, a prostate-specific gene, is overexpressed in prostate cancer. Proc. Natl. Acad. Sci. USA 97:12216-12221) and the gene cluster P704P, P712P, and P775P (Stolk et al., 2004. P704P, P712P, and P775P: A genomic cluster of prostate-specific genes. Prostate 60:214-226). Only a fraction of these markers have been associated with prostate cancer prognosis, progression and/or metastatic capacity and as such, their potential as valuable biomarkers and/or therapeutic targets is largely unknown.

In one embodiment, the prostate cancer is a prostate cancer characterized by overexpression of filamin A. In another embodiment, the prostate cancer is a prostate cancer characterized by overexpression of filamin A and overexpression of one or more additional markers selected from the group consisting of filamin B, LY9, keratin 5, keratin 7, keratin 8, keratin 15, keratin 18, keratin 19, tubulin-beta 3, or prostate specific antigen (PSA). In another embodiment, the prostate cancer is a prostate cancer characterized by overexpression of filamin A and overexpression of one or more additional markers selected from the group consisting of filamin B, LY9, keratin 5, keratin 7, keratin 8, keratin 15, keratin 18, keratin 19, tubulin-beta 3, or prostate specific antigen (PSA), and increased patient age. In another embodiment, the prostate cancer is a prostate cancer characterized by overexpression of filamin A and increased patient age. In another embodiment, the prostate cancer is a prostate cancer characterized by underexpression of filamin A and overexpression of one or more additional markers selected from the group consisting of filamin B, LY9, keratin 5, keratin 7, keratin 8, keratin 15, keratin 18, keratin 19, tubulin-beta 3, or prostate specific antigen (PSA). In another embodiment, the prostate cancer is a prostate cancer characterized by underexpression of filamin A and overexpression of one or more additional markers selected from the group consisting of filamin B, LY9, keratin 5, keratin 7, keratin 8, keratin 15, keratin 18, keratin 19, tubulin-beta 3, or prostate specific antigen (PSA), and increased patient age. In another embodiment, the prostate cancer is a prostate cancer characterized by underexpression of filamin A and increased patient age.

In certain embodiments, the biological sample can be selected from the group consisting of blood, serum, urine, organ tissue, biopsy tissue, feces, skin, hair, and cheek tissue.

In various embodiments, the level of filamin A can be determined by an assay, such as an immunoassay or ELISA. Other suitable assays may be employed.

In certain embodiments, the step of determining the level of filamin A in the biological sample can comprise (i) contacting the biological sample with a reagent that selectively binds to the filamin A polypeptide to form a biomarker complex, and (ii) detecting the biomarker complex.

In some embodiments, the reagent can be an anti-filamin A antibody that selectively binds to at least one epitope of filamin A. In certain other embodiments, the anti-filamin A antibody may further comprise a detectable label. In other embodiments, the method may include a further step that contacts the anti-filamin A antibody/filamin A complex with a secondary antibody which selectively binds to the anti-filamin A antibody, and which itself carries a detectable tag or label.

In certain other embodiments, the step of determining the level of filamin A in the biological sample can be based on determining the amount of filamin A mRNA in the biological sample.

In some embodiments, an amplification reaction can be used for determining the amount of filamin A mRNA in the biological sample. The amplification reaction can include, but is not limited to, (a) a polymerase chain reaction (PCR); (b) a nucleic acid sequence-based amplification assay (NASBA); (c) a transcription mediated amplification (TMA); (d) a ligase chain reaction (LCR); or (e) a strand displacement amplification (SDA).

In still other embodiments, the step of determining the level of filamin A in the biological sample can be based on a hybridization assay, which can include using an oligonucleotide or probe that is complementary to a portion of a filamin A mRNA to hybridize thereto, wherein the oligonucleotide further comprises a detectable label or tag.

In certain embodiments, the prostate cancer is a prostatic intraepithelial neoplasia, adenocarcinoma, small cell carcinoma, or squamous cell carcinoma. In other embodiments, the prostate cancer can be an androgen-dependent prostate cancer. In still other embodiments, the prostate cancer can be an androgen-independent prostate cancer. In yet other embodiments, the prostate cancer can be an aggressive prostate cancer or a metastasized cancer. In still other embodiments, the prostate cancer can be a non-aggressive prostate cancer.

In embodiments where a diagnosis of prostate cancer is made, the invention also contemplates administering a therapeutic anti-cancer treatment, wherein the anti-cancer treatment is selected from the group consisting of (a) radiation therapy, (b) chemotherapy, (c) surgery, (d) hormone therapy, (e) antibody therapy, (f) immunotherapy, (g) cytokine therapy, (h) growth factor therapy, and (d) any combination of (a)-(h).

In various embodiments, the methods of the invention can involve first selecting a subject suspected of having or being at risk of having prostate cancer and obtaining a biological sample from that subject suspected of having or being at risk of having prostate cancer.

In still other embodiments, the diagnostic methods of the invention may further comprise comparing the level of the one or more prostate cancer related markers in the biological sample, e.g., filamin A and one or more of PSA, filamin B, LY9, keratin 4, keratin 7, keratin 8, keratin 15, kertin 18, keratin 19, tubulin-beta 3, PSM, PSCA, TMPRSS2, PDEF, HPG-1, PCA3, and PCGEM1 with the level of the one or more prostate cancer related markers in a control sample selected from the group consisting of: a sample obtained from the same subject at an earlier time point than the biological sample, a sample from a subject with benign prostatic hyperplasia (BPH), a sample from a subject with non-metastatic prostate cancer, a sample from a subject with metastatic prostate cancer, a sample from a subject with androgen sensitive prostate cancer, a sample from a subject with androgen insensitive prostate cancer, a sample from a subject with aggressive prostate cancer, and a sample from a subject with non-aggressive prostate cancer.

In still other embodiments, the diagnostic methods of the invention can comprise differentiating between two prostate cancer states selected from the group consisting of: normal prostate and prostate cancer, benign prostate hyperplasia and prostate cancer, benign prostate hyperplasia and normal prostate, androgen dependent and androgen independent prostate cancer, aggressive prostate cancer and non-aggressive prostate cancer, and metastatic prostate cancer and non-metastatic prostate cancer.

In yet another aspect, the present invention provides a method for monitoring prostate cancer in a subject, the method comprising: (1) determining a level of filamin A in a first biological sample obtained at a first time from a subject having prostate cancer; (2) determining a level of filamin A in a second biological sample obtained from the subject at a second time, wherein the second time is later than the first time; and (3) comparing the level of filamin A in the second sample with the level of filamin A in the first sample, wherein a change in the level of filamin A is indicative of a change in prostate cancer status in the subject.

In certain embodiments, the determining steps (1) and (2) above further comprise determining the level of one or more additional prostate cancer related markers selected from the group consisting of PSA, filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1. In certain embodiments, the determining steps (1) and (2) above further comprise determining the level of the patient's age.

In certain embodiments, the subject is actively treated for prostate cancer prior to obtaining the second sample. In other embodiments, the subject is not actively treated for prostate cancer prior to obtaining the second sample.

In certain embodiments relating to monitoring prostate cancer, the increased level of filamin A and/or the one or more additional prostate cancer related markers in the second biological sample as compared to the first biological sample is indicative of progression of the prostate cancer in the subject.

In certain other embodiments relating to monitoring prostate cancer, a decreased or equivalent level of filamin A and/or the one or more additional prostate cancer related markers in the second biological sample as compared to the first biological sample is indicative of non-progression of the prostate cancer in the subject.

In other embodiments relating to monitoring prostate cancer, wherein the method further comprises comparing the level of the one or more prostate cancer related markers in the first biological sample or the second biological sample with the level of the one or more prostate cancer related markers in a control sample selected from the group consisting of: a normal control sample, a sample from a subject with benign prostatic hyperplasia (BPH), a sample from a subject with non-metastatic prostate cancer, a sample from a subject with metastatic prostate cancer, a sample from a subject with androgen sensitive prostate cancer, a sample from a subject with androgen insensitive prostate cancer, a sample from a subject with aggressive prostate cancer, and a sample from a subject with non-aggressive prostate cancer.

In still other embodiments, any of the methods of the invention can include detecting the size of the prostate tumor in the subject.

In still other embodiments, any of the methods further comprise obtaining a first sample and a second sample from the subject.

In still other embodiments, the diagnostic methods of the invention further comprise the step of selecting and/or administering a different treatment regimen for the subject based on progression of the prostate cancer in the subject.

In yet other embodiments, the diagnostic methods of the invention further comprise administering a therapeutic anti-cancer based on progression of the prostate cancer in the subject, wherein the anti-cancer treatment is selected from the group consisting of (a) radiation therapy, (b) chemotherapy, (c) surgery, (d) hormone therapy, (e) antibody therapy, (f) immunotherapy, (g) cytokine therapy, (h) growth factor therapy, and (d) any combination of (a)-(h).

In still other embodiments, the methods of the invention further comprise withholding an active treatment of the prostate cancer in the subject based on non-progression of the prostate cancer in the subject.

In another aspect, the present invention provides a method of treating prostate cancer in a subject, comprising: (a) obtaining a biological sample from a subject suspected of having prostate cancer, (b) submitting the biological sample to obtain diagnostic information as to the level of filamin A, (c) administering a therapeutically effective amount of an anti-cancer therapy if the level of filamin A is above a threshold level.

In yet another aspect, the present invention provides a method of treating prostate cancer in a subject, comprising: (a) obtaining diagnostic information as to the level of filamin A in a biological sample, and (b) administering a therapeutically effective amount of an anti-cancer therapy if the level of filamin A is above a threshold level.

In still another aspect, the present invention provides a method of treating prostate cancer in a subject, comprising: (a) obtaining a biological sample from a subject suspected of having prostate cancer for use in identifying diagnostic information as to the level of filamin A, (b) measuring the level of filamin A in the biological sample, (c) recommending to a healthcare provider to administer an anti-cancer therapy if the level of filamin A is above a threshold level.

In certain embodiments, the method of the invention further comprises obtaining diagnostic information as to the level of one or more additional markers of prostate cancer.

In still other embodiments, the method of the invention further comprises obtaining diagnostic information as to the level of one or more additional markers of prostate cancer. The one or more additional markers of prostate cancer can include, but are not limited to, PSA, filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1. In another embodiment, the patient's age is determined. Age can be used as a continuous predictive variable. For example, increased age is associated with increased risk of prostate cancer. Conversely, decreased age is associated with decreased risk of prostate cancer.

In certain other embodiments, the method of the invention involves administering a therapeutically effective amount of an anti-cancer therapy if the level of filamin A and at least one of the additional markers of prostate cancer are above a threshold level.

In still other embodiments, the method of the invention involves recommending to a healthcare provider to administer an anti-cancer therapy if the level of filamin A and at least one of the additional markers of prostate cancer are above a threshold level.

The biological sample of any of the methods of the invention can be obtained from the blood, serum, urine, organ tissue, biopsy tissue, feces, skin, hair, or cheek tissue, or any other suitable tissue or bodily site.

In still further embodiments, the methods of treatment of the invention can measure the level of filamin A as determined by immunoassay or ELISA. In still other embodiments, the level of filamin A can be determined by (i) contacting the biological sample with a reagent that selectively binds to the filamin A to form a biomarker complex, and (ii) detecting the biomarker complex. The reagent can be an anti-filamin A antibody that selectively binds to at least one epitope of filamin A.

In certain other embodiments, the level of filamin A can be determined by measuring the amount of filamin A mRNA in the biological sample. The filamin A mRNA level can be determine by an amplification reaction, including (a) a polymerase chain reaction (PCR); (b) a nucleic acid sequence-based amplification assay (NASBA); (c) a transcription mediated amplification (TMA); (d) a ligase chain reaction (LCR); or (e) a strand displacement amplification (SDA). The level of filamin A mRNA can also be determined by a hybridization assay using an oligonucleotide that is complementary to a portion of a filamin A mRNA.

In still another aspect, the present invention relates to a kit for detecting filamin A in a biological sample comprising at least one reagent for measuring the level of filamin A in the biological sample, and a set of instructions for measuring the level of filamin A. The reagent can be an anti-filamin A antibody. The kit can also comprise a means to detect the anti-filamin A antibody, such as a detectable secondary antibody.

The kit of the invention may also include a reagent that is an oligonucleotide that is complementary to a filamin A mRNA.

The kit of the invention can also include a set of instructions which set forth an immunoassay or ELISA for detecting the filamin A level in the biological sample. The instruction may set forth an amplification or hybridization reaction for assaying the level of filamin A mRNA in the biological sample. The amplification reaction can be (a) a polymerase chain reaction (PCR); (b) a nucleic acid sequence-based amplification assay (NASBA); (c) a transcription mediated amplification (TMA); (d) a ligase chain reaction (LCR); or (e) a strand displacement amplification (SDA).

In still another aspect, the present invention provides a panel for use in a method of detecting at least two markers for prostate cancer, the panel comprising at least two detection reagents, wherein each detection reagent is specific for the detection of at least one prostate cancer marker of a set of markers, wherein the set of markers comprises filamin A and at least one other prostate cancer related marker selected from the group consisting of PSA, filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1. In another embodiment, the patient's age is also used as a continuous predictor variable.

In yet another aspect, the present invention provides a panel for use in a method of treating prostate cancer, the panel comprising at least two detection reagents, wherein each detection reagent is specific for the detection of at least one prostate cancer marker of a set of markers, wherein the set of markers comprises filamin A and at least one other prostate cancer related marker selected from the group consisting of PSA, filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1. In another embodiment, the patient's age is also used as a continuous predictor variable.

In still another aspect, the invention provides a panel for use in a method of monitoring the treatment of prostate cancer, the panel comprising at least two detection reagents, wherein each detection reagent is specific for the detection of at least one prostate cancer marker of a set of markers, wherein the set of markers comprises filamin A and at least one other prostate cancer related marker selected from the group consisting of PSA, filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1. In another embodiment, the patient's age is also used as a continuous predictor variable.

In still another aspect, the present invention relates to the use of a panel comprising a plurality of detection reagents specific for detecting markers of prostate cancer in a method for diagnosing and/or treating prostate cancer, wherein at least one detection reagent of the panel is specific for detecting filamin A, and wherein the remaining one or more detection reagents are specific for detecting a prostate cancer marker selected from the group consisting of PSA, filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1. In another embodiment, the patient's age is also used as a continuous predictor variable.

In yet another aspect, the invention provides methods for diagnosing an abnormal prostate state in a subject comprising: (1) determining a level of filamin A in combination with one or more additional prostate cancer related markers selected from the group consisting of PSA, filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1 in a biological sample from the subject; and (2) comparing the level of the filamin A and level of the one or more prostate cancer related markers in the biological sample with the corresponding levels in a normal control sample, wherein an altered level of the filamin A and the one or more prostate cancer related markers in the biological sample relative to the normal control sample is indicative of an abnormal prostate state in the subject. In another embodiment, the patient's age is also used as a continuous predictor variable.

In certain embodiments, the one or more prostate cancer related markers is selected from the group consisting of filamin B, LY9, and keratin 19. In certain embodiments, an increased level of filamin A and at least one or more prostate cancer related markers selected from the group consisting of filamin B, LY9, and keratin 19 in the biological sample relative to a normal control sample is indicative of an abnormal prostate state in the subject. In another embodiment, the patient's age is also used as a continuous predictor variable.

In certain embodiments, no increase in the detected level of expression of filamin A and at least one of the prostate-cancer related markers selected from the group consisting of filamin B, LY9, and keratin 19 in the biological sample relative to a normal control sample is indicative of a normal prostate state in the subject. In such embodiments, levels of one, two, or all three of filamin B, LY9, and keratin 19 can be detected. In certain embodiments, none of the markers have increased levels. In another embodiment, the patient's age is also used as a continuous predictor variable.

In certain embodiments, the method further comprises detecting the level of prostate specific antigen (PSA) in the biological sample and preferably further comprising comparing the level of PSA in the biological sample to the level of PSA in a normal control sample. In certain embodiments, an increase in the level of filamin A and at least one or more prostate cancer related markers selected from the group consisting of filamin B, LY9, and keratin 19 in the biological sample relative to the normal control sample, in combination with an increase in the level of PSA in the biological sample as compared to a normal control sample has greater predictive value of the subject having an abnormal prostate state than the predictive value of a single marker alone. In certain embodiments, no increase in the detected level of expression of filamin A and in combination with the one or more prostate-cancer related markers selected from the group consisting of filamin B, LY9, and keratin 19 in the biological sample relative to the normal control sample, in further combination with a decreased or normal level of PSA in the biological sample as compared to the level of PSA in the normal control sample has a greater predictive value of the subject having a normal prostate state than any single marker alone. In another embodiment, the patient's age is also used as a continuous predictor variable.

Throughout the methods, kits, and panels of the invention, filamin A in combination with one or more of filamin B, LY9 and keratin 19 is understood filamin A in combination with any of filamin B; LY9; keratin 19; filamin B and LY9; filamin B and keratin 19; LY9 and keratin 19; or filamin B, LY9, and keratin 19. In one embodiment, the methods, kits and panels of the invention include filamin A in combination with filamin B, and Keratin 19 (KRT19). In one embodiment, the methods, kits and panels of the invention include filamin A in combination with filamin B, Keratin 19 (KRT19), and a determination of the patient's age.

Further, the invention contemplates that filamin A may be combined with any one, two, three, four, five, six, seven, eight, nine, ten, eleven, twelve, thirteen, fourteen, fifteen, sixteen, seventeen, eighteen, nineteen, twenty or more other prostate cancer related markers in any combinations, including any of PSA, filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1. In one embodiment, the methods, kits and panels of the invention include filamin A in combination with filamin B, and Keratin 19 (KRT19).

In certain embodiments of the invention, the abnormal prostate state is prostate cancer.

In certain embodiments of the invention, the prostate cancer is androgen-dependent prostate cancer. In certain embodiments of the invention, the prostate cancer is androgen-independent prostate cancer. In certain embodiments of the invention, the prostate cancer is aggressive prostate cancer. In certain embodiments of the invention, the prostate cancer is non-aggressive prostate cancer.

In certain embodiments of the invention, the abnormal prostate state is benign prostate hyperplasia.

In another aspect, the invention provides a method for identifying a subject as being at increased risk for developing prostate cancer, the method comprising: (1) determining a level of filamin A in combination with one or more additional prostate cancer related markers selected from the group consisting of PSA, filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1 in a biological sample from the subject; and (2) comparing the level of filamin A and the one or more prostate cancer related markers in the biological sample with the level of the markers in a normal control sample, wherein an altered level of the markers in the biological sample relative to the control sample is indicative of an increased risk for developing prostate cancer in the subject. In another embodiment, the patient's age is also used as a continuous predictor variable.

In certain embodiments, filamin A detection is combined with detection of one or more prostate cancer related markers selected from the group consisting of filamin B, LY9, and keratin 19. In certain embodiments, an increased level of filamin A and one or more prostate cancer related markers selected from the group consisting of filamin B, LY9, and keratin 19 in the biological sample relative to the normal control sample is indicative of an increased risk for developing prostate cancer in the subject. In certain embodiments, no increase in the detected level of expression of filamin A and of each of the one or more prostate-cancer related markers selected from the group consisting of filamin B, LY9, and keratin 19 in the biological sample relative to the normal control sample is indicative of no increased risk for developing prostate cancer in the subject. In another embodiment, the patient's age is also used as a continuous predictor variable.

In certain embodiments, the method further comprises detecting the level filamin A together with prostate specific antigen (PSA) in the biological sample. In this embodiment, the method involves comparing the levels of filamin A and PSA in the biological sample to the corresponding levels in a normal control sample. In certain embodiments, the method further comprises measuring the levels of one or more additional prostate cancer related markers selected from the group consisting of filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1 in the biological sample relative to the normal control sample, thereby increasing the predictive value of developing prostate cancer in the subject. In certain other embodiments, no increase in the detected level of expression of filamin A and PSA in the biological sample relative to the normal sample is indicative of having no increased risk for developing prostate cancer. In still further embodiments, no increase in the detected levels of one or more additional prostate cancer related markers selected from the group consisting of filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1 is indicative of no increased risk of prostate cancer, which has a greater predictive value of no increased risk of prostate cancer than evaluating filamin A and/or PSA alone. In another embodiment, the patient's age is also used as a continuous predictor variable.

In certain embodiments of the diagnostic or prognostic methods of the invention, the method of diagnosis of the invention is carried out on the basis of filamin A, optionally on the additional basis of PSA, and still optionally on the basis of one or more additional prostate cancer related markers selected from the group consisting of filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1. In certain embodiments, the one or more additional prostate cancer related markers is selected from the group consisting of keratin 7, keratin 8, and keratin 15. In certain other embodiments, the one or more additional prostate cancer related markers is selected from the group consisting of keratin 7 and keratin 15. In certain other embodiments, the one or more additional prostate cancer markers is selected from the group consisting of keratin 7, 15, and 19. In another embodiment, the patient's age is also used as a continuous predictor variable.

In certain embodiments, the control sample for filamin A and PSA is the same control sample as for the one or more additional prostate cancer related markers of the invention. In certain embodiments, the control sample for the filamin A and PSA is different from the control sample used for the one or more additional prostate cancer related markers of the invention. In still other embodiments, the control sample for the filamin A is different from the control sample used for PSA, which are each also different from the control sample used to measure the one or more additional prostate cancer markers.

In certain embodiments of the diagnostic methods of the invention, wherein one or more prostate cancer related markers that are combined with filamin A is selected from the group consisting of filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1, an increased level of one or more of the prostate cancer related markers in the biological sample relative to a normal control sample is indicative of an abnormal prostate state in the subject. In certain embodiments of the diagnostic methods of the invention, wherein one or more additional prostate cancer related markers is selected from the group consisting of filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1, a decreased or normal level of one or more of the additional prostate cancer related markers in the biological sample relative to a normal control sample is indicative of an abnormal prostate state in the subject. In certain embodiments of the diagnostic methods of the invention, wherein one or more prostate cancer related markers is selected from the group consisting of filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1, an increased level of one or more of the additional prostate cancer related markers in the biological sample relative to a normal control sample is indicative of a normal prostate state in the subject. In certain embodiments of the diagnostic methods of the invention, wherein one or more prostate cancer related markers is selected from the group consisting of filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1, a decreased or normal level of one or more of the prostate cancer related markers in the biological sample relative to a normal control sample is indicative of a normal prostate state in the subject. In another embodiment, the patient's age is also used as a continuous predictor variable.

In certain embodiments of the prognostic methods of the invention, wherein the one or more additional prostate cancer related markers that are combined with filamin A is selected from the group consisting of PSA, filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1, an increased level of one or more of the additional prostate cancer related markers in the biological sample relative to a normal control sample—in addition to increased filamin A—is indicative of an increased risk of developing prostate cancer in the subject. In certain embodiments of the prognostic methods of the invention, wherein one or more additional prostate cancer related markers is selected from the group consisting of PSA, filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1, a decreased or normal level of one or more of the additional prostate cancer related markers in the biological sample relative to a normal control sample—in addition to decreased filamin A—is indicative of a decreased risk of developing prostate cancer in the subject. In certain embodiments of the prognostic methods of the invention, wherein one or more additional prostate cancer related markers is selected from the group consisting of PSA, filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1, an increased level of one or more of the prostate cancer related markers in the biological sample relative to a normal control sample—in addition to increased filamin A—is indicative of increased risk of developing prostate cancer in the subject. In certain embodiments of the prognostic methods of the invention, wherein one or more additional prostate cancer related markers is selected from the group consisting of PSA, filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1, a decreased or normal level of one or more of the additional prostate cancer related markers in the biological sample—in addition to decreased filamin A—relative to a normal control sample is indicative of no increased risk of developing prostate cancer in the subject. In another embodiment, the patient's age is also used as a continuous predictor variable.

In certain embodiments that involve the detection of both filamin A and PSA, the method of the invention can comprise detection of one or more additional prostate cancer related markers that are selected from the group consisting of filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1. In certain embodiments, an increase in the level of both filamin A and PSA in combination with an increase in the level of at least one of the additional prostate cancer related markers selected from the group consisting of filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1 is indicative of an abnormal prostate state in the subject wherein the method has greater diagnostic or predictive value than the value of any of the individual markers alone. In certain other embodiments, a decrease in the level of both filamin A and PSA in combination with a decrease in the level of at least one of the additional prostate cancer related markers selected from the group consisting of filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1 is indicative of a normal prostate state in the subject wherein the method has greater diagnostic or predictive value than the value of any of the individual markers alone. In another embodiment, the patient's age is also used as a continuous predictor variable.

In various embodiments of any of the diagnostic or prognostic methods of the invention, the method may further comprise comparing the level of the one or more prostate cancer related markers in the biological sample with the level of the one or more prostate cancer related markers in a control sample selected from the group consisting of: a sample obtained from the same subject at an earlier time point than the biological sample, a sample from a subject with benign prostatic hyperplasia (BPH), a sample from a subject with non-metastatic prostate cancer, a sample from a subject with metastatic prostate cancer, a sample from a subject with androgen sensitive prostate cancer, a sample from a subject with androgen insensitive prostate cancer, a sample from a subject with aggressive prostate cancer, and a sample from a subject with non-aggressive prostate cancer. In such embodiments, comparison with one or more additional control sample can facilitate differentiating between two prostate cancer states selected from the group consisting of: normal prostate and prostate cancer, benign prostate hyperplasia and prostate cancer, benign prostate hyperplasia and normal prostate, androgen dependent and androgen independent prostate cancer, aggressive prostate cancer and non-aggressive prostate cancer, and metastatic prostate cancer and non-metastatic prostate cancer; or differentiating between any two or more of normal prostate, prostate cancer, benign prostate hyperplasia, androgen dependent prostate cancer, androgen independent prostate cancer, aggressive prostate cancer, non-aggressive prostate cancer, metastatic prostate cancer, and non-metastatic prostate cancer.

In certain embodiments of the invention, when a tumor is present, the method further comprises detecting the size of the prostate tumor in the subject.

In certain embodiments of the diagnostic and prognostic methods the invention, the method further comprises obtaining a sample from a subject.

In certain embodiments of the diagnostic and prognostic methods the invention, the method further comprises selecting a subject who has or is suspected of having prostate cancer.

In certain embodiments of the invention, the method further comprises selecting a treatment regimen for the subject based on the level of the one or more prostate cancer markers. In certain embodiments of the invention, the method further comprises treating the subject with a treatment regimen based on the level of the one or more prostate cancer markers. In certain embodiments, a treatment regimen comprises one or more treatments selected from the group consisting of surgery, radiation, hormone therapy, antibody therapy, growth factor therapy, cytokine therapy, and chemotherapy.

Where applicable or not specifically disclaimed, any one of the embodiments described herein are contemplated to be able to combine with any other one or more embodiments, even though the embodiments are described under different aspects of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

(FIG. 3A) KRT8-KRT15 association is abolished upon ubidecaronone treatment. Note change of direction of arrow between and positions of KRT7 and KRT15 before treatment (FIG. 3A) and after treatment (FIG. 3B). (FIG. 3C) Tubulin-beta 3 interacts with a number of proteins. (FIG. 3D) Expression levels of keratin 19 in biological samples from subjects with prostate cancer or control samples.

(FIG. 9A) ROC curve analysis of sensitivity and false positive rate (FPR) of PSA, FLNB and the combination of PSA and FLNB and (FIG. 9B) area under the curve values (AUC) calculated based on the analysis. The combination of PSA and FLNB was more sensitive than either marker alone.

(FIG. 10A) ROC curve analysis of PSA, FLNB, LY9 and combinations of PSA, FLNB, and LY9 using linear and (FIG. 10B) non-linear scoring functions. The combination of PSA, LY9, and FLNB was more sensitive than any marker alone.

FIG. 11: Medical annotations for the serum samples used in connection with filamin A ELISA, as described in the Example 13.

FIG. 12: Medical annotations for the serum samples used in connection with keratin 19 ELISA, as described in the Example 13.

FIG. 17: AUC summary of AUC for PSA, Age, Filamin A (FLNA), Filamin B (FLNB), Keratin 19 (KRT19), and combinations thereof.

FIG. 18: PCA versus Else: Sensitivity match PSA.

FIG. 20: Accuracy analysis for PCA versus Else.

FIG. 21: Super High Gleason versus Else.

FIG. 23: Accuracy Analysis for Super High Gleason (8-10) versus Else.

FIG. 24: High Gleason Versus Else.

FIG. 26: Accuracy Analysis for High Gleason (7 and above) versus Else.

FIG. 27: Prostate Cancer (PCA) versus Benign Prostatic Hyperplasia (BPH) Sensitivity.

FIG. 29: Accuracy analysis for Prostate Cancer (PCA) versus Benign Prostatic Hyperplasia (BPH).

FIG. 30: FLNA, FLNB, and KRT19 expression in prostate cancer cells in vitro.

DETAILED DESCRIPTION OF THE INVENTION

A. Overview

Figure 1:
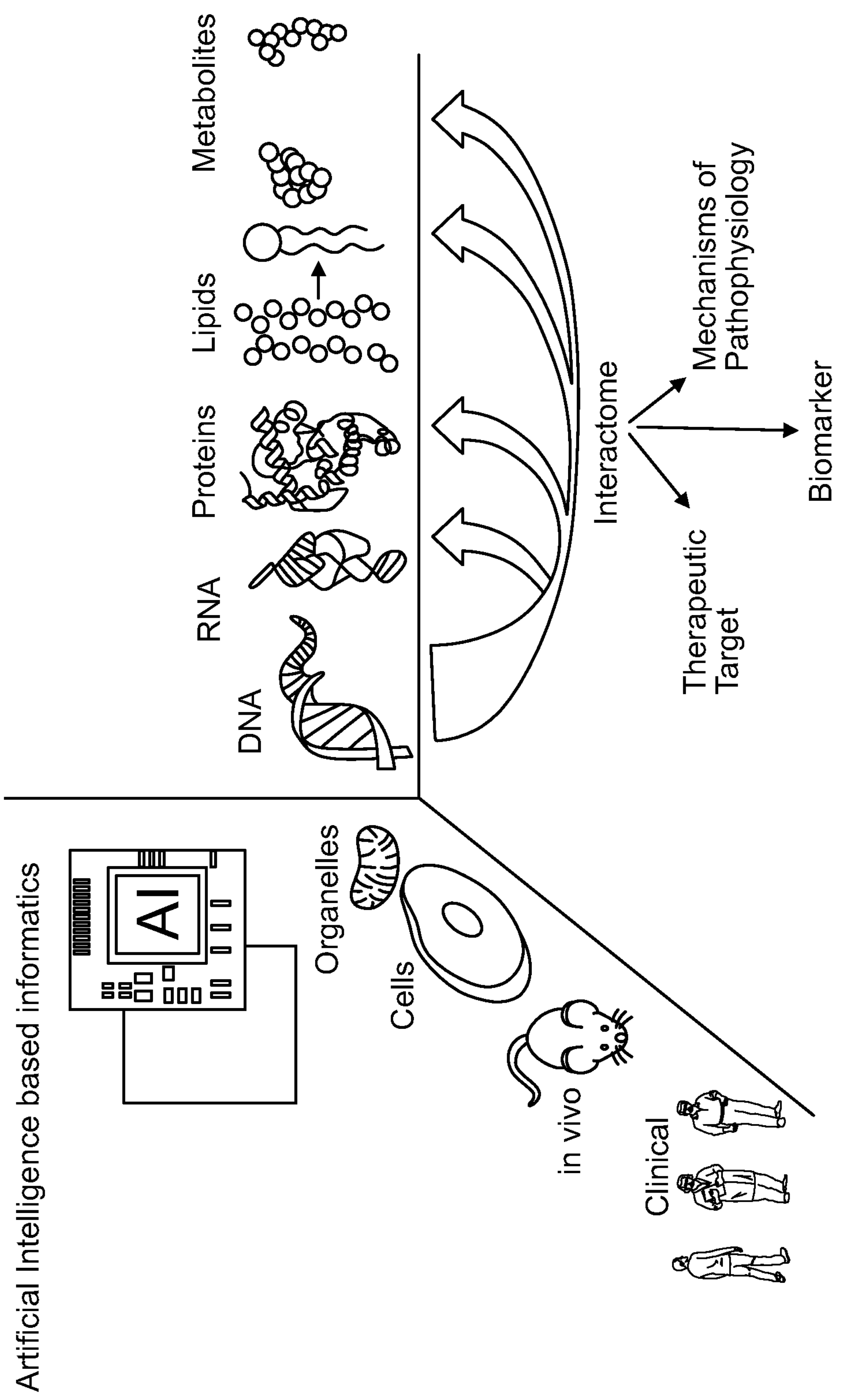
FIG. 1: Schematic representing the underlying principles of the Interrogative Platform Technology (a.k.a. Interrogative Biology™) provided in WO2012119129, the entire contents of which are incorporated herein by reference.

The identification of tumor markers or antigens associated with prostate cancer has stimulated considerable interest as promising tools for the screening, diagnosis, prognosis, clinical management and potential treatment of prostate cancer, and in particular, early detection of prostate cancer. Indeed, early detection mitigates the risk that the cancer will metastasize. Non-metastasized, local prostate tumors can often be cured by radical prostatectomy or radiation therapy, however for patients with distantly spread disease, no curative treatment is available. This emphasizes the need for new prostate (cancer) specific diagnostic tools that may improve the chances for accurate early detection.

While some prostate-specific markers are known, e.g., prostate-specific antigen and prostate stem cell antigen, very few biomarkers are in widespread or routine use as molecular diagnostics for prostate cancer. Accordingly, there remains a need for efficient, accurate, and rapid molecular diagnosis means, particularly which do not suffer from a high proportion of false results. The development of molecular tests for the accurate detection of prostate cancer will also lead to improved management of appropriate therapies, and an overall improved survival rate. Thus, there remains a need to provide an improved diagnostic test for the detection of prostate cancer which is more reliable and accurate than PSA and other current screening tests. The present invention addresses this need by providing the use of a new biomarker, filamin A, either used alone or in combination with other markers, for the accurate and reliable detection of prostate cancer.

As presently described herein, the invention at hand is based, at least in part, on the discovery that filamin A ("FLNA") is differentially regulated in prostate cancer cells and serves as a useful biomarker of prostate cancer. In one embodiment, filamin A can serve as a useful diagnostic biomarker to predict and/or detect the presence of prostate cancer in a subject. In another embodiment, filamin A can serve as a useful prognostic biomarker, serving to inform on the likely progression of prostate cancer in a subject with or without treatment. In still another embodiment, filamin A can serve as a useful predictive biomarker for helping to assess the likely response of prostate cancer to a particular treatment. Accordingly, the invention provides methods that use biomarkers, e.g., filamin A, in the diagnosis of prostate cancer (e.g., prediction of the presence of prostate cancer in a subject), in the prognosis of prostate cancer (e.g., prediction of the course or outcome of prostate cancer with or without treatment), and in the assessment of therapies intended to treat prostate cancer (i.e., filamin A as a theragnostic or predictive marker). The invention further provides compositions of matter (e.g., oligonucleotide probes specific for filamin A mRNA, antibodies specific for filamin A, therapeutic agents that target filamin A), including panels comprising binding or detection reagents specific for filamin A and optionally other biomarkers for use in the methods of the invention, as well as kits for practicing the methods of the invention.

The following is a detailed description of the invention provided to aid those skilled in the art in practicing the present invention. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, figures and other references mentioned herein are expressly incorporated by reference in their entirety.

Although any methods and materials similar or equivalent to those described herein can also be used in the practice or testing of the present invention, the preferred methods and materials are now described. All publications mentioned herein are incorporated herein by reference to disclose and described the methods and/or materials in connection with which the publications are cited.

B. Definitions

Unless defined otherwise, all technical and scientific terms used herein have the meaning commonly understood by a person skilled in the art to which this invention belongs. The following references, the entire disclosures of which are incorporated herein by reference, provide one of skill with a general definition of many of the terms (unless defined otherwise herein) used in this invention: Singleton et al., Dictionary of Microbiology and Molecular Biology ($2^{nd}$ ed. 1994); The Cambridge Dictionary of Science and Technology (Walker ed., 1988); The Glossary of Genetics, $5^{th}$ Ed., R. Rieger et al. (eds.), Springer Verlag (1991); and Hale & Marham, the Harper Collins Dictionary of Biology (1991). Generally, the procedures of molecular biology methods described or inherent herein and the like are common methods used in the art. Such standard techniques can be found in reference manuals such as for example Sambrook et al., (2000, Molecular Cloning—A Laboratory Manual, Third Edition, Cold Spring Harbor Laboratories); and Ausubel et al., (1994, Current Protocols in Molecular Biology, John Wiley & Sons, New-York).

The following terms may have meanings ascribed to them below, unless specified otherwise. However, it should be understood that other meanings that are known or understood by those having ordinary skill in the art are also possible, and within the scope of the present invention. All publications, patent applications, patents, and other references mentioned herein are incorporated by reference in their entirety. In the case of conflict, the present specification, including definitions, will control. In addition, the materials, methods, and examples are illustrative only and not intended to be limiting.

As used herein, the singular forms “a”, “and”, and “the” include plural references unless the context clearly dictates otherwise. All technical and scientific terms used herein have the same meaning.

Unless specifically stated or obvious from context, as used herein, the term “about” is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

As used herein, the term “age” refers to the length of time that a subject has been alive. For example, the age of a subject is calculated from the date of birth of the subject to the current date. Age can be used as a continuous predictive variable for the presence of prostate cancer. For example, increased age is associated with increased risk of prostate cancer. Conversely, decreased age is associated with decreased risk of prostate cancer. Similarly, age can be used as a continuous predictive variable for the stage, or category, of the prostate cancer. For example, age can be used as a continuous predictive variable for the Gleason score of the prostate cancer.

As used herein, the term “amplification” refers to any known in vitro procedure for obtaining multiple copies (“amplicons”) of a target nucleic acid sequence or its complement or fragments thereof. In vitro amplification refers to production of an amplified nucleic acid that may contain less than the complete target region sequence or its complement. Known in vitro amplification methods include, e.g., transcription-mediated amplification, replicase-mediated amplification, polymerase chain reaction (PCR) amplification, ligase chain reaction (LCR) amplification and strand-displacement amplification (SDA including multiple strand-displacement amplification method (MSDA)). Replicase-mediated amplification uses self-replicating RNA molecules, and a replicase such as Q-β-replicase (e.g., Kramer et al., U.S. Pat. No. 4,786,600). PCR amplification is well known and uses DNA polymerase, primers and thermal cycling to synthesize multiple copies of the two complementary strands of DNA or cDNA (e.g., Mullis et al., U.S. Pat. Nos. 4,683,195, 4,683,202, and 4,800,159). LCR amplification uses at least four separate oligonucleotides to amplify a target and its complementary strand by using multiple cycles of hybridization, ligation, and denaturation (e.g., EP Pat. App. Pub. No. 0 320 308). SDA is a method in which a primer contains a recognition site for a restriction endonuclease that permits the endonuclease to nick one strand of a hemimodified DNA duplex that includes the target sequence, followed by amplification in a series of primer extension and strand displacement steps (e.g., Walker et al., U.S. Pat. No. 5,422,252). Two other known strand-displacement amplification methods do not require endonuclease nicking (Dattagupta et al., U.S. Pat. Nos. 6,087,133 and 6,124,120 (MSDA)). Those skilled in the art will understand that the oligonucleotide primer sequences of the present invention may be readily used in any in vitro amplification method based on primer extension by a polymerase. (see generally Kwoh et al., 1990, Am. Biotechnol. Lab. 8:14-25 and (Kwoh et al., 1989, Proc. Natl. Acad. Sci. USA 86, 1173-1177; Lizardi et al., 1988, BioTechnology 6:1197-1202; Malek et al., 1994, Methods Mol. Biol., 28:253-260; and Sambrook et al., 2000, Molecular Cloning—A Laboratory Manual, Third Edition, CSH Laboratories). As commonly known in the art, the oligos are designed to bind to a complementary sequence under selected conditions.

As used herein, the term “antigen” refers to a molecule, e.g., a peptide, polypeptide, protein, fragment, or other biological moiety, which elicits an antibody response in a subject, or is recognized and bound by an antibody.

As used herein, the term “area under the curve” or “AUC” refers to the area under the curve in a plot of sensitivity versus specificity. For example, see FIGS. 18, 21, 24, and 27. In one embodiment, the AUC for a biomarker, or combination of biomarkers, of the invention is 0.5. In another embodiment, the AUC for a biomarker, or combination of biomarkers, of the invention is 0.6. In another embodiment, the AUC for a biomarker, or combination of biomarkers, of the invention is 0.7. In another embodiment, the AUC for a biomarker, or combination of biomarkers, of the invention is 0.8. In another embodiment, the AUC for a biomarker, or combination of biomarkers, of the invention is 0.9. In another embodiment, the AUC for a biomarker, or combination of biomarkers, of the invention is 1.0. In specific embodiments, the AUC for a biomarker, or combination of biomarkers, of the invention is 0.5, 0.51, 0.52, 0.53, 0.54, 0.55, 0.56, 0.57, 0.58, 0.59, 0.6, 0.61, 0.62, 0.63, 0.64, 3.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99 or 1.0. In one embodiment, the AUC for a biomarker, or combination of biomarkers, of the invention is at least 0.5. In another embodiment, the AUC for a biomarker, or combination of biomarkers, of the invention is at least 0.6. In another embodiment, the AUC for a biomarker, or combination of biomarkers, of the invention is at least 0.7. In another embodiment, the AUC for a biomarker, or combination of biomarkers, of the invention is at least 0.8. In another embodiment, the AUC for a biomarker, or combination of biomarkers, of the invention is at least 0.9. In another embodiment, the AUC for a biomarker, or combination of biomarkers, of the invention is at least 1.0. In specific embodiments, the AUC for a biomarker, or combination of biomarkers, of the invention is at least 0.5, 0.51, 0.52, 0.53, 0.54, 0.55, 0.56, 0.57, 0.58, 0.59, 0.6, 0.61, 0.62, 0.63, 0.64, 3.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99 or 1.0

As used herein, the term "biomarker" is understood to mean a measurable characteristic that reflects in a quantitative or qualitative manner the physiological state of an organism. The physiological state of an organism is inclusive of any disease or non-disease state, e.g., a subject having prostate cancer or a subject who is otherwise healthy. Said another way, biomarkers are characteristics that can be objectively measured and evaluated as indicators of normal processes, pathogenic processes, or pharmacologic responses to a therapeutic intervention. Biomarkers can be clinical parameters (e.g., age, performance status), laboratory measures (e.g., molecular biomarkers, such as prostate specific antigen), imaging-based measures, or genetic or other molecular determinants, such as phosphorylation or acetylation state of a protein marker, methylation state of nucleic acid, or any other detectable molecular modification to a biological molecule. Examples of biomarkers include, for example, polypeptides, peptides, polypeptide fragments, proteins, antibodies, hormones, polynucleotides, RNA or RNA fragments, microRNA (miRNAs), lipids, polysaccharides, and other bodily metabolites. Other examples of biomarkers include the age of the patient.

Preferably, a biomarker of the present invention is modulated (e.g., increased or decreased level) in a biological sample from a subject or a group of subjects having a first phenotype (e.g., having a disease) as compared to a biological sample from a subject or group of subjects having a second phenotype (e.g., not having the disease, e.g., a control). A biomarker may be differentially present at any level, but is generally present at a level that is increased relative to normal or control levels by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more; or is generally present at a level that is decreased relative to normal or control levels by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent). A biomarker is preferably differentially present at a level that is statistically significant (e.g., a p-value less than 0.05 and/or a q-value of less than 0.10 as determined using either Welch's T-test or Wilcoxon's rank-sum Test).

As used herein, the term "biopsy" or "biopsy tissue" refers to a sample of tissue (e.g., prostate tissue) that is removed from a subject for the purpose of determining if the sample contains cancerous tissue. The biopsy tissue is then examined (e.g., by microscopy) for the presence or absence of cancer.

As used herein, the term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "control sample," as used herein, refers to any clinically relevant comparative sample, including, for example, a sample from a healthy subject not afflicted with an oncological disorder, e.g., prostate cancer, or a sample from a subject from an earlier time point, e.g., prior to treatment, an earlier tumor assessment time point, at an earlier stage of treatment. A control sample can be a purified sample, protein, and/or nucleic acid provided with a kit. Such control samples can be diluted, for example, in a dilution series to allow for quantitative measurement of levels of analytes, e.g., markers, in test samples. A control sample may include a sample derived from one or more subjects. A control sample may also be a sample made at an earlier time point from the subject to be assessed. For example, the control sample could be a sample taken from the subject to be assessed before the onset of an oncological disorder, e.g., prostate cancer, at an earlier stage of disease, or before the administration of treatment or of a portion of treatment. The control sample may also be a sample from an animal model, or from a tissue or cell line derived from the animal model of oncological disorder, e.g., prostate cancer. The level of activity or expression of one or more markers (e.g., 1, 2, 3, 4, 5, 6, 7, 8, or 9 or more markers) in a control sample consists of a group of measurements that may be determined, e.g., based on any appropriate statistical measurement, such as, for example, measures of central tendency including average, median, or modal values. Different from a control is preferably statistically significantly different from a control.

As used herein, "changed as compared to a control" sample or subject is understood as having a level of the analyte or diagnostic or therapeutic indicator (e.g., marker) to be detected at a level that is statistically different than a sample from a normal, untreated, or abnormal state control sample. Changed as compared to control can also include a difference in the rate of change of the level of one or more markers obtained in a series of at least two subject samples obtained over time. Determination of statistical significance is within the ability of those skilled in the art and can include any acceptable means for determining and/or measuring statistical significance, such as, for example, the number of standard deviations from the mean that constitute a positive or negative result, an increase in the detected level of a biomarker in a sample (e.g., prostate cancer sample) versus a control or healthy sample, wherein the increase is above some threshold value, or a decrease in the detected level of a biomarker in a sample (e.g., prostate cancer sample) versus a control or healthy sample, wherein the decrease is below some threshold value. The threshold value can be determine by any suitable means by measuring the biomarker levels in a plurality of tissues or samples known to have a disease, e.g., prostate cancer, and comparing those levels to a normal sample and calculating a statistically significant threshold value.

The term "control level" refers to an accepted or predetermined level of a marker in a subject sample. A control level can be a range of values. Marker levels can be compared to a single control value, to a range of control values, to the upper level of normal, or to the lower level of normal as appropriate for the assay.

In one embodiment, the control is a standardized control, such as, for example, a control which is predetermined using an average of the levels of expression of one or more markers from a population of subjects having no cancer, especially subjects having no prostate cancer. In still other embodiments of the invention, a control level of a marker is the level of the marker in a non-cancerous sample(s) derived from the subject having cancer. For example, when a biopsy or other medical procedure reveals the presence of cancer in one portion of the tissue, the control level of a marker may be determined using the non-affected portion of the tissue, and this control level may be compared with the level of the marker in an affected portion of the tissue.

In certain embodiments, the control can be from a subject, or a population of subject, having an abnormal prostate state. For example, the control can be from a subject suffering from benign prostate hyperplasia (BPH), androgen sensitive prostate cancer, androgen insensitive or resistant prostate cancer, aggressive prostate cancer, non-aggressive prostate cancer, metastatic prostate cancer, or non-metastatic prostate cancer. It is understood that not all markers will have different levels for each of the abnormal prostate states listed. It is understood that a combination of marker levels may be most useful to distinguish between abnormal prostate states, possibly in combination with other diagnostic methods. Further, marker levels in biological samples can be compared to more than one control sample (e.g., normal, abnormal, from the same subject, from a population control). Marker levels can be used in combination with other signs or symptoms of an abnormal prostate state to provide a diagnosis for the subject.

A control can also be a sample from a subject at an earlier time point, e.g., a baseline level prior to suspected presence of disease, before the diagnosis of a disease, at an earlier assessment time point during watchful waiting, before the treatment with a specific agent (e.g., chemotherapy, hormone therapy) or intervention (e.g., radiation, surgery). In certain embodiments, a change in the level of the marker in a subject can be more significant than the absolute level of a marker, e.g., as compared to control.

As used herein, "detecting", "detection", "determining", and the like are understood to refer to an assay performed for identification of filamin A and/or an additional one or more specific markers in a sample, e.g., one or more (e.g., 1, 2, 3, 4, 5, 6, 7, 8, or 9 or more) markers selected from the group consisting of PSA, filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1. The amount of marker expression or activity detected in the sample can be none or below the level of detection of the assay or method.

As used herein, the term "DNA" or "RNA" molecule or sequence (as well as sometimes the term "oligonucleotide") refers to a molecule comprised generally of the deoxyribonucleotides adenine (A), guanine (G), thymine (T) and/or cytosine (C). In "RNA", T is replaced by uracil (U).

The terms "disorders", "diseases", and "abnormal state" are used inclusively and refer to any deviation from the normal structure or function of any part, organ, or system of the body (or any combination thereof). A specific disease is manifested by characteristic symptoms and signs, including biological, chemical, and physical changes, and is often associated with a variety of other factors including, but not limited to, demographic, environmental, employment, genetic, and medically historical factors. Certain characteristic signs, symptoms, and related factors can be quantitated through a variety of methods to yield important diagnostic information. As used herein the disorder, disease, or abnormal state is an abnormal prostate state, including benign prostate hyperplasia and cancer, particularly prostate cancer. The abnormal prostate state of prostate cancer can be further subdivided into stages and grades of prostate cancer as provided, for example in Prostate. In: Edge S B, Byrd D R, Compton C C, et al., eds.: AJCC Cancer Staging Manual. 7th ed. New York, N.Y.: Springer, 2010, pp 457-68 (incorporated herein by reference in its entirety). Further, abnormal prostate states can be classified as one or more of benign prostate hyperplasia (BPH), androgen sensitive prostate cancer, androgen insensitive or resistant prostate cancer, aggressive prostate cancer, non-aggressive prostate cancer, metastatic prostate cancer, and non-metastatic prostate cancer.

As used herein, a sample obtained at an "earlier time point" is a sample that was obtained at a sufficient time in the past such that clinically relevant information could be obtained in the sample from the earlier time point as compared to the later time point. In certain embodiments, an earlier time point is at least four weeks earlier. In certain embodiments, an earlier time point is at least six weeks earlier. In certain embodiments, an earlier time point is at least two months earlier. In certain embodiments, an earlier time point is at least three months earlier. In certain embodiments, an earlier time point is at least six months earlier. In certain embodiments, an earlier time point is at least nine months earlier. In certain embodiments, an earlier time point is at least one year earlier. Multiple subject samples (e.g., 3, 4, 5, 6, 7, or more) can be obtained at regular or irregular intervals over time and analyzed for trends in changes in marker levels. Appropriate intervals for testing for a particular subject can be determined by one of skill in the art based on ordinary considerations.

The term "expression" is used herein to mean the process by which a polypeptide is produced from DNA. The process involves the transcription of the gene into mRNA and the translation of this mRNA into a polypeptide. Depending on the context in which used, "expression" may refer to the production of RNA, or protein, or both.

As used herein, "greater predictive value" is understood as an assay that has significantly greater sensitivity and/or specificity, preferably greater sensitivity and specificity, than the test to which it is compared. The predictive value of a test can be determined using an ROC analysis. In an ROC analysis a test that provides perfect discrimination or accuracy between normal and disease states would have an area under the curve (AUC)=1, whereas a very poor test that provides no better discrimination than random chance would have AUC=0.5. As used herein, a test with a greater predictive value will have a statistically improved AUC as compared to another assay. The assays are preformed in an appropriate subject population.

A "higher level of expression", "higher level", and the like of a marker refers to an expression level in a test sample that is greater than the standard error of the assay employed to assess expression, and is preferably at least 25% more, at least 50% more, at least 75% more, at least two, at least three, at least four, at least five, at least six, at least seven, at least eight, at least nine, or at least ten times the expression level of the marker in a control sample (e.g., sample from a healthy subject not having the marker associated disease, i.e., an abnormal prostate state) and preferably, the average expression level of the marker or markers in several control samples.

As used herein, the term "hybridization," as in "nucleic acid hybridization," refers generally to the hybridization of two single-stranded nucleic acid molecules having complementary base sequences, which under appropriate conditions will form a thermodynamically favored double-stranded structure. Examples of hybridization conditions can be found in the two laboratory manuals referred above (Sambrook et al., 2000, supra and Ausubel et al., 1994, supra, or further in Higgins and Hames (Eds.) "Nucleic acid hybridization, a practical approach" IRL Press Oxford, Washington D.C., (1985)) and are commonly known in the art. In the case of a hybridization to a nitrocellulose filter (or other such support like nylon), as for example in the well-known Southern blotting procedure, a nitrocellulose filter can be incubated overnight at a temperature representative of the desired stringency condition (60-65° C. for high stringency, 50-60° C. for moderate stringency and 40-45° C. for low stringency conditions) with a labeled probe in a solution containing high salt (6×SSC or 5×SSPE), 5×Denhardt's solution, 0.5% SDS, and 100 g/ml denatured carrier DNA (e.g., salmon sperm DNA). The non-specifically binding probe can then be washed off the filter by several washes in 0.2×SSC/0.1% SDS at a temperature which is selected in view of the desired stringency: room temperature (low stringency), 42° C. (moderate stringency) or 65° C. (high stringency). The salt and SDS concentration of the washing solutions may also be adjusted to accommodate for the desired stringency. The selected temperature and salt concentration is based on the melting temperature (Tm) of the DNA hybrid. Of course, RNA-DNA hybrids can also be formed and detected. In such cases, the conditions of hybridization and washing can be adapted according to well-known methods by the person of ordinary skill. Stringent conditions will be preferably used (Sambrook et al., 2000, supra). Other protocols or commercially available hybridization kits (e.g., ExpressHyb® from BD Biosciences Clonetech) using different annealing and washing solutions can also be used as well known in the art. As is well known, the length of the probe and the composition of the nucleic acid to be determined constitute further parameters of the hybridization conditions. Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility. Hybridizing nucleic acid molecules also comprise fragments of the above described molecules. Furthermore, nucleic acid molecules which hybridize with any of the aforementioned nucleic acid molecules also include complementary fragments, derivatives and allelic variants of these molecules. Additionally, a hybridization complex refers to a complex between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., Cot or Rot analysis) or between one nucleic acid sequence present in solution and another nucleic acid sequence immobilized on a solid support (e.g., membranes, filters, chips, pins or glass slides to which, e.g., cells have been fixed).

As used herein, the term "identical" or "percent identity" in the context of two or more nucleic acid or amino acid sequences, refers to two or more sequences or subsequences that are the same, or that have a specified percentage of amino acid residues or nucleotides that are the same (e.g., 60% or 65% identity, preferably, 70-95% identity, more preferably at least 95% identity), when compared and aligned for maximum correspondence over a window of comparison, or over a designated region as measured using a sequence comparison algorithm as known in the art, or by manual alignment and visual inspection. Sequences having, for example, 60% to 95% or greater sequence identity are considered to be substantially identical. Such a definition also applies to the complement of a test sequence. Preferably the described identity exists over a region that is at least about 15 to 25 amino acids or nucleotides in length, more preferably, over a region that is about 50 to 100 amino acids or nucleotides in length. Those having skill in the art will know how to determine percent identity between/among sequences using, for example, algorithms such as those based on CLUSTALW computer program (Thompson Nucl. Acids Res. 2 (1994), 4673-4680) or FASTDB (Brutlag Comp. App. Biosci. 6 (1990), 237-245), as known in the art. Although the FASTDB algorithm typically does not consider internal non-matching deletions or additions in sequences, i.e., gaps, in its calculation, this can be corrected manually to avoid an overestimation of the % identity.

CLUSTALW, however, does take sequence gaps into account in its identity calculations. Also available to those having skill in this art are the BLAST and BLAST 2.0 algorithms (Altschul Nucl. Acids Res. 25 (1977), 3389-3402). The BLASTN program for nucleic acid sequences uses as defaults a word length (W) of 11, an expectation (E) of 10, M=5, N=4, and a comparison of both strands. For amino acid sequences, the BLASTP program uses as defaults a wordlength (W) of 3, and an expectation (E) of 10. The BLOSUM62 scoring matrix (Henikoff Proc. Natl. Acad. Sci., USA, 89, (1989), 10915) uses alignments (B) of 50, expectation (E) of 10, M=5, N=4, and a comparison of both strands. Moreover, the present invention also relates to nucleic acid molecules the sequence of which is degenerate in comparison with the sequence of an above-described hybridizing molecule. When used in accordance with the present invention the term "being degenerate as a result of the genetic code" means that due to the redundancy of the genetic code different nucleotide sequences code for the same amino acid. The present invention also relates to nucleic acid molecules which comprise one or more mutations or deletions, and to nucleic acid molecules which hybridize to one of the herein described nucleic acid molecules, which show (a) mutation(s) or (a) deletion(s).

The term "including" is used herein to mean, and is used interchangeably with, the phrase "including but not limited to."

A subject at "increased risk for developing prostate cancer" may or may not develop prostate cancer. Identification of a subject at increased risk for developing prostate cancer should be monitored for additional signs or symptoms of prostate cancer. The methods provided herein for identifying a subject with increased risk for developing prostate cancer can be used in combination with assessment of other known risk factors or signs of prostate cancer including, but not limited to decreased urinary stream, urgency, hesitancy, nocturia, incomplete bladder emptying, and age.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

As used herein, a "label" refers to a molecular moiety or compound that can be detected or can lead to a detectable signal. A label is joined, directly or indirectly, to a molecule, such as an antibody, a nucleic acid probe or the protein/antigen or nucleic acid to be detected (e.g., an amplified sequence). Direct labeling can occur through bonds or interactions that link the label to the nucleic acid (e.g., covalent bonds or non-covalent interactions), whereas indirect labeling can occur through the use of a "linker" or bridging moiety, such as oligonucleotide(s) or small molecule carbon chains, which is either directly or indirectly labeled. Bridging moieties may amplify a detectable signal. Labels can include any detectable moiety (e.g., a radionuclide, ligand such as biotin or avidin, enzyme or enzyme substrate, reactive group, chromophore such as a dye or colored particle, luminescent compound including a bioluminescent, phosphorescent or chemiluminescent compound, and fluorescent compound). Preferably, the label on a labeled probe is detectable in a homogeneous assay system, i.e., in a mixture, the bound label exhibits a detectable change compared to an unbound label.

The terms "level of expression of a gene", "gene expression level", "level of a marker", and the like refer to the level of mRNA, as well as pre-mRNA nascent transcript(s), transcript processing intermediates, mature mRNA(s) and degradation products, or the level of protein, encoded by the gene in the cell. The "level" of one of more biomarkers means the absolute or relative amount or concentration of the biomarker in the sample.

A "lower level of expression" or "lower level" of a marker refers to an expression level in a test sample that is less than 90%, 85%, 80%, 75%, 70%, 65%, 60%, 55%, 50%, 45%, 40%, 35%, 30%, 25%, 20%, 15%, or 10% of the expression level of the marker in a control sample (e.g., sample from a healthy subjects not having the marker associated disease, i.e., an abnormal prostate state) and preferably, the average expression level of the marker in several control samples.

The term "modulation" refers to upregulation (i.e., activation or stimulation), down-regulation (i.e., inhibition or suppression) of a response (e.g., level of expression of a marker), or the two in combination or apart. A "modulator" is a compound or molecule that modulates, and may be, e.g., an agonist, antagonist, activator, stimulator, suppressor, or inhibitor.

As used herein, "negative fold change" refers to "down-regulation" or "decrease (of expression)" of a gene that is listed herein.

As used herein, "nucleic acid molecule" or "polynucleotides", refers to a polymer of nucleotides. Non-limiting examples thereof include DNA (e.g., genomic DNA, cDNA), RNA molecules (e.g., mRNA) and chimeras thereof. The nucleic acid molecule can be obtained by cloning techniques or synthesized. DNA can be double-stranded or single-stranded (coding strand or non-coding strand [antisense]). Conventional ribonucleic acid (RNA) and deoxyribonucleic acid (DNA) are included in the term "nucleic acid" and polynucleotides as are analogs thereof. A nucleic acid backbone may comprise a variety of linkages known in the art, including one or more of sugar-phosphodiester linkages, peptide-nucleic acid bonds (referred to as "peptide nucleic acids" (PNA); Hydig-Hielsen et al., PCT Intl Pub. No. WO 95/32305), phosphorothioate linkages, methylphosphonate linkages or combinations thereof. Sugar moieties of the nucleic acid may be ribose or deoxyribose, or similar compounds having known substitutions, e.g., 2' methoxy substitutions (containing a 2'-O-methylribofuranosyl moiety; see PCT No. WO 98/02582) and/or 2' halide substitutions. Nitrogenous bases may be conventional bases (A, G, C, T, U), known analogs thereof (e.g., inosine or others; see The Biochemistry of the Nucleic Acids 5-36, Adams et al., ed., 11th ed., 1992), or known derivatives of purine or pyrimidine bases (see, Cook, PCT Int'l Pub. No. WO 93/13121) or "abasic" residues in which the backbone includes no nitrogenous base for one or more residues (Arnold et al., U.S. Pat. No. 5,585,481). A nucleic acid may comprise only conventional sugars, bases and linkages, as found in RNA and DNA, or may include both conventional components and substitutions (e.g., conventional bases linked via a methoxy backbone, or a nucleic acid including conventional bases and one or more base analogs). An "isolated nucleic acid molecule", as is generally understood and used herein, refers to a polymer of nucleotides, and includes, but should not limited to DNA and RNA. The "isolated" nucleic acid molecule is purified from its natural in vivo state, obtained by cloning or chemically synthesized.

As used herein, the term "obtaining" is understood herein as manufacturing, purchasing, or otherwise coming into possession of.

As used herein, "oligonucleotides" or "oligos" define a molecule having two or more nucleotides (ribo or deoxyribonucleotides). The size of the oligo will be dictated by the particular situation and ultimately on the particular use thereof and adapted accordingly by the person of ordinary skill. An oligonucleotide can be synthesized chemically or derived by cloning according to well-known methods. While they are usually in a single-stranded form, they can be in a double-stranded form and even contain a "regulatory region". They can contain natural rare or synthetic nucleotides. They can be designed to enhance a chosen criteria like stability for example. Chimeras of deoxyribonucleotides and ribonucleotides may also be within the scope of the present invention.

As used herein, "one or more" is understood as each value 1, 2, 3, 4, 5, 6, 7, 8, 9, 10, and any value greater than 10.

The term "or" is used inclusively herein to mean, and is used interchangeably with, the term "and/or," unless context clearly indicates otherwise. For example, as used herein, filamin B or LY9 is understood to include filamin B alone, LY9 alone, and the combination of filamin B and LY9.

As used herein, "patient" or "subject" can mean either a human or non-human animal, preferably a mammal. By "subject" is meant any animal, including horses, dogs, cats, pigs, goats, rabbits, hamsters, monkeys, guinea pigs, rats, mice, lizards, snakes, sheep, cattle, fish, and birds. A human subject may be referred to as a patient. It should be noted that clinical observations described herein were made with human subjects and, in at least some embodiments, the subjects are human.

As used herein, "positive fold change" refers to "up-regulation" or "increase (of expression)" of a gene that is listed herein.

As used herein, "preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease). Prevention does not require that the disease or condition never occurs in the subject. Prevention includes delaying the onset or severity of the disease or condition.

As used herein, a "predetermined threshold value" or "threshold value" of a biomarker refers to the level of the biomarker (e.g., the expression level or quantity (e.g., ng/ml) in a biological sample) in a corresponding control/normal sample or group of control/normal samples obtained from normal or healthy subjects, e.g., those males that do not have prostate cancer. The predetermined threshold value may be determined prior to or concurrently with measurement of marker levels in a biological sample. The control sample may be from the same subject at a previous time or from different subjects.

As used herein, a "probe" is meant to include a nucleic acid oligomer or oligonucleotide that hybridizes specifically to a target sequence in a nucleic acid or its complement, under conditions that promote hybridization, thereby allowing detection of the target sequence or its amplified nucleic acid. Detection may either be direct (i.e., resulting from a probe hybridizing directly to the target or amplified sequence) or indirect (i.e., resulting from a probe hybridizing to an intermediate molecular structure that links the probe to the target or amplified sequence). A probe's "target" generally refers to a sequence within an amplified nucleic acid sequence (i.e., a subset of the amplified sequence) that hybridizes specifically to at least a portion of the probe sequence by standard hydrogen bonding or "base pairing." Sequences that are "sufficiently complementary" allow stable hybridization of a probe sequence to a target sequence, even if the two sequences are not completely complementary. A probe may be labeled or unlabeled. A probe can be produced by molecular cloning of a specific DNA sequence or it can also be synthesized. Numerous primers and probes which can be designed and used in the context of the present invention can be readily determined by a person of ordinary skill in the art to which the present invention pertains.

As used herein, the terminology "prognosis", "staging" and "determination of aggressiveness" are defined herein as the prediction of the degree of severity of the prostate cancer and of its evolution as well as the prospect of recovery as anticipated from usual course of the disease. According to the present invention, once the aggressiveness of the prostate cancer has been determined appropriate methods of treatments can be chosen.

As used herein, "prophylactic" or "therapeutic" treatment refers to administration to the subject of one or more agents or interventions to provide the desired clinical effect. If it is administered prior to clinical manifestation of the unwanted condition (e.g., disease or other unwanted state of the host animal) then the treatment is prophylactic, i.e., it protects the host against developing at least one sign or symptom of the unwanted condition, whereas if administered after manifestation of the unwanted condition, the treatment is therapeutic (i.e., it is intended to diminish, ameliorate, or maintain at least one sign or symptom of the existing unwanted condition or side effects therefrom).

As used herein, "prostate cancer," refers to any malignant or pre-malignant form of cancer of the prostate. The term includes prostate in situ carcinomas, invasive carcinomas, metastatic carcimomas and pre-malignant conditions. The term also encompasses any stage or grade of cancer in the prostate. Where the prostate cancer is "metastatic," the cancer has spread or metastasized beyond the prostate gland to a distant site, such as a lymph node or to the bone.

As used herein, a "reference level" of a biomarker means a level of the biomarker that is indicative of a particular disease state, phenotype, or lack thereof, as well as combinations of disease states, phenotypes, or lack thereof. A "positive" reference level of a biomarker means a level that is indicative of a particular disease state or phenotype. A "negative" reference level of a biomarker means a level that is indicative of a lack of a particular disease state or phenotype. For example, a "prostate cancer-positive reference level" of a biomarker means a level of a biomarker that is indicative of a positive diagnosis of prostate cancer in a subject, and a "prostate cancer-negative reference level" of a biomarker means a level of a biomarker that is indicative of a negative diagnosis of prostate cancer in a subject. A "reference level" of a biomarker may be an absolute or relative amount or concentration of the biomarker, a presence or absence of the biomarker, a range of amount or concentration of the biomarker, a minimum and/or maximum amount or concentration of the biomarker, a mean amount or concentration of the biomarker, and/or a median amount or concentration of the biomarker; and, in addition, "reference levels" of combinations of biomarkers may also be ratios of absolute or relative amounts or concentrations of two or more biomarkers with respect to each other. Appropriate positive and negative reference levels of biomarkers for a particular disease state, phenotype, or lack thereof may be determined by measuring levels of desired biomarkers in one or more appropriate subjects, and such reference levels may be tailored to specific populations of subjects (e.g., a reference level may be age-matched so that comparisons may be made between biomarker levels in samples from subjects of a certain age and reference levels for a particular disease state, phenotype, or lack thereof in a certain age group). Such reference levels may also be tailored to specific techniques that are used to measure levels of biomarkers in biological samples (e.g., LC-MS, GC-MS, etc.), where the levels of biomarkers may differ based on the specific technique that is used.

As used herein, "sample" or "biological sample" includes a specimen or culture obtained from any source. Biological samples can be obtained from blood (including any blood product, such as whole blood, plasma, serum, or specific types of cells of the blood), urine, saliva, and the like. Biological samples also include tissue samples, such as biopsy tissues or pathological tissues that have previously been fixed (e.g., formaline snap frozen, cytological processing, etc.). In an embodiment, the biological sample is from blood. In another embodiment, the biological sample is a biopsy tissue from the prostate gland.

As use herein, the phrase "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabeled A) in a reaction containing labeled "A" and the antibody will reduce the amount of labeled A bound to the antibody.

The phrase "specific identification" is understood as detection of a marker of interest with sufficiently low background of the assay and cross-reactivity of the reagents used such that the detection method is diagnostically useful. In certain embodiments, reagents for specific identification of a marker bind to only one isoform of the marker. In certain embodiments, reagents for specific identification of a marker bind to more than one isoform of the marker. In certain embodiments, reagents for specific identification of a marker bind to all known isoforms of the marker.

As used herein, the phrase "subject suspected of having cancer" refers to a subject that presents one or more symptoms indicative of a cancer or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received an initial diagnosis (e.g., a CT scan showing a mass or increased PSA level) but for whom the stage of cancer is not known. The term further includes people who once had cancer (e.g., an individual in remission).

The term "such as" is used herein to mean, and is used interchangeably, with the phrase "such as but not limited to."

As used herein, the term "stage of cancer" refers to a qualitative or quantitative assessment of the level of advancement of a cancer. Criteria used to determine the stage of a cancer include, but are not limited to, the size of the tumor, whether the tumor has spread to other parts of the body and where the cancer has spread (e.g., within the same organ or region of the body or to another organ).

As used herein, the term "staging" refers to commonly used systems for grading/stating cancer, e.g., prostate cancer. In one aspect, staging can take the form of the "Gleason Score", as well known in the art, is the most commonly used system for the grading/staging and prognosis of adenocarcinoma. The system describes a score between 2 and 10, with 2 being the least aggressive and 10 being the most aggressive. The score is the sum of the two most common patterns (grade 1-5) of tumor growth found. To be counted a pattern (grade) needs to occupy more than 5% of the biopsy specimen. The scoring system requires biopsy material (core biopsy or operative specimens) in order to be accurate; cytological preparations cannot be used. The "Gleason Grade" is the most commonly used prostate cancer grading system. It involves assigning numbers to cancerous prostate tissue, ranging from 1 through 5, based on how much the arrangement of the cancer cells mimics the way normal prostate cells form glands. Two grades are assigned to the most common patterns of cells that appear; these two grades (they can be the same or different) are then added together to determine the Gleason score (a number from 1 to 10). The Gleason system is based exclusively on the architectural pattern of the glands of the prostate tumor. It evaluates how effectively the cells of any particular cancer are able to structure themselves into glands resembling those of the normal prostate. The ability of a tumor to mimic normal gland architecture is called its differentiation, and experience has shown that a tumor whose structure is nearly normal (well differentiated) will probably have a biological behavior relatively close to normal, i.e., that is not very aggressively malignant.

A Gleason grading from very well differentiated (grade 1) to very poorly differentiated (grade 5) is usually done for the most part by viewing the low magnification microscopic image of the cancer. There are important additional details which require higher magnification, and an ability to accurately grade any tumor is achieved only through much training and experience in pathology. Gleason grades 1 and 2: These two grades closely resemble normal prostate. They are the least important grades because they seldom occur in the general population and because they confer a prognostic benefit which is only slightly better than grade 3. Both of these grades are composed by mass; in grade 2 they are more loosely aggregated, and some glands wander (invade) into the surrounding muscle (stroma). Gleason grade 3 is the most common grade and is also considered well differentiated (like grades 1 and 2). This is because all three grades have a normal "gland unit" like that of a normal prostate; that is, every cell is part of a circular row which forms the lining of a central space (the lumen). The lumen contains prostatic secretion like normal prostate, and each gland unit is surrounded by prostate muscle which keeps the gland units apart. In contrast to grade 2, wandering of glands (invading) into the stroma (muscle) is very prominent and is the main defining feature. The cells are dark rather than pale and the glands often have more variable shapes.

Gleason Grade 4 is probably the most important grade because it is fairly common and because of the fact that if a lot of it is present, patient prognosis is usually (but not always) worsened by a considerable degree. Grade 4 also shows a considerable loss of architecture. For the first time, disruption and loss of the normal gland unit is observed. In fact, grade 4 is identified almost entirely by loss of the ability to form individual, separate gland units, each with its separate lumen (secretory space). This important distinction is simple in concept but complex in practice. The reason is that there are a variety of different-appearing ways in which the cancer's effort to form gland units can be distorted. Each cancer has its own partial set of tools with which it builds part of the normal structure. Grade 4 is like the branches of a large tree, reaching in a number of directions from the (well differentiated) trunk of grades 1, 2, and 3. Much experience is required for this diagnosis, and not all patterns are easily distinguished from grade 3. This is the main class of poorly differentiated prostate cancer, and its distinction from grade 3 is the most commonly important grading decision.

Gleason grade 5 is an important grade because it usually predicts another significant step towards poor prognosis. Its overall importance for the general population is reduced by the fact that it is less common than grade 4, and it is seldom seen in men whose prostate cancer is diagnosed early in its development. This grade too shows a variety of patterns, all of which demonstrate no evidence of any attempt to form gland units. This grade is often called undifferentiated, because its features are not significantly distinguishing to make it look any different from undifferentiated cancers which occur in other organs. When a pathologist looks at prostate cancer specimens under the microscope and gives them a Gleason grade, an attempt to identify two architectural patterns and assign a Gleason grade to each one is made. There may be a primary or most common pattern and then a secondary or second most common pattern which the pathologist will seek to describe for each specimen; alternatively, there may often be only a single pure grade. In developing his system, Dr. Gleason discovered that by giving a combination of the grades of the two most common patterns he could see in any particular patient's specimens, that he was better able to predict the likelihood that a particular patient would do well or badly. Therefore, although it may seem confusing, the Gleason score which a physician usually gives to a patient, is actually a combination or sum of two numbers which is accurate enough to be very widely used. These combined Gleason sums or scores may be determined as follows:

The lowest possible Gleason score is 2 (1+1), where both the primary and secondary patterns have a Gleason grade of 1 and therefore when added together their combined sum is 2.

Very typical Gleason scores might be 5 (2+3), where the primary pattern has a Gleason grade of 2 and the secondary pattern has a grade of 3, or 6 (3+3), a pure pattern.

Another typical Gleason score might be 7 (4+3), where the primary pattern has a Gleason grade of 4 and the secondary pattern has a grade of 3.

Finally, the highest possible Gleason score is 10 (5+5), when the primary and secondary patterns both have the most disordered Gleason grades of 5.

Another way of staging prostate cancer is by using the TNM System. It describes the extent of the primary tumor (T stage), the absence or presence of spread to nearby lymph nodes (N stage) and the absence or presence of distant spread, or metastasis (M stage). Each category of the TNM classification is divided into subcategories representative of its particular state. For example, primary tumors (T stage) may be classified into:

T1: The tumor cannot be felt during a digital rectal exam, or seen by imaging studies, but cancer cells are found in a biopsy specimen;

T2: The tumor can be felt during a DRE and the cancer is confined within the prostate gland;

T3: The tumor has extended through the prostatic capsule (a layer of fibrous tissue surrounding the prostate gland) and/or to the seminal vesicles (two small sacs next to the prostate that store semen), but no other organs are affected;

T4: The tumor has spread or attached to tissues next to the prostate (other than the seminal vesicles).

Lymph node involvement is divided into the following 4 categories:

N0: Cancer has not spread to any lymph nodes;

N1: Cancer has spread to a single regional lymph node (inside the pelvis) and is not larger than 2 centimeters;

N2: Cancer has spread to one or more regional lymph nodes and is larger than 2 centimeters, but not larger than 5 centimeters; and N3: Cancer has spread to a lymph node and is larger than 5 centimeters (2 inches).

Metastasis is generally divided into the following two categories:

M0: The cancer has not metastasized (spread) beyond the regional lymph nodes; and M1: The cancer has metastasized to distant lymph nodes (outside of the pelvis), bones, or other distant organs such as lungs, liver, or brain.

In addition, the Tstage is further divided into subcategories T1a-c T2a-c, T3a-c and T4a-b. The characteristics of each of these subcategories are well known in the art and can be found in a number of textbooks.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention. In some embodiments of the present invention, test compounds include antisense compounds.

The term "therapeutic effect" refers to a local or systemic effect in animals, particularly mammals, and more particularly humans caused by a pharmacologically active substance. The term thus means any substance intended for use in the diagnosis, cure, mitigation, treatment, or prevention of disease, or in the enhancement of desirable physical or mental development and conditions in an animal or human. A therapeutic effect can be understood as a decrease in tumor growth, decrease in tumor growth rate, stabilization or decrease in tumor burden, stabilization or reduction in tumor size, stabilization or decrease in tumor malignancy, increase in tumor apoptosis, and/or a decrease in tumor angiogenesis.

As used herein, "therapeutically effective amount" means the amount of a compound that, when administered to a patient for treating a disease, is sufficient to effect such treatment for the disease, e.g., the amount of such a substance that produces some desired local or systemic effect at a reasonable benefit/risk ratio applicable to any treatment, e.g., is sufficient to ameliorate at least one sign or symptom of the disease, e.g., to prevent progression of the disease or condition, e.g., prevent tumor growth, decrease tumor size, induce tumor cell apoptosis, reduce tumor angiogenesis, prevent metastasis. When administered for preventing a disease, the amount is sufficient to avoid or delay onset of the disease. The "therapeutically effective amount" will vary depending on the compound, its therapeutic index, solubility, the disease and its severity and the age, weight, etc., of the patient to be treated, and the like. For example, certain compounds discovered by the methods of the present invention may be administered in a sufficient amount to produce a reasonable benefit/risk ratio applicable to such treatment. Administration of a therapeutically effective amount of a compound may require the administration of more than one dose of the compound.

A "transcribed polynucleotide" or "nucleotide transcript" is a polynucleotide (e.g. an mRNA, hnRNA, a cDNA, or an analog of such RNA or cDNA) which is complementary to or having a high percentage of identity (e.g., at least 80% identity) with all or a portion of a mature mRNA made by transcription of a marker of the invention and normal post-transcriptional processing (e.g. splicing), if any, of the RNA transcript, and reverse transcription of the RNA transcript.

As used herein, “treatment,” particularly “active treatment,” refers to performing an intervention to treat prostate cancer in a subject, e.g., reduce at least one of the growth rate, reduction of tumor burden, reduce or maintain the tumor size, or the malignancy (e.g., likelihood of metastasis) of the tumor; or to increase apoptosis in the tumor by one or more of administration of a therapeutic agent, e.g., chemotherapy or hormone therapy; administration of radiation therapy (e.g., pellet implantation, brachytherapy), or surgical resection of the tumor, or any combination thereof appropriate for treatment of the subject based on grade and stage of the tumor and other routine considerations. Active treatment is distinguished from “watchful waiting” (i.e., not active treatment) in which the subject and tumor are monitored, but no interventions are performed to affect the tumor. Watchful waiting can include administration of agents that alter effects caused by the tumor (e.g., incontinence, erectile dysfunction) that are not administered to alter the growth or pathology of the tumor itself.

The recitation of a listing of chemical group(s) in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Reference will now be made in detail to exemplary embodiments of the invention. While the invention will be described in conjunction with the exemplary embodiments, it will be understood that it is not intended to limit the invention to those embodiments. To the contrary, it is intended to cover alternatives, modifications, and equivalents as may be included within the spirit and scope of the invention as defined by the appended claims.

Exemplary compositions and methods of the present invention are described in more detail in the following sections: (C) Biomarkers of the invention; (D) Prostate tissue samples; (E) Detection and/or measurement of the biomarkers of the invention; (F) Isolated biomarkers; (G) Applications of biomarkers of the invention; (H) Therapeutics; (I) Drug screening; and (J) Kits/panels.

C. Biomarkers of the Invention

The present invention is based, at least in part, on the discovery that filamin A is differentially regulated in prostate cancer cells. In particular, the invention is based on the surprising discovery that filamin A levels are significantly elevated in the serum of patients with prostate cancer. Accordingly, the invention provides methods for diagnosing and/or monitoring (e.g., monitoring of disease progression or treatment) and/or prognosing an oncological disease state, e.g., prostate cancer, in a mammal. The invention also provides methods for treating or for adjusting treatment regimens based on diagnostic information relating to the levels of filamin A in the serum of a subject with an oncological disease state, e.g., prostate cancer. The invention further provides panels and kits for practicing the methods of the invention.

The present invention provides new biomarkers and combinations of biomarkers for use in diagnosing and/or prognosing an oncological disorder, and in particular, biomarkers for use in diagnosing and/or prognosing prostate cancer. The biomarkers of the invention are meant to encompass any measurable characteristic that reflects in a quantitative or qualitative manner the physiological state of an organism, e.g, whether the organism has prostate cancer. The physiological state of an organism is inclusive of any disease or non-disease state, e.g., a subject having prostate cancer or a subject who is otherwise healthy. Said another way, the biomarkers of the invention include characteristics that can be objectively measured and evaluated as indicators of normal processes, pathogenic processes, or pharmacologic responses to a therapeutic intervention, including, in particular, prostate cancer. Biomarkers can be clinical parameters (e.g., age, performance status), laboratory measures (e.g., molecular biomarkers, such as prostate specific antigen), imaging-based measures, or genetic or other molecular determinants, as well as combinations thereof. Examples of biomarkers include, for example, polypeptides, peptides, polypeptide fragments, proteins, antibodies, hormones, polynucleotides, RNA or RNA fragments, microRNA (miRNAs), lipids, polysaccharides, and other bodily metabolites that are diagnostic and/or indicative and/or predictive of an oncological disease, e.g., prostate cancer. Examples of biomarkers also include polypeptides, peptides, polypeptide fragments, proteins, antibodies, hormones, polynucleotides, RNA or RNA fragments, microRNA (miRNAs), lipids, polysaccharides, and other bodily metabolites which are diagnostic and/or indicative and/or predictive of any stage or clinical phase of an oncological disease, such as, prostate cancer. Clinical stage or phase can be represented by any means known in the art, for example, based on the Gleason Score system, e.g., Gleason grade 1, grade 2, grade 3, grade 4, or grade 5 prostate cancer.

In one aspect, the present invention relates to using, measuring, detecting, and the like of filamin A alone, or together with one or more additional biomarkers of prostate cancer, which can include, but are not limited to prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1. Other markers that may be used in combination with filamin A include any measurable characteristic described herein that reflects in a quantitative or qualitative manner the physiological state of an organism, e.g, whether the organism has prostate cancer. The physiological state of an organism is inclusive of any disease or non-disease state, e.g., a subject having prostate cancer or a subject who is otherwise healthy. The biomarkers of the invention that may be used in combination with filamin A include characteristics that can be objectively measured and evaluated as indicators of normal processes, pathogenic processes, or pharmacologic responses to a therapeutic intervention, including, in particular, prostate cancer. Such combination biomarkers can be clinical parameters (e.g., age, performance status), laboratory measures (e.g., molecular biomarkers, such as prostate specific antigen), imaging-based measures, or genetic or other molecular determinants. Examples of biomarkers for use in combination with filamin A include, for example, polypeptides, peptides, polypeptide fragments, proteins, antibodies, hormones, polynucleotides, RNA or RNA fragments, microRNA (miRNAs), lipids, polysaccharides, and other bodily metabolites that are diagnostic and/or indicative and/or predictive of prostate cancer, or any particular stage or phase of prostate cancer, e.g., Gleason grade 1, grade 2, grade 3, grade 4, or grade 5 prostate cancer or TNM classifications. In other embodiments, the present invention also involves the analysis and consideration of any clinical and/or patient-related health data, for example, data obtained from an Electronic Medical Record (e.g., collection of electronic health information about individual patients or populations relating to various types of data, such as, demographics, medical history, medication and allergies, immunization status, laboratory test results, radiology images, vital signs, personal statistics like age and weight, and billing information).

In certain embodiments, filamin A may be used in combination with at least one other biomarker, or more preferably, with at least two other biomarkers, or still more preferably, with at least three other biomarkers, or even more preferably with at least four other biomarkers. Still further, filamin A in certain embodiments, may be used in combination with at least five other markers, or at least six other biomarkers, or at least seven other biomarkers, or at least eight other biomarkers, or at least nine other biomarkers, or at least ten other biomarkers, or at least eleven other biomarkers, or at least twelve other biomarkers, or at least thirteen other biomarkers, or at least fourteen other biomarkers, or at least fifteen other biomarkers, or at least sixteen other biomarkers, or at least seventeen other biomarkers, or at least eighteen other biomarkers, or at least nineteen other biomarkers, or at least twenty other biomarkers. Further, filamin A may be used in combination with a multitude of other biomarkers, including, for example, with between about 20-50 other biomarkers, or between 50-100, or between 100-500, or between 500-1000, or between 1000-10,000 or biomarkers or more.

In certain embodiments, the present invention involves the detection and/or analysis filamin A I combination with at least one of the following set of biomarkers: prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1. The known function of these proteins is provided as follows, without wishing to be bound by theory:

Filamin A (FLN-A).

Filamin A (also known as FLN-A, FLN1, ABP-280, OPD1, OPD2, Endothelial Actin-Binding Protein, CVD1, FMD, MNS, NHBP, XLVD, XMVD, Actin Binding Protein 280, Alpha-Filamin, Filamin-1, Filamin-A—each of which may appear herein and are considered equivalent terms as used herein) is a 280-kD protein that is thought to crosslink actin filaments into orthogonal networks in cortical cytoplasm. The large molecular-weight protein also participates in the anchoring of membrane proteins to the actin cytoskeleton. Remodeling of the cytoskeleton is central to the modulation of cell shape and migration cells. Filamin A, encoded by the FLNA gene, is a widely expressed protein that regulates reorganization of the actin cytoskeleton by interacting with integrins, transmembrane receptor complexes, and second messengers. At least two different isoforms are know, isoform 1 and isoform 2, all of which are contemplated by the invention and encompassed by the term "filamin A." It will be appreciated that isoform 1 is the predominant transcript encoding filamin A. Isoform 2 includes an alternate in-frame exon and encodes a slightly longer protein isoform. Interaction with FLNA may allow neuroblast migration from the ventricular zone into the cortical plate. FLNA tethers cell surface-localized furin, modulates its rate of internalization and directs its intracellular trafficking. Further reference to filamin A can be found in the scientific literature, for example, in Gorlin J B et al., (October 1993). "Actin-binding protein (ABP-280) filamin gene (FLN) maps telomeric to the color vision locus (R/GCP) and centromeric to G6PD in Xq28". Genomics 17 (2): 496-8, and Robertson S P et al. (March 2003). "Localized mutations in the gene encoding the cytoskeletal protein filamin A cause diverse malformations in humans". Nat Genet 33 (4): 487-91, each of which are incorporated herein by reference. The nucleotide and amino acid sequences of filamin A can be found as GenBank Accession No. NM_001456.3 (filamin A—isoform 1—mRNA transcript sequence—SEQ ID NO: 46) and the corresponding polypeptide sequence of NP_001447.2 (filamin A—isoform 1—polypeptide sequence—SEQ ID NO: 47) and as GenBank Accession No. NM_001110556.1 (filamin A—isoform 2—mRNA transcript sequence—SEQ ID NO: 48) and the corresponding polypeptide sequence of NP_001104026.1 (filamin A—isoform 2—polypeptide sequence—SEQ ID NO: 49). These GenBank numbers are incorporated herein by reference in the versions available on the earliest effective filing date of this application.

The present invention is based, at least in part, on the discovery that filamin A is differentially regulated in prostate cancer cells. In particular, the invention is based on the surprising discovery that filamin A levels are significantly elevated in the serum of patients with prostate cancer. Accordingly, the invention provides methods for diagnosing and/or monitoring (e.g., monitoring of disease progression or treatment) and/or prognosing an oncological disease state, e.g., prostate cancer, in a mammal. The invention also provides methods for treating or for adjusting treatment regimens based on diagnostic information relating to the levels of filamin A in the serum of a subject with an oncological disease state, e.g., prostate cancer. The invention further provides panels and kits for practicing the methods of the invention.

It is understood that the invention includes the use of any combination of one or more of the filamin A sequences provided in the sequence listing or any fragments thereof as long as the fragment can allow for the specific identification of filamin A. Methods of the invention and reagents can be used to detect single isoforms of filamin A, e.g., isoform 1 and isoform 2, combinations of filamin A isoforms, or all of the filamin A isoforms simultaneously. Unless specified, filamin A can be considered to refer to one or more isoforms of filamin A, including total filamin A. Moreover, it is understood that there are naturally occurring variants of filamin A, which may or may not be associated with a specific disease state, the use of which are also included in the instant application.

It is understood that the invention includes the use of any fragments of filamin A polypeptide as long as the fragment allows for the specific identification of filamin A by a detection method of the invention. For example, an ELISA antibody must be able to bind to the filamin A fragment so that detection is possible. Moreover, it is understood that there are naturally occurring variants of filamin A which may or may not be associated with a specific disease state, the use of which are also included in this application. Accordingly, the present inventions also contemplates fragments and variants of filamin A which may be associated with a disease state, e.g., prostate cancer, and/or a particular stage or phase of a disease state, e.g., grades 1-5 of prostate cancer. It is also understood that the invention encompasses the use of nucleic acid molecules encoding filamin A, including for example, filamin A-encoding DNA, filamin A mRNA, and fragments and/or variants thereof. Reference to "filamin A" may refer to filamin A polypeptide or to the filamin A gene, unless otherwise indicated.

Keratin 4.

Keratin 4, also known as K4; CK4; CK-4; CYK4, is a member of the keratin gene family. The type II cytokeratins consist of basic or neutral proteins which are arranged in pairs of heterotypic keratin chains coexpressed during differentiation of simple and stratified epithelial tissues. This type II cytokeratin is specifically expressed in differentiated layers of the mucosal and esophageal epithelia with family member KRT13. Mutations in these genes have been associated with White Sponge Nevus, characterized by oral, esophageal, and anal leukoplakia. The type II cytokeratins are clustered in a region of chromosome 12q12-q13.

As used herein, keratin 4 refers to both the gene and the protein unless clearly indicated otherwise by context. The NCBI Gene ID for human keratin 4 is 3851 and detailed information can be found at the NCBI website (incorporated herein by reference in the version available on the filing date of the application to which this application claims priority). *Homo sapiens* keratin 4, GenBank Accession No. NM_002272 amino acid and nucleotide sequences, respectively, are provided in SEQ ID NOs: 1 and 2. (The GenBank number is incorporated herein by reference in the version available on the filing date of the application to which this application claims priority.)

It is understood that the invention includes the use of any fragments of keratin 4 polypeptide as long as the fragment allow for the specific identification of keratin 4 by a detection method of the invention. For example, an ELISA antibody must be able to bind to the keratin 4 fragment so that detection is possible. Moreover, it is understood that there are naturally occurring variants of keratin 4 which may or may not be associated with a specific disease state, the use of which are also included in this application. Accordingly, the present inventions also contemplates fragments and variants of keratin 4 which may be associated with a disease state, e.g., prostate cancer, and/or a particular stage or phase of a disease state, e.g., grades 1-5 of prostate cancer. It is also understood that the invention encompasses the use of nucleic acid molecules encoding keratin 4, including for example, keratin 4-encoding DNA, keratin 4 mRNA, and fragments and/or variants thereof. Reference to "keratin 4" may refer to keratin 4 polypeptide or to the keratin 4 gene, unless otherwise indicated.

Keratin 7.

Keratin 7, also known as CK7, K2C7, K7, SCL, CK-7; cytokeratin 7; cytokeratin-7; keratin, 55K type II cytoskeletal; keratin, simple epithelial type I, K7; keratin, type II cytoskeletal 7; keratin-7; sarcolectin; type II mesothelial keratin K7; and type-II keratin Kb7, is a member of the keratin gene family. The type II cytokeratins consist of basic or neutral proteins which are arranged in pairs of heterotypic keratin chains co-expressed during differentiation of simple and stratified epithelial tissues. This type II cytokeratin is specifically expressed in the simple epithelia lining the cavities of the internal organs and in the gland ducts and blood vessels. The genes encoding the type II cytokeratins are clustered in a region of chromosome 12q12-q13. Alternative splicing may result in several transcript variants; however, not all variants have been fully described.

As used herein, keratin 7 refers to both the gene and the protein unless clearly indicated otherwise by context. The NCBI Gene ID for human keratin 7 is 3855 and detailed information can be found at the NCBI website (incorporated herein by reference in the version available on the filing date of the application to which this application claims priority). *Homo sapiens* keratin 7, GenBank Accession No. NM_005556 amino acid and nucleotide sequences, respectively, are provided in SEQ ID NOs: 3 and 4. (The GenBank number is incorporated herein by reference in the version available on the filing date of the application to which this application claims priority.)

It is understood that the invention includes the use of any fragments of keratin 7 polypeptide as long as the fragment allow for the specific identification of keratin 7 by a detection method of the invention. For example, an ELISA antibody must be able to bind to the keratin 7 fragment so that detection is possible. Moreover, it is understood that there are naturally occurring variants of keratin 7 which may or may not be associated with a specific disease state, the use of which are also included in this application. Accordingly, the present inventions also contemplates fragments and variants of keratin 7 which may be associated with a disease state, e.g., prostate cancer, and/or a particular stage or phase of a disease state, e.g., grades 1-5 of prostate cancer. It is also understood that the invention encompasses the use of nucleic acid molecules encoding keratin 7, including for example, keratin 7-encoding DNA, keratin 7 mRNA, and fragments and/or variants thereof. Reference to "keratin 7" may refer to keratin 7 polypeptide or to the keratin 7 gene, unless otherwise indicated.

Keratin 8.

Keratin 8, also known as K8; KO; CK8; CK-8; CYK8; K2C8; CARD2 is a member of the type II keratin family clustered on the long arm of chromosome 12. Type I and type II keratins heteropolymerize to form intermediate-sized filaments in the cytoplasm of epithelial cells. The product of this gene typically dimerizes with keratin 18 to form an intermediate filament in simple single-layered epithelial cells. This protein plays a role in maintaining cellular structural integrity and also functions in signal transduction and cellular differentiation. Mutations in this gene cause cryptogenic cirrhosis. Alternatively spliced transcript variants have been found for this gene.

As used herein, keratin 8 refers to both the gene and the protein unless clearly indicated otherwise by context. The NCBI Gene ID for human keratin 8 is 3856 and detailed information can be found at the NCBI website (incorporated herein by reference in the version available on the filing date of the application to which this application claims priority). *Homo sapiens* keratin 8, variant 1, GenBank Accession No. NM_001256282 amino acid and nucleotide sequences, respectively, are provided in SEQ ID NOs: 5 and 6; and *Homo sapiens* keratin 8, variant 3, GenBank Acession No. NM_001256293 amino acid and nucleotide sequences, respectively, are provided in SEQ ID NOs: 7 and 8. (The GenBank numbers are incorporated herein by reference in the version available on the filing date of the application to which this application claims priority.)

It is understood that the invention includes the use of any fragments of keratin 8 polypeptide as long as the fragment allow for the specific identification of keratin 8 by a detection method of the invention. For example, an ELISA antibody must be able to bind to the keratin 8 fragment so that detection is possible. Moreover, it is understood that there are naturally occurring variants of keratin 8 which may or may not be associated with a specific disease state, the use of which are also included in this application. Accordingly, the present inventions also contemplates fragments and variants of keratin 8 which may be associated with a disease state, e.g., prostate cancer, and/or a particular stage or phase of a disease state, e.g., grades 1-5 of prostate cancer. It is also understood that the invention encompasses the use of nucleic acid molecules encoding keratin 8, including for example, keratin 8-encoding DNA, keratin 8 mRNA, and fragments and/or variants thereof. Reference to "keratin 8" may refer to keratin 8 polypeptide or to the keratin 8 gene, unless otherwise indicated.

Keratin 15.

Keratin 15, also known as K15; CK15; K1CO, is a member of the keratin gene family. The keratins are intermediate filament proteins responsible for the structural integrity of epithelial cells and are subdivided into cytokeratins and hair keratins. Most of the type I cytokeratins consist of acidic proteins which are arranged in pairs of heterotypic keratin chains and are clustered in a region on chromosome 17q21.2.

As used herein, keratin 15 refers to both the gene and the protein unless clearly indicated otherwise by context. The NCBI Gene ID for human keratin 15 is 3866 and detailed information can be found at the NCBI website (incorporated herein by reference in the version available on the filing date of the application to which this application claims priority). *Homo sapiens* keratin 15, GenBank Accession No. NM_002275 amino acid and nucleotide sequences, respectively, are provided in SEQ ID NOs: 9 and 10. (The GenBank number is incorporated herein by reference in the version available on the filing date of the application to which this application claims priority.)

It is understood that the invention includes the use of any fragments of keratin 15 polypeptide as long as the fragment allow for the specific identification of keratin 15 by a detection method of the invention. For example, an ELISA antibody must be able to bind to the keratin 15 fragment so that detection is possible. Moreover, it is understood that there are naturally occurring variants of keratin 15 which may or may not be associated with a specific disease state, the use of which are also included in this application. Accordingly, the present inventions also contemplates fragments and variants of keratin 15 which may be associated with a disease state, e.g., prostate cancer, and/or a particular stage or phase of a disease state, e.g., grades 1-5 of prostate cancer. It is also understood that the invention encompasses the use of nucleic acid molecules encoding keratin 15, including for example, keratin 15-encoding DNA, keratin 15 mRNA, and fragments and/or variants thereof. Reference to "keratin 15" may refer to keratin 15 polypeptide or to the keratin 15 gene, unless otherwise indicated.

Keratin 18.

Keratin 18, also known as K18; CYK18, encodes the type I intermediate filament chain keratin 18. Keratin 18, together with its filament partner keratin 8, are perhaps the most commonly found members of the intermediate filament gene family. They are expressed in single layer epithelial tissues of the body. Mutations in this gene have been linked to cryptogenic cirrhosis. Two transcript variants encoding the same protein have been found for this gene.

As used herein, keratin 18 refers to both the gene and the protein unless clearly indicated otherwise by context. The NCBI Gene ID for human keratin 18 is 3875 and detailed information can be found at the NCBI website (incorporated herein by reference in the version available on the filing date of the application to which this application claims priority). *Homo sapiens* keratin 18, variant 1, GenBank Accession No. NM_000224 amino acid and nucleotide sequences, respectively, are provided in SEQ ID NOs: 11 and 12, and *Homo sapiens* keratin 18, variant 2, GenBank Accession No. 199187 amino acid and nucleotide sequences, respectively, are provided in SEQ ID NOs: 13 and 14. (The GenBank numbers are incorporated herein by reference in the version available on the filing date of the application to which this application claims priority.)

It is understood that the invention includes the use of any fragments of keratin 18 polypeptide as long as the fragment allow for the specific identification of keratin 18 by a detection method of the invention. For example, an ELISA antibody must be able to bind to the keratin 18 fragment so that detection is possible. Moreover, it is understood that there are naturally occurring variants of keratin 18 which may or may not be associated with a specific disease state, the use of which are also included in this application. Accordingly, the present inventions also contemplates fragments and variants of keratin 18 which may be associated with a disease state, e.g., prostate cancer, and/or a particular stage or phase of a disease state, e.g., grades 1-5 of prostate cancer. It is also understood that the invention encompasses the use of nucleic acid molecules encoding keratin 18, including for example, keratin 18-encoding DNA, keratin 18 mRNA, and fragments and/or variants thereof. Reference to "keratin 18" may refer to keratin 18 polypeptide or to the keratin 18 gene, unless otherwise indicated.

Keratin 19.

Keratin 19, also known as K19; CK19; K1CS, is a member of the keratin gene family. The keratins are intermediate filament proteins responsible for the structural integrity of epithelial cells and are subdivided into cytokeratins and hair keratins. The type I cytokeratins consist of acidic proteins which are arranged in pairs of heterotypic keratin chains. Unlike its related family members, this smallest known acidic cytokeratin is not paired with a basic cytokeratin in epithelial cells. It is specifically expressed in the periderm, the transiently superficial layer that envelopes the developing epidermis. The type I cytokeratins are clustered in a region of chromosome 17q12-q21.

As used herein, keratin 19 refers to both the gene and the protein unless clearly indicated otherwise by context. The NCBI Gene ID for human keratin 19 is 3880 and detailed information can be found at the NCBI website (incorporated herein by reference in the version available on the filing date of the application to which this application claims priority). *Homo sapiens* keratin 19, GenBank Accession No. NM_002276 amino acid and nucleotide sequences, respectively, are provided in SEQ ID NOs: 15 and 16. (The GenBank number is incorporated herein by reference in the version available on the filing date of the application to which this application claims priority.)

It is understood that the invention includes the use of any fragments of keratin 19 polypeptide as long as the fragment allow for the specific identification of keratin 19 by a detection method of the invention. For example, an ELISA antibody must be able to bind to the keratin 19 fragment so that detection is possible. Moreover, it is understood that there are naturally occurring variants of keratin 19 which may or may not be associated with a specific disease state, the use of which are also included in this application. Accordingly, the present inventions also contemplates fragments and variants of keratin 19 which may be associated with a disease state, e.g., prostate cancer, and/or a particular stage or phase of a disease state, e.g., grades 1-5 of prostate cancer. It is also understood that the invention encompasses the use of nucleic acid molecules encoding keratin 19, including for example, keratin 19-encoding DNA, keratin 19 mRNA, and fragments and/or variants thereof. Reference to "keratin 19" may refer to keratin 19 polypeptide or to the keratin 8 gene, unless otherwise indicated.

Tubulin-Beta 3.

Tubulin-beta 3, also known as CDCBM; TUBB4; beta-4; CFEOM3A, is a class III member of the beta tubulin protein family. Beta tubulins are one of two core protein families (alpha and beta tubulins) that heterodimerize and assemble to form microtubules. This protein is primarily expressed in neurons and may be involved in neurogenesis and axon guidance and maintenance. Mutations in this gene are the cause of congenital fibrosis of the extraocular muscles type 3. Alternate splicing results in multiple transcript variants. A pseudogene of this gene is found on chromosome 6.

As used herein, Tubulin-beta 3 refers to both the gene and the protein unless clearly indicated otherwise by context. The NCBI Gene ID for human Tubulin-beta 3 is 10381 and detailed information can be found at the NCBI website (incorporated herein by reference in the version available on the filing date of the application to which this application claims priority). *Homo sapiens* Tubulin-beta 3, variant 2, GenBank Accession No. NM_001197181 amino acid and nucleotide sequences, respectively, are provided in SEQ ID NOs: 17 and 18. *Homo sapiens* Tubulin-beta 3, variant 1, GenBank Accession No. NM_006086 amino acid and nucleotide sequences, respectively, are provided in SEQ ID NOs: 19 and 20. (The GenBank numbers are incorporated herein by reference in the versions available on the filing date of the application to which this application claims priority.)

It is understood that the invention includes the use of any fragments of Tubulin-beta 3 polypeptide as long as the fragment allow for the specific identification of Tubulin-beta 3 by a detection method of the invention. For example, an ELISA antibody must be able to bind to the Tubulin-beta 3 fragment so that detection is possible. Moreover, it is understood that there are naturally occurring variants of Tubulin-beta 3 which may or may not be associated with a specific disease state, the use of which are also included in this application. Accordingly, the present inventions also contemplates fragments and variants of Tubulin-beta 3 which may be associated with a disease state, e.g., prostate cancer, and/or a particular stage or phase of a disease state, e.g., grades 1-5 of prostate cancer. It is also understood that the invention encompasses the use of nucleic acid molecules encoding Tubulin-beta 3, including for example, Tubulin-beta 3-encoding DNA, Tubulin-beta 3 mRNA, and fragments and/or variants thereof. Reference to "Tubulin-beta 3" may refer to Tubulin-beta 3 polypeptide or to the Tubulin-beta 3 gene, unless otherwise indicated.

Filamin B.

Filamin B is also known as filamin-3, beta-filamin, ABP-280 homolog, filamin homolog 1, thyroid autoantigen, actin binding protein 278, actin-binding-like protein, Larsen syndrome 1 (autosomal dominant), AOI; FH1; SCT; TAP; LRS1; TABP; FLN-B; FLN1L; ABP-278; and ABP-280. The gene encodes a member of the filamin family. The encoded protein interacts with glycoprotein Ib alpha as part of the process to repair vascular injuries. The platelet glycoprotein Ib complex includes glycoprotein Ib alpha, and it binds the actin cytoskeleton. Mutations in this gene have been found in several conditions: atelosteogenesis type 1 and type 3; boomerang dysplasia; autosomal dominant Larsen syndrome; and spondylocarpotarsal synostosis syndrome. Multiple alternatively spliced transcript variants that encode different protein isoforms have been described for this gene.

As used herein, filamin B refers to both the gene and the protein unless clearly indicated otherwise by context. The NCBI gene ID for filamin B is 2317 and detailed information can be found at the NCBI website (incorporated herein by reference in the version available on the filing date of the application to which this application claims priority).

*Homo sapiens* filamin B, beta (FLNB), RefSeqGene on chromosome 3, locus NG_012801 is shown in SEQ ID NO: 21. *Homo sapiens* filamin B, beta (FLNB), transcript variant 1, GenBank Accession No. NM_001164317.1 amino acid and nucleotide sequences, respectively, are provided in SEQ ID NOs: 22 and 23. *Homo sapiens* filamin B, beta (FLNB), transcript variant 3, GenBank Accession No. NM_001164318.1 amino acid and nucleotide sequences, respectively, are provided in SEQ ID NOs: 24 and 25. *Homo sapiens* filamin B, beta (FLNB), transcript variant 4, GenBank Accession No. NM_001164319.1 amino acid and nucleotide sequences, respectively, are provided in SEQ ID NOs: 26 and 27. *Homo sapiens* filamin B, beta (FLNB), transcript variant 2, GenBank Accession No. NM_001457.3 amino acid and nucleotide sequences, respectively, are provided in SEQ ID NOs: 28 and 29. (Each GenBank number is incorporated herein by reference in the version available on the filing date of the application to which this application claims priority.)

It is understood that the invention includes the use of any combination of one or more of the filamin B sequences provided in the sequence listing or any fragments thereof as long as the fragment can allow for the specific identification of filamin B. Methods of the invention and reagents can be used to detect single isoforms of filamin B, combinations of filamin B isoforms, or all of the filamin B isoforms simultaneously. Unless specified, filamin B can be considered to refer to one or more isoforms of filamin B, including total filamin B. Moreover, it is understood that there are naturally occurring variants of filamin B, which may or may not be associated with a specific disease state, the use of which are also included in the instant application.

In addition, it is understood that the invention includes the use of any fragments of filamin B polypeptide as long as the fragment allow for the specific identification of filamin B by a detection method of the invention. For example, an ELISA antibody must be able to bind to the filamin B fragment so that detection is possible. Moreover, it is understood that there are naturally occurring variants of filamin B which may or may not be associated with a specific disease state, the use of which are also included in this application. Accordingly, the present inventions also contemplates fragments and variants of filamin B which may be associated with a disease state, e.g., prostate cancer, and/or a particular stage or phase of a disease state, e.g., grades 1-5 of prostate cancer. It is also understood that the invention encompasses the use of nucleic acid molecules encoding filamin B, including for example, filamin B-encoding DNA, filamin B mRNA, and fragments and/or variants thereof. Reference to "filamin B" may refer to filamin B polypeptide or to the filamin B gene, unless otherwise indicated.

Lymphocyte Antigen 9.

Lymphocyte antigen 9 (LY9) is also known as RP11-312J18.1, CD229, SLAMF3, hly9, mLY9, T-lymphocyte surface antigen Ly-9; and cell surface molecule Ly-9. LY9 belongs to the SLAM family of immunomodulatory receptors (see SLAMF1; MIM 603492) and interacts with the adaptor molecule SAP (SH2D1A; MIM 300490) (Graham et al., 2006).

As used herein, LY9 refers to both the gene and the protein unless clearly indicated otherwise by context. The NCBI gene ID for LY9 is 4063 and detailed information can be found at the NCBI website (incorporated herein by reference in the version available on the filing date of the application to which this application claims priority).

*Homo sapiens* lymphocyte antigen 9 (LY9), transcript variant 2, GenBank Accession No. NM_001033667 amino acid and nucleotide sequences, respectively, are provided in SEQ ID NOs: 30 and 31. *Homo sapiens* lymphocyte antigen 9 (LY9), transcript variant 3, GenBank Accession No. NM_001261456 amino acid and nucleotide sequences, respectively, are provided in SEQ ID NOs: 32 and 33. *Homo sapiens* lymphocyte antigen 9 (LY9), transcript variant 4, GenBank Accession No. NM_001261457 amino acid and nucleotide sequences, respectively, are provided in SEQ ID NOs: 34 and 35. *Homo sapiens* lymphocyte antigen 9 (LY9), transcript variant 1, GenBank Accession No. NM_002348 is shown amino acid and nucleotide sequences, respectively, are provided in SEQ ID NOs: 36 and 37. (Each GenBank number is incorporated herein by reference in the version available on the filing date of the application to which this application claims priority.)

It is understood that the invention includes the use of any combination of one or more of the LY9 sequences provided in the sequence listing or any fragments thereof as long as the fragment can allow for the specific identification of LY9. Methods of the invention and reagents can be used to detect single isoforms of LY9, combinations of LY9 isoforms, or all of the LY9 isoforms simultaneously. Unless specified, LY9 can be considered to refer to one or more isoforms of LY9, including total LY9. Moreover, it is understood that there are naturally occurring variants of LY9, which may or may not be associated with a specific disease state, the use of which are also included in the instant application.

In addition, it is understood that the invention includes the use of any fragments of LY9 polypeptide as long as the fragment allow for the specific identification of LY9 by a detection method of the invention. For example, an ELISA antibody must be able to bind to the LY9 fragment so that detection is possible. Moreover, it is understood that there are naturally occurring variants of LY9 which may or may not be associated with a specific disease state, the use of which are also included in this application. Accordingly, the present inventions also contemplates fragments and variants of LY9 which may be associated with a disease state, e.g., prostate cancer, and/or a particular stage or phase of a disease state, e.g., grades 1-5 of prostate cancer. It is also understood that the invention encompasses the use of nucleic acid molecules encoding LY9, including for example, LY9-encoding DNA, LY9 mRNA, and fragments and/or variants thereof. Reference to “LY9” may refer to LY9 polypeptide or to the LY9 gene, unless otherwise indicated.

Prostate Specific Antigen.

Prostate-specific antigen (PSA) is also known as kallikrein-3, seminin, P-30 antigen, semenogelase, gamma-seminoprotein, APS, hK3, and KLK2A1. Kallikreins are a subgroup of serine proteases having diverse physiological functions. Growing evidence suggests that many kallikreins are implicated in carcinogenesis and some have potential as novel cancer and other disease biomarkers. This gene is one of the fifteen kallikrein subfamily members located in a cluster on chromosome 19. Its protein product is a protease present in seminal plasma. It is thought to function normally in the liquefaction of seminal coagulum, presumably by hydrolysis of the high molecular mass seminal vesicle protein. Serum level of this protein, called PSA in the clinical setting, is useful in the diagnosis and monitoring of prostatic carcinoma. Alternate splicing of this gene generates several transcript variants encoding different isoforms.

As used herein, PSA refers to both the gene and the protein, in both processed and unprocessed forms, unless clearly indicated otherwise by context. The NCBI gene ID for PSA is 354 and detailed information can be found at the NCBI website (incorporated herein by reference in the version available on the filing date of the application to which this application claims priority).

*Homo sapiens* PSA is located on chromosome 19 at 19q13.41Sequence: NC_000019.9 (51358171 . . . 51364020). Four splice variants of human PSA are known. Prostate-specific antigen isoform 3 preproprotein, NM_001030047.1, is provided as SEQ ID NOs: 38 and 39. Prostate-specific antigen isoform 4 preproprotein, NM_001030048.1, is provided as SEQ ID NOs: 40 and 41. Prostate-specific antigen isoform 6 preproprotein, NM_001030050.1, is provided as SEQ ID NOs: 42 and 43. Prostate-specific antigen isoform 1 preproprotein, NM_001648.2, is provided in SEQ ID NOs: 44 and 45. (Each GenBank number is incorporated herein by reference in the version available on the filing date of the application to which this application claims priority).

It is understood that the invention includes the use of any combination of one or more of the PSA sequences provided in the sequence listing or any fragments thereof as long as the fragment can allow for the specific identification of PSA. Methods of the invention and reagents can be used to detect single isoforms of PSA, combinations of PSA isoforms, or all of the PSA isoforms simultaneously. Unless specified, PSA can be considered to refer to one or more isoforms of PSA, including total PSA. Moreover, it is understood that there are naturally occurring variants of PSA, which may or may not be associated with a specific disease state, the use of which are also included in the instant application.

In addition, it is understood that the invention includes the use of any fragments of PSA polypeptide as long as the fragment allow for the specific identification of PSA by a detection method of the invention. For example, an ELISA antibody must be able to bind to the PSA fragment so that detection is possible. Moreover, it is understood that there are naturally occurring variants of PSA which may or may not be associated with a specific disease state, the use of which are also included in this application. Accordingly, the present inventions also contemplates fragments and variants of PSA which may be associated with a disease state, e.g., prostate cancer, and/or a particular stage or phase of a disease state, e.g., grades 1-5 of prostate cancer. It is also understood that the invention encompasses the use of nucleic acid molecules encoding PSA, including for example, PSA-encoding DNA, PSA mRNA, and fragments and/or variants thereof. Reference to “PSA” may refer to PSA polypeptide or to the PSA gene, unless otherwise indicated.

Age.

The age of a subject can be used as a continuous predictive variable for the presence of prostate cancer. For example, increased age is associated with increased risk of prostate cancer. Conversely, decreased age is associated with decreased risk of prostate cancer. Similarly, age can be used as a continuous predictive variable for the stage, or category, of the prostate cancer. For example, age can be used as a continuous predictive variable for the Gleason score of the prostate cancer.

The biomarkers of the invention, including in particular filamin A alone or in combination with any one or more of PSA, keratin 4, keratin 7, keratin 8, keratin 15, keratin 18, keratin 19, tubulin-beta 3, filamin B (FLNB), and lymphocyte antigen 9 (LY9), may be detected as a polypeptide or a detectable fragment thereof. Alternatively, the biomarkers of the invention, including in particular filamin A alone or in combination with any one or more of PSA, keratin 4, keratin 7, keratin 8, keratin 15, keratin 18, keratin 19, tubulin-beta 3, filamin B (FLNB), and lymphocyte antigen 9 (LY9), may be detected as nucleic acid molecules, such as DNA, RNA, mRNA, microRNA, and the like. In addition, combinations of biomarkers, including filamin A alone or in combination with any one or more of PSA, keratin 4, keratin 7, keratin 8, keratin 15, keratin 18, keratin 19, tubulin-beta 3, filamin B (FLNB), and lymphocyte antigen 9 (LY9), may be detected as any combination of polypeptides and nucleic acid molecules. In certain embodiments, all of the biomarkers are in the form of polypeptides. In certain other embodiments, all of the biomarkers are in the form of polynucleotides. In certain other embodiments, at least filamin A is in the form of a polypeptide, whereas any other markers tested can be a polypeptide or nucleic acid molecule. In still other embodiments, at least filamin A is in the form of a nucleic acid molecule, whereas any other markers tested can be a polypeptide or nucleic acid molecule.

In other embodiments, the biomarkers of the invention, including in particular filamin A alone or in combination with any one or more of PSA, keratin 4, keratin 7, keratin 8, keratin 15, keratin 18, keratin 19, tubulin-beta 3, filamin B (FLNB), lymphocyte antigen 9 (LY9), prostate-specific membrane antigen (PSM), prostate stem cell antigen (PSCA), TMPRSS2, PDEF, prostate-specific gene-1 (HPG-1), and non-coding RNAs (ncRNAs), including PCA3, PCGEM1, and the gene cluster P704P, P712P, and P775P, may be detected as a polypeptide or a detectable fragment thereof. Alternatively, the biomarkers of the invention, including in particular filamin A alone or in combination with any one or more of PSA, keratin 4, keratin 7, keratin 8, keratin 15, keratin 18, keratin 19, tubulin-beta 3, filamin B (FLNB), lymphocyte antigen 9 (LY9), prostate-specific membrane antigen (PSM), prostate stem cell antigen (PSCA), TMPRSS2, PDEF, prostate-specific gene-1 (HPG-1), and non-coding RNAs (ncRNAs), including PCA3, PCGEM1, and the gene cluster P704P, P712P, and P775P, may be detected as nucleic acid molecules, such as DNA, RNA, mRNA, microRNA, and the like. In addition, combinations of biomarkers, including filamin A alone or in combination with any one or more of PSA, keratin 4, keratin 7, keratin 8, keratin 15, keratin 18, keratin 19, tubulin-beta 3, filamin B (FLNB), lymphocyte antigen 9 (LY9), prostate-specific membrane antigen (PSM), prostate stem cell antigen (PSCA), TMPRSS2, PDEF, prostate-specific gene-1 (HPG-1), and non-coding RNAs (ncRNAs), including PCA3, PCGEM1, and the gene cluster P704P, P712P, and P775P, may be detected as any combination of polypeptides and nucleic acid molecules. In certain embodiments, all of the biomarkers are in the form of polypeptides. In certain other embodiments, all of the biomarkers are in the form of polynucleotides. In certain other embodiments, at least filamin A is in the form of a polypeptide, whereas any other markers tested can be a polypeptide or nucleic acid molecule. In still other embodiments, at least filamin A is in the form of a nucleic acid molecule, whereas any other markers tested can be a polypeptide or nucleic acid molecule.

The specific marker identified herein as prostate-specific membrane antigen (PSM) is further described in Sokoll et al., 1997, Prostate-specific antigen—Its discovery and biochemical characteristics, Urol. Clin. North Am., 24:253-259, which is incorporated herein by reference.

The specific marker identified herein as prostate stem cell antigen (PSCA) is further described in Fair et al., 1997, Prostate-specific membrane antigen, Prostate, 32:140-148, which is incorporated herein by reference.

The specific marker identified herein as TMPRSS2 is further described in Lin et al., 1999, Prostate-localized and androgen-regulated expression of the membrane-bound serine protease TMPRSS2, Cancer Res., 59:4180-4184, which is incorporated herein by reference.

The specific marker identified herein as PDEF is further described in Oettgen et al., PDEF, a novel prostate epithelium-specific ETS transcription factor interacts with the androgen receptor and activates prostate-specific antigen gene expression, J. Biol. Chem., 275: 1216-1225, which is incorporated herein by reference.

The specific marker identified herein as prostate-specific gene-1 (HPG-1) is further described in Herness, A novel human prostate-specific gene-1 (HPG-1): molecular cloning, sequencing, and its potential involvement in prostate carcinogenesis, 2003, Cancer Res. 63:329-336, which is incorporated herein by reference.

The non-coding RNA's (ncRNA's) identified as PCA3 is further described in Bussemakers et al., 1999, DD3: a new prostate-specific gene, highly overexpressed in prostate cancer, Cancer Res. 59:5975-5979, which is incorporated herein by reference.

The non-coding RNA identified as PCGEM1 is further described in Srikantan et al., 2000. PCGEM1, a prostate-specific gene, is overexpressed in prostate cancer. Proc. Natl. Acad. Sci. USA 97:12216-12221, which is incorporated herein by reference.

The gene cluster P704P, P712P, and P775P is further described in Stolk et al., 2004. P704P, P712P, and P775P: A genomic cluster of prostate-specific genes. Prostate 60:214-226), which is incorporated herein by reference.

The present invention also contemplates the use of particular combinations of biomarkers.

In one embodiment, the invention contemplates marker sets with at least two (2) members, which may include, but are not limited to the following sets: filamin A together with PSA; filamin A together with PSA; filamin A together with LY9; filamin A together with keratin 4; filamin A together with kertain 7; filamin A together with keratin 8; filamin A together with keratin 15; filamin A together with keratin 18; filamin A together with keratin 19; filamin A together with tubulin-beta 3; filamin A together with prostate-specific membrane antigen (PSM); filamin A together with prostate stem cell antigen (PSCA); filamin A together with TMPRSS2; filamin A together with PDEF; filamin A together with prostate-specific gene-1 (HPG-1); filamin A together with PCA3; filamin A together with PCGEM1; and filamin A together with gene cluster P704P, P712P, and P775P; and filamin A together with patient age. Any marker set can additionally be used in combination with PSA.

In another embodiment, the invention contemplates marker sets with at least three (3) members, wherein one member is filamin A and the additional two members are selected from the following sets of two markers: filamin B, LY9; filamin B, keratin 4; filamin B, keratin 7; filamin B, keratin 8; filamin B, keratin 15; filamin B, keratin 18; filamin B, keratin 19; filamin B, tubulin-beta 3; filamin B, PSM; filamin B, PSCA; filamin B, TMPRSS2; filamin B, PDEF; filamin B, HPG-1; filamin B, PCA3; filamin B, PCGEM1; filamin B, P704P/P712P/P775P; LY9, keratin 4; LY9, keratin 7; LY9, keratin 8; LY9, keratin 15; LY9, keratin 18; LY9, keratin 19; LY9, tubulin-beta 3; LY9, PSM; LY9, PSCA; LY9, TMPRSS2; LY9, PDEF; LY9, HPG-1; LY9, PCA3;

LY9, PCGEM1; LY9, P704P/P712P/P775P; keratin 4, keratin 7; keratin 4, keratin 8; keratin 4, keratin 15; keratin 4, keratin 18; keratin 4, keratin 19; keratin 4, tubulin-beta 3; keratin 4, PSM; keratin 4, PSCA; keratin 4, TMPRSS2; keratin 4, PDEF; keratin 4, HPG-1; keratin 4, PCA3; keratin 4, PCGEM1; keratin 4, P704P/P712P/P775P; keratin 7, keratin 8; keratin 7, keratin 15; keratin 7, keratin 18; keratin 7, keratin 19; keratin 7, tubulin-beta 3; keratin 7, PSM; keratin 7, PSCA; keratin 7, TMPRSS2; keratin 7, PDEF; keratin 7, HPG-1; keratin 7, PCA3; keratin 7, PCGEM1; keratin 7, P704P/P712P/P775P; keratin 8, keratin 15; keratin 8, keratin 18; keratin 8, keratin 19; keratin 8, tubulin-beta 3; keratin 8, PSM; keratin 8, PSCA; keratin 8, TMPRSS2; keratin 8, PDEF; keratin 8, HPG-1; keratin 8, PCA3; keratin 8, PCGEM1; keratin 8, P704P/P712P/P775P; keratin 15, keratin 18; keratin 15, keratin 19; keratin 15, tubulin-beta 3; keratin 15, PSM; keratin 15, PSCA; keratin 15, TMPRSS2; keratin 15, PDEF; keratin 15, HPG-1; keratin 15, PCA3; keratin 15, PCGEM1; keratin 15, P704P/P712P/P775P; keratin 18, tubulin-beta 3; keratin 18, keratin 19; and keratin 19, tubulin-beta 3; keratin 18, PSM; keratin 18, PSCA; keratin 18, TMPRSS2; keratin 18, PDEF; keratin 18, HPG-1; keratin 18, PCA3; keratin 18, PCGEM1; keratin 18, P704P/P712P/P775P. Any marker set can be used in combination with patient age. Any marker set can additionally be used in combination with PSA.

In another embodiment, the invention contemplates marker sets with at least four (4) members, wherein one member is filamin A and the additional three members may include, but are not limited to the following sets: filamin B, LY9, keratin 4; filamin B, LY9, keratin 7; filamin B, LY9, keratin 8; filamin B, LY9, keratin 15; filamin B, LY9, keratin 18; filamin B, LY9, keratin 19; filamin B, LY9, tubulin-beta 3; filamin B, keratin 4, keratin 7; filamin B, keratin 4, keratin 8; filamin B, keratin 4, keratin 15; filamin B, keratin 4, keratin 18; filamin B, keratin 4, keratin 19; filamin B, keratin 4, tubulin-beta 3; filamin B, keratin 7, keratin 8; filamin B, keratin 7, keratin 15; filamin B, keratin 7, keratin 18; filamin B, keratin 7, keratin 19; filamin B, keratin 7, tubulin-beta 3; filamin B, keratin 8, keratin 15; filamin B, keratin 8, keratin 18; filamin B, keratin 8, keratin 19; filamin B, keratin 8, tubulin-beta 3; filamin B, keratin 15, keratin 18; filamin B, keratin 15, keratin 19; filamin B, keratin 15, tubulin-beta 3; filamin B, keratin 18, keratin 19; filamin B, keratin 18, tubulin-beta 3; filamin B, keratin 19, tubulin-beta 3; LY9, keratin 4, keratin 7; LY9, keratin 4, keratin 8; LY9, keratin 4, keratin 15; LY9, keratin 4, keratin 18; LY9, keratin 4, keratin 19; LY9, keratin 4, tubulin-beta 3; LY9, keratin 7, keratin 8; LY9, keratin 7, keratin 15; LY9, keratin 7, keratin 18; LY9, keratin 7, keratin 19; LY9, keratin 7, tubulin-beta 3; LY9, keratin 8, keratin 15; LY9, keratin 8, keratin 18; LY9, keratin 8, keratin 19; LY9, keratin 8, tubulin-beta 3; LY9, keratin 15, keratin 18; LY9, keratin 15, keratin 19; LY9, keratin 15, tubulin-beta 3; LY9, keratin 18, keratin 19; LY9, keratin 18, tubulin-beta 3; LY9, keratin 19, tubulin-beta 3; keratin 4, keratin 7, keratin 8; keratin 4, keratin 7, keratin 15; keratin 4, keratin 7, keratin 18; keratin 4, keratin 7, keratin 19; keratin 4, keratin 7, tubulin-beta 3; keratin 4, keratin 8, keratin 15; keratin 4, keratin 8, keratin 18; keratin 4, keratin 8, keratin 19; keratin 4, keratin 8, tubulin-beta 3; keratin 4, keratin 15, keratin 18; keratin 4, keratin 15, keratin 19; keratin 4, keratin 15, tubulin-beta 3; keratin 4, keratin 18, keratin 19; keratin 4, keratin 19, tubulin-beta 3; keratin 7, keratin 8, keratin 15; keratin 7, keratin 8, keratin 18; keratin 7, keratin 8, keratin 19; keratin 7, keratin 8, tubulin-beta 3; keratin 7, keratin 8, tubulin-beta 3; keratin 7, keratin 15, keratin 18; keratin 7, keratin 15, keratin 19; keratin 7, keratin 15, tubulin-beta 3; keratin 7, keratin 18, keratin 19; keratin 7, keratin 18, tubulin-beta 3; keratin 15, keratin 18, keratin 19; keratin 15, keratin 18, tubulin-beta 3; and keratin 18, keratin 19, tubulin-beta 3. Any marker set can be used in combination with patient age. Any marker set can be used in combination with PSA. In addition, any of the above sets may be modified to replace one or more markers in the marker set with one or more of the following additional markers: prostate-specific membrane antigen (PSM), prostate stem cell antigen (PSCA), TMPRSS2, PDEF, prostate-specific gene-1 (HPG-1), PCA3, PCGEM1, and the gene cluster P704P, P712P, and P775P.

In another embodiment, the invention contemplates marker sets with at least five (5) members, wherein one member is filamin A and the additional four members may include, but are not limited to the following sets: filamin B, LY9, keratin 4, keratin 7; filamin B, LY9, keratin 4, keratin 8; filamin B, LY9, keratin 4, keratin 15; filamin B, LY9, keratin 4, keratin 18; filamin B, LY9, keratin 4, keratin 19; filamin B, LY9, keratin 4, tubulin-beta 3; filamin B, keratin 4, keratin 7, keratin 8; filamin B, keratin 4, keratin 7, keratin 15; filamin B, keratin 4, keratin 7, keratin 18; filamin B, keratin 4, keratin 7, tubulin-beta 3; filamin B, keratin 4, keratin 7, tubulin-beta 3; filamin B, keratin 7, keratin 8, keratin 15; filamin B, keratin 7, keratin 8, keratin 18; filamin B, keratin 7, keratin 8, keratin 19; filamin B, keratin 7, keratin 8, tubulin-beta 3; filamin B, keratin 8, keratin 15, keratin 18; filamin B, keratin 8, keratin 15, keratin 19; filamin B, keratin 8, keratin 15, tubulin-beta 3; filamin B, keratin 15, keratin 18, keratin 19; filamin B, keratin 15, keratin 18, tubulin-beta 3; filamin B, keratin 18, keratin 19, and tubulin-beta 3; LY9, keratin 4, keratin 7, keratin 8; LY9, keratin 4, keratin 7, keratin 15; LY9, keratin 4, keratin 7, keratin 18; LY9, keratin 4, keratin 7, keratin 19; LY9, keratin 4, keratin 7, tubulin-beta 3; LY9, keratin 7, keratin 8, keratin 15; LY9, keratin 7, keratin 8, keratin 18; LY9, keratin 7, keratin 8, keratin 19; LY9, keratin 7, keratin 8, tubulin-beta 3; LY9, keratin 8, keratin 15, keratin 18; LY9, keratin 8, keratin 15, keratin 19; LY9, keratin 8, keratin 15, tubulin-beta 3; LY9, keratin 15, keratin 18, keratin 19; LY9, keratin 15, keratin 18, tubulin-beta 3; LY9, keratin 18, keratin 19, and tubulin-beta 3; keratin 4, keratin 7, keratin 8, keratin 15; keratin 4, keratin 7, keratin 8, keratin 18; keratin 4, keratin 7, keratin 8, keratin 19; keratin 4, keratin 7, keratin 8, tubulin-beta 3; keratin 4, keratin 8, keratin 15, keratin 18; keratin 4, keratin 8, keratin 15, keratin 19; keratin 4, keratin 8, keratin 15, tubulin-beta 3; keratin 4, keratin 15, keratin 18, keratin 19; keratin 4, keratin 15, keratin 18, tubulin-beta 3; keratin 4, keratin 18, keratin 19, tubulin-beta 3; keratin 8, keratin 15, keratin 18, keratin 19; keratin 8, keratin 15, keratin 18, tubulin-beta 3; and keratin 15, keratin 18, keratin 19, tubulin-beta 3. Any marker set can be used in combination with PSA. In addition, any of the above sets may be modified to replace one or more markers in the marker set with one or more of the following additional markers: prostate-specific membrane antigen (PSM), prostate stem cell antigen (PSCA), TMPRSS2, PDEF, prostate-specific gene-1 (HPG-1), PCA3, PCGEM1, and the gene cluster P704P, P712P, and P775P. Any marker set can be used in combination with patient age.

In another embodiment, the invention contemplates marker sets with at least six (6) members, wherein one member is filamin A and the additional five members may include, but are not limited to the following sets: keratin 8, keratin 15, keratin 18, keratin 19 tubulin-beta 3; keratin 7, keratin 15, keratin 18, keratin 19 tubulin-beta 3; keratin 7, keratin 8, keratin 18, keratin 19 tubulin-beta 3; keratin 7, keratin 8, keratin 15, keratin 19 tubulin-beta 3; keratin 7, keratin 8, keratin 15, keratin 18 tubulin-beta 3; keratin 7, keratin 8, keratin 15, keratin 18, keratin 19; keratin 4, keratin 15, keratin 18, keratin 19 tubulin-beta 3; keratin 4, keratin 8, keratin 18, keratin 19 tubulin-beta 3; keratin 4, keratin 8, keratin 15, keratin 19 tubulin-beta 3; keratin 4, keratin 8, keratin 15, keratin 18 tubulin-beta 3; keratin 4, keratin 8, keratin 15, keratin 18, keratin 19; LY9, keratin 15, keratin 18, keratin 19, tubulin-beta 3; LY9, keratin 8, keratin 18, keratin 19 tubulin-beta 3; LY9, keratin 8, keratin 15, keratin 19 tubulin-beta 3; LY9, keratin 8, keratin 15, keratin 18, and tubulin-beta 3; LY9, keratin 8, keratin 15, keratin 18, keratin 19; filamin B, keratin 15, keratin 18, keratin 19 tubulin-beta 3; filamin B, keratin 8, keratin 18, keratin 19 tubulin-beta 3; filamin B, keratin 8, keratin 15, keratin 19 tubulin-beta 3; filamin B, keratin 8, keratin 15, keratin 18, and tubulin-beta 3; filamin B, keratin 8, keratin 15, keratin 18, keratin 19; filamen B, LY9, keratin 18, keratin 19 tubulin-beta 3; filamen B, LY9, keratin 15, keratin 19 tubulin-beta 3; filamen B, LY9, keratin 15, keratin 18, tubulin-beta 3; filamen B, LY9, keratin 15, keratin 18, keratin 19; filamen B, keratin 4, keratin 18, keratin 19 tubulin-beta 3; filamen B, keratin 4, keratin 15, keratin 19 tubulin-beta 3; filamen B, keratin 4, keratin 15, keratin 18, tubulin-beta 3; filamen B, keratin 4, keratin 15, keratin 18, keratin 19; filamen B keratin 7, keratin 18, keratin 19 tubulin-beta 3; filamen B keratin 7, keratin 15, keratin 19, tubulin-beta 3; filamen B keratin 7, keratin 15, keratin 18, tubulin-beta 3; filamen B keratin 7, keratin 15, keratin 18, keratin 19; filamen B, keratin 8, keratin 18, keratin 19 tubulin-beta 3; filamen B, keratin 8, keratin 15, keratin 19 tubulin-beta 3; filamen B, keratin 8, keratin 15, keratin 18 tubulin-beta 3; filamen B, keratin 8, keratin 15, keratin 18, keratin 19; LY9, keratin 4, keratin 18, keratin 19 and tubulin-beta 3; LY9, keratin 4, keratin 15, keratin 19 tubulin-beta 3; LY9, keratin 4, keratin 15, keratin 18, tubulin-beta 3; LY9, keratin 4, keratin 15, keratin 18, keratin 19; LY9, keratin 7, keratin 18, keratin 19 tubulin-beta 3; LY9, keratin 7, keratin 15, keratin 19 tubulin-beta 3; LY9, keratin 7, keratin 15, keratin 18, and tubulin-beta 3; LY9, keratin 7, keratin 15, keratin 18, keratin 19; LY9, keratin 8, keratin 18, keratin 19 tubulin-beta 3; LY9, keratin 8, keratin 15, keratin 19 tubulin-beta 3; LY9, keratin 8, keratin 15, keratin 18, and tubulin-beta 3; LY9, keratin 8, keratin 15, keratin 18, keratin 19; keratin 4, keratin 7, keratin 18, keratin 19 tubulin-beta 3; keratin 4, keratin 7, keratin 15, keratin 19 tubulin-beta 3; keratin 4, keratin 7, keratin 15, keratin 18, and tubulin-beta 3; keratin 4, keratin 7, keratin 15, keratin 18, keratin 19; keratin 4, keratin 8, keratin 18, keratin 19 tubulin-beta 3; keratin 4, keratin 8, keratin 15, keratin 19 tubulin-beta 3; keratin 4, keratin 8, keratin 15, keratin 18, and tubulin-beta 3; keratin 4, keratin 8, keratin 15, keratin 18, keratin 19; keratin 7, keratin 8, keratin 18, keratin 19 tubulin-beta 3; keratin 7, keratin 8, keratin 15, keratin 19 tubulin-beta 3; keratin 7, keratin 8, keratin 15, keratin 18, and tubulin-beta 3; keratin 7, keratin 8, keratin 15, keratin 18, keratin 19; filamen B, LY9, keratin 4, keratin 19, tubulin-beta 3; filamen B, LY9, keratin 4, keratin 18, ubulin-beta 3; filamen B, LY9, keratin 4, keratin 18, keratin 19; filamen B, LY9, keratin 7, keratin 19, tubulin-beta 3; filamen B, LY9, keratin 7, keratin 18, tubulin-beta 3; filamen B, LY9, keratin 7, keratin 18, keratin 19; filamen B, LY9, keratin 8, keratin 19, tubulin-beta 3; filamen B, LY9, keratin 8, keratin 18, tubulin-beta 3; filamen B, LY9, keratin 8, keratin 18, keratin 19; filamen B, LY9, keratin 15, keratin 19, tubulin-beta 3; filamen B, LY9, keratin 15, keratin 18, tubulin-beta 3; filamen B, LY9, keratin 15, keratin 18, keratin 19; filamen B, keratin 4, keratin 7, keratin 19, tubulin-beta 3; filamen B, keratin 4, keratin 7, keratin 18, tubulin-beta 3; filamen B, keratin 4, keratin 7, keratin 18, keratin 19; filamen B, keratin 4, keratin 8, keratin 19, tubulin-beta 3; filamen B, keratin 4, keratin 8, keratin 18, tubulin-beta 3; filamen B, keratin 4, keratin 8, keratin 18, keratin 19; filamen B, keratin 4, keratin 15, keratin 19, tubulin-beta 3; filamen B, keratin 4, keratin 15, keratin 18, tubulin-beta 3; filamen B, keratin 4, keratin 15, keratin 18, keratin 19; filamen B, keratin 7, keratin 8, keratin 19, tubulin-beta 3; filamen B, keratin 7, keratin 8, keratin 18, tubulin-beta 3; filamen B, keratin 7, keratin 8, keratin 18, keratin 19; filamen B, keratin 8, keratin 15, keratin 19, tubulin-beta 3; filamen B, keratin 8, keratin 15, keratin 18, tubulin-beta 3; filamen B, keratin 8, keratin 15, keratin 18, keratin 19; LY9, keratin 4, keratin 7, keratin 19, tubulin-beta 3; LY9, keratin 4, keratin 7, keratin 18, tubulin-beta 3; LY9, keratin 4, keratin 7, keratin 18, keratin 19; LY9, keratin 4, keratin 8, keratin 19, tubulin-beta 3; LY9, keratin 4, keratin 8, keratin 18, tubulin-beta 3; LY9, keratin 4, keratin 8, keratin 18, keratin 19; LY9, keratin 4, keratin 15, keratin 19, tubulin-beta 3; LY9, keratin 4, keratin 15, keratin 18, tubulin-beta 3; LY9, keratin 4, keratin 15, keratin 18, keratin 19; LY9, keratin 7, keratin 8, keratin 19, tubulin-beta 3; LY9, keratin 7, keratin 8, keratin 18, tubulin-beta 3; LY9, keratin 7, keratin 8, keratin 18, keratin 19; LY9, keratin 7, keratin 15, keratin 19, tubulin-beta 3; LY9, keratin 7, keratin 15, keratin 18, tubulin-beta 3; LY9, keratin 7, keratin 15, keratin 18, keratin 19; LY9, keratin 8, keratin 15, keratin 19, tubulin-beta 3; LY9, keratin 8, keratin 15, keratin 18, tubulin-beta 3; LY9, keratin 8, keratin 15, keratin 18, keratin 19; keratin 4, keratin 7, keratin 8, keratin 19, tubulin-beta 3; keratin 4, keratin 7, keratin 8, keratin 18, tubulin-beta 3; keratin 4, keratin 7, keratin 8, keratin 18, keratin 19; keratin 4, keratin 7, keratin 15, keratin 19, tubulin-beta 3; keratin 4, keratin 7, keratin 15, keratin 18, tubulin-beta 3; keratin 4, keratin 7, keratin 15, keratin 18, keratin 19; keratin 4, keratin 8, keratin 15, keratin 19, tubulin-beta 3; keratin 4, keratin 8, keratin 15, keratin 18, tubulin-beta 3; keratin 4, keratin 8, keratin 15, keratin 18, keratin 19; keratin 7, keratin 8, keratin 15, keratin 19, tubulin-beta 3; keratin 7, keratin 8, keratin 15, keratin 18, tubulin-beta 3; and keratin 7, keratin 8, keratin 15, keratin 18, keratin 19. Any marker set can be used in combination with PSA. In addition, any of the above sets may be modified to replace one or more markers in the marker set with one or more of the following additional markers: prostate-specific membrane antigen (PSM), prostate stem cell antigen (PSCA), TMPRSS2, PDEF, prostate-specific gene-1 (HPG-1), PCA3, PCGEM1, and the gene cluster P704P, P712P, and P775P. Any marker set can be used in combination with patient age.

In another embodiment, the invention contemplates marker sets with at least seven (7) members, wherein one member is filamin A and the additional six members may include, but are not limited to the following sets: keratin 7, keratin 8, keratin 15, keratin 18, keratin 19, and tubulin-beta 3; keratin 4, keratin 8, keratin 15, keratin 18, keratin 19, and tubulin-beta 3; keratin 4, keratin 7, keratin 15, keratin 18, keratin 19, tubulin-beta 3; keratin 4, keratin 7, keratin 8, keratin 18, keratin 19, tubulin-beta 3; keratin 4, keratin 7, keratin 8, keratin 15, keratin 19, tubulin-beta 3; keratin 4, keratin 7, keratin 8, keratin 15, keratin 18, tubulin-beta 3; keratin 4, keratin 7, keratin 8, keratin 15, keratin 18, keratin 19; LY9, keratin 8, keratin 15, keratin 18, keratin 19, tubulin-beta 3; LY9, keratin 7, keratin 15, keratin 18, keratin 19, tubulin-beta 3; LY9, keratin 7, keratin 8, keratin 18, keratin 19, tubulin-beta 3; LY9, keratin 7, keratin 8, keratin 15, keratin 19, tubulin-beta 3; LY9, keratin 7, keratin 8, keratin 15, keratin 18, tubulin-beta 3; LY9, keratin 7, keratin 8, keratin 15, keratin 18, keratin 19; LY9, keratin 4, keratin 15, keratin 18, keratin 19, tubulin-beta 3; LY9, keratin 4, keratin 8, keratin 18, keratin 19, tubulin-beta 3; LY9, keratin 4, keratin 8, keratin 15, keratin 19, tubulin-beta 3; LY9, keratin 4, keratin 8, keratin 15, keratin 18, tubulin-beta 3; LY9, keratin 4, keratin 8, keratin 15, keratin 18, keratin 19; LY9, keratin 4, keratin 7, keratin 18, keratin 19, and tubulin-beta 3; LY9, keratin 4, keratin 7, keratin 15, keratin 19, and tubulin-beta 3; LY9, keratin 4, keratin 7, keratin 15, keratin 18, tubulin-beta 3; LY9, keratin 4, keratin 7, keratin 15, keratin 18, keratin 19; LY9, keratin 4, keratin 7, keratin 8, keratin 19, tubulin-beta 3; LY9, keratin 4, keratin 7, keratin 8, keratin 18, tubulin-beta 3; LY9, keratin 4, keratin 7, keratin 8, keratin 18, keratin 19; LY9, keratin 4, keratin 7, keratin 8, keratin 15, tubulin-beta 3; LY9, keratin 4, keratin 7, keratin 8, keratin 15, keratin 19; and LY9, keratin 4, keratin 7, keratin 8, keratin 15, keratin 18. Any marker set can be used in combination with PSA. In addition, any of the above sets may be modified to replace one or more markers in the marker set with one or more of the following additional markers: prostate-specific membrane antigen (PSM), prostate stem cell antigen (PSCA), TMPRSS2, PDEF, prostate-specific gene-1 (HPG-1), PCA3, PCGEM1, and the gene cluster P704P, P712P, and P775P. Any maker set can be used in combination with patient age.

In another embodiment, the invention contemplates marker sets with at least eight (8) members, wherein one member is filamin A and the additional seven members may include, but are not limited to the following sets: keratin 4, keratin 7, keratin 8, keratin 15, keratin 18, keratin 19, tubulin-beta 3; LY9, keratin 7, keratin 8, keratin 15, keratin 18, keratin 19, tubulin-beta 3; LY9, keratin 4, keratin 8, keratin 15, keratin 18, keratin 19, tubulin-beta 3; LY9, keratin 4, keratin 7, keratin 15, keratin 18, keratin 19, tubulin-beta 3; LY9, keratin 4, keratin 7, keratin 8, keratin 18, keratin 19, tubulin-beta 3; LY9, keratin 4, keratin 7, keratin 8, keratin 15, keratin 19, tubulin-beta 3; LY9, keratin 4, keratin 7, keratin 8, keratin 15, keratin 18, tubulin-beta 3; LY9, keratin 4, keratin 7, keratin 8, keratin 15, keratin 18, keratin 19; filamin B, keratin 7, keratin 8, keratin 15, keratin 18, keratin 19, tubulin-beta 3; filamin B, keratin 4, keratin 8, keratin 15, keratin 18, keratin 19, tubulin-beta 3; filamin B, keratin 4, keratin 7, keratin 15, keratin 18, keratin 19, tubulin-beta 3; filamin B, keratin 4, keratin 7, keratin 8, keratin 18, keratin 19, tubulin-beta 3; filamin B, keratin 4, keratin 7, keratin 8, keratin 15, keratin 19, tubulin-beta 3; filamin B, keratin 4, keratin 7, keratin 8, keratin 15, keratin 18, tubulin-beta 3; filamin B, keratin 4, keratin 7, keratin 8, keratin 15, keratin 18, keratin 19; filamin B, LY9, keratin 8, keratin 15, keratin 18, keratin 19, tubulin-beta 3; filamin B, LY9, keratin 7, keratin 15, keratin 18, keratin 19, tubulin-beta 3; filamin B, LY9, keratin 7, keratin 8, keratin 18, keratin 19, tubulin-beta 3; filamin B, LY9, keratin 7, keratin 8, keratin 15, keratin 19, tubulin-beta 3; filamin B, LY9, keratin 7, keratin 8, keratin 15, keratin 18, tubulin-beta 3; filamin B, LY9, keratin 7, keratin 8, keratin 15, keratin 18, keratin 19; filamin B, LY9, keratin 4, keratin 15, keratin 18, keratin 19, tubulin-beta 3; filamin B, LY9, keratin 4, keratin 8, keratin 18, keratin 19, tubulin-beta 3; filamin B, LY9, keratin 4, keratin 8, keratin 15, keratin 19, tubulin-beta 3; filamin B, LY9, keratin 4, keratin 8, keratin 15, keratin 18, tubulin-beta 3; filamin B, LY9, keratin 4, keratin 8, keratin 15, keratin 18, keratin 19; filamin B, LY9, keratin 4, keratin 7, keratin 18, keratin 19, and tubulin-beta 3; filamin B, LY9, keratin 4, keratin 7, keratin 15, keratin 19, and tubulin-beta 3; filamin B, LY9, keratin 4, keratin 7, keratin 15, keratin 18, tubulin-beta 3; filamin B, LY9, keratin 4, keratin 7, keratin 15, keratin 18, keratin 19; filamin B, LY9, keratin 4, keratin 7, keratin 8, keratin 19, tubulin-beta 3; filamin B, LY9, keratin 4, keratin 7, keratin 8, keratin 18, tubulin-beta 3; filamin B, LY9, keratin 4, keratin 7, keratin 8, keratin 18, keratin 19; filamin B, LY9, keratin 4, keratin 7, keratin 8, keratin 15, tubulin-beta 3; filamin B, LY9, keratin 4, keratin 7, keratin 8, keratin 15, keratin 19; and filamin B, LY9, keratin 4, keratin 7, keratin 8, keratin 15, keratin 18. Any marker set can be used in combination with PSA. In addition, any of the above sets may be modified to replace one or more markers in the marker set with one or more of the following additional markers: prostate-specific membrane antigen (PSM), prostate stem cell antigen (PSCA), TMPRSS2, PDEF, prostate-specific gene-1 (HPG-1), PCA3, PCGEM1, and the gene cluster P704P, P712P, and P775P. Any marker set can be used in combination with patient age.

In another embodiment, the invention contemplates marker sets with at least nine (9) members, wherein one member is filamin A and the additional eight members may include, but are not limited to the following sets: LY9, keratin 4, keratin 7, keratin 8, keratin 15, keratin 18, keratin 19, tubulin-beta 3; filamin B, keratin 4, keratin 7, keratin 8, keratin 15, keratin 18, keratin 19, tubulin-beta 3; filamin B, LY9, keratin 7, keratin 8, keratin 15, keratin 18, keratin 19, tubulin-beta 3; filamin B, LY9, keratin 4, keratin 8, keratin 15, keratin 18, keratin 19, tubulin-beta 3; filamin B, LY9, keratin 4, keratin 7, keratin 15, keratin 18, keratin 19, tubulin-beta 3; filamin B, LY9, keratin 4, keratin 7, keratin 8, keratin 18, keratin 19, tubulin-beta 3; filamin B, LY9, keratin 4, keratin 7, keratin 8, keratin 15, keratin 19, tubulin-beta 3; filamin B, LY9, keratin 4, keratin 7, keratin 8, keratin 15, keratin 18, tubulin-beta 3; and filamin B, LY9, keratin 4, keratin 7, keratin 8, keratin 15, keratin 18, keratin 19. Any marker set can be used in combination with PSA. In addition, any of the above sets may be modified to replace one or more markers in the marker set with one or more of the following additional markers: prostate-specific membrane antigen (PSM), prostate stem cell antigen (PSCA), TMPRSS2, PDEF, prostate-specific gene-1 (HPG-1), PCA3, PCGEM1, and the gene cluster P704P, P712P, and P775P. Any marker set can be used in combination with patient age.

In another embodiment, the invention contemplates marker sets with at least ten (10) members, wherein one member is filamin A and the additional nine members may include, but are not limited to the following sets: filamin B, LY9, keratin 4, keratin 7, keratin 8, keratin 15, keratin 18, keratin 19, and tubulin-beta 3. In addition, any of the above sets may be modified to replace one or more markers in the marker set with one or more of the following additional markers: prostate-specific membrane antigen (PSM), prostate stem cell antigen (PSCA), TMPRSS2, PDEF, prostate-specific gene-1 (HPG-1), PCA3, PCGEM1, and the gene cluster P704P, P712P, and P775P. Any marker set can be used in combination with patient age.

Any marker set can be used in combination with PSA.

The invention provides for the use of various combinations and sub-combinations of markers. It is understood that any single marker or combination of the markers provided herein can be used in the invention unless clearly indicated otherwise. Further, any single marker or combination of the markers of the invention can be used in conjunction with patient age. Alternatively, any single marker or combination of the markers of the invention can be used in conjunction with PSA. Alternatively, any single marker or combination of the markers of the invention can be used in conjunction with patient age and PSA.

Throughout the application, one or more of filamin B, LY9 and keratin 19 is understood as any of: filamin B; LY9; keratin 19; filamin B and LY9; filamin B and keratin 19; LY9 and keratin 19; or filamin B, LY9, and keratin 19. Further, any single marker or combination of the markers of the invention can be used in conjunction with PSA. Further, any single marker or combination of the markers of the invention can be used in conjunction with patient age. Preferably, each marker set includes, in addition if not already indicated, filamin A.

Throughout the application, combination of the filamin B and LY9 with PSA is understood as any of filamin B; LY9; filamin B and PSA; filamin B and LY9; LY9 and PSA; filamin B, LY9, and PSA. Preferably, each marker set includes, in addition if not already indicated, filamin A. Preferably, each marker set includes, in addition if not already indicated, patient age.

Throughout the application, one or more prostate cancer markers selected from the group consisting of keratin 4, keratin 7, keratin 8, keratin 15, keratin 18, and tubulin beta-3 is understood as any of keratin 4; keratin 7; keratin 8; keratin 15; keratin 18; tubulin beta-3; keratin 4 and keratin 7; keratin 4 and keratin 8; keratin 4 and keratin 15; keratin 4 and keratin 18; keratin 4 and tubulin beta-3; keratin 7 and keratin 8; keratin 7 and keratin 15; keratin 7 and keratin 18; keratin and tubulin beta-3; keratin 8 and keratin 15; keratin 8 and keratin 18; keratin 8 and tubulin beta-3; keratin 15 and keratin 18; keratin 15 and tubulin beta-3; keratin 18 and tubulin beta-3; keratin 4, keratin 7 and keratin 8; keratin 4, keratin 7 and keratin 15; keratin 4, keratin 7 and keratin 18; keratin 4, keratin 7 and tubulin beta-3; keratin 4, keratin 8 and keratin 15; keratin 4, keratin 8 and keratin 18; keratin 4, keratin 8 and tubulin beta-e; keratin 4, keratin 15 and keratin 18; keratin 4, keratin 15 and tubulin beta-e; keratin 4, keratin 18 and tubulin beta-3; kertin 4, keratin 7, keratin 8 and keratin 15; keratin 4, keratin 7, keratin 8 and keratin 18; keratin 4, keratin 7, keratin 8 and tubulin beta-3; keratin 4, keratin 8, keratin 15 and keratin 18; keratin 4, keratin 8, keratin 15 and tubulin beta-3; keratin 4, keratin 15, keratin 18 and tubulin beta-3; keratin 4, keratin 7, keratin 8, keratin 15 and keratin 18; keratin 4, keratin 7, keratin 8, keratin 15, and tubulin beta-3; keratin 4, keratin 7, keratin 8, keratin 18, and tubulin beta-3; keratin 4, keratin 7, keratin 15, keratin 18, and tubulin beta-3; keratin 4, keratin 8, keratin 15, keratin 18, and tubulin beta-3; or keratin 7, keratin 8, keratin 15, keratin 18, and tubulin beta-3. Further, any single marker or combination of the markers of the invention can be used in conjunction with PSA. Preferably, each marker set includes, in addition if not already indicated, filamin A. Preferably, each marker set includes, in addition if not already indicated, patient age.

Throughout the application, one or more prostate cancer markers selected from the group consisting of keratin 7, 15, and 19 is understood as any of keratin 7; keratin 15; keratin 19; keratin 7 and 15; keratin 7 and 19; keratin 15 and 19; and keratin 7, 15, and 19. Further, any single marker or combination of the markers of the invention can be used in conjunction with PSA. Preferably, each marker set includes, in addition if not already indicated, filamin A. Preferably, each marker set includes, in addition if not already indicated, patient age.

Throughout the application, one or more prostate cancer markers selected from the group consisting of keratin 7, 8, and 15 is understood as any of keratin 7; keratin 8; keratin 15; keratin 7 and 8; keratin 7 and 15; keratin 8 and 15; and keratin 7, 8, and 15. Further, any single marker or combination of the markers of the invention can be used in conjunction with PSA. Preferably, each marker set includes, in addition if not already indicated, filamin A. Preferably, each marker set includes, in addition if not already indicated, patient age.

Throughout the application, one or more prostate cancer markers selected from the group consisting of keratin 7 and 15 is understood as any of keratin 7; keratin 15; or keratin 7 and 15. Further, any single marker or combination of the markers of the invention can be used in conjunction with PSA. Preferably, each marker set includes, in addition if not already indicated, filamin A. Preferably, each marker set includes, in addition if not already indicated, patient age.

Throughout the application, one or more prostate cancer markers selected from the group consisting filamin B, LY9, or keratin 19 is understood as any of filamin B; LY9; keratin 19; filamin B and LY9; filamin B and keratin 19; LY9, and keratin 19; and filamin B, LY9, and keratin 19. Further, any single marker or combination of the markers of the invention can be used in conjunction with PSA. Preferably, each marker set includes, in addition if not already indicated, filamin A. Preferably, each marker set includes, in addition if not already indicated, patient age.

In another aspect, the present invention provides for the identification of a "diagnostic signature" or "disease profile" based on the levels of the biomarkers of the invention in a biological sample, including in a diseased tissue (e.g., prostate tumor) or directly from the serum or blood, that correlates with the presence and/or risk and/or prognosis of prostate cancer. The "levels of the biomarkers" can refer to the expression level of the biomarker genes, e.g., by measuring the expression levels of the biomarker mRNAs. The "levels of the biomarkers" can also refer to level of biomarker polypeptides in a biological sample, e.g., prostate tissue or serum. The collection or totality of expression levels of biomarker polypeptides and/or nucleic acid molecules provide a diagnostic signature that correlates with the presence and/or diagnosis and/or progression of prostate cancer. The biomarkers for obtaining a diagnostic signature or disease profile of the invention are meant to encompass any measurable characteristic that reflects in a quantitative or qualitative manner the physiological state of an organism, e.g, whether the organism has prostate cancer. The physiological state of an organism is inclusive of any disease or non-disease state, e.g., a subject having prostate cancer or a subject who is otherwise healthy. Said another way, the biomarkers used for identifying a diagnostic signature or disease profile of the invention include characteristics that can be objectively measured and evaluated as indicators of normal processes, pathogenic processes, or pharmacologic responses to a therapeutic intervention, including, in particular, prostate cancer. Biomarkers can be clinical parameters (e.g., age, performance status), laboratory measures (e.g., molecular biomarkers, such as prostate specific antigen), imaging-based measures, or genetic or other molecular determinants. Examples of biomarkers include, for example, polypeptides, peptides, polypeptide fragments, proteins, antibodies, hormones, polynucleotides, RNA or RNA fragments, microRNA (miRNAs), lipids, polysaccharides, and other bodily metabolites that are diagnostic and/or indicative and/or predictive of an oncological disease, e.g., prostate cancer. Examples of biomarkers also include polypeptides, peptides, polypeptide fragments, proteins, antibodies, hormones, polynucleotides, RNA or RNA fragments, microRNA (miRNAs), lipids, polysaccharides, and other bodily metabolites which are diagnostic and/or indicative and/or predictive of any stage or clinical phase of an oncological disease, e.g., Gleason grade 1, grade 2, grade 3, grade 4, or grade 5 prostate cancer.

In a particular embodiment, a prostate cancer disease profile or diagnostic signature is determined on the basis of the combination of filamin A together with one or more additional biomarkers of prostate cancer, which can include, but are not limited to prostate specific antigen (PSA), filamin B, LY9, keratin 4, keratin 7, keratin 8, keratin 15, keratin 18, keratin 19, and tubulin-beta 3, as well as additional markers PSM, PSCA, TMPRSS2, PDEF, HPG-1, PCA3, and PCGEM1. Other markers that may be used in combination with filamin A include any measurable characteristic that reflects in a quantitative or qualitative manner the physiological state of an organism, e.g, whether the organism has prostate cancer. Such characteristics may include patient age. The physiological state of an organism is inclusive of any disease or non-disease state, e.g., a subject having prostate cancer or a subject who is otherwise healthy. Said another way, the biomarkers of the invention that may be used in combination with filamin A include characteristics that can be objectively measured and evaluated as indicators of normal processes, pathogenic processes, or pharmacologic responses to a therapeutic intervention, including, in particular, prostate cancer. Such combination biomarkers can be clinical parameters (e.g., age, performance status), laboratory measures (e.g., molecular biomarkers, such as prostate specific antigen), imaging-based measures, or genetic or other molecular determinants. Example of biomarkers for use in combination with filamin A include, for example, polypeptides, peptides, polypeptide fragments, proteins, antibodies, hormones, polynucleotides, RNA or RNA fragments, microRNA (miRNAs), lipids, polysaccharides, and other bodily metabolites that are diagnostic and/or indicative and/or predictive of prostate cancer, or any particular stage or phase of prostate cancer, e.g., Gleason grade 1, grade 2, grade 3, grade 4, or grade 5 prostate cancer. In certain embodiments, biomarkers for use in combination with filamin A include polypeptides, peptides, polypeptide fragments, proteins, antibodies, hormones, polynucleotides, RNA or RNA fragments, microRNA (miRNAs), lipids, polysaccharides, and other bodily metabolites which are diagnostic and/or indicative and/or predictive of prostate cancer, or any stage or clinical phase thereof, e.g., Gleason grade 1, grade 2, grade 3, grade 4, or grade 5 prostate cancer or TNM classifications. In other embodiments, the present invention also involves the analysis and consideration of any clinical and/or patient-related health data, for example, data obtained from an Electronic Medical Record (e.g., collection of electronic health information about individual patients or populations relating to various types of data, such as, demographics, medical history, medication and allergies, immunization status, laboratory test results, radiology images, vital signs, personal statistics like age and weight, and billing information).

In certain embodiments, the diagnostic signature is obtained by (1) detecting the level of filamin A in a biological sample, (2) detecting the level(s) of one or more additional biomarkers that may include, but are not limited to prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1, and (3) comparing the levels of filamin A and the one or more additional biomarkers to the levels of the same biomarkers from a control sample, (4) determining if the filamin A and the one or more additional biomarkers detected in the biological sample are above a certain threshold level. If filamin A and at least 1 additionally detected biomarker is above the threshold level, then the diagnostic signature is indicative of prostate cancer in the biological sample. In certain embodiments, the diagnostic signature can be determined based on an algorithm or computer program that predicts whether the biological sample is cancerous based on the levels of filamin A and the one or more additional biomarkers.

In certain other embodiments, the diagnostic signature is obtained by (1) detecting the level of filamin A in a biological sample, (2) detecting the level(s) of two or more additional biomarkers that may include, but are not limited to prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1, and (3) comparing the levels of filamin A and the two or more additional biomarkers to the levels of the same biomarkers from a control sample, (4) determining if the filamin A and the two or more additional biomarkers detected in the biological sample are above a certain threshold level. If filamin A and at least 2 additionally detected biomarkers are above the threshold level, then the diagnostic signature is indicative of prostate cancer in the biological sample. In certain embodiments, the diagnostic signature can be determined based on an algorithm or computer program that predicts whether the biological sample is cancerous based on the levels of filamin A and the two or more additional biomarkers. In other embodiments, the diagnostic signature also takes into account the patient's age.

In certain other embodiments, the diagnostic signature is obtained by (1) detecting the level of filamin A in a biological sample, (2) detecting the level(s) of three or more additional biomarkers that may include, but are not limited to prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1, and (3) comparing the levels of filamin A and the three or more additional biomarkers to the levels of the same biomarkers from a control sample, (4) determining if the filamin A and the three or more additional biomarkers detected in the biological sample are above a certain threshold level. If filamin A and at least 3 additionally detected biomarkers are above the threshold level, then the diagnostic signature is indicative of prostate cancer in the biological sample. In certain embodiments, the diagnostic signature can be determined based on an algorithm or computer program that predicts whether the biological sample is cancerous based on the levels of filamin A and the three or more additional biomarkers. In other embodiments, the diagnostic signature also takes into account the patient's age.

In other embodiments, the diagnostic signature is obtained by (1) detecting the level of filamin A in a biological sample, (2) detecting the level(s) of four or more additional biomarkers that may include, but are not limited to prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1, and (3) comparing the levels of filamin A and the four or more additional biomarkers to the levels of the same biomarkers from a control sample, (4) determining if the filamin A and the four or more additional biomarkers detected in the biological sample are above a certain threshold level. If filamin A and at least 4 additionally detected biomarkers are above the threshold level, then the diagnostic signature is indicative of prostate cancer in the biological sample. In certain embodiments, the diagnostic signature can be determined based on an algorithm or computer program that predicts whether the biological sample is cancerous based on the levels of filamin A and the four or more additional biomarkers. In other embodiments, the diagnostic signature also takes into account the patient's age.

In other embodiments, the diagnostic signature is obtained by (1) detecting the level of filamin A in a biological sample, (2) detecting the level(s) of five or more additional biomarkers that may include, but are not limited to prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1, and (3) comparing the levels of filamin A and the five or more additional biomarkers to the levels of the same biomarkers from a control sample, (4) determining if the filamin A and the five or more additional biomarkers detected in the biological sample are above a certain threshold level. If filamin A and at least 5 additionally detected biomarkers are above the threshold level, then the diagnostic signature is indicative of prostate cancer in the biological sample. In certain embodiments, the diagnostic signature can be determined based on an algorithm or computer program that predicts whether the biological sample is cancerous based on the levels of filamin A and the five or more additional biomarkers. In other embodiments, the diagnostic signature also takes into account the patient's age.

In other embodiments, the diagnostic signature is obtained by (1) detecting the level of filamin A in a biological sample, (2) detecting the level(s) of six or more additional biomarkers that may include, but are not limited to prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1, and (3) comparing the levels of filamin A and the six or more additional biomarkers to the levels of the same biomarkers from a control sample, (4) determining if the filamin A and the six or more additional biomarkers detected in the biological sample are above a certain threshold level. If filamin A and at least 6 additionally detected biomarkers are above the threshold level, then the diagnostic signature is indicative of prostate cancer in the biological sample. In certain embodiments, the diagnostic signature can be determined based on an algorithm or computer program that predicts whether the biological sample is cancerous based on the levels of filamin A and the six or more additional biomarkers. In other embodiments, the diagnostic signature also takes into account the patient's age.

In other embodiments, the diagnostic signature is obtained by (1) detecting the level of filamin A in a biological sample, (2) detecting the level(s) of seven or more additional biomarkers that may include, but are not limited to prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1, and (3) comparing the levels of filamin A and the seven or more additional biomarkers to the levels of the same biomarkers from a control sample, (4) determining if the filamin A and the seven or more additional biomarkers detected in the biological sample are above a certain threshold level. If filamin A and at least 7 additionally detected biomarkers are above the threshold level, then the diagnostic signature is indicative of prostate cancer in the biological sample. In certain embodiments, the diagnostic signature can be determined based on an algorithm or computer program that predicts whether the biological sample is cancerous based on the levels of filamin A and the seven or more additional biomarkers. In other embodiments, the diagnostic signature also takes into account the patient's age.

In other embodiments, the diagnostic signature is obtained by (1) detecting the level of filamin A in a biological sample, (2) detecting the level(s) of eight or more additional biomarkers that may include, but are not limited to prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1, and (3) comparing the levels of filamin A and the eight or more additional biomarkers to the levels of the same biomarkers from a control sample, (4) determining if the filamin A and the eight or more additional biomarkers detected in the biological sample are above a certain threshold level. If filamin A and at least 8 additionally detected biomarkers are above the threshold level, then the diagnostic signature is indicative of prostate cancer in the biological sample. In certain embodiments, the diagnostic signature can be determined based on an algorithm or computer program that predicts whether the biological sample is cancerous based on the levels of filamin A and the eight or more additional biomarkers. In other embodiments, the diagnostic signature also takes into account the patient's age.

In other embodiments, the diagnostic signature is obtained by (1) detecting the level of filamin A in a biological sample, (2) detecting the level(s) of nine or more additional biomarkers that may include, but are not limited to prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1, and (3) comparing the levels of filamin A and the nine or more additional biomarkers to the levels of the same biomarkers from a control sample, (4) determining if the filamin A and the nine or more additional biomarkers detected in the biological sample are above a certain threshold level. If filamin A and at least 9 additionally detected biomarkers are above the threshold level, then the diagnostic signature is indicative of prostate cancer in the biological sample. In certain embodiments, the diagnostic signature can be determined based on an algorithm or computer program that predicts whether the biological sample is cancerous based on the levels of filamin A and the nine or more additional biomarkers. In other embodiments, the diagnostic signature also takes into account the patient's age.

In accordance with various embodiments, algorithms may be employed to predict whether or not a biological sample is likely to be diseased, e.g., have prostate cancer. The skilled artisan will appreciate that an algorithm can be any computation, formula, statistical survey, nomogram, look-up table, decision tree method, or computer program which processes a set of input variables (e.g., number of markers (n) which have been detected at a level exceeding some threshold level, or number of markers (n) which have been detected at a level below some threshold level) through a number of well-defined successive steps to eventually produce a score or "output," e.g., a diagnosis of prostate cancer. Any suitable algorithm—whether computer-based or manual-based (e.g., look-up table)—is contemplated herein.

In certain embodiments, an algorithm of the invention used to predict whether a biological sample has prostate cancer producing a score on the basis of the detected level of filamin A in the sample and the level(s) at least one, or two, or three, or four, or five, or six, or seven, or eight, or nine or more additional prostate cancer markers (e.g., selected from the group consisting of prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1), wherein if the score is above a certain threshold score, then the biological sample has prostate cancer. In certain embodiments, the algorithm also produces a score using the patient's age as a continuous predictor variable. For example, increased age is associated with higher risk of prostate cancer.

In certain embodiments, an algorithm of the invention used to predict whether a biological sample has prostate cancer producing a score on the basis of the detected level of filamin A in the sample and the level(s) at least one, or two, or three, or four, or five, or six, or seven, or eight, or nine or more additional prostate cancer markers (e.g., selected from the group consisting of prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1), wherein if the score is below a certain threshold score, then the biological sample has prostate cancer. In certain embodiments, the algorithm also produces a score using the patient's age as a continuous predictor variable.

In certain embodiments, an algorithm of the invention used to predict whether a biological sample has prostate cancer producing a score on the basis of the detected level of filamin A in the sample and the level(s) at least one, or two, or three, or four, or five, or six, or seven, or eight, or nine or more additional prostate cancer markers (e.g., selected from the group consisting of prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1), wherein if the score is above a certain threshold score, then the biological sample does not have prostate cancer. In certain embodiments, the algorithm also produces a score using the patient's age as a continuous predictor variable.

In certain embodiments, an algorithm of the invention used to predict whether a biological sample has prostate cancer producing a score on the basis of the detected level of filamin A in the sample and the level(s) at least one, or two, or three, or four, or five, or six, or seven, or eight, or nine or more additional prostate cancer markers (e.g., selected from the group consisting of prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1), wherein if the score is below a certain threshold score, then the biological sample does not have prostate cancer. In certain embodiments, the algorithm also produces a score using the patient's age as a continuous predictor variable.

Moreover, a prostate cancer disease profile or signature may be obtained by detecting filamin A in combination with at least one other biomarker, or more preferably, with at least two other biomarkers, or still more preferably, with at least three other biomarkers, or even more preferably with at least four other biomarkers. Still further, filamin A in certain embodiments, may be used in combination with at least five other markers, or at least six other biomarkers, or at least seven other biomarkers, or at least eight other biomarkers, or at least nine other biomarkers, or at least ten other biomarkers, or at least eleven other biomarkers, or at least twelve other biomarkers, or at least thirteen other biomarkers, or at least fourteen other biomarkers, or at least fifteen other biomarkers, or at least sixteen other biomarkers, or at least seventeen other biomarkers, or at least eighteen other biomarkers, or at least nineteen other biomarkers, or at least twenty other biomarkers. Further still, filamin A may be used in combination with a multitude of other biomarkers, including, for example, with between about 20-50 other biomarkers, or between 50-100, or between 100-500, or between 500-1000, or between 1000-10,000 or biomarkers or more. In certain embodiments, the patient's age is also used as a continuous predictor variable. For example, increased age is associated with increased risk of prostate cancer diagnosis.

In certain embodiments, the biomarkers of the invention can include variant sequences. More particularly, the binding agents/reagents used for detecting the biomarkers of the invention can bind and/or identify variants of the biomarkers of the invention. As used herein, the term "variant" comprehends nucleotide or amino acid sequences different from the specifically identified sequences, wherein one or more nucleotides or amino acid residues is deleted, substituted, or added. Variants may be naturally occurring allelic variants, or non-naturally occurring variants. Variant sequences (polynucleotide or polypeptide) preferably exhibit at least 80%, 85%, 90%, 95%, 96%, 97%, 98% or 99% identity to a sequence disclosed herein. The percentage identity is determined by aligning the two sequences to be compared as described below, determining the number of identical residues in the aligned portion, dividing that number by the total number of residues in the inventive (queried) sequence, and multiplying the result by 100.

In addition to exhibiting the recited level of sequence identity, variants of the disclosed polypeptide biomarkers are preferably themselves expressed in subjects with prostate cancer at levels that are higher or lower than the levels of expression in normal, healthy individuals.

Variant sequences generally differ from the specifically identified sequence only by conservative substitutions, deletions or modifications. As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. Variants may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptide and polynucleotide sequences may be aligned, and percentages of identical amino acids or nucleotides in a specified region may be determined against another polypeptide or polynucleotide sequence, using computer algorithms that are publicly available. The percentage identity of a polynucleotide or polypeptide sequence is determined by aligning polynucleotide and polypeptide sequences using appropriate algorithms, such as BLASTN or BLASTP, respectively, set to default parameters; identifying the number of identical nucleic or amino acids over the aligned portions; dividing the number of identical nucleic or amino acids by the total number of nucleic or amino acids of the polynucleotide or polypeptide of the present invention; and then multiplying by 100 to determine the percentage identity.

Two exemplary algorithms for aligning and identifying the identity of polynucleotide sequences are the BLASTN and FASTA algorithms. The alignment and identity of polypeptide sequences may be examined using the BLASTP algorithm. BLASTX and FASTX algorithms compare nucleotide query sequences translated in all reading frames against polypeptide sequences. The FASTA and FASTX algorithms are described in Pearson and Lipman, Proc. Natl. Acad. Sci. USA 85:2444-2448, 1988; and in Pearson, Methods in Enzymol. 183:63-98, 1990. The FASTA software package is available from the University of Virginia, Charlottesville, Va. 22906-9025. The FASTA algorithm, set to the default parameters described in the documentation and distributed with the algorithm, may be used in the determination of polynucleotide variants. The readme files for FASTA and FASTX Version 2.0x that are distributed with the algorithms describe the use of the algorithms and describe the default parameters.

The BLASTN software is available on the NCBI anonymous FTP server and is available from the National Center for Biotechnology Information (NCBI), National Library of Medicine, Building 38A, Room 8N805, Bethesda, Md. 20894. The BLASTN algorithm Version 2.0.6 [Sep. 10, 1998] and Version 2.0.11 [Jan. 20, 2000] set to the default parameters described in the documentation and distributed with the algorithm, is preferred for use in the determination of variants according to the present invention. The use of the BLAST family of algorithms, including BLASTN, is described at NCBI's website and in the publication of Altschul, et al., "Gapped BLAST and PSI-BLAST: a new generation of protein database search programs," Nucleic Acids Res. 25:3389-3402, 1997.

In an alternative embodiment, variant polypeptides are encoded by polynucleotide sequences that hybridize to a disclosed polynucleotide under stringent conditions. Stringent hybridization conditions for determining complementarity include salt conditions of less than about 1 M, more usually less than about 500 mM, and preferably less than about 200 mM. Hybridization temperatures can be as low as 5° C., but are generally greater than about 22° C., more preferably greater than about 30° C., and most preferably greater than about 37° C. Longer DNA fragments may require higher hybridization temperatures for specific hybridization. Since the stringency of hybridization may be affected by other factors such as probe composition, presence of organic solvents and extent of base mismatching, the combination of parameters is more important than the absolute measure of any one alone. An example of "stringent conditions" is prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

D. Tissue Samples

The present invention may be practiced with any suitable biological sample that potentially contains, expresses, includes, a detectable disease biomarker, e.g., a polypeptide biomarker, a nucleic acid biomarkers, a mRNA biomarker, a microRNA biomarker. For example, the biological sample may be obtained from sources that include whole blood and serum to diseased and/or healthy tissue, for example, biopsy of prostate tumor. The methods of the invention may especially be applied to the study of any prostate tissue sample, i.e., a sample of prostate tissue or fluid, as well as cells (or their progeny) isolated from such tissue or fluid. In another embodiment, the present invention may be practiced with any suitable Prostate tissue samples which are freshly isolated or which have been frozen or stored after having been collected from a subject, or archival tissue samples, for example, with known diagnosis, treatment and/or outcome history. Prostate tissue may be collected by any non-invasive means, such as, for example, fine needle aspiration and needle biopsy, or alternatively, by an invasive method, including, for example, surgical biopsy.

The inventive methods may be performed at the single cell level (e.g., isolation and testing of cancerous cells from the prostate tissue sample). However, preferably, the inventive methods are performed using a sample comprising many cells, where the assay is "averaging" expression over the entire collection of cells and tissue present in the sample. Preferably, there is enough of the prostate tissue sample to accurately and reliably determine the expression levels of the set of genes of interest. In certain embodiments, multiple samples may be taken from the same prostate tissue in order to obtain a representative sampling of the tissue. In addition, sufficient biological material can be obtained in order to perform duplicate, triplicate or further rounds of testing.

Any commercial device or system for isolating and/or obtaining prostate tissue and/or blood or other biological products, and/or for processing said materials prior to conducting a detection reaction is contemplated.

In certain embodiments, the present invention relates to detecting biomarker nucleic acid molecules (e.g., mRNA encoding filamin A, antigen (PSA), filamin B, LY9, keratin 4, keratin 7, keratin 8, keratin 15, kertin 18, keratin 19, and tubulin-beta 3). In such embodiments, RNA can be extracted from a biological sample, e.g., a prostate tissue sample, before analysis. Methods of RNA extraction are well known in the art (see, for example, J. Sambrook et al., "Molecular Cloning: A Laboratory Manual", 1989, $2^{nd}$ Ed., Cold Spring Harbour Laboratory Press: New York). Most methods of RNA isolation from bodily fluids or tissues are based on the disruption of the tissue in the presence of protein denaturants to quickly and effectively inactivate RNases. Generally, RNA isolation reagents comprise, among other components, guanidinium thiocyanate and/or beta-mercaptoethanol, which are known to act as RNase inhibitors. Isolated total RNA is then further purified from the protein contaminants and concentrated by selective ethanol precipitations, phenol/chloroform extractions followed by isopropanol precipitation (see, for example, P. Chomczynski and N. Sacchi, Anal. Biochem., 1987, 162: 156-159) or cesium chloride, lithium chloride or cesium trifluoroacetate gradient centrifugations.

Numerous different and versatile kits can be used to extract RNA (i.e., total RNA or mRNA) from bodily fluids or tissues (e.g., prostate tissue samples) and are commercially available from, for example, Ambion, Inc. (Austin, Tex.), Amersham Biosciences (Piscataway, N.J.), BD Biosciences Clontech (Palo Alto, Calif.), BioRad Laboratories (Hercules, Calif.), GIBCO BRL (Gaithersburg, Md.), and Giagen, Inc. (Valencia, Calif.). User Guides that describe in great detail the protocol to be followed are usually included in all these kits. Sensitivity, processing time and cost may be different from one kit to another. One of ordinary skill in the art can easily select the kit(s) most appropriate for a particular situation.

In certain embodiments, after extraction, mRNA is amplified, and transcribed into cDNA, which can then serve as template for multiple rounds of transcription by the appropriate RNA polymerase. Amplification methods are well known in the art (see, for example, A. R. Kimmel and S. L. Berger, Methods Enzymol. 1987, 152: 307-316; J. Sambrook et al., "Molecular Cloning: A Laboratory Manual", 1989, 2.sup.nd Ed., Cold Spring Harbour Laboratory Press: New York; "Short Protocols in Molecular Biology", F. M. Ausubel (Ed.), 2002, 5.sup.th Ed., John Wiley & Sons; U.S. Pat. Nos. 4,683,195; 4,683,202 and 4,800,159). Reverse transcription reactions may be carried out using non-specific primers, such as an anchored oligo-dT primer, or random sequence primers, or using a target-specific primer complementary to the RNA for each genetic probe being monitored, or using thermostable DNA polymerases (such as avian myeloblastosis virus reverse transcriptase or Moloney murine leukemia virus reverse transcriptase).

In certain embodiments, the RNA isolated from the prostate tissue sample (for example, after amplification and/or conversion to cDNA or cRNA) is labeled with a detectable agent before being analyzed. The role of a detectable agent is to facilitate detection of RNA or to allow visualization of hybridized nucleic acid fragments (e.g., nucleic acid fragments hybridized to genetic probes in an array-based assay). Preferably, the detectable agent is selected such that it generates a signal which can be measured and whose intensity is related to the amount of labeled nucleic acids present in the sample being analyzed. In array-based analysis methods, the detectable agent is also preferably selected such that it generates a localized signal, thereby allowing spatial resolution of the signal from each spot on the array.

Methods for labeling nucleic acid molecules are well-known in the art. For a review of labeling protocols, label detection techniques and recent developments in the field, see, for example, L. J. Kricka, Ann. Clin. Biochem. 2002, 39: 114-129; R. P. van Gijlswijk et al., Expert Rev. Mol. Diagn. 2001, 1: 81-91; and S. Joos et al., J. Biotechnol. 1994, 35: 135-153. Standard nucleic acid labeling methods include: incorporation of radioactive agents, direct attachment of fluorescent dyes (see, for example, L. M. Smith et al., Nucl. Acids Res. 1985, 13: 2399-2412) or of enzymes (see, for example, B. A. Connoly and P. Rider, Nucl. Acids. Res. 1985, 13: 4485-4502); chemical modifications of nucleic acid fragments making them detectable immunochemically or by other affinity reactions (see, for example, T. R. Broker et al., Nucl. Acids Res. 1978, 5: 363-384; E. A. Bayer et al., Methods of Biochem. Analysis, 1980, 26: 1-45; R. Langer et al., Proc. Natl. Acad. Sci. USA, 1981, 78: 6633-6637; R. W. Richardson et al., Nucl. Acids Res. 1983, 11: 6167-6184; D. J. Brigati et al., Virol. 1983, 126: 32-50; P. Tchen et al., Proc. Natl Acad. Sci. USA, 1984, 81: 3466-3470; J. E. Landegent et al., Exp. Cell Res. 1984, 15: 61-72; and A. H. Hopman et al., Exp. Cell Res. 1987, 169: 357-368); and enzyme-mediated labeling methods, such as random priming, nick translation, PCR and tailing with terminal transferase (for a review on enzymatic labeling, see, for example, J. Temsamani and S. Agrawal, Mol. Biotechnol. 1996, 5: 223-232).

Any of a wide variety of detectable agents can be used in the practice of the present invention. Suitable detectable agents include, but are not limited to: various ligands, radionuclides, fluorescent dyes, chemiluminescent agents, microparticles (such as, for example, quantum dots, nanocrystals, phosphors and the like), enzymes (such as, for example, those used in an ELISA, i.e., horseradish peroxidase, beta-galactosidase, luciferase, alkaline phosphatase), colorimetric labels, magnetic labels, and biotin, dioxigenin or other haptens and proteins for which antisera or monoclonal antibodies are available.

However, in some embodiments, the expression levels are determined by detecting the expression of a gene product (e.g., protein) thereby eliminating the need to obtain a genetic sample (e.g., RNA) from the prostate tissue sample.

In still other embodiments, the present invention relates to preparing a prediction model for prostate and/or the likelihood of relapse of prostate cancer by preparing a model for prostate cancer based on measuring the biomarkers of the invention in known control samples. More particularly, the present invention relates in some embodiments to preparing a predictive model by evaluating the biomarkers of the invention, e.g., filamin A in combination with one or more of prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1.

The skilled person will appreciate that patient tissue samples containing prostate cells or prostate cancer cells may be used in the methods of the present invention including, but not limited to those aimed at predicting relapse probability. In these embodiments, the level of expression of the signature gene can be assessed by assessing the amount, e.g. absolute amount or concentration, of a signature gene product, e.g., protein and RNA transcript encoded by the signature gene and fragments of the protein and RNA transcript) in a sample, e.g., stool and/or blood obtained from a patient. The sample can, of course, be subjected to a variety of well-known post-collection preparative and storage techniques (e.g. fixation, storage, freezing, lysis, homogenization, DNA or RNA extraction, ultrafiltration, concentration, evaporation, centrifugation, etc.) prior to assessing the amount of the signature gene product in the sample.

The invention further relates to the preparation of a model for prostate cancer or prostate cancer relapse by evaluating the biomarkers of the invention in known samples of prostate cancer. More particularly, the present invention relates to a prostate cancer model for diagnosing and/or monitoring and/or prognosing prostate cancer or prostate cancer relapse using the biomarkers of the invention, which can include filamin A and at least one other prostate cancer related marker selected from the group consisting of filamin B, LY9, keratin 4, keratin 7, keratin 8, keratin 15, keratin 18, keratin 19, tubulin-beta 3, PSA, PSM, PSCA, TMPRSS2, PDEF, HPG-1, PCA3, and PCGEM1.

In the methods of the invention aimed at preparing a model for prostate cancer and/or prostate cancer relapse prediction, it is understood that the particular clinical outcome associated with each sample contributing to the model preferably should be known. Consequently, the model can be established using archived tissue samples. In the methods of the invention aimed at preparing a model for prostate cancer and/or prostate cancer relapse prediction, total RNA can be generally extracted from the source material of interest, generally an archived tissue such as a formalin-fixed, paraffin-embedded tissue, and subsequently purified. Methods for obtaining robust and reproducible gene expression patterns from archived tissues, including formalin-fixed, paraffin-embedded (FFPE) tissues are taught in U.S. Publ. No. 2004/0259105, which is incorporated herein by reference in its entirety. Commercial kits and protocols for RNA extraction from FFPE tissues are available including, for example, ROCHE High Pure RNA Paraffin Kit (Roche) MasterPure™ Complete DNA and RNA Purification Kit (EPICENTRE® Madison, Wis.); Paraffin Block RNA Isolation Kit (Ambion, Inc.) and RNeasy™ Mini kit (Qiagen, Chatsworth, Calif.).

The use of FFPE tissues as a source of RNA for RT-PCR has been described previously (Stanta et al., Biotechniques 11:304-308 (1991); Stanta et al., Methods Mol. Biol. 86:23-26 (1998); Jackson et al., Lancet 1:1391 (1989); Jackson et al., J. Clin. Pathol. 43:499-504 (1999); Finke et al., Biotechniques 14:448-453 (1993); Goldsworthy et al., Mol. Carcinog. 25:86-91 (1999); Stanta and Bonin, Biotechniques 24:271-276 (1998); Godfrey et al., J. Mol. Diagnostics 2:84 (2000); Specht et al., J. Mol. Med. 78:B27 (2000); Specht et al., Am. J. Pathol. 158:419-429 (2001)). For quick analysis of the RNA quality, RT-PCR can be performed utilizing a pair of primers targeting a short fragment in a highly expressed gene, for example, actin, ubiquitin, gapdh or other well-described commonly used housekeeping gene. If the cDNA synthesized from the RNA sample can be amplified using this pair of primers, then the sample is suitable for the a quantitative measurements of RNA target sequences by any method preferred, for example, the DASL assay, which requires only a short cDNA fragment for the annealing of query oligonucleotides.

There are numerous tissue banks and collections including exhaustive samples from all stages of a wide variety of disease states, most notably cancer and in particular, prostate cancer. The ability to perform genotyping and/or gene expression analysis, including both qualitative and quantitative analysis on these samples enables the application of this methodology to the methods of the invention. In particular, the ability to establish a correlation of gene expression and a known predictor of disease extent and/or outcome by probing the genetic state of tissue samples for which clinical outcome is already known, allows for the establishment of a correlation between a particular molecular signature and the known predictor, such as a Gleason score, to derive a score that allows for a more sensitive prognosis than that based on the known predictor alone. The skilled person will appreciate that by building databases of molecular signatures from tissue samples of known outcomes, many such correlations can be established, thus allowing both diagnosis and prognosis of any condition. Thus, such approaches may be used to correlate the expression levels of the biomarkers of the invention, e.g., filamin A and at least one other prostate cancer related marker selected from the group consisting of filamin B, LY9, keratin 4, keratin 7, keratin 8, keratin 15, keratin 18, keratin 19, tubulin-beta 3 and PSA, to a particular stage of prostate cancer.

Tissue samples useful for preparing a model for prostate cancer prediction include, for example, paraffin and polymer embedded samples, ethanol embedded samples and/or formalin and formaldehyde embedded tissues, although any suitable sample may be used. In general, nucleic acids isolated from archived samples can be highly degraded and the quality of nucleic preparation can depend on several factors, including the sample shelf life, fixation technique and isolation method. However, using the methodologies taught in U.S. Publ. No. 2004/0259105, which have the significant advantage that short or degraded targets can be used for analysis as long as the sequence is long enough to hybridize with the oligonucleotide probes, highly reproducible results can be obtained that closely mimic results found in fresh samples.

Archived tissue samples, which can be used for all methods of the invention, typically have been obtained from a source and preserved. Preferred methods of preservation include, but are not limited to paraffin embedding, ethanol fixation and formalin, including formaldehyde and other derivatives, fixation as are known in the art. A tissue sample may be temporally "old", e.g. months or years old, or recently fixed. For example, post-surgical procedures generally include a fixation step on excised tissue for histological analysis. In a preferred embodiment, the tissue sample is a diseased tissue sample, particularly a prostate cancer tissue, including primary and secondary tumor tissues as well as lymph node tissue and metastatic tissue.

Thus, an archived sample can be heterogeneous and encompass more than one cell or tissue type, for example, tumor and non-tumor tissue. Preferred tissue samples include solid tumor samples including, but not limited to, tumors of the prostate. It is understood that in applications of the present invention to conditions other than prostate cancer, the tumor source can be brain, bone, heart, breast, ovaries, prostate, uterus, spleen, pancreas, liver, kidneys, bladder, stomach and muscle. Similarly, depending on the condition, suitable tissue samples include, but are not limited to, bodily fluids (including, but not limited to, blood, urine, serum, lymph, saliva, anal and vaginal secretions, perspiration and semen, of virtually any organism, with mammalian samples being preferred and human samples being particularly preferred). In embodiments directed to methods of establishing a model for prostate cancer relapse prediction, the tissue sample is one for which patient history and outcome is known. Generally, the invention methods can be practiced with the signature gene sequence contained in an archived sample or can be practiced with signature gene sequences that have been physically separated from the sample prior to performing a method of the invention.

E. Detection and/or Measurement of Biomarkers

The present invention contemplates any suitable means, techniques, and/or procedures for detecting and/or measuring the biomarkers of the invention. The skilled artisan will appreciate that the methodologies employed to measure the biomarkers of the invention will depend at least on the type of biomarker being detected or measured (e.g., mRNA biomarker or polypeptide biomarker) and the source of the biological sample (e.g., whole blood versus prostate biopsy tissue). Certain biological sample may also require certain specialized treatments prior to measuring the biomarkers of the invention, e.g., the preparation of mRNA from a biopsy tissue in the case where mRNA biomarkers are being measured.

1. Detection of Nucleic Acid Biomarkers

In certain embodiments, the invention involves the detection of nucleic acid biomarkers, e.g., mRNA biomarkers of filamin A alone or filamin A in combination with at least one other prostate cancer related marker selected from the group consisting of filamin B, LY9, keratin 4, keratin 7, keratin 8, keratin 15, keratin 18, keratin 19, tubulin-beta 3, PSA, PSM, PSCA, TMPRSS2, PDEF, HPG-1, PCA3, and PCGEM1.

In various embodiments, the diagnostic/prognostic methods of the present invention generally involve the determination of expression levels of a set of genes in a prostate tissue sample. Determination of gene expression levels in the practice of the inventive methods may be performed by any suitable method. For example, determination of gene expression levels may be performed by detecting the expression of mRNA expressed from the genes of interest and/or by detecting the expression of a polypeptide encoded by the genes.

For detecting nucleic acids encoding biomarkers of the invention, any suitable method can be used, including, but not limited to, Southern blot analysis, Northern blot analysis, polymerase chain reaction (PCR) (see, for example, U.S. Pat. Nos. 4,683,195; 4,683,202, and 6,040,166; "PCR Protocols: A Guide to Methods and Applications", Innis et al. (Eds), 1990, Academic Press: New York), reverse transcriptase PCR (RT-PCT), anchored PCR, competitive PCR (see, for example, U.S. Pat. No. 5,747,251), rapid amplification of cDNA ends (RACE) (see, for example, "Gene Cloning and Analysis: Current Innovations, 1997, pp. 99-115); ligase chain reaction (LCR) (see, for example, EP 01 320 308), one-sided PCR (Ohara et al., Proc. Natl. Acad. Sci., 1989, 86: 5673-5677), in situ hybridization, Taqman-based assays (Holland et al., Proc. Natl. Acad. Sci., 1991, 88: 7276-7280), differential display (see, for example, Liang et al., Nucl. Acid. Res., 1993, 21: 3269-3275) and other RNA fingerprinting techniques, nucleic acid sequence based amplification (NASBA) and other transcription based amplification systems (see, for example, U.S. Pat. Nos. 5,409,818 and 5,554,527), Qbeta Replicase, Strand Displacement Amplification (SDA), Repair Chain Reaction (RCR), nuclease protection assays, subtraction-based methods, Rapid-Scan®, etc.

In other embodiments, gene expression levels of biomarkers of interest may be determined by amplifying complementary DNA (cDNA) or complementary RNA (cRNA) produced from mRNA and analyzing it using a microarray. A number of different array configurations and methods of their production are known to those skilled in the art (see, for example, U.S. Pat. Nos. 5,445,934; 5,532,128; 5,556,752; 5,242,974; 5,384,261; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,599,695; 5,624,711; 5,658,734; and 5,700,637). Microarray technology allows for the measurement of the steady-state mRNA level of a large number of genes simultaneously. Microarrays currently in wide use include cDNA arrays and oligonucleotide arrays. Analyses using microarrays are generally based on measurements of the intensity of the signal received from a labeled probe used to detect a cDNA sequence from the sample that hybridizes to a nucleic acid probe immobilized at a known location on the microarray (see, for example, U.S. Pat. Nos. 6,004,755; 6,218,114; 6,218,122; and 6,271,002). Array-based gene expression methods are known in the art and have been described in numerous scientific publications as well as in patents (see, for example, M. Schena et al., Science, 1995, 270: 467-470; M. Schena et al., Proc. Natl. Acad. Sci. USA 1996, 93: 10614-10619; J. J. Chen et al., Genomics, 1998, 51: 313-324; U.S. Pat. Nos. 5,143,854; 5,445,934; 5,807,522; 5,837,832; 6,040,138; 6,045,996; 6,284,460; and 6,607,885).

In one particular embodiment, the invention comprises a method for identification of prostate cancer cells in a biological sample by amplifying and detecting nucleic acids corresponding to the novel prostate cancer biomarkers, and or panels of biomarkers that include filamin A alone or filamin A in combination with one or more markers selected from the group consisting of filamin B, LY9, keratin 4, keratin 7, keratin 8, keratin 15, keratin 18, keratin 19, tubulin-beta 3, PSA, PSM, PSCA, TMPRSS2, PDEF, HPG-1, PCA3, and PCGEM1. The biological sample may be any tissue or fluid in which prostate cancer cells might be present. Various embodiments include radical prostatectomy specimens, pathological specimens, bone marrow aspirate, bone marrow biopsy, lymph node aspirate, lymph node biopsy, spleen tissue, fine needle aspirate, skin biopsy or organ tissue biopsy. Other embodiments include samples where the body fluid is peripheral blood, serum, plasma, lymph fluid, ascites, serous fluid, pleural effusion, sputum, cerebrospinal fluid, lacrimal fluid, stool, prostatic fluid or urine.

Nucleic acid used as a template for amplification can be isolated from cells contained in the biological sample, according to standard methodologies. (Sambrook et al., 1989) The nucleic acid may be genomic DNA or fractionated or whole cell RNA. Where RNA is used, it may be desired to convert the RNA to a complementary cDNA. In one embodiment, the RNA is whole cell RNA and is used directly as the template for amplification.

Pairs of primers that selectively hybridize to nucleic acids corresponding to any of the prostate cancer biomarker nucleotide sequences identified herein are contacted with the isolated nucleic acid under conditions that permit selective hybridization. Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced. Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (Affymax technology; Bellus, 1994). Following detection, one may compare the results seen in a given patient with a statistically significant reference group of normal patients and prostate, cancer patients. In this way, it is possible to correlate the amount of nucleic acid detected with various clinical states.

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences may be employed. Primers may be provided in double-stranded or single-stranded form, although the single-stranded form is preferred.

A number of template dependent processes are available to amplify the nucleic acid sequences present in a given template sample. One of the best known amplification methods is the polymerase chain reaction (referred to as PCR) which is described in detail in U.S. Pat. Nos. 4,683,195, 4,683,202 and 4,800,159, and in Innis et al., 1990, each of which is incorporated herein by reference in its entirety.

In PCR, two primer sequences are prepared which are complementary to regions on opposite complementary strands of the target nucleic acid sequence. An excess of deoxynucleoside triphosphates are added to a reaction mixture along with a DNA polymerase, e.g., Taq polymerase. If the target nucleic acid sequence is present in a sample, the primers will bind to the target nucleic acid and the polymerase will cause the primers to be extended along the target nucleic acid sequence by adding on nucleotides. By raising and lowering the temperature of the reaction mixture, the extended primers will dissociate from the target nucleic acid to form reaction products, excess primers will bind to the target nucleic acid and to the reaction products and the process is repeated.

A reverse transcriptase PCR amplification procedure may be performed in order to quantify the amount of mRNA amplified. Methods of reverse transcribing RNA into cDNA are well known and described in Sambrook et al., 1989.

Alternative methods for reverse transcription utilize thermostable DNA polymerases. These methods are described in WO 90/07641 filed Dec. 21, 1990. Polymerase chain reaction methodologies are well known in the art.

Another method for amplification is the ligase chain reaction ("LCR"), disclosed in European Application No. 320 308, incorporated herein by reference in its entirely. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, also may be used as still another amplification method in the present invention. In this method, a replicative sequence of RNA which has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[α-thio]-triphosphates in one strand of a restriction site also may be useful in the amplification of nucleic acids in the present invention. Walker et al. (1992), incorporated herein by reference in its entirety.

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases may be added as biotinylated derivatives for easy detection. A similar approach is used in SDA. Target specific sequences also may be detected using a cyclic probe reaction (CPR). In CPR, a probe having 3' and 5' sequences of non-specific DNA and a middle sequence of specific RNA is hybridized to DNA which is present in a sample. Upon hybridization, the reaction is treated with RNase H, and the products of the probe identified as distinctive products which are released after digestion. The original template is annealed to another cycling probe and the reaction is repeated.

Still other amplification methods described in GB Application No. 2 202 328, and in PCT Application No. PCT/US89/01025, each of which is incorporated herein by reference in its entirety, may be used in accordance with the present invention. In the former application, "modified" primers are used in a PCR like, template and enzyme dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other contemplated nucleic acid amplification procedures include transcription-based amplification systems (TAS), including nucleic acid sequence based amplification (NASBA) and 3SR. Kwoh et al. (1989); Gingeras et al., PCT Application WO 88/10315, incorporated herein by reference in their entirety. In NASBA, the nucleic acids may be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by a polymerase such as T7 or SP6. In an isothermal cyclic reaction, the RNA's are reverse transcribed into double stranded DNA, and transcribed once against with a polymerase such as T7 or SP6. The resulting products, whether truncated or complete, indicate target specific sequences.

Davey et al., European Application No. 329 822 (incorporated herein by reference in its entirely) disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from the resulting DNA:RNA duplex by the action of ribonuclease H(RNase H, an RNase specific for RNA in duplex with either DNA or RNA). The resultant ssDNA is a second template for a second primer, which also includes the sequences of an RNA polymerase promoter (exemplified by T7 RNA polymerase) 5' to its homology to the template. This primer is then extended by DNA polymerase (exemplified by the large "Klenow" fragment of *E. coli* DNA polymerase 1), resulting in a double-stranded DNA ("dsDNA") molecule, having a sequence identical to that of the original RNA between the primers and having additionally, at one end, a promoter sequence. This promoter sequence may be used by the appropriate RNA polymerase to make many RNA copies of the DNA. These copies may then re-enter the cycle leading to very swift amplification. With proper choice of enzymes, this amplification may be done isothermally without addition of enzymes at each cycle. Because of the cyclical nature of this process, the starting sequence may be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR™." Frohman (1990) and Ohara et al. (1989), each herein incorporated by reference in their entirety.

Methods based on ligation of two (or more) oligonucleotides in the presence of nucleic acid having the sequence of the resulting "di-oligonucleotide", thereby amplifying the di-oligonucleotide, also may be used in the amplification step of the present invention. Wu et al. (1989), incorporated herein by reference in its entirety.

Oligonucleotide probes or primers of the present invention may be of any suitable length, depending on the particular assay format and the particular needs and targeted sequences employed. In a preferred embodiment, the oligonucleotide probes or primers are at least 10 nucleotides in length (preferably, 10, 11, 12, 13, 14, 15, 16, 17, 18, 19, 20, 21, 22, 23, 24, 25, 26, 27, 28, 29, 30, 31, 32 . . . ) and they may be adapted to be especially suited for a chosen nucleic acid amplification system and/or hybridization system used. Longer probes and primers are also within the scope of the present invention as well known in the art. Primers having more than 30, more than 40, more than 50 nucleotides and probes having more than 100, more than 200, more than 300, more than 500 more than 800 and more than 1000 nucleotides in length are also covered by the present invention. Of course, longer primers have the disadvantage of being more expensive and thus, primers having between 12 and 30 nucleotides in length are usually designed and used in the art. As well known in the art, probes ranging from 10 to more than 2000 nucleotides in length can be used in the methods of the present invention. As for the % of identity described above, non-specifically described sizes of probes and primers (e.g., 16, 17, 31, 24, 39, 350, 450, 550, 900, 1240 nucleotides, . . . ) are also within the scope of the present invention. In one embodiment, the oligonucleotide probes or primers of the present invention specifically hybridize with a filamin A RNA (or its complementary sequence) or a filamin A mRNA. More preferably, the filamin A primers and probes will be chosen to detect a filamin A RNA which is associated with prostate cancer.

In other embodiments, the detection means can utilize a hybridization technique, e.g., where a specific primer or probe is selected to anneal to a target biomarker of interest, e.g., filamin A, and thereafter detection of selective hybridization is made. As commonly known in the art, the oligonucleotide probes and primers can be designed by taking into consideration the melting point of hybridization thereof with its targeted sequence (see below and in Sambrook et al., 1989, Molecular Cloning—A Laboratory Manual, 2nd Edition, CSH Laboratories; Ausubel et al., 1994, in Current Protocols in Molecular Biology, John Wiley & Sons Inc., N.Y.).

To enable hybridization to occur under the assay conditions of the present invention, oligonucleotide primers and probes should comprise an oligonucleotide sequence that has at least 70% (at least 71%, 72%, 73%, 74%), preferably at least 75% (75%, 76%, 77%, 78%, 79%, 80%, 81%, 82%, 83%, 84%, 85%, 86%, 87%, 88%, 89%) and more preferably at least 90% (90%, 91%, 92%, 93%, 94%, 95%, 96%, 97%, 98%, 99%, 100%) identity to a portion of a filamin A or polynucleotide of another biomarker of the invention. Probes and primers of the present invention are those that hybridize under stringent hybridization conditions and those that hybridize to biomarker homologs of the invention under at least moderately stringent conditions. In certain embodiments probes and primers of the present invention have complete sequence identity to the biomarkers of the invention (filamin A, gene sequences (e.g., cDNA or mRNA). It should be understood that other probes and primers could be easily designed and used in the present invention based on the biomarkers of the invention disclosed herein by using methods of computer alignment and sequence analysis known in the art (cf. Molecular Cloning: A Laboratory Manual, Third Edition, edited by Cold Spring Harbor Laboratory, 2000).

2. Detection of Polypeptide Biomarkers

The present invention contemplates any suitable method for detecting polypeptide biomarkers of the invention. In certain embodiments, the detection method is an immunodetection method involving an antibody that specifically binds to one or more of the biomarkers of the invention, e.g., filamin A alone or filamin A in combination with at least one other prostate cancer related marker selected from the group consisting of filamin B, LY9, keratin 4, keratin 7, keratin 8, keratin 15, keratin 18, keratin 19, tubulin-beta 3, PSA, PSM, PSCA, TMPRSS2, PDEF, HPG-1, PCA3, and PCGEM1. The steps of various useful immunodetection methods have been described in the scientific literature, such as, e.g., Nakamura et al. (1987), which is incorporated herein by reference.

In general, the immunobinding methods include obtaining a sample suspected of containing a biomarker protein, peptide or antibody, and contacting the sample with an antibody or protein or peptide in accordance with the present invention, as the case may be, under conditions effective to allow the formation of immunocomplexes.

The immunobinding methods include methods for detecting or quantifying the amount of a reactive component in a sample, which methods require the detection or quantitation of any immune complexes formed during the binding process. Here, one would obtain a sample suspected of containing a prostate specific protein, peptide or a corresponding antibody, and contact the sample with an antibody or encoded protein or peptide, as the case may be, and then detect or quantify the amount of immune complexes formed under the specific conditions.

In terms of biomarker detection, the biological sample analyzed may be any sample that is suspected of containing a prostate cancer-specific biomarker, such as, filamin A and at least one other prostate cancer related marker selected from the group consisting of filamin B, LY9, keratin 4, keratin 7, keratin 8, keratin 15, keratin 18, keratin 19, tubulin-beta 3 and PSA. The biological sample may be, for example, a prostate or lymph node tissue section or specimen, a homogenized tissue extract, an isolated cell, a cell membrane preparation, separated or purified forms of any of the above protein-containing compositions, or even any biological fluid that comes into contact with prostate tissues, including blood or lymphatic fluid.

Contacting the chosen biological sample with the protein (e.g., filamin A or antigen thereof to bind with a anti-filamin A antibody in the blood), peptide (e.g., filamin A fragment that binds with a anti-filamin A antibody in the blood), or antibody (e.g., as a detection reagent that binds filamin A in a biological sample) under conditions effective and for a period of time sufficient to allow the formation of immune complexes (primary immune complexes). Generally, complex formation is a matter of simply adding the composition to the biological sample and incubating the mixture for a period of time long enough for the antibodies to form immune complexes with, i.e., to bind to, any antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

The encoded protein (e.g., filamin A), peptide (e.g., filamin A peptide) or corresponding antibody (anti-filamin A antibody as detection reagent) employed in the detection may itself be linked to a detectable label, wherein one would then simply detect this label, thereby allowing the amount of the primary immune complexes in the composition to be determined.

Alternatively, the first added component that becomes bound within the primary immune complexes may be detected by means of a second binding ligand that has binding affinity for the encoded protein, peptide or corresponding antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the encoded protein, peptide or corresponding antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

The immunodetection methods of the present invention have evident utility in the diagnosis of conditions such as prostate cancer. Here, a biological or clinical sample suspected of containing either the encoded protein or peptide or corresponding antibody is used. However, these embodiments also have applications to non-clinical samples, such as in the tittering of antigen or antibody samples, in the selection of hybridomas, and the like.

The present invention, in particular, contemplates the use of ELISAs as a type of immunodetection assay. It is contemplated that the biomarker proteins or peptides of the invention will find utility as immunogens in ELISA assays in diagnosis and prognostic monitoring of prostate cancer. Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and Western blotting, dot blotting, FACS analyses, and the like also may be used.

In one exemplary ELISA, antibodies binding to the biomarkers of the invention are immobilized onto a selected surface exhibiting protein affinity, such as a well in a polystyrene microtiter plate. Then, a test composition suspected of containing the prostate cancer marker antigen, such as a clinical sample, is added to the wells. After binding and washing to remove non-specifically bound immunecomplexes, the bound antigen may be detected. Detection is generally achieved by the addition of a second antibody specific for the target protein, that is linked to a detectable label. This type of ELISA is a simple "sandwich ELISA." Detection also may be achieved by the addition of a second antibody, followed by the addition of a third antibody that has binding affinity for the second antibody, with the third antibody being linked to a detectable label.

In another exemplary ELISA, the samples suspected of containing the prostate cancer marker antigen are immobilized onto the well surface and then contacted with the anti-biomarker antibodies of the invention. After binding and washing to remove non-specifically bound immunecomplexes, the bound antigen is detected. Where the initial antibodies are linked to a detectable label, the immunecomplexes may be detected directly. Again, the immunecomplexes may be detected using a second antibody that has binding affinity for the first antibody, with the second antibody being linked to a detectable label.

Irrespective of the format employed, ELISAs have certain features in common, such as coating, incubating or binding, washing to remove non-specifically bound species, and detecting the bound immunecomplexes. These are described as follows.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the control human prostate, cancer and/or clinical or biological sample to be tested under conditions effective to allow immunecomplex (antigen/antibody) formation. Detection of the immunecomplex then requires a labeled secondary binding ligand or antibody, or a secondary binding ligand or antibody in conjunction with a labeled tertiary antibody or third binding ligand.

The phrase "under conditions effective to allow immunecomplex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background.

The "suitable" conditions also mean that the incubation is at a temperature and for a period of time sufficient to allow effective binding. Incubation steps are typically from about 1 to 2 to 4 h, at temperatures preferably on the order of 25 to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immunecomplexes between the test sample and the originally bound material, and subsequent washing, the occurrence of even minute amounts of immunecomplexes may be determined.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immunecomplex with a urease, glucose oxidase, alkaline phosphatase or hydrogen peroxidase-conjugated antibody for a period of time and under conditions that favor the development of further immunecomplex formation (e.g., incubation for 2 h at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple. Quantitation is then achieved by measuring the degree of color generation, e.g., using a visible spectra spectrophotometer.

The protein biomarkers of the invention (e.g., filamin A alone or in combination with any one or more of filamin B, LY9, keratin 4, keratin 7, keratin 8, keratin 15, keratin 18, keratin 19, tubulin-beta 3, PSA, PSM, PSCA, TMPRSS2, PDEF, HPG-1, PCA3, and PCGEM1) can also be measured, quantitated, detected, and otherwise analyzed using protein mass spectrometry methods and instrumentation. Protein mass spectrometry refers to the application of mass spectrometry to the study of proteins. Although not intending to be limiting, two approaches are typically used for characterizing proteins using mass spectrometry. In the first, intact proteins are ionized and then introduced to a mass analyzer. This approach is referred to as "top-down" strategy of protein analysis. The two primary methods for ionization of whole proteins are electrospray ionization (ESI) and matrix-assisted laser desorption/ionization (MALDI). In the second approach, proteins are enzymatically digested into smaller peptides using a protease such as trypsin. Subsequently these peptides are introduced into the mass spectrometer and identified by peptide mass fingerprinting or tandem mass spectrometry. Hence, this latter approach (also called "bottom-up" proteomics) uses identification at the peptide level to infer the existence of proteins.

Whole protein mass analysis of the biomarkers of the invention can be conducted using time-of-flight (TOF) MS, or Fourier transform ion cyclotron resonance (FT-ICR). These two types of instruments are useful because of their wide mass range, and in the case of FT-ICR, its high mass accuracy. The most widely used instruments for peptide mass analysis are the MALDI time-of-flight instruments as they permit the acquisition of peptide mass fingerprints (PMFs) at high pace (1 PMF can be analyzed in approx. 10 sec). Multiple stage quadrupole-time-of-flight and the quadrupole ion trap also find use in this application.

The biomarkers of the invention can also be measured in complex mixtures of proteins and molecules that co-exist in a biological medium or sample, however, fractionation of the sample may be required and is contemplated herein. It will be appreciated that ionization of complex mixtures of proteins can result in situation where the more abundant proteins have a tendency to "drown" or suppress signals from less abundant proteins in the same sample. In addition, the mass spectrum from a complex mixture can be difficult to interpret because of the overwhelming number of mixture components. Fractionation can be used to first separate any complex mixture of proteins prior to mass spectrometry analysis. Two methods are widely used to fractionate proteins, or their peptide products from an enzymatic digestion. The first method fractionates whole proteins and is called two-dimensional gel electrophoresis. The second method, high performance liquid chromatography (LC or HPLC) is used to fractionate peptides after enzymatic digestion. In some situations, it may be desirable to combine both of these techniques. Any other suitable methods known in the art for fractionating protein mixtures are also contemplated herein.

Gel spots identified on a 2D Gel are usually attributable to one protein. If the identity of the protein is desired, usually the method of in-gel digestion is applied, where the protein spot of interest is excised, and digested proteolytically. The peptide masses resulting from the digestion can be determined by mass spectrometry using peptide mass fingerprinting. If this information does not allow unequivocal identification of the protein, its peptides can be subject to tandem mass spectrometry for de novo sequencing.

Characterization of protein mixtures using HPLC/MS may also be referred to in the art as "shotgun proteomics" and MuDPIT (Multi-Dimensional Protein Identification Technology). A peptide mixture that results from digestion of a protein mixture is fractionated by one or two steps of liquid chromatography (LC). The eluent from the chromatography stage can be either directly introduced to the mass spectrometer through electrospray ionization, or laid down on a series of small spots for later mass analysis using MALDI.

The biomarkers of the present invention (e.g., filamin A alone or in combination with any one or more of filamin B, LY9, keratin 4, keratin 7, keratin 8, keratin 15, keratin 18, keratin 19, tubulin-beta 3, PSA, PSM, PSCA, TMPRSS2, PDEF, HPG-1, PCA3, and PCGEM1) can be identified using MS using a variety of techniques, all of which are contemplated herein. Peptide mass fingerprinting uses the masses of proteolytic peptides as input to a search of a database of predicted masses that would arise from digestion of a list of known proteins. If a protein sequence in the reference list gives rise to a significant number of predicted masses that match the experimental values, there is some evidence that this protein was present in the original sample. It will be further appreciated that the development of methods and instrumentation for automated, data-dependent electrospray ionization (ESI) tandem mass spectrometry (MS/MS) in conjunction with microcapillary liquid chromatography (LC) and database searching has significantly increased the sensitivity and speed of the identification of gel-separated proteins. Microcapillary LC-MS/MS has been used successfully for the large-scale identification of individual proteins directly from mixtures without gel electrophoretic separation (Link et al., 1999; Opitek et al., 1997).

Several recent methods allow for the quantitation of proteins by mass spectrometry. For example, stable (e.g., non-radioactive) heavier isotopes of carbon ($^{13}C$) or nitrogen ($^{15}N$) can be incorporated into one sample while the other one can be labeled with corresponding light isotopes (e.g. $^{12}C$ and $^{14}N$). The two samples are mixed before the analysis. Peptides derived from the different samples can be distinguished due to their mass difference. The ratio of their peak intensities corresponds to the relative abundance ratio of the peptides (and proteins). The most popular methods for isotope labeling are SILAC (stable isotope labeling by amino acids in cell culture), trypsin-catalyzed $^{18}O$ labeling, ICAT (isotope coded affinity tagging), iTRAQ (isobaric tags for relative and absolute quantitation). "Semi-quantitative" mass spectrometry can be performed without labeling of samples. Typically, this is done with MALDI analysis (in linear mode). The peak intensity, or the peak area, from individual molecules (typically proteins) is here correlated to the amount of protein in the sample. However, the individual signal depends on the primary structure of the protein, on the complexity of the sample, and on the settings of the instrument. Other types of "label-free" quantitative mass spectrometry, uses the spectral counts (or peptide counts) of digested proteins as a means for determining relative protein amounts.

In one embodiment, any one or more of the biomarkers of the invention (e.g., filamin A alone or in combination with any one or more of filamin B, LY9, keratin 4, keratin 7, keratin 8, keratin 15, keratin 18, keratin 19, tubulin-beta 3, PSA, PSM, PSCA, TMPRSS2, PDEF, HPG-1, PCA3, and PCGEM1) can be identified and quantified from a complex biological sample using mass spectroscopy in accordance with the following exemplary method, which is not intended to limit the invention or the use of other mass spectrometry-based methods.

In the first step of this embodiment, (A) a biological sample, e.g., a biological sample suspected of having prostate cancer, which comprises a complex mixture of protein (including at least one biomarker of interest) is fragmented and labeled with a stable isotope X. (B) Next, a known amount of an internal standard is added to the biological sample, wherein the internal standard is prepared by fragmenting a standard protein that is identical to the at least one target biomarker of interest, and labeled with a stable isotope Y. (C) This sample obtained is then introduced in an LC-MS/MS device, and multiple reaction monitoring (MRM) analysis is performed using MRM transitions selected for the internal standard to obtain an MRM chromatogram. (D) The MRM chromatogram is then viewed to identify a target peptide biomarker derived from the biological sample that shows the same retention time as a peptide derived from the internal standard (an internal standard peptide), and quantifying the target protein biomarker in the test sample by comparing the peak area of the internal standard peptide with the peak area of the target peptide biomarker.

Any suitable biological sample may be used as a starting point for LC-MS/MS/MRM analysis, including biological samples derived blood, urine, saliva, hair, cells, cell tissues, biopsy materials, and treated products thereof; and protein-containing samples prepared by gene recombination techniques.

Each of the above steps (A) to (D) is described further below.

Step (A) (Fragmentation and Labeling). In step (A), the target protein biomarker is fragmented to a collection of peptides, which is subsequently labeled with a stable isotope X. To fragment the target protein, for example, methods of digesting the target protein with a proteolytic enzyme (protease) such as trypsin, and chemical cleavage methods, such as a method using cyanogen bromide, can be used. Digestion by protease is preferable. It is known that a given mole quantity of protein produces the same mole quantity for each tryptic peptide cleavage product if the proteolytic digest is allowed to proceed to completion. Thus, determining the mole quantity of tryptic peptide to a given protein allows determination of the mole quantity of the original protein in the sample. Absolute quantification of the target protein can be accomplished by determining the absolute amount of the target protein-derived peptides contained in the protease digestion (collection of peptides). Accordingly, in order to allow the proteolytic digest to proceed to completion, reduction and alkylation treatments are preferably performed before protease digestion with trypsin to reduce and alkylate the disulfide bonds contained in the target protein.

Subsequently, the obtained digest (collection of peptides, comprising peptides of the target biomarker in the biological sample) is subjected to labeling with a stable isotope X. Examples of stable isotopes X include $^{1}H$ and $^{2}H$ for hydrogen atoms, $^{12}C$ and $^{13}C$ for carbon atoms, and $^{14}N$ and $^{15}N$ for nitrogen atoms. Any isotope can be suitably selected therefrom. Labeling by a stable isotope X can be performed by reacting the digest (collection of peptides) with a reagent containing the stable isotope. Preferable examples of such reagents that are commercially available include mTRAQ (registered trademark) (produced by Applied Biosystems), which is an amine-specific stable isotope reagent kit. mTRAQ is composed of 2 or 3 types of reagents (mTRAQ-light and mTRAQ-heavy; or mTRAQ-D0, mTRAQ-D4, and mTRAQ-D8) that have a constant mass difference therebetween as a result of isotope-labeling, and that are bound to the N-terminus of a peptide or the primary amine of a lysine residue.

Step (B) (Addition of the Internal Standard). In step (B), a known amount of an internal standard is added to the sample obtained in step (A). The internal standard used herein is a digest (collection of peptides) obtained by fragmenting a protein (standard protein) consisting of the same amino acid sequence as the target protein (target biomarker) to be measured, and labeling the obtained digest (collection of peptides) with a stable isotope Y. The fragmentation treatment can be performed in the same manner as above for the target protein. Labeling with a stable isotope Y can also be performed in the same manner as above for the target protein. However, the stable isotope Y used herein must be an isotope that has a mass different from that of the stable isotope X used for labeling the target protein digest. For example, in the case of using the aforementioned mTRAQ (registered trademark) (produced by Applied Biosystems), when mTRAQ-light is used to label a target protein digest, mTRAQ-heavy should be used to label a standard protein digest.

Step (C) (LC-MS/MS and MRM Analysis). In step (C), the sample obtained in step (B) is first placed in an LC-MS/MS device, and then multiple reaction monitoring (MRM) analysis is performed using MRM transitions selected for the internal standard. By LC (liquid chromatography) using the LC-MS/MS device, the sample (collection of peptides labeled with a stable isotope) obtained in step (B) is separated first by one-dimensional or multi-dimensional high-performance liquid chromatography. Specific examples of such liquid chromatography include cation exchange chromatography, in which separation is conducted by utilizing electric charge difference between peptides; and reversed-phase chromatography, in which separation is conducted by utilizing hydrophobicity difference between peptides. Both of these methods may be used in combination.

Subsequently, each of the separated peptides is subjected to tandem mass spectrometry by using a tandem mass spectrometer (MS/MS spectrometer) comprising two mass spectrometers connected in series. The use of such a mass spectrometer enables the detection of several fmol levels of a target protein. Furthermore, MS/MS analysis enables the analysis of internal sequence information on peptides, thus enabling identification without false positives. Other types of MS analyzers may also be used, including magnetic sector mass spectrometers (Sector MS), quadrupole mass spectrometers (QMS), time-of-flight mass spectrometers (TOFMS), and Fourier transform ion cyclotron resonance mass spectrometers (FT-ICRMS), and combinations of these analyzers.

Subsequently, the obtained data are put through a search engine to perform a spectral assignment and to list the peptides experimentally detected for each protein. The detected peptides are preferably grouped for each protein, and preferably at least three fragments having an m/z value larger than that of the precursor ion and at least three fragments with an m/z value of, preferably, 500 or more are selected from each MS/MS spectrum in descending order of signal strength on the spectrum. From these, two or more fragments are selected in descending order of strength, and the average of the strength is defined as the expected sensitivity of the MRR transitions. When a plurality of peptides is detected from one protein, at least two peptides with the highest sensitivity are selected as standard peptides using the expected sensitivity as an index.

Step (D) (Quantification of the Target Protein in the Test Sample). Step (D) comprises identifying, in the MRM chromatogram detected in step (C), a peptide derived from the target protein (a target biomarker of interest) that shows the same retention time as a peptide derived from the internal standard (an internal standard peptide), and quantifying the target protein in the test sample by comparing the peak area of the internal standard peptide with the peak area of the target peptide. The target protein can be quantified by utilizing a calibration curve of the standard protein prepared beforehand.

The calibration curve can be prepared by the following method. First, a recombinant protein consisting of an amino acid sequence that is identical to that of the target biomarker protein is digested with a protease such as trypsin, as described above. Subsequently, precursor-fragment transition selection standards (PFTS) of a known concentration are individually labeled with two different types of stable isotopes (i.e., one is labeled with a stable isomer used to label an internal standard peptide (labeled with IS), whereas the other is labeled with a stable isomer used to label a target peptide (labeled with T). A plurality of samples are produced by blending a certain amount of the IS-labeled PTFS with various concentrations of the T-labeled PTFS. These samples are placed in the aforementioned LC-MS/MS device to perform MRM analysis. The area ratio of the T-labeled PTFS to the IS-labeled PTFS (T-labeled PTFS/IS-labeled PTFS) on the obtained MRM chromatogram is plotted against the amount of the T-labeled PTFS to prepare a calibration curve. The absolute amount of the target protein contained in the test sample can be calculated by reference to the calibration curve.

3. Antibodies and Labels (e.g., Fluorescent Moieties, Dyes)

In some embodiments, the invention provides methods and compositions that include labels for the highly sensitive detection and quantitation of the biomolecules of the invention, e.g., filamin A alone or in combination with at least one other prostate cancer related marker selected from the group consisting of filamin B, LY9, keratin 4, keratin 7, keratin 8, keratin 15, keratin 18, keratin 19, tubulin-beta 3, PSA, PSM, PSCA, TMPRSS2, PDEF, HPG-1, PCA3, and PCGEM1. One skilled in the art will recognize that many strategies can be used for labeling target molecules to enable their detection or discrimination in a mixture of particles (e.g., labeled anti-filamin A antibody or labeled secondary antibody, or labeled oligonucleotide probe that specifically hybridizes to filamin A mRNA). The labels may be attached by any known means, including methods that utilize non-specific or specific interactions of label and target. Labels may provide a detectable signal or affect the mobility of the particle in an electric field. In addition, labeling can be accomplished directly or through binding partners.

In some embodiments, the label comprises a binding partner that binds to the biomarker of interest, where the binding partner is attached to a fluorescent moiety. The compositions and methods of the invention may utilize highly fluorescent moieties, e.g., a moiety capable of emitting at least about 200 photons when simulated by a laser emitting light at the excitation wavelength of the moiety, wherein the laser is focused on a spot not less than about 5 microns in diameter that contains the moiety, and wherein the total energy directed at the spot by the laser is no more than about 3 microJoules. Moieties suitable for the compositions and methods of the invention are described in more detail below.

In some embodiments, the invention provides a label for detecting a biological molecule comprising a binding partner for the biological molecule that is attached to a fluorescent moiety, wherein the fluorescent moiety is capable of emitting at least about 200 photons when simulated by a laser emitting light at the excitation wavelength of the moiety, wherein the laser is focused on a spot not less than about 5 microns in diameter that contains the moiety, and wherein the total energy directed at the spot by the laser is no more than about 3 microJoules. In some embodiments, the moiety comprises a plurality of fluorescent entities, e.g., about 2 to 4, 2 to 5, 2 to 6, 2 to 7, 2 to 8, 2 to 9, 2 to 10, or about 3 to 5, 3 to 6, 3 to 7, 3 to 8, 3 to 9, or 3 to 10 fluorescent entities. In some embodiments, the moiety comprises about 2 to 4 fluorescent entities. In some embodiments, the biological molecule is a protein or a small molecule. In some embodiments, the biological molecule is a protein. The fluorescent entities can be fluorescent dye molecules. In some embodiments, the fluorescent dye molecules comprise at least one substituted indolium ring system in which the substituent on the 3-carbon of the indolium ring contains a chemically reactive group or a conjugated substance. In some embodiments, the dye molecules are Alexa Fluor molecules selected from the group consisting of Alexa Fluor 488, Alexa Fluor 532, Alexa Fluor 647, Alexa Fluor 680 or Alexa Fluor 700. In some embodiments, the dye molecules are Alexa Fluor molecules selected from the group consisting of Alexa Fluor 488, Alexa Fluor 532, Alexa Fluor 680 or Alexa Fluor 700. In some embodiments, the dye molecules are Alexa Fluor 647 dye molecules. In some embodiments, the dye molecules comprise a first type and a second type of dye molecules, e.g., two different Alexa Fluor molecules, e.g., where the first type and second type of dye molecules have different emission spectra. The ratio of the number of first type to second type of dye molecule can be, e.g., 4 to 1, 3 to 1, 2 to 1, 1 to 1, 1 to 2, 1 to 3 or 1 to 4. The binding partner can be, e.g., an antibody.

In some embodiments, the invention provides a label for the detection of a biological marker of the invention, wherein the label comprises a binding partner for the marker and a fluorescent moiety, wherein the fluorescent moiety is capable of emitting at least about 200 photons when simulated by a laser emitting light at the excitation wavelength of the moiety, wherein the laser is focused on a spot not less than about 5 microns in diameter that contains the moiety, and wherein the total energy directed at the spot by the laser is no more than about 3 microJoules. In some embodiments, the fluorescent moiety comprises a fluorescent molecule. In some embodiments, the fluorescent moiety comprises a plurality of fluorescent molecules, e.g., about 2 to 10, 2 to 8, 2 to 6, 2 to 4, 3 to 10, 3 to 8, or 3 to 6 fluorescent molecules. In some embodiments, the label comprises about 2 to 4 fluorescent molecules. In some embodiments, the fluorescent dye molecules comprise at least one substituted indolium ring system in which the substituent on the 3-carbon of the indolium ring contains a chemically reactive group or a conjugated substance. In some embodiments, the fluorescent molecules are selected from the group consisting of Alexa Fluor 488, Alexa Fluor 532, Alexa Fluor 647, Alexa Fluor 680 or Alexa Fluor 700. In some embodiments, the fluorescent molecules are selected from the group consisting of Alexa Fluor 488, Alexa Fluor 532, Alexa Fluor 680 or Alexa Fluor 700. In some embodiments, the fluorescent molecules are Alexa Fluor 647 molecules. In some embodiments, the binding partner comprises an antibody. In some embodiments, the antibody is a monoclonal antibody. In other embodiments, the antibody is a polyclonal antibody.

In various embodiments, the binding partner for detecting a biomarker of interest, e.g., filamin A or filamin B, LY9, keratin 4, keratin 7, keratin 8, keratin 15, keratin 18, keratin 19, tubulin-beta 3 and PSA, is an antibody or antigen-binding fragment thereof. The term "antibody," as used herein, is a broad term and is used in its ordinary sense, including, without limitation, to refer to naturally occurring antibodies as well as non-naturally occurring antibodies, including, for example, single chain antibodies, chimeric, bifunctional and humanized antibodies, as well as antigen-binding fragments thereof. An "antigen-binding fragment" of an antibody refers to the part of the antibody that participates in antigen binding. The antigen binding site is formed by amino acid residues of the N-terminal variable ("V") regions of the heavy ("H") and light ("L") chains. It will be appreciated that the choice of epitope or region of the molecule to which the antibody is raised will determine its specificity, e.g., for various forms of the molecule, if present, or for total (e.g., all, or substantially all of the molecule).

Methods for producing antibodies are well-established. One skilled in the art will recognize that many procedures are available for the production of antibodies, for example, as described in Antibodies, A Laboratory Manual, Ed Harlow and David Lane, Cold Spring Harbor Laboratory (1988), Cold Spring Harbor, N.Y. One skilled in the art will also appreciate that binding fragments or Fab fragments which mimic antibodies can also be prepared from genetic information by various procedures (Antibody Engineering: A Practical Approach (Borrebaeck, C., ed.), 1995, Oxford University Press, Oxford; J. Immunol. 149, 3914-3920 (1992)). Monoclonal and polyclonal antibodies to molecules, e.g., proteins, and markers also commercially available (R and D Systems, Minneapolis, Minn.; HyTest, HyTest Ltd., Turku Finland; Abcam Inc., Cambridge, Mass., USA, Life Diagnostics, Inc., West Chester, Pa., USA; Fitzgerald Industries International, Inc., Concord, Mass. 01742-3049 USA; BiosPacific, Emeryville, Calif.).

In some embodiments, the antibody is a polyclonal antibody. In other embodiments, the antibody is a monoclonal antibody.

Antibodies may be prepared by any of a variety of techniques known to those of ordinary skill in the art (see, for example, Harlow and Lane, Antibodies: A Laboratory Manual, Cold Spring Harbor Laboratory, 1988). In general, antibodies can be produced by cell culture techniques, including the generation of monoclonal antibodies as described herein, or via transfection of antibody genes into suitable bacterial or mammalian cell hosts, in order to allow for the production of recombinant antibodies.

Monoclonal antibodies may be prepared using hybridoma methods, such as the technique of Kohler and Milstein (Eur. J. Immunol. 6:511-519, 1976), and improvements thereto. These methods involve the preparation of immortal cell lines capable of producing antibodies having the desired specificity. Monoclonal antibodies may also be made by recombinant DNA methods, such as those described in U.S. Pat. No. 4,816,567. DNA encoding antibodies employed in the disclosed methods may be isolated and sequenced using conventional procedures. Recombinant antibodies, antibody fragments, and/or fusions thereof, can be expressed in vitro or in prokaryotic cells (e.g. bacteria) or eukaryotic cells (e.g. yeast, insect or mammalian cells) and further purified as necessary using well known methods.

More particularly, monoclonal antibodies (MAbs) may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified expressed protein, polypeptide or peptide. The immunizing composition is administered in a manner effective to stimulate antibody producing cells. The methods for generating monoclonal antibodies (MAbs) generally begin along the same lines as those for preparing polyclonal antibodies. Rodents such as mice and rats are preferred animals, however, the use of rabbit, sheep or frog cells is also possible. The use of rats may provide certain advantages (Goding, 1986, pp. 60-61), but mice are preferred, with the BALB/c mouse being most preferred as this is most routinely used and generally gives a higher percentage of stable fusions.

The animals are injected with antigen as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals. Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of the animal with the highest antibody titer will be removed and the spleen lymphocytes obtained by homogenizing the spleen with a syringe.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

The selected hybridomas would then be serially diluted and cloned into individual antibody-producing cell lines, which clones may then be propagated indefinitely to provide MAbs. The cell lines may be exploited for MAb production in two basic ways. A sample of the hybridoma may be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, may then be tapped to provide MAbs in high concentration. The individual cell lines also may be cultured in vitro, where the MAbs are naturally secreted into the culture medium from which they may be readily obtained in high concentrations. MAbs produced by either means may be further purified, if desired, using filtration, centrifugation and various chromatographic methods such as HPLC or affinity chromatography.

Large amounts of the monoclonal antibodies of the present invention also may be obtained by multiplying hybridoma cells in vivo. Cell clones are injected into mammals which are histocompatible with the parent cells, e.g., syngeneic mice, to cause growth of antibody-producing tumors. Optionally, the animals are primed with a hydrocarbon, especially oils such as pristane (tetramethylpentadecane) prior to injection.

In accordance with the present invention, fragments of the monoclonal antibody of the invention may be obtained from the monoclonal antibody produced as described above, by methods which include digestion with enzymes such as pepsin or papain and/or cleavage of disulfide bonds by chemical reduction. Alternatively, monoclonal antibody fragments encompassed by the present invention may be synthesized using an automated peptide synthesizer.

Antibodies may also be derived from a recombinant antibody library that is based on amino acid sequences that have been designed in silico and encoded by polynucleotides that are synthetically generated. Methods for designing and obtaining in silico-created sequences are known in the art (Knappik et al., J. Mol. Biol. 296:254:57-86, 2000; Krebs et al., J. Immunol. Methods 254:67-84, 2001; U.S. Pat. No. 6,300,064).

Digestion of antibodies to produce antigen-binding fragments thereof can be performed using techniques well known in the art. For example, the proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "F(ab').sub.2" fragment, which comprises both antigen-binding sites. "Fv" fragments can be produced by preferential proteolytic cleavage of an IgM, IgG or IgA immunoglobulin molecule, but are more commonly derived using recombinant techniques known in the art. The Fv fragment includes a non-covalent V.sub.H::V.sub.L heterodimer including an antigen-binding site which retains much of the antigen recognition and binding capabilities of the native antibody molecule (Inbar et al., Proc. Natl. Acad. Sci. USA 69:2659-2662 (1972); Hochman et al., Biochem. 15:2706-2710 (1976); and Ehrlich et al., Biochem. 19:4091-4096 (1980)).

Antibody fragments that specifically bind to the polypeptide biomarkers disclosed herein can also be isolated from a library of scFvs using known techniques, such as those described in U.S. Pat. No. 5,885,793.

A wide variety of expression systems are available in the art for the production of antibody fragments, including Fab fragments, scFv, VL and VHs. For example, expression systems of both prokaryotic and eukaryotic origin may be used for the large-scale production of antibody fragments. Particularly advantageous are expression systems that permit the secretion of large amounts of antibody fragments into the culture medium. Eukaryotic expression systems for large-scale production of antibody fragments and antibody fusion proteins have been described that are based on mammalian cells, insect cells, plants, transgenic animals, and lower eukaryotes. For example, the cost-effective, large-scale production of antibody fragments can be achieved in yeast fermentation systems. Large-scale fermentation of these organisms is well known in the art and is currently used for bulk production of several recombinant proteins.

Antibodies that bind to the polypeptide biomarkers employed in the present methods are well known to those of skill in the art and in some cases are available commercially or can be obtained without undue experimentation.

In still other embodiments, particularly where oligonucleotides are used as binding partners to detect and hybridize to mRNA biomarkers or other nucleic acid based biomarkers, the binding partners (e.g., oligonucleotides) can comprise a label, e.g., a fluorescent moiety or dye. In addition, any binding partner of the invention, e.g., an antibody, can also be labeled with a fluorescent moiety. The fluorescence of the moiety will be sufficient to allow detection in a single molecule detector, such as the single molecule detectors described herein. A "fluorescent moiety," as that term is used herein, includes one or more fluorescent entities whose total fluorescence is such that the moiety may be detected in the single molecule detectors described herein. Thus, a fluorescent moiety may comprise a single entity (e.g., a Quantum Dot or fluorescent molecule) or a plurality of entities (e.g., a plurality of fluorescent molecules). It will be appreciated that when "moiety," as that term is used herein, refers to a group of fluorescent entities, e.g., a plurality of fluorescent dye molecules, each individual entity may be attached to the binding partner separately or the entities may be attached together, as long as the entities as a group provide sufficient fluorescence to be detected.

Typically, the fluorescence of the moiety involves a combination of quantum efficiency and lack of photobleaching sufficient that the moiety is detectable above background levels in a single molecule detector, with the consistency necessary for the desired limit of detection, accuracy, and precision of the assay. For example, in some embodiments, the fluorescence of the fluorescent moiety is such that it allows detection and/or quantitation of a molecule, e.g., a marker, at a limit of detection of less than about 10, 5, 4, 3, 2, 1, 0.1, 0.01, 0.001, 0.00001, or 0.000001 pg/ml and with a coefficient of variation of less than about 20, 15, 14, 13, 12, 11, 10, 9, 8, 7, 6, 5, 4, 3, 2, 1% or less, e.g., about 10% or less, in the instruments described herein. In some embodiments, the fluorescence of the fluorescent moiety is such that it allows detection and/or quantitation of a molecule, e.g., a marker, at a limit of detection of less than about 5, 1, 0.5, 0.1, 0.05, 0.01, 0.005, 0.001 pg/ml and with a coefficient of variation of less than about 10%, in the instruments described herein. "Limit of detection," or LoD, as those terms are used herein, includes the lowest concentration at which one can identify a sample as containing a molecule of the substance of interest, e.g., the first non-zero value. It can be defined by the variability of zeros and the slope of the standard curve. For example, the limit of detection of an assay may be determined by running a standard curve, determining the standard curve zero value, and adding 2 standard deviations to that value. A concentration of the substance of interest that produces a signal equal to this value is the "lower limit of detection" concentration.

Furthermore, the moiety has properties that are consistent with its use in the assay of choice. In some embodiments, the assay is an immunoassay, where the fluorescent moiety is attached to an antibody; the moiety must have properties such that it does not aggregate with other antibodies or proteins, or experiences no more aggregation than is consistent with the required accuracy and precision of the assay. In some embodiments, fluorescent moieties that are preferred are fluorescent moieties, e.g., dye molecules that have a combination of 1) high absorption coefficient; 2) high quantum yield; 3) high photostability (low photobleaching); and 4) compatibility with labeling the molecule of interest (e.g., protein) so that it may be analyzed using the analyzers and systems of the invention (e.g., does not cause precipitation of the protein of interest, or precipitation of a protein to which the moiety has been attached).

Any suitable fluorescent moiety may be used. Examples include, but are not limited to, Alexa Fluor dyes (Molecular Probes, Eugene, Oreg.). The Alexa Fluor dyes are disclosed in U.S. Pat. Nos. 6,977,305; 6,974,874; 6,130,101; and 6,974,305 which are herein incorporated by reference in their entirety. Some embodiments of the invention utilize a dye chosen from the group consisting of Alexa Fluor 647, Alexa Fluor 488, Alexa Fluor 532, Alexa Fluor 555, Alexa Fluor 610, Alexa Fluor 680, Alexa Fluor 700, and Alexa Fluor 750. Some embodiments of the invention utilize a dye chosen from the group consisting of Alexa Fluor 488, Alexa Fluor 532, Alexa Fluor 647, Alexa Fluor 700 and Alexa Fluor 750. Some embodiments of the invention utilize a dye chosen from the group consisting of Alexa Fluor 488, Alexa Fluor 532, Alexa Fluor 555, Alexa Fluor 610, Alexa Fluor 680, Alexa Fluor 700, and Alexa Fluor 750. Some embodiments of the invention utilize the Alexa Fluor 647 molecule, which has an absorption maximum between about 650 and 660 nm and an emission maximum between about 660 and 670 nm. The Alexa Fluor 647 dye is used alone or in combination with other Alexa Fluor dyes.

In some embodiments, the fluorescent label moiety that is used to detect a biomarker in a sample using the analyzer systems of the invention is a quantum dot. Quantum dots (QDs), also known as semiconductor nanocrystals or artificial atoms, are semiconductor crystals that contain anywhere between 100 to 1,000 electrons and range from 2-10 nm. Some QDs can be between 10-20 nm in diameter. QDs have high quantum yields, which makes them particularly useful for optical applications. QDs are fluorophores that fluoresce by forming excitons, which are similar to the excited state of traditional fluorophores, but have much longer lifetimes of up to 200 nanoseconds. This property provides QDs with low photobleaching. The energy level of QDs can be controlled by changing the size and shape of the QD, and the depth of the QDs' potential. One optical feature of small excitonic QDs is coloration, which is determined by the size of the dot. The larger the dot, the redder, or more towards the red end of the spectrum the fluorescence. The smaller the dot, the bluer or more towards the blue end it is. The bandgap energy that determines the energy and hence the color of the fluoresced light is inversely proportional to the square of the size of the QD. Larger QDs have more energy levels which are more closely spaced, thus allowing the QD to absorb photons containing less energy, i.e., those closer to the red end of the spectrum. Because the emission frequency of a dot is dependent on the bandgap, it is possible to control the output wavelength of a dot with extreme precision. In some embodiments the protein that is detected with the single molecule analyzer system is labeled with a QD. In some embodiments, the single molecule analyzer is used to detect a protein labeled with one QD and using a filter to allow for the detection of different proteins at different wavelengths.

F. Isolated Biomarkers

1. Isolated Polypeptide Biomarkers

One aspect of the invention pertains to isolated marker proteins and biologically active portions thereof, as well as polypeptide fragments suitable for use as immunogens to raise antibodies directed against a marker protein or a fragment thereof. In one embodiment, the native marker protein can be isolated from cells or tissue sources by an appropriate purification scheme using standard protein purification techniques. In another embodiment, a protein or peptide comprising the whole or a segment of the marker protein is produced by recombinant DNA techniques. Alternative to recombinant expression, such protein or peptide can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a marker protein include polypeptides comprising amino acid sequences sufficiently identical to or derived from the amino acid sequence of the marker protein, which include fewer amino acids than the full length protein, and exhibit at least one activity of the corresponding full-length protein. Typically, biologically active portions comprise a domain or motif with at least one activity of the corresponding full-length protein. A biologically active portion of a marker protein of the invention can be a polypeptide which is, for example, 10, 25, 50, 100 or more amino acids in length. Moreover, other biologically active portions, in which other regions of the marker protein are deleted, can be prepared by recombinant techniques and evaluated for one or more of the functional activities of the native form of the marker protein.

Preferred marker proteins are encoded by nucleotide sequences provided in the sequence listing. Other useful proteins are substantially identical (e.g., at least about 40%, preferably 50%, 60%, 70%, 80%, 90%, 91%, 92%, 93%, 94%, 95%, 96%, 97%, 98% or 99%) to one of these sequences and retain the functional activity of the corresponding naturally-occurring marker protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. Preferably, the percent identity between the two sequences is calculated using a global alignment. Alternatively, the percent identity between the two sequences is calculated using a local alignment. The percent identity between the two sequences is a function of the number of identical positions shared by the sequences (i.e., % identity=# of identical positions/total # of positions (e.g., overlapping positions)×100). In one embodiment the two sequences are the same length. In another embodiment, the two sequences are not the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the BLASTN and BLASTX programs of Altschul, et al. (1990) *J. Mol. Biol.* 215:403-410. BLAST nucleotide searches can be performed with the BLASTN program, score=100, wordlength=12 to obtain nucleotide sequences homologous to a nucleic acid molecules of the invention. BLAST protein searches can be performed with the BLASTP program, score=50, wordlength=3 to obtain amino acid sequences homologous to a protein molecules of the invention. To obtain gapped alignments for comparison purposes, a newer version of the BLAST algorithm called Gapped BLAST can be utilized as described in Altschul et al. (1997) *Nucleic Acids Res.* 25:3389-3402, which is able to perform gapped local alignments for the programs BLASTN, BLASTP and BLASTX. Alternatively, PSI-Blast can be used to perform an iterated search which detects distant relationships between molecules. When utilizing BLAST, Gapped BLAST, and PSI-Blast programs, the default parameters of the respective programs (e.g., BLASTX and BLASTN) can be used. See the NCBI website. Another preferred, non-limiting example of a mathematical algorithm utilized for the comparison of sequences is the algorithm of Myers and Miller, (1988) *CABIOS* 4:11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

Another aspect of the invention pertains to antibodies directed against a protein of the invention. In preferred embodiments, the antibodies specifically bind a marker protein or a fragment thereof. The terms "antibody" and "antibodies" as used interchangeably herein refer to immunoglobulin molecules as well as fragments and derivatives thereof that comprise an immunologically active portion of an immunoglobulin molecule, (i.e., such a portion contains an antigen binding site which specifically binds an antigen, such as a marker protein, e.g., an epitope of a marker protein). An antibody which specifically binds to a protein of the invention is an antibody which binds the protein, but does not substantially bind other molecules in a sample, e.g., a biological sample, which naturally contains the protein. Examples of an immunologically active portion of an immunoglobulin molecule include, but are not limited to, single-chain antibodies (scAb), F(ab) and $F(ab')_2$ fragments.

An isolated protein of the invention or a fragment thereof can be used as an immunogen to generate antibodies. The full-length protein can be used or, alternatively, the invention provides antigenic peptide fragments for use as immunogens. The antigenic peptide of a protein of the invention comprises at least 8 (preferably 10, 15, 20, or 30 or more) amino acid residues of the amino acid sequence of one of the proteins of the invention, and encompasses at least one epitope of the protein such that an antibody raised against the peptide forms a specific immune complex with the protein. Preferred epitopes encompassed by the antigenic peptide are regions that are located on the surface of the protein, e.g., hydrophilic regions. Hydrophobicity sequence analysis, hydrophilicity sequence analysis, or similar analyses can be used to identify hydrophilic regions. In preferred embodiments, an isolated marker protein or fragment thereof is used as an immunogen.

The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope. Preferred polyclonal and monoclonal antibody compositions are ones that have been selected for antibodies directed against a protein of the invention. Particularly preferred polyclonal and monoclonal antibody preparations are ones that contain only antibodies directed against a marker protein or fragment thereof. Methods of making polyclonal, monoclonal, and recombinant antibody and antibody fragments are well known in the art.

2. Isolated Nucleic Acid Biomarkers

One aspect of the invention pertains to isolated nucleic acid molecules, including nucleic acids which encode a marker protein or a portion thereof. Isolated nucleic acids of the invention also include nucleic acid molecules sufficient for use as hybridization probes to identify marker nucleic acid molecules, and fragments of marker nucleic acid molecules, e.g., those suitable for use as PCR primers for the amplification of a specific product or mutation of marker nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. In one embodiment, an "isolated" nucleic acid molecule (preferably a protein-encoding sequences) is free of sequences which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. In another embodiment, an "isolated" nucleic acid molecule, such as a cDNA molecule, can be substantially free of other cellular material, or culture medium when produced by recombinant techniques, or substantially free of chemical precursors or other chemicals when chemically synthesized. A nucleic acid molecule that is substantially free of cellular material includes preparations having less than about 30%, 20%, 10%, or 5% of heterologous nucleic acid (also referred to herein as a "contaminating nucleic acid").

A nucleic acid molecule of the present invention can be isolated using standard molecular biology techniques and the sequence information in the database records described herein. Using all or a portion of such nucleic acid sequences, nucleic acid molecules of the invention can be isolated using standard hybridization and cloning techniques (e.g., as described in Sambrook et al., ed., *Molecular Cloning: A Laboratory Manual,* 2nd ed., Cold Spring Harbor Laboratory Press, Cold Spring Harbor, N.Y., 1989).

A nucleic acid molecule of the invention can be amplified using cDNA, mRNA, or genomic DNA as a template and appropriate oligonucleotide primers according to standard PCR amplification techniques. The nucleic acid so amplified can be cloned into an appropriate vector and characterized by DNA sequence analysis. Furthermore, nucleotides corresponding to all or a portion of a nucleic acid molecule of the invention can be prepared by standard synthetic techniques, e.g., using an automated DNA synthesizer.

In another preferred embodiment, an isolated nucleic acid molecule of the invention comprises a nucleic acid molecule which has a nucleotide sequence complementary to the nucleotide sequence of a marker nucleic acid or to the nucleotide sequence of a nucleic acid encoding a marker protein. A nucleic acid molecule which is complementary to a given nucleotide sequence is one which is sufficiently complementary to the given nucleotide sequence that it can hybridize to the given nucleotide sequence thereby forming a stable duplex.

Moreover, a nucleic acid molecule of the invention can comprise only a portion of a nucleic acid sequence, wherein the full length nucleic acid sequence comprises a marker nucleic acid or which encodes a marker protein. Such nucleic acids can be used, for example, as a probe or primer. The probe/primer typically is used as one or more substantially purified oligonucleotides. The oligonucleotide typically comprises a region of nucleotide sequence that hybridizes under stringent conditions to at least about 15, more preferably at least about 25, 50, 75, 100, 125, 150, 175, 200, 250, 300, 350, or 400 or more consecutive nucleotides of a nucleic acid of the invention.

Probes based on the sequence of a nucleic acid molecule of the invention can be used to detect transcripts or genomic sequences corresponding to one or more markers of the invention. In certain embodiments, the probes hybridize to nucleic acid sequences that traverse splice junctions. The probe comprises a label group attached thereto, e.g., a radioisotope, a fluorescent compound, an enzyme, or an enzyme co-factor. Such probes can be used as part of a diagnostic test kit or panel for identifying cells or tissues which express or mis-express the protein, such as by measuring levels of a nucleic acid molecule encoding the protein in a sample of cells from a subject, e.g., detecting mRNA levels or determining whether a gene encoding the protein or its translational control sequences have been mutated or deleted.

The invention further encompasses nucleic acid molecules that differ, due to degeneracy of the genetic code, from the nucleotide sequence of nucleic acids encoding a marker protein (e.g., protein having the sequence provided in the sequence listing), and thus encode the same protein.

It will be appreciated by those skilled in the art that DNA sequence polymorphisms that lead to changes in the amino acid sequence can exist within a population (e.g., the human population). Such genetic polymorphisms can exist among individuals within a population due to natural allelic variation and changes known to occur in cancer. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

As used herein, the phrase "allelic variant" refers to a nucleotide sequence which occurs at a given locus or to a polypeptide encoded by the nucleotide sequence.

As used herein, the terms "gene" and "recombinant gene" refer to nucleic acid molecules comprising an open reading frame encoding a polypeptide corresponding to a marker of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

In another embodiment, an isolated nucleic acid molecule of the invention is at least 15, 20, 25, 30, 40, 60, 80, 100, 150, 200, 250, 300, 350, 400, 450, 550, 650, 700, 800, 900, 1000, 1200, 1400, 1600, 1800, 2000, 2200, 2400, 2600, 2800, 3000, 3500, 4000, 4500, or more nucleotides in length and hybridizes under stringent conditions to a marker nucleic acid or to a nucleic acid encoding a marker protein. As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

G. Biomarker Applications

The invention provides methods for diagnosing an abnormal prostate state, e.g., BPH or an oncological disease state, e.g., prostate cancer, in a subject. The invention further provides methods for prognosing or monitoring progression or monitoring response of an abnormal prostate state, e.g., BPH or prostate cancer, to a therapeutic treatment during active treatment or watchful waiting.

In one aspect, the present invention constitutes an application of diagnostic information obtainable by the methods of the invention in connection with analyzing, detecting, and/or measuring the prostate cancer biomarkers of the present invention, including filamin A alone or filamin A in combination with one or more of filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1, which goes well beyond the discovered correlation between prostate cancer and the biomarkers of the invention.

For example, when executing the methods of the invention for detecting and/or measuring a polypeptide biomarkers of the present invention, as described herein, one contacts a biological sample with a detection reagent, e.g, a monoclonal antibody, which selectively binds to the biomarker of interest, forming a protein-protein complex, which is then further detected either directly (if the antibody comprises a label) or indirectly (if a secondary detection reagent is used, e.g., a secondary antibody, which in turn is labeled). Thus, the method of the invention transforms the polypeptide markers of the invention to a protein-protein complex that comprises either a detectable primary antibody or a primary and further secondary antibody. Forming such protein-protein complexes is required in order to identify the presence of the biomarker of interest and necessarily changes the physical characteristics and properties of the biomarker of interest as a result of conducting the methods of the invention.

The same principal applies when conducting the methods of the invention for detecting nucleic acid biomarkers of the invention. In particular, when amplification methods are used to detect a biomarker of the invention (e.g., filamin A mRNA), the amplification process, in fact, results in the formation of a new population of amplicons—i.e., molecules that are newly synthesized and which were not present in the original biological sample, thereby physically transforming the biological sample. Similarly, when hybridization probes are used to detect a target biomarker, a physical new species of molecules is in effect created by the hybridization of the probes (optionally comprising a label) to the target biomarker mRNA (or other nucleic acid), which is then detected. Such polynucleotide products are effectively newly created or formed as a consequence of carrying out the method of the invention.

The invention provides, in one embodiment, methods for diagnosing an oncological disorder, e.g., prostate cancer. The methods of the present invention can be practiced in conjunction with any other method used by the skilled practitioner to prognose the occurrence or recurrence of an oncologic disorder and/or the survival of a subject being treated for an oncologic disorder. The diagnostic and prognostic methods provided herein can be used to determine if additional and/or more invasive tests or monitoring should be performed on a subject. It is understood that a disease as complex as an oncological disorder is rarely diagnosed using a single test. Therefore, it is understood that the diagnostic, prognostic, and monitoring methods provided herein are typically used in conjunction with other methods known in the art. For example, the methods of the invention may be performed in conjunction with a morphological or cytological analysis of the sample obtained from the subject, imaging analysis, and/or physical exam. Cytological methods would include immunohistochemical or immunofluorescence detection (and quantitation if appropriate) of any other molecular marker either by itself, in conjunction with other markers. Other methods would include detection of other markers by in situ PCR, or by extracting tissue and quantitating other markers by real time PCR. PCR is defined as polymerase chain reaction.

Methods for assessing tumor progression during watchful waiting or the efficacy of a treatment regimen, e.g., chemotherapy, radiation therapy, surgery, hormone therapy, or any other therapeutic approach useful for treating an oncologic disorder in a subject are also provided. In these methods the amount of marker in a pair of samples (a first sample obtained from the subject at an earlier time point or prior to the treatment regimen and a second sample obtained from the subject at a later time point, e.g., at a later time point when the subject has undergone at least a portion of the treatment regimen) is assessed. It is understood that the methods of the invention include obtaining and analyzing more than two samples (e.g., 3, 4, 5, 6, 7, 8, 9, or more samples) at regular or irregular intervals for assessment of marker levels. Pairwise comparisons can be made between consecutive or non-consecutive subject samples. Trends of marker levels and rates of change of marker levels can be analyzed for any two or more consecutive or non-consecutive subject samples.

The invention also provides a method for determining whether an oncologic disorder, e.g., prostate cancer, is aggressive. The method comprises determining the amount of a marker present in a sample and comparing the amount to a control amount of the marker present in one or more control samples, as defined in Definitions, thereby determining whether an oncologic disorder is aggressive. Marker levels can be compared to marker levels in samples obtained at different times from the same subject or marker levels from normal or abnormal prostate state subjects. A rapid increase in the level of marker may be indicative of a more aggressive cancer than a slow increase or no increase or change in the marker level.

The methods of the invention may also be used to select a compound that is capable of modulating, i.e., decreasing, the aggressiveness of an oncologic disorder, e.g., prostate cancer. In this method, a cancer cell is contacted with a test compound, and the ability of the test compound to modulate the expression and/or activity of a marker in the invention in the cancer cell is determined, thereby selecting a compound that is capable of modulating aggressiveness of an oncologic disorder.

Using the methods described herein, a variety of molecules, may be screened in order to identify molecules which modulate, e.g., increase or decrease the expression and/or activity of a marker of the invention, e.g., filamin A alone or filamin A in combination with one or more of PSA, keratin 4, keratin 7, keratin 8, keratin 15, keratin 18, keratin 19, tubulin-beta 3, filamin B (FLNB), and lymphocyte antigen 9 (LY9), PSM, PSCA, TMPRSS2, PDEF, HPG-1, PCA3, and PCGEM1. Compounds so identified can be provided to a subject in order to inhibit the aggressiveness of an oncologic disorder in the subject, to prevent the recurrence of an oncologic disorder in the subject, or to treat an oncologic disorder in the subject.

The present invention pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining the level of expression of one or more marker proteins or nucleic acids, in order to determine whether an individual is at risk of developing a disease or disorder, such as, without limitation, an oncological disorder, e.g., prostate cancer. Such assays can be used for prognostic or predictive purposes to thereby prophylactically treat an individual prior to the onset of the disorder.

Yet another aspect of the invention pertains to monitoring the influence of agents (e.g., drugs or other therapeutic compounds) on the expression or activity of a biomarker of the invention in clinical trials. These and other applications are described in further detail in the following sections.

1. Diagnostic Assays

An exemplary method for detecting the presence or absence or change of expression level of a marker protein or nucleic acid in a biological sample involves obtaining a biological sample (e.g. an oncological disorder-associated body fluid) from a test subject and contacting the biological sample with a compound or an agent capable of detecting the polypeptide or nucleic acid (e.g., mRNA, genomic DNA, or cDNA). The detection methods of the invention can thus be used to detect mRNA, protein, cDNA, or genomic DNA, for example, in a biological sample in vitro as well as in vivo.

Methods provided herein for detecting the presence, absence, change of expression level of a marker protein or nucleic acid in a biological sample include obtaining a biological sample from a subject that may or may not contain the marker protein or nucleic acid to be detected, contacting the sample with a marker-specific binding agent (i.e., one or more marker-specific binding agents) that is capable of forming a complex with the marker protein or nucleic acid to be detected, and contacting the sample with a detection reagent for detection of the marker-marker-specific binding agent complex, if formed. It is understood that the methods provided herein for detecting an expression level of a marker in a biological sample includes the steps to perform the assay. In certain embodiments of the detection methods, the level of the marker protein or nucleic acid in the sample is none or below the threshold for detection.

The methods include formation of either a transient or stable complex between the marker and the marker-specific binding agent. The methods require that the complex, if formed, be formed for sufficient time to allow a detection reagent to bind the complex and produce a detectable signal (e.g., fluorescent signal, a signal from a product of an enzymatic reaction, e.g., a peroxidase reaction, a phosphatase reaction, a beta-galactosidase reaction, or a polymerase reaction).

In certain embodiments, all markers are detected using the same method. In certain embodiments, all markers are detected using the same biological sample (e.g., same body fluid or tissue). In certain embodiments, different markers are detected using various methods. In certain embodiments, markers are detected in different biological samples.

2. Protein Detection

In certain embodiments of the invention, the marker to be detected is a protein. Proteins are detected using a number of assays in which a complex between the marker protein to be detected and the marker specific binding agent would not occur naturally, for example, because one of the components is not a naturally occurring compound or the marker for detection and the marker specific binding agent are not from the same organism (e.g., human marker proteins detected using marker-specific binding antibodies from mouse, rat, or goat). In a preferred embodiment of the invention, the marker protein for detection is a human marker protein. In certain detection assays, the human markers for detection are bound by marker-specific, non-human antibodies, thus, the complex would not be formed in nature. The complex of the marker protein can be detected directly, e.g., by use of a labeled marker-specific antibody that binds directly to the marker, or by binding a further component to the marker-marker-specific antibody complex. In certain embodiments, the further component is a second marker-specific antibody capable of binding the marker at the same time as the first marker-specific antibody. In certain embodiments, the further component is a secondary antibody that binds to a marker-specific antibody, wherein the secondary antibody preferably linked to a detectable label (e.g., fluorescent label, enzymatic label, biotin). When the secondary antibody is linked to an enzymatic detectable label (e.g., a peroxidase, a phosphatase, a beta-galactosidase), the secondary antibody is detected by contacting the enzymatic detectable label with an appropriate substrate to produce a colorimetric, fluorescent, or other detectable, preferably quantitatively detectable, product. Antibodies for use in the methods of the invention can be polyclonal, however, in a preferred embodiment monoclonal antibodies are used. An intact antibody, or a fragment or derivative thereof (e.g., Fab or $F(ab')_2$) can be used in the methods of the invention. Such strategies of marker protein detection are used, for example, in ELISA, RIA, western blot, and immunofluorescence assay methods.

In certain detection assays, the marker present in the biological sample for detection is an enzyme and the detection reagent is an enzyme substrate. For example, the enzyme can be a protease and the substrate can be any protein that includes an appropriate protease cleavage site. Alternatively, the enzyme can be a kinase and the substrate can be any substrate for the kinase. In preferred embodiments, the substrate which forms a complex with the marker enzyme to be detected is not the substrate for the enzyme in a human subject.

In certain embodiments, the marker-marker-specific binding agent complex is attached to a solid support for detection of the marker. The complex can be formed on the substrate or formed prior to capture on the substrate. For example, in an ELISA, RIA, immunoprecipitation assay, western blot, immunofluorescence assay, in gel enzymatic assay the marker for detection is attached to a solid support, either directly or indirectly. In an ELISA, RIA, or immunofluorescence assay, the marker is typically attached indirectly to a solid support through an antibody or binding protein. In a western blot or immunofluorescence assay, the marker is typically attached directly to the solid support. For in-gel enzyme assays, the marker is resolved in a gel, typically an acrylamide gel, in which a substrate for the enzyme is integrated.

3. Nucleic Acid Detection

In certain embodiments of the invention, the marker is a nucleic acid. Nucleic acids are detected using a number of assays in which a complex between the marker nucleic acid to be detected and a marker-specific probe would not occur naturally, for example, because one of the components is not a naturally occurring compound. In certain embodiments, the analyte comprises a nucleic acid and the probe comprises one or more synthetic single stranded nucleic acid molecules, e.g., a DNA molecule, a DNA-RNA hybrid, a PNA, or a modified nucleic acid molecule containing one or more artificial bases, sugars, or backbone moieties. In certain embodiments, the synthetic nucleic acid is a single stranded is a DNA molecule that includes a fluorescent label. In certain embodiments, the synthetic nucleic acid is a single stranded oligonucleotide molecule of about 12 to about 50 nucleotides in length. In certain embodiments, the nucleic acid to be detected is an mRNA and the complex formed is an mRNA hybridized to a single stranded DNA molecule that is complementary to the mRNA. In certain embodiments, an RNA is detected by generation of a DNA molecule (i.e., a cDNA molecule) first from the RNA template using the single stranded DNA that hybridizes to the RNA as a primer, e.g., a general poly-T primer to transcribe poly-A RNA. The cDNA can then be used as a template for an amplification reaction, e.g., PCR, primer extension assay, using a marker-specific probe. In certain embodiments, a labeled single stranded DNA can be hybridized to the RNA present in the sample for detection of the RNA by fluorescence in situ hybridization (FISH) or for detection of the RNA by northern blot.

For example, in vitro techniques for detection of mRNA include northern hybridizations, in situ hybridizations, and rtPCR. In vitro techniques for detection of genomic DNA include Southern hybridizations. Techniques for detection of mRNA include PCR, northern hybridizations and in situ hybridizations. Methods include both qualitative and quantitative methods.

A general principle of such diagnostic, prognostic, and monitoring assays involves preparing a sample or reaction mixture that may contain a marker, and a probe, under appropriate conditions and for a time sufficient to allow the marker and probe to interact and bind, thus forming a complex that can be removed and/or detected in the reaction mixture. These assays can be conducted in a variety of ways known in the art, e.g., ELISA assay, PCR, FISH.

4. Detection of Expression Levels

Marker levels can be detected based on the absolute expression level or a normalized or relative expression level. Detection of absolute marker levels may be preferable when monitoring the treatment of a subject or in determining if there is a change in the prostate cancer status of a subject. For example, the expression level of one or more markers can be monitored in a subject undergoing treatment for prostate cancer, e.g., at regular intervals, such a monthly intervals. A modulation in the level of one or more markers can be monitored over time to observe trends in changes in marker levels. Expression levels of the biomarkers of the invention, e.g., filamin A alone or in combination with one or more of prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1 in the subject may be higher than the expression level of those markers in a normal sample, but may be lower than the prior expression level, thus indicating a benefit of the treatment regimen for the subject. Similarly, rates of change of marker levels can be important in a subject who is not subject to active treatment for prostate cancer (e.g., watchful waiting). Changes, or not, in marker levels may be more relevant to treatment decisions for the subject than marker levels present in the population. Rapid changes in marker levels in a subject who otherwise appears to have a normal prostate may be indicative of an abnormal prostate state, even if the markers are within normal ranges for the population.

As an alternative to making determinations based on the absolute expression level of the marker, determinations may be based on the normalized expression level of the marker. Expression levels are normalized by correcting the absolute expression level of a marker by comparing its expression to the expression of a gene that is not a marker, e.g., a housekeeping gene that is constitutively expressed. Suitable genes for normalization include housekeeping genes such as the actin gene, or epithelial cell-specific genes. This normalization allows the comparison of the expression level in one sample, e.g., a patient sample, to another sample, e.g., a non-cancer sample, or between samples from different sources.

Alternatively, the expression level can be provided as a relative expression level as compared to an appropriate control, e.g., population control, adjacent normal tissue control, earlier time point control, etc. Preferably, the samples used in the baseline determination will be from non-cancer cells. The choice of the cell source is dependent on the use of the relative expression level. Using expression found in normal tissues as a mean expression score aids in validating whether the marker assayed is cancer specific (versus normal cells). In addition, as more data is accumulated, the mean expression value can be revised, providing improved relative expression values based on accumulated data. Expression data from cancer cells provides a means for grading the severity of the cancer state.

5. Diagnostic, Prognostic, and Treatment Methods

The invention provides methods for detecting an abnormal prostate state in a subject by (1) contacting a biological sample from a subject with a panel of one or more detection reagents wherein each detection reagent is specific for one prostate-cancer related protein; wherein the prostate-cancer related proteins are selected from the prostate-cancer related protein set as follows: filamin A alone or filamin A in combination with one or more of prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1;

(2) measuring the amount of each prostate-cancer related marker detected in the biological sample by each detection reagent; and (3) comparing the level of expression of the one or more prostate-cancer related protein in the biological sample obtained from the subject with a level of expression of the one or more prostate-cancer related protein in a control sample, thereby detecting an abnormal prostate state.

In certain embodiments, detecting an abnormal prostate state comprises diagnosing prostate cancer status in a subject. In certain embodiments, an abnormal prostate state comprises identifying a predisposition to developing prostate cancer.

The invention provides methods for monitoring the treatment of prostate cancer in a subject by (1) contacting a first biological sample obtained from the subject prior to administering at least a portion of a treatment regimen to the subject with a panel of one or more detection reagents wherein each detection reagent is specific for one prostate-cancer related protein; wherein the prostate-cancer related proteins are selected from the prostate protein set as follows: filamin A alone or in combination with one or more of prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1;

(2) contacting a second biological sample obtained from the subject after administering at least a portion of a treatment regimen to the subject with a panel of one or more detection reagents wherein each detection reagent is specific for one prostate-cancer related protein; wherein the prostate-cancer related proteins are selected from the prostate protein set as follows: filamin A alone or in combination with one or more of prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1;

(3) measuring the amount of prostate-cancer related marker detected in each the first biological sample and the second biological sample by each detection reagent; and (4) comparing the level of expression of the one or more prostate-cancer related markers in the first sample with the expression level of the one or more prostate-cancer related markers in the second sample, thereby monitoring the treatment of prostate cancer in the subject.

The invention provides method of selecting for administration of active treatment or against administration of active treatment of prostate cancer in a subject by (1) contacting a first biological sample obtained from the subject prior to administering a treatment regimen to the subject with a panel of one or more detection reagents wherein each detection reagent is specific for one prostate-cancer related protein; wherein the prostate-cancer related proteins are selected from the prostate protein set as follows: filamin A alone or in combination with prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1;

(2) contacting a second biological sample obtained from the subject prior to administering a treatment regimen to the subject with a panel of one or more detection reagents wherein each detection reagent is specific for one prostate-cancer related protein; wherein the prostate-cancer related proteins are selected from the prostate protein set as follows: filamin A alone or in combination with one or more of prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1;

(3) measuring the amount of prostate-cancer related marker detected in each the first biological sample and the second biological sample by each detection reagent; and (4) comparing the level of expression of the one or more prostate-cancer related markers in the first sample with the expression level of the one or more prostate-cancer related markers in the second sample, wherein selecting for administration of active treatment or against administration of active treatment of prostate cancer is based on the presence or absence of changes in the level of expression of one or more markers between the first sample and the second sample.

In certain embodiments of the diagnostic and monitoring methods provided herein, one or more prostate-cancer related markers is two or more markers. In certain embodiments of the diagnostic and monitoring methods provided herein, one or more prostate-cancer related markers is three or more markers. In certain embodiments of the diagnostic and monitoring methods provided herein, one or more prostate-cancer related markers is four or more markers. In certain embodiments of the diagnostic and monitoring methods provided herein, one or more prostate-cancer related markers is five or more markers. In certain embodiments of the diagnostic and monitoring methods provided herein, one or more prostate-cancer related markers is six or more markers. In certain embodiments of the diagnostic and monitoring methods provided herein, one or more prostate-cancer related markers is seven or more markers. In certain embodiments of the diagnostic and monitoring methods provided herein, one or more prostate-cancer related markers is eight or more markers. In certain embodiments of the diagnostic and monitoring methods provided herein, one or more prostate-cancer related markers is nine or more markers.

In certain embodiments of the diagnostic methods provided herein, an increase in the level of expression of one or more prostate-cancer related markers selected from the group consisting of filamin A alone or in combination with one or more of prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1 in the biological sample as compared to the level of expression of the one or more prostate-cancer related markers in a normal control sample is an indication that the subject is afflicted with prostate cancer. In certain embodiments of the diagnostic methods provided herein, no increase in the detected expression level of filamin A or one or more of prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1 in the biological sample as compared to the expression level in a normal control sample is an indication that the subject is not afflicted with prostate cancer or not predisposed to developing prostate cancer. In one embodiment, the age of the patient is also determined and used as a predictor variable. For example, increased patient age is an indication that the subject is afflicted with prostate cancer or is predisposed to developing prostate cancer.

In certain embodiments of the diagnostic methods provided herein, an increase in the level of expression of one or more prostate-cancer related markers selected from the group consisting of filamin A alone or in combination with one or more of prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1 in the biological sample as compared to the level of expression of the one or more prostate-cancer related markers in a normal control sample is an indication that the subject is predisposed to developing prostate cancer. In one embodiment, the age of the patient is also determined and used as a predictor variable. For example, increased patient age is an indication that the subject is afflicted with prostate cancer or is predisposed to developing prostate cancer.

In certain embodiments of the monitoring methods provided herein, no increase in the detected level of expression of any of the one or more prostate-cancer related markers selected from the group consisting of filamin A alone or in combination with one or more of prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1 in the second sample as compared to the level of expression of the one or more prostate-cancer related markers in the first sample is an indication that the therapy is efficacious for treating prostate cancer in the subject. In certain embodiments the monitoring methods provided herein, further comprise comparing the level of expression of one or more prostate-cancer related markers selected from the group consisting of filamin A alone or in combination with one or more of prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1 in the first sample or the level of expression of one or more prostate-cancer related markers selected from the group consisting of filamin A alone or in combination with one or more of prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1 in the second sample with the expression of the one or more prostate-cancer related markers in a control sample.

In certain embodiments of the monitoring methods provided herein, an increase in the level of expression of the one or more prostate-cancer related markers selected from the group consisting of filamin A alone or in combination with one or more of prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1 in the second sample as compared to the level of expression of the one or more prostate-cancer related markers in the first sample is an indication for selection of active treatment of prostate cancer in the subject. In certain embodiments of the monitoring methods provided herein, no increase in the detected level of expression of any of the one or more prostate-cancer related markers selected from the group consisting of filamin A alone or in combination with one or more of prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1 in the second sample as compared to the level of expression of the one or more prostate-cancer related markers in the first sample is an indication against selection of active treatment of prostate cancer in the subject. In certain embodiments of the monitoring methods provided herein, wherein an increased expression level of filamin A alone or in combination with one or more of prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1 in the second sample as compared to the expression level in the first sample is an indication that the therapy is not efficacious in the treatment of prostate cancer.

In certain embodiments of the diagnostic and monitoring methods provided herein, the one or more prostate-cancer related markers is selected from the group of filamin A alone or in combination with one or more of prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1. In certain embodiments of the diagnostic and monitoring methods provided herein, the one or more prostate-cancer related markers comprise at least keratin 7, keratin 8, and keratin 15. In certain embodiments of the diagnostic and monitoring methods provided herein, the one or more prostate-cancer related markers is selected from the group of keratin 7, keratin 15, and keratin 19. In certain embodiments of the diagnostic and monitoring methods provided herein, the one or more prostate-cancer related markers comprise at least keratin 7 or keratin 15. In certain embodiments of the diagnostic and monitoring methods provided herein, the one or more prostate-cancer related markers comprise at least keratin 4, keratin 7, keratin 8, keratin 15, keratin 18, and tubulin beta-3 in the biological sample is compared to the level of the one or more prostate-cancer related markers in a normal control sample is indicative of a modulation in prostate cancer status.

In certain embodiments of the monitoring methods provided herein, modulation of the level of expression of the one or more prostate-cancer related markers selected from the group consisting of filamin A alone or in combination with one or more of prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1 in the second sample as compared to the level of expression of the corresponding marker(s) in the first sample is indicative of a change in prostate cancer status in response to treatment of the prostate cancer in the subject. In certain embodiments of the monitoring methods provided herein, the methods further comprise comparing the level of expression of one or more prostate-cancer related markers selected from the group consisting of keratin 4, keratin 7, keratin 8, keratin 15, keratin 18, and tubulin beta-3 in the first sample; or the level of expression of one or more prostate-cancer related markers selected from the group consisting of keratin 4, keratin 7, keratin 8, keratin 15, keratin 18, and tubulin beta-3 in the second sample to the level of expression of one or more prostate-cancer related markers in a normal control sample.

In any of the aforementioned embodiments, the methods may also include a step of determining whether a subject having prostate cancer or who is being treated for prostate cancer is responsive to a particular treatment. Such a step can include, for example, measuring the level of expression of one or more prostate-cancer related markers selected from the group consisting of filamin A alone or in combination with one or more of prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1 prior to administering an anti-prostate cancer treatment, and measuring the level of expression of one or more prostate-cancer related markers selected from the group consisting of filamin A alone or in combination with one or more of prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1 after administering the anti-prostate cancer treatment, and comparing the expression level before and after treatment. Determining that the prostate cancer is responsive to the treatment if the expression level of the one or more markers is lower than before treatment as compared to after treatment. The method may further include the step of adjusting the treatment to a higher dose in order to increase the responsiveness to the treatment, or adjusting the treatment to a lower dose in order to descrease the responsiveness to the treatment.

In any of the aforementioned embodiments, the methods may also include a step of determining whether a subject having prostate cancer or who is being treated for prostate cancer is responsive to a particular treatment. Such a step can include, for example, measuring the level of expression of one or more prostate-cancer related markers selected from the group consisting of filamin A alone or in combination with one or more of prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1 prior to administering an anti-prostate cancer treatment, and measuring the level of expression of one or more prostate-cancer related markers selected from the group consisting of filamin A alone or in combination with one or more of prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1 after administering the anti-prostate cancer treatment, and comparing the expression level before and after treatment. Determining that the prostate cancer is responsive to the treatment if the expression level of the one or more markers is higher than before treatment as compared to after treatment. The method may further include the step of adjusting the treatment to a higher dose in order to increase the responsiveness to the treatment, or adjusting the treatment to a lower dose in order to descrease the responsiveness to the treatment.

In any of the aforementioned embodiments, the methods may also include a step of determining whether a subject having prostate cancer or who is being treated for prostate cancer is not responsive to a particular treatment. Such a step can include, for example, measuring the level of expression of one or more prostate-cancer related markers selected from the group consisting of filamin A alone or in combination with one or more of prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1 prior to administering an anti-prostate cancer treatment, and measuring the level of expression of one or more prostate-cancer related markers selected from the group consisting of filamin A alone or in combination with one or more of prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1 after administering the anti-prostate cancer treatment, and comparing the expression level before and after treatment. Determining that the prostate cancer is not responsive to the treatment if the expression level of the one or more markers is lower than before treatment as compared to after treatment. The method may further include the step of adjusting the treatment to a higher dose in order to increase the responsiveness to the treatment.

In any of the aforementioned embodiments, the methods may also include a step of determining whether a subject having prostate cancer or who is being treated for prostate cancer is not responsive to a particular treatment. Such a step can include, for example, measuring the level of expression of one or more prostate-cancer related markers selected from the group consisting of filamin A alone or in combination with one or more of prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1 prior to administering an anti-prostate cancer treatment, and measuring the level of expression of one or more prostate-cancer related markers selected from the group consisting of filamin A alone or in combination with one or more of prostate specific antigen (PSA), filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1 after administering the anti-prostate cancer treatment, and comparing the expression level before and after treatment. Determining that the prostate cancer is not responsive to the treatment if the expression level of the one or more markers is higher than before treatment as compared to after treatment. The method may further include the step of adjusting the treatment to a higher dose in order to increase the responsiveness to the treatment.

In certain embodiments the diagnostic methods provided herein further comprise detecting the level of expression of prostate specific antigen (PSA) in the biological sample and preferably further comprise comparing the level of expression of PSA in the biological sample to a PSA expression level in a normal control sample. In certain embodiments, the combination of PSA level with one or more of the prostate-cancer maker levels increases the predictive value of the method.

In certain embodiments the monitoring methods provided herein further comprise detecting the level of expression of prostate specific antigen (PSA) in the first sample and the second sample, and preferably further comprising comparing the level of expression of PSA in the first sample with the level of expression of PSA in the second sample. In certain monitoring methods, the change in PSA level in combination with the change in prostate-cancer maker level increases the predictive value of the method.

In certain embodiments the diagnostic and monitoring methods provided herein further comprise comparing the detected level of the one or more prostate markers in the biological samples with one or more control samples wherein the control sample is one or more of a sample from the same subject at an earlier time point than the biological sample, a sample from a subject with benign prostatic hyperplasia (BPH), a sample from a subject with non-metastatic prostate cancer, a sample from a subject with metastatic prostate cancer, a sample from a subject with androgen sensitive prostate cancer, a sample from a subject with androgen insensitive prostate cancer, a sample from a subject with aggressive prostate cancer, and sample obtained from a subject with non-aggressive prostate cancer. Comparison of the marker levels in the biological samples with control samples from subjects with various normal and abnormal prostate states facilitates the differentiation between various prostate states including normal prostate and prostate cancer, benign prostate hyperplasia and prostate cancer, benign prostate hyperplasia and normal prostate, androgen dependent and androgen independent prostate cancer, aggressive prostate cancer and non-aggressive prostate cancer, aggressive prostate cancer and non-aggressive prostate cancer, or between any two or more prostate states including normal prostate, prostate cancer, benign prostate hyperplasia, androgen dependent prostate cancer, androgen independent prostate cancer, aggressive prostate cancer, non-aggressive prostate cancer, metastatic prostate cancer, and non-metastatic prostate cancer.

In certain embodiments the diagnostic and monitoring methods provided herein further comprising detecting the size of the prostate tumor in the subject. In certain embodiments the monitoring methods provided herein further comprise detecting a change in the size or relative aggressiveness of the tumor. In certain embodiments, the size of the prostate tumor in the subject is detected prior to administering the at least a portion of a treatment regimen to the subject. In certain embodiments, the size of the prostate tumor in the subject is detected after administering the at least a portion of a treatment regimen to the subject. Certain monitoring methods, further comprise comparing the size of the prostate tumor in the subject prior to administering the at least a portion of a treatment regimen to the subject to the size of the prostate tumor in the subject after administering the at least a portion of a treatment regimen to the subject. Certain other embodiments of the diagnostic and monitoring methods further comprise determining the particular stage or grade of prostate cancer, e.g., Gleason grade 1, grade 2, grade 3, grade 4, or grade 5 prostate cancer or TNM classifications. In other embodiments, the present invention also involves the analysis and consideration of any clinical and/or patient-related health data, for example, data obtained from an Electronic Medical Record (e.g., collection of electronic health information about individual patients or populations relating to various types of data, such as, demographics, medical history, medication and allergies, immunization status, laboratory test results, radiology images, vital signs, personal statistics like age and weight, and billing information).

In certain embodiments the diagnostic and monitoring methods provided herein further comprising obtaining a subject sample.

In certain embodiments the diagnostic and monitoring methods provided herein further comprising selecting a treatment regimen for the subject based on the level of expression of one or more of the prostate-cancer related markers selected from the group consisting of filamin A alone or filamin A in combination with one or more of filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1.

In certain embodiments the diagnostic and monitoring methods provided herein further comprise selecting a subject for having or being suspected of having prostate cancer.

In certain embodiments the diagnostic and monitoring methods provided herein further comprising treating the subject with a regimen including one or more treatments selected from the group consisting of surgery, radiation, hormone therapy, antibody therapy, therapy with growth factors, cytokines, and chemotherapy.

In certain embodiments the diagnostic and monitoring methods provided herein further comprise selecting the one or more specific treatment regimens for the subject based on the results of the diagnostic and monitoring methods provided herein. In one embodiment, a treatment regimen known to be effective against prostate cancer having the biomarker signature detected in the subject/sample is selected for the subject. In certain embodiments, the treatment method is started, change, revised, or maintained based on the results from the diagnostic or prognostic methods of the invention, e.g., when it is determined that the subject is responding to the treatment regimen, or when it is determined that the subject is not responding to the treatment regimen, or when it is determined that the subject is insufficiently responding to the treatment regimen. In certain embodiments, the treatment method is changed based on the results from the diagnostic or prognostic methods.

In certain other embodiments the diagnostic and monitoring methods provided herein further comprise introducing one or more specific treatment regimens for the subject based on the results of the diagnostic and monitoring methods provided herein. In one embodiment, a treatment regimen known to be effective against prostate cancer is selected for the subject. In certain embodiments, the treatment method is started, change, revised, or maintained based on the results from the diagnostic or prognostic methods of the invention, e.g., when it is determined that the subject is responding to the treatment regimen, or when it is determined that the subject is not responding to the treatment regimen, or when it is determined that the subject is insufficiently responding to the treatment regimen. In certain embodiments, the treatment method is changed based on the results from the diagnostic or prognostic methods.

In yet other embodiments the diagnostic and monitoring methods provided herein further comprise the step of administering a therapeutically effective amount of an anti-prostate cancer therapy based on the results of the diagnostic and monitoring methods provided herein. In one embodiment, a treatment regimen known to be effective against prostate cancer is selected for the subject. In certain embodiments, the treatment method is administered based on the results from the diagnostic or prognostic methods of the invention, e.g., when it is determined that the subject expresses one or more biomarkers of the invention (e.g., filamin A alone or filamin A in combination with one or more of filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1) above some threshold level that is indicative of prostate cancer.

In yet other embodiments the diagnostic and monitoring methods provided herein further comprise the step of administering a therapeutically effective amount of an anti-prostate cancer therapy based on the results of the diagnostic and monitoring methods provided herein. In one embodiment, a treatment regimen known to be effective against prostate cancer is selected for the subject. In certain embodiments, the treatment method is administered based on the results from the diagnostic or prognostic methods of the invention, e.g., when it is determined that the subject expresses one or more biomarkers of the invention (e.g., filamin A alone or filamin A in combination with one or more of filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1) below some threshold level that is indicative of prostate cancer.

In yet other embodiments the diagnostic and monitoring methods provided herein further comprise the step of increasing, decreasing, or changing the dose of an anti-prostate cancer therapy based on the results of the diagnostic and monitoring methods provided herein. In one embodiment, a treatment regimen known to be effective against prostate cancer is selected for the subject. In certain embodiments, the treatment method is administered based on the results from the diagnostic or prognostic methods of the invention, e.g., when it is determined that the subject expresses one or more biomarkers of the invention (e.g., filamin A alone or filamin A in combination with one or more of filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1) above some threshold level that is indicative of prostate cancer.

In yet other embodiments the diagnostic and monitoring methods provided herein further comprise the step of increasing, decreasing, or changing the dose of an anti-prostate cancer therapy based on the results of the diagnostic and monitoring methods provided herein. In one embodiment, a treatment regimen known to be effective against prostate cancer is selected for the subject. In certain embodiments, the treatment method is administered based on the results from the diagnostic or prognostic methods of the invention, e.g., when it is determined that the subject expresses one or more biomarkers of the invention (e.g., filamin A alone or filamin A in combination with one or more of filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1) below some threshold level that is indicative of prostate cancer.

In certain embodiments, a change in the treatment regimen comprises changing a hormone based therapy treatment. In certain embodiments, treatments for prostate cancer include one or more of surgery, radiation, hormone therapy, antibody therapy, therapy with growth factors, cytokines, or chemotherapy based on the results of a method of any one of claims 1-64 for an interval prior to performing a subsequent diagnostic, prognostic, or monitoring method provided herein.

In certain embodiments of the diagnostic and monitoring methods provided herein, the method further comprises isolating a component of the biological sample.

In certain embodiments of the diagnostic and monitoring methods provided herein, the method further comprises labeling a component of the biological sample.

In certain embodiments of the diagnostic and monitoring methods provided herein, the method further comprises amplifying a component of a biological sample.

In certain embodiments of the diagnostic and monitoring methods provided herein, the method comprises forming a complex with a probe and a component of a biological sample. In certain embodiments, forming a complex with a probe comprises forming a complex with at least one non-naturally occurring reagent. In certain embodiments of the diagnostic and monitoring methods provided herein, the method comprises processing the biological sample. In certain embodiments of the diagnostic and monitoring methods provided herein, the method of detecting a level of at least two markers comprises a panel of markers. In certain embodiments of the diagnostic and monitoring methods provided herein, the method of detecting a level comprises attaching the marker to be detected to a solid surface.

The invention provides methods of selecting for administration of active treatment or against administration of active treatment of prostate cancer in a subject comprising:

(1) detecting a level of one or more markers selected from the group consisting of filamin B, LY9, keratin 4, keratin 7, keratin 8, keratin 15, keratin 18, keratin 19, and tubulin-beta in a first sample obtained from the subject having prostate cancer at a first time wherein the subject has not been actively treated for prostate cancer;

(2) detecting a level of one or more markers selected from the group consisting of filamin B, LY9, keratin 4, keratin 7, keratin 8, keratin 15, keratin 18, keratin 19, and tubulin-beta 3 in a second sample obtained from the subject at a second time, e.g., wherein the subject has not been actively treated;

(3) comparing the level of one or more markers selected from the group consisting of filamin B, LY9, keratin 4, keratin 7, keratin 8, keratin 15, keratin 18, keratin 19, and tubulin-beta 3 in the first sample with the level of one or more markers selected from the group consisting of filamin B, LY9, keratin 4, keratin 7, keratin 8, keratin 15, keratin 18, keratin 19, and tubulin-beta 3 in the second sample;

wherein selecting for administration of active treatment or against administration of active treatment of prostate cancer is based on the presence or absence of changes in the level of expression of one or more markers between the first sample and the second sample.

In certain embodiments, the method further comprising obtaining a third sample obtained from the subject at a third time (e.g., wherein the subject has not been actively treated), detecting a level of one or more markers selected from the group consisting of filamin B, LY9, keratin 4, keratin 7, keratin 8, keratin 15, keratin 18, keratin 19, and tubulin-beta 3 in the third sample, and comparing the level of one or more markers selected from the group consisting of filamin B, LY9, keratin 4, keratin 7, keratin 8, keratin 15, keratin 18, keratin 19, and tubulin-beta 3 in the third sample with the level of the one or more markers in the first sample and/or the one or more markers in the second sample.

In certain embodiments, an increased level of filamin A alone or filamin A in combination with one or more of filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1, in the second sample as compared to the level of the markers in the first sample is an indication that the therapy is not efficacious in the treatment of prostate cancer.

In certain embodiments, an increased level of filamin A alone or filamin A in combination with one or more of filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1, in the second sample as compared to the level of the markers in the first sample is an indication for selecting active treatment for prostate cancer.

In certain embodiments, the method further comprises comparing the level of one or more markers selected from the group consisting of ilamin A alone or filamin A in combination with one or more of filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1, in the first sample or the level of one or more markers selected from the group consisting of ilamin A alone or filamin A in combination with one or more of filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1, in the second sample with the level of one or more of ilamin A alone or filamin A in combination with one or more of filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1, in a control sample. In certain embodiments, the method comprises detecting the level of filamin A in combination with one or more of keratin 4, keratin 7, keratin 8, keratin 15, keratin 18, and tubulin beta-3 in the first sample; detecting the level of filamin A in combination with one or more of keratin 4, keratin 7, keratin 8, keratin 15, keratin 18, and tubulin beta-3 in the second sample; and comparing the level of filamin A in combination with one or more of one or more of keratin 4, keratin 7, keratin 8, keratin 15, keratin 18, and tubulin beta-3 in the second sample with the one or more of the level of filamin A in combination with keratin 4, keratin 7, keratin 8, keratin 15, keratin 18, and tubulin beta-3 in the first sample. In certain embodiments, the method comprises detection of a subset of keratins such as keratin 7, keratin 8, and keratin 15; keratin 7, 15, and 19 in combination with filamin A; and keratin 7 or keratin 15. In certain embodiments, the method further comprises comparing the level of one or more of keratin 4, keratin 7, keratin 8, keratin 15, keratin 18, and tubulin beta-3 in combination with filamin A in the first sample; or the level of expression of one or more of keratin 4, keratin 7, keratin 8, keratin 15, keratin 18, and tubulin beta-3 in combination with filamin A in the second sample to the level of one or more of keratin 4, keratin 7, keratin 8, keratin 15, keratin 18, and tubulin beta-3 in combination with filamin A in a control sample.

In certain embodiments, no change in the level of expression of one or more markers selected from the group consisting of filamin A alone or filamin A in combination with one or more of filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1, between the first sample and the second sample is an indication for selecting against active treatment for prostate cancer.

In certain embodiments, the methods further comprise detecting the level of prostate specific antigen (PSA) in the first sample and the second sample, and then preferably further comprising comparing the level of PSA in the first sample with the level of PSA in the second sample.

In certain embodiments, a decrease in the level of one or more of filamin A alone or filamin A in combination with one or more of filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1, in the second sample as compared to the level of one or more of filamin A alone or filamin A in combination with one or more of filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1, in the first sample in combination with a decrease in the level of PSA in the second sample as compared to the level of PSA in the first sample has greater predictive value that the therapy is efficacious in treating prostate cancer in the subject than analysis of a single marker alone.

In certain embodiments, a decrease in the level of one or more of filamin A alone or filamin A in combination with one or more of filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1, in the second sample as compared to the level of one or more of filamin A alone or filamin A in combination with one or more of filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1, in the first sample in combination with a decrease in the level of expression of PSA in the second sample as compared to the level of PSA in the first sample has greater predictive value for selecting against active treatment for prostate cancer than analysis of a single marker alone.

6. Monitoring Clinical Trials

Monitoring the influence of agents (e.g., drug compounds) on the level of expression of a marker of the invention can be applied not only in basic drug screening or monitoring the treatment of a single subject, but also in clinical trials. For example, the effectiveness of an agent to affect marker expression can be monitored in clinical trials of subjects receiving treatment for an oncological disorder. In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate) comprising the steps of (i) obtaining a pre-administration sample from a subject prior to administration of the agent; (ii) detecting the level of expression of one or more selected markers of the invention (e.g., filamin B, LY9, keratin 4, keratin 7, keratin 8, keratin 15, keratin 18, keratin 19, tubulin-beta 3, optionally in combination with PSA) in the pre-administration sample; (iii) obtaining one or more post-administration samples from the subject; (iv) detecting the level of expression of the marker(s) in the post-administration samples; (v) comparing the level of expression of the marker(s) in the pre-administration sample with the level of expression of the marker(s) in the post-administration sample or samples; and (vi) altering the administration of the agent to the subject accordingly. For example, increased expression of the marker gene(s) during the course of treatment may indicate ineffective dosage and the desirability of increasing the dosage. Conversely, decreased expression of the marker gene(s) may indicate efficacious treatment and no need to change dosage.

H. Treatment/Therapeutics

The present invention provides methods for use of one or more (e.g., 1, 2, 3, 4, 5, 6, 7, 8, or 9) markers selected from the group consisting of filamin A, keratin 4, keratin 7, keratin 8, keratin 15, keratin 18, keratin 19, tubulin-beta 3, filamin B (FLNB), and lymphocyte antigen 9 (LY9) to treat disease states in a subject, e.g., a mammal, e.g., a human.

The present invention also provides methods for treatment of a subject with prostate cancer with a therapeutic, e.g., a nucleic acid based therapeutic, that modulates (e.g., reduces, or increases, and preferably reduces) the expression or activity of one or more (e.g., 1, 2, 3, 4, 5, 6, 7, 8, or 9) markers selected from the group consisting of filamin A alone or filamin A in combination with one or more of filamin B, LY9, keratin 4, keratin 7, keratin 8, keratin 15, keratin 18, keratin 19, tubulin-beta 3, PSM, PSCA, TMPRSS2, PDEF, HPG-1, PCA3, and PCGEM1.

The invention also provides methods for selection and/or administration of known treatment agents, especially hormone based therapies vs. non-hormone based therapies, and aggressive or active treatment vs. “watchful waiting”, depending on the detection of a change in the level of one or more (e.g., 1, 2, 3, 4, 5, 6, 7, 8, or 9) markers selected from the group consisting of filamin A, keratin 4, keratin 7, keratin 8, keratin 15, keratin 18, keratin 19, tubulin-beta 3, filamin B (FLNB), and lymphocyte antigen 9 (LY9), as compared to a control. The selection of treatment regimens can further include the detection of PSA to assist in selection of the therapeutic methods. Selection of treatment methods can also include other diagnostic considerations and patient characteristics including results from imaging studies, tumor size or growth rates, risk of poor outcomes, disruption of daily activities, and age, Gleason scores (e.g., grade 1, grade 2, grade 3, grade 4, or grade 5 prostate cancer), TNM classifications, clinical and/or patient-related health data (e.g., data obtained from an Electronic Medical Record (e.g., collection of electronic health information about individual patients or populations relating to various types of data, such as, demographics, medical history, medication and allergies, immunization status, laboratory test results, radiology images, vital signs, personal statistics like age and weight, and billing information).

As used herein, the term “aggressive oncological disorder”, such as aggressive prostate cancer, refers to an oncological disorder involving a fast-growing tumor. An aggressive oncological disorder typically does not respond, responds poorly, or loses response to therapeutic treatment. For example, an prostate cancer may be considered to become an aggressive prostate cancer upon loss of response to hormone therapy, necessitating treatment with chemotherapy, surgery, and/or radiation. As used herein, an aggressive prostate cancer, for example, is one that will likely or has metastasized. As used herein, an aggressive prostate cancer is one that will result in significant changes in quality of life as the tumor grows. Active treatment is therapeutically indicated for an aggressive oncological disorder, e.g., aggressive prostate cancer.

As used herein, the term “non-aggressive oncological disorder” such as a non-aggressive prostate cancer, refers to an oncological disorder involving a slow-growing tumor. A non-aggressive oncological disorder typically responds favorably or moderately to therapeutic treatment or grows so slowly that immediate treatment is not warranted. A non-aggressive prostate tumor is one that a person skilled in the art, e.g., an oncologist, may decide to not actively treat with routine interventions for the treatment of cancer, e.g., chemotherapy, radiation, surgery, as the active treatment may do more harm than the disease, particularly in an older subject. A non-aggressive prostate tumor is one that a person skilled in the art may decide to monitor with “watchful waiting” rather than subjecting the person to any active therapeutic interventions to alter the presence or growth of the tumor (e.g., radiation, surgery, chemotherapy, hormone therapy).

1. Nucleic Acid Therapeutics

Nucleic acid therapeutics are well known in the art. Nucleic acid therapeutics include both single stranded and double stranded (i.e., nucleic acid therapeutics having a complementary region of at least 15 nucleotides in length that may be one or two nucleic acid strands) nucleic acids that are complementary to a target sequence in a cell. Nucleic acid therapeutics can be delivered to a cell in culture, e.g., by adding the nucleic acid to culture media either alone or with an agent to promote uptake of the nucleic acid into the cell. Nucleic acid therapeutics can be delivered to a cell in a subject, i.e., in vivo, by any route of administration. The specific formulation will depend on the route of administration.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

Sequences can be "fully complementary" with respect to each when there is base-pairing of the nucleotides of the first nucleotide sequence with the nucleotides of the second nucleotide sequence over the entire length of the first and second nucleotide sequences. However, where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs as is common in double stranded nucleic acid therapeutics, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes described herein.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but not limited to, G:U Wobble or Hoogstein base pairing.

The terms "complementary," "fully complementary", and "substantially complementary" herein may be used with respect to the base matching between the sense strand and the antisense strand of a dsRNA, or between an antisense nucleic acid or the antisense strand of dsRNA and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding filamin B, LY9, a keratin, tubulin-beta 3, or PSA) including a 5' UTR, an open reading frame (ORF), or a 3' UTR. For example, a polynucleotide is complementary to at least a part of filamin B, LY9, a keratin, tubulin-beta 3, or PSA mRNA if the sequence is substantially complementary to a non-interrupted portion of an mRNA encoding filamin B, LY9, a keratin, tubulin-beta 3, or PSA.

Nucleic acid therapeutics typically include chemical modifications to improve their stability and to modulate their pharmacokinetic and pharmacodynamic properties. For example, the modifications on the nucleotides can include, but are not limited to, LNA, HNA, CeNA, 2'-hydroxyl, and combinations thereof.

Nucleic acid therapeutics may further comprise at least one phosphorothioate or methylphosphonate internucleotide linkage. The phosphorothioate or methylphosphonate internucleotide linkage modification may occur on any nucleotide of the sense strand or antisense strand or both (in nucleic acid therapeutics including a sense strand) in any position of the strand. For instance, the internucleotide linkage modification may occur on every nucleotide on the sense strand or antisense strand; each internucleotide linkage modification may occur in an alternating pattern on the sense strand or antisense strand; or the sense strand or antisense strand may contain both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand.

A. Single Stranded Therapeutics

Antisense nucleic acid therapeutic agent single stranded nucleic acid therapeutics, typically about 16 to 30 nucleotides in length and are complementary to a target nucleic acid sequence in the target cell, either in culture or in an organism.

Patents directed to antisense nucleic acids, chemical modifications, and therapeutic uses are provided, for example, in U.S. Pat. No. 5,898,031 related to chemically modified RNA-containing therapeutic compounds, and U.S. Pat. No. 6,107,094 related methods of using these compounds as therapeutic agent. U.S. Pat. No. 7,432,250 related to methods of treating patients by administering single-stranded chemically modified RNA-like compounds; and U.S. Pat. No. 7,432,249 related to pharmaceutical compositions containing single-stranded chemically modified RNA-like compounds. U.S. Pat. No. 7,629,321 is related to methods of cleaving target mRNA using a single-stranded oligonucleotide having a plurality RNA nucleosides and at least one chemical modification. Each of the patents listed in the paragraph are incorporated herein by reference.

B. Double Stranded Therapeutics

In many embodiments, the duplex region is 15-30 nucleotide pairs in length. In some embodiments, the duplex region is 17-23 nucleotide pairs in length, 17-25 nucleotide pairs in length, 23-27 nucleotide pairs in length, 19-21 nucleotide pairs in length, or 21-23 nucleotide pairs in length.

In certain embodiments, each strand has 15-30 nucleotides.

The RNAi agents that are used in the methods of the invention include agents with chemical modifications as disclosed, for example, in Publications WO 2009/073809 and WO/2012/037254, the entire contents of each of which are incorporated herein by reference.

Nucleic acid therapeutic agents for use in the methods of the invention also include double stranded nucleic acid therapeutics. An "RNAi agent," "double stranded RNAi agent," double-stranded RNA (dsRNA) molecule, also referred to as "dsRNA agent," "dsRNA", "siRNA", "iRNA agent," as used interchangeably herein, refers to a complex of ribonucleic acid molecules, having a duplex structure comprising two anti-parallel and substantially complementary, as defined below, nucleic acid strands. As used herein, an RNAi agent can also include dsiRNA (see, e.g., US Patent publication 20070104688, incorporated herein by reference). In general, the majority of nucleotides of each strand are ribonucleotides, but as described herein, each or both strands can also include one or more non-ribonucleotides, e.g., a deoxyribonucleotide and/or a modified nucleotide. In addition, as used in this specification, an "RNAi agent" may include ribonucleotides with chemical modifications; an RNAi agent may include substantial modifications at multiple nucleotides. Such modifications may include all types of modifications disclosed herein or known in the art. Any such modifications, as used in a siRNA type molecule, are encompassed by "RNAi agent" for the purposes of this specification and claims. The RNAi agents that are used in the methods of the invention include agents with chemical modifications as disclosed, for example, in U.S. Provisional Application No. 61/561,710, filed on Nov. 18, 2011, International Application No. PCT/US2011/051597, filed on Sep. 15, 2010, and PCT Publication WO 2009/073809, the entire contents of each of which are incorporated herein by reference. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi agent may comprise one or more nucleotide overhangs. The term "siRNA" is also used herein to refer to an RNAi agent as described above.

In another aspect, the agent is a single-stranded antisense RNA molecule. An antisense RNA molecule is complementary to a sequence within the target mRNA. Antisense RNA can inhibit translation in a stoichiometric manner by base pairing to the mRNA and physically obstructing the translation machinery, see Dias, N. et al., (2002) Mol Cancer Ther 1:347-355. The antisense RNA molecule may have about 15-30 nucleotides that are complementary to the target mRNA. For example, the antisense RNA molecule may have a sequence of at least 15, 16, 17, 18, 19, 20 or more contiguous nucleotides complementary to the filamin B or LY9 sequences provided herein.

The term "antisense strand" refers to the strand of a double stranded RNAi agent which includes a region that is substantially complementary to a target sequence (e.g., a human TTR mRNA). As used herein, the term "region complementary to part of an mRNA encoding transthyretin" refers to a region on the antisense strand that is substantially complementary to part of a TTR mRNA sequence. Where the region of complementarity is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus.

The term "sense strand," as used herein, refers to the strand of a dsRNA that includes a region that is substantially complementary to a region of the antisense strand.

The invention also includes molecular beacon nucleic acids having at least one region which is complementary to a nucleic acid of the invention, such that the molecular beacon is useful for quantitating the presence of the nucleic acid of the invention in a sample. A "molecular beacon" nucleic acid is a nucleic acid comprising a pair of complementary regions and having a fluorophore and a fluorescent quencher associated therewith. The fluorophore and quencher are associated with different portions of the nucleic acid in such an orientation that when the complementary regions are annealed with one another, fluorescence of the fluorophore is quenched by the quencher. When the complementary regions of the nucleic acid are not annealed with one another, fluorescence of the fluorophore is quenched to a lesser degree. Molecular beacon nucleic acids are described, for example, in U.S. Pat. No. 5,876,930.

I. Drug Screening

As noted above, sets of biomarkers whose expression levels correlate with one or more selected prostate disease characteristics (e.g., prostate cancer progression) are attractive targets for identification of new therapeutic agents via screens to detect compounds or entities that inhibit or enhance expression of these biomarker genes and/or their products. Accordingly, the present invention provides methods for the identification of compounds potentially useful for modulating prostate cancer progression. In particular, the present invention provides methods for the identification of compounds potentially useful for modulating prostate cancer progression wherein the compounds modulate (e.g., increase or decrease, preferably decrease or inhibit) the expression of filamin A, and/or filamin A in combination with other biomarkers, including prostate specific antigen (PSA), filamin B, LY9, keratin 4, keratin 7, keratin 8, keratin 15, kertin 18, keratin 19, and tubulin-beta 3.

Such assays typically comprise a reaction between a marker of the invention and one or more assay components. The other components may be either the test compound itself, or a combination of test compounds and a natural binding partner of a marker of the invention. Compounds identified via assays such as those described herein may be useful, for example, for modulating, e.g., inhibiting, ameliorating, treating, or preventing the disease. Compounds identified for modulating the expression level of one or more of keratin 4, keratin 7, keratin 8, keratin 15, keratin 18, keratin 19, tubulin-beta 3, filamin B, or LY9; optionally in combination with PSA, are preferably further tested for activity useful in the treatment of cancer, preferably prostate cancer, e.g., inhibiting tumor cell growth, inhibiting tumor angiogenesis, inducing tumor cell apoptosis, etc.

The test compounds used in the screening assays of the present invention may be obtained from any available source, including systematic libraries of natural and/or synthetic compounds. Test compounds may also be obtained by any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al., 1994, *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, Anticancer Drug Des. 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten, 1992, *Biotechniques* 13:412-421), or on beads (Lam, 1991, *Nature* 354:82-84), chips (Fodor, 1993, *Nature* 364:555-556), bacteria and/or spores, (Ladner, U.S. Pat. No. 5,223,409), plasmids (Cull et al, 1992, *Proc Natl Acad Sci USA* 89:1865-1869) or on phage (Scott and Smith, 1990, *Science* 249:386-390; Devlin, 1990, *Science* 249:404-406; Cwirla et al, 1990, *Proc. Natl. Acad. Sci.* 87:6378-6382; Felici, 1991, *J. Mol. Biol.* 222:301-310; Ladner, supra.).

The screening methods of the invention comprise contacting a cell, e.g., a diseased cell, especially a prostate cancer cell, with a test compound and determining the ability of the test compound to modulate the expression and/or activity of filamin B, LY9, or keratin 19, optionally in combination with PSA, in the cell. The expression and/or activity of filamin B, LY9, or keratin 19; optionally in combination with PSA, can be determined using any methods known in the art, such as those described herein.

In another embodiment, the invention provides assays for screening candidate or test compounds which are substrates of a marker of the invention or biologically active portions thereof. In yet another embodiment, the invention provides assays for screening candidate or test compounds which bind to a marker of the invention or biologically active portions thereof. Determining the ability of the test compound to directly bind to a marker can be accomplished, for example, by any method known in the art.

This invention further pertains to novel agents identified by the above-described screening assays. Accordingly, it is within the scope of this invention to further use an agent identified as described herein in an appropriate animal model. For example, an agent capable of modulating the expression and/or activity of a marker of the invention identified as described herein can be used in an animal model to determine the efficacy, toxicity, or side effects of treatment (e.g., of prostate cancer) with such an agent. Alternatively, an agent identified as described herein can be used in an animal model to determine the mechanism of action of such an agent. Furthermore, this invention pertains to uses of novel agents identified by the above-described screening assays for treatment as described above.

In certain embodiments, the screening methods are performed using cells contained in a plurality of wells of a multi-well assay plate. Such assay plates are commercially available, for example, from Stratagene Corp. (La Jolla, Calif.) and Corning Inc. (Acton, Mass.) and include, for example, 48-well, 96-well, 384-well and 1536-well plates.

Reproducibility of the results may be tested by performing the analysis more than once with the same concentration of the same candidate compound (for example, by incubating cells in more than one well of an assay plate). Additionally, since candidate compounds may be effective at varying concentrations depending on the nature of the compound and the nature of its mechanism(s) of action, varying concentrations of the candidate compound may be tested. Generally, candidate compound concentrations from 1 fM to about 10 mM are used for screening. Preferred screening concentrations are generally between about 10 pM and about 100 μM.

The screening methods of the invention will provide "hits" or "leads," i.e., compounds that possess a desired but not optimized biological activity. Lead optimization performed on these compounds to fulfill all physicochemical, pharmacokinetic, and toxicologic factors required for clinical usefulness may provide improved drug candidates. The present invention also encompasses these improved drug candidates and their use as therapeutics for modulating prostate cancer progression.

J. Kits/Panels

The invention also provides compositions and kits for diagnosing, prognosing, or monitoring a disease or disorder, recurrence of a disorder, or survival of a subject being treated for a disorder (e.g., an abnormal prostate state, BPH, an oncologic disorder, e.g., prostate cancer). These kits include one or more of the following: a detectable antibody that specifically binds to a marker of the invention, a detectable antibody that specifically binds to a marker of the invention, reagents for obtaining and/or preparing subject tissue samples for staining, and instructions for use.

The invention also encompasses kits for detecting the presence of a marker protein or nucleic acid in a biological sample. Such kits can be used to determine if a subject is suffering from or is at increased risk of developing an abnormal prostate state. For example, the kit can comprise a labeled compound or agent capable of detecting a marker protein or nucleic acid in a biological sample and means for determining the amount of the protein or mRNA in the sample (e.g., an antibody which binds the protein or a fragment thereof, or an oligonucleotide probe which binds to DNA or mRNA encoding the protein). Kits can also include instructions for use of the kit for practicing any of the methods provided herein or interpreting the results obtained using the kit based on the teachings provided herein. The kits can also include reagents for detection of a control protein in the sample not related to the abnormal prostate state, e.g., actin for tissue samples, albumin in blood or blood derived samples for normalization of the amount of the marker present in the sample. The kit can also include the purified marker for detection for use as a control or for quantitation of the assay performed with the kit.

Kits include a panel of reagents for use in a method to diagnose prostate cancer in a subject (or to identify a subject predisposed to developing prostate cancer, etc.), the panel comprising at least two detection reagents, wherein each detection reagent is specific for one prostate cancer-specific protein, wherein said prostate cancer-specific proteins are selected from the prostate cancer-specific protein sets provided herein.

For antibody-based kits, the kit can comprise, for example: (1) a first antibody (e.g., attached to a solid support) which binds to a first marker protein; and, optionally, (2) a second, different antibody which binds to either the first marker protein or the first antibody and is conjugated to a detectable label. In certain embodiments, the kit includes (1) a second antibody (e.g., attached to a solid support) which binds to a second marker protein; and, optionally, (2) a second, different antibody which binds to either the second marker protein or the second antibody and is conjugated to a detectable label. The first and second marker proteins are different. In an embodiment, the first and second markers are markers of the invention, e.g., filamin A, keratin 4, keratin 7, keratin 8, keratin 15, keratin 18, keratin 19, tubulin-beta 3, filamin B, LY9, and PSA. In certain embodiments, neither the first marker nor the second marker is PSA. In certain embodiments, the kit comprises a third antibody which binds to a third marker protein which is different from the first and second marker proteins, and a second different antibody that binds to either the third marker protein or the antibody that binds the third marker protein wherein the third marker protein is different from the first and second marker proteins.

For oligonucleotide-based kits, the kit can comprise, for example: (1) an oligonucleotide, e.g., a detectably labeled oligonucleotide, which hybridizes to a nucleic acid sequence encoding a marker protein or (2) a pair of primers useful for amplifying a marker nucleic acid molecule. In certain embodiments, the kit can further include, for example: (1) an oligonucleotide, e.g., a second detectably labeled oligonucleotide, which hybridizes to a nucleic acid sequence encoding a second marker protein or (2) a pair of primers useful for amplifying the second marker nucleic acid molecule. The first and second markers are different. In an embodiment, the first and second markers are markers of the invention, e.g., filamin A, keratin 4, keratin 7, keratin 8, keratin 15, keratin 18, keratin 19, tubulin-beta 3, filamin B, LY9, and PSA. In certain embodiments, neither the first marker nor the second marker is PSA. In certain embodiments, the kit can further include, for example: (1) an oligonucleotide, e.g., a third detectably labeled oligonucleotide, which hybridizes to a nucleic acid sequence encoding a third marker protein or (2) a pair of primers useful for amplifying the third marker nucleic acid molecule wherein the third marker is different from the first and second markers. In certain embodiments, the kit includes a third primer specific for each nucleic acid marker to allow for detection using quantitative PCR methods.

For chromatography methods, the kit can include markers, including labeled markers, to permit detection and identification of one or more markers of the invention, e.g., filamin A, keratin 4, keratin 7, keratin 8, keratin 15, keratin 18, keratin 19, tubulin-beta 3, filamin B, LY9, and optionally PSA, by chromatography. In certain embodiments, kits for chromatography methods include compounds for derivatization of one or more markers of the invention. In certain embodiments, kits for chromatography methods include columns for resolving the markers of the method.

Reagents specific for detection of a marker of the invention, e.g., filamin A, keratin 4, keratin 7, keratin 8, keratin 15, keratin 18, keratin 19, tubulin-beta 3, filamin B, LY9, and PSA, allow for detection and quantitation of the marker in a complex mixture, e.g., serum, tissue sample. In certain embodiments, the reagents are species specific. In certain embodiments, the reagents are not species specific. In certain embodiments, the reagents are isoform specific. In certain embodiments, the reagents are not isoform specific. In certain embodiments, the reagents detect total keratin 8, keratin 18, filamin B, PSA, or LY9.

In certain embodiments, the kits for the diagnosis, monitoring, or characterization of prostate cancer comprise at least one reagent specific for the detection of the level of expression of at least one marker selected from the group consisting of keratin 4, keratin 7, keratin 8, keratin 15, keratin 18, keratin 19, and tubulin-beta 3, filamin B, and LY9. In certain embodiments, the kits further comprise instructions for the diagnosis, monitoring, or characterization of prostate cancer based on the level of expression of the at least one marker selected from the group consisting of keratin 4, keratin 7, keratin 8, keratin 15, keratin 18, keratin 19, and tubulin-beta 3, filamin B, and LY9. In certain embodiments, the kits further comprise instructions to detect the level of PSA in a sample in which the at least one marker selected from the group consisting of keratin 4, keratin 7, keratin 8, keratin 15, keratin 18, keratin 19, and tubulin-beta 3, filamin B, and LY9 is detected. In certain embodiments, the kits further comprise at least one reagent for the specific detection of PSA.

The invention provides kits comprising at least one reagent specific for the detection of a level of expression of at least one marker selected from the group consisting of keratin 4, keratin 7, keratin 8, keratin 15, keratin 18, keratin 19, and tubulin-beta 3, filamin B, and LY9 and at least one reagent specific for the detection of a level of expression of PSA.

In certain embodiments, the kits can also comprise, e.g., a buffering agents, a preservative, a protein stabilizing agent, reaction buffers. The kit can further comprise components necessary for detecting the detectable label (e.g., an enzyme or a substrate). The kit can also contain a control sample or a series of control samples which can be assayed and compared to the test sample. The controls can be control serum samples or control samples of purified proteins or nucleic acids, as appropriate, with known levels of target markers. Each component of the kit can be enclosed within an individual container and all of the various containers can be within a single package, along with instructions for interpreting the results of the assays performed using the kit.

The kits of the invention may optionally comprise additional components useful for performing the methods of the invention.

The invention further provides panels of reagents for detection of one or more prostate-related marker in a subject sample and at least one control reagent. In certain embodiments, the control reagent is to detect the marker for detection in the biological sample wherein the panel is provided with a control sample containing the marker for use as a positive control and optionally to quantitate the amount of marker present in the biological sample. In certain embodiments, the panel includes a detection reagent for a maker not related to an abnormal prostate state that is known to be present or absent in the biological sample to provide a positive or negative control, respectively. The panel can be provided with reagents for detection of a control protein in the sample not related to the abnormal prostate state, e.g., actin for tissue samples, albumin in blood or blood derived samples for normalization of the amount of the marker present in the sample. The panel can be provided with a purified marker for detection for use as a control or for quantitation of the assay performed with the panel.

In a preferred embodiment, the panel includes reagents for detection of two or more markers of the invention (e.g., 2, 3, 4, 5, 6, 7, 8, 9), preferably in conjunction with a control reagent. In the panel, each marker is detected by a reagent specific for that marker. In certain embodiments, the panel further includes a reagent for the detection of PSA. In certain embodiments, the panel includes replicate wells, spots, or portions to allow for analysis of various dilutions (e.g., serial dilutions) of biological samples and control samples. In a preferred embodiment, the panel allows for quantitative detection of one or more markers of the invention.

In certain embodiments, the panel is a protein chip for detection of one or more markers. In certain embodiments, the panel is an ELISA plate for detection of one or more markers. In certain embodiments, the panel is a plate for quantitative PCR for detection of one or more markers.

In certain embodiments, the panel of detection reagents is provided on a single device including a detection reagent for one or more markers of the invention and at least one control sample. In certain embodiments, the panel of detection reagents is provided on a single device including a detection reagent for two or more markers of the invention and at least one control sample. In certain embodiments, multiple panels for the detection of different markers of the invention are provided with at least one uniform control sample to facilitate comparison of results between panels.

This invention is further illustrated by the following examples which should not be construed as limiting. The contents of all references and published patents and patent applications cited throughout the application are hereby incorporated by reference.

EXAMPLES

This invention is further illustrated by the following examples which should not be construed as limiting. The contents of all references, GenBank Accession and Gene numbers, and published patents and patent applications cited throughout the application are hereby incorporated by reference. Those skilled in the art will recognize that the invention may be practiced with variations on the disclosed structures, materials, compositions and methods, and such variations are regarded as within the ambit of the invention.

Example 1: Identification of Keratins and Tubulin as Prostate Cancer Markers Extracellular Keratins are known to influence the cell proliferation and metastasis of epithelial derived prostate cancers. Androgen refractory prostate cancers exhibit differential expression keratin 8 (K8) when compared to normal tissue. Modulation and degradation of keratins is in turn mediated by mitochondrial generation of Reactive Oxygen Species (ROS). Despite these advances a systematic approach to understanding of keratins and other EC proteins in prostate cancer metastasis and proliferation is lacking.

Figure 2A:
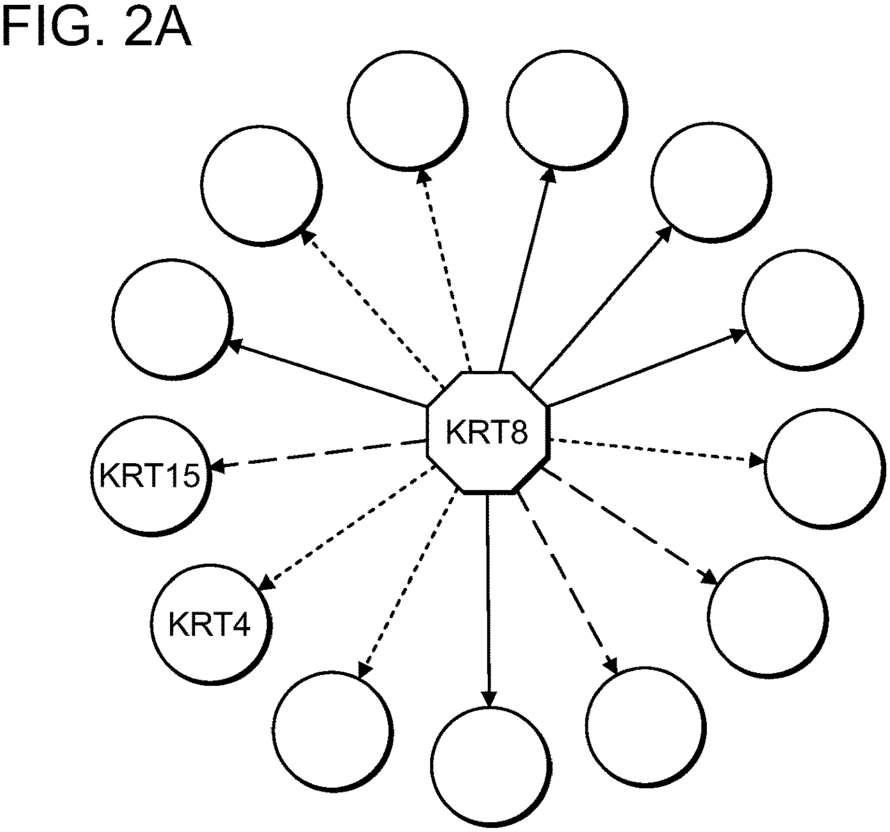
FIG. 2A, FIG. 2B, and FIG. 2C: Causal associations of keratins, including (FIG. 2A) KRT4, KRT8, KRT15 and (FIG. 2B) KRT18 and (FIG. 2C) KRT19 in human prostate cancer cells as inferred by the Interrogative Platform Technology.
Figure 2B:
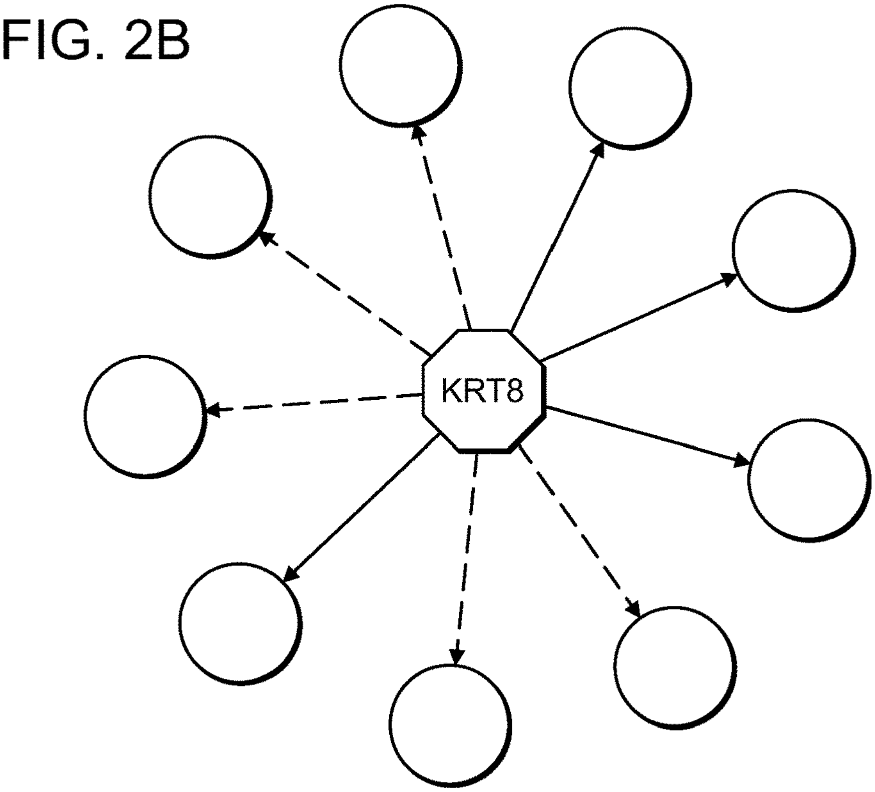
Figure 2C:
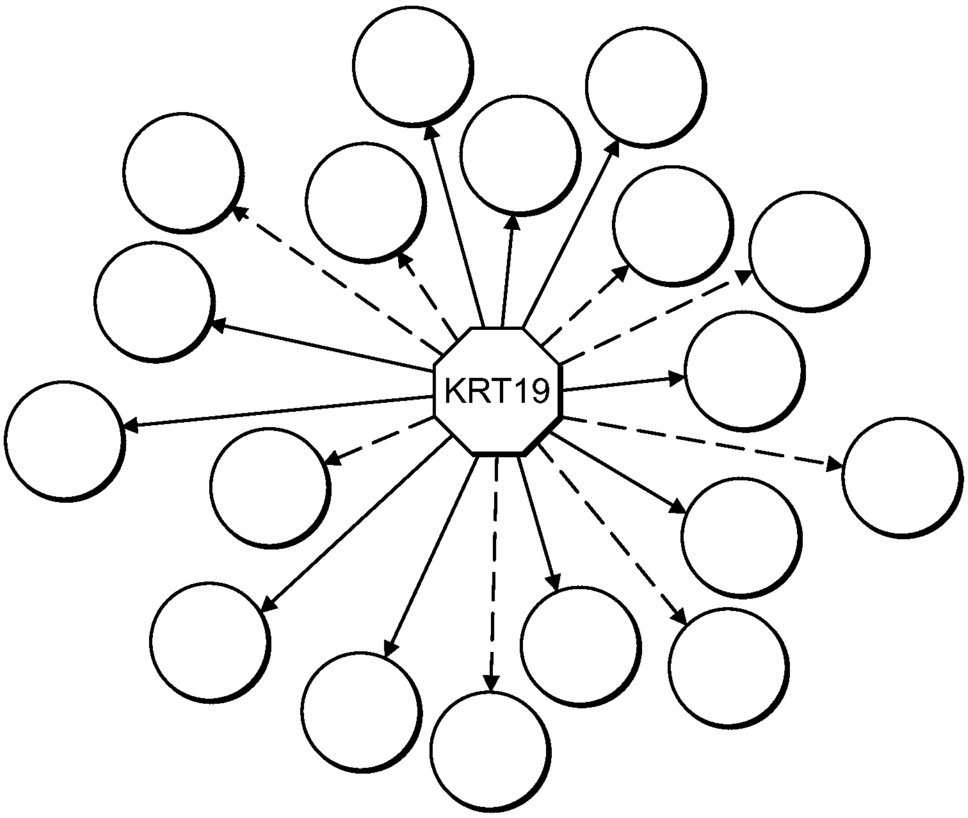
Figure 3A:
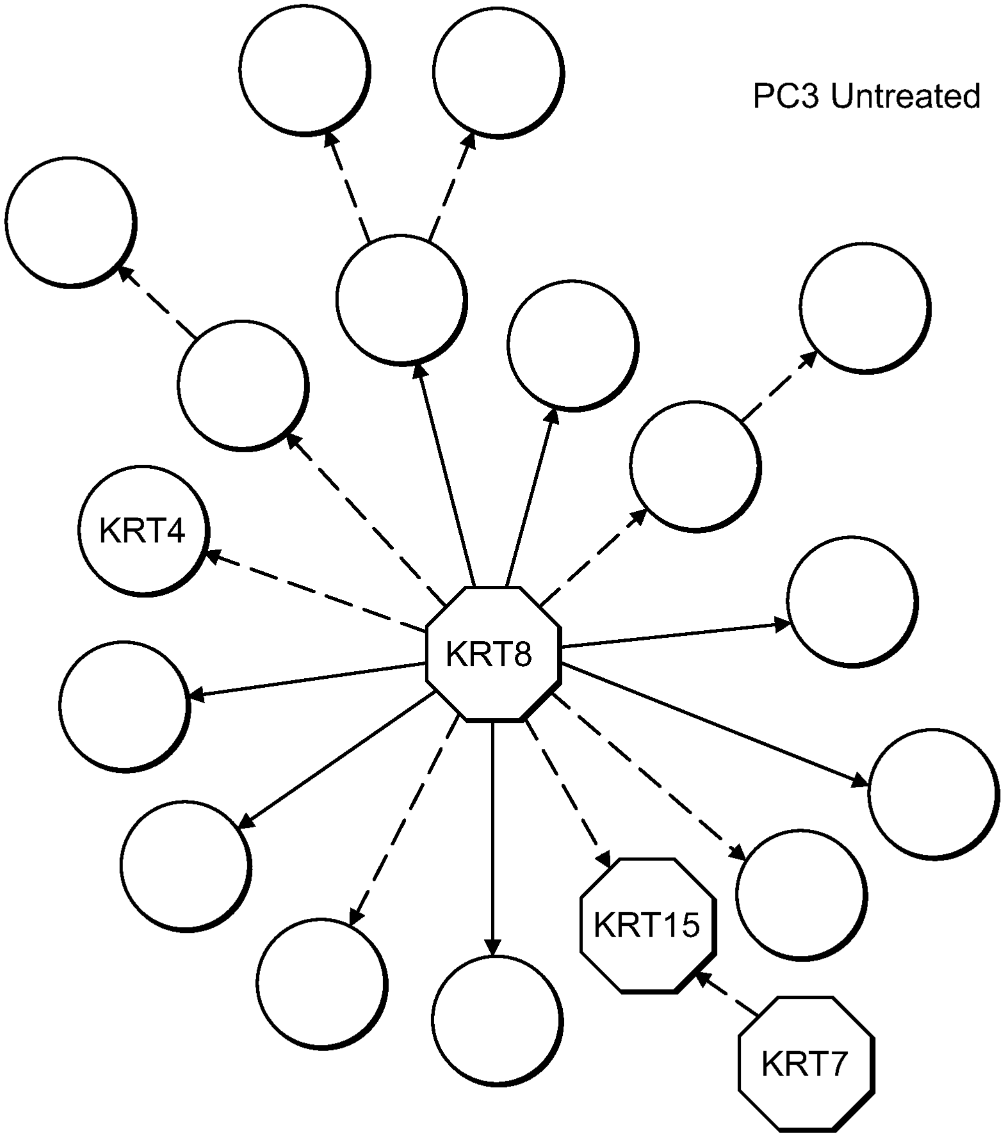
FIG. 3A, FIG. 3B, FIG. 3C, and FIG. 3D: Mechanistic insight into regulation of keratins by mitochondrial function inferred by the Interrogative Platform Technology.
Figure 3B:
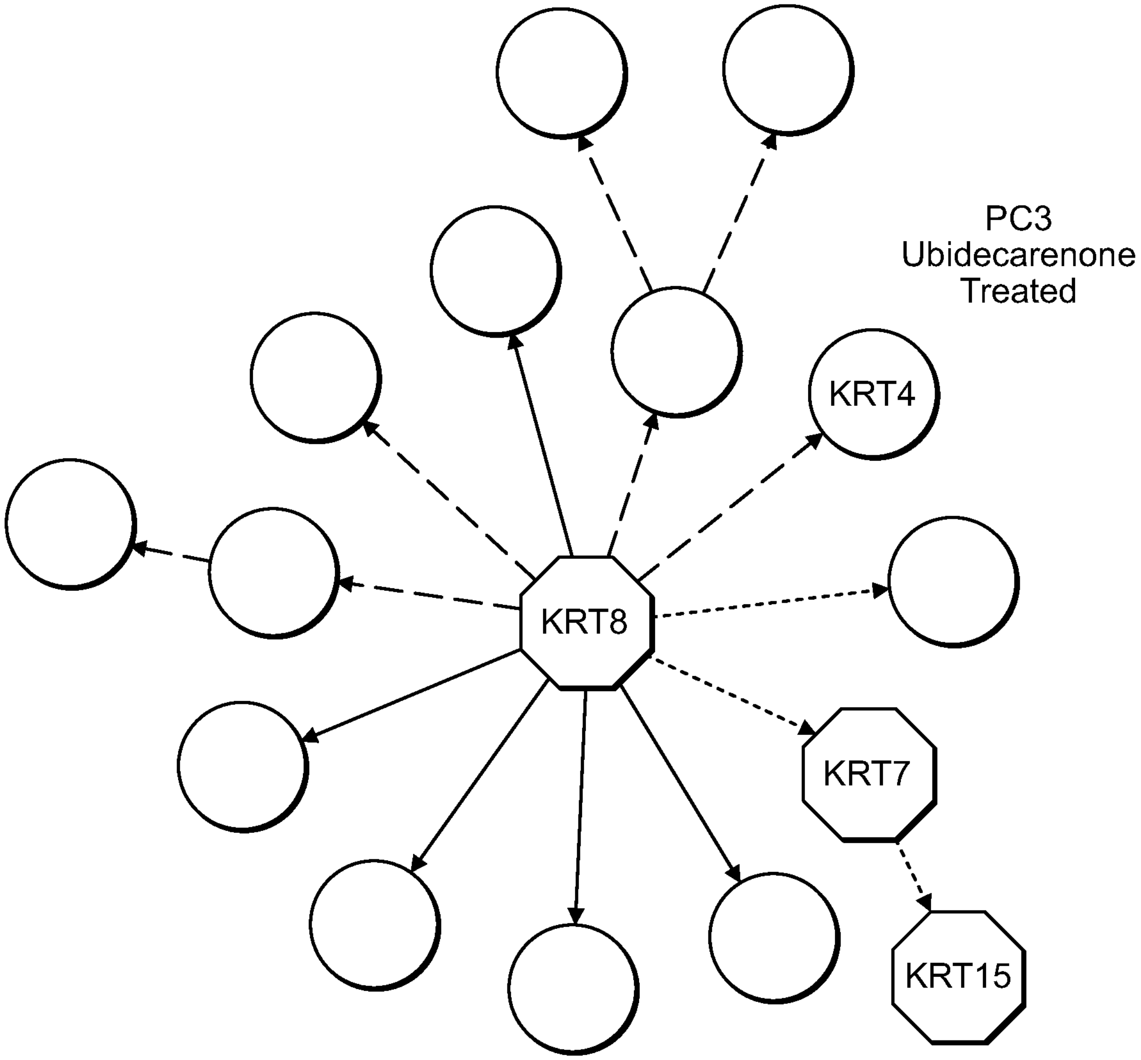
Figure 3C:
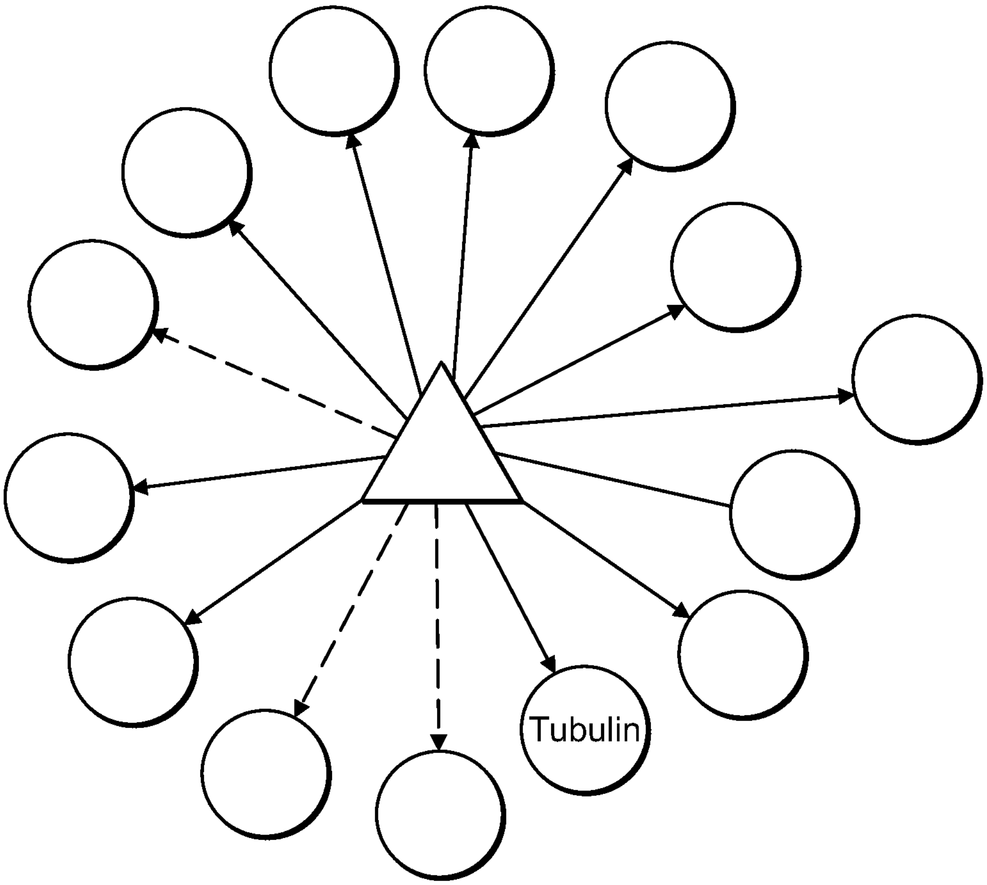
Figure 3D:
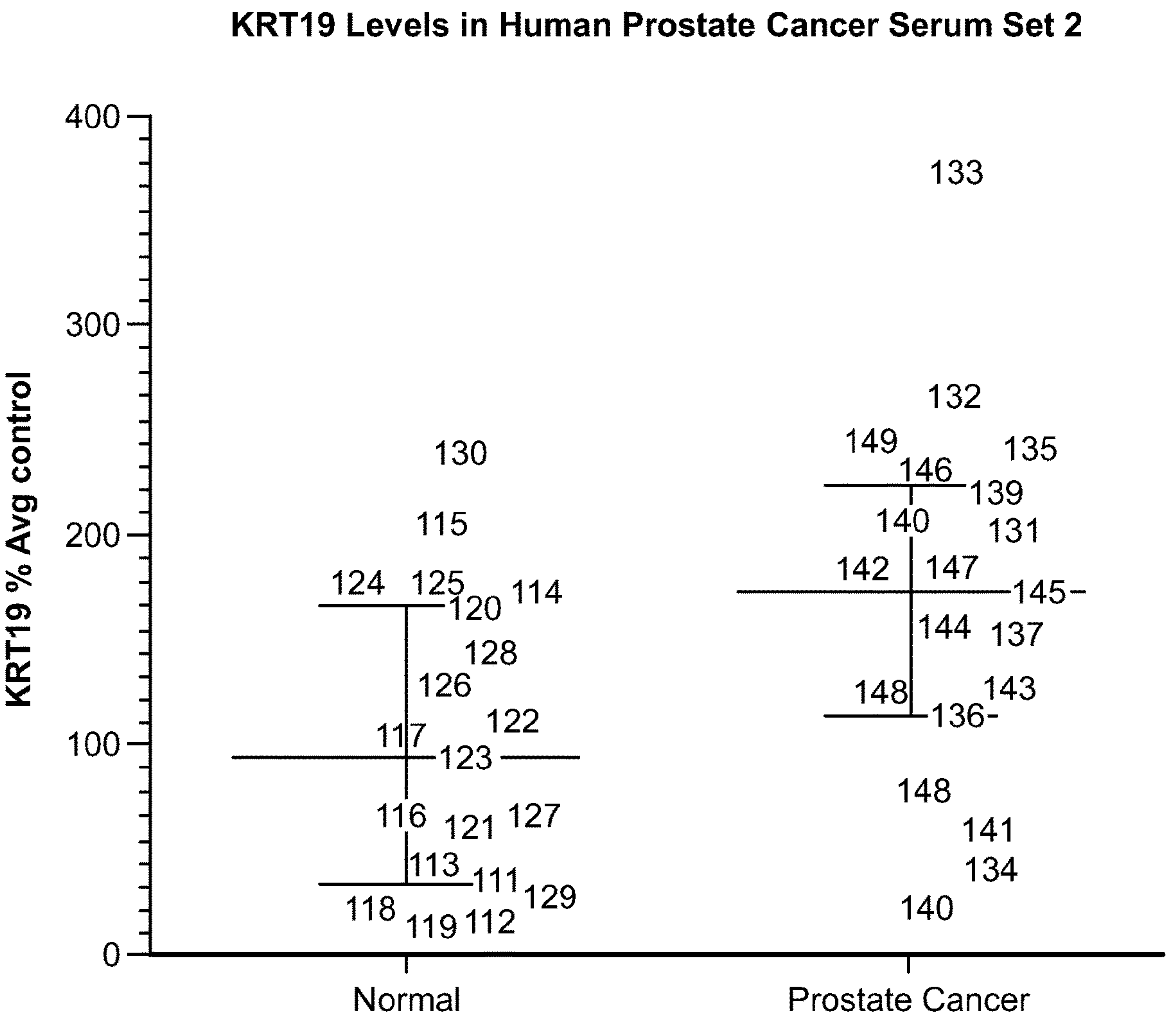

An interrogative systems biology based discovery platform (i.e., Interrogative Platform Technology or a.k.a. Interrogative Biology™) disclosed in WO2012119129 (incorporated herein by reference), and shown schematically in FIG. 1, provides new mechanistic insights into understanding mitochondrial role in behavior of prostate cancer cells. The discovery platform involves discovery across a hierarchy of systems including in vitro human cell based models and human serum samples from prostate cancer patients and downstream data integration and mathematical modeling employing an Artificial Intelligence (AI) based informatic module. For cellular models, androgen sensitive LnCAP cell line and metastatic, androgen refractory PC3 cell line were treated with ubidecarenone (coenzyme Q10) in order to engage the mitochondrial machinery. Proteomic signatures were captured using a 2D LC-MS orbitrap technology. Total protein signatures were input to an AI based informatics module to generate causal protein networks (FIG. 2). Wet lab assays that specifically measure mitochondrial ROS, ATP and caspase 3 activation confirmed changes in intracellular levels of these markers.

As shown in FIG. 3, several novel protein causal interactions that govern induction of mitochondrial machinery by ubidecarenone in PC3 cells were observed. Causal protein maps revealed association of keratins 8 and 15 in PC3 models and not LnCAP. The keratin 8/15 association was lost upon treatment with ubidecarenone, and a direct association of keratins 7 and 15 was established (FIG. 3).

These results suggest that a change in the interaction among keratins 7, 8, and 15 is particularly useful in demonstrating a response to treatment or a change in prostate cancer status in a subject. Further, keratins 8 and 15 were differentially associated in the androgen refractory, metastatic PC3 cell line and the androgen sensitive LnCAP cell line. This indicates that keratins 8 and 15 could be useful do differentiate between prostate cancer states, e.g., between androgen sensitive and metastatic, androgen refractory prostate cancer.

An increase in the expression of keratin 19 in relation to prostate cancer was confirmed using a panel of serum samples from subjects suffering from prostate cancer as compared to an appropriate matched control population. (See FIG. 2C and FIG. 3D).

Thus novel mechanistic insight into prostate cancer proliferation and mitochondrial role in modulating metastasis was gained with a novel chemical systems biology approach.

The results provided herein demonstrate that modulation of keratin and potential causal association in androgen refractory prostate cancer was inferred by the Platform technology. This provides a potential mechanisms of keratin regulation in response to modulation of mitochondrial function was deciphered by the Platform technology. Thus, novel drivers of cancer pathophysiology were validated in patient serum samples.

Example 2: Identification of Filamin B as a Prostate Cancer Marker

An interrogative systems biology based discovery platform (i.e., Interrogative Platform Technology or a.k.a. Interrogative Biology™) was used to obtain mechanistic insights into understanding the mitochondrial role in behavior of prostate cancer cells. The Platform technology, which is described in detail in WO2012119129, involves discovery across a hierarchy of systems including in vitro human cell based models and human serum samples from prostate cancer patients and downstream data integration and mathematical modeling employing an Artificial Intelligence (AI) based informatics module.

The results provided in this Example demonstrate the modulation of filamin B and LY9, and the potential causal association in androgen refractory prostate cancer that was inferred using the Platform technology. The Example provides potential mechanisms of filamin B and LY9 regulation in response to modulation of mitochondrial function that was deciphered by the Platform technology, and provides validation of the markers in patient serum samples.

Using the Platform methods, human prostate cancer cells PC3 (androgen insensitive, metastatic) and LnCap (androgen sensitive) were modeled in cancer microenvironments including hypoxia, reduced environments, and hyperglycemia and in presence of coenzyme Q10. Normal cells (human dermal fibroblasts (HDFa) and SV40 transformed human liver cells (THLE2)) were modeled under similar conditions mentioned above in Example 2. Proteomics of cellular proteins and proteins secreted in the supernatant were carried out by LCMS. Data were input into the Bayesian Network Inference (BNI) algorithms REFS™.

Figure 4:
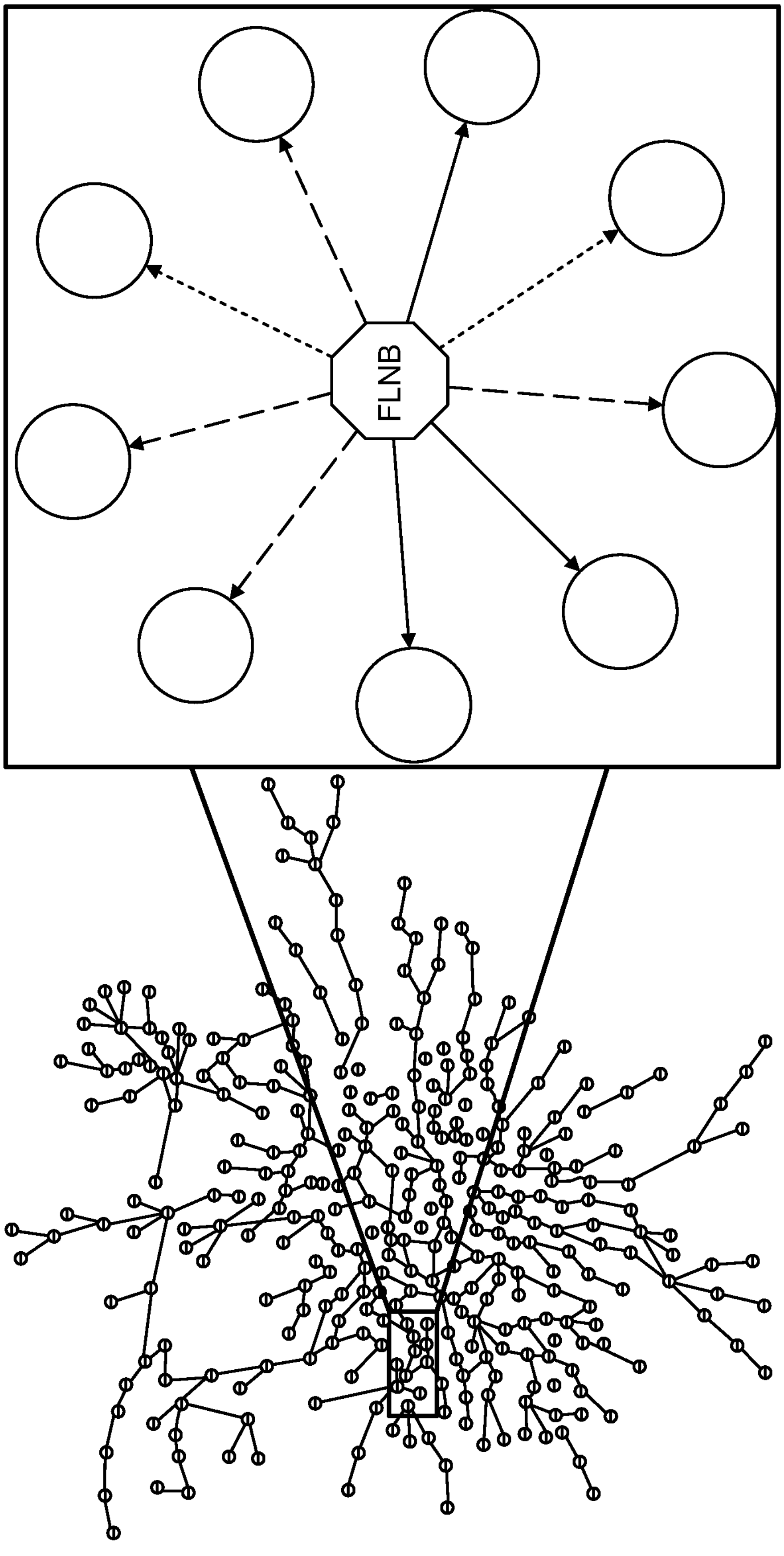
FIG. 4: Inference of filamin B (FLNB) as a hub of activity in prostate cancer and as a biomarker using the Interrogative Platform Technology provided in WO2012119129.
Figure 5:
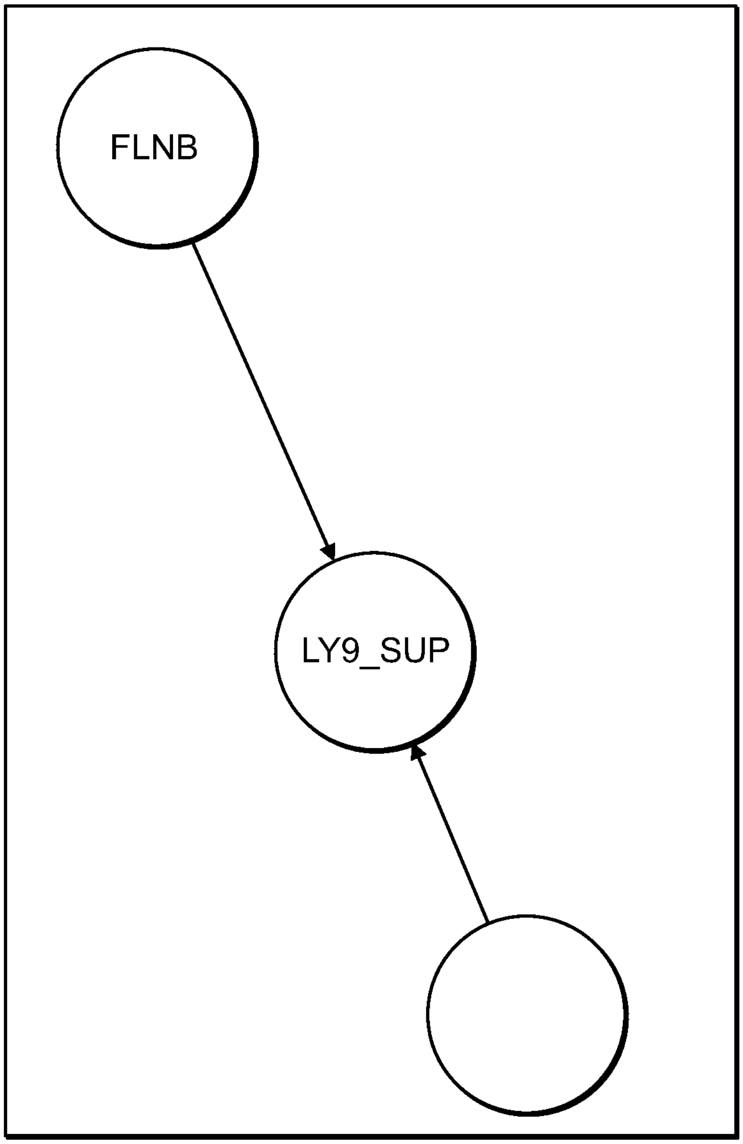
FIG. 5: Portion of an inference map showing filamin B is connected directly to LY9, which is, in turn, connected to at least one other marker.

Causal associations between proteins were derived by the BNI. Differential network analysis was employed to tease out the hubs of activity in prostate cancer when compared to normal cells in normal microenviroments. Filamin B was identified as differential hub of activity in PC3 and not in LnCap and normal cells. That is, Filamin B was found to differ between androgen sensitive LnCAP cell line and metastatic, androgen refractory PC3 cell line. This indicates that Filamin B could be useful to differentiate between prostate cancer states, e.g., between androgen sensitive and metastatic, androgen refractory prostate cancer. The interaction matrix placing filamin B at the center of an interaction hub is shown in FIG. 4. The interaction of LY9 with filamin B is shown in FIG. 5.

Example 3: Validation of Filamin B as a Prostate Cancer Marker in Human Samples

Having identified filamin B as a prostate cancer marker using the platform technology, human serum samples from normal subjects and subjects with prostate cancer were used to confirm filamin B as a prostate cancer marker.

Specifically, human serum samples were procured from a commercial vendor that sources human serum. Twenty samples were from normal donors and 20 samples were from patients diagnosed with prostate cancer. Prostate cancer samples were from patients with different prognosis and aggressiveness of cancers reported. Clinical characteristics of the subjects are provided in the table.

| | Prostate Cancer | Control Group |
|---|---|---|
| Median Age | 61 (47-86) | 58 (45-72) |
| Ethnicity | | |
| Caucasian | 75% | 85% |
| African American | 15% | 10% |
| Hispanic | 10% | 5% |
| Tumor Stage | | |
| Stage I | 20% | |
| Stage II | 35% | |
| Stage III | 5% | |
| Stage IV | 40% | |

Figure 6A:
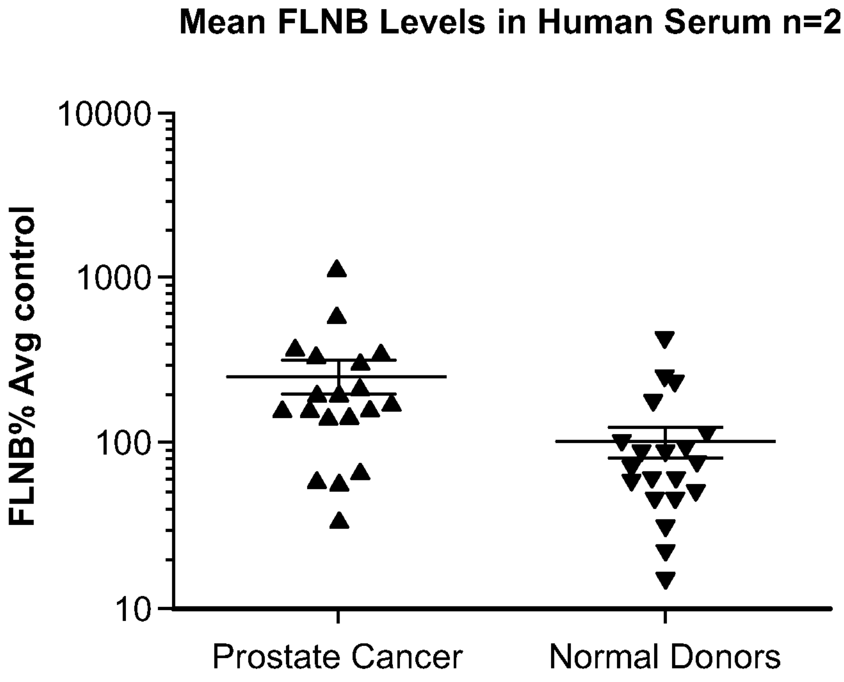
FIG. 6A and FIG. 6B: Validation of filamin B levels in human serum samples. Levels of filamin B (FIG. 6A) and PSA (FIG. 6B) were elevated in prostate cancer samples when compared to normal serum. Data represents percent average change, with normal donors set to 100% on a log scale.
Figure 6B:
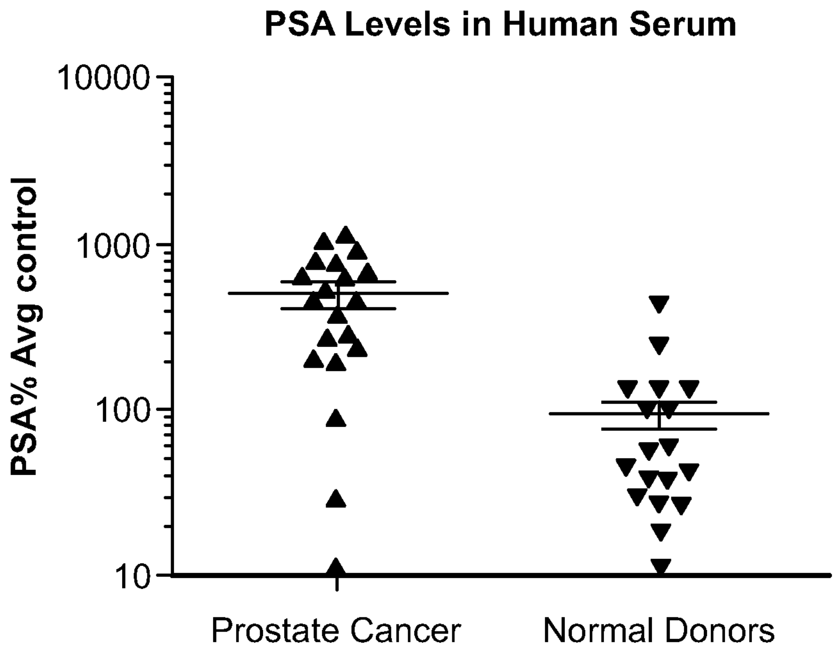

Commercially available ELISA tests for filamin B and PSA were procured from commercial source. The assays were performed using the manufacturer's instructions. The results from the assay are shown in FIG. 6. The results show the differential levels of FlnB and PSA in patients with a diagnosis for prostate cancer as compared to control subjects without prostate cancer.

As shown, both filamin B and PSA levels were elevated in serum samples from patients diagnosed with prostate cancer. The correlation between PSA and FlnB expression in serum samples is 0.20075, indicating a relatively low correlation between the variables. This demonstrates that filamin B and PSA are useful for the detection of prostate cancer in different subjects. These results demonstrate that filamin B is useful for the diagnosis of prostate cancer, and that filamin B is useful for improving the detection of prostate cancer by PSA.

Example 4: Validation of LY9 as a Prostate Cancer Marker in Human Samples

Figure 7:
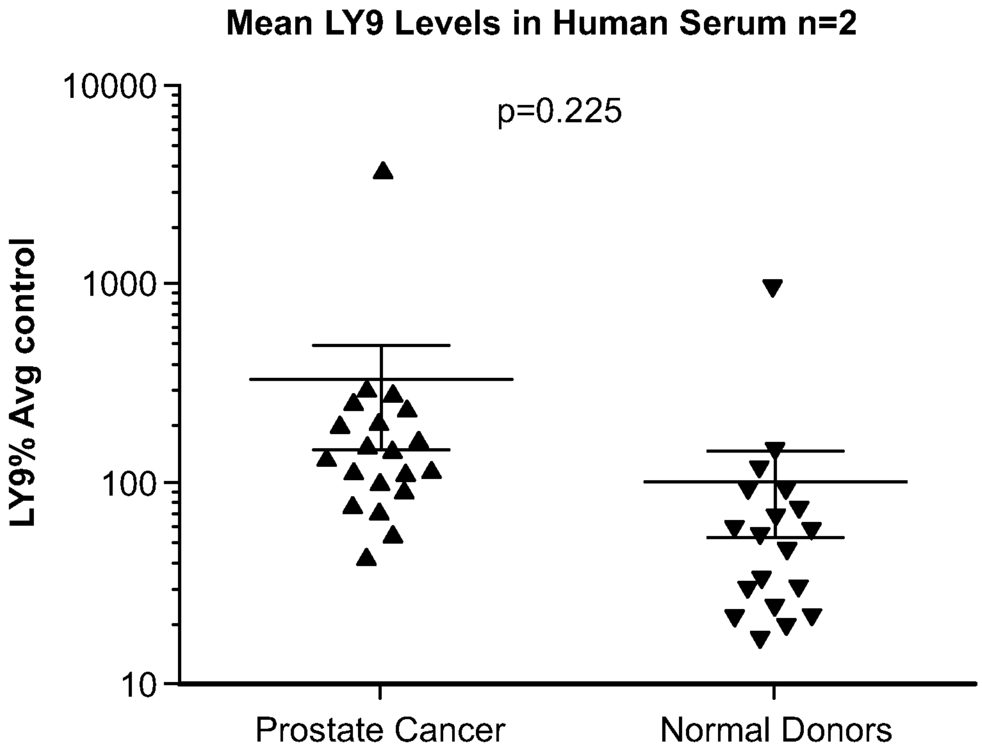
FIG. 7: Validation of LY9 levels in human serum samples. Levels of LY9 were elevated in prostate cancer samples when compared to normal serum. Data represents percent average change, with normal donors set to 100% on a log scale.

The same human serum samples used in Example 3 were further tested to detect the presence of LY9. A commercially available ELISA test for LY9 was procured from commercial source. The assay was performed using the manufactures' instructions. The results from the assay are shown in FIG. 7.

Figure 8A:
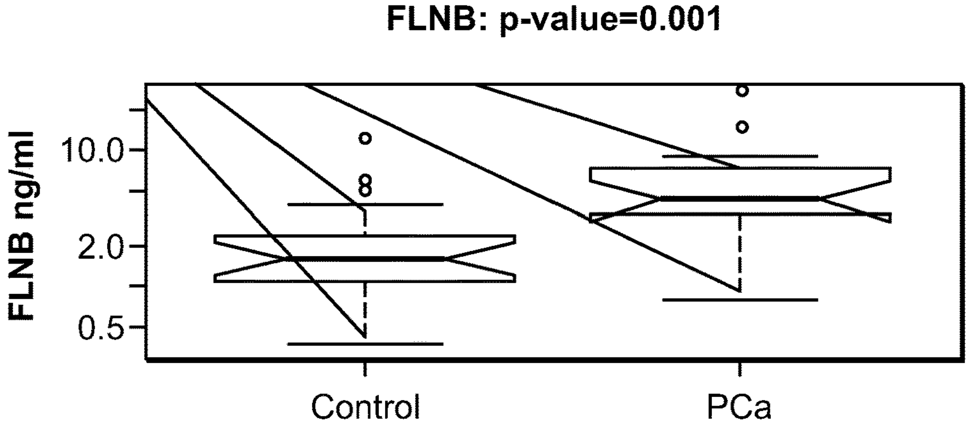
FIG. 8A, FIG. 8B, and FIG. 8C: Validation of filamin B (FIG. 8A), LY9 (FIG. 8B), and PSA (FIG. 8C) levels in human serum samples. Data are shown as ng/ml of the marker in serum.
Figure 8B:
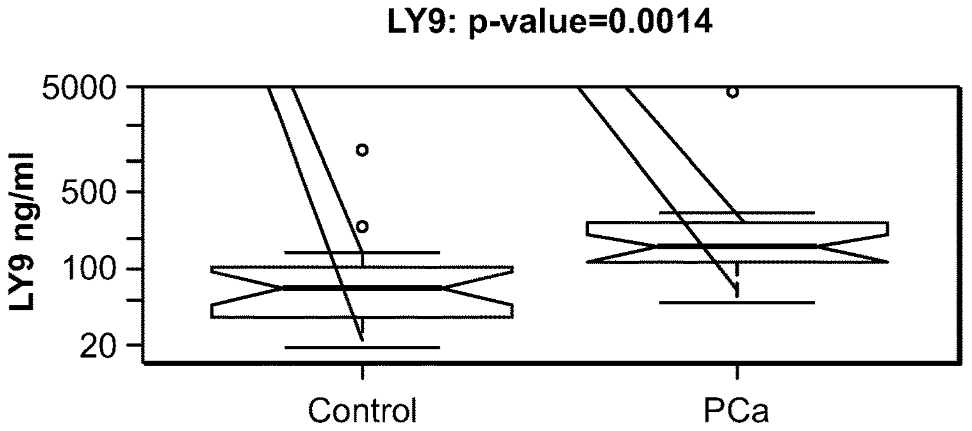
Figure 8C:
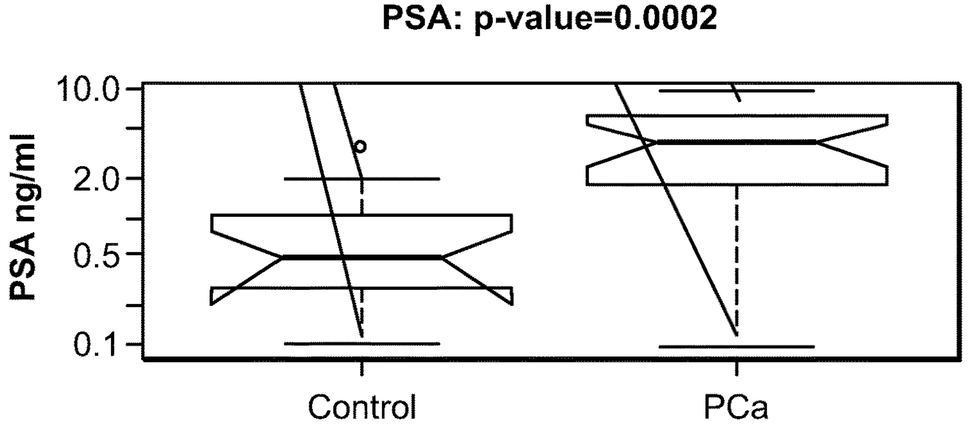

The results show the differential levels of LY9 in patients with a diagnosis for prostate cancer as compared to control subjects without prostate cancer. As shown, samples from subjects with prostate cancer were found to have higher levels of LY9 as compared to normal subjects. Results from assays of expression levels of both filamin B and LY9 in human serum with results expressed as ng/ml of protein are shown in FIG. 8.

Figures 9A, 9B:
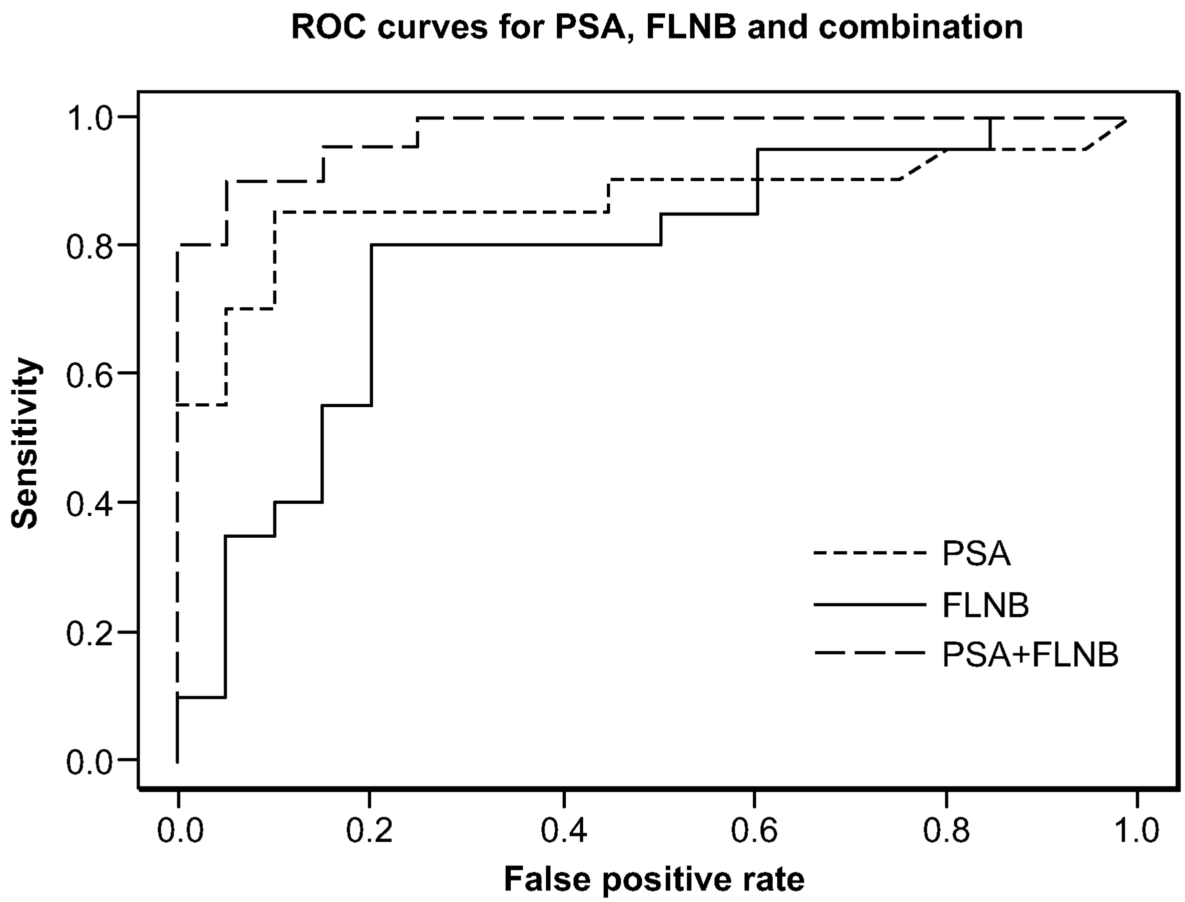
FIG. 9A and FIG. 9B.

Example 5: Analysis of Filamin B Levels Improves the Detection of Prostate Cancer as Compared to PSA Alone Having demonstrated that the level of filamin B is increased in the serum of subjects with prostate cancer, the results were analyzed in conjunction with the study of PSA levels in the same samples to determine if the predictive value of filamin B and PSA together was better than either of the markers alone. Receiver operating characteristic (ROC) curve analysis of sensitivity and false positive rate (FPR) of PSA, filamin B, and the combination of PSA and filamin B was generated. The curves and the area under the curve (AUC) values are shown in FIGS. 9A and B. The goal of this analysis was to gauge the predictive power of the test independent of a specific cut-off. When using an ROC analysis, a test that provides perfect discrimination or accuracy between normal and disease states would have AUC=1, whereas a very poor test that provides no better discrimination than random chance would have AUC=0.5

As demonstrated by the analysis, filamin B alone performs very well and most importantly somewhat orthogonal to PSA. PSA is reported to have a very high false positive rate, e.g., about 75% (as reported in, Gilligan, "The new data on prostate cancer screening: What should we do now?," Cleveland Clin. J. Med. 76: 446-448, 2009, incorporated herein by reference). That is, it has a high sensitivity and low specificity. In the specific study presented, the AUC for FLNB is lower than that for PSA. However, the correlation level of 0.20075 determined in Example 3, indicates a relatively low correlation between the variables. That is, subjects identified as having an elevated filamin B level did not necessarily have a high PSA level, and the reverse was also true, suggesting that the markers in combination can provide a more predictive test than either marker alone.

This was confirmed in the ROC analysis. As shown, the combination of PSA and filamin B was found to have a higher AUC indicating better discrimination of the test than PSA alone, and to be more predictive than either of the markers alone. The combination of PSA and filamin B is a very good predictor of prostate cancer and provides a drastic increase over the PSA test specificity, which is the primary problem with the test.

Figure 10A:
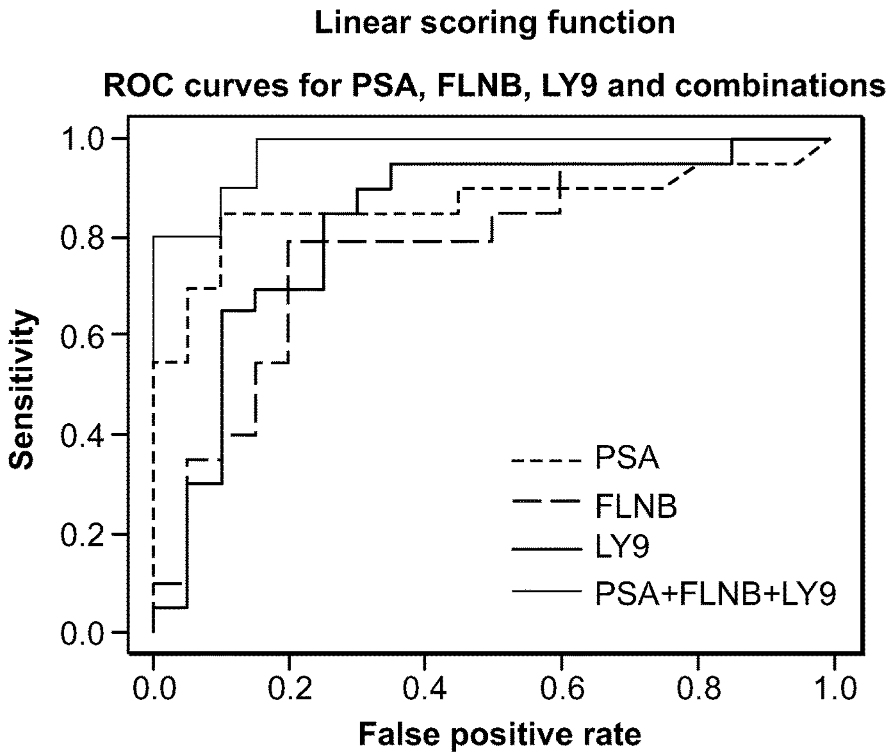
FIG. 10A and FIG. 10B.
Figure 10B:
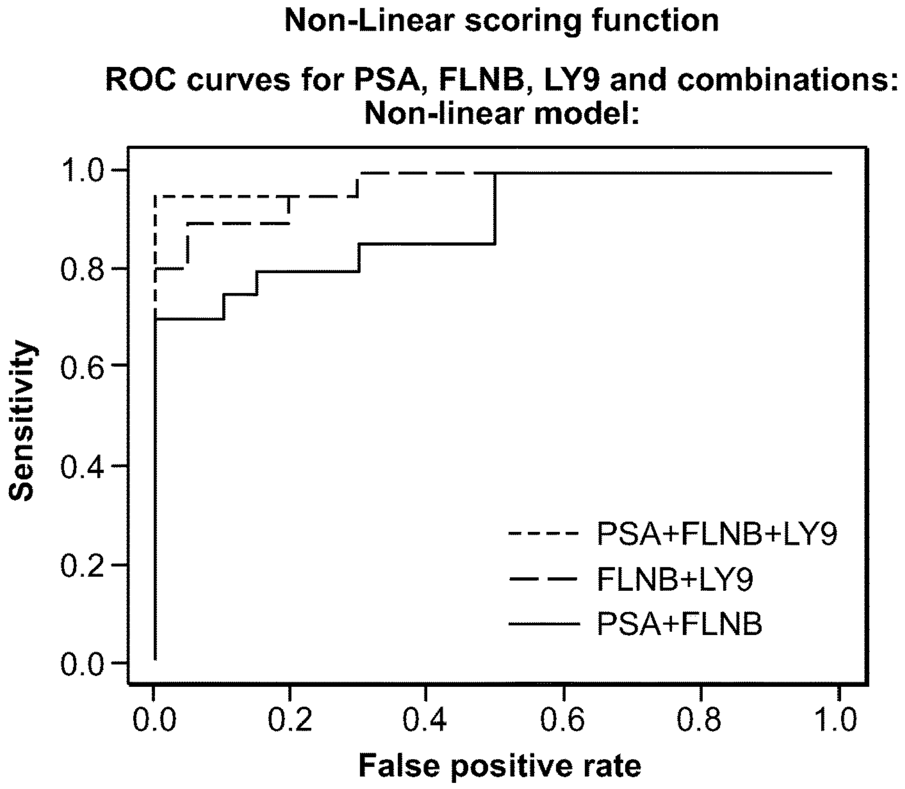

Example 6: Analysis of Filamin B, LY9, and PSA Levels Together Improves the Detection of Prostate Cancer as Compared to any Marker Alone Having demonstrated that each of filamin B, LY9, and PSA are all elevated in serum samples from subjects with prostate cancer, the ROC curve analysis was performed comparing each of the three markers individually to the combination of all three markers using a linear scoring function, and comparing the combination of filamin B and LY9, and the combination of filamin B and PSA, against the combination of all three markers using a non-linear scoring function to determine which combinations of the markers were more effective than each single marker for the detection of prostate cancer in a subject. As shown, the combination of all three markers was more predictive than any of the markers alone (FIG. 10A). The combination of filamin B with PSA, either with or without LY9, was more predictive than the combination of filamin B with LY9 (FIG. 10B). Additional samples can be analyzed to further refine the results. The AUC results are summarized in the table.

| Marker | AUC |
|---|---|
| LY9 | 0.85 |
| FLNB | 0.78 |
| PSA | 0.87 |
| LY9 + FLNB + PSA | 0.98 |

Example 7: Stratification of Subjects with Prostate Cancer Using Keratin 4, Keratin 7, Keratin 8, Keratin 15, Keratin 18, Keratin 19, Tubulin-Beta 3

As demonstrated in Examples 3 and 4 respectively, filamin B levels and LY9 levels can be used to distinguish subjects who are or are not suffering from prostate cancer. Further, as demonstrated in Examples 5 and 6, the analysis of both filamin B and PSA, optionally further in combination with LY9, is more sensitive than an analysis based on either marker alone. The markers keratin 4, keratin 7, keratin 8, keratin 15, keratin 18, keratin 19, and tubulin-beta 3 are similarly analyzed, as described in Examples 3-6, in human samples.

A series of subject samples are obtained from an appropriate source, e.g., a commercial source, wherein the samples were obtained from subjects with different stages of prostate cancer, e.g., aggressive prostate cancer, androgen sensitive, androgen insensitive, metastatic; or from subjects not suffering from prostate cancer, e.g., subjects with normal prostate or subjects with BPH. The samples are analyzed for the expression level of at least one of keratin 4, keratin 7, keratin 8, keratin 15, keratin 18, keratin 19, tubulin-beta 3, preferably at least one of keratin 7, keratin 15, and keratin 19; and optionally further at least one of filamin B, LY9, and PSA. The level of the expression of the makers, alone and in various combinations, correlate with the presence or absence of disease, and with the severity of prostate cancer. For example, an increase in the expression level of one or more of keratin 19, filamin B, LY9, and PSA, as compared to a normal sample from a subject not suffering from prostate cancer, is indicative of prostate cancer in the subject. Expression levels of keratins 7, 8, and 15 may also be particularly useful in the stratification of subjects with prostate cancer.

Example 8: Monitoring of Prostate Cancer Treatment Using Keratin 4, Keratin 7, Keratin 8, Keratin 15, Keratin 18, Keratin 19, Tubulin-Beta 3

At the time of diagnosis with prostate cancer, subjects are invited to participate in a trial. A subject sample, e.g., blood, is obtained. Periodically, throughout the monitoring, watchful waiting, or active treatment of the subject, e.g., chemotherapy, radiation therapy, surgery, hormone therapy, a new subject sample is obtained. At the end of the study, all subject samples are tested for the expression level of at least one of keratin 4, keratin 7, keratin 8, keratin 15, keratin 18, keratin 19, tubulin-beta 3, preferably at least one of keratin 7, keratin 15, and keratin 19; and optionally further at least one of filamin B, LY9, and PSA. The subject samples are matched to the medical records of the subjects to correlate marker levels with prostate cancer status at the time of diagnosis, rate of progression of disease, response of subjects to one or more interventions, and transitions between androgen dependent and independent status. An increase in the expression level of one or more of keratin 19, filamin B, LY9, and PSA, as compared to a normal sample from a subject not suffering from prostate cancer, is indicative of prostate cancer in the subject. Expression levels of keratins 7, 8, and 15 may also be particularly useful in the diagnosis and monitoring of subjects with prostate cancer.

Example 9: Detection and Monitoring of Prostate Cancer Using Keratin 4, Keratin 7, Keratin 8, Keratin 15, Keratin 18, Keratin 19, Tubulin-Beta 3

Despite its limitations, including a positive predictive value of only 25-40%, PSA remains the only generally accepted biomarker for prostate cancer. Moreover, as prostate cancer is most commonly a slow growing tumor in men of advanced age, treatment of the cancer may do more harm to the subject than the tumor itself would. Therefore, the tests together for the expression level of at least one of keratin 4, keratin 7, keratin 8, keratin 15, keratin 18, keratin 19, tubulin-beta 3, preferably at least one of keratin 7, keratin 15, and keratin 19; and optionally further at least one of filamin B, LY9, and PSA are used for the detection an monitoring of prostate cancer. The level of the expression of the makers, alone and in various combinations are used in detection, including in routine, preventative, screening methods in men having an increased risk of prostate cancer (e.g., increased age, family history, race, etc.) or in monitoring of subjects diagnosed with prostate cancer prior to or during treatment may be useful to better identify subjects in need of further, potentially more invasive, diagnostic tests, e.g., prostate exam or biopsy, digital rectal exam; or more aggressive treatment. Detection of levels of expression of the markers, or various combinations thereof, may also be indicative of a good or poor response to a specific treatment regimen prior to changes in other signs or symptoms, e.g., loss of tumor response to hormone therapy.

In routine screening methods for prostate cancer, a serum sample from a subject is tested for the level of expression of at least one of keratin 4, keratin 7, keratin 8, keratin 15, keratin 18, keratin 19, tubulin-beta 3, preferably at least one of keratin 7, keratin 15, and keratin 19; and optionally further at least one of filamin B, LY9, and PSA. The levels are compared to one or more appropriate controls, e.g., other normal subjects, subjects with prostate cancer. Detection of an abnormal level of one or more of at least one of keratin 4, keratin 7, keratin 8, keratin 15, keratin 18, keratin 19, tubulin-beta 3, preferably at least one of keratin 7, keratin 8, keratin 15, and keratin 19; indicates that the subject should be considered for further tests for the presence of prostate cancer. Changes in the level of at least one of keratin 4, keratin 7, keratin 8, keratin 15, keratin 18, keratin 19, tubulin-beta 3, preferably at least one of keratin 7, keratin 8, keratin 15, and keratin 19, in the subject may be more indicative of a change in prostate cancer status than comparison to a population control.

In determining a therapeutic regimen for a subject with prostate cancer not yet being actively treated for prostate cancer (i.e., watchful waiting) can be tested at regular intervals to determine if there is a change in the level of expression of at least one of keratin 4, keratin 7, keratin 8, keratin 15, keratin 18, keratin 19, tubulin-beta 3, preferably at least one of keratin 7, keratin 15, and keratin 19; and optionally further at least one of filamin B, LY9, and PSA. An modulation in the level of at least one of keratin 4, keratin 7, keratin 8, keratin 15, keratin 18, keratin 19, tubulin-beta 3, preferably at least one of keratin 7, keratin 8, keratin 15, and keratin 19; and optionally further at least one of filamin B, LY9, and PSA indicates that the subject should be considered for further tests to monitor the prostate cancer and more active therapeutic interventions should be considered.

In a subject undergoing treatment for prostate cancer (e.g., hormone therapy, chemotherapy, radiation therapy, surgery) is tested prior to the initiation of the treatment and during and/or after the treatment to determine if the treatment results in a decrease in the level of expression of at least one of keratin 4, keratin 7, keratin 8, keratin 15, keratin 18, keratin 19, tubulin-beta 3, preferably at least one of keratin 7, keratin 15, and keratin 19; and optionally further at least one of filamin B, LY9, and PSA. A decrease in the level of keratin 19, filamin B, LY9, or PSA is indicative of response to treatment. Expression levels of keratins 7, 8, and 15 may also be particularly useful in the diagnosis and monitoring of subjects with prostate cancer.

Example 10: Stratification of Subjects with Prostate Cancer Using Filamin B, PSA, or LY9

As demonstrated in Examples 3 and 4 respectively, filamin B levels and LY9 levels can be used to distinguish subjects who are or are not suffering from prostate cancer. Further, as demonstrated in Examples 5 and 6, the analysis of both filamin B and PSA, optionally further in combination with LY9, is more sensitive than an analysis based on either marker alone.

A series of subject samples are obtained from an appropriate source, e.g., a commercial source, wherein the samples were obtained from subjects with different stages of prostate cancer, e.g., aggressive prostate cancer, androgen sensitive, androgen insensitive, metastatic; or from subjects not suffering from prostate cancer, e.g., subjects with normal prostate or subjects with BPH. The samples are analyzed for the expression level of filamin B and PSA, and optionally the level of LY9, and further with one or more of keratin 4, keratin 7, keratin 8, keratin 15, keratin 18, keratin 19, and tubulin-beta 3, especially keratin 19. The level of filamin B, LY9, and PSA, alone and in various combinations, optionally with other markers, e.g., keratin 4, keratin 7, keratin 8, keratin 15, keratin 18, keratin 19, and tubulin-beta 3, especially keratin 19, correlate with the presence or absence of disease, and with the severity of prostate cancer.

Example 11: Monitoring of Prostate Cancer Treatment Using Filamin B, PSA, or LY9

At the time of diagnosis with prostate cancer, subjects are invited to participate in a trial. A subject sample, e.g., blood, is obtained. Periodically, throughout the monitoring, watchful waiting, or active treatment of the subject, e.g., chemotherapy, radiation therapy, surgery, hormone therapy, a new subject sample is obtained. At the end of the study, all subject samples are tested for the level of filamin B, PSA, and optionally in further combination with one or more of LY9, keratin 4, keratin 7, keratin 8, keratin 15, keratin 18, keratin 19, and tubulin-beta 3. The subject samples are matched to the medical records of the subjects to correlate filamin B, PSA, LY9, keratin 4, keratin 7, keratin 8, keratin 15, keratin 18, keratin 19, or tubulin-beta 3 levels, as appropriate, with prostate cancer status at the time of diagnosis, rate of progression of disease, response of subjects to one or more interventions, and transitions between androgen dependent and independent status.

Example 12: Detection and Monitoring of Prostate Cancer Using Filamin B, PSA, or LY9

Despite its limitations, including a positive predictive value of only 25-40%, PSA remains the only generally accepted biomarker for prostate cancer. Moreover, as prostate cancer is most commonly a slow growing tumor in men of advanced age, treatment of the cancer may do more harm to the subject than the tumor itself would. As demonstrated herein, there is a low correlation between elevated levels of filamin B and PSA in subjects with prostate cancer. Further, elevated levels of LY9 have been demonstrated to be associated with prostate cancer. Therefore, the tests together, particularly filamin B and PSA, optionally in combination with one or more of LY9, keratin 4, keratin 7, keratin 8, keratin 15, keratin 18, keratin 19, and tubulin-beta 3, especially keratin 19, in detection, including in routine, preventative, screening methods in men having an increased risk of prostate cancer (e.g., increased age, family history, race, etc.) or in monitoring of subjects diagnosed with prostate cancer prior to or during treatment may be useful to better identify subjects in need of further, potentially more invasive, diagnostic tests, e.g., prostate exam or biopsy, digital rectal exam; or more aggressive treatment. Detection of levels of expression of filamin B, PSA, LY9 keratin 4, keratin 7, keratin 8, keratin 15, keratin 18, keratin 19, and tubulin-beta 3, especially keratin 19, may also be indicative of a good or poor response to a specific treatment regimen prior to changes in other signs or symptoms, e.g., loss of tumor response to hormone therapy.

In routine screening methods for prostate cancer, a serum sample from a subject is tested for the level of expression of both filamin B and PSA, and optionally one or more of LY9, keratin 4, keratin 7, keratin 8, keratin 15, keratin 18, keratin 19, and tubulin-beta 3, especially keratin 19. The levels are compared to one or more appropriate controls, e.g., other normal subjects, subjects with prostate cancer. Detection of an abnormal level of one or more of filamin B, PSA, LY9, keratin 4, keratin 7, keratin 8, keratin 15, keratin 18, keratin 19, and tubulin-beta 3, especially keratin 19 indicates that the subject should be considered for further tests for the presence of prostate cancer. Changes in the level of filamin B, optionally in combination with one or more of PSA, LY9, keratin 4, keratin 7, keratin 8, keratin 15, keratin 18, keratin 19, or tubulin-beta 3, especially keratin 19 with PSA in the subject may be more indicative of a change in prostate cancer status than comparison to a population control.

In determining a therapeutic regimen for a subject with prostate cancer not yet being actively treated for prostate cancer (i.e., watchful waiting) can be tested at regular intervals to determine if there is a change in the level of expression of filamin B, PSA, LY9 keratin 4, keratin 7, keratin 8, keratin 15, keratin 18, keratin 19, and tubulin-beta 3. An increase in the level of filamin B, PSA, keratin 19, or LY9 indicates that the subject should be considered for further tests to monitor the prostate cancer and more active therapeutic interventions should be considered.

In a subject undergoing treatment for prostate cancer (e.g., hormone therapy, chemotherapy, radiation therapy, surgery)

is tested prior to the initiation of the treatment and during and/or after the treatment to determine if the treatment results in a change in the level of expression of one or more of filamin B, PSA, LY9, keratin 4, keratin 7, keratin 8, keratin 15, keratin 18, keratin 19, and tubulin-beta 3. A decrease in the level of filamin B, PSA, keratin 19, or LY9 is indicative of response to treatment.

Example 13: Detection of Filamin a and Keratin 19 by ELISA in Human Serum from Patients with and without Prostate Cancer ELISA assays were conducted on commercially available human serum samples to detect the levels of filamin A and keratin 19 in samples from patients with and without prostate cancer.

The commercial human serum samples used for the filamin A ELISA are shown in FIG. 11, the data/annotation of which is publicly available at the Asterand and Bioreclamation websites. The commercial human serum samples used for the keratin 19 ELISA are shown in FIG. 12, the data/annotation of which is publicly available at the Asterand and Bioreclamation websites.

For the filamin A test, the ELISA was conducted in accordance with the Human Filamin A (FLNa) ELISA kit, Catalog No. CSB-EL008724HU, which is commercially and publicly available from CEDARLANE (Cusabio), the contents of which are incorporated herein by reference.

For the keratin 19 test, the ELISA was conducted in accordance with the Human Keratin-19 (KRT19) ELISA Kit, Catalog No. E91239HU, which is commercially and publicly available from CEDARLANE (Cusabio), the contents of which are incorporated herein by reference.

Figure 13:
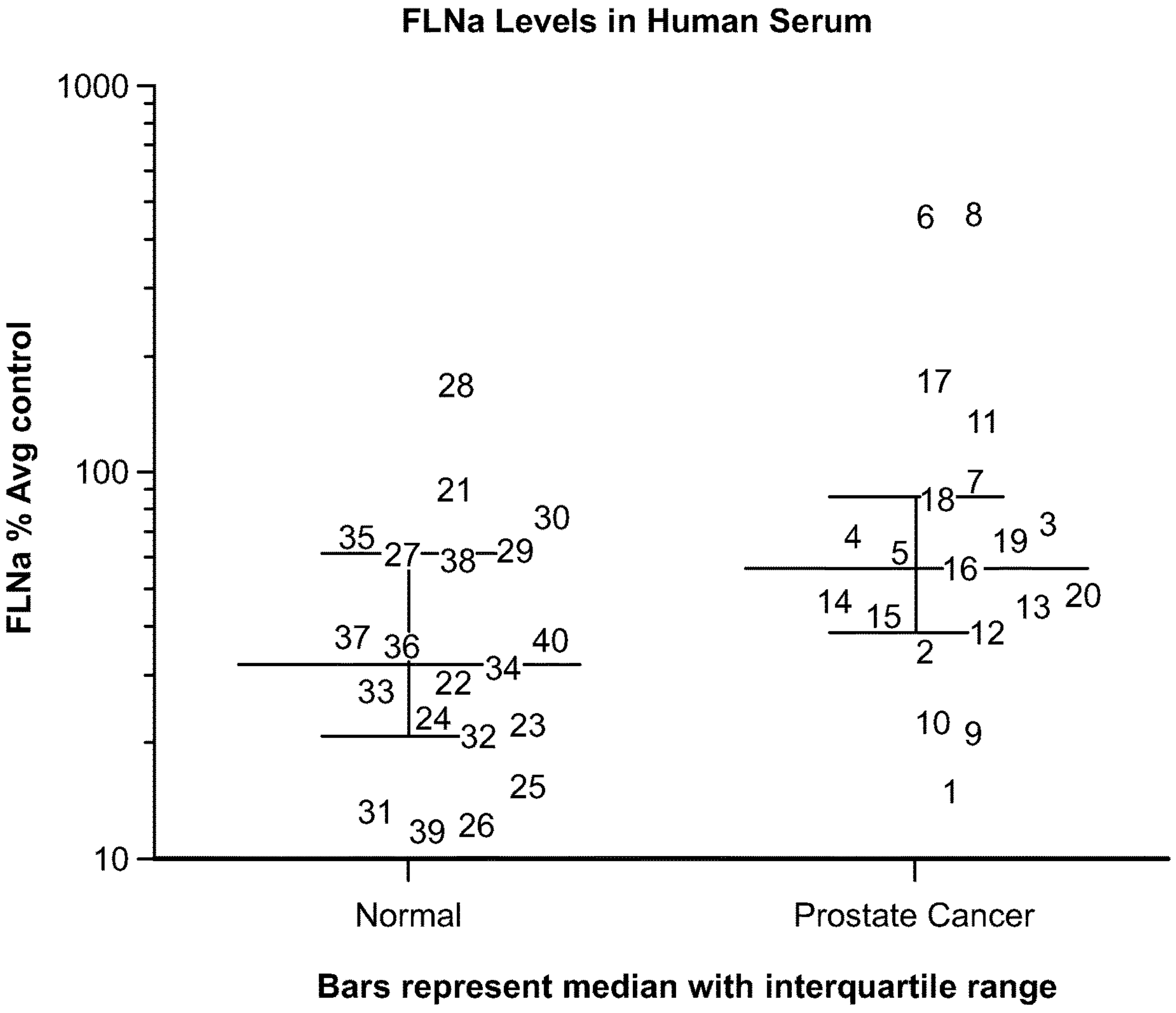
FIG. 13: Filamin A protein levels in serum from patients with and without prostate cancer as determined by ELISA.

FIG. 13 shows the filamin A protein levels in serum from patients with and without prostate cancer as determined by ELISA.

Figure 14:
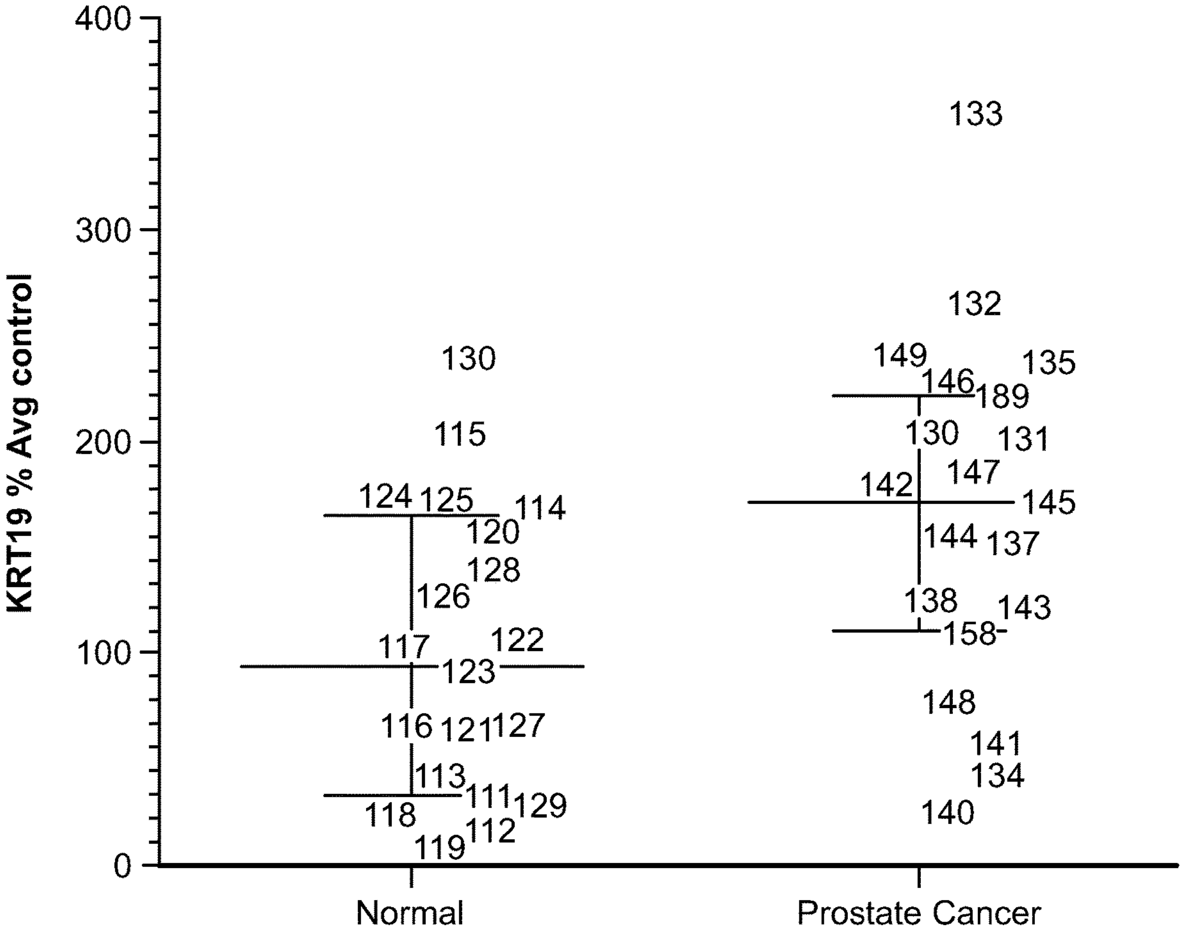
FIG. 14: Keratin 19 protein levels in serum from patients with and without prostate cancer as determined by ELISA.

FIG. 14. shows the keratin 19 protein levels in serum from patients with and without prostate cancer as determined by ELISA.

Example 14: Filamin a and Keratin 19 Differentiate Between Patients with Prostate Cancer and Normal Individuals The inventors have developed in-vitro models of prostate cancer based on a number of cancer and normal cell lines including the androgen independent PC3 and the androgen dependent LNCaP prostate cancer cell lines. Key regulatory nodes inferred by Berg Interrogative Biology™ were selected for a proof-of-concept validation in human serum as biomarkers of prostate cancer.

The initial two biomarkers FLNB and LY9 showed predictive power to differentiate between normal serum and serum from prostate cancer patients. This report reviews statistical characteristics of additional biomarkers, FLNA, FLNC, KRT18 and KRT19.

Statistical Performance of Candidate Markers: Bioreclamation Sample Set #1:

Human serum samples from normal individuals and individuals with prostate cancer were acquired from a commercial source, as per Example 13. The panel of biomarkers was measured by commercially available ELISA kits, as per Example 13.

Figure 15:
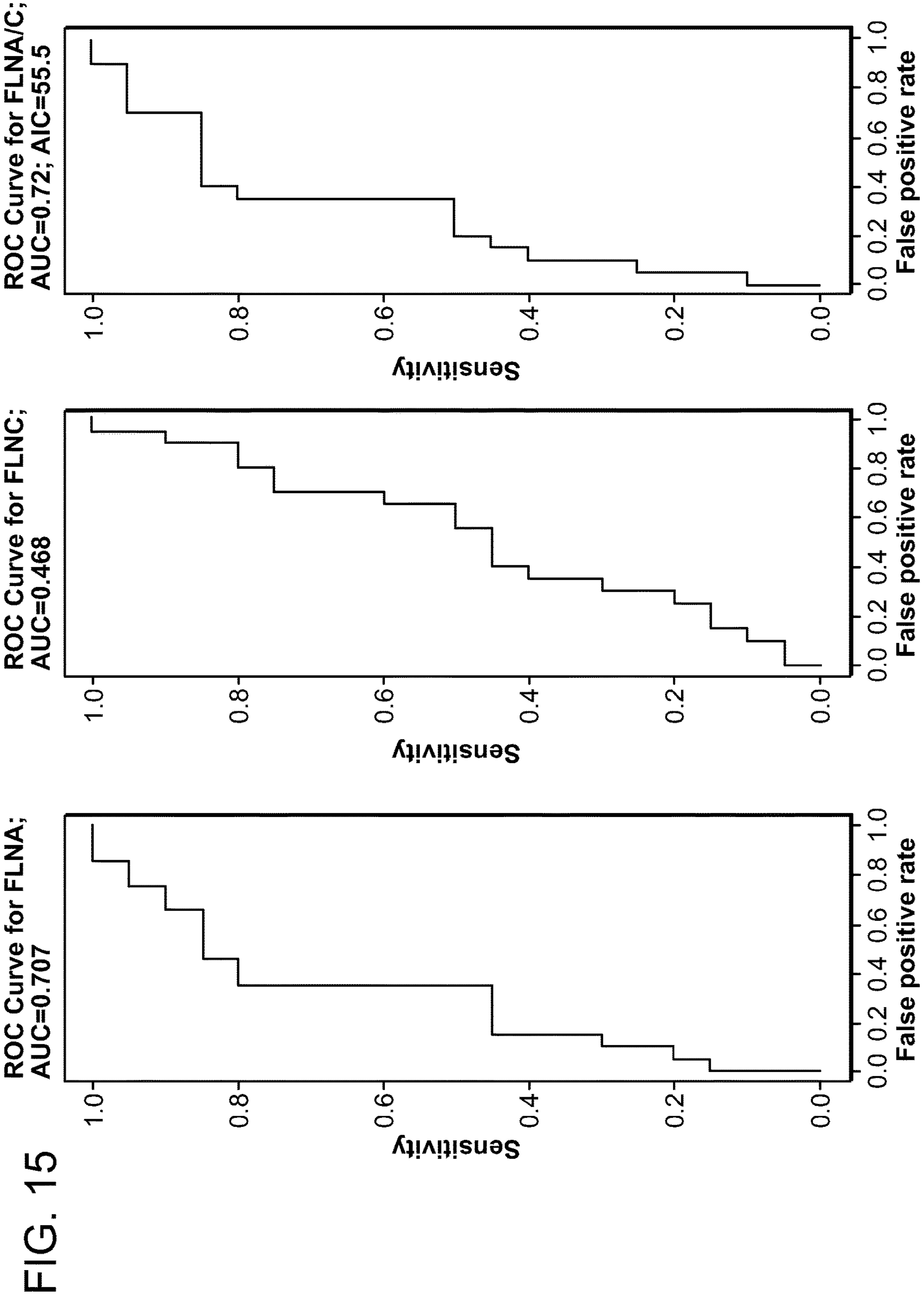
FIG. 15: ROC curve analysis for filamin A (FLNA) and filamin C (FLNC) and the combination (FLNA/C), as per Example 14.

FIG. 15 demonstrates the performance of the candidate markers in the set of 20 normal and 20 prostate cancer samples. FLN-A showed predictive power to differentiate between normal and cancer patients, whereas FLN-C did not show any positive trend. The combination panel of FLN-A and FLN-C did not improve on the performance of FLN-A alone.

Statistical Performance of Candidate Markers: Bioreclamation and Asterand Sample Set #2:

Human serum samples from normal individuals and individuals with prostate cancer were acquired from two commercial sources, as per Example 13. The panel of biomarkers was measured by commercially available ELISA kits, as per Example 13.

Figure 16:
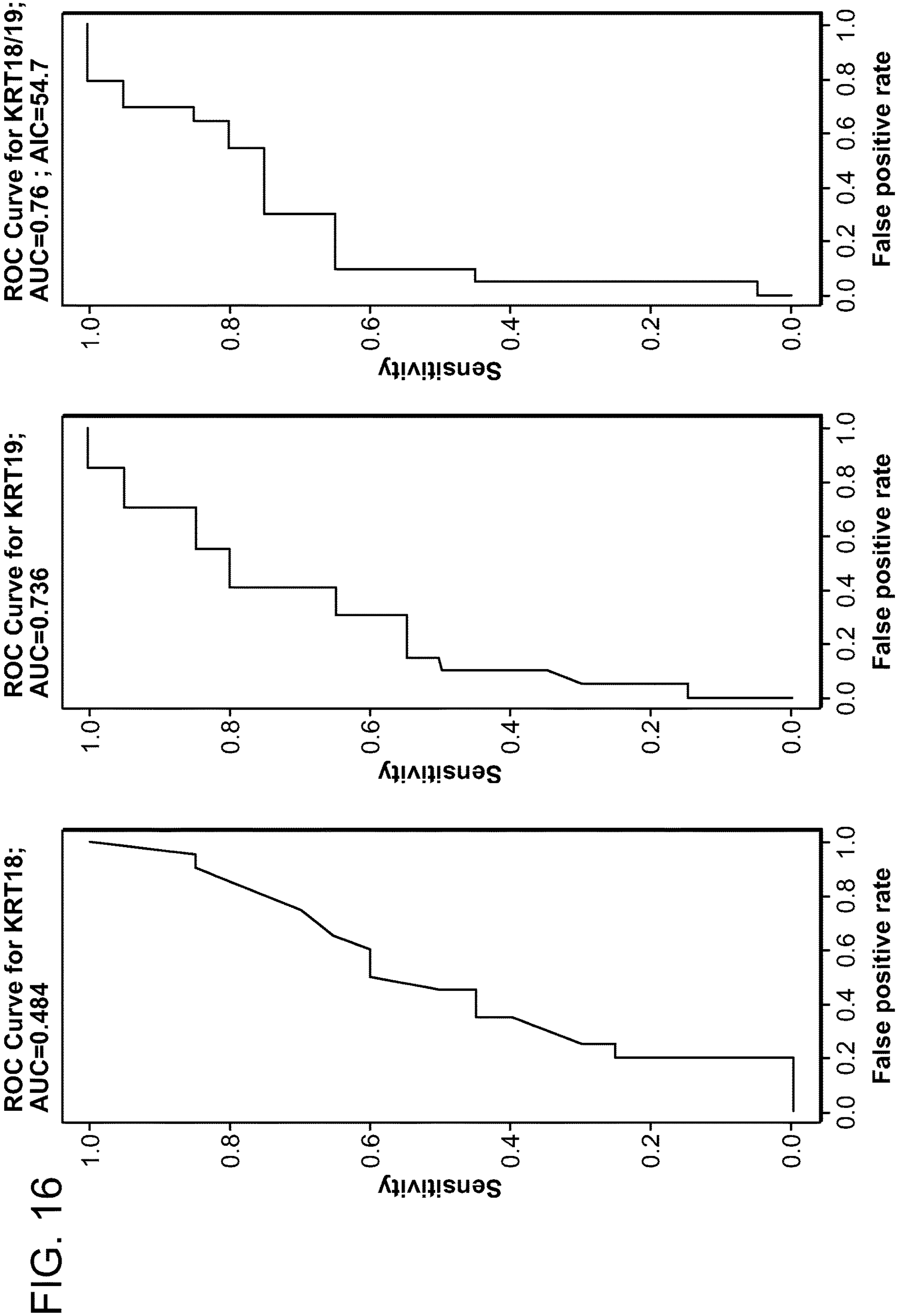
FIG. 16: ROC curve analysis for keratin 18 (KRT18) and kertain 19 (KRT19) and the combination (KRT18/19), as per Example 14.

FIG. 16 demonstrates the performance of the candidate markers in the set of 20 normal and 20 prostate cancer samples. KRT19 showed predictive power to differentiate between normal and cancer patients. KRT18 did not show any differentiation between normal and cancer specimens. The combination panel of KRT18 and KRT19 did not improve on the performance of KRT19 alone.

Conclusion:

Based on the results of this proof-of-concept study, KRT19 and FLNA have the potential to differentiate between patients with prostate cancer and normal individuals. These two biomarkers may be evaluated in a larger clinical validation study by either a commercial or in-house developed ELISA assay. The results above demonstrate that FLNa and KRT19 are statistically significant biomarkers of prostate cancer and therefore may be a significant improvement over the current screening tools.

Example 15: Filamin a, Filamin B, Keratin 19, and Age Differentiate Between Patients with Prostate Cancer and Normal Individuals To study whether the Prostate Cancer Panel test is equivalent, better, or weaker than PSA in screening for prostate cancer, we studied the above 4 comparisons with 4 different MVI (Multivariate Index) models to best study the utility of the panel.

Samples were divided as training/verification set and validation set. The verification set consisting of 332 samples was used to develop the models. The validation set of 171 samples were used to test the model.

The annotations of the validation samples were blinded. Probability unit linear regression models were estimated using the verification part of the sample set. Regression models were created to classify samples from the patients with diagnosed prostate cancer, with high Gleason Score (>6 and >7), and with benign prostate hyperplasia. Prostate cancer panel predictive algorithms were implemented based on the regression models and the probability cut-offs selected to achieve a certain level of test sensitivity or specificity. Each predictive algorithm was validated on the left-out validation sample set.

The biomarkers in the panel are:

1) Filamin-A
2) Filamin-B
3) Keratin-19
4) Age was used as a continuous predictor variable.

Using the panel in various combinations along with clinical information, the predictive power in screening for prostate cancer compared to PSA alone was tested. The specific study objectives were:

1) Determine the predictive power and the utility of the Biomarker panel to differentiate between samples from patients with and without prostate cancer.

2) Determine the predictive power of the Biomarker panel to differentiate between samples from patients with HIGH Gleason Score (8-10), INTERMEDIATE Gleason Score (7), and LOW Gleason Score (6) prostate cancer.

3) Determine the predictive power of the Biomarker panel to identify samples from patients with prostate cancer but low PSA (less than 4 ng/ml) concentration.

4) Determine the predictive power of the Biomarker panel to differentiate between samples from patients with prostate cancer and benign prostatic hyperplasia.

The terminology used for categories of cancer is:

Super High=Gleason Score 8 and above.

High=Gleason Score 7 and above

Low=Gleason score 6

Else=All other samples when a certain specified category is being compared with the rest of the samples.

Study Design

A retrospective and clinically annotated sample set from Mt. Sinai Hospital, Toronto, Canada was obtained. The sample matrix is serum and is frozen since its collection and processing.

This is a clinically annotated sample set with 662 samples from the patients at a Prostate Center. The patients were all comers for prostate gland biopsy. 120 samples from this set were used as a proof of concept set for the proposed Prostate Cancer Panel. The remaining samples were sorted as per the volume available. Anything short of 350 ul was excluded and the samples were then segregated in 2:1 ratio and identified as 'Verification' set and 'Validation' set.

All samples, irrespective of the verification or validation set, were analyzed using the prostate Cancer Panel in the CLIA certified laboratory. The laboratory was blinded to the sample's designation of 'verification' or 'validation' set.

The samples were randomized and separated as 'verification' and 'validation' set.

Participant Recruitment and Sampling

Serum samples were collected from 662 male patients. All patients were referred to a Prostate Center for a prostatic biopsy. These patients were suspicious for prostate cancer based on either clinical symptoms, digital-rectal examination, or, more frequently, due to a serum PSA elevation (beyond 3 ng/ml). The patients were consented to participate in this study by a personal interview and blood was drawn before any clinical manipulations or prostatic biopsy.

To establish the final diagnosis, the pathology report was examined by a clinical associate and patients were categorized as prostate cancer with Gleason score assigned (n=311), benign conditions (n=122), atypical small acini proliferation (n=26), prostatic intraepithelial neoplasia (n=69), benign prostatic hyperplasia (n=60), inflammation (n=58), microfocus adenocarcinoma (n=16).

Sample Collection Protocol

Venous blood was collected in SST tube, 5 mL from BD

Tubes were kept vertically at room temperature for ½-1 hour, allowing the blood to clot.

Samples were centrifuged at 2000 RCF for 10 minutes at 4° C.

The supernatant serum was collected, aliquoted into 0.5 ml sterile screw-capped tubes, and labeled with the appropriate Identification Number.

Samples were immediately stored at −80° C.

Data Collection

There are 332 samples in the training and 171 samples in the validation dataset. Samples were randomized to make two groups.

No. of total samples=332

No. of Gleason above 8=19

No. of samples with Gleason 6=103

No. of samples with No-Cancer=159

No. of BPH samples=23

Study Population

The samples were transferred on dry ice and were stored at −80° C. in the CLIA certified laboratory.

The samples are from a retrospective sample set with the following annotation:

PSA test values

Diagnosis

Patient age

Reason for biopsy

Total biopsy cores, staging, and grading (Gleason score)

Number of positive cores

Tumor location

Reference standard and Rationale

The PSA test is the reference standard against which the outcome of the Panel was compared.

This retrospective sample set has documented PSA values which were used in data analysis.

This set also had documented biopsy results with Gleason scores.

Validated Assays

All samples were tested using the assays described below:

FLN-A ELISA: which measures FLN-A in serum and plasma by ELISA in the range of 3.125-200 ng/ml FLN-B ELISA which measures concentration of FLN-B in human serum and plasma by ELISA in the range of 0.156-10 pM Keratin-19 ELISA which measures soluble cytokeratin 19 fragments in human serum FLN-A IP MRM which measures the concentration of FLN A peptides from human serum using Immunoprecipitation and LC-MS/MS in the range of 125 pg/ml-2000 pg/ml for P2, 250 pg/ml-6000 pg/ml for P3 and 1125 pg/ml-36000 pg/ml for P4.

Definition and Rationale of Units

PSA is reported in units of ng/ml. The values are taken from the annotations of the sample set.

Filamin A ELISA: ng/ml

Filamin A Peptide IP-MRM: pg/ml

Keratin-19 fragment ELISA: ng/ml

Filamin-B ELISA; picomole, pM

Results

The models generated from the verification set samples generated the following AUC data in Table 1 and the predictive power data in Table 2.

TABLE 1

AUC summary for all dataset (Peptide in Log scale)

| | CA vs Others | | CA vs BPH | | High Gleason vs. Low | | High Gleason vs. Others | | Super High Gleason vs. Others | |
|---|---|---|---|---|---|---|---|---|---|---|
| | Biomarker | AUC | Biomarker | AUC | Biomarker | AUC | Biomarker | AUC | Biomarker | AUC |
| Individual | PSA | 0.569 | PSA | 0.564 | PSA | 0.619 | PSA | 0.631 | PSA | 0.67 |
| | Age | 0.62 | Age | 0.621 | Age | 0.622 | Age | 0.662 | Age | 0.7 |
| | FLNA | 0.574 | FLNA | 0.696 | FLNA | 0.515 | FLNA | 0.56 | FLNA | 0.542 |
| | FLNB | 0.51 | FLNB | 0.516 | FLNB | 05.28 | FLNB | 0.515 | FLNB | 0.515 |
| | Krt19 | 0.519 | Krt19 | 0.618 | Krt19 | 0.573 | Krt19 | 0.567 | Krt19 | 0.574 |
| | P2-1 | 0.55 | P2-1 | 0.636 | P2-1 | 0.527 | P2-1 | 0.551 | P2-1 | 0.528 |
| | P2-2 | 0.502 | P2-2 | 0.582 | P2-2 | 0.528 | P2-2 | 0.552 | P2-2 | 0.53 |
| | P3-1 | 0.51 | P3-1 | 0.524 | P3-1 | 0.547 | P3-1 | 0.529 | P3-1 | 0.5 |
| | P4-2 | 0.522 | P4-2 | 0.595 | P4-2 | 0.551 | P4-2 | 0.555 | P4-2 | 0.578 |
| Two Combined (top) | Age & FLNB | 0.63 | FLNA & KRT19 | 0.717 | Age & PSA | 0.659 | Age & PSA | 0.696 | Age & PSA | 0.765 |
| Three Combined (top) | Age & FLNB & PSA | 0.635 | FLNA & KRT19 & Age | 0.735 | PSA & Age & FLNB | 0.685 | PSA & Age & FLNB | 0.717 | PSA & Age & FLNB | 0.804 |
| Four Combined (top) | Age & FLNA & P2-1 & P2-2 | 0.637 | FLNA & KRT19 & P2-1 & Age | 0.746 | PSA & Age & FLNB & P3-1 | 0.693 | PSA & Age & FLNP & P3-1 | 0.723 | PSA & Age & FLNB & P2-2 | 0.81 |
| | | | FLAN & KRT19 & Age & P4-2 | 0.746 | | | | | PSA & Age & FLNB & P2-2 | 0.81 |
| Five Combined (top) | Age & FLNA & PSA & P2-2 & P2-1 | 0.644 | FLNA & KRT19 & Age & P2-1 & P3-1 | 0.764 | PSA & Age & FLNA & P3-1 & KRT19 | 0.694 | No improvement | | PSA & Age & FLNB & P2-2 & P2-1 | 0.811 |

TABLE 2

Summary of Predictive Power analysis of Verification Samples

| Goal | Cut off | Sensitivity | Specificity | PPV | NPV |
|---|---|---|---|---|---|
| Differentiate between Cancer and Non Cancer samples | | | | | |
| Verification Set<br>Gleason Score 8 and above Vs. Other samples | 0.4455 | 0.7712 | 0.3380 | 0.5566 | 0.5783 |
| Verification Set<br>Gleason Score 7 and above Vs. Other samples | 0.01997 | 1.0000 | 0.2482 | 0.0752 | 1.0000 |
| Verification Set<br>Prostate Cancer Vs. BPH samples | 0.1603 | 0.8136 | 0.4915 | 0.2857 | 0.9134 |
| Verification Set | 0.8758 | 0.8035 | 0.6087 | 0.9392 | 0.2917 |

The predictive power and the utility of the Biomarker panel to differentiate between samples from patients with and without prostate cancer is shown below:

| Goal<br>Differentiate between<br>Cancer and Non Cancer | Cut off | Sensitivity | Specificity | PPV | NPV | Comments |
|---|---|---|---|---|---|---|
| Verification Set | 0.4455 | 0.7712 | 0.3380 | 0.5566 | 0.5783 | |
| Validation Set | 0.4455 | 0.8442 | 0.3580 | 0.5556 | 0.7073 | p value significant for Odds Ratio |

Verification Set

This model was trained to match the sensitivity of PSA=4 cutoff and test the specificity of the above-identified biomarker panel compared to the PSA test. FIG. 18 depicts PCA vs. Else: Sensitivity match PSA with a cutoff of 0.4455.

Validation Set

Figure 19:
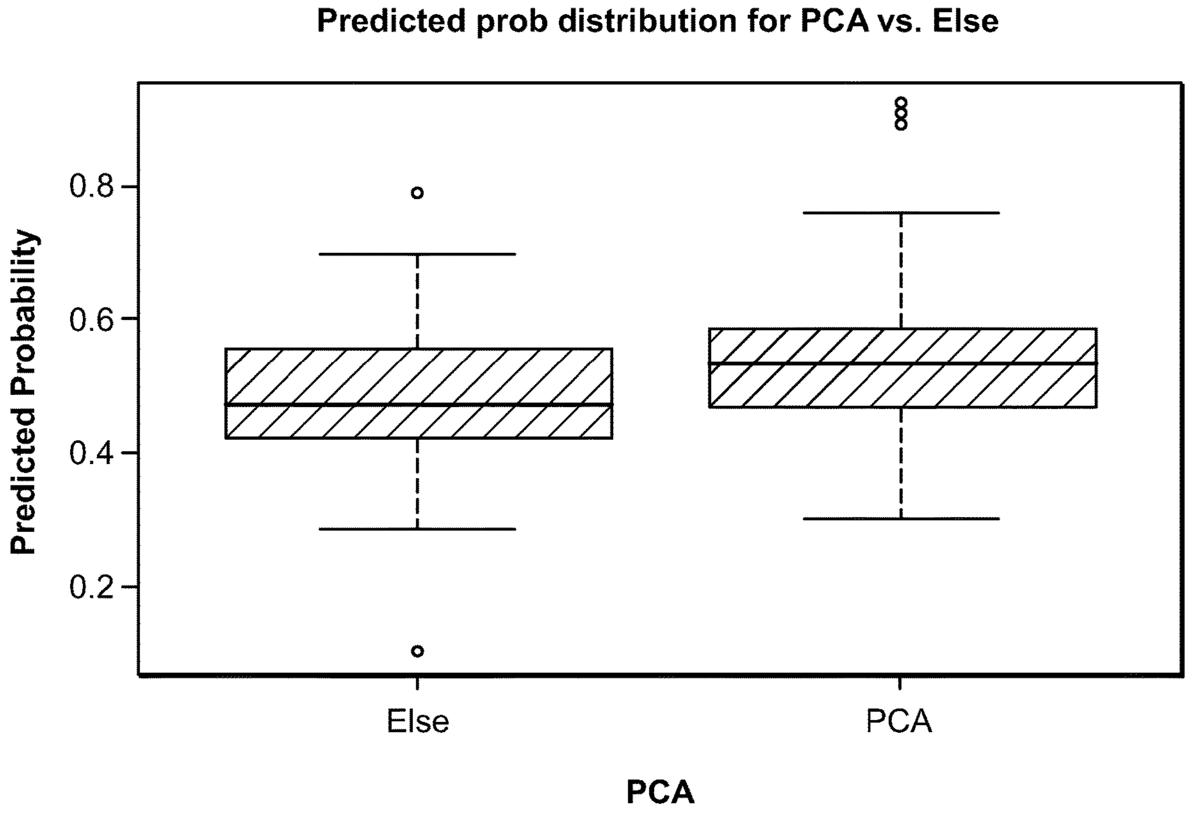
FIG. 19: Predicted probability distribution for PCA versus Else.

A boxplot of the predicted probability and the accuracy analysis are shown in FIGS. 19 and 20, respectively.

Next, the predictive power of the biomarker panel to differentiate between samples from patients with SUPER HIGH Gleason Score (8-10), HIGH Gleason Score (7 and above), and LOW Gleason Score (6) prostate cancer was determined.

| Goal | Cut off | Sensitivity | Specificity | PPV | NPV | Comments |
|---|---|---|---|---|---|---|
| Gleason Score 8 and above Vs. Other samples | | | | | | |
| Verification Set | 0.01997 | 1.0000 | 0.2482 | 0.0752 | 1.0000 | |
| Validation Set | 0.01997 | 0.7500 | 0.2583 | 0.0509 | 0.9512 | |
| Gleason Score 7 and above Vs. Other samples | | | | | | |
| Verification Set | 0.1603 | 0.8136 | 0.4915 | 0.2857 | 0.9134 | |
| Validation Set | 0.1603 | 0.7000 | 0.5116 | 0.2500 | 0.8800 | p value significant for Odds Ratio |

Verification Set

The model was trained to give a Sensitivity > or =0.95. As per this model, the cut off generated was 0.01997. See FIG. 21.

Validation Set

Figure 22:
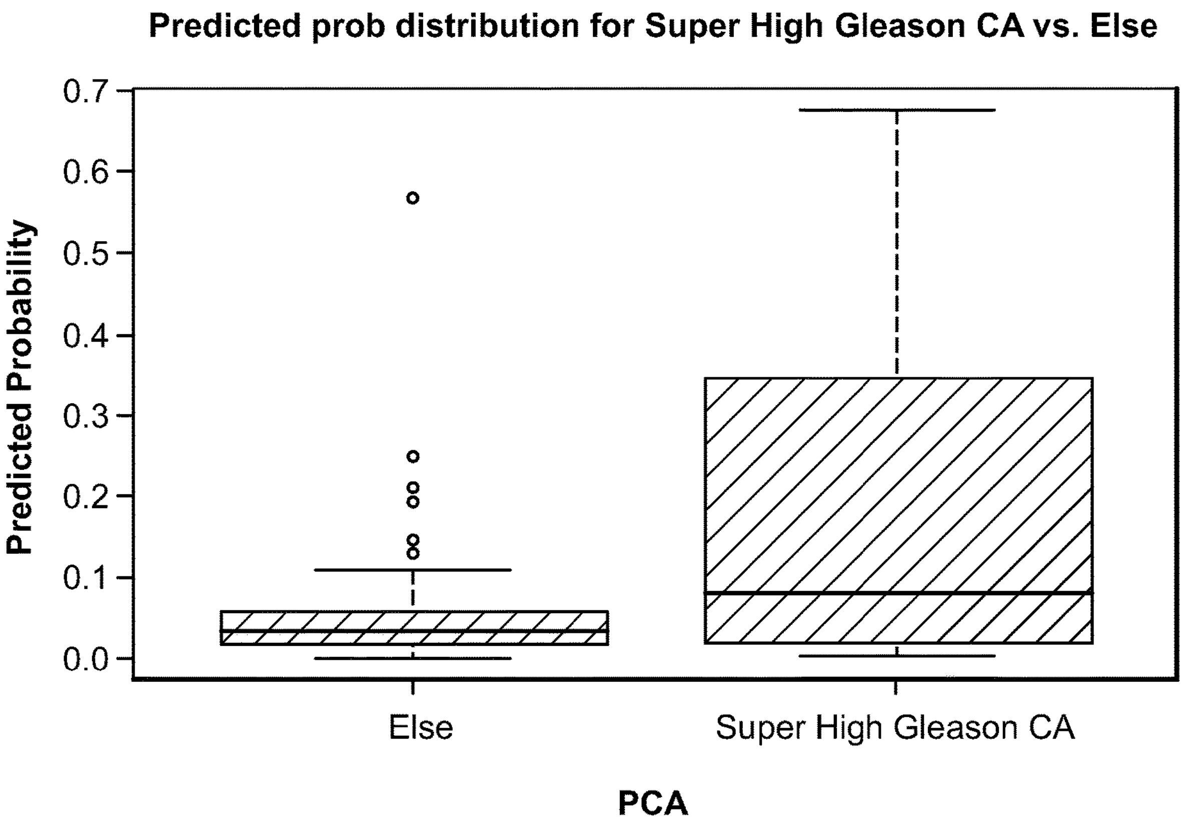
FIG. 22: Predicted probability distribution for Super High Gleason (8-10) versus Else.

A boxplot of the predicted probability and the accuracy analysis are shown in FIG. 22 and FIG. 23, respectively.

Next, the predictive power of the biomarker panel to differentiate between samples from patients with a HIGH Gleason Score versus Everything Else was determined.

Verification Set

The model was trained to have sensitivity of greater than or equal to 0.8. The outcome was a cut off value for the Biomarker panel which was 0.1603. See FIG. 24.

Validation Set

Figure 25:
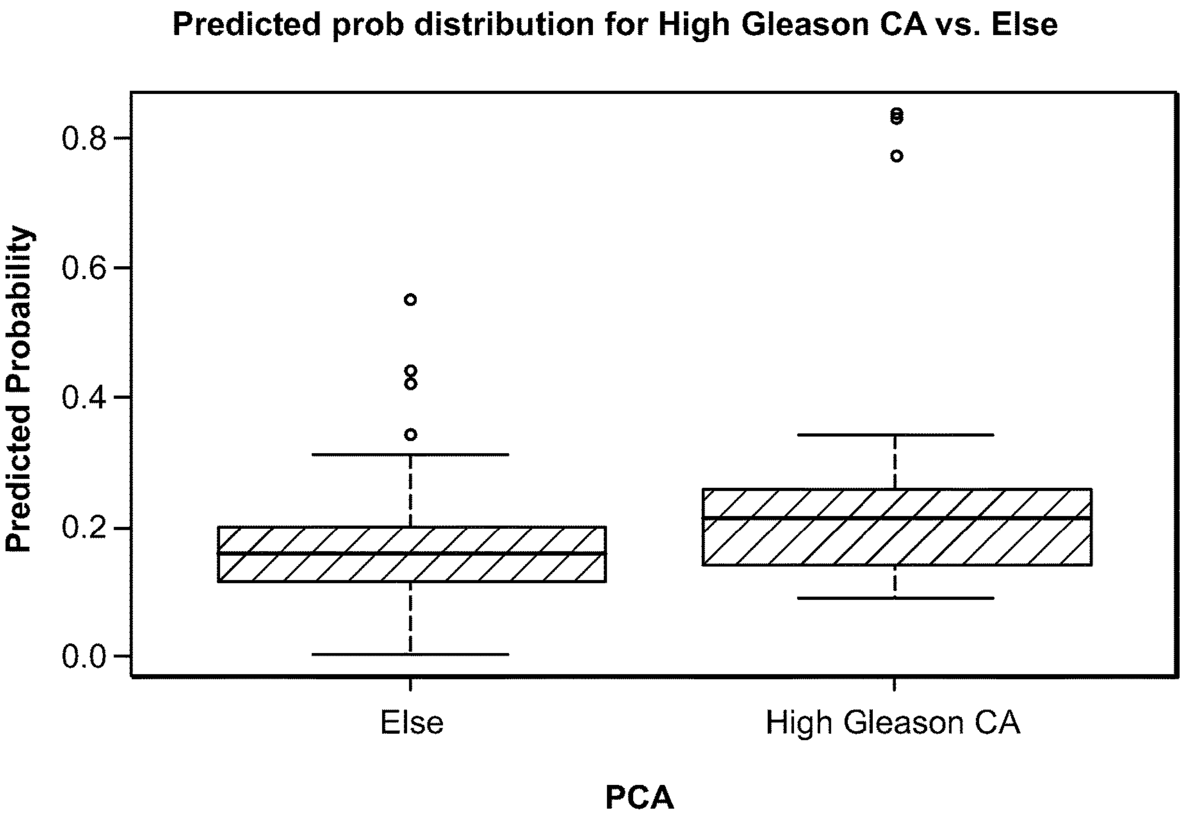
FIG. 25: Predicted probability distribution for High Gleason (7 and above) versus Else.

A boxplot of the predicted probability and the accuracy analysis are shown in FIG. 25 and FIG. 26, respectively.

Next, the predictive power of the biomarker panel to identify samples from patients with prostate cancer but low PSA (less than 4 ng/ml) concentration was determined. For this test, verification samples that had cancer were differentiated as low PSA (less than 4 ng/ml) and high PSA (greater than 4 ng/ml). Thus, the PSA AUC was equal to 1. Next, the low PSA and high PSA were predicted using the above-identified biomarker panel. The Table, below, depicts the AUC Summary for High PSA cancer versus Low PSA cancer.

AUC Summary for High PSA Cancer Vs. Low PSA Cancer

| | High PSA CA versus LPSA CA | |
|---|---|---|
| | Biomarker | AUC |
| | Age | 0.598 |
| | FLNA | 0.608 |
| | FLNB | 0.517 |
| | KRT19 | 0.517 |
| | P3-1 | 0.532 |
| | P4-2 | 0.506 |
| Two Combined (top) | FLNA & Age | 0.664 |
| Three Combined (top) | FLNA & Age & P4-2 | 0.669 |
| Four Combined (top) | No improvement | |
| Five Combined (top) | No improvment | |

Next, the predictive power of the biomarker panel to differentiate between samples from patients with prostate cancer and benign prostatic hyperplasia was determined. See Table, below.

| Goal<br>Prostate Cancer Vs. BPH | Cut off | Sensitivity | Specificity | PPV | NPV | Comments |
|---|---|---|---|---|---|---|
| Verification Set | 0.8758 | 0.8035 | 0.6087 | 0.9392 | 0.2917 | |
| Validation Set | 0.8758 | 0.6790 | 0.3636 | 0.8871 | 0.1333 | |

Verification Set

The biomarker panel was set to get sensitivity greater than or equal to 0.8. The cut off generated by this model was 0.8758. See FIG. 27.

Validation Set

Figure 28:
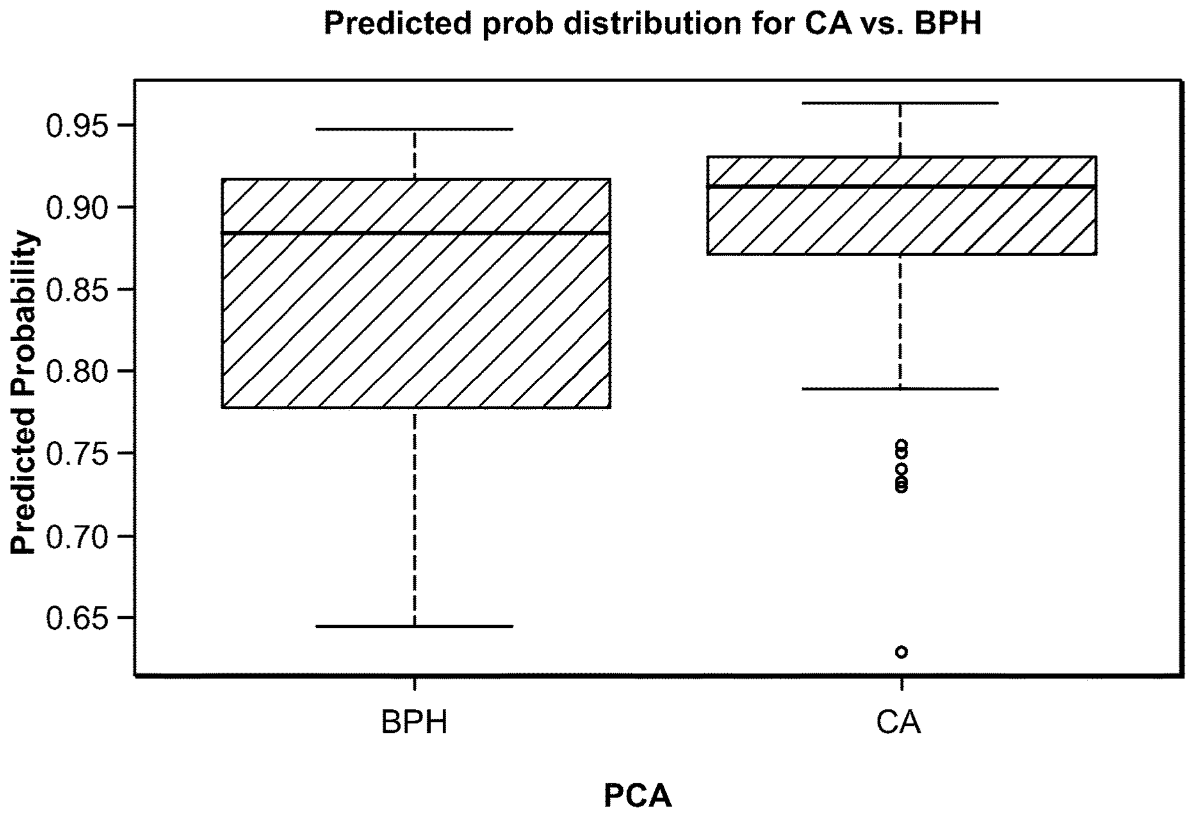
FIG. 28: Predicted probability distribution for Prostate Cancer (PCA) versus Benign Prostatic Hyperplasia (BPH).

A boxplot of the predicted probability and the accuracy analysis are shown in FIG. 28 and FIG. 29, respectively.

Conclusion

The verification and validation study indicates utility in four clinical applications of the PCA panel. The developed model significantly improved the ability to discriminate less aggressive forms from more aggressive forms. The AUC for discriminating samples taken from patients with Gleason Scores 8 and higher was 0.8 (versus 0.67 for PSA alone). The negative predictive value was very high for this model, if the patient value was below the model cutoff, the probability of the patient being disease free was 95%.

The model also performed well in discriminating patients with BPH versus prostate cancer. A patient value greater than the model cut-off was associated with an approximately 90% probability of the patient having prostate cancer instead of BPH. The AUC for this model was 0.75 (versus 0.56 for PSA alone).

The capabilities to discriminate samples from patients with prostate cancer from those without prostate cancer had predictive values in the 55-70 precentiles. However, AUC's were improved compared to the use of PSA alone.

Summary of Predictive Power Analysis of Vervification/Validation Samples

| Goal | Cut off | Sensitivity | Specificity | PPV | NPV | Comments |
|---|---|---|---|---|---|---|
| Differentiate between Cancer and Non Cancer | | | | | | |
| Verification Set | 0.4455 | 0.7712 | 0.3380 | 0.5566 | 0.5783 | |
| Validation Set | 0.4455 | 0.8442 | 0.3580 | 0.5556 | 0.7073 | p value significant for Odds Ratio |
| Gleason Score 8 and above Vs. Other samples | | | | | | |
| Verification Set | 0.01997 | 1.0000 | 0.2482 | 0.0752 | 1.0000 | |
| Validation Set | 0.01997 | 0.7500 | 0.2583 | 0.0509 | 0.9512 | |
| Gleason Score 7 and above Vs. Other samples | | | | | | |
| Verification Set | 0.1603 | 0.8136 | 0.4915 | 0.2857 | 0.9134 | |
| Validation Set | 0.1603 | 0.7000 | 0.5116 | 0.2500 | 0.8800 | p value significant for Odds Ratio |
| Prostate Cancer Vs. BPH | | | | | | |
| Verification Set | 0.8758 | 0.8035 | 0.6087 | 0.9392 | 0.2917 | |
| Validation Set | 0.8758 | 0.6790 | 0.3636 | 0.8871 | 0.1333 | |

Example 16: Identification and Validatin of Novel Prostate Cancer Biomarkers

Prostate cancer is the most frequent cancer diagnosis among men and the second leading cause of cancer-related death. Despite the widespread use of digital rectal exam (DRE) and blood-based screening of prostate-specific antigen (PSA) for prostate cancer screening, there are significant limitations in their specificity and prognostic value. Biomarkers which distinguish i) PSA-low prostate cancer from benign prostatic hyperplasia (BPH) and (ii) indolent versus aggressive disease course represent unment clinical needs. Experimentally, a panel of prostate cancer cell lines and non-tumorigenic, human primary cells were exposed to in vitro conditions designed to stimulate poor oxygenation, low pH, diminished nutrient microenvironments, and metabolic preturbations (24-48 h) followed by iTRAQ proteomic analysis of cell lysates. Using an Interrogative Biology platform, proteomic data were then subjected to Bayesian network learning to map molecular interactions, with cytoskeletal and scaffolding proteins Filamin A (FLNA), Filamin B (FLNB), and Keratin 19 (KRT19) identified as candidate prostate cancer biomarkers.

Figure 31:
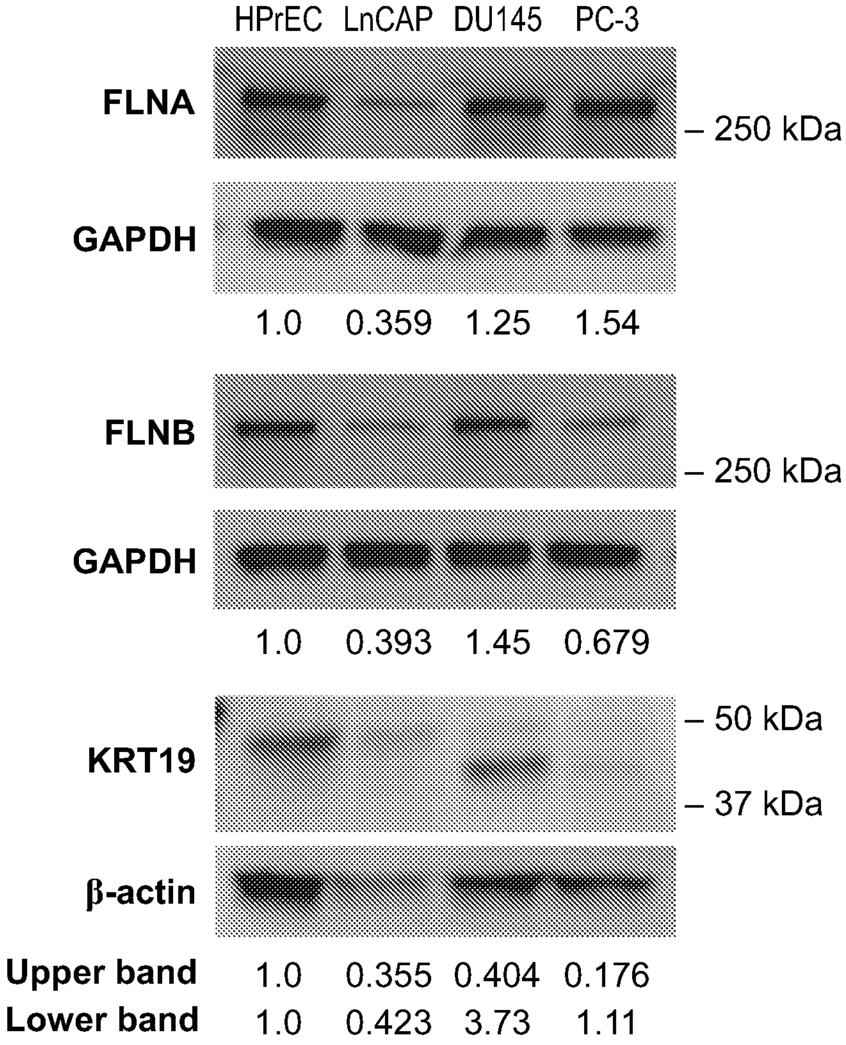
FIG. 31: FLNA, FLNB, and KRT19 expression in prostate cancer cells in vitro.

To validate biomarker expression, mRNA and protein was quantified in a panel of primary human prostate epithelial cells (HPrEC) and androgen-sensitive (LnCAP) or refractory (DU145, PC-3) prostate cancer cells, and each was differentially detected in one or more prostate cancer cell lines compared to HPrEC (FIGS. 30 and 31). Specifically, basal expression of FLNA, FLNB, and KRT19 in prostate cancer cells in vitro was assessed. mRNA and cell lysates were prepared from HPrEC, LnCAP, DU145, and PC-3 cells. Expression of FLNA, FLNB, and KRT19 was assessed by quantitative RT-PCR and normalized to TBP. Cell lysates were resolved by SDS-PAGE and probed with antibodies specific for FLNA, FLNB, and KRT19. Representative images are shown in FIGS. 30 and 31. Densitometric analysis for FLNA, FLNB, and KRT19 are reported below each blot. Values represent means+SEM, N=3. * $p<0.05$ compared to HPrEC.

Figure 32:
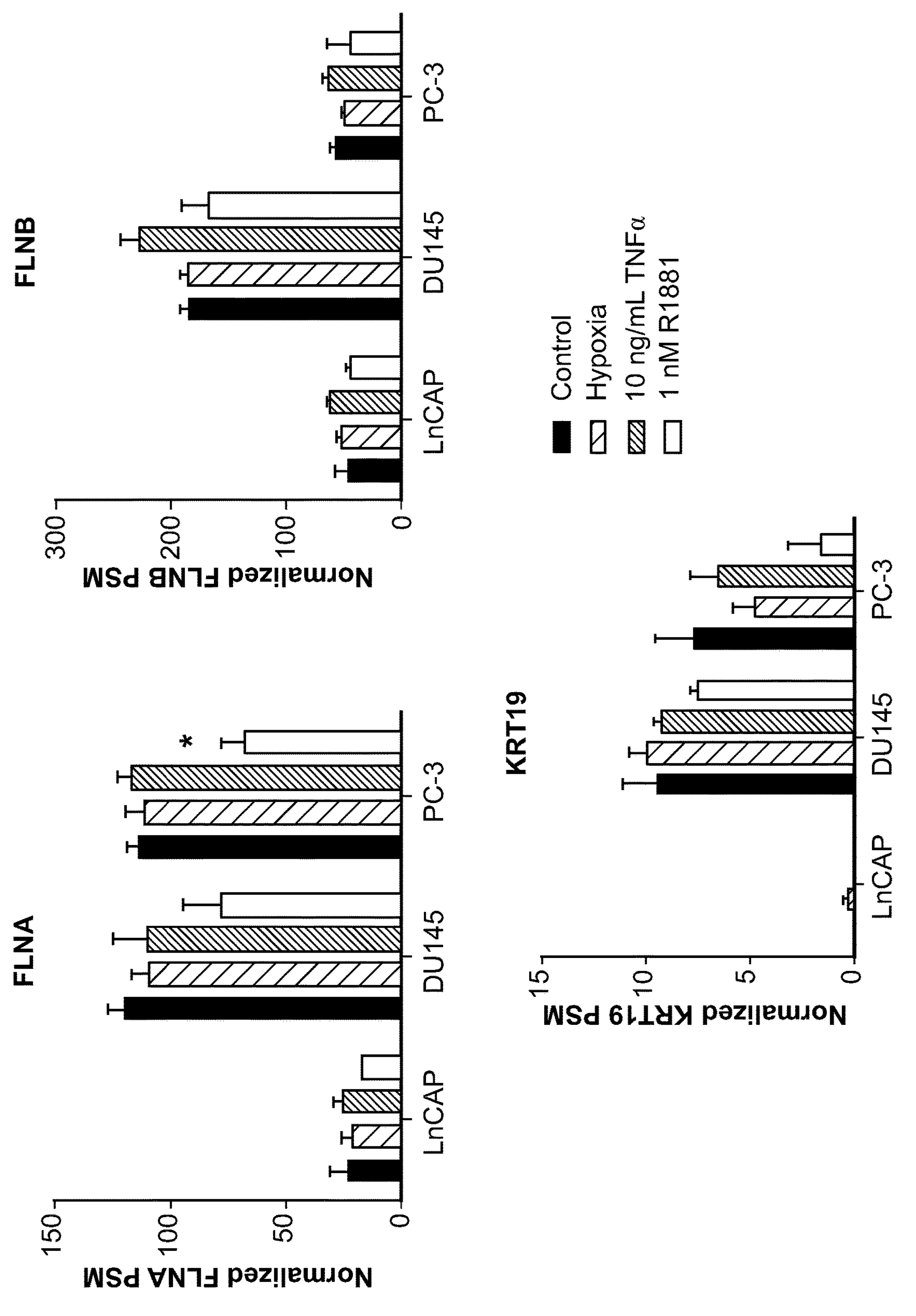
FIG. 32: Secretion of FLNA, FLNB, and KRT19 from prostate cancer cells in vitro.

Using proteomic analysis, peptides from FLNA, FLNB and KRT19 were also detected in cell culture media conditioned by prostate cancer cells (24 h), indicating that they can be secreted (FIG. 32). Specifically, conditioned media from LnCAP, DU145, and PC-3 cells exposed to lypoxia (1% oxygen), TNFα (10 ng/mL), or R1881 (1 nM) for 24 hours was harvested, and proteomic analysis was performed. Values represent means+SEM, N=3. * $p<0.05$ compared to normoxia control.

Figure 33:
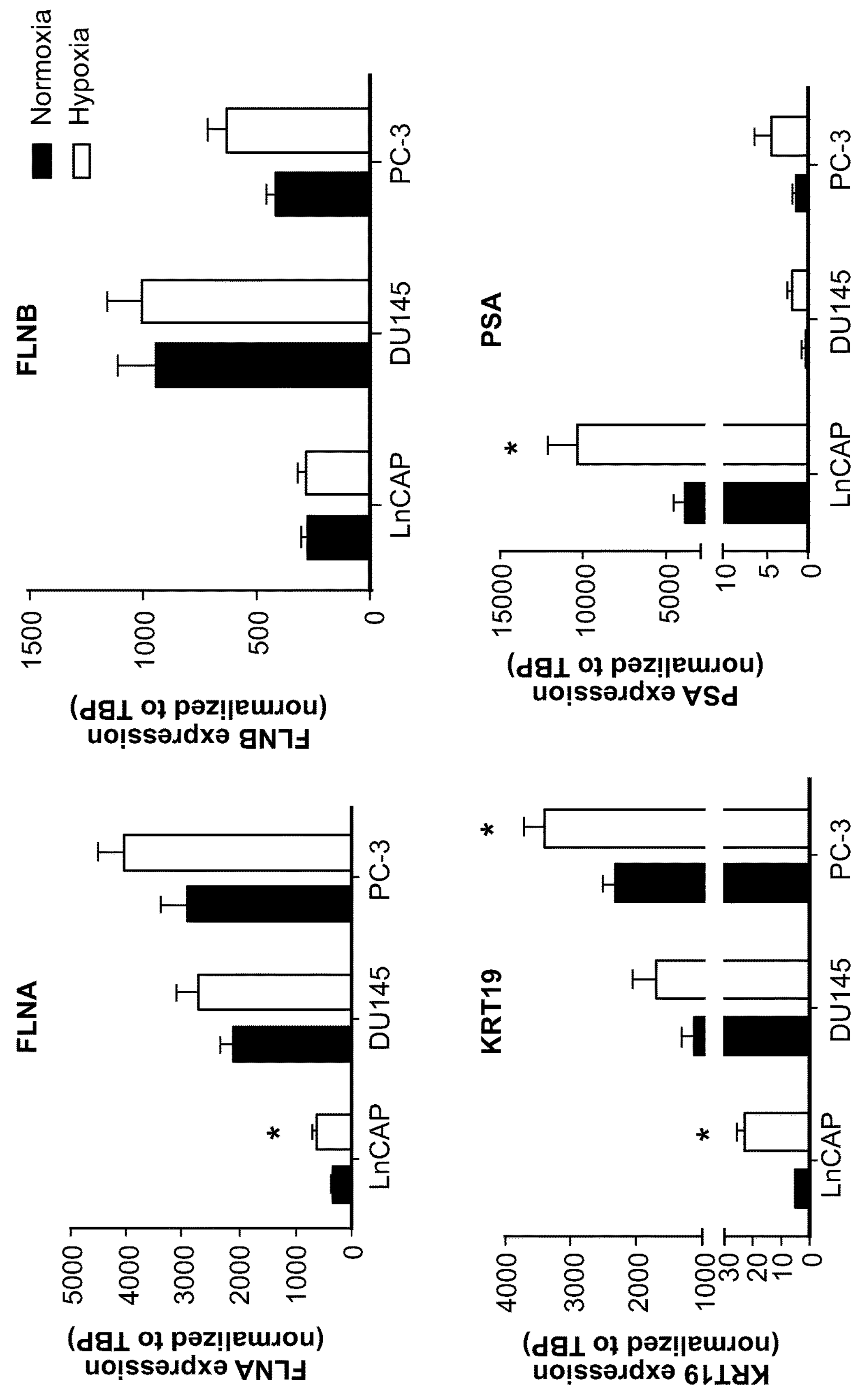
FIG. 33: Transcriptional regulation of FLNA, FLNB, KRT19, and PSA expression by prostate-relevant stimuli of hypoxia (1% oxygen) in vitro.
Figure 34:
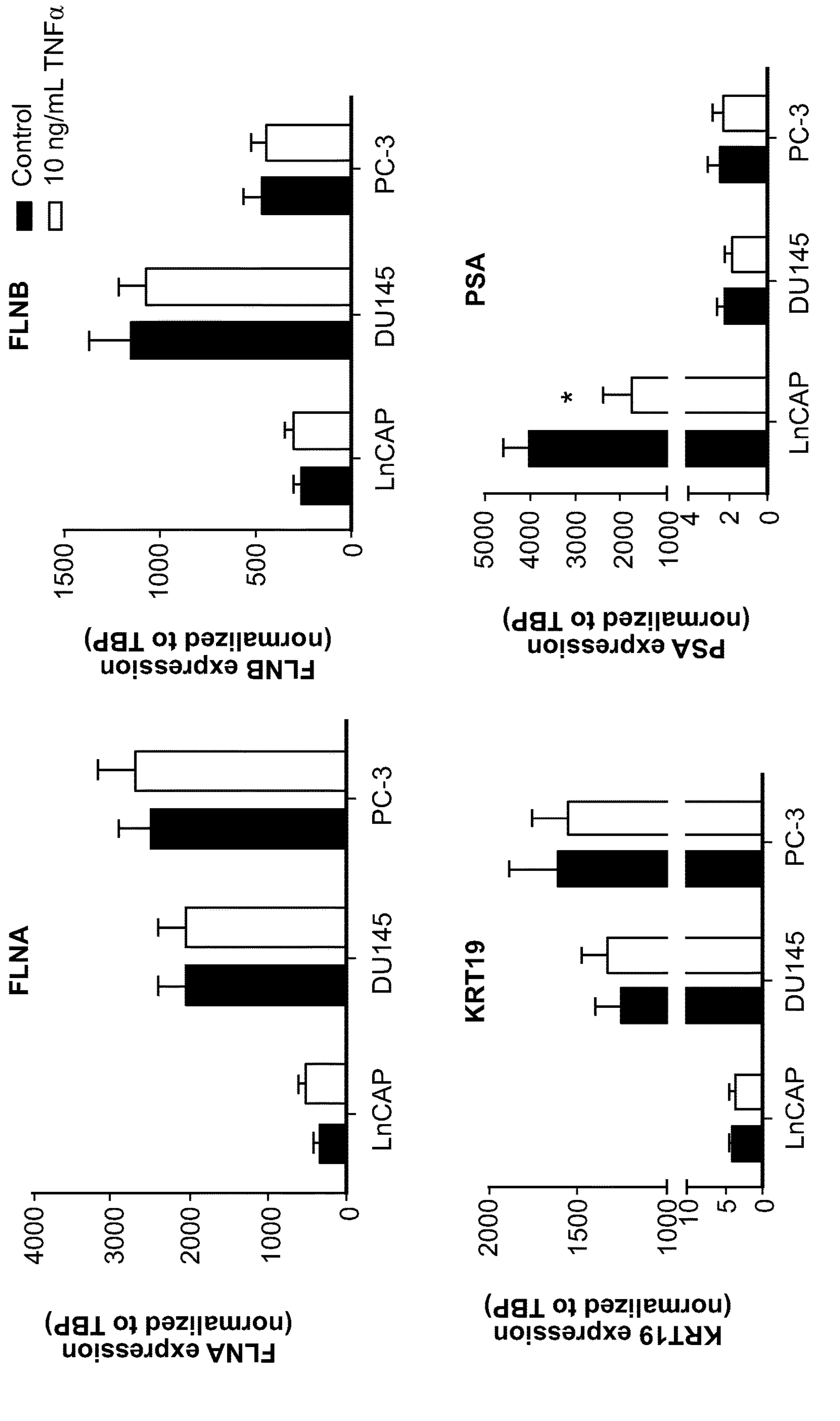
FIG. 34: Transcriptional regulation of FLNA, FLNB, KRT19, and PSA expression by prostate-relevant stimuli of TNFα (10 ng/mL) in vitro.
Figure 35:
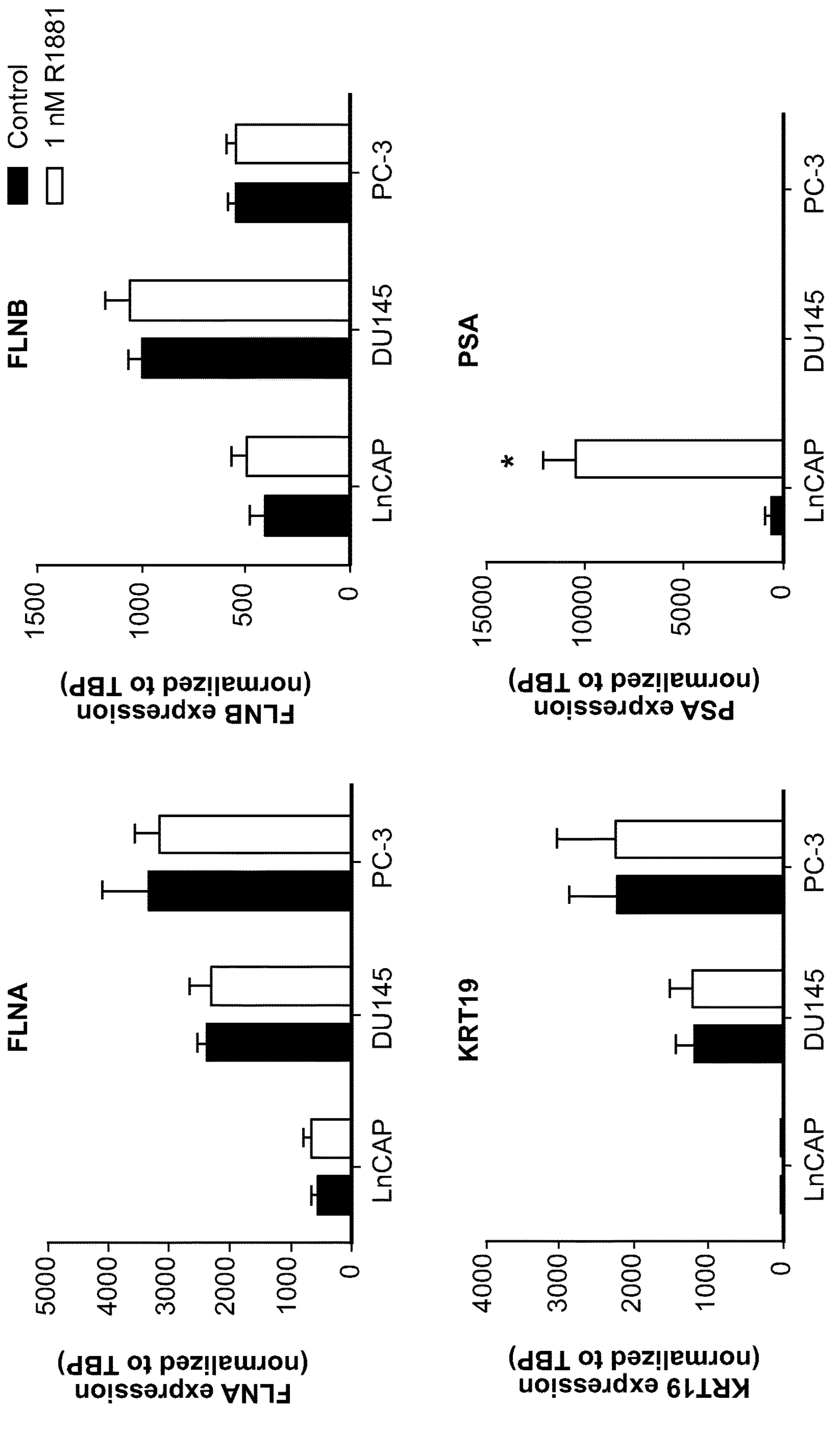
FIG. 35: Transcriptional regulation of FLNA, FLNB, KRT19, and PSA expression by prostate-relevant stimuli of R1881 (1 nM) in vitro.

Importantly, unlike PSA expression, global regulation of FLNA, FLNB, and KRT19 expression remained unaltered after treatment with multiple prostate-cancer relevant stimula (e.g., hypoxia, androgens, and inflammatory stimula) (FIGS. 33-35). Specifically, mRNA was prepared from LnCAP, DU145, and PC-3 cells exposed to hypoxia (1% oxygen; A), TNFα (10 ng/mL; B), or R1881 (1 nM; C) for 24 h. Expression of FLNA, FLNB, and KRT19 was assessed by quantitative RT-PCR, normalized to TBP, and compared to PSA. Values represent means+SEM, N=3. * $p<0.05$ compared to normoxia/control.

Figure 36:
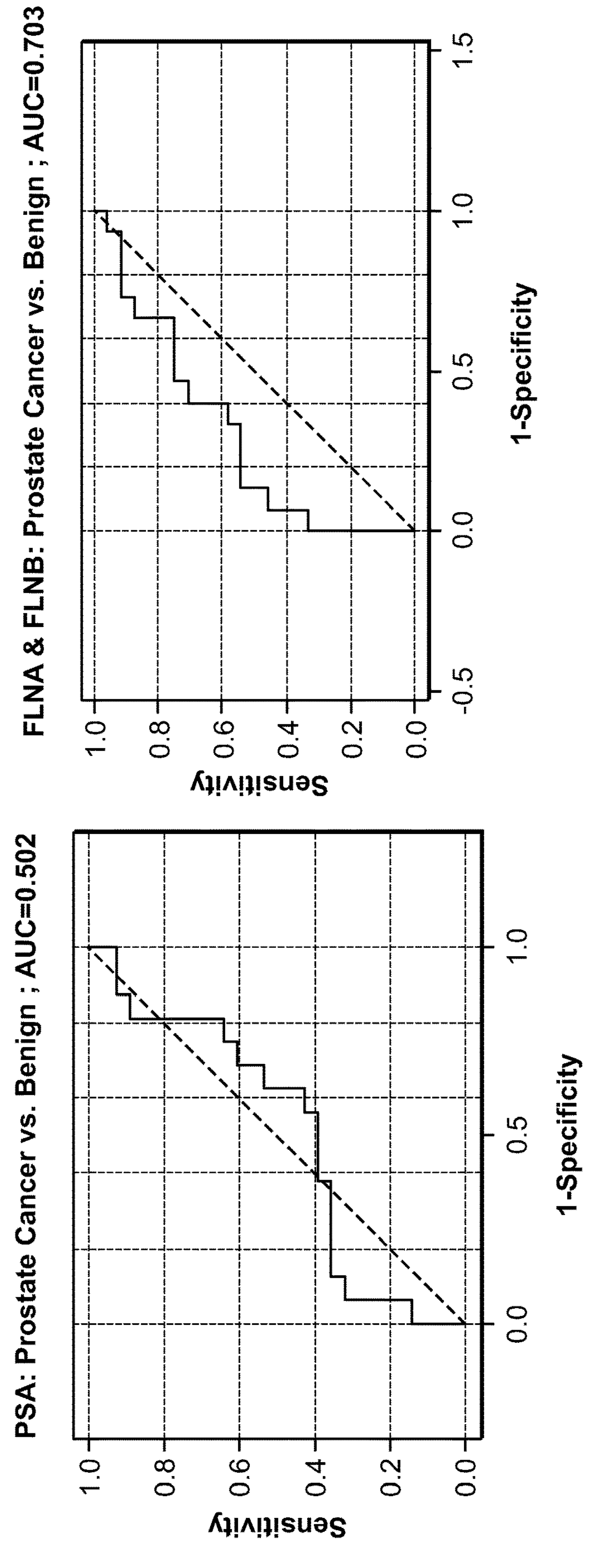
FIG. 36: Assessment of plasma FLNA and FLNB levels as biomarkers for prostate cancer.

Assessment of plasma FLNA and FLNB levels as screening markers were assessed in a proof-of-concept sample cohort of 47 plasma samples (FIG. 36). Residual lithium herpain plasma was collected from patient samples after the ordered tests were completed. The inclusion criteria were elevated PSA results (≥2.6 ng/mL), age of 45-70 years, and minimum volume of 700 μL. Results demonstrate that FLNA and FLNB were detected in human plasma and have predictive power in identifying prostate cancer patients.

Finally, in vivo validation was next conducted in sera from men (N-447) with confirmed prostate cancer, benign prostate tumors, or BPH using LDT ELISA assays in a CLIA-certified laboratory. To assess the sensitivity and specificity of FLNA, FLNB, and KRT19 compared to PSA, ROC curve analysis was performed. The individual predictive power of each biomarker alone was comparable to that of PSA. However, the combination of age, levels of FLNA, FLNB, and KRT19 and PSA out-performed PSA alone in identification of patients with prostate cancer stratified compared to benign status, Gleason scores, and incidence of BPH. Together, these data indicate that FLNA, FLNB, and KRT19 can be used in conjunction with PSA and/or age for more sensitive and specific prostate cancer screening, a critical unment need in the field.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present invention will be apparent from the appended claims. Moreover, those skilled in the art will recognize, or be able to ascertain using no more than routine experimentation, many equivalents to the specific embodiments of the invention described herein. Such equivalents are intended to be encompassed by the following claims.

The invention claimed is:

1. A method of treating prostate cancer in a subject suspected of having prostate cancer, comprising: (i) obtaining a serum sample or a plasma sample from the subject, wherein the subject has elevated PSA and is symptomatic of prostate cancer, (ii) submitting the sample from the subject to obtain diagnostic information as to the protein level of filamin A, (iii) administering a therapeutically effective amount of an anti-cancer therapy to the subject if the protein level of filamin A in the sample is increased relative to the protein level of filamin A in a normal control sample, wherein the anti-cancer therapy is selected from the group consisting of (a) radiation therapy, (b) chemotherapy, (c) surgery for resecting tumor tissues, (d) hormone therapy, (e) antibody therapy, (f) immunotherapy, (g) cytokine therapy, (h) growth factor therapy, and (i) any combination of (a)-(h).

2. The method of claim 1, further comprising submitting the sample from the subject to obtain diagnostic information as to the protein level of one or more additional markers of prostate cancer.

3. The method of claim 2, wherein the one or more additional markers of prostate cancer is selected from the group consisting of filamin B, LY9, keratin 4, keratin 7, keratin 8, keratin 15, keratin 18, keratin 19, and tubulin-beta 3.

4. The method of claim 2 or 3, further comprising administering a therapeutically effective amount of the anti-cancer therapy to the subject if the protein level of filamin A and the protein level of at least one of the one or more additional markers of prostate cancer in the sample from the subject are increased relative to the protein level of filamin A and at least one of the one or more additional markers in a normal control sample.

5. A method of treating prostate cancer in a subject, comprising: (i) obtaining diagnostic information as to the protein level of filamin A in a serum sample or a plasma sample from the subject, wherein the subject has elevated PSA and is symptomatic of prostate cancer, and (ii) administering a therapeutically effective amount of an anti-cancer therapy to the subject if the protein level of filamin A in the sample is increased relative to the protein level of filamin A in a normal control sample, wherein the anti-cancer therapy is selected from the group consisting of (a) radiation therapy, (b) chemotherapy, (c) surgery for resecting tumor tissues, (d) hormone therapy, (e) antibody therapy, (f) immunotherapy, (g) cytokine therapy, (h) growth factor therapy, and (i) any combination of (a)-(h).

6. The method of claim 5, further comprising obtaining diagnostic information as to the protein level of one or more additional markers of prostate cancer.

7. The method of claim 6, wherein the one or more additional markers of prostate cancer is selected from the group consisting of filamin B, LY9, keratin 4, keratin 7, keratin 8, keratin 15, keratin 18, keratin 19, and tubulin-beta 3.

8. The method of claim 6 or 7, further comprising administering a therapeutically effective amount of the anti-cancer therapy to the subject if the protein level of filamin A and the protein level of at least one of the additional markers of prostate cancer in the sample from the subject are increased relative to the protein level of filamin A and the protein level of at least one of the additional markers in a normal control sample.

9. A method of treating prostate cancer in a subject suspected of having prostate cancer, comprising: (i) obtaining a serum sample or a plasma sample from the subject for use in identifying diagnostic information as to the protein level of filamin A, wherein the subject has elevated PSA and is symptomatic of prostate cancer, (ii) determining the protein level of filamin A in the sample from the subject, (iii) administering a therapeutically effective amount of an anti-cancer therapy to the subject if the protein level of filamin A is increased relative to the protein level of filamin A in a normal control sample, wherein the anti-cancer therapy is selected from the group consisting of (a) radiation therapy, (b) chemotherapy, (c) surgery for resecting tumor tissues, (d) hormone therapy, (e) antibody therapy, (f) immunotherapy, (g) cytokine therapy, (h) growth factor therapy, and (i) any combination of (a)-(h).

10. The method of claim 9, wherein determining the protein level of filamin A comprises: (a) detecting the protein level of filamin A in a sample of the subject, and (b) comparing the protein level of filamin A in the sample with the protein level of filamin A in a normal control sample.

11. The method of claim 9, further comprising determining the protein level of one or more additional markers of prostate cancer.

12. The method of claim 11, wherein the one or more additional markers of prostate cancer is selected from the group consisting of filamin B, LY9, keratin 4, keratin 7, keratin 8, keratin 15, keratin 18, keratin 19, and tubulin-beta 3.

13. The method of claim 9, further comprising administering the anti-cancer therapy to the subject if the protein level of filamin A and the protein level of at least one of the additional markers of prostate cancer in the sample from the subject are increased relative to the protein level of filamin A and the protein level of at least one of the additional markers in a normal control sample.

14. The method of claim 9, wherein the protein level of filamin A protein is determined by immunoassay or mass spectrometry.

15. The method of claim 14, wherein the immunoassay is selected from the group consisting of ELISA, radioimmunoassay (RIA), and immunohistochemistry.

16. The method of claim 14, wherein the mass spectrometry is multiple reaction monitoring (MRM).

17. The method of claim 9, wherein the protein level of filamin A is determined by contacting the sample with a reagent that selectively binds to the filamin A to form a biomarker complex.

18. The method of claim 17, wherein the reagent is an anti-filamin A antibody that selectively binds to at least one epitope of filamin A.

19. The method of any one of claim 1, 5, or 9, wherein the anti-cancer therapy is suitable for treating a prostate cancer characterized by filamin A overexpression.

20. The method of any one of claims 1, 5, or 9, wherein the surgery is resection of a prostate tumor.

21. The method of any one of claims 1, 5, or 9, wherein the radiation therapy is brachytherapy.

22. The method of any one of claim 1, 5, or 9, further comprising determining the age of the subject.

23. The method of claim 22, wherein increased age of the subject as compared to a control is indicative of a change in prostate cancer status in the subject.

* * * * *